US010273465B2

(12) United States Patent
Bower et al.

(10) Patent No.: US 10,273,465 B2
(45) Date of Patent: Apr. 30, 2019

(54) GLYCOSYL HYDROLASE ENZYMES AND USES THEREOF

(71) Applicant: Danisco US Inc., Palo Alto, CA (US)

(72) Inventors: Benjamin Bower, Newark, CA (US); Megan Yee Hsi, San Jose, CA (US); Thijs Kaper, Half Moon Bay, CA (US); Bradley R. Kelemen, Menlo Park, CA (US); Suzanne E. Lantz, San Carlos, CA (US); Edmund A. Larenas, Moss Beach, CA (US); Colin Mitchinson, Half Moon Bay, CA (US); Steven Kim, Fremont, CA (US); William D. Hitz, Wilmington, DE (US); Mark Emptage, Wilmington, DE (US); Keith Dumont Wing, Wilmington, DE (US)

(73) Assignee: DANISCO US INC., Palo Alto, CA (US)

( * ) Notice: Subject to any disclaimer, the term of this patent is extended or adjusted under 35 U.S.C. 154(b) by 96 days.

(21) Appl. No.: 14/810,434

(22) Filed: Jul. 27, 2015

(65) Prior Publication Data
US 2016/0177279 A1  Jun. 23, 2016

Related U.S. Application Data

(63) Continuation of application No. 13/498,069, filed as application No. PCT/US2010/049849 on Sep. 22, 2010, now abandoned.

(60) Provisional application No. 61/245,273, filed on Sep. 23, 2009, provisional application No. 61/289,886, filed on Dec. 23, 2009.

(51) Int. Cl.
| | | |
|---|---|---|
| *C12P 19/00* | (2006.01) | |
| *C12N 9/16* | (2006.01) | |
| *C12N 9/24* | (2006.01) | |
| *C12P 19/14* | (2006.01) | |
| *C12N 9/04* | (2006.01) | |
| *C12N 9/08* | (2006.01) | |
| *C12N 9/20* | (2006.01) | |
| *C12N 9/42* | (2006.01) | |
| *C12P 19/02* | (2006.01) | |

(52) U.S. Cl.
CPC ............ *C12N 9/248* (2013.01); *C12N 9/0006* (2013.01); *C12N 9/0065* (2013.01); *C12N 9/16* (2013.01); *C12N 9/20* (2013.01); *C12N 9/2402* (2013.01); *C12N 9/2437* (2013.01); *C12N 9/2445* (2013.01); *C12N 9/2485* (2013.01); *C12P 19/00* (2013.01); *C12P 19/02* (2013.01); *C12P 19/14* (2013.01); *C12Y 302/01008* (2013.01); *C12Y 302/01037* (2013.01); *C12Y 302/01055* (2013.01); *C12Y 302/01* (2013.01); *C12Y 302/01004* (2013.01); *C12Y 302/01021* (2013.01)

(58) Field of Classification Search
CPC .................................. C12N 9/16; C12P 19/00
See application file for complete search history.

(56) References Cited

U.S. PATENT DOCUMENTS

| | | | |
|---|---|---|---|
| 4,797,361 | A | 1/1989 | Montenencourt |
| 5,405,769 | A | 4/1995 | Campbell et al. |
| 5,426,043 | A | 6/1995 | De Graaff et al. |
| 5,437,992 | A | 8/1995 | Bodie et al. |
| 5,536,325 | A | 7/1996 | Brink |
| 5,681,732 | A | 10/1997 | De Graaff et al. |
| 5,705,369 | A | 1/1998 | Torget et al. |
| 5,817,499 | A | 10/1998 | Dalboge et al. |
| 5,830,734 | A | 11/1998 | Christgau et al. |
| 5,997,913 | A | 12/1999 | Fowler et al. |
| 6,022,725 | A | 2/2000 | Fowler et al. |
| 6,132,727 | A | 10/2000 | Rohde, Jr. et al. |
| 6,409,841 | B1 | 6/2002 | Lombard |
| 6,423,145 | B1 | 7/2002 | Nguyen et al. |
| 6,509,171 | B1 | 1/2003 | Berka et al. |
| 6,555,335 | B1 | 4/2003 | Saloheimo et al. |
| 6,573,086 | B1 | 6/2003 | Ernalfarb et al. |
| 6,660,506 | B2 | 12/2003 | Nguyen et al. |
| 6,768,001 | B2 | 7/2004 | Saloheimo et al. |
| 6,982,159 | B2 | 1/2006 | Dunn-Coleman et al. |
| 7,005,289 | B2 | 2/2006 | Dunn-Coleman et al. |
| 7,045,332 | B2 | 5/2006 | Dunn-Coleman et al. |
| 7,314,743 | B2 | 1/2008 | Clarkson et al. |
| 7,459,299 | B2 | 12/2008 | Goedegebuur et al. |
| 7,960,146 | B2 | 6/2011 | Dunn-Coleman et al. |
| 7,960,147 | B2 | 6/2011 | Danenberg et al. |
| 8,288,148 | B2 | 10/2012 | Cervin et al. |
| 8,476,048 | B2 | 7/2013 | Caimi et al. |

(Continued)

FOREIGN PATENT DOCUMENTS

| | | |
|---|---|---|
| DE | 10043662 | 2/2001 |
| EP | 2397491 | 12/2011 |

(Continued)

OTHER PUBLICATIONS

Akel, et al., "Molecular Regulation of arabinan and L-Arabinose Metabolism in Hypocrea jecorina (Trichoderma reesel),"Eukaryotic Cell, vol. 8, No. 12, Dec. 1, 2009, pp. 1837-1844.
Brown, et al., "Comparative Analysis of 87,000 Expressed Sequence Tags from the Fumonisin-producingfungus Fusarium Verticillioides," Fungal Genetics and Biology, CA, US, San Diego, vol. 42, No. 10, Oct. 1, 2005, pp. 848-861.
Database EMBL [Online], Database Accession No. DR631218 sequence, Jul. 12, 2005, "EST1021346 Fvl Gibberella moiliformis cDNA clone FVIE185, mRNA sequence," retrieved from EBI Accession No. EMBL: DR631218.

(Continued)

*Primary Examiner* — Maryam Monshipouri

(57) ABSTRACT

The present disclosure is generally directed to glycosyl hydrolase enzymes, compositions comprising such enzymes, and methods of using the enzymes and compositions, for example for the saccharification of cellulosic and hemicellulosic materials into sugars.

12 Claims, 80 Drawing Sheets

Figure 25:
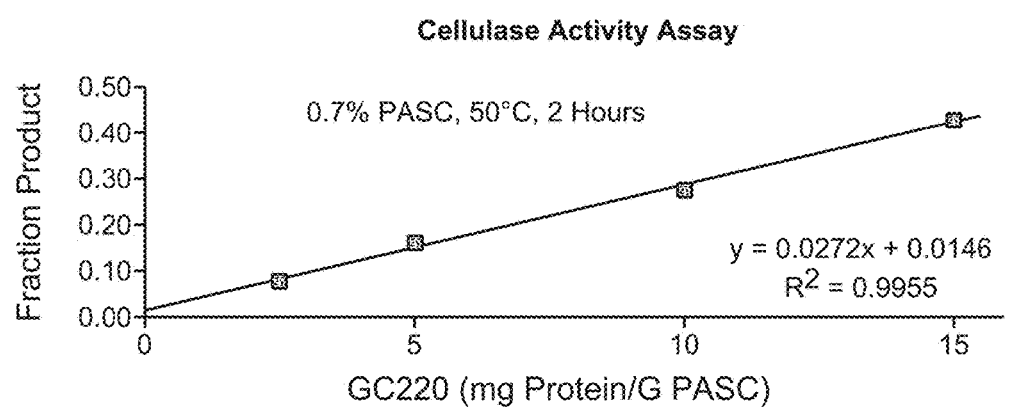

Specification includes a Sequence Listing.

(56) References Cited

U.S. PATENT DOCUMENTS

| | | |
|---|---|---|
| 8,518,684 B2 | 8/2013 | Brown et al. |
| 8,647,850 B2 * | 2/2014 | Hitz .................. C12N 1/20 435/161 |
| 8,673,618 B2 | 3/2014 | Gusakov et al. |
| 8,721,794 B2 | 5/2014 | Hennessey et al. |
| 8,906,235 B2 | 12/2014 | Hennessey et al. |
| 9,175,275 B2 | 11/2015 | Gray et al. |
| 9,279,112 B2 | 3/2016 | Scott et al. |
| 9,447,400 B2 | 9/2016 | Bott et al. |
| 2002/0084046 A1 | 7/2002 | Hsu et al. |
| 2003/0113732 A1 | 6/2003 | Dunn-Coleman et al. |
| 2003/0113734 A1 | 6/2003 | Dunn-Coleman et al. |
| 2003/0113735 A1 | 6/2003 | Dunn-Coleman et al. |
| 2003/0114330 A1 | 6/2003 | Dunn-Coleman et al. |
| 2004/0102619 A1 | 5/2004 | Dunn-Coleman et al. |
| 2005/0191736 A1 | 9/2005 | Brown et al. |
| 2006/0003408 A1 | 1/2006 | Dunn-Coleman et al. |
| 2006/0075522 A1 | 4/2006 | Cleveland et al. |
| 2006/0258554 A1 | 11/2006 | Dunn-Coleman et al. |
| 2007/0031918 A1 | 2/2007 | Dunson et al. |
| 2007/0031919 A1 | 2/2007 | Dunson et al. |
| 2007/0031953 A1 | 2/2007 | Dunson et al. |
| 2007/0037259 A1 | 2/2007 | Hennessey et al. |
| 2007/0077630 A1 | 4/2007 | Harris et al. |
| 2008/0076159 A1 | 3/2008 | Baez-Vasquez et al. |
| 2008/0293109 A1 | 11/2008 | Berka et al. |
| 2008/0299613 A1 | 12/2008 | Merino et al. |
| 2009/0050134 A1 | 2/2009 | Friend et al. |
| 2009/0099079 A1 | 4/2009 | Emalfarb et al. |
| 2009/0280541 A1 | 11/2009 | Jordan et al. |
| 2010/0124769 A1 | 5/2010 | Brown et al. |
| 2011/0039320 A1 | 2/2011 | Li et al. |
| 2011/0086408 A1 | 4/2011 | Power et al. |
| 2011/0136182 A1 | 6/2011 | Huang et al. |
| 2011/0212505 A1 | 9/2011 | Dunn-Coleman et al. |
| 2011/0318803 A1 | 12/2011 | Hitz et al. |
| 2012/0135499 A1 | 5/2012 | Bower et al. |
| 2013/0143277 A1 | 6/2013 | Gutierrez et al. |
| 2013/0143301 A1 | 6/2013 | Bott et al. |
| 2013/0337508 A1 | 12/2013 | Fujdaia et al. |
| 2014/0073017 A1 | 3/2014 | Kaper et al. |
| 2014/0106408 A1 | 4/2014 | Mitchinson et al. |
| 2014/0134677 A1 | 5/2014 | Mitchinson et al. |
| 2014/0295475 A1 | 10/2014 | England et al. |
| 2015/0010981 A1 | 1/2015 | Yang et al. |
| 2013/0177947 A1 | 3/2016 | Bower et al. |
| 2016/0060665 A1 | 3/2016 | Power et al. |
| 2016/0177279 A1 | 6/2016 | Bower et al. |
| 2016/0272956 A1 | 9/2016 | Diez Garcia et al. |
| 2017/0096651 A1 | 4/2017 | Mitchinson et al. |

FOREIGN PATENT DOCUMENTS

| | | |
|---|---|---|
| WO | 97/00964 | 1/1997 |
| WO | 9815633 | 4/1998 |
| WO | 9902693 | 1/1999 |
| WO | 0149859 | 7/2001 |
| WO | 02095014 | 11/2002 |
| WO | 03027306 | 4/2003 |
| WO | 03052118 | 6/2003 |
| WO | 03093420 A2 | 11/2003 |
| WO | 2004016760 | 2/2004 |
| WO | 2004033646 | 4/2004 |
| WO | 2004043980 | 5/2004 |
| WO | 2004078919 | 9/2004 |
| WO | 2004081185 | 9/2004 |
| WO | 2005001036 | 1/2005 |
| WO | 2005001065 | 1/2005 |
| WO | 2005028636 | 3/2005 |
| WO | 2005074647 A2 | 8/2005 |
| WO | 2005074656 A2 | 8/2005 |
| WO | 2005093050 | 10/2005 |
| WO | 2005093073 | 10/2005 |
| WO | 2005118769 A1 | 12/2005 |
| WO | 2006074005 | 7/2006 |
| WO | 2006110901 | 10/2006 |
| WO | 2006110902 A1 | 10/2006 |
| WO | 2006114095 A1 | 11/2006 |
| WO | 2007071818 A1 | 6/2007 |
| WO | 2007/094852 | 8/2007 |
| WO | 2007089290 A2 | 8/2007 |
| WO | 2008025165 A1 | 3/2008 |
| WO | 2008039370 | 4/2008 |
| WO | 2008045977 | 4/2008 |
| WO | 2008140749 A2 | 11/2008 |
| WO | 2008147396 | 12/2008 |
| WO | 2008151079 | 12/2008 |
| WO | 2008153712 | 12/2008 |
| WO | 2008153903 | 12/2008 |
| WO | 2009003167 | 12/2008 |
| WO | 2009009142 A2 | 1/2009 |
| WO | 2009033071 A2 | 3/2009 |
| WO | 2009035537 | 3/2009 |
| WO | 2009045627 A2 | 4/2009 |
| WO | 2009074685 | 6/2009 |
| WO | 2009076676 | 6/2009 |
| WO | 2009085859 A2 | 7/2009 |
| WO | 2009/108941 | 9/2009 |
| WO | 2009117689 A1 | 9/2009 |
| WO | 2009132008 A2 | 10/2009 |
| WO | 2009149202 | 12/2009 |
| WO | 2010096673 | 8/2010 |
| WO | 2010138754 A1 | 12/2010 |
| WO | 2010141779 | 12/2010 |
| WO | 2010148148 A2 | 12/2010 |
| WO | 2011/038019 | 3/2011 |
| WO | 2011063308 | 5/2011 |
| WO | 2011079048 A2 | 6/2011 |
| WO | 2011137150 | 11/2011 |
| WO | 2011153276 | 12/2011 |
| WO | 2011161063 | 12/2011 |
| WO | 2012030845 | 3/2012 |
| WO | 2012125925 A2 | 9/2012 |
| WO | 2012125937 A2 | 9/2012 |
| WO | 2012125951 | 9/2012 |
| WO | 2012154735 | 11/2012 |
| WO | 2013090053 | 6/2013 |
| WO | 2014070837 | 5/2014 |
| WO | 2014070841 | 5/2014 |
| WO | 2014093275 | 6/2014 |
| WO | 2015/017254 A1 | 2/2015 |
| WO | 2015/017255 A1 | 2/2015 |
| WO | 2015/017256 A1 | 2/2015 |
| WO | 2015084596 | 6/2015 |

OTHER PUBLICATIONS

Database EMBL [Online], Database Accession No. DR628222 sequence, Jul. 12, 2005, "EST1018350 Fvl Gibberella moniliformis cDNA clone FVICQ42, mRNA sequence,"retrieved from EBI Accession No. EM EST: DR628222.

Database EMBL [Online]Database Accession No. DR630608 sequence, Jul. 12, 2005, "EST1018350 Fvl Gibberella moniliformis cDNA clone FVIDS84, mRNA sequence," retrieved from EBI Accession No. EM EST: DR630608.

Database UniProt [Online], Database Accession No, Q09LXO sequence, Oct. 17, 2006, "SubName: Full=Beta-xylosidase", retrieved from EBI Accession No. UNIPROT: Q09LXO.

Database UniProt [Online], Database Accession No. A4UVM8 Sequence, May 15, 2007, retrieved from EBI Accession No. Uniprot: A4UVM8.

Database Geneseq [Online] Database Accession No. AXR37961 sequence, Nov. 26, 2009, "Plant biomass degradation related protein SEQ 1D No. 107," retrieved from EBI Accession No. GSP: AXR37961 xp002672566.

Database Geneseq [Online], Database Accession No. AXR38055 sequence, Nov. 26, 2009, "Plant biomass degradation related SEQ 1D No.199," retrieved from EBI Accession No. GSP: AXR38055.

Database Geneseq [Online], Accession No. AXR38027, Nov. 26, 2009, "Plant biomass degradation related SEQ 1D No. 172," retrieved from EBI Accession No. GSP: AXR38027.

(56) References Cited

OTHER PUBLICATIONS

Database Geneseq [Online], Database Accession No. AXR38047 sequence, Nov. 26, 2009, "Plant biomass degradation related SEQ ID No. 192," retrieved from EBI Accession No. GSP: AXR38047.

Kitamoto; et al., "Sequence Analysis, Overexpression, and Antisense Inhibition of a b-Xyiosidase Gene; xylA, from Aspergillus orvzae KBN616," Applied and Environmenta Microbiology, Jan. 1999, pp. 20-24.

Zhang, et al., "Formation of Ethyl Beta-xylopyranoside During Simultaneous Saccharification and Co-fermentation of Paper Sludge," Enzyme and Microbial Technology, Stoneham, MA, US, vol. 44, No, 4, Apr. 6, 2009, pp. 196-202.

International Search Report dated on May 7, 2012, for PCT Patent Application No. PCT/US2010/061082, filed Dec. 17, 2010.

Akel, Eda, "Molecular Regulation of Arabinan and I-Arabinose Metabolism in Hypocrea jecorina (Trichoderma reesei)," Eukaryotic Cell, Dec. 1, 2009, vol. 8; No. 12, pp. 1837-1844.

Brux, Christian, et al., "Crystallization and preliminary crystallographic analysis of a family 43 β-D-xylosidase from Geobacillus stearothermophilus T-6," Acta Crystallographica, Section F., Nov. 12, 2005, pp. 1054-1057.

Dogaris, Ioannis, et al. Induction of Cellulases and hemicellulases from Neurospora crassa under solid-state cultivated for bioconversion of sorghum bagasse into alcohol, Industrial Crops and Products, Mar. 2009, vol. 29, No. 2-3, pp. 401-411.

Drouet, Philippe, et al., "Production of Nkyl P-D-Xylosides with the Trichoderma reesei β-Xylosidase," Annals of the New York Academy of Sciences, Mar. 1, 1995, vol. 750, pp. 306-311.

Gargouri, Mohamed, et al., "Fungus β-glycosidases: immobilization and use in alkyl-β-glycoside synthesis," Journal of Molecular Catalysis B: Enzymatic, Jun. 1, 2004, vol. 29, No. 1-6, pp. 89-94.

GENESEQ Accession No. AXR37961 (Plant biomass degradation related protein; SEQ ID No. 107 from WO2009108941-A2, published Sep. 3, 2009), printed Mar. 29, 2012.

GenBank Accession No. EGU86020 (hypothetical protein FOXB_03424 [Fusariurn oxysporum Fo5176]): last modification date Aug. 5, 2011; printed on Mar. 9, 2016, pp. 1-2.

GenBank Accession No. CAK96229 (unnamed protein product [Aspergillus niger]): last modification date Mar. 14, 2015); printed on Mar. 9, 2016, pp. 1-2.

GenBank Accession No. AAD13106 (beta-xylosidase [Aspergillus niger]]): last modification date Dec. 4, 2001; printed on Mar. 9, 2016, pp. 1-2.

Zhang, et al,, "Formation of Ethyl β-xylopyranoside during simultaneous saccharification and co-fermation of papers sludge," Enzyme and Microbial Technology, Apr. 2009, vol. 44, No. 4, pp. 196-202.

Matsuo, M., et al., "Four Types of β-Xylosidases from Penicillium wortmanni IFO 7237," Agricultural and Biological Chemistry, 1987, vol. 51, No. 9, pp. 2367-2380.

Saha, B.C., "Xylanase from a newly isolated Fusarium verticillioides capable of utilizing corn fiber xylan," Applied microbiol and Biotechnol, Sep. 1, 2001, vol. 56, No. 5-6, pp. 762-766.

Shinoyama, Hirofurni, et al., "Enzymatic Synthesis of Alkyl β-Xylosides from Xylobiose by Application of the Transxylosyl Reaction of Aspergillus niger β-Xylosidase," Agricultural and Biological Chemistry, Jan. 1, 1988, vol. 52, No. 9, pp. 2197-2202.

Smaali, Issam, et al., "Biocatalytic conversion of wheat bran hydrolysate using an immobilized GH43 beta- xylosidase", Bioresource Technology, Jan. 1, 2009, vol. 100, No. 1, pp. 338-344.

Sorensen, HR, et al., "Enzymatic hydrolysis of water-soluble wheat arabinoxylan. 1. Synergy between α-L- arabinofuranosidases, endo-1,4-β-xylanases, and β-xylosidase activities," Biotechnology and Bioengineering, Mar. 20, 2003, vol. 81, No. 6, pp. 726-731.

Sorensen, HR, et al., "Enzymatic Hydrolysis of Wheat Arabinoxylan by a Recombinant "Minimal" Enzyme Cocktail Containing β-Xylosidase and Novel endo-1,4-β-Xylanase and α-L-Arabinofuranosidase Activities," Biotechnology Progress, Jan. 1, 2007, vol. 23, No. 1, pp. 100-107.

UniProtKB/Swiss-Prot: Accession No. Q4X0K2 (Xylosidase : arabinofuranosidase): last modification date Oct. 31, 2006; printed on Mar. 10, 2016, pp. 1-2.

UniProtKB/Swiss-Prot: Accession No. P45702 (RecName: Full= Beta-xylosidase; AltName: Full=1,4-beta-D-xylan xylohydrolase; AltName: Full=Xylan 1,4-beta-xylosiciase; Flags: Precursor): last modification date Jan. 7, 2015, printed Mar. 10, 2016, pp. 1-2.

UniProtKB/Swiss-Prot: Accession No. P36906 (RecName: Full= Beta-xylosiciase; AltName: Full=1,4-beta-D-xylan xylohydrolase; AltName: Full=Xylan 1,4-beta-xylosidase): last modification date Oct. 14, 2015, printed Mar. 10, 2016, pp. 1-7.

UniProtKB/Swiss-Prot: Accession No. P48792 (RecName: Full= Arabinofuranosidase/B-xylosidase; Includes:.RecName: Full=Alpha-L-arabinofuranosidase; Short=Arabinosidase; Includes: RecName: Full=Beta-xylosidase; AltName: Full=1,4-beta-D-xylan xylohydrolase; AltName: Full=Xylan 1,4-beta-xylosidase; Flags: Precursor): last modification date Dec. 9, 2015, printed Mar. 10, 2016, pp. 1-2.

Wakiyama, M. et al, "Purification and Properties of an Extracellular β-Xylosidase from Aspergillus japonicus and Sequence Analysis of the Encoding Gene," Journal of Bioscience and Bioengineering, Oct. 1, 2008, vol. 106, No. 4, pp. 398-404.

Abdelkader et al., 'In-vitro studies on wood degradation in soil by soft-rot fungi: Aspergillus niger and Penicilliurn chrysogenum,' International Biodeterioration & Biodegradation, 2013, vol. 78, pp. 98-108.

Altschul et al., 'Blast Manual,' J. Mol. Biol., 1990, vol. 215, pp. 403-410.

Altschul et al., 'Gapped Blast and PSI-Blast: a new generation of protein database search programs,' Nucleic Acids Research, 1997, vol. 25:17, pp. 3389-3402.

Ausubel et al., (eds.) 'Current Protocols in Molecular Biology,' 1987, Supplement 30, Section 7.7.18 (copy not provided as book is commonly available).

Berka et al., 'Molecular cloning and deletion of the gene encoding aspergillopepsin A from Aspergillus awamori,' Gene, 1990, vol. 86, pp. 153-162.

Biely et al., 'Proceedings of the second TRICEL symposium on Trichoderma reesei Cellulases and other Hydrolases,' Espoo, Finland 1993, Souminen, P. and Reinikainen, R. (eds.), Foundation for Biotechnical and Industrial Fermentation Research, 1993, vol. 8, pp. 125-135.

Harris et al., 'Stimulation of lignocellulosic biomass hydrolysis by proteins of glycoside hydrolase family 61: structure and function of a large, enigmatic family,' Biochemistry, American Chemical Society, Us, vol. 49, No. 15, Apr. 1, 2010, pp. 3305-3316, XP002608645, issn: 0006-2960, Doi: 10.1021./Bi100009p [Retrieved on Mar. 15, 2010].

Herpoel-Gimbert et al., 'Comparative secretorne analysis of two Trichoderma reesei RUT-C30 and CL847 hypersecretory strains,' Biotechnology for Biofuels, 2008, 1:18 doi:10.1186/1754-6834-1-18.

Juturu et al., 'Insight into microbial hemicellulases other than xylanases: a review,' J Chem Technol Biotechnol, 2013, vol. 88, pp. 353-363.

Mach-Aigner et al., 'Transcriptional regulation of xryl, encoding the main regulator of the xylanolytic and cellulolytic enzyme system in Hypocrea jecorina,' Applied and Environmental Microbiology, Nov. 2008, vol. 74, pp. 6554-6562.

Mandels, Cellulases Annu. Rep. Ferment, Process., 1982, 5, 35.

Margolles-Clark, 'Expression patterns of ten hemicellulase genes of the filamentous fungus Trichoderma reesei on various carbon sources' Journal of Biotechnology, Sep. 16, 1997, vol. 57, pp. 167-17.

Ogasawara et al,, 'Cloning, Functional Expression and Promoter Analysis of Xylanase III Gene from Trichoderma reesei,' Applied Microbiology and Biotechnology, 2006, vol. 72:5, pp. 995-1003.

Pearson et al., 'Improved tools for biological sequence comparison,' Proc. Natl. Acad. Sci, USA, 1988, 85, pp. 2444-2448.

Persson et al., 'Fungal cellulolytic enzyme production: a review,' Process Biochemistry, 1991, vol. 26, pp. 65-74.

Pollet et al., 'Structural determinants of the substrate specificities of xylanases from different glycoside hydrolase families,' Critical Reviews in Biotechnology, 2010, vol. 30:3, pp. 176-191.

(56) References Cited

OTHER PUBLICATIONS

Prior et al., 'Hydrolysis of Ammonia-pretreated Sugar Cane Bagasse with Cellulase, β-Glucosidase and Hemicellulase Preparations,' Applied Biochemistry and Biotechnology, Mar. 2008, vol. 146, issue 1-3, pp. 151-164.
Saha et al., 'a-L-Arabinofuranosidases: biochemistry, molecular biology and application in biotechnology,' Biotechnology Advances, 2000, vol. 18, pp. 403-423.
Schulte et al., UniProt, Accession No. Q9P3R7, version 15, Apr. 14, 2009.
Shallom et al., 'Microbial Hemicellulases,' Current Opinion in Microbiology, 2003, vol. 6:3, pp. 219-228.
Sheir-Neiss et al., 'Characterization of the secreted cellulases of Trichoderma reesei wild type and mutants during controlled fermentations,' Appl. Microbiol. Biotechnology, 1984, vol. 20, pp. 46-53.
Shirkot et al., 'Effect of Dithiocarbamates on Cellulase Activity in Culture Filtrates of Trichoderma reesei,' Biotechnology and Bioengineering, 1982, vol. XXIV, pp. 1233-1240.
Sorensen et al., 'Enzymatic hydrolysis of water-soluble wheat arabinoxylan. 1.Synergy between alpha-L-arabinofuranosidases, endo-1,4-beta-xylanases, and beta-xlyosidase activities,' Biotechnology and Bioengineering, 2003, 81:6, pp. 726-731.
Tabka et al., 'Enzymatic Saccharification of wheat straw for bioethanol production by a combined cellulase xylanase and feruloyl esterase treatment,' Enzyme and Microbial Technology, 2006, vol. 39, pp. 897-902.
Tangnu et al., 'Enhanced production of cellulase, hemicellulase, and P-Glucosidase by Trichoderma reesei (Rut C-30),' Biotechnology and Bioengineering, 1981, vol. XXIII, pp. 1837-1849.
Tenkanen et al., 'Two major xylaneses of Trichoderma reesei,' Enzyme Microb. Technol., 1992, 14:566-574.
Thygesen et al., 'Production of cellulose and hemicellulose-degrading enzymes by filamentous fungi cultivated on wet-oxidised wheat straw,' Enzyme and Microbial Technology, 2003, 32:5, pp. 606-615.
Torronen et al., 'The two major xylanases from trichoderma reesei: characterizationof both enzymes and gens,' Biotechnology, 1992, vol. 10, pp. 1461-1465.
Xu et al., 'A third xylanase from trichoderma reesei PC-3-7,' Appl. Microbiol. Biotechnol. 1998, 49:718-724.
UniProt Acc# Q9P973 from Ogasawara et al., Appl Microbial Biotechnol, 2006, 72: 995-1003, Alignment with SEQ ID No. 2.
UniProt Acc# Q92458 from Margolles-Clark et al., Appl. Environ. Microbiol., vol. 62, No. 10 Oct. 1996, pp. 3840-3846, Alignment with SEQ ID No. 17.
UniProt Acc# Q92455 from Margolles-Clark et al., Appl. Environ. Microbiol., vol. 62, No. 10 Oct. 1996, pp. 3840-3846, Alignment with SEQ ID No. 3.
Database EMBL, Database Accession No. AB093564, 'Penicillium herquei mRNA for xylosidase, complete cds.', Apr. 15, 2003, XP002633644.
Database EMBL, Database Accession No. EF490448, 'Penicillium purpurogenum alpha-L-arabinofuranosidase 2 (abf2) gene, complete cds.', Apr. 19, 2007, XP002633645.
Database REFSEQ, Database Accession No. XP_383785, NCBI reference sequence collection Hypothetical protein FG03609 [Giberella zeae PH-1], Apr. 9, 2008, XP002660306.
Database REFSEQ, Database Accession No. XP_386639.1, NCBI reference sequence collection Hypothetical protein FG06463.1 [Giberella zeae PH-1], Apr. 9, 2008, XP002660307.
Database EMBL, Database Accession No. FJ040192, '*Trichoderma* sp. SSL endoglucanase IV mRNA, complete cds.', Sep. 22, 2008, XP002683383.
PCT International Search Report issued for PCT/US2009/037853, dated Jul. 16, 2009.
PCT Written Opinion issued for PCT/US2009/037853, dated Jul. 16, 2009.
PCT International Search Report issued for PCT/US2010/049849, dated Sep. 30, 2011.
PCT Written Opinion issued for PCT/US2010/049849, dated Sep. 30, 2011.
PCT Written Opinion issued for PCT/US2010/061082, dated May 7, 2012.
PCT International Search Report issued for PCT/US2012/029445 dated Oct. 22, 2012.
PCT Written Opinon issued for PCT/US2012/029445 dated Oct. 22, 2012.
PCT International Search Report issued for PCT/US2012/029470, dated Sep. 14, 2012.
PCT Written Opinion issued for PCT/US2012/029470, dated Sep. 14, 2012.
U.S. Appl. No. 15/647,775, filed Jul. 12, 2017.
U.S. Appl. No. 61/245,273, filed Sep. 23, 2009.
Brux et al., The Structure of an Inverting GH43 13-Xylosidase from Geobacillus stearothermophilus with its Substrate Reveals the Role of the Three Catalytic Residues, J. Mol. Bioi., 2006, 359, 97-109.
Drouet et al., Enzymatic synthesis of alkyl 13-D-xylosides by transylosylation and reverse hydrolysis, Biotech. Bioeng., 1994, 43, 1075-80.
GenBank, Accession No. AY690618.1, 2004, www.ncbi.nlm.nih.gov.
Knob et al., 13-xylosidases from filamentous fungi, World J. Microbial. Biotechnol., Oct. 26, 2009, 389-407.
Margolles-Ciark et al., Cloning of genes encoding a-L-arabinofuranosidase and 13-xylosidase from Trichoderma reesei by expression in *Saccharomyces cerevisiae*, Appl. Environ. Microbial., 1996, 62, 3840-46.
Nagendran et al., Reduced genomic potential for secreted plant cell-wall-degrading enzymes in the ectomycorrhizal fungus Amanita bisporigera, based on the secretome of Trichoderma reesei, Fungal Genetics Bioi., 2009, 46, 427-35.
Olofsson et al., A short review on SSF—an interesting process option for ethanol production from lignocellulosic feedstocks, Biotech. Biofuels, 2008, 1, 7.
Saha, Purification and characterization of an extracellular 13-xylosidase from a newly isolated Fusarium verticillioides, J. Indust. Microbial. Biotechnol., 2001, 27, 241-45.
Shallom et al., Biochemical Characterization and Identification of the Catalytic Residues of a Family 43 beta-D-Xylosidase from Geobacillus stearothermophilus T-6, Biochemistry, 2005, 44, 287-97.
Smaali et al., Expression in *Escherichaia coli* and characterization of 13-xylosidase GH39 and GH-43 from Bacillus halodurans C-125, Appl. Microbial. Biotechnol., 2006, 73, 582-90.
Zhang et al., Formation of ethyl13-xylopyranoside during simultaneous saccharification and co-fermentation of paper sludge, Enz. Microbial Tech., Apr. 2009, 44, 196-202.
Mamma et al., Fungal multienzyme production on industrial by-products of the citrus-processing industry, Bioresource Tech., Jun. 2007, 99,2373-83.
UniProt, Accession No. N1 S321, 2013, www.uniprot.org.
Megazyme, 1 ,4-13-D-xylohexaose (Lot 121206), 2013.
Genbank Accession No. XM_018379765, *Fusarium Oxysporum F.* Sp. Lycopersici 4287 Beta-Glucosidase, mRNA, last modification date Sep. 26, 2016; printed on Feb. 28, 2017, pp. 1-2.
Genbank Accession No. XP_018235878, Beta-Glucosidase [*Fusarium Oxysporum F.* Sp. Lycopersici 4287]), last modification date Sep. 26, 2016; printed on Feb. 28, 2017, pp. 1-2.
*Fusarium Oxysporum F.*Sp. Lycopersici Genome, *Fusarium Oxysporum f.* sp. Lycopersici Ensembl Genomes 34, pp. 1-2; fungi.ensembl.org/Fusarium_oxysporum/Info/Annotation/; printed Mar. 3, 2017.
U.S. Appl. No. 15/440,341, filed Feb. 23, 2017.
PCT International Search Report issued for PCT/US2012/029498 dated May 8, 2012.
PCT Written Opinion issued for PCT/US2012/029498 dated May 8, 2012.
Andrade et al., 'Effect of carbon source on the biochemical properties of β-xylosidases produced by Aspergillus versicolor,' Process Biochem., 2004, vol. 39, pp. 1931-1938.
Barnett et al., 'Cloning and amplification of the gene encoding an extracellular β-glucosidase from Trichoderma reesei: evidence for

(56) References Cited

OTHER PUBLICATIONS improved rates of saccharification of cellulosic substrates,' Biotechnology, 1991, vol. 9, No. 6, pp. 562-567.
Bernier et al., 'Molecular cloning of a Bacillus subtilis xylanase gene in *Escherichia coli.*' Gene, 1983, vol. 26, No. 1, pp. 59-65.
Campbell et al., 'Improved transformation efficiency of Aspergillus niger using the homologous niaD gene for nitrate reductase,' Current Genetics, 1989, vol. 16, pp. 53-56.
Canals et al., 'Structure of xylanase Xys1 from Steptomyces halstedii,' Acta Crystalogr. Section D Biological Chrystallography, 2003, vol. 59, pp. 1447-1453.
Cantarel et al., 'The carbohydrate-active enzymes database (CAZy): an expert resource for Glycogenomics,' Nucleic Acids Res., 2009, vol. 37, pp. D233-38.
Chacon-Martinez et al., 'Identification and characterization of the α-L-arabinofuranosidase B of *Fusarium oxysporurn f.* sp, Dianthi,' Physiol. Mol. Plant Pathol., 2004, vol. 64, pp. 201-208.
Chen et al., 'Potential of agricultural residues and hay for bioethanol production,' Appl Biochem Biotechnol., Sep. 2007, vol. 142(3), pp. 276-290.
Chen et al., 'Purification and characterization of two extracellular β-glucosidases from Trichoderma reesei,' Biochimica et Biophysica Acta, 1992, vol. 1121, pp. 54-60.
Clarke et al,, 'A modular xylanase from mesophilic Cellulomonas fimi contains the same cellulose-binding and therrnostabilizing domains as xylanases from thermophilic bacteria,' Fems Microbiology Letters, 1996, vol. 139, pp. 27-35.
Coutinho et al., 'The modular structure of cellulases and other carbohydrate-active enzymes: an integrated database approach,' Genetics, Biochemistry, and Ecology of Cellulse Degradation UNI Publishers Co., 1999, pp. 15-23.
Database Geneseq ID: AXR39051 )Plant biomass degrading enzyme encoding DNA #271): SEQ ID No. 2785 from International Patent Application Publication No. WO2009108941-A2, published Sep. 3, 2009, printed Mar. 18, 2016, pp. 1-2.
Database EMBL, Database Accession No. GY256384, 'Sequence 1 from U.S. Pat No. 7,960,146,' Jun. 21, 2011.
Debeche et al., 'Probing the catalytically residues of the α-L-arabinofuranosidase from Thermobacillus kylanilyticus,' Protein Engineering, 2002, vol. 15, No. 1, pp. 21-28.
Deog et al., 'Construction and characterization of novel chimeric beta-glucosidases with Ceiivibrio gilvus (CG) and thermotoga maritima TM by overlapping PCR,' Biotechnology and Bioprocess Engineering, Jun. 1, 2009, vol. 14, No. 3, pp. 266-273.
Dominguez et al., 'A common protein fold and similar active site in two distinct families of β-glycanases,' Nature Structural Biology, Jul. 1995, vol. 2, No. 7, pp. 569-576.
Emsley et al., 'Features and development of Coot,' ACTA Cryst., 2010, vol. D66, pp. 486-501.
Foreman et al., 'Transcirptional regulation of biomass-degrading enzymes in the filamentous fungus trichoderma reesei,' Journal of Biological Chemistry, Aug. 22, 2003, vol. 278, No. 34, pp. 31968-31997.
Galbe et al., 'A review of the production of ethanol from softwood,' Appl. Microbio. Biotechnol., 2002, vol. 59, pp. 618-628.
GenBank Accession No. KNA97832, Beta-glucosidase, *Fusarium Oxysporurn F.* Sp. Lycopersici 4287), last modification date Jul. 23, 2015; printed on Mar. 3, 2017, pp. 1-2.
GenbankAccession No. XM_018379766, *Fusariurn Oxysporurn F.* Sp. Lycopersici 4287 beta glucosidase mRNA, last modification date Sep. 26, 2016; printed on Mar. 3, 2017, pp. 1-2.
Genbank Accession No. XM_018893759, Fusarium Verticilloides 7600 beta-glucosidase mRNA, last modification date Oct. 27, 2016; printed on Mar. 3, 2017, pp. 1-2.
Genbank Accession No. XP_018235880, Beta glucosidase *Fusarium oxysporum f.* sp. Lycopersici 4287, last modification date Sep. 26, 2016; printed on Mar. 3, 2017; pp. 1-2.
Genbank Accession No. XP_018750667, Beta-glucosidase fusarium verticilloides 7600, last modification date Oct. 27, 2016; printed on Mar. 3, 2017; pp. 1-2.

Genbank Accession No. XM_018379764, *Fusarium oxysporum f.* sp. Lycopersici 4287 beta glucosidase mRNA, last modification date Sep. 26, 2016; printed on Mar. 3, 2017, pp. 1-2.
Genbank Accession No. AY281374.1, Trichoderma reesei strain QM6a Cel3b (cel3b) mRNA, Last modification date Mar. 25, 2015; printed on Mar. 17, 2016; pp. 1-2.
Genbank Accession No. XM_006965219, Trichoderma reesei QM6a glycosidase hydolase family 3 (TRIREDRAFT_121735), Mrna, Last modification date Mar. 15, 2014; printed on Mar. 18, 2016; pp. 1-3.
Genbank Accession No. XP_386781, Hypothetical protein FG06605.1, [Fusarium graminearum PH-1], Last modification date Oct. 19, 2010; printed Mar. 18, 2016, p. 1.
Genbank Accession No. XP_001912683, Hypothetical protein [Podospora anserina S mat+], last modification date May 5, 2010; printed on Nov. 24, 2015, pp. 1-2.
Genbank Accession No. XP_003045443, Hypothetical protein NECHADRAFT_39290 [Nectria haematococca mpV177-13-4], last modification date Aug. 14, 2010; printed on Nov. 24, 2015, pp. 1-2.
Genbank Accession No. CAK48740, beta-glucosidase bgl1-Aspergillus niger, last modification date Mar. 14, 2015; printed on Nov. 24, 2015, pp. 1-2.
Genbank Accession No. AAL69548, beta-glucosidase [Rasamsonia emersonii], last modification date Jul. 10, 2003; printed on Nov. 25, 2015; pp. 1-2.
Genbank Accession No. AAP57755, Cei3b [Trichoderma reese]), last modification date Mar. 26, 2003; printed on Nov. 25, 2015; pp. 1-2.
Genbank Accession No. AAA18473, beta-D-glucoside glucohydrolase [Trichoderma reesei], last modification date May 26, 1994; printed on Nov. 25, 2015; pp. 1-2.
Genbank Accession No. QOGC07, Beta-glucosidase) last modification date Nov. 28, 2006; printed on Nov. 25, 2015, pp. 1-2.
Genbank Accession No. Q7Z9M5, Cel3b, last modification date Oct. 31, 2006; printed on Nov. 25, 2015, pp. 1-2.
Ghose, 'International union of pure and applied chemistry,' Pure and Applied Chemistry, 1987, vol. 59, No. 2, pp. 257-268.
Gilbert et al., 'Molecular cloning of multiple xylanase genes from *pseudornonas fluorescens* subsp. Cellulosa,' Journal of General Microbiology, 1988, vol. 134, pp. 3239-3247.
Gornall et al., 'Determination of serum proteins by means of the biuret reaction,' J. Biol. Chem., 1949, vol. 177, pp. 752-766.
Gould et al., 'Alkaline peroxide delignification of agricultural residues to enhance enzymatic saccharification,' Biotech and Bioeng., 1984, vol. 26, pp. 46-52.
Goyal et al., 'Enhancement of transglycosylation activity by construction by chimeras between mesophilic and thermophilic beta-glucosidase,' Archives of Biochemistry and Biophysics, Nov. 1, 2002, vol. 407, No. 1, pp. 125-134.
Henrissat et al., 'A scheme for designating enzymes that hydrolyse the polysaccharides in the cell walls of plants,' Febs Letters, 1998, vol. 425, No. 2, pp. 352-354.
Iwashita et al., 'The bglA gene of *Aspergillus kawachii* encodes both extracellular and cell wall-bound β-glucosidases,' Appl. Environ. Microbiol., 1999, vol. 65, pp. 5546-5553.
Jung et al., 'Purification and characterization of α-L-arabinosidase from *Trichoderma* sp. SY,' Agric. Chem. Biotechnol., 2005, vol. 48, pp. 7-10.
Karlsson et al., 'Homologous expression and characterization of Ce161A (EG IV) reesei,' Eur. J. Biochem., 2001, vol. 268, pp. 6498-6507.
Kawaguchi et al., 'Cloning and sequencing of the cDNA encoding β-glucosidase 1 from Aspergillus aculeatus,' Gene, 1996, vol. 173, pp. 287-288.
Kim et al., 'Characterization of the arfA gene from Bacillus stearothermophilus No. 236 and its protein product, α-L-arabinofuranosidase,' J. Microbiol. Biotechnol., 2004, vol. 14, pp. 474-482.
Kim et al., 'Purification and characterization of β-xylosidase from *Trichoderma* sp. SY,' J. Microbiol. Biotechnol., 2004, vol. 14, pp. 643-645.

(56) References Cited

OTHER PUBLICATIONS

Kinoshita et al., 'Cloning of the xynNB gene encoding xylanase B from Aspergillus niger and its expression in Aspergillus kawachii,' Journal of Fermentation and Bioengineering, 1995, vol. 79, No. 5, pp. 422-428.
Kluepfel et al., 'Purification and characterization of a new xylanase (xylanase B) produced by Streptomyces lividans 66,' Biochem J., 1990, vol. 287, pp. 45-50.
Knowles et al., 'Cellulase families and their genes,' Trends in Biotechnology, 1987, vol. 5, No. 9, pp. 255-261.
Kosecki et al., 'Mutational analysis of N-glycosylation recognition sites on the biochemical properties of Aspergillus kawachii α-L-arabinofuranosidase 54,' Biochim. Biophys. Acta, 2006, vol. 1760, pp. 1458-1464.
Kotake et al., 'An α-L-arabinofuranosidase/β-D-xylosidase from immature seeds of radish (Raphanus sativus L),' J. Exp. Botany, 2006, vol. 57, pp. 2353-2362.
Kurakake et al., 'Characteristics of transxylosylation by β-xylosidase from Aspergillus awamori K4,' Biochim. Biophys. Acta, 2005, vol. 1726, pp. 272-279.
Lee et al., 'Bifunctional family of 3 glycoside hydrolases from barley with α-L-arabinofuranosidase and β-D-xylosidase activity. Characterization, primary structures and COOH-terminal processing,' J. Biol, Chem., 2003, vol. 278, pp. 5377-5387.
Li et al., 'Catalytic mechanism of a family 3 β-glucosidase and mutagenesis study on residue ASP-24,' Biochem. J., 2001, vol. 355, pp. 835-840.
Luthi et al., 'Xylanase from the extremely thermophilic bacterium "Caldocellurn saccharolyticurn": overexpression of the gene in Escherichia coli and characterization of the gene product,' Appl. Environ. Microbiol., 1990, vol. 56, No. 9, pp. 2677-2683.
Machida et al., 'Nucelotide sequences of saccharomycopsis fibuligera genes for extracellular β-glucosidases as expressed in saccharomyces cerevisiae,' Appl. Environ. Microbiol., 1988, vol. 54, pp. 3147-3155.
Margolles et al., 'Purificationa nd functional characterization of a novel α-l-arabinofuranosidase from bifidobacterium longum B66,' Appl. Environ. Microbiol., 2003, vol. 69, pp. 5096-5103.
Miyazaki et al., 'Hyperthermophilic α-L-arabinofuranosidase from thermotoga maritima MSB8: molecular cloning, gene expression, and characterization of the recombinant protein,' Extremophiles, 2005, vol. 9, pp. 399-406.
Morosoli et al., 'Purification and properties of a xylanase from Streptomyces lividans,' Biochem. J., 1986, vol. 239, pp. 587-592.
Numan et al., 'α-L-arabinofuranosidases: the potential applications in biotechnology,' J. Ind. Microbiol. Biotechnol., 2006, vol. 33, pp. 247-260.
Nuyens et al., Heterologous expression of the bacillus pumilus endo-β-xylanase (xynA) gene in the yeast Saccharomyces cerevisiae, Applied Microbiology and Biotechnology, 2001, vol. 56, pp. 431-434.
Oguntimein et al., 'Properties of soluble and immobilized Aspergillus niger β-xylosidase,' Biotechnol. Bioeng., 1980, vol. 22, pp. 1143-1154.
Olsson et al., 'Fermentation of lignocellulosic hydrolysates for ethanol production,' Enzyme Microb Technol., 1996, vol. 18, pp. 312-331.
Oshima et al., 'Purification and characterization of an Exo-1, 5-alpha-L-arabinanase from Aspergillus sojae,' Journal of Applied Glycoscience, 2005, vol. 52, pp. 261-265.
Pace et al., 'How to measure and predict the molar absorption coefficient of a protein,' Protein Science, 1995, vol. 4, pp. 2411-2423.
Panagiotou et al., 'Induction, purification and characterization of two extracellular-L-arabinofuranosidases from Fusarium oxysporum,' Can. J. Microbiol., 2003, vol. 49, pp. 639-644.
Pentilla et al., 'A versatile transformation system for the cellulolytic filamentous fungus Trichoderma reesei,' Gene, 1987, vol. 61, pp. 155-164.
Pinphanichakarn et al., 'Purification and characterization of β-xylosidase from streptomyces sp. CH7 and its gene sequence analysis,' World J. Microbiol. Biotechnol., 2004, vol. 20, pp. 727-733.
Pozzo et al., 'Structural and functional analysis of β-glucosidase 3B from thermotoga neapolitana: A thermostable three-domain representative of glycoside hydrolase 3,' J. Mol. Biol., 2010, vol. 397, pp. 724-739.
Rahman et al., 'A role of xylanase,-L-arabinofuranosidase and xylosidase in xylan degradation,' Can. J. Microbiol., 2003, vol. 49, pp. 58-64.
Rahman et al., 'Substrate specificity of the α-L-arabinofuranosidase from Rhizornucor pusillus HHT-1,' Carbohydrate Research, 2003, vol. 338, pp. 1469-1476.
Reen et al., 'Molecular characterization and expression analysis of the first hemicellulase gene (bxl1) encoding β-xylosidase from the thermophilic fungus Talarornyces ernersonii,' Biochem. Biophys. Res. Commun., 2003, vol. 305, No. 3, pp. 579-585.
Rose et al., 'Crystallization and preliminary x-ray diffraction study of a xylanase from trichoderma harzianum,' J. Mol. Biol., 1987, vol. 194, No. 4, pp. 755-756.
Sader et al., 'Application of Kjeldahl and Dumas combustion methods for nitrogen analysis,' Archives of Veterinary Science, 2004, vol. 9, No. 2, pp. 73-79.
Sakamoto et al., 'Purification and properties of two type-β α-L-arabinofuranosidases produced by Penicillurn chrysogenum,' Biochimic et Biophys. Acta, 2003, vol. 1621, pp. 204-210.
Schmidt et al., 'Xylanases and β-xylosidase of trichoderma lignorum,' Methods in Enzymology, 1988, vol. 160, pp. 662-671.
Schulein et al., 'Cellulases of trichoderma reesei,' Methods in Enzymology, 1988, vol. 160, pp. 234-242.
Shallom et al., 'Detailed kinetic analysis and identification of the nucleophile in α-L-arabinofuranosidase from Geobacillus stearothermophilus T-6, a family 51 glycoside hydrolase,' J, Biol. Chem., 2002, vol. 277, pp. 43667-43673.
Shareck et al., 'Sequences of three genes specifying xylanases in Streptomyces lividans,' Gene, 1991, vol. 107, pp. 75-82.
Shin et al., 'Purification and characterization of α-L-arabinopyranosidase and α-L-arabinofuranosidase from bifidobacterium breve K-110, a human intestinal anaerobic bacterium metabolizing ginsenoside Rb2 and Rc,' Appl. Environ. Microbiol., 2003, vol. 69, pp. 7116-7123.
Simpson et al., 'An extremely thermostable xylanase from the thermophilic eubacterium thermotoga,' Biochem. J., 1991, vol. 277, pp. 413-417.
Sluiter et al., 'Determination of structural carbohydrates and lignin in biomass,' National Renewable Energy Laboratory, 2008, Golden, CO, pp. 1-15.
Taylor et al., 'Structural insight into the ligand specificity of a thermostable family 51 arabinofuranosidase, Araf51, from Clostridium thermocellum,' Biochem, J., 2006, vol. 395, pp. 31-37.
Teixeira et al., 'Alkaline and peracetic acid pretreatments of biomass for ethanol production,' Appl, Biochem and Biotech., 1999, vol. 77, pp. 19-34.
Teymouri et al., 'Ammonia fiber explosion treatment of corn stover,' Applied Biochemistry and Biotechnology, 2004, vol. 113-116, pp. 951-963.
Tuncer et al., 'Purification and partial characterization of α-L-arabinofuranosidase produced by thermonospora fusca,' Folia Microbiol., 2008, vol. 48, No. 2, pp. 168-172.
Walseth et al., 'Occurrence of cellulases in enzyme preparations from microorganisms,' TAPPI, May 1952, vol. 35, No. 5, pp. 228-233.
Weichselbaum et al., 'An accurate and rapid method for the determination of proteins in small amounts of blood serum arid plasma,' American Journal of Clinical Pathology, Mar. 1946, pp. 40-49.
Winterhalter et al., 'Two extremely thermostable xylanases of the hyperthermophilic bacterium thermotoga maritima MSB8,' Appl. Environ. Microbiol., 1995, vol. 61, No. 5, pp. 1810-1815.
Wong et al., 'The cloning, expression and characterization of a cellobiase gene encoding a secretory enzyme from cellulomonas biazotea,' Gene, 1998, vol. 207, pp. 79-86.
Wood et al., 'The genome sequence of Schizosaccharomyces pombe,' Nature, 2002, vol. 415, pp. 871-880.

(56) References Cited

OTHER PUBLICATIONS

Wood et al., 'The cellulase of fusarium solani,' Biochem. J. 1971, vol. 121, pp. 353-362.

Xue et al., 'Expression and characterization of a thermostable β-xylosidase from the hyperthermophile, thermotoga maritima,' Biotechnol. Lett., 2004, vol. 26, pp. 1511-1515.

Yang et al., 'Nucleotide sequence of a *bacillus circulans xylanese* gene,' Nucleic Acids Res., 1988, vol. 16, No. 14, p. 7187.

Zaldivar et al., 'Fuel ethanol production from lignocellulose: a challenge for metabolic engineering and process integration,' Appl. Microbiol. Biotechnol., 2001, vol. 56, pp. 17-34.

Zanoelo et al., 'Purification and biochemical properties of a thermostable xylose-tolerant β-D-xylosidase from Scytalidium thermophilum,' J. Ind. Microbiol. Biotechnol., 2004, vol. 31, pp. 170-176.

Zappe et al., 'Nucleotide sequence of a clostridium acetobutylicum P262 xylanase gene (xynB),' Nucleic Acids Res., 1990, vol. 18, No. 8, p. 2179.

UniProt Accession No. Q9ZFM2, (Recname: Full=Beta-Xylosidase; Altname: Full=1,4-Beta-D-XylanXylohydrolase; Altname: Full=Xylan 1, 4-Beta-Xylosidase), last modification date Nov. 2, 2016;.printed on Feb. 28, 2017, pp. 1-2.

Ma et al., Comparative genomics reveals mobile pathogenicity chromosomes in Fusarium, Nature, Mar. 18, 2010, pp. 367-373, vol. 464.

Supplementary Information, Figures Sl-S20, from Ma et al. Comparative genomics reveals mobile pathogenicity chromosomes in Fusarium, Nature, 2010, pp. 367-373, vol. 464, No. 18.

Supplementary Information, pp. 1-31, from Ma et al. Comparative genomics reveals mobile pathogenicity chromosomes in Fusarium, Nature, 2010, pp. 367-373, vol. 464, No. 18.

Supplementary Information, Tables Sl-S25, from Ma et al. Comparative genomics reveals mobile pathogenicity chromosomes in Fusarium, Nature, 2010, pp. 367-373, vol. 464, No. 18.

Fusarium Comparative Genome Project, Broad Institute, pp. 1-6; www.broadinstitute.org/scientific-community/science/projects/fungal-genome-initiative/fusarium-comparative-genome-project; printed Mar. 3, 2017.

Genbank Accession No. XP018761619, alpha-N-arabinofuranosidase [Fusarium verticilloides 7600], last modification date Oct. 27 2016.

Genbank Accession No. XM_018902798, Fusarium verticillioides 7600 alpha-N-arabinofuranosidase partial mRNA, last modification date Oct. 27, 2016.

Cuomo et al. The *Fusarium Graminearum* Genome Reveals a Link Between Localized Polymorphism and Pathogen Specialization, Science, 2007, vol. 317, No. 5843, pp. 1400-2.

\* cited by examiner

SEQ ID NO:1
Nucleotide sequence for Fv3A, a GH3 family enzyme from *Fusarium verticillioides* atgctgctcaatcttcaggtcgctgccagcgctttgtcgctttctcttttaggtggattggctgaggctg
ctacgccatataccttccggactgtaccaaaggacctttgagcaagaatggaatctgcgatacttcgtt
atctccagctaaaagagcggctgctctagttgctgctctgacgcccgaagagaaggtgggcaatctggtc
aggtaaaatataccccccccataatcactattcggagattggagctgacttaacgcagcaatgcaactg
gtgcaccaagaatcggacttccaaggtacaactggtggaacgaagcccttcatggcctcgctggatctcc
aggtggtcgctttgccgacactcctccctacgacgcggccacatcatttcccatgcctcttctcatggcc
gctgctttcgacgatgatctgatccacgatatcggcaacgtcgtcggcaccgaagcgcgtgcgttcacta
acggcggttggcgcggagtcgacttctggacacccaacgtcaaccttttaaagatcctcgctggggtcg
tggctccgaaactccaggtgaagatgcccttcatgtcagccggtatgctcgctatatcgtcagggctc
gaaggcgataaggagcaacgacgtattgttgctacctgcaagcactatgctggaaacgactttgaggact
ggggaggcttcacgcgtcacgactttgatgccaagattactcctcaggacttggctgagtactacgtcag
gcctttccaggagtgcacccgtgatgcaaaggttggttccatcatgtgcgcctacaatgccgtgaacggc
attcccgcatcgcaaactcgtatctgcaggagacgatcctcagagggcactggaactggacgcgcgata
acaactggatcactagtgattgtggcgccatgcaggatatctggcagaatcacaagtatgtcaagaccaa
cgctgaaggtgcccaggtagcttttgagaacggcatggattctagctgcgagtatactactaccagcgat
gtctccgattcgtacaagcaaggcctcttgactgagaagctcatggatcgttcgttgaagcgccttttcg
aagggcttgttcatactggtttctttgacggtgccaaagcgcaatggaactcgctcagttttgcggatgt
caacaccaaggaagctcaggatcttgcactcagatctgctgtggagggtgctgttcttcttaagaatgac
ggcactttgcctctgaagctcaagaagaaggatagtgttgcaatgatcggattctgggccaacgatactt
ccaagctgcagggtggttacagtggacgtgctccgttcctccacagcccgcttatgcagctgagaagct
tggtcttgacaccaacgtggcttggggtccgacactgcagaacagctcatctcatgataactggaccacc
aatgctgttgctgcggcgaagaagtctgattacattctctactttggtggtcttgacgcctctgctgctg
gcgaggacagagatcgtgagaaccttgactggcctgagagccagctgaccctcttcagaagctctctag
tctcggcaagccactggttgttatccagcttggtgatcaagtcgatgacaccgctcttttgaagaacaag
aagattaacagtattctttgggtcaattaccctggtcaggatggcggcactgcagtcatggacctgtca
ctggacgaaagagtcctgctggccgactacccgtcacgcaatatcccagtaaatacactgagcagattgg
catgactgacatggacctcagacctaccaagtcgttgccagggagaacttatcgctggtactcaactcca
gttcttccctacggctttggcctccactacaccaagttccaagccaagttcaagtccaacaagttgacgt
tgacatccagaagcttctcaagggctgcagtgctcaatactccgatacttgcgcgctgcccccatcca
agttagtgtcaagaacaccggccgcattacctccgactttgtctctctggtctttatcaagagtgaagtt
ggacctaagccttaccctctcaagacccttgcggcttatggtcgcttgcatgatgtcgcgccttcatcga
cgaaggatatctcactggagtggacgttggataacattgcgcgacggggagagaatggtgatttggttgt
ttatcctgggacttacactctgttgctggatgagcctacgcaagccaagatccaggttacgctgactgga
aagaaggctatttggataagtggcctcaagaccccaagtctgcgtaa

FIG. 1A

SEQ ID NO:2
Protein sequence of Fv3A

<u>mllnlqvaasalslsllqqlaea</u>atpytlpdctkgplskngicdtslspakraaalvaaltpeekvgnlv
sn**ATGAPRIGLPRYNWWNEALHGLAGSPGGRFADTPPYDAATSFPMPLLMAAAFDDDLIHDIGNVVGTEA
RAFTNGGWRGVDFWTPNVNPFKDPRWGRGSETPGEDALHVSRYARYIVRGLEGDKEQRRIVATCKHYAGN
DFEDWGGFTRHDFDAKITPQDLAEYYVRPFQECTRDAKVGSIMCAYNAVNGIPACANSYLQETILRGHWN
WTRDNNWITSDCGAMQDIWQNHKYVKTNAEGAQVAFENGMD**ssceytttsdvsdsykqglltekImdrsl
krlfeglvhtgffdgakaqwnslsfadvntkeaqdlalrsaveg**AVLLKNDGTLPLKLKKKDSVAMIGFW
ANDTSKLQGGYSGRAPFLHSPLYAAEKLGLDTNVAWGPTLQNSSSHDNWTTNAVAAAKKSDYILYFGGLD
ASAAGEDRDRENLDWPESQLTLLQKLSSLGKPLVVIQLGDQVDDTALLKNKKINSILWVNYPGQDGGTAV
MDLLTGRKSPAGRLPVTQYPSKYTEQIGMTDMDLRPTKSLPGRTYRWYSTPVLPYGFGLHYT**kfqakfks
nkltfdiqkllkgcsaqysdtcalppiqvsvkntgritsdfvslvfiksevgpkpyplktlaaygrihdv
apsstkdislewtldniarrgengdlvvypgtytllldeptqakiqvtltgkkaildkwpqdpksa

FIG. 1B

SEQ ID NO:3
Nucleotide sequence for Pf43A, a GH43 family enzyme from *Penicillium funiculosum* atgcttcagcgatttgcttatattttaccactggctctattgagtgttggagtgaaagccgacaacccct
ttgtgcagagcatctacaccgctgatccggcaccgatggtatacaatgaccgcgtttatgtcttcatgga
ccatgacaacaccggagctacctactacaacatgacagactggcatctgttctcgtcagcagatatggcg
aattggcaagatcatggcattccaatgagcctggccaatttcacctgggccaacgcgaatgcgtgggccc
cgcaagtcatccctcgcaacggccaattctactttttatgctcctgtccgacacaacgatggttctatggc
tatcggtgtgggagtgagcagcaccatcacaggtccataccatgatgctatcggcaaaccgctagtagag
aacaacgagattgatccaccgtgttcatcgacgatgacggtcaggcatacctgtactggggaaatccag
acctgtggtacgtcaaattgaaccaagatatgatatcgtacagcgggagccctactcagattccactcac
cacggctggatttggtactcgaacgggcaatgctcaacggccgaccacttttgaagaagctccatgggta
tacaaacgcaacggcatctactatatcgcctatgcagccgattgttgttctgaggatattcgctactcca
cgggaaccagtgccactggtccgtggacttatcgaggcgtcatcatgccgacccaaggtagcagcttcac
caatcacgagggtattatcgacttccagaacaactcctactttttctatcacaacggcgctcttcccggc
ggaggcggctaccaacgatctgtatgtgtggagcaattcaaatacaatgcagatggaaccattccgacga
tcgaaatgaccaccgccggtccagctcaaattgggactctcaaccctacgtgcgacaggaagccgaaac
ggcggcatggtcttcaggcatcactacggagggtttgtagcgaaggcggaattgacgtcgggtttatcaac
aatggcgattacatcaaagttaaaggcgtagctttcggttcaggagcccattctttctcagcgcgggttg
cttctgcaaatagcggcggcactattgcaatacacctcggaagcacaactggtacgctcgtgggcacttg
tactgtcccagcactggcggttggcagacttggactaccgttacctgttctgtcagtggcgcatctggg
acccaggatgtgtatttgttttcggtggtagcggaacaggataccgtcaactttgattattggcagt
tcgcataa

*FIG. 2A*

SEQ ID NO:4
Protein sequence of Pf43A

<u>mlqrfayilplallsvgvka</u>dnpfvqsiytadpapmvyndrvyvfmdhdntgatyynmtdwhlfssadma
nwqdhgipmslanftwananawapqviprngqfyfyapvrhndgsmaigvgvsstitgpyhdaigkplve
nneidptvfidddgqaylywgnpdlwyvklnqdmisysgsptqipltaggftrtgnaqrpttfeeapwv
ykrngiyyiayaadccsediryststsatgpwtyrgvimptqgssftnhegiidfqnnsyffyhngalpg
gggyqrsvcveqfkynadgti*ptiemttagpaqigtlnpyvrq*EAETAAWSSGITTEVCSEGGIDVGFIN
NGDYIKVKGVAFGSGAHSFSARVASANSGGTIAIHLGSTTGTLVGTCTVPSTGGWQTWTTVTCSVSGASG
TQDVYFVFGGSGTGYLFNFDYWQFa

*FIG. 2B*

SEQ ID NO:5
**Nucleotide sequence for Fv43E, a GH43 family enzyme from *Fusarium verticillioides*** atgaaggtatactggctcgtggcgtgggccacttctttgacgccggcactggctggcttgattggacacc
gtcgcgccaccaccttcaacaatcctatcatctactcagacttttccagataacgatgtattcctcggtcc
agataactactactacttctctgcttccaacttccacttcagcccaggagcacccgttttgaagtctaaa
gatctgctaaactgggatctcatcggccattcaattccccgcctgaactttggcgacggctatgatcttc
ctcctggctcacgttattaccgtggaggtacttgggcatcatccctcagatacagaagagcaatggaca
gtggtactggatcggctgcatcaacttctgcagacctgggtatacactgcctcatcgccggaaggtcca
tggtacaacaagggaaacttcggtgataacaattgctactacgacaatggcatactgatcgatgacgatg
ataccatgtatgtcgtatacggttccggtgaggtcaaagtatctcaactatctcaggacggattcagcca
ggtcaaatctcaggtagttttcaagaacactgatattgggtccaagacttggagggtaaccgcatgtac
aagatcaacgggctctactatatcctaaacgatagcccaagtggcagtcagacctggatttggaagtcga
aatcaccctggggcccttatgagtctaaggtcctcgccgacaaagtcaccccgcctatctctggtggtaa
ctcgccgcatcagggtagtctcataaagactcccaatggtggctggtacttcatgtcattcacttgggcc
tatcctgccggccgtcttccggttcttgcaccgattacgtggggtagcgatggtttccccattcttgtca
agggtgctaatggccgatggggatcatcttacccaacacttcctggcacggatggtgtgacaaagaattg
gacaaggactgataccttccgcggaacctcacttgctccgtcctgggagtggaaccataatccggacgtc
aactccttcactgtcaacaacggcctgactctccgcactgctagcattacgaaggatatttaccaggcga
ggaacacgctatctcaccgaactcatggtgatcatccaacaggaatagtgaagattgatttctctccgat
gaaggacggcgaccgggccgggctttcagcgtttcgagaccaaagtgcatacatcggtattcatcgagat
aacggaaagttcacaatcgctacgaagcatgggatgaatatggatgagtggaacggaacaacaacagacc
tgggacaaataaaagccacagctaatgtgccttctggaaggaccaagatctggctgagacttcaacttga
taccaacccagcaggaactggcaacactatcttttcttacagttgggatggagtcaagtatgaaacactg
ggtcccaacttcaaactgtacaatggttgggcattctttattgcttaccgattcggcatcttcaacttcg
ccgagacggctttaggaggctcgatcaaggttgagtctttcacagctgcatag

FIG. 3A

SEQ ID NO:6
Protein sequence of Fv43E

<u>mkvywlvawatsltpalag</u>lighrrattfnnpiiysdfpdndvflgpdnyyyfsasnfhfspgapvlksk
dllnwdlighsiprlnfgdgydlppgsryyrggtwasslryrksngqwywigcinfwqtwvytasspegp
wynkgnfgdnncyydngiliddddtmyvvygsgevkvsqlsqdgfsqvksqvvfkntdigvqdlegnrmy
kinglyyilndspsgsqtwiwkskspwgpyeskvladkvtppisggnsphqgsliktpnggwyfmsftwa
ypagrlpvlapitwgsdgfpilvkqanggwgssyptlpgtdgvtknwtrtdtfrgtslapswewnhnpdv
nsftvnngltlrtasitkdiyqarntlshrthgdhptgivkidfspmkdgdraqlsafrdqsayigihrd
ngkftiatkhgmnmdewngttdlgqikatanvpsgrtkiwlrlqldtnpagtgntifsyswdgvkyetl
qpnfklyngwaffiayrfgifnfaetalggsikvesftaa

FIG. 3B

SEQ ID NO:7
Nucleotide sequence for Fv39A, a GH39 family enzyme from *Fusarium verticillioides* atgcactacgctaccctcaccactttggtgctggctctgaccaccaacgtcgctgcacagcaaggcacag
caactgtcgacctctccaaaaatcatggaccggcgaaggcccttggttcaggcttcatatacggctggcc
tgacaacggaacaagcgtcgacacctccataccagatttcttggtaactgacatcaaattcaactcaaac
cgcggcggtggcgcccaaatcccatcactgggttgggccagaggtggctatgaaggatacctcggccgct
tcaactcaaccttatccaactatcgcaccacgcgcaagtataacgctgactttatcttgttgcctcatga
cctctggggtgcggatggcgggcaggttcaaactccccgtttcctggcgacaatggcaattggactgag
atggagttattctggaatcagcttgtgtctgacttgaaggctcataatatgctggaaggtcttgtgattg
atgtttggaatgagcctgatattgatatcttttgggatcgcccgtggtcgcagtttcttgagtattacaa
tcgcgcgaccaaactacttcggtgagtctactactgatccatacgtatttacagtgagctgactggtcga
attagaaaaacacttcccaaaactcttctcagtggcccagccatggcacattctcccattctgtccgatg
ataaatggcatacctggcttcaatcagtagcgggtaacaagacagtccctgatatttactcctggcatca
gattggcgcttgggaacgtgagccggacagcactatccccgactttaccaccttgcgggcgcaatatggc
gttcccgagaagccaattgacgtcaatgagtacgctgcacgcgatgagcaaaatccagccaactccgtct
actacctctctcaactagagcgtcataaccttagaggtcttcgcgcaaactggggtagcggatctgacct
ccacaactggatgggcaacttgatttacagcactaccggtacctcggaggggacttactacccctaatggt
gaatggcaggcttacaagtactatgcggccatggcagggcagagacttgtgaccaaagcatcgtcggact
tgaagtttgatgtctttgccactaagcaaggccgtaagattaagattatagccggcacgaggaccgttca
agcaaagtataacatcaaaatcagcggtttggaagtagcaggacttcctaagatgggtacggtaaaggtc
cggacttatcggttcgactgggctggccgaatggaaaggttgacgggcctgttgatttgggggagaaga
agtatacttattcggccaatacggtgagcagcccctctacttga

*FIG. 4A*

SEQ ID NO:8
Protein sequence of Fv39A

<u>mhyatlttlvlalttnvaa</u>qqgtatvdlsknhgpakalgsgfiygwpdngtsvdtsipdflvtdikfnsn
rgggaqipslgwarggyegylgrfnstlsnyrttrkynadfillphdlwgadggqgsnspfpgdngnwte
me l **fwnqlvsdlkahnmleglvidvwnepdidifwdrpwsqfleyynratkllrktlpktllsgpamahs
pilsddkwhtwlqsvagnktvpdiyswhqigawerepdstipdfttlraqygvpekpidvneyaardeqn
pansvyylsql**erhnlrglranwgsgsdlhnwmgnliysttgtsegtyypngewqaykyyaamagqrlvt
kassdlkfdvfatkqgrkikiiagtrtvqakynikisglevaglpkmgtvkvrtyrfdwagpngkvdgpv
dlgekkytysantvsspst

*FIG. 4B*

SEQ ID NO:9
Nucleotide sequence for Fv43A, a GH43 family enzyme from *Fusarium verticillioides* atgtggctgacctccccattgctgttcgccagcaccctcctgggcctcactggcgttgctctagcagaca
accccatcgtccaagacatctacaccgcagacccagcaccaatggtctacaatggccgcgtctacctctt
cacaggccatgacaacgacggctctaccgacttcaacatgacagactggcgtctcttctcgtcagcagac
atggtcaactggcagcaccatggtgtccccatgagcttaaagaccttcagctgggccaacagcagagcct
gggctggtcaagtcgttgcccgaaacggaaagttttacttctatgttcctgtccgtaatgccaagacggg
tggaatggctattggtgtcggtgttagtaccaacatccttgggcctacactgatgcccttggaaagcca
ttggtcgagaacaatgagatcgacccaactgtctacatcgacactgatggccaggcctatctctactggg
gcaaccctggattgtactacgtcaagctcaaccaagacatgctctcctacagtggtagcatcaacaaagt
atcgctcacaacagctggattcggcagccgcccgaacaacgcgcagcgtcctactactttcgaggaagga
ccgtggctgtacaagcgtggaaatctctactacatgatctacgcagccaactgctgttccgaggacattc
gctactcaactggacccagcgccactggaccttggacttaccgcggtgtcgtgatgaacaaggcgggtcg
aagcttcaccaaccatcctggcatcatcgactttgagaacaactcgtacttctttaccacaatggcgct
cttgatggaggtagcggttatactcggtctgtggctgtcgagagcttcaagtatggttcggacggtctga
tccccgagatcaagatgactacgcaaggcccagcgcagctcaagtctctgaacccatatgtcaagcagga
ggccgagactatcgcctggtctgagggtatcgagactgaggtctgcagcgaaggtggtctcaacgttgct
ttcatcgacaatggtgactacatcaaggtcaagggagtcgactttggcagcaccggtgcaaagacgttca
gcgcccgtgttgcttccaacagcagcggaggcaagattgagcttcgacttggtagcaagaccggtaagtt
ggttggtacctgcacggtaacgactacgggaaactggcagacttataagactgtggattgccccgtcagt
ggtgctactggtacgagcgatctattctttgtcttcacgggctctgggtctggctctctgttcaacttca
actggtggcagtttagctaa

FIG. 5A

SEQ ID NO:10
Protein sequence of Fv43A

<u>mwltspllfastllqltqvala</u>dnpivqdiytadpapmvyngrvylftghdndgstdfnmtdwrlfssad
mvnwqhhgvpmslktfswansrawagqvvarngkfyfyvpvrnaktggmaigvqvstnilgpytdalgkp
lvenneidptvyidtdgqaylywgnpglyyvklnqdmlsysgsinkvslttagfgsrpnnaqrpttfeeg
pwlykrgnlyymiyaanccsedirystgpsatgpwtyrgvvmnkagrsftnhpgiidfennsyffyhnga
ldggsgytrsvavesfkygsdg*lipelkmttqgpaqlksl*NPYVKQEAETIAWSEGIETEVCSEGGLNVA
FIDNGDYIKVKGVDFGSTGAKTFSARVASNSSGGKIELRLGSKTGKLVGTCTVTTTGNWQTYKTVDCPVS
GATGTSDLFFVFTGSGSGSLFNFNWWQFs

FIG. 5B

SEQ ID NO:11
**Nucleotide sequence for Fv43B, a GH43 family enzyme from *Fusarium verticillioides*** atgcgcttctcttggctattgtgcccccttctagcgatgggaagtgctcttcctgaaacgaagacggatg
tttcgacatacaccaaccctgtccttccaggatggcactcggatccatcgtgtatccagaaagatggcct
ctttctctgcgtcacttcaacattcatctccttccaggtcttcccgtctatgcctcagggatctagtc
aactggcgtctcatcagccatgtctggaaccgcgagaaacagttgcctggcattagctggaagacggcag
gacagcaacagggaatgtatgcaccaaccattcgataccacaagggaacatactacgtcatctgcgaata
cctgggcgttggagatattattggtgtcatcttcaagaccaccaatccgtgggacgagagtagctggagt
gaccctgttaccttcaagccaaatcacatcgacccgatctgttctgggatgatgacggaaaggtttatt
gtgctacccatggcatcactctgcaggagattgatttggaaactggagagcttagcccggagcttaatat
ctggaacggcacaggaggtgtatgcctgagggtccccatatctacaagcgcgacggttactactatctc
atgattgccgagggtggaactgccgaagaccacgctatcacaatcgctcgggcccgcaagatcaccggcc
cctatgaagcctacaataacaacccaatcttgaccaaccgcgggacatctgagtacttccagactgtcgg
tcacggtgatctgttccaagataccaagggcaactggtgggtctttgtcttgctactcgcatcacagca
cagggagtttcacccatgggccgtgaagctgttttgttcaatggcacatggaacaagggcgaatggccca
agttgcaaccagtacgaggtcgcatgcctggaaacctcctcccaaagccgacgcgaaacgttccgggaga
tgggcccttcaacgctgacccagacaactacaacttgaagaagactaagaagatccctcctcactttgtg
caccatagagtcccaagagacggtgccttctctttgtcttccaagggtctgcacatcgtgcctagtcgaa
acaacgttaccggtagtgtgttgccaggagatgagattgagctatcaggacagcgaggtctagctttcat
cggacgccgccaaactcacactctgttcaaatatagtgttgatatcgacttcaagcccaagtccgatgat
caggaagctggaatcaccgttttccgcacgcagttcgaccatatcgatcttggcattgttcgtcttccta
caaaccaaggcagcaacaagaaatctaagcttgccttccgattccgggccacaggagctcagaatgttcc
tgcaccgaaggtagtaccggtccccgatggctgggagaagggcgtaatcagtctacatatcgaggcagcc
aacgcgacgcactacaaccttggagcttcgagccacagaggcaagactctcgacatcgcgacagcatcag
caagtcttgtgagtggaggcacgggttcatttgttggtagtttgcttggaccttatgctacctgcaacgg
caaaggatctggagtggaatgtcccaagggaggtgatgtctatgtgacccaatggacttataagcccgtg
gcacaagagattgatcatggtgttttgtgaaatcagaattgtag

FIG. 6A

SEQ ID NO:12
Protein sequence of Fv43B mrfswllcpllamgsalpetktdvstytnpvlpqwhsdpsciqkdglflcvtstfisfpglpvyasrdlv
nwrlishvwnrekqlpgiswktagqqqgmyaptiryhkgtyyviceylgvgdiigvifkttnpwdessws
dpvtfkpnhidpdlfwdddgkvycathgitlqeidletgelspelniwngtggvwpegphiykrdgyyyl
miaeggtaedhaitiararkitgpyeaynnnpiltnrgtseyfqtvghgdlfqdtkgnwwglclatrita
qgvspmgreavlfngtwnkgewpklqpvrgrmpgnllpkptrnvpgdgpfnadpdnynlkkktkkipphfv
hhrvprdgafslsskglhivpsrnnvtgsvlpgdeielsgqrglafigrrqthtlfkysvdidfkpksdd
qeagitvfrtqfdhidlgivrlptnqgsnkksklafrfratgaqnvpapkvvpvpdgwekgvislhieaa
nathynlqasshrgktldiatasaslvsggtgsfvgsllgpyatcngkgsqvecpkggdvyv
tqwtykpvaqeidhgvfvksel

FIG. 6B

SEQ ID NO:13
Nucleotide sequence for Pa51A, a GH51 family enzyme from *Podospora anserina*

```
atgatccacctcaagccagccctcgcggctgttgttggcgctgtcgacgcaatgtgtggctattgattgttgtcaagtc
ttcgggggggaataagacgactgatatcatgtatgtcttatgcacgagtgttgttttgcgagatctcccttttgttt
ttgcgcactgctgacatgagactgcaaactgcaaccaggatatccactccaacctcgacaactggagccggccatctacgccgagctaatctcc
aaccgcgttgccaaggagtgagaaccccttcctctgcgttgccttactccgtcaatgttgccaacccacggaggccaaggagggcaaggcaagg
tcagaagcttgccaagcccccttcctctgcgttgccttactccgtcaatgttgccaacccacggaggccaaggagggcaagg
gcaaggacaccaaggagaaggttgctggcttgccaatgctgtggtttgagttatgatgtcaagaggcagaagtacact
ggtagcttccacgttactgtgagtacaaggggtaggtagttagcttgcagcgcgattaccgggagaccttttgg
caagaagtggtgaaggtggggtggagaagggaagtggaccgagaaggagttgagttgggtcctttcaaggatgcgc
ccaacagcaacaccttgttgtcaggcgccaaggacaggatctttgggatgctcttcttatttatgctgagataaagttggg
ttgacatgatgtgttgcagggcgagaattgatctgcgcagacgatggttggtgagctcaagccggtaagtctctctctagtcagaaaag
gaagaagaatggcttgttaacgttgacacagaccttggcccctcgaaggatcgccccggcatggctggtgtctgagggtaaacatgctccagcagccctt
tagagccttttgttgttaacgttgacacagaccttggcccctcgaaggatcgccccggcatggtggtgtctgagggtaaacatgctccagcagccctt
gtggaagtggtacgagaccattggccctcgagtggccgatgacatgaactgggagccccagtatgtgatcccattctcggagtg
gcttggtctgtcgaggtacaggtatccacagttgtcgagtgctctctgtcgttctgcactgctcgttcgttcccgaattcga
actctcttgctaacgtatccaacaggtgcatcggcgaaatcgagttcctcactgacgatcgagatcggtcaagtgggttgagatcgaggatgggcttgccggacgc
gatggatgggtcatccaacaggtcacccaagccttggaagtcaagttggagatcgtcaagtgggttgagatcgaggatgggcttgccggacgc
tccgcgcgcaagcttggtcacccaagccttggtacaccgcttcaactaccgcttcccatgatgatgaaggccttcaacgaaaagtacccgacatcaa
cctgctggcttcgagtcgtacatcaactaccgcttcccatgatgatgaaggccttcaacgaaaagtacccgacatcaa
gatcatcgcgccctccatcttcgaccaacatgacaatcccccgggtgctgcggtgatcaccaccccgtacctgactc
ccgatgagttcgttgagcgattcgccaagtcgtcagttgagcaagatcatcgccgcggttgagcaaggatataacgtgacgctcatcgcgaggctgctgtcg
acgcatcctaacggtgtatcgtgaggagaacggtgacaaggtgacaagatcatcgcggcttctacgccgctcgcagcttgaccgct
cttcttgatcagcactgagagaaacggtgacaagatcatcggtcgatcatcggtcgtactcgcgcctcgtcagcttgaccgct
gcaatggagcatgaccgtgtgcagcatgcgagacgcaccggatcgccaagcccaacttgacccctctgttcta
atcctcgccccaccacatcatccgtgagagagcatcccgtgagagctgcggtgcccggtatcttcaaggctgcgtcctacaactcgatccgtgtcgt
cgttgccggaaagagcgagagttgtgtcaacaggagcggtgcctcctccaaccaggccgaaaagcgcggcgaagttcacctttcac
tgaagttgattatgttgtctcaacggtgtatcaatgtttgtcaaggagaagaccaccttcatcaaggccgaaaagcgcggcaagttcacctttcac
gaccccttcactggttatcagtgtctcaacggtgtatcaatgtttgtcaaggagaagaccaccttcatcaaggccgaaaagcgcggcaagttcacctttcac
cctgccggcttgagtgttgcttgctgttgctgttggagacgccgacggcggcatccatcttggagacgccgacggcggcgacgcggtggtcg
agggtaactga
```

FIG. 7A

SEQ ID NO:14
Protein sequence of Pa51A mihlkpalaallalstccvaidlfvkssggnkttdimyglmhedinnsgdggiyaelisnrafggsekfp
snldnwspvggatltlqklakplssalpysvnvanpkegkgkgkdtkgkkvglanagfwgmdvkrqkytg
sfhvtgeykgdfevslrsaltgetfgkkvvkggskkgkwtekefelvpfkdapnsnntfvvqwdaegakd
gsldinlislfpptfkgrknglridlaqtmvelkptflrfpggnmlegntldtwwkwyetigplkdrpgm
agvweygqtlglglveymewaddmnlepivgvfaglaldgsfvpesemgwviqqaldeiefltgdakttk
wgavraklghpkpwkvkvweignedwlagrpagfeesyinyrfpmmmkafnekypdikiliaspsifdnmti
pagaagdhhpyltpdefverfakfdnlskdnvtligeaasthpnggiawegdlmplpwwggsvaeaifli
sterngdkiigatyapglrsldrwqwsmtwvqhaadpalttrstswyvwrilahhiiretlpvdapagkp
nfdplfyvagksesgtgifkaavynstesipvslkfdglnegavanltvltgpedpygyndpftginvvk
akttfikagkggkfftlpglsvavletadavkggkgkgkgkgn

FIG. 7B

SEQ ID NO:15
Nucleotide sequence for Gz43A, a GH43 family enzyme from Gibberella zeae atgaagtccaagtgttgttattccactcctctcttcgttggtcaaagtcttgccaccaacgacgactgtcctctcatcactagtag
atggactgcggatccttcggctcatgtcttaacgacacacctttgtgctctcataccgtctcatgacatcgatgctgagaatg
atcctgatggaggccagtacgccagtacgccatgagagattaccatgtctactctatcgacaagatctacgttccctgcgtcgatcacggt
acggccctgtcagtggagatcgagggtcccatgccgtctgacagatgtggctcctgacgctgccacaacccccggcgaccattggcgtcccgaca
atacttccctgccaaagacaagatggatgatatcttcagatcggcgttgctgtgctcgatgatgatgacagaccctactggcatggggtgtatc
atggtggccagctcacacttcaacgatggcaaggatggcaaggataacaagtacactctggcaacgaatctggcactgagcccgacaatctggcactgagccactgagccactgagccactgagccactgagccactgagccactgagccactgagccactgagccactgagccactgagccactgagccactgagccactgagccactgagccactgagccactgagccactgagcactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagccactgagc

FIG. 8A

SEQ ID NO:16
Protein sequence of Gz43A

<u>mkskllfpllsfvqqsla</u>tnddcplitsrwtadpsahvfndtlwlypshdidagfendpdgqyamrdyh
vysidkiygslpvdhgtalsvedvpwasrqmwapdaahkngkyylyfpakdkddifrigvavsptpggpf
vpdkswiphtfsidpasfvddddraylawggimggqlqrwqdknkynesgtepgngtaalspqiaklskd
mhtlaekprdmlildpktgkpllsedearrffegpwihkrnkiyyltystgtthylvyatsktpygpyty
qgrilepvdgwtthssivkyqgqwwlfyhdaktsgkdylrqvkakkiwydskg<u>kiltkkp</u>

*FIG. 8B*

SEQ ID NO:17
Nucleotide sequence for Fo43A, a GH43 family enzyme from *Fusarium oxysporum* atgcagctcaagtttctgtcttcagcattgctgttctctctgaccagcaaatgcgctgcgcaagacacta
atgacattcctccctgatcaccgaccctctggtccgcagatccctcggctcatgttttcgaaggcaagct
ctgggtttacccatctcacgacatcgaagccaatgttgtcaacggcacaggaggcgctcaatacgccatg
agggattaccataccatcctccatgaagagcatctatggtaaagatccgttgtcgaccacggcgtcgctc
tctcagtcgatgacgttccctgggcgaagcagcaaatgtgggctcctgacgcagctcataagaacggcaa
atattatctgtacttccccgccaaggacaaggatgagatcttcagaattggagttgctgtctccaacaag
ccagcggtcctttcaaggccgacaagagctggatccctggcacgtacagtatcgatcctgctagctacg
tgacactgataacgaggcctacctcatctggggcggtatctgggcggccagctccaagcctggcagga
taaaaagaactttaacgagtcgtggattggagacaaggctgctcctaacggcaccaatgccctatctcct
cagatcgccaagctaagcaaggacatgcacaagatcaccgaaacaccccgcgatctcgtcattctcgccc
ccgagacaggcaagcctcttcaggctgaggacaacaagcgacgattcttcgagggccttggatccacaa
gcgcggcaagctttactacctcatgtactccaccggtgatacccacttccttgtctacgctacttccaag
aacatctacggtcctttatacctaccggggcaagattcttgatcctgttgatgggtggactactcatggaa
gtattgttgagtataagggacagtggtggctttttctttgctgatgcgcatacgtctggtaaggattacct
tcgacaggtgaaggcgaggaagatctggtatgacaagaacggcaagatcttgcttcaccgtccttag

*FIG. 9A*

SEQ ID NO:18
Protein sequence of Fo43A

<u>mqlkflssallfsltskcaa</u>qdtndipplitdlwsadpsahvfegklwvypshdieanvvngtggaqyam
rdyhtysmksiygkdpvvdhgvalsvddvpwakqqmwapdaahkngkyylyfpakdkdeifrigvavsnk
psgpfkadkswipgtysidpasyvdtdneayliwggiwggqlqawqdkknfneswigdkaapngtnalsp
qiaklskdmhkitetprdlvilapetgkplqaednkrrffegpwihkrgklyylmystgdthflvyatsk
niygpytyrgkildpvdgwtthgsiveykgqwwlffadahtsgkdylrqvkarkiwydkng<u>killhrp</u>

*FIG. 9B*

SEQ ID NO:19
Nucleotide sequence for Af43A, a GH43 family enzyme from *Aspergillus fumigatus* atggcagctccaagtttatcctaccccacaggtatccaatcgtataccaatcctctcttccctggttggc
actccgatcccagctgtgctacgtagcggagcaagacaccttttctgcgtgacgtccactttcattgc
cttccccggtcttcctctttatgcaagccgagatctgcagaactggaaactggcaagcaatatttcaat
cggcccagccagatccctgatcttcgcgtcacggatggacagcagtcgggtatctatgcgcccactctgc
gctatcatgagggccagttctacttgatcgtttcgtacctgggcccgcagactaagggcttgctgttcac
ctcgtctgatccgtacgacatgccgcgtggagcgatccgtcgaattcgcggtacatggcatcgacccg
gatatcttctgggatcacgacgggacggtctatgtcacgtccgccgaggaccagatgattaagcagtaca
cactcgatctgaagacggggcgattggcccggttgactacctctggaacggcaccggaggagtctggcc
cgagggccgcacatttacaagagagacggatactactacctcatgatcgcagagggaggtaccgagctc
ggccactcggagaccatggcgcgatctagaacccggacaggtcctgggagccataccccgcacaatccgc
tcttgtcgaacaagggcacctcggagtacttccagactgtgggccatgcggacttgttccaggatggaa
cggcaactggtgggccgtggcgttgagcacccgatcagggcctgcatggaagaactatcccatgggtcgg
gagacggtgctcgccccgccgcttgggagaagggtgagtggcctgtcattcagcctgtgagaggccaaa
tgcaggggccgtttccaccaccaaataagcgagttcctcgcggcgagggcggatggatcaagcaacccga
caaagtggatttcaggcccggatcgaagataccggcgcacttccagtactggcgatatcccaagacagag
gattttaccgtctcccctcggggccaccgaatactcttcggctcacaccctccttttacaacctcaccg
gaactgcggacttcaagccggatgatggcctgtcgcttgttatgcgcaaacagaccgacaccttgttcac
gtacactgtggacgtgtcttttgacccaaggttgccgatgaagaggcgggtgtgactgttttccttacc
cagcagcagcacatcgatcttggtattgtccttctccagacaaccgaggggctgtcgttgtccttccggt
tccgcgtggaaggccgcggtaactacgaaggtcctcttccagaagccaccgtgcctgttcccaaggaatg
gtgtggacagaccatccggcttgagattcaggccgtgagtgacaccgagtatgtctttgcggctgccccg
gctcggcaccctgcacagaggcaaatcatcagccgcgccaactcgttgattgtcagtggtgatacgggac
ggtttactggctcgcttgttggcgtgtatgccacgtcgaacggggtgccggatccacgcccgcatatat
cagcagatggagatacgaaggacggggccagatgattgatttggtcgagtggtcccgagctactga

*FIG. 10A*

SEQ ID NO:20
Protein sequence of Af43A maapsisyptgiqsytnplfpgwhsdpscayvaeqdtffcvtstfiafpglplyasrdlqnwklasnifn
rpsqipdlrvtdgqqsgiyaptlryhegqfylivsylgpqtkgllftssdpyddaawsdplefavhgidp
difwdhdgtvyvtsaedqmikqytldlktgaigpvdylwngtggvwpegphiykrdgyyylmiaeggtel
ghsetmarsrtrtgpwepyphnpllsnkgtseyfqtvghadlfqdgngnwwavalstrsgpawknypmgr
etvlapaawekgewpviqpvrgqmqgpfpppnkrvprgeqgwikqpdkvdfrpgskipahfqywrypkte
dftvsprghpntlrltpsfynltgtadfkpddglslvmrkqtdtlftytvdvsfdpkvadeeagvtvflt
qqqhidlgivllqttegislsfrfrvegrgnyegplpeatvpvpkewcgqtirleiqavsdteyvfaaap
arhpaqrqiisranslivsgdtgrftgslvgvyatsnggagstpayisrwryegrgqmidfgrvvpsy

*FIG. 10B*

SEQ ID NO:21
Nucleotide sequence for Pf51A, a GH51 family enzyme from *Penicillium funiculosum* atggaaagatgtggcattcgatcttgttgtgtttgggcttattgtctgtcgggcatgccatcactactcaacgtgtcccaaagtgg
cggcaataagaccagtccttttgcaatatggtctgatgttcgaggtaatcctctcttatccacacatataaaagttgcgtcatttct
aagacaagtcaaggacataaatcacggcgtgatggcggttcggttcgtgtatgcagagcttgttcgaaaccgagcattcaaggtagcaccg
tctatccagcaaacctcgatggatacgaccggtccaacaatggaaagcatcggtttcgcaaatgaaggctggtggggatagaagtcaa
atgcctagctctctcaacgtcgccaaggggtccagtcctcacgtctacgtcttctacggagattcgacatcctctcttcagtcgaaattgacacaag
gccgcaaagatacgcgggctcattctacgtcctcaccagtctccggaaacacgagactgggttcaatacaagtcgagttggtgccaaaaggca
aagtcttcgcaacgcaataacactctgaccattactttttgactcactttgggtttagttcgatgtctggcaattgt
cttcaaacaccaatacgtagggatcgacctgtttgaagctaggctattggctgaactagaggggtgatgtgtggacgtacgaagctcttacaagctcttacaaatcaactttatcttttacgaagactaa
atggcctaagaatcgacctgtttgaagctaggctattggctgaactagaggggtgatgtggacgtagcgatatggctattccagcccagtgcccagtgagtgagtgaacgaagtgatatcgaacacggaccatatccgaagccgtgacgattaact
atgtgaaaacttagaaatttctgcgttccaggcgtagcgatagctattggctccaggcggagtgagtgaacgaagtgatatcgaacacggaccatatccgaagccgtgacgattaact
acgtgagattgaaacgaagacaatctatacggggactagaacatatcggggtaatgtctttgaccggagatcgatgaatctttgaccggagatcagatgccagtcactaataataataataataagaaccgttatccagattgcaacgttatccagatgccagatatgatccaccgcatatccgaagccgtgacgattaacctaataataataataataataagaaccgttatccagattgcaacgttatccatccgatccgttatccgataatcctagtaattc
acagctaaatatccccatatgacggtcatgtcttttaatgtattaaccatcttcatggagagatttggtcgttcagaagctgtttttcctaattgtgaagagaga
ttctactcctgatggtttgtttccccagttcaactacttttgatcagtccagatgtccagtcactaatagaacactgaacgttatcaataatcctagtaattc
ccccttttttaatatgctttaatgttataaccatcttcatggagagatttggtcgttcagaagctgtttttcctaattgtgaagagaga
ggttggcctgggaagccatttcccccattcgtatccttgtatccttgtggattgggtccgttcagaagctgtttttcctaattgtgaagagaga
attcgccaaagataatcggttgctacgtacgaattctactttcgagatttctactttcgaattctactttcgagatttctactttcgagcttttgacgctgactctcgcgtacaagtcg
caggtccaatgttcagaaatatcaagatgttcagaaatatcaaaatggcagtggtctccaacactcgttttgacgctgactctcgcgtacaagtcg
ttcaacaagctggcatgtgcatgtgatcaagtatgtcaatttcctcctcattcaaaacccgagatgtgagctgtagctgagctgtagctaactttccgaagcttctc
tcgaacaacaaatcgaacatattcaaggccgtgtttacacgacgatccgacgcatccgaacgatccgaacatccctgtcctgttcaatttgcaccgttcaattgcaggatgcaacga
caatacaggatcgaacatattcaaggccgtgtttacacgacgatccgacgcatccgaacgatccgaacatccctgtcctgttcaatttgcaccgttcaattgcaggatgcaacga
caaagagcgcaaatttgaccatcttgtcatccgacgcatttgtcatggagagcatttgtcatggagagcatttgaggcccgaaggtgtggctgttctcaaaaacggagtaa
atccagtctgtcactgcaaatgctcaaatgctcactgcaaatgctcactgcaaatgctcaaatgctcactgcaaatgctcactgcaaatgctcactgcaaatgctcactgcaaatgctcactgtcctccgaacctaagtgtgctgttctcaaaaacggagtaa

*FIG. 11A*

SEQ ID NO:22
Protein sequence of Pf51A

<u>mqkmwhsilvvlgllsvqha</u>itinvsqsggnktsplqyglmfedinhqgdgglyaelvrnrafqgstvyp
anldgydsvngailalqnltnplspsmpsslnvakgsnngsigfanegwwgievkpqryagsfyvqgdyq
gdfdislqskltqevfatakvrssgkhedwvqykyelvpkkaasntnntltitfdskglkdgslnfnlis
lfpptynnrpnglridlveamaelegkflrfpggsdvegvqapywykwnetvgdlkdrysrpsawtyees
ngiglieymnwcddmglepilavwdghylsnevisendlqpyiddtlnqleflmgapdtpygswraslgy
pkpwtinyveignednlyggletyiayrfqayydaitakyphmtvmesltempgpaaaasdyhqystpdg
fvsqfnyfdqmpvtnrtlngeiatvypnnpsnsvawgspfplyp**wwigsvaeavfligeernspkiigas
yapmfrninnwqwsptliafdadssrtsrstswhvikllstnkitqnlpttwsggdigplywvagrndnt
gsnifkaavynstsdvpvtvqfagcnaksanltilssddpnasnypggpevvkteiqsvtanahgafefs
lpnls**vavlkte

FIG. 11B

SEQ ID NO:23
**Nucleotide sequence for AfuXyn2, a GH11 family enzyme from *Aspergillus fumigatus*** atggtttctttctcctacctgctgctggcgtgctccgccattggagctctggctgcccccgtcgaacccg
agaccacctcgttcaatgagactgctcttcatgagttcgctgagcgcgccggcacccccaagctccaccgg
ctgaacaacggctactactactccttctggactgatggcggcggcgacgtgacctacaccaatggcgcc
ggtggctcgtactccgtcaactggaggaacgtgggcaactttgtcggtggaaagggctggaaccctggaa
gcgctaggtaccgagctttgtcaacgtcggatgtgcagacctgtgctgacagaagtagaaccatcaact
acggaggcagcttcaaccccagcggcaatggctacctggctgtctacggctggaccaccaaccccttgat
tgagtactacgttgttgagtcgtatggtacatacaaccccggcagcggcggtaccttcaggggcactgtc
aacaccgacggtggcacttacaacatctacacggccgttcgctacaatgctccctccatcgaaggcacca
agaccttcacccagtactggtctgtgcgcacctccaagcgtaccggcggcactgtcaccatggccaacca
cttcaacgcctggagcagactgggcatgaacctgggaactcacaactaccagattgtcgccactgagggt
taccagagcagcggatctgcttccatcactgtctactag

FIG. 12A

SEQ ID NO:24
Protein sequence of AfuXyn2

<u>mvsfsvllacsaigala</u>apvepettsfnetalhefaeragtpsst**gwnngyyysfwtdgggdvtytnga
ggsysvnwrnvgnfvggkgwnpgsartinyggsfnpsgngylavygwttnplieyyvvesygtynpgsgg
tfrgtvntdggtyniytavrynapsiegtktftqywsvrtskrtggtvtmanhfnawsrlgmnlgthnyq
ivategyqssgsasitvy**

FIG. 12B

SEQ ID NO:25
Nucleotide sequence for AfuXyn5, a GH11 family enzyme from *Aspergillus fumigatus* atgatctccatttcctcgctcagctttggactcgccgctatcgccggcgcatatgctcttccgagtgaca
aatccgtcagcttagcggaacgtcagacgatcacgaccagccagacaggcacaaacaatggctactacta
ttccttctggaccaacggtgccggatcagtgcaatatacaaatggtgctggtggcgaatatagtgtgacg
tgggcgaaccagaacggtggtgactttacctgtgggaagggctggaatccagggagtgaccagtaggcaa
cgcccgagaactatagaagaggacgcaaagaaagcactaaactctctactagtgacattaccttctctgg
cagcttcaatccttccggaaatgcttacctgtccgtgtatggatggactaccaaccccctagtcgaatac
tacatcctcgagaactatggcagttacaatcctggctcgggcatgacgcacaagggcaccgtcaccagcg
atggatccacctacgacatctatgagcaccaacaggtcaaccagccttcgatcgtcggcacggccacctt
caaccaatactggtccatccgccaaaacaagcgatccagcggcacagtcaccaccgcgaatcacttcaag
gcctgggctagtctggggatgaacctgggtacccataactatcagattgtttccactgagggatatgaga
gcagcggtacctcgaccatcactgtctcgtctggtggttcttcttctggtggaagtggtggcagctcgtc
tactacttcctcaggcagctcccctactggtggctccggcagtgtaagtcttcttccatatggttgtggc
tttatgtgtattctgactgtgatagtgctctgctttgtgggccagtgcggtggaattggctggtctggt
cctacttgctgctcttcgggcacttgccaggtttcgaactcgtactactcccagtgcttgtagtaccttc
ttgcagggttatatccaagtga

FIG. 13A

SEQ ID NO:26
Protein sequence of AfuXyn5

<u>MISISSLSFGLAAIAGAYA</u>LPSDKSVSLAERQTITTSQT**GTNNGYYYSFWTNGAGSVQYTNGAGGEYSVT
WANQNGGDFTCGKGWNPGSDHDITFSGSFNPSGNAYLSVYGWTTNPLVEYYILENYGSYNPGSGMTHKGT
VTSDGSTYDIYEHQQVNQPSIVGTATFNQYWSIRQNKRSSGTVTTANHFKAWASLGMNLGTHNYQIVSTE
GYESSGTSTITVSSGGSSSGGSGGSSSTTSSGSSPTGGSGSCSALWGQCGGIGWSGPTCCSSGTCQVSNS
YY**SQCL

FIG. 13B

SEQ ID NO:27
**Nucleotide sequence for Fv43D, GH43 family enzyme from *Fusarium verticillioides*** atgcagctcaagtttctgtcttcagcattgttgctgtctttgacggcaattgcgctgcgcaagacacta
atgatatccctcctctgatcaccgacctctggtctgcggatccctcggctcatgttttcgagggcaaact
ctgggtttacccatctcacgacatcgaagccaatgtcgtcaacggcaccggaggcgctcagtacgccatg
agagattatcacacctattccatgaagaccatctatggaaaagatcccgttatcgaccatggcgtcgctc
tgtcagtcgatgatgtcccatgggccaagcagcaaatgtgggctcctgacgcagcttacaagaacggcaa
atattatctctacttccccgccaaggataaagatgagatcttcagaattggagttgctgtctccaacaag
cccagcggtccttttcaaggcgacaagagctggatccccggtacttacagtatcgatcctgctagctatg
tcgacactaatggcgaggcatacctcatctggggcggtatctggggcggccagcttcaggcctggcagga
tcacaagacctttaatgagtcgtggctcggcgacaaagctgctcccaacggcaccaacgccctatctcct
cagatcgccaagctaagcaaggacatgcacaagatcaccgagacaccccgcgatctcgtcatcctggccc
ccgagacaggcaagccccttcaagcagaggacaataagcgacgattttcgagggcgcctggggttcacaa
gcgcggcaagctgtactacctcatgtactctaccggcgacacgcacttcctcgtctacgcgacttccaag
aacatctacggtccttatacctatcagggcaagattctcgaccctgttgatgggtggactacgcatggaa
gtattgttgagtacaagggacagtggtggttgttctttgcggatgcgcatacttctggaaaggattatct
gagacaggttaaggcgaggaagatctggtatgacaaggatggcaagattttgcttactcgtcctaagatt
tag

FIG. 14A

SEQ ID NO:28
Protein sequence of Fv43D

<u>mglkflssalllsltqncaa</u>qdtndipplitdlwsadpsahvfegklwvypshdieanvvngtggaqyam
rdyhtysmktiygkdpvidhgvalsvddvpwakqqmwapdaaykngkyylyfpakdkdeifrigvavsnk
psgpfkadkswipgtysidpasyvdtngeayliwggiwggqlqawqdhktfneswlgdkaapngtnalsp
qiaklskdmhkitetprdlvilapetgkplqaednkrrffegpwvhkrgklyylmystgdthflvyatsk
niygpytyqgkildpvdgwtthgsiveykgqwwlffadahtsgkdylrqvkarkiwydkdgkilltrpki

FIG. 14B

SEQ ID NO:29
Nucleotide sequence for Pf43B, GH43 family enzyme from *Penicillium funiculosum* atgagtcgcagcatccttccgtacgcctctgttttcgcctcctgggcggggctatcgccgaaccgtttt
tggttctcaatagcgattttcccgatcccagtctcatagagacatccagcggatactatgcattcggtac
caccggaaacggagtcaatgcgcaggttgcttcttcaccagactttaatacctggactttgctttccggc
acagatgccctcccgggaccatttccgtcatgggtagcttcgtctccacaaatctgggcgccagatgttt
tggttaaggtatgttcttatggaataacagtttaggagtaggtcagccaggatattgacaaaattataa
taggccgatggtacctatgtcatgtactttcggcatctgctgcgagtgactcgggcaaacactgcgttg
gtgccgcaactgcgacctcaccggaaggacctacaccccggtcgatagcgctgttgcctgtccattaga
ccagggaggagctattgatgccaatggatttattgacaccgacggcactatatacgttgtatacaaaatt
gatggaaacagtctagacggtgatggaaccacacatcctaccccatcatgcttcaacaaatggaggcag
acggaacaaccccaaccggcagcccaatccaactcattgaccgatccgacctcgacggacctttgatcga
ggctcctagtttgctcctctccaatggaatctactacctcagtttctcttccaactactacaacactaat
tactacgacacttcatacgcctatgcctcgtcgattactggtccttggaccaaacaatctgcgccttatg
caccottgttggttactggaaccgagactagcaatgacggcgcattgagcgccctggtggtgccgattt
ctccgtcgatggcaccaagatgttgttccacgcaaacctcaatggacaagatatctcgggcggacgcgcc
ttatttgctgcgtcaattactgaggccagcgatgtggttacattgcagtag

FIG. 15A

SEQ ID NO:30
Protein sequence of Pf43B

<u>msrsilpyasvfallqqaiae</u>pflvlnsdfpdpslietssgyyafgttgngvnaqvasspdfntwtllsg
tdalpgpfpswvasspqiwapdvlvkadgtyvmyfsasaasdsgkhcvgaatatspegpytpvdsavacp
ldqggaidangfidtdgtiyvvykidgnsldgdgtthptpimlqqmeadgttptgspiqlidrsdldgpl
ieapslllsngiyylsfssnyyntnyydtsyayassitgpwtkqsapyapllvtgtetsndgalsapgga
dfsvdgtkmlfhanlngqdisggralfaasiteasdvvtlq

FIG. 15B

SEQ ID NO:31

**Nucleotide sequence of Fv51A, a GH51 family enzyme from *Fusarium verticillioides*** atggttcgcttcagttcaatcctagcggctgcggcttgcttcgtggctgttgagtcagtcaacatcaaggtcgacag
caagggcggaaacgctactagcggtcaccaatatggcttccttcacgaggttggtattgacacaccactggcgatga
ttgggatgctaacttggagctaggatatcaacaattccggtgatggtggcatctacgctgagctcatccgcaatcgt
gctttccagtacagcaagaaataccctgtttctctatctggctggagacccatcaacgatgctaagctctccctcaa
ccgtctcgacactcctctctccgacgctctccccgtttccatgaacgtgaagcctggaaagggcaaggccaaggaga
ttggtttcctcaacgagggttactggggaatggatgtcaagaagcaaaagtacactggctctttctgggttaagggc
gcttacaagggccactttacagcttctttgcgatctaaccttaccgacgatgtctttggcagcgtcaaggtcaagtc
caaggccaacaagaagcagtgggttgagcatgagtttgtgcttactcctaacaagaatgcccctaacagcaacaaca
cttttgctatcacctacgatcccaaggtgagtaacaatcaaaactgggacgtgatgtatactgacaatttgtagggc
gctgatggagctcttgacttcaacctcattagcttgttccctcccacctacaagggccgcaagaacggtcttcgagt
tgatcttgccgaggctctcgaaggtctccaccccgtaaggtttaccgtctcacgtgtatcgtgaacagtcgctgact
tgtagaaaagagcctgctgcgcttccccggtggtaacatgctcgagggcaacaccaacaagacctggtgggactgga
aggataccctcggacctctccgcaaccgtcctggtttcgagggtgtctggaactaccagcagacccatggtcttgga
atcttggagtacctccagtgggctgaggacatgaaccttgaaatcagtaggttctataaaattcagtgacggttatg
tgcatgctaacagatttcagttgtcggtgtctacgctggcctctccctcgacggctccgtcacccccaaggaccaac
tccagcccctcatcgacgacgcgctcgacgagatcgaattcatccgaggtcccgtcacttcaaagtggggaaagaag
cgcgctgagctcggccaccccaagcctttcagactctcctacgttgaagtcggaaacgaggactggctcgctggtta
tcccactggctggaactcttacaaggagtaccgcttccccatgttcctcgaggctatcaagaaagctcaccccgatc
tcaccgtcatctcctctggtgcttctattgaccccgttggtaagaaggatgctggtttcgatattcctgctcctgga
atcggtgactaccacccttaccgcgagcctgatgttcttgttgaggagttcaacctgtttgataacaataagtatgg
tcacatcattggtgaggttgcttctacccaccccaacggtggaactggctggagtggtaaccttatgccttacccct
ggtggatctctggtgttggcgaggccgtcgctctctgcggttatgagcgcaacgccgatcgtattcccggaacattc
tacgctcctatcctcaagaacgagaaccgttggcagtgggctatcaccatgatccaattcgccgccgactccgccat
gaccacccgctccaccagctggtatgtctggtcactcttcgcaggccaccccatgacccatactctccccaccaccg
ccgacttcgacccccctctactacgtcgctggtaagaacgaggacaagggaactcttatctggaagggtgctgcgtat
aacaccaccaagggtgctgacgttcccgtgtctctgtccttcaagggtgtcaagcccggtgctcaagctgagcttac
tcttctgaccaacaaggagaaggatccttttgcgttcaatgatcctcacaagggcaacaatgttgttgatactaaga
agactgttctcaaggccgatggaaagggtgctttcaacttcaagcttcctaacctgagcgtcgctgttcttgagacc
ctcaagaagggaaagccttactctagctag

*FIG. 16A*

SEQ ID NO:32
Protein sequence of Fv51A mvrfssilaaaacfvavesvnikvdskggnatsqhqygflhedinnsgdggiyaelirnrafqyskkypv
slsgwrpindaklslnrldtplsdalpvsmnvkpgkgkakeigflnegywgmdvkkqkytgsfwvkgayk
ghftaslrsnltddvfgsvkvkskankkqwvehefvltpnknapnsnntfaitydpkgadgaldfnlisl
fpptykgrknglrvdlaealeglhpsllrfpggnmlegntnktwwdwkdtlgplrnrpgfegvwnyqqth
glgileylqwaedmnleiivgvyaglsldgsvtpkdqlqpliddaldeiefirgpvtskwgkkraelghp
kpfrlsyvevgnedwlagyptgwnsykeyrfpmfleaikkahpdltvissgasidpvgkkdagfdipapg
igdyhpyrepdvlveefnlfdnnkyghii**gevasthpnggtgwsgnlmpypwwisgvgeavalcgyerna
dripgtfyapilknenrwqwaitmiqfaadsamttrstswyvwslfaghpmthtlpttadfdplyyvagk
nedkgtliwkgaaynttkgadvpvslsfkgvkpgaqaeltlltnkekdpfafndphkgnnvvdtkktvlk
adgkgafnfklpnls**vavletlkkgkpyss

FIG. 16B

SEQ ID NO:33
**Nucleotide sequence for Cg51B, a GH51 family enzyme from *Chaetomium globosum*** atggcgccctttcgcttcgggccctctcgctgctcgcgctcacaggagccgcagccgcggtgaccctat
cggtcgcgaactctggcggtaatgatacgtctccgtacatgtatggcatcatgttcgaggacatcaatca
gagcggtgacggcgggctgtaagttctgtcgcggcttcccctgacaagcttgcatgatgcttaactaaag
tccttaggtacgccgagctgattcgcaaccgagccttccataatagctccctccaggcctggaccgcgt
ggggggacagcactctcgaggtcgtaacctctgcaccgttatcggatgccctgcctcgctcggtcaaggtc
acgagtggaaagggcaaggcgggcttgaagaatgccggctactggggaatggacgtccagaagaccgaca
agtatagcggcagcttctactcgtacggcgcctacgacggaaagtttaccctctctctggtgtcggacat
cacaaatgagaccctggccaccaccaagatcaagtccaggtcggtggagcatgcctggaccgagcacaag
ttcgagcttctcccgaccaagagcgcggcgaacagcaacaacagcttcgtgctggagttccgcccctgcc
accagacggagctccagttcaacctcatcagcttgttcccgccgacgtataagaacaggcccaacggcat
gcgccgagagctcatggagaagctcgcagacctcaagcccagtttccttcggattccaggaggcaacaac
ctgtaagtgcttccggcgaaactagcagtagttgcctgagagacactaatctcagcgaacaacagcgagg
gcaactatgctggcaactactggaactggtcaagcacacttggcccgctgaccgaccggccggtcgtga
cggcgtgtggacgtacgccaacacggacggcatcgggctggtcgagtacatgcactgggccgaggacctc
gacgtggaggttgtgctggcggtcgccgcaggcctgtacctgaacggcgatgtggtcccggaggaggagc
tgcacgtcttcgtggaggatgcgctgaacgagctcgagttcctcatgggcgacgtctcgacccccttgggg
cgcgcgccgcgctaagctcggctaccccaagccgtggaacatcaagttcgtcgaggtcggcaacgaggac
aacctgtggggcggcctcgactcgtacaagagctaccggctgaagactttctacgacgccatcaaggcga
agtaccccgacatctccatcttttcgtcgaccgacgagtttgtgtacaaggagtcgggccaggactacca
caagtacaccggccggactactccgtgtcccagttcgacctgtttgacaactgggccgacggccaccccc
atcatcatcggagagtgagtgaacggcgacccccacctccccctaacgcgggatcgcgagctgatagatc
acccccaggtatgcgaccatccagaacaacacgggcaagctcgaggacacggactgggacgcgcccaagaa
caagtggtccaactggatcggctccgtgccgaggccgtcttcatcctcggagccgagcgcaacggcgac
cgggtctggggcaccaccttcgcgccgatcctccagaacctcaacagctaccaatgggctgtaagtacat
acatacataccgcaccccaaccccaacccccaaagcgcacctccacccacccacccaaacacaccac
aactacctagctaacccgccacacaaacaaacagcccgacctaatctccttcaccgccaacccggccgac
accacgccagcgtctcgtacccgatcatccagctgctcgcctcgcaccgcatcacgcacaccctccccg
tcagcagcgccgacgccttcggcccggcctactgggtggccggtcgcggcgccgacgacggctcgtacat
cctcaaggcggccgtgtacaacagcacgggggtgcgcgatgtaccggtgagggtgcagtttgaggcgggg
ggtggtggtggtggtggtggtggtggtggtggtggtggtgatgggaaggggaagggtaaagggaagg
gaggggagggtggtgagggtgtgaagaagggtgaccgcgcgcagttgaccgtgttgacggcgccggaggg
gccctgggcgcataatacgccggagaataagggggcggtcaagacgacagtgacgacgttgaaggccggg
aggggtggggtgtttgagtttagtctgccggatttgtcggtggcggtgttggtggtggagggggagaagt
ga

FIG. 17A

SEQ ID NO:34
Protein sequence of Cg51B maplslralsllaltqaaaavtlsvansggndtspymygimfedinqsgdgglyaelirnrafhnsslqa
wtavgdstlevvtsaplsdalprsvkvtsgkgkaglknagywgmdvqktdkysgsfysygaydgkftlsl
vsditnetlattkiksrsvehawtehkfellptksaansnnsfvlefrpchqtelqfnlislfpptyknr
pngmrrelmekladlkpsflripggnnlegnyagnywnwsstlgpltdrpgrdgvwtyantdgiglveym
hwaedldvevvlavaaglylngdvvpeeelhvfvedalneleflmgdvstpwgarraklgypkpwnikfv
evgnednlwggldsyksyrlktfydaikakypdisifsstdefvykesgqdyhkytrpdysvsqfdlfdn
wadghpiiigeyatiqnntgkledtdwdapknkwsnwigsvaeavfilgaerngdrvwgttfapilqnln
syqwapdlisftanpadttpsvsypiiqllashrithtlpvssadafgpaywvagrgaddgsyilkaavy
nstggadvpvrvqfeagggggggggggggggdgkgkgkgkggeggegvkkgdraqltvltapegpwahnt
penkgavkttvttlkagrggvfefslpdlsvavlvveqek

FIG. 17B

SEQ ID NO:35
Nucleotide sequence for Fv43C, a GH43 family enzyme from *Fusarium verticillioides* atgcgtcttctatcgtttcccagccatctcctcgtggccttcctaaccctcaaagaggcttcatccctcg
ccctcagcaaacgggatagccctgtcctccccggcctctgggcggaccccaacatcgccatcgtcgacaa
gacatactacatcttccctaccaccgacggtttcgaaggctggggcggcaacgtcttctactggtggaaa
tcaaagatctcgtatcatggacaaagagcgacaagccattccttactctcaatggtacgaatggcaacg
ttccctggctacaggtaatgcctggctcctgctttcgctgctcgcggaggcaagtattacttctacca
tagtgggaataatccctctgtgagtgatgggcataagagtattggtgcggcggtggctgatcatcctgag
gggccgtggaaggcacaggataagccgatgatcaagggaacttctgatgaggagattgtcagcaaccagg
ctatcgatcccgctgcctttgaagaccctgagactggaaagtggtatatctactggggaaacggtgtccc
cattgtcgcagagctcaacgacgacatggtctctctcaaagcaggctggcacaaaatcacaggtcttcag
aatttccgcgagggtcttttcgtcaactatcgcgatggaacatatcatctgacatactctatcgacgata
cgggctcagagaactatcgcgttgggtacgctacggcggataaccccattggaccttggacatatcgtgg
tgttcttctggagaaggacgaatcgaagggcattcttgctacgggacataactccatcatcaacattcct
ggaacggatgagtggtatatcgcgtatcatcgcttccatattcccgatggaaatgggtataataggaga
ctacgattgatagggtacccatcgacaaggatacggtttgtttggaaaggttacgccgactttgcagag
tgttgatcctaggcctttgtag

FIG. 18A

SEQ ID NO:36
Protein sequence for Fv43C mrllsfpshllvaflltlkeasslalskrdspvlpglwadpniaivdktyyifpttdgfegwggnvfywwk
skdlvswtksdkpfltlngtngnvpwatgnawapafaarggkyyfyhsgnnpsvsdghksigaavadhpe
gpwkaqdkpmikgtsdeeivsnqaidpaafedpetgkwyiywgngvpivaelnddmvslkagwhkitglq
nfreglfvnyrdgtyhltysiddtgsenyrvgyatadnpigpwtyrgvllekdeskgilatghnsiinip
gtdewyiayhrfhipdgngynrettidrvpidkdtglfgkvtptlqsvdprpl

FIG. 18B

SEQ ID NO:37
**Nucleotide sequence for Fv30A, a GH30 family enzyme from *Fusarium verticillioides*** atgctcttctcgctcgttcttcctacccttgcctttcaagccagcctggcgctcggcgatacatccgtta
ctgtcgacaccagccagaaactccaggtcatcgatggctttggtgtctcagaagcctacggccacgccaa
acaattccaaaacctcggtcctggaccacagaaagagggcctcgatcttctcttcaacactacaaccggc
gcaggcttatccatcatccgaaacaagatcggctgcgacgcctccaactccatcaccagcaccaacaccg
acaacccagataagcaggctgtttaccattttgacggcgatgatgatggtcaggtatggtttagcaaaca
ggccatgagctatggtgtagatactatctacgctaatgcttggtctgcgcctgtatacatgaagtcagcc
cagagtatgggccgtctctgcggtacacctggtgtgtcgtgctcctctggagattggagacatcgttacg
ttgagatgatagctgagtacctctcctactacaagcaggctggcatcccagtgtcgcacgttggattcct
caatgagggtgacggctcggactttatgctctcaactgccgaacaggctgcagatgtcattcctcttcta
cacagcgctttgcagtccaagggccttggcgatatcaagatgacgtgctgtgataacatcggttggaagt
cacagatggactataccgccaagctggctgagcttgaggtggagaagtatctatctgtcatcacatccca
cgagtactccagcagccccaaccagcctatgaacactacattgccaacctggatgtccgagggagctgcc
aatgaccaggcatttgccacagcgtggtacgtcaacggcggttccaacgaaggtttcacatgggcagtca
agatcgcacaaggcatcgtcaatgccgacctctcagcgtatatctactgggagggcgttgagaccaacaa
caaggggtctctatctcacgtcatcgacacggacggtaccaagtttaccatatcctcgattctctgggcc
attgctcactggtcgcgccatattcgccctggtgcgcatagactttcgacttcaggtgttgtgcaagata
cgattgttggtgcgtttgagaacgttgatggcagtgtcgtcatggtgctcaccaactctggcactgctgc
tcagactgtggacctgggtgtttcgggaagtagcttctcaacagctcaggctttcacttcggatgctgag
gcgcagatggtcgataccaaggtgactctgtccgacggtcgtgtcaaggttacggtcccggtgcacggtg
tcgtcactgtgaagctcacaacagcaaaaagctccaaaccggtctcaactgctgtttctgcgcaatctgc
cccactccaactagtgttaagcacaccttgactcaccagaagacttcttcaacaacactctcgaccgcc
aaggccccaacctccactcagactacctctgtagttgagtcagccaaggcggtgaaataccctgtccccc
ctgtagcatccaagggatcctcgaagagtgctcccaagaagggtaccaagaagaccactacgaagaaggg
ctcccaccaatcgcacaaggcgcatagtgctactcatcgtcgatgccgccatggaagttaccgtcgtggc
cactgcaccaactaa

*FIG. 19A*

SEQ ID NO:38
Protein sequence of Fv30A mlfslvlptlafqaslalgdtsvtvdtsqklqvidgfgvseayghakqfqnlgpgpqkegldllfntttg
aglsiirnkigcdasnsitstntdnpdkqavyhfdgdddgqsaqsmgrlcgtpgvscssgdwrhryvemi
aeylsyykqagipvshvgflnegdgsdfmlstaeqaadvipllhsalqskglgdikmtccdnigwksqmd
ytaklaelevekylsvitsheysspnqpmnttlptwmsegaandqafatawyvnggsnegftwavkiaq
givnadlsayiywegvetnnkgslshvidtdgtkftissilwaiahwsrhirpgahrlstsgvvqdtivg
afenvdgsvvmvltnsgtaaqtvdlgvsgssfstaqaftsdaeaqmvdtkvtlsdgrvkvtvpvhgvvtv
klttaksskpvstavsaqsaptptsvkhtlthqktssttlstakaptstqttsvvesakavkypvppvas
kgssksapkkgtkktttkkgshqshkahsathrrcrhgsyrrghctn

*FIG. 19B*

SEQ ID NO:39
**Nucleotide sequence for Fv43F, a GH43 family enzyme from *Fusarium verticillioides*** atgtggaaactcctcgtcagcggtcttgtcgccgtcgcgtccctcagcggcgtgaacgctgcttatccta
accctggtcccgtcaccggcgatactcgtgttcacgaccctacggttgtcaagactcccagcggtggata
cttgctggctcatactggcgataacgtttcgctcaagacttcttctgatcgaactgcttggaaggatgca
ggtgctgttttccccaacggtgcgccttggactacgcagtacaccaagggcgacaagaacctctgggccc
ctgatatctcctaccacaacggccagtactatctgtactactccgcctcttccttcggtcagcgtacctc
tgccattttctcgctaccagcaagaccggtgcatccggctcgtggaccaaccaaggcgtcgtcgtcgag
tccaacaacaacaacgactacaatgccattgacggaaatctctttgtcgactctgatggaaaatggtggc
tctccttcggctctttctggtccggcatcaagctcatccaactcgaccccaagaccggcaagcgcaccgg
ctcaagcatgtactccctcgccaaacgcgacgcctccgtcgaaggcgccgtcgaggctccgttcatcacc
aaacgcggaagcacctactacctctgggtgtcgttcgacaagtgttgccagggcgctgctagcacgtacc
gtgtcatggttggacggtcgagcagcattactggtccttatgttgacaaggctggtaagcagatgatgtc
tggtggaggaacggagattatggctagtcacggatctattcatggaccgggacataatgctgttttcact
gataacgatgcggacgttcttgtctatcattactacgataacgctggcacagcgctgttgggcatcaact
tgctcagatatgacaatggctggcctgttgcttattag

*FIG. 20A*

SEQ ID NO:40
Protein sequence for Fv43F

<u>mwkllvsglvavaslsqvna</u>aypnpgpvtgdtrvhdptvvktpsggyllahtgdnvslktssdrtawkda
gavfpnqapwttqytkgdknlwapdisyhngqyylyysassfgqrtsaiflatsktqasgswtnqgvvve
snnnndynaidgnlfvdsdgkwwlsfgsfwsgikliqldpktgkrtgssmyslakrdasvegaveapfit
krgstyylwvsfdkccqgaastyrvmvgrsssitgpyvdkagkqmmsgggteimashgsihgpghnavft
dndadvlvyhyydnagtallginllrydngwpvay

*FIG. 20B*

SEQ ID NO:41
Nucleotide sequence for Xyn3, a GH10 xylanase from *Trichoderma reesei* atgaaagcaaacgtcatcttgtgcctcctggcccccctggtcgccgctctccccaccgaaaccatccacc
tcgaccccgagctcgccgctctccgcgccaacctcaccgagcgaacagccgacctctgggaccgccaagc
ctctcaaagcatcgaccagctcatcaagagaaaaggcaagctctactttggcaccgccaccgaccgcggc
ctcctccaacgggaaaagaacgcggccatcatccaggcagacctcggccaggtgacgccggagaacagca
tgaagtggcagtcgctcgagaacaaccaaggccagctgaactggggagacgccgactatctcgtcaactt
tgccagcaaaacggcaagtcgatacgcggccacactctgatctggcactcgcagctgcctgcgtgggtg
aacaatatcaacaacgcggatactctgcggcaagtcatccgcacccatgtctctactgtggttgggcggt
acaagggcaagattcgtgcttgggtgagttttgaacaccacatgccccttttcttagtccgctcctcctc
ctcttggaacttctcacagttatagccgtatacaacattcgacaggaaatttaggatgacaactactgac
tgacttgtgtgtgatggcgataggacgtggtcaatgaaatcttcaacgaggatggaacgctgcgctct
tcagtcttttccaggctcctcggcgaggagtttgtctcgattgcctttcgtgctgctcgagatgctgacc
cttctgcccgtctttacatcaacgactacaatctcgaccgcgccaactatggcaaggtcaacgggttgaa
gacttacgtctccaagtggatctctcaaggagttcccattgacggtattggtgagccacgaccctaaat
gtccccattagagtctctttctagagccaaggcttgaagccattcagggactgacacgagagccttctc
tacaggaagccagtcccatctcagcggcggcggaggctctggtacgctgggtgcgctccagcagctggca
acggtacccgtcaccgagctggccattaccgagctggacattcaggggcaccgacgacggattacaccc
aagttgttcaagcatgcctgagcgtctccaagtgcgtcggcatcaccgtgtgggcatcagtgacaggt
aagttgcttcccctgtctgtgcttatcaactgtaagcagcaacaactgatgctgtctgtctttacctagg
actcgtggcgtgccagcaccaaccctcttctgtttgacgcaaacttcaaccccaagccggcatataacag
cattgttggcatcttacaatag

FIG. 21A

SEQ ID NO:42
Protein sequence for Xyn3

<u>mkanvilcllaplvaal</u>ptetihldpelaalranltertadlwdrqasqsidqlikrkgklyfgtatdrg
llqreknaaiiqadlgqvtpensmkwqslennqgqlnwgdadylvnfaqqngksirghtliwhsqlpawv
nninnadtlrqvirthvstvvgrykgkirawdvvneifnedgtlrssvfsrllgeefvsiafraardadp
sarlyindynldranygkvnglktyvskwisqgvpidgigsqshlsgggsgtlgalqqlatpvtelai
teldiqgapttdytqvvqaclsvskcvgitvwgisdkdswrastnpllfdanfnpkpaynsivgilq

FIG. 21B

SEQ ID NO:43
Protein sequence of Xyn2, a GH11 family xylanase from *Trichoderma reesei* mvsftsllaasppsrascrpaaevesvavekrqtiqpgtgynngyfysywndghggvtytngpggqfsvn
wsnsgnfvggkgwqpgtknkvinfsgsynpngnsylsvygwsrnplieyyivenfgtynpstgatklgev
tsdgsvydiyrtqrvnqpsiigtatfyqywsvrrnhrssgsvntanhfnawaqqgltlgtmdyqivaveg
yfssgsasitvs

FIG. 22

SEQ ID NO:44
Protein sequence of Bxl1, a GH3 family β-xylosidase from *Trichoderma reesei* mvnnaallaalsallptalaqnnqtyanysaqgqpdlypetlatltlsfpdcehgplknnlvcdssagyv
eraqalislftleelilntqnsgpgvprlglpnyqvwnealhgldranfatkggqfewatsfpmpiltta
alnrtlihqiadiistqarafsnsgrygldvyapnvngfrsplwgrgqetpgedafflssaytyeyitgi
qggvdpehlkvaatvkhfagydlenwnnqsrlgfdaiitqqdlseyytpqflaaaryaksrslmcaynsv
ngvpscansfflqtllreswgfpewgyvssdcdavynvfnphdyasnqssaaasslragtdidcgqtypw
blnesfvagevsrgeiersvtrlyanlvrlgyfdkknqyrslgwkdvvktdawnisyeaavegivllknd
gtlpiskkvrsialigpwanattqmqgnyygpapylispleaakkagyhvnfelgteiagnsttgfakai
aaakksdaiiylggidntieqegadrtdiawpgnqldlikqlsevgkplvvlqmgggqvdssslksnkkv
nslvwggypgqsggvalfdilsgkrapagrlvttqypaeyvhqfpqndmnlrpdgksnpgqtyiwytgkp
vyefgsglfyttfketlashpkslkfntssilsaphpgytyseqipvftfeaniknsgktespytamlfv
rtsnaqpapypnkwlvgfdrladikpghssklsipipvsalarvdshgnrivypgkyelalntdesvkle
felvgeevtienwpleeqqikdatpda

FIG. 23

SEQ ID NO:45
Protein sequence of Bgl1, a GH3 family β-glucosidase from *Trichoderma reesei* mrvrtaaalalatqpfaradshstsqasaeavvppaqtpwgtaydkakaalakinlqdkvgivsgvgwng
gpcvgntspaskisypslclqdgplgvrystgstaftpgvqaastwdvnlirergqfigeevkasgihvi
lgpvagplgktpqggrnwegfgvdpyltgiamgqtingiqsvgvqatakhyilneqelnretissnpddr
tlhelytwpfadavqanvasvmcsynkvnttwacedqytlqtvlkdqlgfpgyvmtdwnaqhttvqsans
gldmsmpgtdfngnnrlwgpaltnavnsnqvptsrvddmvtrilaawyltgqdqagypsfnisrnvqgnh
ktnvraiardgivllkndanilplkkpasiavvgsaaiignharnspscndkgcddgalgmgwgsgavny
pyfvapydaintrassqgtqvtlsntdntssgasaargkdvaivfitadsgegyitvegnagdrnnldpw
hngnalvqavagansnvivvvhsvgaiileqilalpqvkavvwaglpsqesgnalvdvlwgdvspsgklv
ytiakspndyntrivsggsdsfseglfidykhfddanitpryefgyglsytkfnysrlsvlstaksgpat
gavvpgqpsdlfqnvatvtvdiansqqvtgaevaqlyitypssaprtppkqlrgfaklnltpgqsgtatf
nirrrdlsywdtasqkwvvpsgsfgisvgassrdirltstlsva

FIG. 24

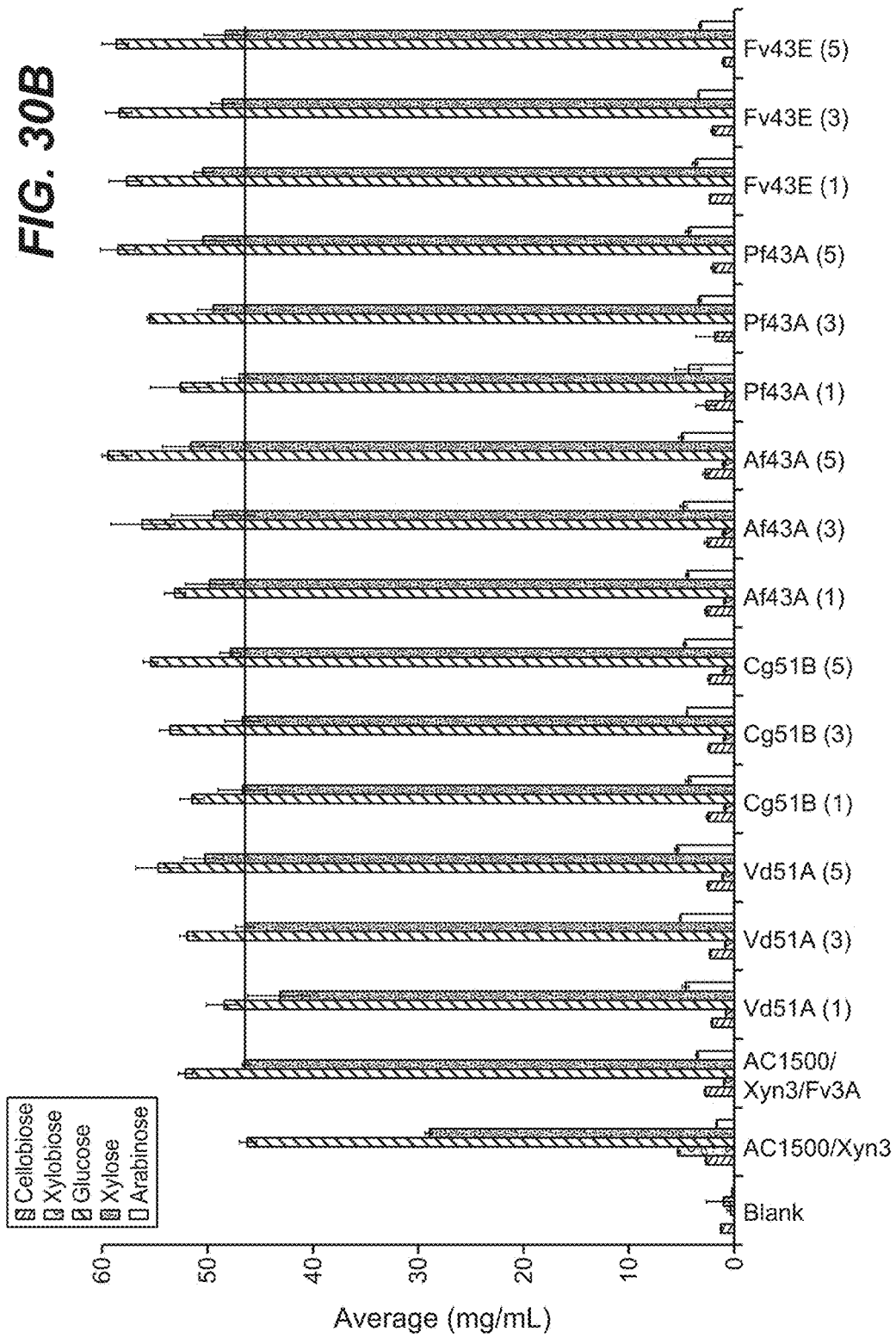

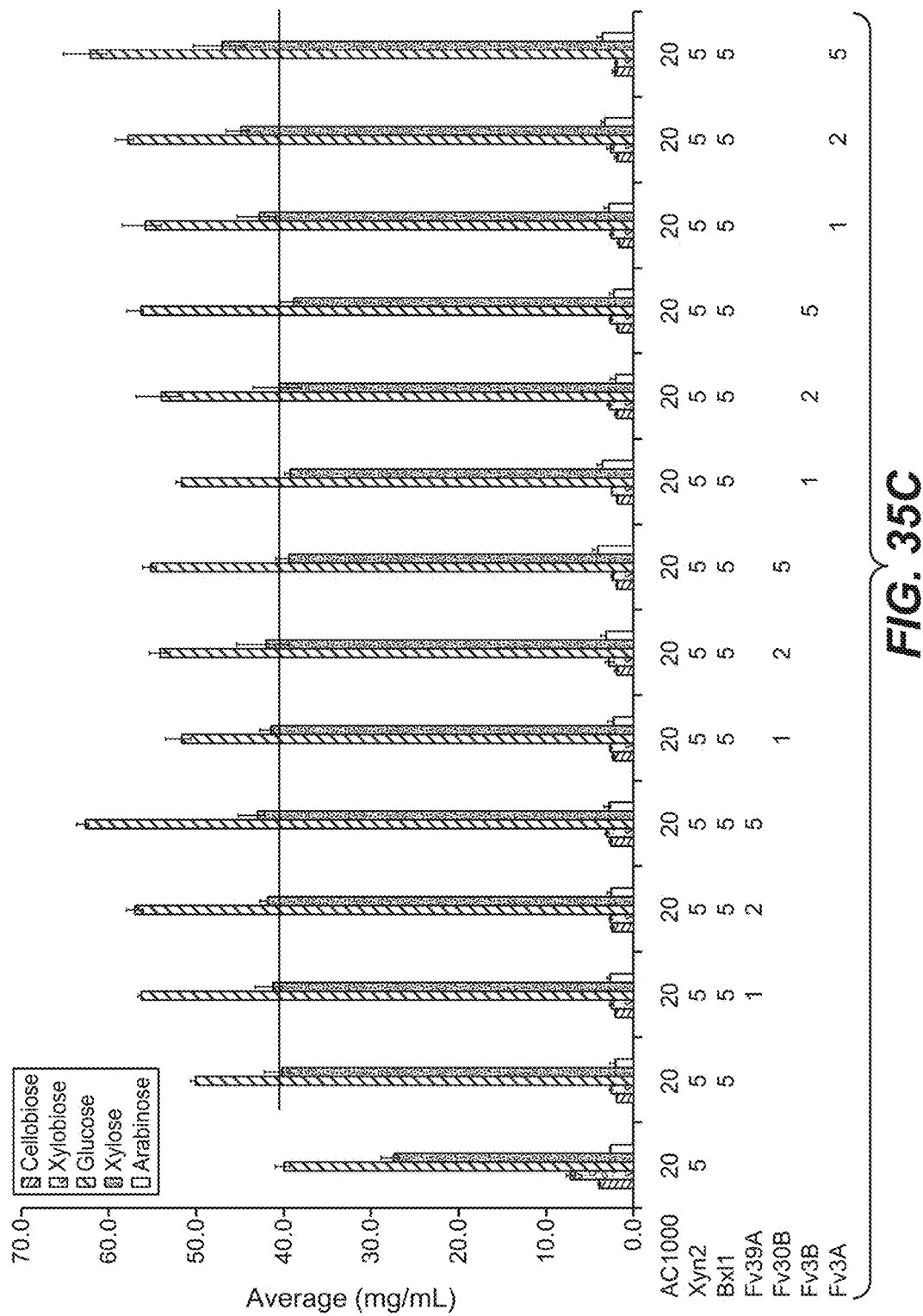

```
gi|reesei|Bx11   -MVNNAALLAALSALLPTALAQNNQTYANYSAQGQPDLYPETLATLTLSFPDCEHGPLKN
gi|fvert| Fv3A   MLLNLQVAASALSLSLLGGLAEAATPYT------------------------LPDCTKGPLSK
                 ::*   .  :***  * .**:    .*:              :***  :***.:

gi|reesei|       NLVCDSSAGYVERAQALISLFTLEELILNTQNSGPGVPRLGLPNYQVWNEALHGLDRAN-
gi|fvert|        NGICDTSLSPAKRAAALVAALTPEEKVGNLVSNATGAPRIGLPRYNWWNEALHGLAGSPG
                 *  :**:*  .  ::** **:: :* **  :  *  ....*.**:***.*: ******** :

gi|reesei|       --FATKGGQFEWATSFPMPILTTAALNRTLIHQIADIISTQARAFSNSGRYGLDVYAPNV
gi|fvert|        GRFADTP-PYDAATSFPMPLLMAAAFDDDLIHDIGNVVGTEARAFTNGGWRGVDFWTPNV
                      .  :: *****:* ;:.  *:*.,:::.*:****:*.*  *:*.::*** gi|reesei|       NGFRSPLWGRGQETPGEDAFFLSSAYTYEYITGIQGGVDPEHLKVAATVKHFAGYDLENW
gi|fvert|        NPFKDPRWGRGSETPGEDALHVS-RYARYIVRGLEG--DKEQRRIVATCKHYAGNDFEDW
                 * *:.* **.*****.::* *:  *::* *  *: ::. :** *:*:* gi|reesei|       NNQSRLGFDAIITQQDLSEYYTPQFLAAARYAKSRSLMCAYNSVNGVPSCANSFFLQTLL
gi|fvert|        GGFTRHDFDAKITPQDLAEYYVRPFQECTRDAKVGSIMCAYNAVNGIPACANSYLQETIL
                 .. :*  .*  *:*.  *  .:* **  *:***:*:*:****:: :*:* gi|reesei|       RESWGFP-EWGYVSSDCDAVYNVFNPHDYASNQSSAAASSLRAGTDIDCGQTYPWHLNES
gi|fvert|        RGHWNWTRDNNWITSDCGAMQDIWQNHKYVKTNAEGAQVAFENGMDSSCEYTTTSDVSDS
                 *  *.:.. :  .::;:***.*: ::::  *.*...::..*  ::. *  * . * .  ..:* gi|reesei|       FVAGEVSRGEIERSVTRLYANLVRLGYFD-KKNQYRSLGWKDVVKTDAWNISYEAAVEGI
gi|fvert|        YKQGLLTEKLMDRSLKRLFEGLVHTGFFDGAKAQWNSLSFADVNTKEAQDLALRSAVEGA
                 :  *  ::..  :::.:   .**.  *;** *  *:..:     ..:*   :::   .:**** gi|reesei|       VLLKNDGTLPLSKKVR-SIALIGPWANATTQMQGNYYGPAPYLISPLEAAKKAGYHVNFE
gi|fvert|        VLLKNDGTLPLKLKKKDSVAMIGFWANDTSKLQGGYSGRAPFLHSPLYAAEKLGLDTNVA
                 ***********. *   *:*:** *** *::.**.* * **:* ***  **:* *  ..*.

gi|reesei|       LGTEIAGNSTTG--FAKAIAAAKKSDAIIYLGGIDNTIEQEGADRTDIAWPGNQLDLIKQ
gi|fvert|        WGPTLQNSSSHDNWTTNAVAAAKKSDYILYFGGLDASAAGEDRDRENLDWPESQLTLLQK
                 *. :  ..*:  .    ::*.******* *:*:**:*  :   *. **  :: **  .** *:::

gi|reesei|       LSEVGKPLVVLQMGGGQVDSSSLKSNKKVNSLVWGGYPGQSGGVALFDILSGKRAPAGRL
gi|fvert|        LSSLGKPLVVIQLG-DQVDDTALLKNKKINSILWVNYPGQDGGTAVMDLLTGRKSPAGRL
                 .:****:*:*  .***.::*  .**::* .**..*:;*;*;*:::***** gi|reesei|       VTTQYPAEYVHQFPQNDMNLRPDGKSNPGQTYIWYTGKPVYEFGSGLFYTTFKETLASHP
gi|fvert|        PVTQYPSKYTEQIGMTDMDLRPT-KSLPGRTYRWYS-TPVLPYGFGLHYTKFQAKFKSN-
                 .****::*..*:  .**:***  ** **:**  .**  :*   **,**,*:  .:  *:

gi|reesei|       KSLKFNTSSILSAPHPGYTYSEQIPVFTFEANIKNSGKTESPYTAMLFVRTSNAGPAPYP
gi|fvert|        -KLTFDIQKLLKG--CSAQYSDFCALPPIQVSVKNTGRITSDFVSLVFIKS-EVGPKPYP
                 .*.*: ...:*..  .  : .: .:::.:.::*:  *  :.:::*:::  ..  * gi|reesei|       NKWLVGFDRLADIKPGHSSKLSIPIPVSALARVDSHGNRIVYPGKYELALNTDESVKLEF
gi|fvert|        LKTLAAYGRLHDVAPSSTKDISLEWTLDNIARRGENGDLVVYPGTYTLLLDEPTQAKIQV
                 * *.::.:.** *: *. .:.: .:*:  .:.  :**   ..:*: :****.* * *:   ..*::.

gi|reesei|       ELVGEEVTIENWPLEEQQIKDATPDA
gi|fvert|        TLTGKKAILDKWPQDPKSA-------
```

FIG. 38

FIG. 52

```
Fv43D   ----MQLKFLSSALLLSLTGNCAAQDTNDIPPLITDLWSADPSAHVFEGKLWVYPSHDIEA
Fo43A   ----MQLKFLSSALLFSLTSKCAAQDTNDIPPLITDLWSADPSAHVFEGKLWVYPSHDIEA
Gz43A   ----MKSKLLFP--LLSFVG--QSLATNDDCPLITSRWTADPSAHVFNDTLWLYPSHDIDA
Pf43A   --MLQRFAYILPLALLSVG--VKADN----PFVQSIYTADPAPMVYNDRVYVFMDHDNTG
Fv43A   -MWLTSPLLFASTLLGLTGVALADN-----PIVQDIYTADPAPMVYNGRVYLFTGHDNDG
Fv43B   --MRFSWLLCPLLAMGSALPETKTDVSTYTNPVLPGWHSDPSC-IQKDGLFLCVTSTFIS
Af43A   ---------------MAAPSLSYPTGIQSYTNPLFPGWHSDPSCAYVAEQDTFFCVTSTFI
Pf43B   ----MSRSILPYASVFALLGGAIAEP----FLVLNSDFPDPSLIETSSGYYAFGTTGNGV
Fv43E   MKVYWLVAWATSLTPALAGLIGHRRATTFNNPIIYSDFPDNDVFLGPDNYYYFSASNFHF

Fv43D   NVVNGTGGAQYAMRDYHTYSMKTIYGKDPVIDHGVALSVDDVPWAKQQMWAPDAAYK--N
Fo43A   NVVNGTGGAQYAMRDYHTYSMKSIYGKDPVVDHGVALSVDDVPWAKQQMWAPDAAHK--N
Gz43A   GFENDPDGGQYAMPDYHVYSIDKIYGSLP-VDHGTALSVEDVPWASRQMWAPDAAHK--N
Pf43A   -------ATYYNMTDWHLFSSADMANWQD---HGIPMSLANFTWANANAWAPQVIPR--N
Fv43A   -------STDFNMTDWRLFSSADMVNWQH---HGVPMSLKTFSWANSRAWAGQVVAR--N
Fv43B   FP-----GLPVYASRDLVNWRLISHVWNRE---KQLPGISWKTAGQQQGMYAPTIRYH--K
Af43A   AFP----GLPLYASRDLQNWKLASNIFNRP----SQIPDLR-VTDGQQSGIYAPTLRYH--E
Pf43B   N-------AQVASSPDFNTWTLLSGT-------DALPGPFPSWVASSPQIWAPDVLVKA-D
Fv43E   SP-----GAPVLKSKDLLNWDLIGHSIPRLNFGDGYDLPPGSRYYRG-GTWASSLRYRKSN

Fv43D   GKYYLYFPAK-DK-DEIFRIGVAVSNKPSGPFK---ADK-SWIPGTYSIDPASYVDTNGE
Fo43A   GKYYLYFPAK-DK-DEIFRIGVAVSNKPSGPFK---ADK-SWIPGTYSIDPASYVDTDNE
Gz43A   GKYYLYFPAK-DK-DDIFRIGVAVSPTPGGPFV---PDK-SWIPHTFSIDPASFVDDDDR
Pf43A   GQFYFYAPVR-HN-DGSMAIGVGVSSTITGPYH----DAIGKPLVENNEIDPTVFIDDDGQ
Fv43A   GKFYFYVPVRNAK-TGGMAIGVGVSTNILGPYT----DALGKPLVENNEIDPTVYIDTDGQ
Fv43B   GTYYVICEYLGVG-DIIGVIFKTTNPWDESSWS---DPV---TFKPNHIDPDLFWDDDGK
Af43A   GQFYLIVSYLGP--QTKGLLFTSSDPYDDAAWS---DPL---EFAVHGIDPDIFWDHDGT
Pf43B   GTYVMYFSASAASDSGKHCVGAATATSPEGPYTPVDSAVACPLDQGGAIDANGFIDTDGT
Fv43E   GQWYWIGCIN--------FWQTWVYTASSPEGPWY----NKGNFGDNNCYYDNGILIDDDDT

Fv43D   AYLIWGGI-WGGQLQAWQDHKTFNESWLGDKAAPNGTNALSPQIAKLSKDMHKITETPRD
Fo43A   AYLIWGGI-WGGQLQAWQDKKNFNESWIGDKAAPNGTNALSPQIAKLSKDMHKITETPRD
Gz43A   AYLAWGGI-MGGQLQRWQDKNKYNES--GTEPG-NGTAALSPQIAKLSKDMHTLAEKPRD
Pf43A   AYLYWG----------------------------------NPDLWYVKLNQDMISYSGSPTQ
Fv43A   AYLYWG----------------------------------NPGLYYVKLNQDMLSYSGSINK
Fv43B   VYCATHG-----ITLQEIDLETGELSPELNIWNGTGGVWPEGPHIYKRDGYYYLMIAEGGT
Af43A   VYVTSAED-QMIKQYTLDLKTGAIGPVDYLWNGTGGVWPEGPHIYKRDGYYYLMIAEGGT
Pf43B   IYVVYKID-----------------------------GNSLDGDGTTHPTPIMLQQMEADGT
Fv43E   MYVVYGSGEVKVSQLSQDGFSQVKSQVVFKNTDIGVQDLEGNRMYKING-------LYYI
```

FIG. 53A

```
Fv43D  LVILAPETGKPLQAEDNKRRFFEGP-----WVHKRGKLYYLMYSTG---------------
Fo43A  LVILAPETGKPLQAEDNKRRFFEGP-----WIHKRGKLYYLMYSTG---------------
Gz43A  MLILDPKTGKPLLSEDEDRRFFEGP-----WIHKRNKIYYLTYSTG---------------
Pf43A  IPLTTAGFGTRTGNAQRPTTFEEAP-----WVYKRNGIYYIAYAAD---------------
Fv43A  VSLTTAGFGSRPNNAQRPTTFEEGP-----WLYKRGNLYYMIYAAN---------------
Fv43B  ----AEDHAITIARARKITGPYEAYNNNPILTNRGTSEYFQTVGHGDLFQDTKGNWWGLC
Af43A  ----ELGHSETMARSRTRTGPWEPYPHNPLLSNKGTSEYFQTVGHADLFQDGNGNWWAVA
Pf43B  --TPTGSPIQLIDRSDLDGPLIEAP-----SLLLSNGIYYLSFSSN---------------
Fv43E  LNDSPSGSQTWIWKSKSPWGPYESKVLADKVTPPISGGNSPHQGSLIKTPNGGWY-----

Fv43D  -DTHFLVYATSKN----IYGPYT--------------YQGKILDPVDG-----------WTTHG
Fo43A  -DTHFLVYATSKN----IYGPYT--------------YRGKILDPVDG-----------WTTHG
Gz43A  -TTHYLVYATSKT----PYGPYT--------------YQGRILEPVDG-----------WTTHS
Pf43A  CCSEDIRYSTGTS---ATGPWT--------------YRGVIMPTQGSS---------FTNHE
Fv43A  CCSEDIRYSTGPS---ATGPWT--------------YRGVVMNKAGRS---------FTNHP
Fv43B  LATRITAQGVSPMGREAVLFNGTWNKGEWPKLQPVRGRMPGNLLPKPTRN-------VPGD
Af43A  LSTRSGPAWKNYPMGRETVLAPAAWEKGEWPVIQPVRGQMQG-PFPPPNKR-----VPRGE
Pf43B  YYNTNYYDTSYAYASSITGPWT-----------KQSAPYAPLLVTGT----------ETSND
Fv43E  FMSFTWAYPAGRLFVLAPITWG------------SDGFPILVKGANGGWGSSYPTLPGT

Fv43D  SIVEYKGQWWLFFAD-AHTSGKDYLRQVKARKIWYDKDG-----KILLTRPKI--------
Fo43A  SIVEYKGQWWLFFAD-AHTSGKDYLRQVKARKIWYDKNG-----KILLHRP----------
Gz43A  SIVKYQGQWWLFYHD-AKTSGKDYLRQVKAKKIWYDSKG-------KILTKKP---------
Pf43A  GIIDFQNNSYFFYHNGALPGGGGYQRSVCVEQFKYNADG-----TIPTIEMTTAG------
Fv43A  GIIDFENNSYFFYHNGALDGGSGYTRSVAVESFKYGSDG-----LIPEIKMTTQG------
Fv43B  GPFNADPDNYNLKKTKKIPPHFVHHRVPRDGAFSLSSKG----LHIVPSRNNVTGSVLPG
Af43A  GGWIKQPDKVDFRPGSKIPAHFQYWRYPKTEDFTVSPRGHPNTLRLTPSFYNLTG-----
Pf43B  GALSAPGGADFSVDGTKMLFHANLNGQDISGGRALFAAS-------ITEASDVVTLQ----
Fv43E  DGVTKNWTRTDTFRGTSLAPSWEWNHNPDVNSFTVNNGLTLRTASITKDIYQARN-----

Fv43D  ----------------------------------------------------------
Fo43A  ----------------------------------------------------------
Gz43A  ----------------------------------------------------------
Pf43A  ---------------PAQIGTLNPYVRQEAETAAWSSGIFTEVCSEGGIDVGFINNG
Fv43A  ---------------PAQLKSLNPYVKQEAETIAWSEGIETEVCSEGGLNVAFIDNG
Fv43B  DEIELSGQRGLAFIGRRQTHTLFKYSVDIDFKPKSDDQEAGITVFRTQFDHIDLGIVRLP
Af43A  -TADFKPDDGLSLVMRKQTDTLFTYTVDVSFDPKVADEEAGVTVFLTQQQHIDLGIVLLQ
Pf43B  ----------------------------------------------------------
Fv43E  ------------TLSHRTHGDHPTGIVKIDFSPMKDGDRAGLSAFRDQSAYIGIHRDNGK
```

*FIG. 53B*

```
Fv43D   ----------------------------------------------------------------
Fo43A   ----------------------------------------------------------------
Gz43A   ----------------------------------------------------------------
Pf43A   DYIK-----------VKGVAFGS-GAHSFSARVASANSGGTIAIHLGSTTGTLVGTCTV
Fv43A   DYIK-----------VKGVDFGSTGAKTFSARVASNSSGGKIELRLGSKTGKLVGTCTV
Fv43B   TNQGSNKKSKLAFRFRATGAQNVPAPK---VVPVPDGWEKGVISLHIEAANATHYNLGAS
Af43A   TTEG----LSLSFRFRVEGRGNYEGPLPEATVPVPKEWCGQTIRLEIQAVSDTEYVFAAA
Pf43B   ----------------------------------------------------------------
Fv43E   FTIAT----KHGMNMDEWNGTTTDLGQIKATANVPSGRTKIWLRLQLDTNPAGTGNTIFS

Fv43D   ----------------------------------------------------------------
Fo43A   ----------------------------------------------------------------
Gz43A   ----------------------------------------------------------------
Pf43A   PSTGGWQTWTTVTCSVSGASGTQ----------DVYFVFGGSGTGYLFN------FDYWQFA
Fv43A   TTTGNWQTYKTVDCPVSGATGTS----------DLFFVFTGSGSGSLFN------FNWWQFS
Fv43B   --SHRGKTLDIATASASLVSGGTGSFVGSLLGPYATCNGKGSGVECPKGGDVYVTQWTYK
Af43A   PARHPAQRQIISRANSLIVSGDTGRFTGSLVGVYATSNG-GAGSTP------AYISRWRYE
Pf43B   ----------------------------------------------------------------
Fv43E   YSWDGVKYETLGPNFKLYNG-----------WAFFIAYRFGIFNFAETALGGSIKVESFT

Fv43D   --------------------
Fo43A   --------------------
Gz43A   --------------------
Pf43A   --------------------
Fv43A   --------------------
Fv43B   PVAQEIDHGVFVKSEL
Af43A   GRGQMIDFGRVVPSY-
Pf43B   --------------------
Fv43E   AA--------------
```

FIG. 53C

```
Pa51A    MIHLKPALAALLALSTQCVAIDLFVKSSGGNKTTDIMYGLMHEDINNSGDGGIYAELISN
Fv51A    MVRFSSILAAAACF-VAVESVNIKVDSKGGNATSGHQYGFLHEDINNSGDGGIYAELIRN
Pf51A    MGKMWHSILVVLGLLSVGHAITINVSQSGGNKTSPLQYGLMFEDINHGGDGGLYAELVRN

Pa51A    RAFQGSEKFPSNLDNWSPVGGATLTLQKLAKPLSSALPYSVNVANPKEGKGKGKDTKGKK
Fv51A    RAFQYSKKYPVSLSGWRPINDAKLSNRLDTPLSDALPVSMNVK---PGKGK-------AKE
Pf51A    RAFQGSTVYPANLDGYDSVNGAILALQNLTNPLSPSMPSSLNVA------KGS-----NNGS

Pa51A    VGLANAGFWGMDVKRQKYTGSFHVTGEYKGDFEVSLRSAITGETFGKKVVKGGSKKGKWT
Fv51A    IGFLNEGYWGMDVKKQKYTGSFWVKGAYKGHFTASLRSNLTDDVFGSVKVKSKANKKQWV
Pf51A    IGFANEGWWGIEVKPQRYAGSFYVQGDYQGDFDISLQSKLTQEVFATAKVRSSGKHEDWV

Pa51A    EKEFELVPFKDAPNSNNTFVVQWDAEGAKDGSLDLNLISLFPPTFKGRKNGLRIDLAQTM
Fv51A    EHEFVLTPNKNAPNSNNTFAITYDPKGA-DGALDFNLISLFPPTYKGRKNGLRVDLAEAL
Pf51A    QYKYELVPKKAASNTNNTLTITFDSKGLKDGSLNFNLISLFPPTYNNRPNGLRIDLVEAM

Pa51A    VELKPTFLRFPGGNMLEGNTLDTWWKWYETIGPLKDRPGMAGVWEYQQTLGLGLVEYMEW
Fv51A    EGLHPSLLRFPGGNMLEGNTNKTWWDWKDTLGPLRNRPGFEGVWNYQQTHGLGILEYLQW
Pf51A    AELEGKFLRFPGGSDVEGVQAPYWYKWNETVGDLKDRYSRPSAWTYEESNGIGLIEYMNW

Pa51A    ADDMNLEPIVGVFAGLALDGSFVPESEMGWVIQQALDEIEFLTGDAKTTKWGAVRAKLGH
Fv51A    AEDMNLEIIVGVYAGLSLDGSVTPKDQLQPLIDDALDEIEFIRG-PVTSKWGKKRAELGH
Pf51A    CDDMGLEPILAVWDGHYLSNEVISENDLQPYIDDTLNQLEFLMG-APDTPYGSWRASLGY

Pa51A    PKPWKVKWVEIGNEDWLAGRPAGFESYINYRFPMMMKAFNEKYPDIKIIASPSIFD----
Fv51A    PKPFRLSYVEVGNEDWLAGYPTGWNSYKEYRFPMFLEAIKKAHPDLTVISSGASIDPVGK
Pf51A    PKPWTINYVEIGNEDNLYG---GLETYIAYRFQAYYDAITAKYPHMTVMESLTEMPG---

Pa51A    ----NMTIPAGAAGDHHPYLTPDEFVERFAKFDNLSKDNVTLIGEAASTHPNG----GIAWE
Fv51A    KDAGFDIPAPGIGDYHPYREPDVLVEEFNLFDNNKYG--HIIGEVASTHPNG---GTGWS
Pf51A    --------PAAAASDYHQYSTPDGFVSQFNYFDQMPVTNRTLNGEIATVYPNNPSNSVAWG

Pa51A    GDLMPLPWWGGSVAEAIFLISTERNGDKIIGATYAPGLRSLDRWQWSMTWVQHAADPALT
Fv51A    GNLMPYPWWISGVGEAVALCGYERNADRIPGTFYAPILKNENRWQWAITMIQFAADSAMT
Pf51A    SPFPLYPWWIGSVAEAVFLIGEERNSPKIIGASYAPMFRNINNWQWSPTLIAFDADSSRT

Pa51A    TRSTSWYVWRILAHHIIRETLPVDAPAGKPNFDPLFYVAGKSES-GTGIFKAAVYNSTES
Fv51A    TRSTSWYVWSLFAGHPMTHTLPTTA-----DFDPLYYVAGKNEDKGTLIWKGAAYNTTKG
Pf51A    SRSTSWHVIKLLSTNKITQNLPTTWSGG--DIGPLYWVAGRNDNTGSNIFKAAVYNSTSD

Pa51A    --IPVSLKFDGLNEGAVANLTVLTGPE-DPYGYNDPFTGINVVKEKTTFIKAGKGGKFTF
Fv51A    ADVPVSLSFKGVKPGAQAELTLLTNKEKDPFAFNDPHKGNNVVDTKKTVLKADGKGAFNF
Pf51A    --VPVTVQFAGCN-AKSANLTILSSDD--PNASNYPG-GPEVVKTEIQSVTANAHGAFEF

Pa51A    TLPGLSVAVLETADAVKGGKGKGKGKGKGN
Fv51A    KLPNLSVAVLETLK--------KGKPYSS
Pf51A    SLPNLSVAVLKTE----------------
```

FIG. 54

```
                    *         20         *         40         *
xyn3    : -MKANVILC---LLAPLVAALPTETIHLDPELAALRANLTERTADLWDRQA :  47
P56588  : ------------------------------------------------QA :   2
P23360  : MVRPTILLTSLLLAPFAAASPI-----------------------LEERQA :  28

*         60         *         80         *        100
xyn3    : SQSIDQLIKRKGKLYFGTATDRGLLQRE-KNAAIIQADLGQVTPENSMKW :  96
P56588  : SVSIDAKFKAHGKKYLGTIGDQYTLTKNTKNPAIIKADFGQLTPENSMKW :  52
P23360  : AQSVDQLIKARGKVYFGVATDQNRLTTG-KNAAIIQADFGQVTPENSMKW :  77

*        120         *        140         *
xyn3    : QSLENNQGQLNWGDADYLVNFAQQNGKSIRGHTLIWHSQLPAWVNNINNA : 146
P56588  : DATEPNRGQFTFSGSDYLVNFAQSNGKLIRGHTLVWHSQLPGWVSSITDK : 102
P23360  : DATEPSQGNFNFAGADYLVNWAQQNGKLIRGHTLVWHSQLPSWVSSITDK : 127

*        160         *        180         *        200
xyn3    : DTLRQVIRTHVSTVVGRYKGKIRAWDVVNEIFNEDGTLRSSVFSRLLGEE : 196
P56588  : NTLISVLKNHITTVMTRYKGKIYAWDVLNEIFNEDGSLRNSVFYNVIGED : 152
P23360  : NTLTNVMKNHITTLMTRYKGKIRAWDVVNEAFNEDGSLRQTVFLNVIGED : 177

*        220         *        240         *
xyn3    : FVSIAFRAARDADPSARLYINDYNLDRANYGKVNGLKTYVSKWISQGVPI : 246
P56588  : YVRIAFETARSVDPNAKLYINDYNLDSAGYSKVNGMVSHVKKWLAAGIPI : 202
P23360  : YIPIAFQTARAADPNAKLYINDYNLDSASYPKTQAIVNRVKQWRAAGVPI : 227

*        260         *        280    N    *        300
xyn3    : DGIGSQSHLSGGGGSGTLGALQQLATVPVTELAITELDIQGAPTTDYTQV : 296
P56588  : DGIGSQTHLGAGAGSAVAGALNALASAGTKEIAITELDIAGASSTDYVNV : 252
P23360  : DGIGSQTHLSAGQGAGVLQALPLLASAGTPEVAITELDVAGASPTDYVNV : 277

*        320         *        340         *
xyn3    : VQACLSVSKCVGITVWGISDKDSWRASTNPLLFDANFNPKPAYNSIVGIL : 346
P56588  : VNACLNQAKCVGITVWGVADPDSWRSSSSPLLFDGNYNPKAAYNAIANAL : 302
P23360  : VNACLNVQSCVGITVWGVADPDSWRASTTPLLFDGNFNPKPAYNAIVQDL : 327 xyn3    : Q- : 347
P56588  : -- :  -
P23360  : QQ : 329
```

*FIG. 55A*

```
  1  M V S F S Y L L L A C S A I G - A L A A P V E P E T T S F N    AfuXyn2
  1  M I S I S S L S F G L A A I A G A Y A L P S D - K S V S L A    AfuXyn5
  1  M V S F T S L L A A S P P S R A S C R P A A E V E S V A V E    Xyn2

30  E T A L H E F A E R A G T P S S T G W N N G Y Y Y S F W T D    AfuXyn2
 30  E R - - - - - - - Q T I T T S Q T G T N N G Y Y Y S F W T N    AfuXyn5
 31  K R - - - - - - - Q T I Q P G - T G Y N N G Y F Y S Y W N D    Xyn2

60  G G G D V T Y T N G A G G S Y S V N W R N - - V G N F V G G    AfuXyn2
 53  G A G S V Q Y T N G A G G E Y S V T W A N Q N G G D F T C G    AfuXyn5
 53  G H G G V T Y T N G P G G Q F S V N W S N - - S G N F V G G    Xyn2

88  K G W N P G S A - R T I N Y G G S F N P S G N G Y L A V Y G    AfuXyn2
 83  K G W N P G S D - H D I T F S G S F N P S G N A Y L S V Y G    AfuXyn5
 81  K G W Q P G T K N K V I N F S G S Y N P N G N S Y L S V Y G    Xyn2
                           N
117  W T T N P L I E Y Y V V E S Y G T Y N P G S G G T F R G T V    AfuXyn2
112  W T T N P L V E Y Y I L E N Y G S Y N P G S G M T H K G T V    AfuXyn5
111  W S R N P L I E Y Y I V E N F G T Y N P S T G A T K L G E V    Xyn2

147  N T D G G T Y N I Y T A V R Y N A P S I E G T K T F T Q Y W    AfuXyn2
142  T S D G S T Y D I Y E H Q Q V N Q P S I V G T A T F N Q Y W    AfuXyn5
141  T S D G S V Y D I Y R T Q R V N Q P S I I G T A T F Y Q Y W    Xyn2

177  S V R T S K R T G G T V T M A N H F N A W S R L G M N L G T    AfuXyn2
172  S I R Q N K R S S G T V T T A N H F K A W A S L G M N L G T    AfuXyn5
171  S V R R N H R S S G S V N T A N H F N A W A Q Q G L T L G T    Xyn2
                           A
207  H N Y Q I V A T E G Y Q S S G S A S I T V Y                    AfuXyn2
202  H N Y Q I V S T E G Y E S S G T S T I T V S S G G S S S G G    AfuXyn5
201  M D Y Q I V A V E G Y F S S G S A S I T V S                    Xyn2

228                                                                AfuXyn2
232  S G G S S T T S S G S S P T G G S G S C S A L W G Q C G G    AfuXyn5
222                                                                Xyn2

228                                                                AfuXyn2
262  I G - W S G P T C C S S G T C Q V S N S Y Y S Q C L            AfuXyn5
222                                                                Xyn2
```

*FIG. 55B*

SEQ ID NO:46
Nucleotide sequence for Pa51A, a GH51 family enzyme from *Podospora anserina*

```
atgatccacctcaagcagccctcgggcgttgttggcgtcgtcgacgcaatgtgtggctattgattgtttgttgtcaagtcttcggg
gggaataagacgactgatatcatgtatgtcttatgcacgaggatatcaacaactccggcgacggcgcatctacgccgagctaa
tctccaaccgcgcgtccaagggagtgagaagttcccctccaacctgacaacctggagccccgtggagctcgtgcgctaccctt
cagaagcttgccaagccccttcctctgcgttgccttactccgtcaatgttgccaaccccaagcaggaggcaaggcaaggcaagga
caccaagggaagaaggttggcttggccaatgctggggttttgggtatgcaagaggcagaagtacactggtagcttccacg
ttactgtgagtaagaaggtgactttgagcttgcgcagccgcgattaccggggagaccttggcaagaaggtggaagggt
ggagtggagtgccgagggcgcagaagggatcttgcgcagaccgacgatggttgagttgtgtctcaacttgatcagctttgtgcctcaatcagcttgcctccggacaccttgcaactgtctcgagggt
atggctgagaattgatcttgccgcagacgatggttgagctcaagccgaccttgcaacatgttgagaccgaggagcacgatggtc
aacacctttgactggcagattccgtgatgtacaagaccatgagtgagtgggccgatggcaccattgcgaacatgtctggagtacca
gcaaaccctttggctggttctcgtcgttcccgatccgcgaatggttgcgcctgcttcgtcaagactctcgacgaactcgagtctcctcgctggtc
ttgcctaagactggctcgtcgttcccgatccgcgctcttggtcacatcaacaacgtctcggaaggttcaagtggttgagatccggtaa
gatgctaagacaccaaatgggtccgcccctgcttgagcgttccgcgcttggtacatcaacattcgcaacaacatgacaaatccccggcggggtcaaggactctcatcggcgaggctgc
cgaggattggctgccggaccatcaagatcatcgccctcgcctccccatctccgccaagtctgagccagacctttcaacgaaa
agtaccccgacactgagaagacgcgccgatgagttcgttgagcgatcgttgagctcgcccgagatccggagctcatcgggcgaggctgc
tacctgactccgatgagttcgttgagcgatcgaagttcgcaagattcgatcgaagataactgagcaagcagatacttgagcaagatgagccacgacgagctcatcggcgaggctgc
gtcgacgcatcctaacggtgtatcgcgtgccgtgcttactggccgagctcgagtccaagctgtgggcgccagtgttgctgaggctatct
tcttgatcagcactgagagaaacggtgcagcatgcgccgaccgaaatcgctcttcgcagcttggacgcctggggctgccaatgg
agcatgacctgggtgcagcgtcccggtcgatgcccgaccgggccccggaccagttgggtatgtctggagaatcctcgcccacca
catcatcctgagacgtatcttcaaggctgcgctgcttactggccgagctccgactgagatccgtatggccaaggcgagga
gtgccacggtccaacttgacggtgccttacggccgagctcgtgcttactggccgaagctccggtcgttgaagtttgatggtctcaacgaggga
gcggttgccaaccttcaaggccgtgccttactggccgagctgcttactggccgaagctccggttcgttgaagttgatcaaggccacc
gaagaccacctcatcaaggccgaaggccggctgaaagggcaaggccggctgaaaggcgaaggccgg
acgcggtcaaggtggcaaggagcaaggcaaggtaaggtaactga
```

FIG. 60A

SEQ ID NO:47
**Codon optimized cDNA for Pa51A, a GH51 family enzyme from *Podospora anserina*** atgatccacctcaagcccgccctcgccgccctcctcgccctcagcacccaatgcgtcgccatcgacctct
tcgtcaagagcagcggcggcaacaagaccaccgacatcatgtacggcctcatgcacgaggacatcaacaa
cagcggcgacggcggcatctacgccgagctgatcagcaaccgcgccttccagggcagcgagaagttcccc
agcaacctcgacaactggtccccgtcggcggcgccacctcaccctccagaagctcgccaagcccctgt
cctctgccctccctactccgtcaacgtcgccaaccccaaggagggtaagggtaagggcaaggacaccaa
gggcaagaaggtcggcctcgccaacgccggcttttggggcatggacgtcaagcgccagaaatacaccggc
agcttccacgtcaccggcgagtacaagggcgacttcgaggtcagcctccgcagcgccattaccggcgaga
cctccggcaagaaggtcgtcaagggcggcagcaagaagggcaagtggaccgagaaggagttcgagctggt
ccccttcaaggacgcccccaacagcaacaacaccttcgtcgtccagtgggacgccgagggcgccaaggac
ggcagcctcgacctcaacctcatcagcctcttcccgcccaccttcaagggccgcaagaacggcctccgca
tcgacctcgcccagaccatggtcgagctgaagcccaccttcctccgctttccggcggcaacatgctcga
gggcaacaccctcgacacctggtggaagtggtacgagaccatcggcccctgaaggaccgccctggcatg
gccggcgtctggagtaccagcagacgctggcctcggcctggtcgagtacatggagtgggccgacgaca
tgaacctcgagcccatcgtcggcgtctttgctggcctggccctggatggcagctttgtcccgagagcga
gatgggctgggtcatccagcaggctctcgatgagatcgagttcctcaccggcgacgccaagaccaccaag
tggggcgccgtccgcgccaagctcggccaccctaagccctggaaggtcaaatgggtcgagatcggcaacg
aggactggctcgccggccgacctgccggcttcgagagctacatcaactaccgcttccccatgatgatgaa
ggccttcaacgagaaatacccgacatcaagatcattgccagcccctccatcttcgacaacatgaccatt
ccagccggtgctgccggtgaccaccaccctacctcaccccgacgaatttgtcgagcgcttcgccaagt
tcgacaacctcagcaaggacaacgtcaccctcattggcgaggccgccagcacccaccccaacggcggcat
tgcctgggagggcgacctcatgccctgccctggtggggcggcagcgtcgccgaggccatcttcctcatc
agcaccgagcgcaacggcgacaagatcatcggcgccacctacgccctggcctccgatctctcgaccgct
ggcagtggagcatgacctgggtccagcacgccgccgaccctgccctcaccacccgcagcaccagctggta
cgtctggcgcatcctcgccaccacatcattcgcgagaccctccccgtcgacgccccgccggcaagccc
aacttcgaccccctcttctacgtcgctggcaagtcggagagcggcaccggcatcttcaaggccgccgtct
acaacagcaccgagagcatccccgtcagcctcaagttcgacggcctcaacgagggcgccgtcgccaacct
caccgtcctcaccggccccgaggacccctacggctacaacgacccttcaccggcatcaacgtcgtcaag
gaaaagaccaccttcatcaaggccggcaagggcggcaagttcaccttaccctccccggcctctctgtcg
ccgtcctcgagaccgccgacgccgtgaagggtggcaagggaaagggaaagggcaagggtaagggtaacta
a

FIG. 60B

SEQ ID NO:48
**Nucleotide sequence for Gz43A, a GH43 family enzyme from *Gibberella zeae*** atgtatcggaagttggccgtcatctcggccttcttggccacagctcgtgctaccaacgacgactgtcctc
tcatcactagtagatggactgcggatccttcggctcatgtctttaacgacaccttgtggctctacccgtc
tcatgacatcgatgctggatttgagaatgatcctgatggaggccagtacgccatgagagattaccatgtc
tactctatcgacaagatctacggttccctgccggtcgatcacggtacggccctgtcagtggaggatgtcc
cctgggcctctcgacagatgtgggctcctgacgctgcccacaagaacggcaaatactacctatacttccc
tgccaaagacaaggatgatatcttcagaatcggcgttgctgtctccaaccccggcggaccattcgtc
cccgacaagagttggatccctcacactttcagcatcgacccgccagtttcgtcgatgatgatgacagag
cctacttggcatggggtggtatcatgggtggccagcttcaacgatgcaggataagaacaagtacaacga
atctggcactgagccaggaaacggcaccgctgccttgagccctcagattgccaagctgagcaaggacatg
cacactctggcagagaagcctcgcgacatgctcattcttgacccaagactggcaagccgctcctttctg
aggatgaagaccgacgcttcttcgaaggaccctggattcacaagcgcaacaagatttactacctcaccta
ctctactggcacaacccactatcttgtctatgcgacttcaaagacccctatggtccttacacctaccag
ggcagaattctggagccagttgatggctggactactcactctagtatcgtcaagtaccagggtcagtggt
ggctattttatcacgatgccaagacatctggcaaggactatcttcgccaggtaaaggctaagaagatttg
gtacgatagcaaaggaaagatcttgacaagaagccttga

FIG. 61

SEQ ID NO:49
**Nucleotide sequence for Fo43A, a GH43 family enzyme from *Fusarium oxysporum*** atgtatcggaagttggccgtcatctcggccttcttggccacagctcgtgctcaagacactaatgacattc
ctccctgatcaccgacctctggtcgcagatccctcggctcatgttttcgaaggcaagctctgggttta
cccatctcacgacatcgaagccaatgttgtcaacggcacaggaggcgctcaatacgccatgagggattac
cataccactccatgaagagcatctatggtaaagatcccgttgtcgaccacggcgtcgctctctcagtcg
atgacgttccctgggcgaagcagcaaatgtgggctcctgacgcagctcataagaacggcaaatattatct
gtacttccccgccaaggacaaggatgagatcttcagaattggagttgctgtctccaacaagcccagcggt
cctttcaaggccgacaagagctggatccctggcacgtacagtatcgatcctgctagctacgtcgacactg
ataacgaggcctacctcatctggggcggtatctggggcggccagctccaagcctggcaggataaaaagaa
ctttaacgagtcgtggattggagacaaggctgctcctaacggcaccaatgccctatctcctcagatcgcc
aagctaagcaaggacatgcacaagatcaccgaaacaccccgcgatctcgtcattctcgccccgagacag
gcaagcctcttcaggctgaggacaacaagcgacgattcttcgagggccttggatccacaagcgcggcaa
gctttactacctcatgtactccaccggtgatacccacttccttgtctacgctacttccaagaacatctac
ggtccttataccctaccggggcaagattcttgatcctgttgatggtggactactcatggaagtattgttg
agtataagggacagtggtggcttttctttgctgatgcgcatacgtctggtaaggattaccttcgacaggt
gaaggcgaggaagatctggtatgacaagaacggcaagatcttgcttcaccgtccttag

FIG. 62

SEQ ID NO:50
**Nucleotide sequence for Pf51A, a GH51 family enzyme from *Penicillium funiculosum*** atgtaccggaagctcgccgtgatcagcgccttcctggcgactgctcgcgccatcaccatcaacgtcagcc
agagcggcggcaacaagaccagcccgctccagtacggcctcatgttcgaggacatcaaccacggcggcga
cggcggcctctacgccgagctggtccggaaccgggccttccagggcagcaccgtctaccggccaaccctc
gacggctacgactcggtgaacggcgcgattctcgcgctccagaacctcaccaacccgctcagcccgagca
tgccctcgtcgtgaacgtcgccaagggctcgaacaacggcagcatcggcttcgccaacgaggggtggtg
gggcatcgaggtcaagccgcagcggtacgccggcagcttctacgtccagggcgactaccagggcgacttc
gacatcagcctccagagcaagctcacccaggaggtcttcgcgacggcgaaggtccggtcgagcggcaagc
acgaggactgggtccagtacaagtacgagctggtcccgaagaaggccgccagcaacaccaacaacaccct
caccatcaccttcgacagcaagggcctcaaggacggcagcctcaacttcaacctcatcagcctcttcccg
ccgacctacaacaaccggccgaacggcctccggatcgacctcgtcgaggccatggcggagctggagggca
agttcctccgcttccccggcggctcggacgtggagggcgtccaggccccgtactggtacaagtggaacga
gacgtcggcgacctcaaggaccgctactcgcgcccgagcgcctggacctacgaggagagcaacggcatc
ggcctcatcgagtacatgaactggtgcgacgacatgggcctcgagccgatcctcgccgtctgggacggcc
actacctcagcaacgaggtcatcagcgagaacgacctccagccgtacatcgacgacaccctcaaccagct
cgagttcctcatgggcgccccggacactccctacgggtcttggagggctagcctcggctacccgaagccg
tggaccatcaactacgtcgagatcggcaacgaggacaacctctacggcggcctcgagacctacatcgcct
accggttccaggcctactacgacgccatcaccgccaagtacccgcacatgaccgtcatggagagcctcac
cgagatgcccggccccgctgccgcggcgtcggactaccaccagtactcgacgcccgacggcttcgtcagc
cagttcaactacttcgaccagatgccggtcaccaaccgcacgctgaacggcgagatcgccaccgtctacc
ccaacaacccgagcaactcggtggcgtggggcagcccgttcccgctctaccgtggtggatcgggtccgt
ggctgaggccgtcttcctcatcggcgaggagcggaacagcccgaagatcatcggcgccagctacgccccc
atgttccgcaacattaacaactggcagtggagcccgaccctgatcgccttcgacgccgacagcagccgga
cgtcgcgctctacttcctggcacgtcatcaagctcctcagcaccaacaagatcacccagaacctgccac
gacgtggtctgggggggacatcggcccgctctactgggtcgccggccggaacgacaacaccggcagcaac
atcttcaaggccgccgtctacaacagcaccagcgacgtcccggtcaccgtccagttcgccggctgcaacg
ccaagagcgccaacctcaccatcctctcgtcggacgacccccaacgccagcaactaccggggcggccccga
ggtcgtcaagaccgagatccagagcgtcaccgccaacgcccacggcgccttcgagttcagcctcccgaac
ctgtcggtggctgtgctgaagacggagtag

*FIG. 63*

```
Fv3A    MLLNLQVAASALSLSLLGGLAEAATPYT---------------------------LPDCTKGPLSK
Bxl1    -MVNNAALLAALSALLPTALAQNNQTYANYSAQGQPDLYPETLATLTLSFPDCEHGPLKN
Bgl1    MRY-RTAAALALATG------PFARADSHSTSG----ASAEAVVP----------------

Fv3A    NGICDTSLSPAKRAAALVAALTPEEKVGNLVSNATGAPRIGLPRYNWWNEALHGLAGSPG
Bxl1    NLVCDSSAGYVERAQALISLFTLEELILNTQNSGPGVPRLGLPNYQVWNEALHGLDRAN-
Bgl1    -PAGTPWGTAYDKAKAALAKLNLQDKVGIVSGVGWNGGPCVGNTSPASKISYPSLCLQDG

Fv3A    GRFADTP-PYDAATSFPMPLLMAAAFDDDLIHDIGNVVGTEARAFTNGGWRGVDFWTPNV
Bxl1    --FATKGGQFEWATSFPMPILTTAALNRTLIHQIADIISTQARAFSNSGRYGLDVYAPNV
Bgl1    ----PLGVRYSTGSTAFTPGVQAASTWDVNLIRERGQFIGEEVKASGIHVILGPVAGPLGK

Fv3A    NPFKDPRWGRGSETPGEDALHVS-RYARYIVRGLEG--DKEQRRIVATCKHYAGNDFEDW
Bxl1    NGFRSPLWGRGQETPGEDAFFLSSAYTYEYITGIQGGVDPEHLKVAATVKHFAGYDLENW
Bgl1    TPQGGRNWEGF---GVDP--YLTGIAMGQTINGIQS------VGVQATAKHYILNEQELN

Fv3A    GGFTR---------HDFDAKITPQDLAEYYVRPFQECTRDAKVGSIMCAYNAVNGIPACA
Bxl1    NNQSR---------LGFDAIITQQDLSEYYTPQFLAAARYAKSRSLMCAYNSVNGVPSCA
Bgl1    R---------------ETISSNPDDRTLHELYTWPFADAVQAN-VASVMCSYNKVNTTWACE

Fv3A    NSYLQETILRGHWNWTRDNNW ITSDCG AMQDIWQNHKYVKTNAEGAQVAFENGMDSSCEY
Bxl1    NSFFLQTLLRESWGFP-EWGY VSSDCD AVYNVFNPHDYASNQSSAAASSLRAGTDIDCGQ
Bgl1    DQYTLQTVLKDQLGFP----GY VMTDWN AQHTTVQSANSGLDMSMPG-TDFNGNNRLWGPA

Fv3A    TTTSDVSDSYKQGLLTEKLMDRSLKRLFEGLVHTGFFDGAKAQWN--------------
Bxl1    TYPWHLNESFVAGEVSRGEIERSVTRLYANLVRLGYFD-KKNQYR---------------
Bgl1    LTNAVNSNQVPTSRVDDMVTRILAAWYLTGQDQAGYPSFNIS-----------------

Fv3A    -SLSFADVNTKEAQDLALRSAVEGAVLLKNDG-TLPLKLKKKDSVAMIGFWAN--------
Bxl1    -SLGWKDVVKTDAWNISYEAAVEGIVLLKNDG-TLPLSKKVR-SIALIGPWAN--------
Bgl1    ------RNVQGNHKTNVRAIARDGIVLLKNDANILPLKKPASIAVVGSAAIIGNHARNSP

Fv3A    -----------DTSKLQGGYSGRAPFLHSPLYAAEKLGLDTNVAWGPTLQNSSSHDNWTTN
Bxl1    -----------ATTQMQGNYYGPAPYLISPLEAAKKAGYHVNFELGTEIAGNSTTG--FAK
Bgl1    SCNDKGCDDGALGMGWGSGAVNYPYFVAPYDAINTRASSQGT--QVTLSNTDNTS---SG

Fv3A    AVAAAKKSDYILYFGGLDAS----AAGEDRDRENLDWPESQLTLLQKLSSLGKPLVVIQL
Bxl1    AIAAAAKKSDAIIYLGGIDNT-----IEQEGADRTDIAWPGNQLDLIKQLSEVGKPLVVLQM
Bgl1    ASAARGKDVAIVFITADSGEGYITVEGNAGDRNNLDPWHNGNALVQAVAGANSNVIVVVH

Fv3A    G-DQVDDTALLKNKKINSILWVNYPGQDGGTAVMDLLTGRKSPAGRLPVTQYP--------
Bxl1    GGGQVDSSSLKSNKKVNSLVWGGYPGQSGGVALFDILSGKRAPAGRLVTTQYP--------
Bgl1    SVGAIILEQILALPQVKAVVWAGLPSQESGNALVDVLWGDVSPSGKLVYTIAKSPNDYNT
```

*FIG. 64A*

```
Fv3A    ---------------------SKYTEQIGMTDMDLRPT-KSLPGRTYRWYS-TPVLPYGFGLHYTKF
Bxl1    ---------------------AEYVHQFPQNDMNLRPDGKSNPGQTYIWYTGKPVYEFGSGLFYTTF
Bgl1    RIVSGGS--------DSFSEGLFIDYKHFDDAN-------------ITPRYEFGYGLSYTKF

Fv3A    QAKFKSN--KLTFDIQKLLKG--CSAQYS--------------------------------
Bxl1    KETLASHPKSLKFNTSSILSAPHPGYTYS--------------------------------
Bgl1    NYSRLSVLSTAKS--GPATGAVVP-------------------------------------

Fv3A    ----------------------------------------------DTCALPPIQVSVKNTGR
Bxl1    ----------------------------------------------EQIPVFTFEANIKNSGK
Bgl1    ----------------------------------------------GGPSDLFQNVATVTVDIANSGQ

Fv3A    ITSDFVSLVFIKS-EVGPKPYPLKTLAAYGRLHDVAPSSTKDISLEWTLDNIARRGENGD
Bxl1    TESPYTAMLFVRTSNAGPAPYPNKWLVGFDRLADIKPGHSSKLSIPIPVSALARVDSHGN
Bgl1    VTGAEVAQLYITYPSSAPR-TPPKQLRGFAKLN-LTPGQSGTATFNIRRRDLSYWDTASQ

Fv3A    LVVYPGTYTLLLDEPTQAKIQVTLTGKKAILDKWPQDPKSA--------
Bxl1    RIVYPGKYELALNTDESVKLEFELVGEEVTIENWPLEEQQIKDATPDA
Bgl1    KWVVPSGSFGISVGASSRDIRLTSTLSVA-------------------
```

*FIG. 64B*

```
Fv30B.pro  MNPLSLGLAALSLLGVVGVNFVAAFPTDSNSGSEVLISVNGHVKHQELDGFGASQAFQRAEDILGKDGLSKEGTQHVIDL     80
Fv30A.pro  ML-FSLVLPTLA--------FQASLALGDTS------VTVDTSQKLQVIDGFGVSEAYGHAKQF----QNLGPGPQKEGLDL   63

Fv30B.pro  LFSKDIGAGESILRNGIGSSNSSDKNFMNSIEPFSPGSPGAKPHYVWDGYDSGQLTVAQEAFKRGLKFLYGDAWSAPGYM   160
Fv30A.pro  LFNTTTGAGLSIIRNKIGCDAS--------NSITSTNTDNPDKQAVYHFDGDDDGQ---                        111

Fv30B.pro  KTNHDENNGGYLCGVTGAACASGDWKQAYADYLLQWVEFYRKSGVKVTNLGFLNEPQFAAPYAGMLSNGTQAADFIRVLG   240
Fv30A.pro  ------SAQSMGRLCGTPGVSCSSGDWRHRYVEMIAEYLSYYKQAGIPVSHVGFLNEGD-GSDF---MLSTAEQAADVIPLLH   184

Fv30B.pro  KTIRKRGIHDLTIACCDGEGWDLQ-------EDMMAGLTAGPDPAINYLSVVTGHGYVSPPNHPLSTTKKTWLTEWADLTGQFT   317
Fv30A.pro  SALQSKGLGDIKMTCCDNIGWKSQMDYTAKLAELEVE------KYLSVITSHEYSSSPNQPMNTTLPTWMSEGAANDQAFA   259

Fv30B.pro  PYTFYNNSGQGEGMTWAGRIQTALVDANVSGFLYWIGAENSTTNS---ALINMIGDKVIPSKRFWAFASFSRFARPGARRI   395
Fv30A.pro  T-AWYVNGGSNEGFTWAVKIAQGIVNADLSAYIYWEGVETNNKGSLSHVIDTDGTKFTISSILWAIAHWSRHIRPGAHRL   338

Fv30B.pro  EATSSVPLVTVSSFLNTDGTVATQVLNNDTVAHSVQLVVSGTG---------------------                    438
Fv30A.pro  STSGVVQDTIVGAFENVDGSSVVMVLTNSGTAAQTVDLGVSGSSFSTAQAFTSDAEAQMVDTKVTLSDGRVKVTVPVHGVV   418

Fv30B.pro  --------------------RNPHSLKPFLTDNSNDLTALKHLKATGKGSFQTTIPPRSLVSFVT-------            483
Fv30A.pro  TVKLITTAKSSKPVSTAVSAQSAPTPTSVKHTLTHQKTSSTTLSTAKAPTSTQTTSVVESAKAVKYPVPPVASKGSSKSAP   498

Fv30B.pro  ---------------DF                                                                  485
Fv30A.pro  KKGTKKTTTKKGSHQSHKAHSATHRRCRHGSYRRGHCTN                                            537
```

FIG. 65

| SEQ ID NO: | Nucleotide or Amino Acid | Description |
|---|---|---|
| 1. | Nucleotide | Nucleotide sequence for Fv3A, a GH3 family enzyme from *Fusarium verticillioides* |
| 2. | Amino acid | Protein sequence of Fv3A |
| 3. | Nucleotide | Nucleotide sequence for Pf43A, a GH43 family enzyme from *Penicillium funiculosum* |
| 4. | Amino acid | Protein sequence of Pf43A |
| 5. | Nucleotide | Nucleotide sequence for Fv43E, a GH43 family enzyme from *Fusarium verticillioides* |
| 6. | Amino acid | Protein sequence of Fv43E |
| 7. | Nucleotide | Nucleotide sequence for Fv39A, a GH39 family enzyme from *Fusarium verticillioides* |
| 8. | Amino acid | Protein sequence of Fv39A |
| 9. | Nucleotide | Nucleotide sequence for Fv43A, a GH43 family enzyme from *Fusarium verticillioides* |
| 10. | Amino acid | Protein sequence of Fv43A |
| 11. | Nucleotide | Nucleotide sequence for Fv43B, a GH43 family enzyme from *Fusarium verticillioides* |
| 12. | Amino acid | Protein sequence of Fv43B |
| 13. | Nucleotide | Nucleotide sequence for Pa51A, a GH51 family enzyme from *Podospora anserina* |
| 14. | Amino acid | Protein sequence of Pa51A |
| 15. | Nucleotide | Nucleotide sequence for Gz43A, a GH43 family enzyme from *Gibberella zeae* |
| 16. | Amino acid | Protein sequence of Gz43A |
| 17. | Nucleotide | Nucleotide sequence for Fo43A, a GH43 family enzyme from *Fusarium oxysporum* |
| 18. | Amino acid | Protein sequence of Fo43A |
| 19. | Nucleotide | Nucleotide sequence for Af43A, a GH43 family enzyme from *Aspergillus fumigatus* |
| 20. | Amino acid | Protein sequence of Af43A |
| 21. | Nucleotide | Nucleotide sequence for Pf51A, a GH51 family enzyme from *Penicillium funiculosum* |
| 22. | Amino acid | Protein sequence of Pf51A |
| 23. | Nucleotide | Nucleotide sequence for AfuXyn2, a GH11 family enzyme from *Aspergillus fumigatus* |
| 24. | Amino acid | Protein sequence of AfuXyn2 |
| 25. | Nucleotide | Nucleotide sequence for AfuXyn5, a GH11 family enzyme from *Aspergillus fumigatus* |

*FIG. 66*

| SEQ ID NO: | Nucleotide or Amino Acid | Description |
|---|---|---|
| 26. | Amino acid | Protein sequence of AfuXyn5 |
| 27. | Nucleotide | Nucleotide sequence for Fv43D, a GH43 family enzyme from *Fusarium verticillioides* |
| 28. | Amino acid | Protein sequence of Fv43D |
| 29. | Nucleotide | Nucleotide sequence for Pf43B, a GH43 family enzyme from *Penicillium funiculosum* |
| 30. | Amino acid | Protein sequence of Pf43B |
| 31. | Nucleotide | Nucleotide sequence for Fv51A, a GH51 family enzyme *Fusarium verticilloides* |
| 32. | Amino acid | Protein sequence of Fv51A |
| 33. | Nucleotide | Nucleotide sequence for Cg51B, a GH51 family enzyme from *Chaetomium globosum* |
| 34. | Amino acid | Protein sequence of Cg51B |
| 35. | Nucleotide | Nucleotide sequence for Fv43C, a GH43 family enzyme from *Fusarium verticillioides* |
| 36. | Amino acid | Fv43C protein sequence |
| 37. | Nucleotide | Nucleotide sequence for Fv30A, a GH30 family enzyme from *Fusarium verticillioides* |
| 38. | Amino acid | Fv30A protein sequence |
| 39. | Nucleotide | Nucleotide sequence for Fv43F, a GH43 family enzyme from *Fusarium verticillioides* |
| 40. | Amino acid | Fv43F protein sequence |
| 41. | Nucleotide | Nucleotide sequence for Xyn3, a GH10 family xylanase from *Trichoderma reesei* |
| 42. | Amino acid | Xyn3 protein sequence |
| 43. | Amino acid | Protein sequence of Xyn2, a GH11 xylanase from *Trichoderma reesei* |
| 44. | Amino acid | Protein sequence of Bxl1, a GH3 β-xylosidase from *Trichoderma reesei* |
| 45. | Amino acid | Protein sequence of Bgl1, a GH3 β-glucosidase from *Trichoderma reesei* |
| 46. | Nucleotide | Deduced cDNA for Pa51A. |
| 47. | Nucleotide | Codon optimized cDNA for Pa51A. |
| 48. | Nucleotide | Coding sequence for CBH1 signal sequence upstream of genomic DNA encoding mature Gz43A. |
| 49. | Nucleotide | Coding sequence for CBH1 signal sequence upstream of genomic DNA encoding mature Fo43A. |
| 50. | Nucleotide | Codon optimized nucleotide sequence for CBH1 signal sequence upstream of codon optimized DNA encoding mature Pf51A |

*FIG. 67*

| Enzyme | Accession No. | Strain of Origin |
|---|---|---|
| Mg51A | XP_369655 (NCBI) | *Magnaporthe grisea* |
| At51A | XP_001212060 (NCBI) | *Aspergillus terreus* |
| Pt51A | XP_001939835 (NCBI) | *Pyrenophora tritici-repentis* |
| Ss51A | XP_001595513 (NCBI) | *Sclerotinia sclerotiorum* |
| Vd51A | EEU33949 (NCBI) | *Verticilium dahliae* |
| AfuXyn3 | Q4WLV2 (Uniprot) | *Aspergillus fumigatus* |
| PfuXyn1 | Q8J0K5 (Uniprot) | *Penicillium funiculosum* |
| SspXyn1 | CAA67143 (NCBI) | *Streptomyces sp.* S38 |

*FIG. 68*

| Expressed Protein | pNPA (xQuad Delete Background) | pNPX (xQuad Delete Background) |
|---|---|---|
| Quad-delete host | 1.0 | 1.0 |
| Fv43A | 51.2 | 43.3 |
| Fv43B | 7.9 | 45.8 |
| Fv43C | 11.1 | 0.7 |
| Fv43D | 59.4 | 715.4 |
| Tr Bxl1 | 52.2 | 1289.4 |
| Pf51A | 0.3 | 26.0 |
| Fv51A | 34.3 | 210.1 |
| Pa51A | 5.0 | 45.0 |
| Fv39A | 9.7 | 9.9 |
| Fv3A | 8.7 | 2763.7 |
| Pf43A | 77.3 | 23.1 |
| Fv43E | 0.7 | 0.9 |
| Gz43A | 9.4 | 42.9 |
| Fo43A | 5.1 | 61.4 |

*FIG. 69*

| Protein | Activity on Birchwood Xylan at 50°C pH5 (Unit/mg Protein) |
|---|---|
| AfuXyn2 | 547 |
| AfuXyn3 | 1192 |
| AfuXyn5 | 1092 |
| PfuXyn1 | 98 |
| SspXyn1 | 454 |
| Tr Xyn2 | 554 |

*FIG. 70*

| Added Enzymes | Glucose | Xylose | Arabinose |
|---|---|---|---|
| Tr Bxl1 | 65.3 | 54.0 | 4.4 |
| Fv3A | 49.8 | 54.9 | 17.7 |
| Fv43A | 3.4 | 5.6 | 2.4 |
| Fv43B | 52.6 | 32.8 | 15.4 |
| Fv43D | 12.0 | 28.3 | 4.0 |
| Fv51A | 17.4 | 22.6 | 10.8 |
| Tr Bxl1 + Fv43A | 68.3 | 63.2 | 15.2 |
| Tr Bxl1 + Fv43B | 66.7 | 61.5 | 29.8 |
| Tr Bxl1 + Fv51A | 74.4 | 59.0 | 15.6 |
| Fv3A + Fv51A | 48.4 | 70.4 | 70.7 |
| Fv3A + Fv43A | 56.9 | 60.8 | 16.3 |
| Fv3A + Fv43B | 55.4 | 77.1 | 64.9 |
| Fv3A + Fv43D | 56.6 | 62.2 | 15.6 |
| Fv43A + Fv43B | 44.0 | 39.2 | 43.8 |
| Fv43D + Fv43A | 23.6 | 43.9 | 19.0 |
| Fv43D + Fv43B | 44.8 | 53.5 | 23.5 |
| Fv43D + Fv51A | 23.5 | 36.6 | 14.1 |
| Tr Bxl1 + Fv43A + Fv43B | 62.3 | 73.2 | 50.4 |
| Tr Bxl1 + Fv43A + Fv51A | 59.9 | 66.0 | 52.7 |
| Fv43D + Fv3A + Fv51A | 56.4 | 77.1 | 71.6 |
| Fv43D + Fv43A + Fv51A | 17.5 | 49.3 | 52.9 |

| Run # | Trial # | Ac1000 | Quad | Tr Xyn3 | Fv43D | Fv51A | Fv43A | Fv43B | Loading ug/mg Carb | Xyl mg/mL | Glu mg/mL | Arab mg/mL | G+X+A mg/mL | Xyl %theor | Glu %theor | Arab %theor |
|---|---|---|---|---|---|---|---|---|---|---|---|---|---|---|---|---|
| 1 | 40 | 0.4 | 0 | 0.02 | 0.3 | 0 | 0 | 0.28 | 21 | 32.435 | 25.610 | 2.632 | 60.68 | 70.39 | 58.94 | 44.53 |
| 2 | 10 | 0.4 | 0 | 0.152 | 0.148 | 0 | 0 | 0.3 | 7 | 28.847 | 14.112 | 2.322 | 45.28 | 62.60 | 32.48 | 39.29 |
| 3 | 47 | 0.4 | 0.3 | 0.02 | 0.02 | 0 | 0 | 0.26 | 21 | 33.809 | 29.948 | 2.706 | 66.46 | 73.37 | 68.93 | 45.79 |
| 4 | 8 | 0.66 | 0.066 | 0.02 | 0.02 | 0.3 | 0 | 0 | 21 | 27.911 | 27.456 | 2.462 | 57.83 | 60.57 | 63.19 | 41.66 |
| 5 | 44 | 0.175 | 0 | 0.067 | 0.009 | 0.3415 | 0.3415 | 0 | 15.99 | 31.691 | 16.036 | 3.226 | 50.95 | 68.77 | 36.91 | 54.59 |
| 6 | 4 | 0.4 | 0 | 0.3 | 0.02 | 0 | 0 | 0.28 | 21 | 35.440 | 27.504 | 2.789 | 65.73 | 76.91 | 63.30 | 47.19 |
| 7 | 46 | 0.76 | 0.2 | 0.02 | 0.02 | 0 | 0 | 0 | 21 | 25.642 | 32.461 | 0.721 | 58.82 | 55.65 | 74.71 | 12.20 |
| 8 | 37 | 0.735 | 0 | 0.02 | 0.02 | 0 | 0.225 | 0 | 6.87 | 19.295 | 15.950 | 0.518 | 35.76 | 41.87 | 36.71 | 8.76 |
| 9 | 49 | 0.68 | 0 | 0.3 | 0.02 | 0.26 | 0 | 0 | 7 | 25.472 | 17.795 | 0.775 | 44.04 | 55.28 | 40.96 | 13.11 |
| 10 | 23 | 0.4 | 0.3 | 0.02 | 0.02 | 0.3 | 0 | 0 | 21 | 28.005 | 28.024 | 2.415 | 58.44 | 60.77 | 64.50 | 40.86 |
| 11 | 32 | 0.4 | 0 | 0.129 | 0.02 | 0.3 | 0.057 | 0.094 | 21 | 34.334 | 25.816 | 3.167 | 63.32 | 74.51 | 59.42 | 53.59 |
| 12 | 9 | 0.4 | 0 | 0.02 | 0.02 | 0 | 0.26 | 0 | 7 | 22.906 | 11.955 | 2.621 | 37.48 | 49.71 | 27.51 | 44.35 |
| 13 | 29 | 0.249 | 0.078 | 0.0125 | 0.0125 | 0 | 0.461 | 0.187 | 33.7 | 33.305 | 26.724 | 3.339 | 63.37 | 72.28 | 61.51 | 56.50 |
| 14 | 42 | 0.4 | 0 | 0.3 | 0.02 | 0.28 | 0 | 0 | 21 | 32.071 | 26.609 | 2.572 | 61.25 | 69.60 | 61.24 | 43.52 |
| 15 | 11 | 0.96 | 0 | 0.02 | 0.02 | 0.3 | 0 | 0 | 7 | 20.257 | 19.160 | 0.460 | 39.88 | 43.96 | 44.10 | 7.78 |
| 16 | 43 | 0.4 | 0 | 0.02 | 0.28 | 0 | 0 | 0 | 21 | 33.822 | 14.959 | 2.673 | 51.45 | 73.40 | 34.43 | 45.23 |
| 17 | 48 | 0.753 | 0 | 0.227 | 0.158 | 0.152 | 0 | 0.123 | 7 | 33.855 | 34.378 | 1.257 | 69.49 | 73.47 | 79.12 | 21.27 |
| 18 | 35 | 0.4 | 0.155 | 0.164 | 0.02 | 0 | 0 | 0 | 21 | 36.727 | 31.042 | 2.638 | 70.41 | 79.70 | 71.44 | 44.64 |
| 19 | 1 | 0.66 | 0 | 0.02 | 0.3 | 0.3 | 0 | 0.3 | 21 | 31.988 | 28.289 | 2.644 | 62.92 | 69.42 | 65.11 | 44.74 |
| 20 | 52 | 0.68 | 0.28 | 0.02 | 0.3 | 0 | 0 | 0 | 7 | 20.053 | 15.878 | 0.375 | 36.31 | 43.52 | 36.54 | 6.35 |
| 21 | 30 | 0.4 | 0 | 0.02 | 0.3 | 0 | 0 | 0.3 | 21 | 31.742 | 29.596 | 0.985 | 62.32 | 68.88 | 68.12 | 16.67 |
| 22 | 41 | 0.4 | 0 | 0.148 | 0.3 | 0.152 | 0 | 0 | 7 | 29.407 | 14.066 | 2.451 | 45.92 | 63.82 | 32.37 | 41.47 |
| 23 | 21 | 0.4 | 0.28 | 0.3 | 0.3 | 0 | 0 | 0 | 21 | 34.797 | 32.721 | 1.456 | 68.97 | 75.51 | 75.31 | 24.64 |
| 24 | 21 | 0.4 | 0 | 0.02 | 0.02 | 0.3 | 0 | 0.3 | 21 | 27.996 | 28.778 | 0.825 | 57.60 | 60.76 | 66.23 | 13.96 |
| 25 | 31 | 0.4 | 0.26 | 0.02 | 0.02 | 0 | 0 | 0 | 7 | 24.278 | 16.366 | 0.775 | 41.42 | 52.69 | 37.67 | 13.11 |
| 26 | 34 | 0.4 | 0 | 0.02 | 0.02 | 0.3 | 0.3 | 0 | 21 | 29.464 | 23.707 | 2.538 | 55.71 | 63.94 | 54.56 | 42.94 |

| | | | | | | | | | | | | | | | | |
|---|---|---|---|---|---|---|---|---|---|---|---|---|---|---|---|---|
| 27 | 2 | 0.4 | 0 | 0.02 | 0.02 | 0 | 0.26 | 0.3 | 7 | 24.484 | 13.033 | 2.612 | 40.13 | 53.13 | 30.00 | 44.20 |
| 28 | 12 | 0.4 | 0 | 0.02 | 0.02 | 0.26 | 0.3 | 0 | 21 | 28.054 | 22.396 | 2.996 | 53.45 | 60.88 | 51.54 | 50.69 |
| 29 | 36 | 0.4 | 0 | 0.02 | 0.02 | 0.3 | 0 | 0.26 | 7 | 23.951 | 13.139 | 1.672 | 38.76 | 51.98 | 30.24 | 28.29 |
| 30 | 25 | 0.4 | 0.3 | 0.28 | 0.28 | 0 | 0 | 0 | 7 | 23.772 | 16.611 | 0.817 | 41.20 | 51.59 | 38.23 | 13.82 |
| 31 | 50 | 0.755 | 0 | 0.02 | 0.02 | 0.205 | 0 | 0 | 21 | 22.539 | 16.844 | 1.475 | 40.86 | 48.91 | 38.77 | 24.96 |
| 32 | 19 | 0.66 | 0 | 0.02 | 0.02 | 0 | 0.3 | 0 | 7 | 26.686 | 27.769 | 1.083 | 55.54 | 57.91 | 63.91 | 18.32 |
| 33 | 7 | 0.4 | 0.3 | 0.02 | 0.02 | 0 | 0 | 0 | 21 | 29.285 | 18.127 | 1.014 | 48.43 | 63.55 | 41.72 | 17.16 |
| 34 | 6 | 0.4 | 0 | 0.02 | 0.02 | 0 | 0.3 | 0 | 7 | 33.763 | 26.607 | 1.341 | 61.71 | 73.27 | 61.24 | 22.69 |
| 35 | 16 | 0.4 | 0 | 0.3 | 0.3 | 0.3 | 0 | 0 | 21 | 20.075 | 12.639 | 0.448 | 33.16 | 43.57 | 29.09 | 7.58 |
| 36 | 26 | 0.4 | 0.26 | 0.02 | 0.02 | 0 | 0 | 0.3 | 7 | 26.736 | 16.644 | 1.615 | 45.00 | 58.02 | 38.31 | 27.33 |
| 37 | 24 | 0.4 | 0 | 0.02 | 0.02 | 0.28 | 0.28 | 0 | 21 | 25.953 | 22.638 | 0.788 | 49.38 | 56.32 | 52.10 | 13.33 |
| 38 | 22 | 0.4 | 0 | 0.3 | 0.3 | 0 | 0 | 0.3 | 7 | 29.727 | 24.463 | 2.016 | 56.21 | 64.51 | 56.30 | 34.11 |
| 39 | 51 | 0.66 | 0 | 0.02 | 0.02 | 0 | 0 | 0.3 | 21 | 23.726 | 17.116 | 1.460 | 42.30 | 51.49 | 39.39 | 24.70 |
| 40 | 38 | 0.4 | 0 | 0.15 | 0.15 | 0 | 0.15 | 0 | 7 | 31.816 | 26.602 | 1.490 | 59.91 | 69.05 | 61.22 | 25.21 |
| 41 | 3 | 0.552 | 0.106 | 0.155 | 0.155 | 0.135 | 0 | 0.138 | 21 | 30.870 | 28.460 | 1.934 | 61.26 | 66.99 | 65.50 | 32.72 |
| 42 | 14 | 0.66 | 0 | 0.02 | 0.02 | 0 | 0 | 0 | 7 | 22.806 | 19.559 | 0.714 | 43.08 | 49.49 | 45.01 | 12.08 |
| 43 | 7 | 0.4 | 0.3 | 0.02 | 0.02 | 0 | 0.3 | 0.26 | 21 | 31.574 | 23.883 | 3.152 | 58.61 | 68.52 | 54.97 | 53.33 |
| 44 | 17 | 0.4 | 0 | 0.02 | 0.02 | 0 | 0.3 | 0 | 7 | 27.356 | 14.697 | 1.005 | 43.06 | 59.37 | 33.83 | 17.01 |
| 45 | 33 | 0.4 | 0.106 | 0.28 | 0.28 | 0 | 0.02 | 0.174 | 21 | 26.208 | 15.846 | 1.521 | 43.58 | 56.88 | 36.47 | 25.74 |
| 46 | 45 | 0.96 | 0 | 0.02 | 0.02 | 0 | 0.3 | 0 | 7 | 24.121 | 32.328 | 0.729 | 57.18 | 52.35 | 74.40 | 12.34 |
| 47 | 20 | 0.4 | 0.26 | 0.02 | 0.02 | 0.3 | 0.02 | 0 | 21 | 25.246 | 16.419 | 1.663 | 43.33 | 54.79 | 37.79 | 28.14 |
| 48 | 27 | 0.4 | 0 | 0.3 | 0.3 | 0 | 0 | 0.168 | 7 | 30.163 | 14.935 | 1.941 | 47.04 | 65.46 | 34.37 | 32.84 |
| 49 | 40 | 0.4 | 0 | 0.02 | 0.02 | 0 | 0.3 | 0.28 | 21 | 28.688 | 25.604 | 1.675 | 55.97 | 62.26 | 58.93 | 28.34 |
| 50 | 5 | 0.4 | 0 | 0.3 | 0.3 | 0.28 | 0.3 | 0 | 7 | 30.932 | 15.365 | 1.881 | 48.18 | 67.13 | 35.36 | 31.83 |
| 51 | 28 | 0.4 | 0 | 0.02 | 0.02 | 0 | 0.02 | 0 | 21 | 27.284 | 15.235 | 0.878 | 43.40 | 59.21 | 35.06 | 14.86 |
| 52 | 15 | 0.4 | 0.3 | 0.02 | 0.02 | 0.3 | 0.02 | 0 | 7 | 33.731 | 30.530 | 1.574 | 65.84 | 73.20 | 70.26 | 26.63 |
| 53 | 8 | 0.66 | 0 | 0.02 | 0.02 | 0 | 0.02 | 0 | 21 | 30.207 | 30.286 | 1.907 | 62.40 | 65.55 | 69.70 | 32.27 |
| 54 | 10 | 0.4 | 0 | 0.152 | 0.148 | 0 | 0 | 0 | 7 | 32.186 | 15.440 | 1.878 | 49.50 | 69.85 | 35.54 | 31.78 |
| 55 | 4 | 0.4 | 0 | 0.3 | 0.3 | 0 | 0.3 | 0.28 | 21 | 40.441 | 30.159 | 2.402 | 73.00 | 87.76 | 69.41 | 40.64 |
| 56 | 18 | 0.4 | 0 | 0.28 | 0.02 | 0.3 | 0.3 | 0 | 21 | 35.302 | 27.592 | 1.840 | 64.73 | 76.61 | 63.50 | 31.13 |

Note: Maximum theoretical xylose, glucose and arabinose were based on 46.08 mg/mL, 53.45 mg/mL, and 5.91 mg/mL, respectively.

*FIG. 72B*

| | Loading Total mg/g Glucose and Xylose | r2 Data Fit to Model (Includes both Loadings) | Fraction Accellerase | Fraction Quad Del Sup | Fraction Purified Xyn3 | Fraction Purified Fv43D | Fraction Purified Fv51A | Fraction Purified Fv43A | Fraction Purified Fv43B |
|---|---|---|---|---|---|---|---|---|---|
| Total mg/mL G+X+A | 21 | 0.97 | 0.4 | 0.3 | 0.16 | 0.02 | 0 | 0.04 | 0.08 |
| | 7 | | 0.4 | 0.3 | 0.15 | 0.02 | 0 | 0.06 | 0.07 |
| % Yield Glucose | 21 | 0.99 | 0.54 | 0.3 | 0.14 | 0.02 | 0 | 0 | 0 |
| | 7 | | 0.52 | 0.3 | 0.12 | 0.02 | 0 | 0.05 | 0 |
| % Yield Xylose | 21 | 0.92 | 0.4 | 0 | 0.22 | 0.02 | 0 | 0.1 | 0.26 |
| | 7 | | 0.4 | 0 | 0.22 | 0.02 | 0 | 0.11 | 0.25 |
| % Yield Arabinose | 21 | 0.94 | 0.4 | 0 | 0.13 | 0.02 | 0 | 0.19 | 0.26 |

Model Calculated Optimal Proportions

*FIG. 73*

| Run # | Accellerase® 1000 | Xyn3 | Fv3A | Fv43D | Fv51A | Fv43A | Fv43B | Glucose Yield | Xylose Yield | Arabinose Yield |
|---|---|---|---|---|---|---|---|---|---|---|
| 20 | 21 | 0 | 0 | 0 | 0 | 0 | 0 | 47.1% | 23.9% | 11.7% |
| 21 | 21 | 0 | 0 | 0 | 0 | 0 | 0 | 47.6% | 24.0% | 11.6% |
| 22 | 21 | 0 | 0 | 0 | 0 | 0 | 0 | 46.0% | 23.4% | 12.2% |
| 1 | 13.125 | 7.875 | 0 | 0 | 0 | 0 | 0 | 50.3% | 40.1% | 17.7% |
| 2 | 12.474 | 7.476 | 0 | 1.05 | 0 | 0 | 0 | 55.6% | 79.4% | 23.1% |
| 3 | 11.55 | 7.35 | 0 | 2.1 | 0 | 0 | 0 | 49.3% | 43.8% | 19.1% |
| 4 | 10.5 | 6.3 | 0 | 4.2 | 0 | 0 | 0 | 46.0% | 45.3% | 19.4% |
| 5 | 10.5 | 6.3 | 0 | 1.05 | 0 | 0 | 3.15 | 52.8% | 78.0% | 31.0% |
| 6 | 10.5 | 6.3 | 0 | 1.05 | 0 | 3.15 | 0 | 51.3% | 80.0% | 28.9% |
| 7 | 10.5 | 6.3 | 0 | 1.05 | 3.15 | 0 | 0 | 51.3% | 80.4% | 33.9% |
| 8 | 10.5 | 6.3 | 0 | 1.05 | 1.05 | 1.05 | 1.05 | 52.7% | 86.0% | 40.4% |
| 9 | 10.5 | 6.3 | 0 | 1.05 | 1.575 | 1.575 | 0 | 53.2% | 87.3% | 39.8% |
| 10 | 10.5 | 6.3 | 0 | 1.05 | 1.575 | 0 | 1.575 | 51.5% | 88.3% | 38.9% |
| 11 | 10.5 | 6.3 | 0 | 1.05 | 0 | 1.575 | 1.575 | 50.4% | 80.4% | 33.8% |
| 12 | 10.5 | 6.3 | 3.15 | 1.05 | 0 | 0 | 0 | 53.8% | 91.6% | 34.3% |
| 13 | 10.5 | 6.3 | 1.575 | 1.05 | 1.575 | 0 | 0 | 49.3% | 90.1% | 50.0% |
| 14 | 10.5 | 6.3 | 1.575 | 1.05 | 0 | 1.575 | 0 | 50.4% | 85.8% | 33.4% |
| 15 | 10.5 | 6.3 | 1.575 | 1.05 | 0 | 0 | 1.575 | 49.8% | 89.4% | 45.5% |
| 16 | 10.5 | 6.3 | 1.05 | 1.05 | 0 | 1.05 | 1.05 | 50.2% | 93.9% | 48.3% |
| 17 | 10.5 | 6.3 | 1.05 | 1.05 | 1.05 | 0 | 1.05 | 49.0% | 85.2% | 47.8% |
| 18 | 10.5 | 6.3 | 1.05 | 1.05 | 1.05 | 1.05 | 0 | 48.8% | 88.1% | 46.1% |
| 19 | 10.5 | 6.3 | 0.7875 | 1.05 | 0.7875 | 0.7875 | 0.7875 | 50.5% | 91.2% | 50.7% |

*FIG. 74*

| Fv3A mg/g Xylan | Fv43D mg/g Xylan | Fv51A mg/g Xylan | >dp2 mg/mL | Cellobiose mg/mL | Xylobiose mg/mL | Glucose mg/mL | Xylose mg/mL |
|---|---|---|---|---|---|---|---|
| 0 | 0 | 0 | 12.8 | 5.3 | 26.8 | 50.7 | 35.6 |
| 0.5 | 0 | 0 | 6.3 | 11.0 | 14.6 | 53.1 | 50.9 |
| 1 | 0 | 0 | 4.1 | 10.7 | 9.2 | 52.5 | 55.1 |
| 2 | 0 | 0 | 3.6 | 11.1 | 6.6 | 53.5 | 60.4 |
| 3 | 0 | 0 | 3.8 | 11.1 | 6.7 | 54.5 | 64.4 |
| 0.5 | 0 | 0.5 | 2.5 | 5.0 | 15.7 | 55.5 | 56.8 |
| 1 | 0 | 0.5 | 2.2 | 4.2 | 14.6 | 56.9 | 64.5 |
| 2 | 0 | 0.5 | 1.5 | 6.2 | 8.2 | 57.5 | 67.4 |
| 3 | 0 | 0.5 | 1.0 | 6.0 | 7.5 | 57.7 | 69.4 |
| 0.5 | 0 | 1 | 5.6 | 5.9 | 16.2 | 55.9 | 59.2 |
| 1 | 0 | 1 | 2.2 | 5.7 | 11.9 | 55.9 | 63.6 |
| 2 | 0 | 1 | 1.0 | 5.0 | 8.5 | 55.7 | 68.4 |
| 3 | 0 | 1 | 0.7 | 5.9 | 7.1 | 57.9 | 68.1 |
| 0.5 | 0 | 2 | 4.4 | 6.2 | 14.9 | 56.1 | 58.7 |
| 1 | 0 | 2 | 1.9 | 5.1 | 12.8 | 55.6 | 64.8 |
| 2 | 0 | 2 | 1.5 | 6.7 | 8.4 | 57.3 | 69.1 |
| 3 | 0 | 2 | 1.5 | 6.0 | 6.7 | 58.7 | 70.5 |
| 0 | 0.5 | 2 | 8.8 | 5.7 | 4.1 | 56.2 | 64.3 |
| 0 | 1 | 2 | 9.3 | 6.1 | 4.2 | 56.0 | 66.8 |
| 0 | 2 | 2 | 8.8 | 5.1 | 3.9 | 55.9 | 66.2 |
| 0 | 3 | 2 | 9.0 | 4.8 | 4.1 | 57.2 | 66.6 |

*FIG. 75*

FIG. 76

| Mix | Glucose Yield | Xylose Yield | Arabinose Yield |
|---|---|---|---|
| A | 1.3% | 64.3% | 57.7% |
| B | 1.0% | 58.5% | 44.0% |
| C | 1.4% | 64.3% | 58.3% |

FIG. 77

| | Cob % Yields | | | Switchgrass % Yields | | | Sorghum % Yields | | | Bagasse % Yields | | |
|---|---|---|---|---|---|---|---|---|---|---|---|---|
| Mix | Glu | Xyl | Ara | Glu | Xyl | Ara | Glu | Xyl | Ara | Glu | Xyl | Ara |
| A | 5.6% | 73.2% | 69.4% | 5.8% | 76.2% | 71.8% | 2.6% | 84.8% | 71.6% | 2.1% | 92.6% | 92.3% |
| B | 3.2% | 62.6% | 42.6% | 4.8% | 72.0% | 64.6% | 59.8% | 83.1% | 70.3% | 2.0% | 95.9% | 93.6% |
| C | 1.8% | 73.3% | 68.3% | 14.3% | 70.6% | 67.0% | 2.5% | 98.5% | 81.1% | 1.8% | 96.1% | 94.6% |

FIG. 78

| Protein | H3A | 39A | 69A | A10A | G6A | 102 | 44A | 11A | G9A |
|---|---|---|---|---|---|---|---|---|---|
| Fv3A | 9.6% | 1.5% | 9.4% | 10.4% | 0.0% | 0.0% | 9.8% | 1.9% | 3.3% |
| Fv51A+Fv43D+EndoH | 14.8% | 38.1% | 6.1% | 24.3% | 14.8% | 38.5% | 17.0% | 41.9% | 15.2% |
| Xyn3 | 12.6% | 8.0% | 15.3% | 10.2% | 12.1% | 10.5% | 0.2% | 11.1% | 14.1% |
| BGL1 | 7.5% | 5.2% | 7.6% | 7.5% | 9.2% | 5.1% | 9.4% | 4.5% | 7.7% |
| CBH1 | 36.4% | 35.2% | 46.5% | 30.2% | 42.8% | 32.1% | 48.6% | 30.5% | 43.7% |
| EGL's | 5.6% | 4.1% | 1.7% | 9.0% | 11.9% | 6.7% | 2.4% | 1.7% | 3.8% |
| CBH2 | 9.5% | 7.8% | 12.7% | 8.3% | 9.2% | 7.2% | 12.4% | 8.2% | 11.9% |
| Other | 4.03% | 0.12% | 0.73% | 0.10% | 0.03% | -0.03% | 0.27% | 0.28% | 0.29% |

FIG. 79

| | Experimental Parameters | | | Response 1 | Response 2 | Response 3 |
|---|---|---|---|---|---|---|
| | Time (Min) | Temp (°C) | % Solids | % NH3 | % Glucan Conversion | % Xylan Conversion | % Total Conversion |
| 1 | 90 | 180 | 47.5 | 14 | 49.3% | 67.4% | 57.1% |
| 2 | 130 | 145 | 40 | 21 | 49.4% | 78.3% | 61.8% |
| 3 | 90 | 180 | 47.5 | 14 | 53.5% | 74.4% | 62.5% |
| 4 | 130 | 145 | 52 | 23 | 51.7% | 78.0% | 63.0% |
| 5 | 90 | 180 | 47.5 | 14 | 53.5% | 76.5% | 63.4% |
| 6 | 90 | 180 | 47.5 | 14 | 47.0% | 67.5% | 55.8% |
| 7 | 90 | 180 | 47.5 | 14 | 51.0% | 71.4% | 59.8% |
| 8 | 170 | 180 | 47.5 | 14 | 50.0% | 64.4% | 56.2% |
| 9 | 90 | 180 | 45.5 | 28 | 60.9% | 84.0% | 70.8% |
| 10 | 90 | 180 | 32.5 | 14 | 52.4% | 74.4% | 61.9% |

FIG. 80

| Dry Solids % | Time (Day) | Enzyme (mg TP/g Glucan) | Glucose (g/L) | Xylose (g/L) | Glucan % | Xylan % |
|---|---|---|---|---|---|---|
| 15% | 2 | 40 | 111.6 | 29.2 | 89.0% | 89.6% |
| 15% | 3 | 20 | 98.7 | 27.1 | 78.7% | 83.1% |
| 20% | 3 | 20 | 90.2 | 27.7 | 54.2% | 63.8% |
| 20% | 4 | 20 | 114.2 | 30.9 | 68.6% | 71.3% |
| 20% | 2-day (fed-batch) | 20 | 92.1 | 27.1 | 55.3% | 62.4% |
| 20% | 3-day (fed-batch) | 20 | 114.7 | 30.1 | 68.9% | 69.4% |

| Sample Name pH / Temp | g/L | | | % Conversion | | |
|---|---|---|---|---|---|---|
| | Cellobiose | Glucose | Xylose | Glucan (Glucose) | Glucan (Cellobiose + Glucose) | Xylan (Xylose) |
| 5.0 / 45 | 5.83 | 71.65 | 16.22 | 92.13% | 100.01% | 80.20% |
| 5.0 / 45 | 5.04 | 71.18 | 15.92 | 91.52% | 98.35% | 78.72% |
| 4.65 / 47.2 | 3.71 | 76.05 | 16.94 | 97.79% | 102.81% | 83.78% |
| 4.65 / 47.2 | 3.62 | 76.21 | 16.81 | 97.99% | 102.89% | 83.09% |
| 5.35 / 47.2 | 6.59 | 69.89 | 16.12 | 89.87% | 98.79% | 79.68% |
| 5.35 / 47.2 | 6.67 | 70.12 | 15.69 | 90.16% | 99.19% | 77.60% |
| 5.0 / 52.5 | 3.38 | 77.32 | 16.79 | 99.42% | 103.99% | 83.00% |
| 5.0 / 52.5 | 3.61 | 77.43 | 16.69 | 99.56% | 104.45% | 82.54% |
| 5.0 / 52.5 | 3.63 | 77.13 | 16.76 | 99.17% | 104.09% | 82.86% |
| 5.0 / 52.5 | 3.84 | 77.65 | 16.85 | 99.85% | 105.05% | 83.31% |
| 5.0 / 52.5 | 3.41 | 77.14 | 16.78 | 99.19% | 103.80% | 82.96% |
| 4.5 / 52.5 | 3.21 | 77.76 | 16.95 | 99.99% | 104.33% | 83.81% |
| 4.5 / 52.5 | 3.26 | 76.88 | 16.79 | 98.85% | 103.26% | 83.04% |
| 5.5 / 52.5 | 6.41 | 72.05 | 16.24 | 92.65% | 101.32% | 80.32% |
| 5.5 / 52.5 | 7.01 | 71.58 | 16.34 | 92.05% | 101.53% | 80.78% |
| 4.65 / 57.8 | 2.59 | 71.04 | 15.62 | 91.35% | 94.85% | 77.21% |
| 4.65 / 57.8 | 2.73 | 70.66 | 15.57 | 90.86% | 94.55% | 76.99% |
| 5.35 / 57.8 | 1.72 | 58.23 | 12.49 | 74.87% | 77.20% | 61.76% |
| 5.35 / 57.8 | 1.80 | 58.91 | 12.40 | 75.75% | 78.19% | 61.29% |
| 5.0 / 60 | 0.13 | 36.64 | 7.37 | 47.12% | 47.29% | 36.46% |
| 5.0 / 60 | 0.15 | 38.21 | 7.67 | 49.13% | 49.32% | 37.93% |

FIG. 81

SEQUENCE LISTING

<160> NUMBER OF SEQ ID NOS: 117

<210> SEQ ID NO 1
<211> LENGTH: 2358
<212> TYPE: DNA
<213> ORGANISM: Fusarium verticillioides

<400> SEQUENCE: 1

| | | | | | |
|---|---|---|---|---|---|
| atgctgctca | atcttcaggt | cgctgccagc | gctttgtcgc | tttctctttt | aggtggattg | 60 |
| gctgaggctg | ctacgccata | tacccttccg | gactgtacca | aaggacctt | gagcaagaat | 120 |
| ggaatctgcg | atacttcgtt | atctccagct | aaaagagcgg | ctgctctagt | tgctgctctg | 180 |
| acgcccgaag | agaaggtggg | caatctggtc | aggtaaaata | taccccccc | cataatcact | 240 |
| attcggagat | tggagctgac | ttaacgcagc | aatgcaactg | gtgcaccaag | aatcggactt | 300 |
| ccaaggtaca | actggtggaa | cgaagcccttt | catggcctcg | ctggatctcc | aggtggtcgc | 360 |
| tttgccgaca | ctcctcccta | cgacgcggcc | acatcatttc | ccatgcctct | tctcatggcc | 420 |
| gctgctttcg | acgatgatct | gatccacgat | atcggcaacg | tcgtcggcac | cgaagcgcgt | 480 |
| gcgttcacta | acggcggttg | gcgcggagtc | gacttctgga | cacccaacgt | caacccttt | 540 |
| aaagatcctc | gctggggtcg | tggctccgaa | actccaggtg | aagatgccct | tcatgtcagc | 600 |
| cggtatgctc | gctatatcgt | cagggtctc | gaaggcgata | aggagcaacg | acgtattgtt | 660 |
| gctacctgca | agcactatgc | tggaaacgac | tttgaggact | ggggaggctt | cacgcgtcac | 720 |
| gactttgatg | ccaagattac | tcctcaggac | ttggctgagt | actacgtcag | gcctttccag | 780 |
| gagtgcaccc | gtgatgcaaa | ggttggttcc | atcatgtgcg | cctacaatgc | cgtgaacggc | 840 |
| attcccgcat | gcgcaaactc | gtatctgcag | gagacgatcc | tcagagggca | ctggaactgg | 900 |
| acgcgcgata | caactggat | cactagtgat | tgtggcgcca | tgcaggatat | ctggcagaat | 960 |
| cacaagtatg | tcaagaccaa | cgctgaaggt | gcccaggtag | cttttgagaa | cggcatggat | 1020 |
| tctagctgcg | agtatactac | taccagcgat | gtctccgatt | cgtacaagca | aggcctcttg | 1080 |
| actgagaagc | tcatggatcg | ttcgttgaag | cgccttttcg | aagggcttgt | tcatactggt | 1140 |
| ttcttgacg | gtgccaaagc | gcaatggaac | tcgctcagtt | ttgcggatgt | caacaccaag | 1200 |
| gaagctcagg | atcttgcact | cagatctgct | gtggagggtg | ctgttcttct | taagaatgac | 1260 |
| ggcactttgc | ctctgaagct | caagaagaag | gatagtgttg | caatgatcgg | attctgggcc | 1320 |
| aacgatactt | ccaagctgca | gggtggttac | agtggacgtg | ctccgttcct | ccacagcccg | 1380 |
| ctttatgcag | ctgagaagct | tggtcttgac | accaacgtgg | cttggggtcc | gacactgcag | 1440 |
| aacagctcat | ctcatgataa | ctggaccacc | aatgctgttg | ctgcggcgaa | gaagtctgat | 1500 |
| tacattctct | actttggtgg | tcttgacgcc | tctgctgctg | gcgaggacag | agatcgtgag | 1560 |
| aaccttgact | ggcctgagag | ccagctgacc | cttcttcaga | agctctctag | tctcggcaag | 1620 |
| ccactggttg | ttatccagct | tggtgatcaa | gtcgatgaca | ccgctctttt | gaagaacaag | 1680 |
| aagattaaca | gtattctttg | ggtcaattac | cctggtcagg | atggcggcac | tgcagtcatg | 1740 |
| gacctgctca | ctggacgaaa | gagtcctgct | ggccgactac | ccgtcacgca | atatcccagt | 1800 |
| aaatacactg | agcagattgg | catgactgac | atggacctca | gacctaccaa | gtcgttgcca | 1860 |
| gggagaactt | atcgctggta | ctcaactcca | gttcttccct | acggctttgg | cctccactac | 1920 |
| accaagttcc | aagccaagtt | caagtccaac | aagttgacgt | tgacatcca | gaagcttctc | 1980 |
| aagggctgca | gtgctcaata | ctccgatact | tgcgcgctgc | ccccccatcca | agttagtgtc | 2040 |
| aagaacaccg | gccgcattac | ctccgacttt | gtctctctgg | tctttatcaa | gagtgaagtt | 2100 |

```
ggacctaagc cttaccctct caagacccctt gcggcttatg gtcgcttgca tgatgtcgcg   2160
ccttcatcga cgaaggatat ctcactggag tggacgttgg ataacattgc gcgacgggga   2220
gagaatggtg atttggttgt ttatcctggg acttacactc tgttgctgga tgagcctacg   2280
caagccaaga tccaggttac gctgactgga agaaggcta ttttggataa gtggcctcaa   2340
gaccccaagt ctgcgtaa                                                  2358
```

<210> SEQ ID NO 2
<211> LENGTH: 766
<212> TYPE: PRT
<213> ORGANISM: Fusarium verticillioides

<400> SEQUENCE: 2

```
Met Leu Leu Asn Leu Gln Val Ala Ala Ser Ala Leu Ser Leu Ser Leu
1               5                   10                  15

Leu Gly Gly Leu Ala Glu Ala Ala Thr Pro Tyr Thr Leu Pro Asp Cys
                20                  25                  30

Thr Lys Gly Pro Leu Ser Lys Asn Gly Ile Cys Asp Thr Ser Leu Ser
            35                  40                  45

Pro Ala Lys Arg Ala Ala Ala Leu Val Ala Ala Leu Thr Pro Glu Glu
50                  55                  60

Lys Val Gly Asn Leu Val Ser Asn Ala Thr Gly Ala Pro Arg Ile Gly
65                  70                  75                  80

Leu Pro Arg Tyr Asn Trp Trp Asn Glu Ala Leu His Gly Leu Ala Gly
                85                  90                  95

Ser Pro Gly Gly Arg Phe Ala Asp Thr Pro Pro Tyr Asp Ala Ala Thr
            100                 105                 110

Ser Phe Pro Met Pro Leu Leu Met Ala Ala Ala Phe Asp Asp Asp Leu
        115                 120                 125

Ile His Asp Ile Gly Asn Val Val Gly Thr Glu Ala Arg Ala Phe Thr
130                 135                 140

Asn Gly Gly Trp Arg Gly Val Asp Phe Trp Thr Pro Asn Val Asn Pro
145                 150                 155                 160

Phe Lys Asp Pro Arg Trp Gly Arg Gly Ser Glu Thr Pro Gly Glu Asp
                165                 170                 175

Ala Leu His Val Ser Arg Tyr Ala Arg Tyr Ile Val Arg Gly Leu Glu
            180                 185                 190

Gly Asp Lys Glu Gln Arg Arg Ile Val Ala Thr Cys Lys His Tyr Ala
        195                 200                 205

Gly Asn Asp Phe Glu Asp Trp Gly Gly Phe Thr Arg His Asp Phe Asp
210                 215                 220

Ala Lys Ile Thr Pro Gln Asp Leu Ala Glu Tyr Tyr Val Arg Pro Phe
225                 230                 235                 240

Gln Glu Cys Thr Arg Asp Ala Lys Val Gly Ser Ile Met Cys Ala Tyr
                245                 250                 255

Asn Ala Val Asn Gly Ile Pro Ala Cys Ala Asn Ser Tyr Leu Gln Glu
            260                 265                 270

Thr Ile Leu Arg Gly His Trp Asn Trp Thr Arg Asp Asn Asn Trp Ile
        275                 280                 285

Thr Ser Asp Cys Gly Ala Met Gln Asp Ile Trp Gln Asn His Lys Tyr
    290                 295                 300

Val Lys Thr Asn Ala Glu Gly Ala Gln Val Ala Phe Glu Asn Gly Met
305                 310                 315                 320
```

```
Asp Ser Ser Cys Glu Tyr Thr Thr Ser Asp Val Ser Asp Ser Tyr
            325                 330                 335

Lys Gln Gly Leu Leu Thr Glu Lys Leu Met Asp Arg Ser Leu Lys Arg
        340                 345                 350

Leu Phe Glu Gly Leu Val His Thr Gly Phe Phe Asp Gly Ala Lys Ala
            355                 360                 365

Gln Trp Asn Ser Leu Ser Phe Ala Asp Val Asn Thr Lys Glu Ala Gln
    370                 375                 380

Asp Leu Ala Leu Arg Ser Ala Val Glu Gly Ala Val Leu Leu Lys Asn
385                 390                 395                 400

Asp Gly Thr Leu Pro Leu Lys Leu Lys Lys Asp Ser Val Ala Met
                405                 410                 415

Ile Gly Phe Trp Ala Asn Asp Thr Ser Lys Leu Gln Gly Gly Tyr Ser
            420                 425                 430

Gly Arg Ala Pro Phe Leu His Ser Pro Leu Tyr Ala Ala Glu Lys Leu
        435                 440                 445

Gly Leu Asp Thr Asn Val Ala Trp Gly Pro Thr Leu Gln Asn Ser Ser
    450                 455                 460

Ser His Asp Asn Trp Thr Thr Asn Ala Val Ala Ala Lys Lys Ser
465                 470                 475                 480

Asp Tyr Ile Leu Tyr Phe Gly Leu Asp Ala Ser Ala Ala Gly Glu
                485                 490                 495

Asp Arg Asp Arg Glu Asn Leu Asp Trp Pro Glu Ser Gln Leu Thr Leu
            500                 505                 510

Leu Gln Lys Leu Ser Ser Leu Gly Lys Pro Leu Val Val Ile Gln Leu
        515                 520                 525

Gly Asp Gln Val Asp Asp Thr Ala Leu Leu Lys Asn Lys Lys Ile Asn
    530                 535                 540

Ser Ile Leu Trp Val Asn Tyr Pro Gly Gln Asp Gly Gly Thr Ala Val
545                 550                 555                 560

Met Asp Leu Leu Thr Gly Arg Lys Ser Pro Ala Gly Arg Leu Pro Val
                565                 570                 575

Thr Gln Tyr Pro Ser Lys Tyr Thr Glu Gln Ile Gly Met Thr Asp Met
            580                 585                 590

Asp Leu Arg Pro Thr Lys Ser Leu Pro Gly Arg Thr Tyr Arg Trp Tyr
        595                 600                 605

Ser Thr Pro Val Leu Pro Tyr Gly Phe Gly Leu His Tyr Thr Lys Phe
    610                 615                 620

Gln Ala Lys Phe Lys Ser Asn Lys Leu Thr Phe Asp Ile Gln Lys Leu
625                 630                 635                 640

Leu Lys Gly Cys Ser Ala Gln Tyr Ser Asp Thr Cys Ala Leu Pro Pro
                645                 650                 655

Ile Gln Val Ser Val Lys Asn Thr Gly Arg Ile Thr Ser Asp Phe Val
            660                 665                 670

Ser Leu Val Phe Ile Lys Ser Glu Val Gly Pro Lys Pro Tyr Pro Leu
        675                 680                 685

Lys Thr Leu Ala Ala Tyr Gly Arg Leu His Asp Val Ala Pro Ser Ser
    690                 695                 700

Thr Lys Asp Ile Ser Leu Glu Trp Thr Leu Asn Ile Ala Arg Arg
705                 710                 715                 720

Gly Glu Asn Gly Asp Leu Val Val Tyr Pro Gly Thr Tyr Thr Leu Leu
                725                 730                 735

Leu Asp Glu Pro Thr Gln Ala Lys Ile Gln Val Thr Leu Thr Gly Lys
```

```
                 740                 745                 750
Lys Ala Ile Leu Asp Lys Trp Pro Gln Asp Pro Lys Ser Ala
            755                 760                 765

<210> SEQ ID NO 3
<211> LENGTH: 1338
<212> TYPE: DNA
<213> ORGANISM: Penicillium funiculosum

<400> SEQUENCE: 3
atgcttcagc gatttgctta tattttacca ctggctctat tgagtgttgg agtgaaagcc      60
gacaacccct tgtgcagag catctacacc gctgatccgg caccgatggt atacaatgac     120
cgcgtttatg tcttcatgga ccatgacaac accggagcta cctactacaa catgacagac     180
tggcatctgt tctcgtcagc agatatggcg aattggcaag atcatggcat tccaatgagc     240
ctggccaatt tcacctgggc aacgcgaat gcgtgggccc cgcaagtcat ccctcgcaac     300
ggccaattct acttttatgc tcctgtccga cacaacgatg ttctatggc tatcggtgtg     360
ggagtgagca gcaccatcac aggtccatac catgatgcta tcggcaaacc gctagtagag     420
aacaacgaga ttgatcccac cgtgttcatc gacgatgacg tcaggcata cctgtactgg     480
ggaaatccag acctgtggta cgtcaaattg aaccaagata tgatatcgta cagcgggagc     540
cctactcaga ttccactcac cacggctgga tttggtactc gaacgggcaa tgctcaacgg     600
ccgaccactt ttgaagaagc tccatgggta tacaaacgca acggcatcta ctatatcgcc     660
tatgcagccg attgttgttc tgaggatatt cgctactcca cgggaaccag tgccactggt     720
ccgtggactt atcgaggcgt catcatgccg acccaaggta gcagcttcac caatcacgag     780
ggtattatcg acttccagaa caactcctac tttttctatc acaacggcgc tcttcccggc     840
ggaggcggct accaacgatc tgtatgtgtg agcaattca aatacaatgc agatggaacc     900
attccgacga tcgaaatgac caccgccggt ccagctcaaa ttgggactct caacccttac     960
gtgcgacagg aagccgaaac ggcggcatgg tcttcaggca tcactacgga ggtttgtagc    1020
gaaggcggaa ttgacgtcgg gtttatcaac aatggcgatt acatcaaagt taaaggcgta    1080
gctttcggtt caggagccca ttctttctca gcgcgggttg cttctgcaaa tagcggcggc    1140
actattgcaa tacacctcgg aagcacaact ggtacgctcg tgggcacttg tactgtcccc    1200
agcactggcg gttggcagac ttggactacc gttacctgtt ctgtcagtgg cgcatctggg    1260
acccaggatg tgtattttgt tttcggtggt agcggaacag gatacctgtt caactttgat    1320
tattggcagt tcgcataa                                                 1338

<210> SEQ ID NO 4
<211> LENGTH: 445
<212> TYPE: PRT
<213> ORGANISM: Penicillium funiculosum

<400> SEQUENCE: 4

Met Leu Gln Arg Phe Ala Tyr Ile Leu Pro Leu Ala Leu Leu Ser Val
1               5                   10                  15

Gly Val Lys Ala Asp Asn Pro Phe Val Gln Ser Ile Tyr Thr Ala Asp
            20                  25                  30

Pro Ala Pro Met Val Tyr Asn Asp Arg Val Tyr Val Phe Met Asp His
        35                  40                  45

Asp Asn Thr Gly Ala Thr Tyr Tyr Asn Met Thr Asp Trp His Leu Phe
    50                  55                  60
```

Ser Ser Ala Asp Met Ala Asn Trp Gln Asp His Gly Ile Pro Met Ser
65                  70                  75                  80

Leu Ala Asn Phe Thr Trp Ala Asn Ala Asn Ala Trp Ala Pro Gln Val
                85                  90                  95

Ile Pro Arg Asn Gly Gln Phe Tyr Phe Tyr Ala Pro Val Arg His Asn
            100                 105                 110

Asp Gly Ser Met Ala Ile Gly Val Gly Val Ser Ser Thr Ile Thr Gly
        115                 120                 125

Pro Tyr His Asp Ala Ile Gly Lys Pro Leu Val Glu Asn Asn Glu Ile
    130                 135                 140

Asp Pro Thr Val Phe Ile Asp Asp Gly Gln Ala Tyr Leu Tyr Trp
145                 150                 155                 160

Gly Asn Pro Asp Leu Trp Tyr Val Lys Leu Asn Gln Asp Met Ile Ser
            165                 170                 175

Tyr Ser Gly Ser Pro Thr Gln Ile Pro Leu Thr Thr Ala Gly Phe Gly
        180                 185                 190

Thr Arg Thr Gly Asn Ala Gln Arg Pro Thr Thr Phe Glu Glu Ala Pro
    195                 200                 205

Trp Val Tyr Lys Arg Asn Gly Ile Tyr Ile Ala Tyr Ala Ala Asp
210                 215                 220

Cys Cys Ser Glu Asp Ile Arg Tyr Ser Thr Gly Thr Ser Ala Thr Gly
225                 230                 235                 240

Pro Trp Thr Tyr Arg Gly Val Ile Met Pro Thr Gln Gly Ser Ser Phe
            245                 250                 255

Thr Asn His Glu Gly Ile Ile Asp Phe Gln Asn Asn Ser Tyr Phe Phe
        260                 265                 270

Tyr His Asn Gly Ala Leu Pro Gly Gly Gly Tyr Gln Arg Ser Val
    275                 280                 285

Cys Val Glu Gln Phe Lys Tyr Asn Ala Asp Gly Thr Ile Pro Thr Ile
290                 295                 300

Glu Met Thr Thr Ala Gly Pro Ala Gln Ile Gly Thr Leu Asn Pro Tyr
305                 310                 315                 320

Val Arg Gln Glu Ala Glu Thr Ala Ala Trp Ser Ser Gly Ile Thr Thr
            325                 330                 335

Glu Val Cys Ser Glu Gly Gly Ile Asp Val Gly Phe Ile Asn Asn Gly
        340                 345                 350

Asp Tyr Ile Lys Val Lys Gly Val Ala Phe Gly Ser Gly Ala His Ser
    355                 360                 365

Phe Ser Ala Arg Val Ala Ser Ala Asn Ser Gly Thr Ile Ala Ile
370                 375                 380

His Leu Gly Ser Thr Thr Gly Thr Leu Val Gly Thr Cys Thr Val Pro
385                 390                 395                 400

Ser Thr Gly Gly Trp Gln Thr Trp Thr Thr Val Thr Cys Ser Val Ser
            405                 410                 415

Gly Ala Ser Gly Thr Gln Asp Val Tyr Phe Val Phe Gly Gly Ser Gly
        420                 425                 430

Thr Gly Tyr Leu Phe Asn Phe Asp Tyr Trp Gln Phe Ala
    435                 440                 445

<210> SEQ ID NO 5
<211> LENGTH: 1593
<212> TYPE: DNA
<213> ORGANISM: Fusarium verticillioides

<400> SEQUENCE: 5

-continued

```
atgaaggtat actggctcgt ggcgtgggcc acttctttga cgccggcact ggctggcttg      60
attggacacc gtcgcgccac caccttcaac aatcctatca tctactcaga ctttccagat     120
aacgatgtat tcctcggtcc agataactac tactacttct ctgcttccaa cttccacttc     180
agcccaggag cacccgtttt gaagtctaaa gatctgctaa actgggatct catcggccat     240
tcaattcccc gcctgaactt tggcgacggc tatgatcttc ctcctggctc acgttattac     300
cgtggaggta cttgggcatc atccctcaga tacagaaaga gcaatggaca gtggtactgg     360
atcggctgca tcaacttctg cagacctggg gtatacactg cctcatcgcc ggaaggtcca     420
tggtacaaca agggaaactt cggtgataac aattgctact acgacaatgg catactgatc     480
gatgacgatg ataccatgta tgtcgtatac ggttccggtg aggtcaaagt atctcaacta     540
tctcaggacg gattcagcca ggtcaaatct caggtagttt caagaacac tgatattggg      600
gtccaagact tggagggtaa ccgcatgtac aagatcaacg gctctacta tatcctaaac     660
gatagcccaa gtgcagtca gacctggatt tggaagtcga atcaccctg gggcccttat       720
gagtctaagg tcctcgccga caaagtcacc ccgcctatct ctggtggtaa ctcgccgcat     780
cagggtagtc tcataaagac tcccaatggt ggctggtact tcatgtcatt cacttgggcc     840
tatcctgccg gccgtcttcc ggttcttgca ccgattacgt ggggtagcga tggtttcccc     900
attcttgtca agggtgctaa tggcggatgg ggatcatctt acccaacact tcctggcacg     960
gatggtgtga caaagaattg gacaaggact gataccttcc gcggaacctc acttgctccg    1020
tcctgggagt ggaaccataa tccggacgtc aactccttca ctgtcaacaa cggcctgact    1080
ctccgcactg ctagcattac gaaggatatt taccaggcga ggaacacgct atctcaccga    1140
actcatggtg atcatccaac aggaatagtg aagattgatt tctctccgat gaaggacggc    1200
gaccgggccg ggctttcagc gtttcgagac caaagtgcat acatcggtat tcatcgagat    1260
aacgaaagt tcacaatcgc tacgaagcat gggatgaata tggatgagtg aacggaaca     1320
acaacagacc tgggacaaat aaaagccaca gctaatgtgc cttctggaag gaccaagatc    1380
tggctgagac ttcaacttga taccaaccca gcaggaactg caacactat cttttcttac     1440
agttgggatg gagtcaagta tgaaacactg ggtcccaact tcaaactgta caatggttgg    1500
gcattcttta ttgcttaccg attcggcatc ttcaacttcg ccgagacggc tttaggaggc    1560
tcgatcaagg ttgagtcttt cacagctgca tag                                 1593
```

<210> SEQ ID NO 6
<211> LENGTH: 530
<212> TYPE: PRT
<213> ORGANISM: Fusarium verticillioides

<400> SEQUENCE: 6

```
Met Lys Val Tyr Trp Leu Val Ala Trp Ala Thr Ser Leu Thr Pro Ala
1               5                   10                  15

Leu Ala Gly Leu Ile Gly His Arg Arg Ala Thr Thr Phe Asn Asn Pro
            20                  25                  30

Ile Ile Tyr Ser Asp Phe Pro Asp Asn Asp Val Phe Leu Gly Pro Asp
        35                  40                  45

Asn Tyr Tyr Tyr Phe Ser Ala Ser Asn Phe His Phe Ser Pro Gly Ala
    50                  55                  60

Pro Val Leu Lys Ser Lys Asp Leu Leu Asn Trp Asp Leu Ile Gly His
65                  70                  75                  80

Ser Ile Pro Arg Leu Asn Phe Gly Asp Gly Tyr Asp Leu Pro Pro Gly
```

```
                    85                  90                  95
Ser Arg Tyr Tyr Arg Gly Gly Thr Trp Ala Ser Ser Leu Arg Tyr Arg
                100                 105                 110

Lys Ser Asn Gly Gln Trp Tyr Trp Ile Gly Cys Ile Asn Phe Trp Gln
                115                 120                 125

Thr Trp Val Tyr Thr Ala Ser Ser Pro Glu Gly Pro Trp Tyr Asn Lys
        130                 135                 140

Gly Asn Phe Gly Asp Asn Asn Cys Tyr Tyr Asp Asn Gly Ile Leu Ile
145                 150                 155                 160

Asp Asp Asp Asp Thr Met Tyr Val Val Tyr Gly Ser Gly Glu Val Lys
                165                 170                 175

Val Ser Gln Leu Ser Gln Asp Gly Phe Ser Gln Val Lys Ser Gln Val
                180                 185                 190

Val Phe Lys Asn Thr Asp Ile Gly Val Gln Asp Leu Glu Gly Asn Arg
                195                 200                 205

Met Tyr Lys Ile Asn Gly Leu Tyr Tyr Ile Leu Asn Asp Ser Pro Ser
        210                 215                 220

Gly Ser Gln Thr Trp Ile Trp Lys Ser Lys Ser Pro Trp Gly Pro Tyr
225                 230                 235                 240

Glu Ser Lys Val Leu Ala Asp Lys Val Thr Pro Pro Ile Ser Gly Gly
                245                 250                 255

Asn Ser Pro His Gln Gly Ser Leu Ile Lys Thr Pro Asn Gly Gly Trp
                260                 265                 270

Tyr Phe Met Ser Phe Thr Trp Ala Tyr Pro Ala Gly Arg Leu Pro Val
        275                 280                 285

Leu Ala Pro Ile Thr Trp Gly Ser Asp Gly Phe Pro Ile Leu Val Lys
        290                 295                 300

Gly Ala Asn Gly Gly Trp Gly Ser Ser Tyr Pro Thr Leu Pro Gly Thr
305                 310                 315                 320

Asp Gly Val Thr Lys Asn Trp Thr Arg Thr Asp Thr Phe Arg Gly Thr
                325                 330                 335

Ser Leu Ala Pro Ser Trp Glu Trp Asn His Asn Pro Asp Val Asn Ser
                340                 345                 350

Phe Thr Val Asn Asn Gly Leu Thr Leu Arg Thr Ala Ser Ile Thr Lys
        355                 360                 365

Asp Ile Tyr Gln Ala Arg Asn Thr Leu Ser His Arg Thr His Gly Asp
        370                 375                 380

His Pro Thr Gly Ile Val Lys Ile Asp Phe Ser Pro Met Lys Asp Gly
385                 390                 395                 400

Asp Arg Ala Gly Leu Ser Ala Phe Arg Asp Gln Ser Ala Tyr Ile Gly
                405                 410                 415

Ile His Arg Asp Asn Gly Lys Phe Thr Ile Ala Thr Lys His Gly Met
                420                 425                 430

Asn Met Asp Glu Trp Asn Gly Thr Thr Thr Asp Leu Gly Gln Ile Lys
        435                 440                 445

Ala Thr Ala Asn Val Pro Ser Gly Arg Thr Lys Ile Trp Leu Arg Leu
        450                 455                 460

Gln Leu Asp Thr Asn Pro Ala Gly Thr Gly Asn Thr Ile Phe Ser Tyr
465                 470                 475                 480

Ser Trp Asp Gly Val Lys Tyr Glu Thr Leu Gly Pro Asn Phe Lys Leu
                485                 490                 495

Tyr Asn Gly Trp Ala Phe Phe Ile Ala Tyr Arg Phe Gly Ile Phe Asn
                500                 505                 510
```

Phe Ala Glu Thr Ala Leu Gly Gly Ser Ile Lys Val Glu Ser Phe Thr
            515                 520                 525

Ala Ala
    530

<210> SEQ ID NO 7
<211> LENGTH: 1374
<212> TYPE: DNA
<213> ORGANISM: Fusarium verticillioides

<400> SEQUENCE: 7

```
atgcactacg ctaccctcac cactttggtg ctggctctga ccaccaacgt cgctgcacag    60
caaggcacag caactgtcga cctctccaaa aatcatggac cggcgaaggc ccttggttca   120
ggcttcatat acggctggcc tgacaacgga acaagcgtcg acacctccat accagatttc   180
ttggtaactg acatcaaatt caactcaaac cgcggcggtg cgcccaaat cccatcactg    240
ggttgggcca gaggtggcta tgaaggatac ctcggccgct tcaactcaac cttatccaac   300
tatcgcacca cgcgcaagta taacgctgac tttatcttgt tgcctcatga cctctggggt   360
gcggatggcg gcagggttc aaactccccg tttcctggcg acaatggcaa ttggactgag   420
atggagttat tctggaatca gcttgtgtct gacttgaagg ctcataatat gctggaaggt   480
cttgtgattg atgtttggaa tgagcctgat attgatatct tttgggatcg cccgtggtcg   540
cagtttcttg agtattacaa tcgcgcgacc aaactacttc ggtgagtcta ctactgatcc   600
atacgtattt acagtgagct gactggtcga attagaaaaa cacttcccaa aactcttctc   660
agtggcccag ccatggcaca ttctcccatt ctgtccgatg ataaatggca tacctggctt   720
caatcagtag cgggtaacaa gacagtccct gatatttact cctggcatca gattggcgct   780
tgggaacgtg agccggacag cactatcccc gactttacca ccttgcgggc gcaatatggc   840
gttcccgaga agccaattga cgtcaatgag tacgctgcac gcgatgagca aaatccagcc   900
aactccgtct actacctctc tcaactagag cgtcataacc ttagaggtct tcgcgcaaac   960
tggggtagcg gatctgacct ccacaactgg atgggcaact tgatttacag cactaccggt  1020
acctcggagg ggacttacta ccctaatggt gaatggcagg cttacaagta ctatgcggcc  1080
atggcagggc agagacttgt gaccaaagca tcgtcggact tgaagtttga tgtctttgcc  1140
actaagcaag gccgtaagat taagattata gccggcacga ggaccgttca agcaaagtat  1200
aacatcaaaa tcagcggttt ggaagtagca ggacttccta agatgggtac ggtaaaggtc  1260
cggacttatc ggttcgactg gctgggccg aatgaaaagg ttgacgggcc tgttgatttg  1320
ggggagaaga agtatactta ttcggccaat acggtgagca gccctctac ttga         1374
```

<210> SEQ ID NO 8
<211> LENGTH: 439
<212> TYPE: PRT
<213> ORGANISM: Fusarium verticillioides

<400> SEQUENCE: 8

Met His Tyr Ala Thr Leu Thr Thr Leu Val Leu Ala Leu Thr Thr Asn
1               5                   10                  15

Val Ala Ala Gln Gln Gly Thr Ala Thr Val Asp Leu Ser Lys Asn His
            20                  25                  30

Gly Pro Ala Lys Ala Leu Gly Ser Gly Phe Ile Tyr Gly Trp Pro Asp
        35                  40                  45

Asn Gly Thr Ser Val Asp Thr Ser Ile Pro Asp Phe Leu Val Thr Asp

```
            50                  55                  60
Ile Lys Phe Asn Ser Asn Arg Gly Gly Ala Gln Ile Pro Ser Leu
 65                  70                  75                  80

Gly Trp Ala Arg Gly Gly Tyr Glu Gly Tyr Leu Gly Arg Phe Asn Ser
                     85                  90                  95

Thr Leu Ser Asn Tyr Arg Thr Arg Lys Tyr Asn Ala Asp Phe Ile
                    100                 105                 110

Leu Leu Pro His Asp Leu Trp Gly Ala Asp Gly Gln Gly Ser Asn
                115                 120                 125

Ser Pro Phe Pro Gly Asp Asn Gly Asn Trp Thr Glu Met Glu Leu Phe
130                 135                 140

Trp Asn Gln Leu Val Ser Asp Leu Lys Ala His Asn Met Leu Glu Gly
145                 150                 155                 160

Leu Val Ile Asp Val Trp Asn Glu Pro Asp Ile Asp Ile Phe Trp Asp
                165                 170                 175

Arg Pro Trp Ser Gln Phe Leu Glu Tyr Tyr Asn Arg Ala Thr Lys Leu
                180                 185                 190

Leu Arg Lys Thr Leu Pro Lys Thr Leu Leu Ser Gly Pro Ala Met Ala
            195                 200                 205

His Ser Pro Ile Leu Ser Asp Asp Lys Trp His Thr Trp Leu Gln Ser
210                 215                 220

Val Ala Gly Asn Lys Thr Val Pro Asp Ile Tyr Ser Trp His Gln Ile
225                 230                 235                 240

Gly Ala Trp Glu Arg Glu Pro Asp Ser Thr Ile Pro Asp Phe Thr Thr
                245                 250                 255

Leu Arg Ala Gln Tyr Gly Val Pro Glu Lys Pro Ile Asp Val Asn Glu
                260                 265                 270

Tyr Ala Ala Arg Asp Glu Gln Asn Pro Ala Asn Ser Val Tyr Tyr Leu
                275                 280                 285

Ser Gln Leu Glu Arg His Asn Leu Arg Gly Leu Arg Ala Asn Trp Gly
            290                 295                 300

Ser Gly Ser Asp Leu His Asn Trp Met Gly Asn Leu Ile Tyr Ser Thr
305                 310                 315                 320

Thr Gly Thr Ser Glu Gly Thr Tyr Tyr Pro Asn Gly Glu Trp Gln Ala
                325                 330                 335

Tyr Lys Tyr Tyr Ala Ala Met Ala Gly Gln Arg Leu Val Thr Lys Ala
                340                 345                 350

Ser Ser Asp Leu Lys Phe Asp Val Phe Ala Thr Lys Gln Gly Arg Lys
            355                 360                 365

Ile Lys Ile Ile Ala Gly Thr Arg Thr Val Gln Ala Lys Tyr Asn Ile
            370                 375                 380

Lys Ile Ser Gly Leu Glu Val Ala Gly Leu Pro Lys Met Gly Thr Val
385                 390                 395                 400

Lys Val Arg Thr Tyr Arg Phe Asp Trp Ala Gly Pro Asn Gly Lys Val
                405                 410                 415

Asp Gly Pro Val Asp Leu Gly Glu Lys Lys Tyr Thr Tyr Ser Ala Asn
                420                 425                 430

Thr Val Ser Ser Pro Ser Thr
            435

<210> SEQ ID NO 9
<211> LENGTH: 1350
<212> TYPE: DNA
<213> ORGANISM: Fusarium verticillioides
```

<400> SEQUENCE: 9

```
atgtggctga cctccccatt gctgttcgcc agcaccctcc tgggcctcac tggcgttgct      60
ctagcagaca accccatcgt ccaagacatc tacaccgcag acccagcacc aatggtctac     120
aatggccgcg tctacctctt cacaggccat gacaacgacg gctctaccga cttcaacatg     180
acagactggc gtctcttctc gtcagcagac atggtcaact ggcagcacca tggtgtcccc     240
atgagcttaa agaccttcag ctgggccaac agcagagcct gggctggtca agtcgttgcc     300
cgaaacggaa agttttactt ctatgttcct gtccgtaatg ccaagacggg tggaatggct     360
attggtgtcg gtgttagtac caacatcctt gggccctaca ctgatgccct ggaaagcca      420
ttggtcgaga caatgagat cgacccaact gtctacatcg acactgatgg ccaggcctat     480
ctctactggg caaccctgg attgtactac gtcaagctca accaagacat gctctcctac     540
agtggtagca tcaacaaagt atcgctcaca acagctggat tcggcagccg cccgaacaac     600
gcgcagcgtc ctactacttt cgaggaagga ccgtggctgt acaagcgtgg aaatctctac     660
tacatgatct acgcagccaa ctgctgttcc gaggacattc gctactcaac tggacccagc     720
gccactggac cttggactta ccgcggtgtc gtgatgaaca aggcgggtcg aagcttcacc     780
aaccatcctg gcatcatcga cttttgagaac aactcgtact tcttttacca caatggcgct    840
cttgatggag gtagcggtta tactcggtct gtggctgtcg agagcttcaa gtatggttcg     900
gacggtctga tccccgagat caagatgact acgcaaggcc agcgcagct caagtctctg     960
aacccatatg tcaagcagga ggccgagact atcgcctggt ctgagggtat cgagactgag    1020
gtctgcagcg aaggtggtct caacgttgct ttcatcgaca atggtgacta catcaaggtc    1080
aagggagtcg actttggcag caccggtgca aagacgttca gcgcccgtgt tgcttccaac    1140
agcagcggag gcaagattga gcttcgactt ggtagcaaga ccggtaagtt ggttggtacc    1200
tgcacggtaa cgactacggg aaactggcag acttataaga ctgtggattg ccccgtcagt    1260
ggtgctactg gtacgagcga tctattcttt gtcttcacgg gctctgggtc tggctctctg    1320
ttcaacttca actggtggca gtttagctaa                                       1350
```

<210> SEQ ID NO 10
<211> LENGTH: 449
<212> TYPE: PRT
<213> ORGANISM: Fusarium verticillioides

<400> SEQUENCE: 10

```
Met Trp Leu Thr Ser Pro Leu Leu Phe Ala Ser Thr Leu Leu Gly Leu
1               5                   10                  15

Thr Gly Val Ala Leu Ala Asp Asn Pro Ile Val Gln Asp Ile Tyr Thr
            20                  25                  30

Ala Asp Pro Ala Pro Met Val Tyr Asn Gly Arg Val Tyr Leu Phe Thr
        35                  40                  45

Gly His Asp Asn Asp Gly Ser Thr Asp Phe Asn Met Thr Asp Trp Arg
    50                  55                  60

Leu Phe Ser Ser Ala Asp Met Val Asn Trp Gln His Gly Val Pro
65                  70                  75                  80

Met Ser Leu Lys Thr Phe Ser Trp Ala Asn Ser Arg Ala Trp Ala Gly
                85                  90                  95

Gln Val Val Ala Arg Asn Gly Lys Phe Tyr Phe Tyr Val Pro Val Arg
            100                 105                 110

Asn Ala Lys Thr Gly Gly Met Ala Ile Gly Val Gly Val Ser Thr Asn
```

```
            115                 120                 125
Ile Leu Gly Pro Tyr Thr Asp Ala Leu Gly Lys Pro Leu Val Glu Asn
130                 135                 140

Asn Glu Ile Asp Pro Thr Val Tyr Ile Asp Thr Asp Gly Gln Ala Tyr
145                 150                 155                 160

Leu Tyr Trp Gly Asn Pro Gly Leu Tyr Tyr Val Lys Leu Asn Gln Asp
                165                 170                 175

Met Leu Ser Tyr Ser Gly Ser Ile Asn Lys Val Ser Leu Thr Thr Ala
                180                 185                 190

Gly Phe Gly Ser Arg Pro Asn Asn Ala Gln Arg Pro Thr Thr Phe Glu
                195                 200                 205

Glu Gly Pro Trp Leu Tyr Lys Arg Gly Asn Leu Tyr Tyr Met Ile Tyr
210                 215                 220

Ala Ala Asn Cys Cys Ser Glu Asp Ile Arg Tyr Ser Thr Gly Pro Ser
225                 230                 235                 240

Ala Thr Gly Pro Trp Thr Tyr Arg Gly Val Val Met Asn Lys Ala Gly
                245                 250                 255

Arg Ser Phe Thr Asn His Pro Gly Ile Ile Asp Phe Glu Asn Asn Ser
                260                 265                 270

Tyr Phe Phe Tyr His Asn Gly Ala Leu Asp Gly Ser Gly Tyr Thr
                275                 280                 285

Arg Ser Val Ala Val Glu Ser Phe Lys Tyr Gly Ser Asp Gly Leu Ile
                290                 295                 300

Pro Glu Ile Lys Met Thr Thr Gln Gly Pro Ala Gln Leu Lys Ser Leu
305                 310                 315                 320

Asn Pro Tyr Val Lys Gln Glu Ala Glu Thr Ile Ala Trp Ser Glu Gly
                325                 330                 335

Ile Glu Thr Glu Val Cys Ser Glu Gly Gly Leu Asn Val Ala Phe Ile
                340                 345                 350

Asp Asn Gly Asp Tyr Ile Lys Val Lys Gly Val Asp Phe Gly Ser Thr
                355                 360                 365

Gly Ala Lys Thr Phe Ser Ala Arg Val Ala Ser Asn Ser Ser Gly Gly
370                 375                 380

Lys Ile Glu Leu Arg Leu Gly Ser Lys Thr Gly Lys Leu Val Gly Thr
385                 390                 395                 400

Cys Thr Val Thr Thr Thr Gly Asn Trp Gln Thr Tyr Lys Thr Val Asp
                405                 410                 415

Cys Pro Val Ser Gly Ala Thr Gly Thr Ser Asp Leu Phe Phe Val Phe
                420                 425                 430

Thr Gly Ser Gly Ser Gly Ser Leu Phe Asn Phe Asn Trp Trp Gln Phe
                435                 440                 445

Ser
```

<210> SEQ ID NO 11
<211> LENGTH: 1725
<212> TYPE: DNA
<213> ORGANISM: Fusarium verticillioides

<400> SEQUENCE: 11
atgcgcttct cttggctatt gtgccccctt ctagcgatgg gaagtgctct tcctgaaacg    60
aagacggatg tttcgacata caccaaccct gtccttccag gatggcactc ggatccatcg   120
tgtatccaga aagatggcct ctttctctgc gtcacttcaa cattcatctc cttcccaggt   180
cttcccgtct atgcctcaag ggatctagtc aactggcgtc tcatcagcca tgtctggaac   240

```
cgcgagaaac agttgcctgg cattagctgg aagacggcag acagcaaca gggaatgtat       300 gcaccaacca ttcgatacca caagggaaca tactacgtca tctgcgaata cctgggcgtt       360
ggagatatta ttggtgtcat cttcaagacc accaatccgt gggacgagag tagctggagt       420
gaccctgtta ccttcaagcc aaatcacatc gaccccgatc tgttctggga tgatgacgga       480
aaggtttatt gtgctaccca tggcatcact ctgcaggaga ttgatttgga aactggagag       540
cttagcccgg agcttaatat ctggaacggc acaggaggtg tatggcctga gggtccccat       600
atctacaagc gcgacggtta ctactatctc atgattgccg agggtggaac tgccgaagac       660
cacgctatca caatcgctcg ggcccgcaag atcaccggcc cctatgaagc ctacaataac       720
aacccaatct tgaccaaccg cgggacatct gagtacttcc agactgtcgg tcacggtgat       780
ctgttccaag ataccaaggg caactggtgg ggtctttgtc ttgctactcg catcacagca       840
cagggagttt cacccatggg ccgtgaagct gttttgttca atggcacatg gaacaagggc       900
gaatggccca agttgcaacc agtacgaggt cgcatgcctg gaaacctcct cccaaagccg       960
acgcgaaacg ttcccggaga tgggcccttc aacgctgacc cagacaacta caacttgaag      1020
aagactaaga agatccctcc tcactttgtg caccatagag tcccaagaga cggtgccttc      1080
tctttgtctt ccaagggtct gcacatcgtg cctagtcgaa caacgttac cggtagtgtg      1140 ttgccaggag atgagattga gctatcagga cagcgaggtc tagctttcat cggacgccgc      1200
caaactcaca ctctgttcaa atatagtgtt gatatcgact tcaagcccaa gtccgatgat      1260
caggaagctg gaatcaccgt tttccgcacg cagttcgacc atatcgatct tggcattgtt      1320
cgtcttccta caaaccaagg cagcaacaag aaatctaagc ttgccttccg attccgggcc      1380
acaggagctc agaatgttcc tgcaccgaag gtagtaccgg tccccgatgg ctgggagaag      1440
ggcgtaatca gtctacatat cgaggcagcc aacgcgacgc actacaacct tggagcttcg      1500
agccacagag gcaagactct cgacatcgcg acagcatcag caagtcttgt gagtggaggc      1560
acgggttcat tgttggtag tttgcttgga ccttatgcta cctgcaacgg caaaggatct      1620
ggagtggaat gtcccaaggg aggtgatgtc tatgtgaccc aatggactta taagcccgtg      1680
gcacaagaga ttgatcatgg tgtttttgtg aaatcagaat tgtag                      1725
```

<210> SEQ ID NO 12
<211> LENGTH: 574
<212> TYPE: PRT
<213> ORGANISM: Fusarium verticillioides

<400> SEQUENCE: 12

```
Met Arg Phe Ser Trp Leu Leu Cys Pro Leu Leu Ala Met Gly Ser Ala
1               5                   10                  15

Leu Pro Glu Thr Lys Thr Asp Val Ser Thr Tyr Thr Asn Pro Val Leu
            20                  25                  30

Pro Gly Trp His Ser Asp Pro Ser Cys Ile Gln Lys Asp Gly Leu Phe
        35                  40                  45

Leu Cys Val Thr Ser Thr Phe Ile Ser Phe Pro Gly Leu Pro Val Tyr
    50                  55                  60

Ala Ser Arg Asp Leu Val Asn Trp Arg Leu Ile Ser His Val Trp Asn
65                  70                  75                  80

Arg Glu Lys Gln Leu Pro Gly Ile Ser Trp Lys Thr Ala Gly Gln Gln
                85                  90                  95

Gln Gly Met Tyr Ala Pro Thr Ile Arg Tyr His Lys Gly Thr Tyr Tyr
            100                 105                 110
```

```
Val Ile Cys Glu Tyr Leu Gly Val Gly Asp Ile Ile Gly Val Ile Phe
        115                 120                 125

Lys Thr Thr Asn Pro Trp Asp Glu Ser Ser Trp Ser Asp Pro Val Thr
        130                 135                 140

Phe Lys Pro Asn His Ile Asp Pro Asp Leu Phe Trp Asp Asp Asp Gly
145                 150                 155                 160

Lys Val Tyr Cys Ala Thr His Gly Ile Thr Leu Gln Glu Ile Asp Leu
                165                 170                 175

Glu Thr Gly Glu Leu Ser Pro Glu Leu Asn Ile Trp Asn Gly Thr Gly
                180                 185                 190

Gly Val Trp Pro Glu Gly Pro His Ile Tyr Lys Arg Asp Gly Tyr Tyr
                195                 200                 205

Tyr Leu Met Ile Ala Glu Gly Gly Thr Ala Glu Asp His Ala Ile Thr
        210                 215                 220

Ile Ala Arg Ala Arg Lys Ile Thr Gly Pro Tyr Glu Ala Tyr Asn Asn
225                 230                 235                 240

Asn Pro Ile Leu Thr Asn Arg Gly Thr Ser Glu Tyr Phe Gln Thr Val
                245                 250                 255

Gly His Gly Asp Leu Phe Gln Asp Thr Lys Gly Asn Trp Trp Gly Leu
                260                 265                 270

Cys Leu Ala Thr Arg Ile Thr Ala Gln Gly Val Ser Pro Met Gly Arg
                275                 280                 285

Glu Ala Val Leu Phe Asn Gly Thr Trp Asn Lys Gly Glu Trp Pro Lys
        290                 295                 300

Leu Gln Pro Val Arg Gly Arg Met Pro Gly Asn Leu Leu Pro Lys Pro
305                 310                 315                 320

Thr Arg Asn Val Pro Gly Asp Gly Pro Phe Asn Ala Asp Pro Asp Asn
                325                 330                 335

Tyr Asn Leu Lys Lys Thr Lys Lys Ile Pro Pro His Phe Val His His
                340                 345                 350

Arg Val Pro Arg Asp Gly Ala Phe Ser Leu Ser Ser Lys Gly Leu His
                355                 360                 365

Ile Val Pro Ser Arg Asn Asn Val Thr Gly Ser Val Leu Pro Gly Asp
        370                 375                 380

Glu Ile Glu Leu Ser Gly Gln Arg Gly Leu Ala Phe Ile Gly Arg Arg
385                 390                 395                 400

Gln Thr His Thr Leu Phe Lys Tyr Ser Val Asp Ile Asp Phe Lys Pro
                405                 410                 415

Lys Ser Asp Asp Gln Glu Ala Gly Ile Thr Val Phe Arg Thr Gln Phe
                420                 425                 430

Asp His Ile Asp Leu Gly Ile Val Arg Leu Pro Thr Asn Gln Gly Ser
                435                 440                 445

Asn Lys Lys Ser Lys Leu Ala Phe Arg Phe Arg Ala Thr Gly Ala Gln
450                 455                 460

Asn Val Pro Ala Pro Lys Val Val Pro Val Pro Asp Gly Trp Glu Lys
465                 470                 475                 480

Gly Val Ile Ser Leu His Ile Glu Ala Ala Asn Ala Thr His Tyr Asn
                485                 490                 495

Leu Gly Ala Ser Ser His Arg Gly Lys Thr Leu Asp Ile Ala Thr Ala
                500                 505                 510

Ser Ala Ser Leu Val Ser Gly Gly Thr Gly Ser Phe Val Gly Ser Leu
                515                 520                 525
```

| | | | | | | | | | | | | |
|---|---|---|---|---|---|---|---|---|---|---|---|---|
| Leu | Gly | Pro | Tyr | Ala | Thr | Cys | Asn | Gly | Lys | Gly | Ser | Gly | Val | Glu | Cys |
| | | 530 | | | | 535 | | | | 540 | | | |

| Pro | Lys | Gly | Gly | Asp | Val | Tyr | Val | Thr | Gln | Trp | Thr | Tyr | Lys | Pro | Val |
| 545 | | | | | 550 | | | | | 555 | | | | | 560 |

| Ala | Gln | Glu | Ile | Asp | His | Gly | Val | Phe | Val | Lys | Ser | Glu | Leu |
| | | | | 565 | | | | | 570 | | | | |

<210> SEQ ID NO 13
<211> LENGTH: 2251
<212> TYPE: DNA
<213> ORGANISM: Podospora anserina

<400> SEQUENCE: 13

```
atgatccacc tcaagccagc cctcgcggcg ttgttggcgc tgtcgacgca atgtgtggct    60
attgatttgt tgtcaagtc ttcgggggg aataagacga ctgatatcat gtatggtctt   120
atgcacgagg tatgtgtttt gcgagatctc ccttttgttt ttgcgcactg ctgacatgga   180
gactgcaaac aggatatcaa caactccggc gacggcggca tctacgccga gctaatctcc   240
aaccgcgcgt tccaagggag tgagaagttc ccctccaacc tcgacaactg gagccccgtc   300
ggtggcgcta cccttaccct tcagaagctt gccaagcccc tttcctctgc gttgccttac   360
tccgtcaatg ttgccaaccc caaggagggc aagggcaagg gcaaggacac caaggggaag   420
aaggttggct tggccaatgc tgggttttgg ggtatggatg tcaagaggca gaagtacact   480
ggtagcttcc acgttactgg tgagtacaag ggtgactttg aggttagctt gcgcagcgcg   540
attaccgggg agacctttgg caagaaggtg gtgaagggtg gagtaagaa ggggaagtgg   600
accgagaagg agtttgagtt ggtgcctttc aaggatgcgc ccaacagcaa caacaccttt   660
gttgtgcagt gggatgccga ggtatgtgct tctttgatat tggctgagat agaagttggg   720
ttgacatgat gtggtgcagg gcgcaaagga cggatctttg gatctcaact tgatcagctt   780
gttccctccg acattcaagg gaaggaagaa tgggctgaga attgatcttg cgcagacgat   840
ggttgagctc aagccggtaa gtcctctcta gtcagaaaag tagagccttt gttaacgctt   900
gacagacctt cttgcgcttc cccggtggca acatgctcga gggtaacacc ttggacactt   960
ggtggaagtg gtacgagacc attggccctc tgaaggatcg cccgggcatg gctggtgtct  1020
gggagtacca gcaaaccctt ggcttgggtc tggtcgagta catggagtgg gccgatgaca  1080
tgaacttgga gcccagtatg tgatcccatt ttctggagtg acttctcttg ctaacgtatc  1140
cacagttgtc ggtgtcttcg ctggtcttgc cctcgatggc tcgttcgttc ccgaatccga  1200
gatgggatgg gtcatccaac aggctctcga cgaaatcgag ttcctcactg gcgatgctaa  1260
gaccaccaaa tggggtgccg tccgcgcgaa gcttggtcac cccaagcctt ggaaggtcaa  1320
gtgggttgag atcggtaacg aggattggct tgccggacgc cctgctggct tcagtcgta   1380
catcaactac cgcttcccca tgatgatgaa ggccttcaac gaaaagtacc ccgacatcaa  1440
gatcatcgcc tcgccctcca tcttcgacaa catgacaatc cccgcgggtg ctgccggtga  1500
tcaccacccg tacctgactc ccgatgagtt cgttgagcga ttcgccaagt tcgataactt  1560
gagcaaggat aacgtgacgc tcatcggcga ggctgcgtcg acgcatccta acggtggtat  1620
cgcttgggag ggagatctca tgcccttgcc ttggtgggc gcagtgttg ctgaggctat  1680
cttcttgatc agcactgaga gaaacggtga caagatcatc ggtgctactt acgcgcctgg  1740
tcttcgcagc ttggaccgct ggcaatggag catgacctgg gtgcagcatg ccgccgaccc  1800
ggcccctcacc actcgctcga ccagttggta tgtctggaga atcctcgccc accacatcat  1860
```

-continued

```
ccgtgagacg ctcccggtcg atgccccggc cggcaagccc aactttgacc ctctgttcta    1920
cgttgccgga aagagcgaga gtggcaccgg tatcttcaag gctgccgtct acaactcgac    1980
tgaatcgatc ccggtgtcgt tgaagtttga tggtctcaac gagggagcgg ttgccaactt    2040
gacggtgctt actgggccgg aggatccgta tggatacaac gacccttca ctggtatcaa     2100 tgttgtcaag gagaagacca ccttcatcaa ggccggaaag ggcggcaagt tcaccttcac    2160
cctgccgggc ttgagtgttg ctgtgttgga gacggccgac gcggtcaagg gtggcaaggg    2220
aaagggcaag ggcaagggaa agggtaactg a                                    2251
```

<210> SEQ ID NO 14
<211> LENGTH: 676
<212> TYPE: PRT
<213> ORGANISM: Podospora anserina

<400> SEQUENCE: 14

```
Met Ile His Leu Lys Pro Ala Leu Ala Ala Leu Leu Ala Leu Ser Thr
1               5                   10                  15

Gln Cys Val Ala Ile Asp Leu Phe Val Lys Ser Ser Gly Gly Asn Lys
            20                  25                  30

Thr Thr Asp Ile Met Tyr Gly Leu Met His Glu Asp Ile Asn Asn Ser
        35                  40                  45

Gly Asp Gly Gly Ile Tyr Ala Glu Leu Ile Ser Asn Arg Ala Phe Gln
    50                  55                  60

Gly Ser Glu Lys Phe Pro Ser Asn Leu Asp Asn Trp Ser Pro Val Gly
65                  70                  75                  80

Gly Ala Thr Leu Thr Leu Gln Lys Leu Ala Lys Pro Leu Ser Ser Ala
                85                  90                  95

Leu Pro Tyr Ser Val Asn Val Ala Asn Pro Lys Glu Gly Lys Gly Lys
            100                 105                 110

Gly Lys Asp Thr Lys Gly Lys Lys Val Gly Leu Ala Asn Ala Gly Phe
        115                 120                 125

Trp Gly Met Asp Val Lys Arg Gln Lys Tyr Thr Gly Ser Phe His Val
    130                 135                 140

Thr Gly Glu Tyr Lys Gly Asp Phe Glu Val Ser Leu Arg Ser Ala Ile
145                 150                 155                 160

Thr Gly Glu Thr Phe Gly Lys Lys Val Val Lys Gly Gly Ser Lys Lys
                165                 170                 175

Gly Lys Trp Thr Glu Lys Glu Phe Glu Leu Val Pro Phe Lys Asp Ala
            180                 185                 190

Pro Asn Ser Asn Asn Thr Phe Val Gln Trp Asp Ala Glu Gly Ala
        195                 200                 205

Lys Asp Gly Ser Leu Asp Leu Asn Leu Ile Ser Leu Phe Pro Pro Thr
    210                 215                 220

Phe Lys Gly Arg Lys Asn Gly Leu Arg Ile Asp Leu Ala Gln Thr Met
225                 230                 235                 240

Val Glu Leu Lys Pro Thr Phe Leu Arg Phe Pro Gly Gly Asn Met Leu
                245                 250                 255

Glu Gly Asn Thr Leu Asp Thr Trp Trp Lys Trp Tyr Glu Thr Ile Gly
            260                 265                 270

Pro Leu Lys Asp Arg Pro Gly Met Ala Gly Val Trp Glu Tyr Gln Gln
        275                 280                 285

Thr Leu Gly Leu Gly Leu Val Glu Tyr Met Glu Trp Ala Asp Asp Met
    290                 295                 300
```

Asn Leu Glu Pro Ile Val Gly Val Phe Ala Gly Leu Ala Leu Asp Gly
305                 310                 315                 320

Ser Phe Val Pro Glu Ser Glu Met Gly Trp Val Ile Gln Gln Ala Leu
            325                 330                 335

Asp Glu Ile Glu Phe Leu Thr Gly Asp Ala Lys Thr Thr Lys Trp Gly
            340                 345                 350

Ala Val Arg Ala Lys Leu Gly His Pro Lys Pro Trp Lys Val Lys Trp
            355                 360                 365

Val Glu Ile Gly Asn Glu Asp Trp Leu Ala Gly Arg Pro Ala Gly Phe
            370                 375                 380

Glu Ser Tyr Ile Asn Tyr Arg Phe Pro Met Met Met Lys Ala Phe Asn
385                 390                 395                 400

Glu Lys Tyr Pro Asp Ile Lys Ile Ile Ala Ser Pro Ser Ile Phe Asp
            405                 410                 415

Asn Met Thr Ile Pro Ala Gly Ala Ala Gly Asp His His Pro Tyr Leu
            420                 425                 430

Thr Pro Asp Glu Phe Val Glu Arg Phe Ala Lys Phe Asp Asn Leu Ser
            435                 440                 445

Lys Asp Asn Val Thr Leu Ile Gly Glu Ala Ala Ser Thr His Pro Asn
450                 455                 460

Gly Gly Ile Ala Trp Glu Gly Asp Leu Met Pro Leu Pro Trp Trp Gly
465                 470                 475                 480

Gly Ser Val Ala Glu Ala Ile Phe Leu Ile Ser Thr Glu Arg Asn Gly
            485                 490                 495

Asp Lys Ile Ile Gly Ala Thr Tyr Ala Pro Gly Leu Arg Ser Leu Asp
            500                 505                 510

Arg Trp Gln Trp Ser Met Thr Trp Val Gln His Ala Ala Asp Pro Ala
            515                 520                 525

Leu Thr Thr Arg Ser Thr Ser Trp Tyr Val Trp Arg Ile Leu Ala His
            530                 535                 540

His Ile Ile Arg Glu Thr Leu Pro Val Asp Ala Pro Ala Gly Lys Pro
545                 550                 555                 560

Asn Phe Asp Pro Leu Phe Tyr Val Ala Gly Lys Ser Glu Ser Gly Thr
            565                 570                 575

Gly Ile Phe Lys Ala Ala Val Tyr Asn Ser Thr Glu Ser Ile Pro Val
            580                 585                 590

Ser Leu Lys Phe Asp Gly Leu Asn Glu Gly Ala Val Ala Asn Leu Thr
            595                 600                 605

Val Leu Thr Gly Pro Glu Asp Pro Tyr Gly Tyr Asn Asp Pro Phe Thr
610                 615                 620

Gly Ile Asn Val Val Lys Glu Lys Thr Thr Phe Ile Lys Ala Gly Lys
625                 630                 635                 640

Gly Gly Lys Phe Thr Phe Thr Leu Pro Gly Leu Ser Val Ala Val Leu
            645                 650                 655

Glu Thr Ala Asp Ala Val Lys Gly Gly Lys Gly Lys Gly Lys Gly Lys
            660                 665                 670

Gly Lys Gly Asn
675

<210> SEQ ID NO 15
<211> LENGTH: 1023
<212> TYPE: DNA
<213> ORGANISM: Gibberella zeae

<400> SEQUENCE: 15

```
atgaagtcca agttgttatt cccactcctc tctttcgttg gtcaaagtct tgccaccaac    60
gacgactgtc ctctcatcac tagtagatgg actgcggatc cttcggctca tgtctttaac   120
gacaccttgt ggctctaccc gtctcatgac atcgatgctg gatttgagaa tgatcctgat   180
ggaggccagt acgccatgag agattaccat gtctactcta tcgacaagat ctacggttcc   240
ctgccggtcg atcacggtac ggccctgtca gtggaggatg tccctgggc ctctcgacag    300
atgtgggctc ctgacgctgc ccacaagaac ggcaaatact acctatactt ccctgccaaa   360
gacaaggatg atatcttcag aatcggcgtt gctgtctcac caaccccgg cggaccattc    420
gtccccgaca gagttggat ccctcacact ttcagcatcg accccgccag tttcgtcgat    480
gatgatgaca gagcctactt ggcatggggt ggtatcatgg gtggccagct caacgatgg    540
caggataaga acaagtacaa cgaatctggc actgagccag aaacggcac cgctgccttg    600
agccctcaga ttgccaagct gagcaaggac atgcacactc tggcagagaa gcctcgcgac   660
atgctcattc ttgaccccaa gactggcaag ccgctccttt ctgaggatga agaccgacgc   720
ttcttcgaag accctggat tcacaagcgc aacaagattt actacctcac ctactctact   780
ggcacaaccc actatcttgt ctatgcgact caaagaccc cctatggtcc ttacacctac    840
cagggcagaa ttctggagcc agttgatggc tggactactc actctagtat cgtcaagtac    900
cagggtcagt ggtggctatt ttatcacgat gccaagacat ctggcaagga ctatcttcgc    960
caggtaaagg ctaagaagat ttggtacgat agcaaaggaa agatcttgac aaagaagcct   1020
tga                                                                 1023
```

<210> SEQ ID NO 16
<211> LENGTH: 340
<212> TYPE: PRT
<213> ORGANISM: Gibberella zeae

<400> SEQUENCE: 16

```
Met Lys Ser Lys Leu Leu Phe Pro Leu Leu Ser Phe Val Gly Gln Ser
1               5                   10                  15

Leu Ala Thr Asn Asp Asp Cys Pro Leu Ile Thr Ser Arg Trp Thr Ala
            20                  25                  30

Asp Pro Ser Ala His Val Phe Asn Asp Thr Leu Trp Leu Tyr Pro Ser
        35                  40                  45

His Asp Ile Asp Ala Gly Phe Glu Asn Asp Pro Asp Gly Gly Gln Tyr
    50                  55                  60

Ala Met Arg Asp Tyr His Val Tyr Ser Ile Asp Lys Ile Tyr Gly Ser
65                  70                  75                  80

Leu Pro Val Asp His Gly Thr Ala Leu Ser Val Glu Asp Val Pro Trp
                85                  90                  95

Ala Ser Arg Gln Met Trp Ala Pro Asp Ala Ala His Lys Asn Gly Lys
            100                 105                 110

Tyr Tyr Leu Tyr Phe Pro Ala Lys Asp Lys Asp Ile Phe Arg Ile
        115                 120                 125

Gly Val Ala Val Ser Pro Thr Pro Gly Gly Pro Phe Val Pro Asp Lys
    130                 135                 140

Ser Trp Ile Pro His Thr Phe Ser Ile Asp Pro Ala Ser Phe Val Asp
145                 150                 155                 160

Asp Asp Asp Arg Ala Tyr Leu Ala Trp Gly Gly Ile Met Gly Gly Gln
                165                 170                 175

Leu Gln Arg Trp Gln Asp Lys Asn Lys Tyr Asn Glu Ser Gly Thr Glu
```

```
            180                 185                 190
Pro Gly Asn Gly Thr Ala Ala Leu Ser Pro Gln Ile Ala Lys Leu Ser
            195                 200                 205

Lys Asp Met His Thr Leu Ala Glu Lys Pro Arg Asp Met Leu Ile Leu
    210                 215                 220

Asp Pro Lys Thr Gly Lys Pro Leu Leu Ser Glu Asp Glu Asp Arg Arg
225                 230                 235                 240

Phe Phe Glu Gly Pro Trp Ile His Lys Arg Asn Lys Ile Tyr Tyr Leu
                245                 250                 255

Thr Tyr Ser Thr Gly Thr Thr His Tyr Leu Val Tyr Ala Thr Ser Lys
            260                 265                 270

Thr Pro Tyr Gly Pro Tyr Thr Tyr Gln Gly Arg Ile Leu Glu Pro Val
        275                 280                 285

Asp Gly Trp Thr Thr His Ser Ser Ile Val Lys Tyr Gln Gly Gln Trp
            290                 295                 300

Trp Leu Phe Tyr His Asp Ala Lys Thr Ser Gly Lys Asp Tyr Leu Arg
305                 310                 315                 320

Gln Val Lys Ala Lys Lys Ile Trp Tyr Asp Ser Lys Gly Lys Ile Leu
                325                 330                 335

Thr Lys Lys Pro
            340

<210> SEQ ID NO 17
<211> LENGTH: 1047
<212> TYPE: DNA
<213> ORGANISM: Fusarium oxysporum

<400> SEQUENCE: 17
atgcagctca agtttctgtc ttcagcattg ctgttctctc tgaccagcaa atgcgctgcg      60
caagacacta atgacattcc tccctgatc accgacctct ggtccgcaga tccctcggct     120
catgttttcg aaggcaagct ctgggtttac ccatctcacg acatcgaagc caatgttgtc     180
aacggcacag gaggcgctca atacgccatg agggattacc ataccctactc catgaagagc    240 atctatggta aagatcccgt tgtcgaccac ggcgtcgctc tctcagtcga tgacgttccc     300
tgggcgaagc agcaaatgtg ggctcctgac gcagctcata gaacggcaa atattatctg      360 tacttccccg ccaaggacaa ggatgagatc ttcagaattg gagttgctgt ctccaacaag     420
cccagcggtc ctttcaaggc cgacaagagc tggatccctg gcacgtacag tatcgatcct     480
gctagctacg tcgacactga taacgaggcc tacctcatct ggggcggtat ctggggcggc     540
cagctccaag cctggcagga taaaaagaac tttaacgagt cgtggattgg agacaaggct    600
gctcctaacg gcaccaatgc cctatctcct cagatcgcca agctaagcaa ggacatgcac     660
aagatcaccg aaacaccccg cgatctcgtc attctcgccc ccgagacagg caagcctctt     720
caggctgagg acaacaagcg acgattcttc gagggcccct tggatccacaa gcgcggcaag    780 ctttactacc tcatgtactc caccggtgat acccacttcc ttgtctacgc tacttccaag     840
aacatctacg gtccttatac ctaccggggc aagattcttg atcctgttga tgggtggact     900
actcatggaa gtattgttga gtataaggga cagtggtggc ttttctttgc tgatgcgcat     960
acgtctggta aggattacct tcgacaggtg aaggcgagga agatctggta tgacaagaac    1020
ggcaagatct tgcttcaccg tccttag                                        1047

<210> SEQ ID NO 18
<211> LENGTH: 348
```

<212> TYPE: PRT
<213> ORGANISM: Fusarium oxysporum

<400> SEQUENCE: 18

Met Gln Leu Lys Phe Leu Ser Ser Ala Leu Leu Phe Ser Leu Thr Ser
1               5                   10                  15

Lys Cys Ala Ala Gln Asp Thr Asn Asp Ile Pro Pro Leu Ile Thr Asp
            20                  25                  30

Leu Trp Ser Ala Asp Pro Ser Ala His Val Phe Glu Gly Lys Leu Trp
        35                  40                  45

Val Tyr Pro Ser His Asp Ile Glu Ala Asn Val Val Asn Gly Thr Gly
    50                  55                  60

Gly Ala Gln Tyr Ala Met Arg Asp Tyr His Thr Tyr Ser Met Lys Ser
65                  70                  75                  80

Ile Tyr Gly Lys Asp Pro Val Val Asp His Gly Val Ala Leu Ser Val
                85                  90                  95

Asp Asp Val Pro Trp Ala Lys Gln Gln Met Trp Ala Pro Asp Ala Ala
            100                 105                 110

His Lys Asn Gly Lys Tyr Tyr Leu Tyr Phe Pro Ala Lys Asp Lys Asp
        115                 120                 125

Glu Ile Phe Arg Ile Gly Val Ala Val Ser Asn Lys Pro Ser Gly Pro
130                 135                 140

Phe Lys Ala Asp Lys Ser Trp Ile Pro Gly Thr Tyr Ser Ile Asp Pro
145                 150                 155                 160

Ala Ser Tyr Val Asp Thr Asp Asn Glu Ala Tyr Leu Ile Trp Gly Gly
                165                 170                 175

Ile Trp Gly Gly Gln Leu Gln Ala Trp Gln Asp Lys Lys Asn Phe Asn
            180                 185                 190

Glu Ser Trp Ile Gly Asp Lys Ala Pro Asn Gly Thr Asn Ala Leu
        195                 200                 205

Ser Pro Gln Ile Ala Lys Leu Ser Lys Asp Met His Lys Ile Thr Glu
    210                 215                 220

Thr Pro Arg Asp Leu Val Ile Leu Ala Pro Glu Thr Gly Lys Pro Leu
225                 230                 235                 240

Gln Ala Glu Asp Asn Lys Arg Arg Phe Phe Glu Gly Pro Trp Ile His
                245                 250                 255

Lys Arg Gly Lys Leu Tyr Tyr Leu Met Tyr Ser Thr Gly Asp Thr His
            260                 265                 270

Phe Leu Val Tyr Ala Thr Ser Lys Asn Ile Tyr Gly Pro Tyr Thr Tyr
        275                 280                 285

Arg Gly Lys Ile Leu Asp Pro Val Asp Gly Trp Thr Thr His Gly Ser
290                 295                 300

Ile Val Glu Tyr Lys Gly Gln Trp Trp Leu Phe Phe Ala Asp Ala His
305                 310                 315                 320

Thr Ser Gly Lys Asp Tyr Leu Arg Gln Val Lys Ala Arg Lys Ile Trp
                325                 330                 335

Tyr Asp Lys Asn Gly Lys Ile Leu Leu His Arg Pro
            340                 345

<210> SEQ ID NO 19
<211> LENGTH: 1677
<212> TYPE: DNA
<213> ORGANISM: Aspergillus fumigatus

<400> SEQUENCE: 19

| | |
|---|---|
| atggcagctc caagtttatc ctaccccaca ggtatccaat cgtataccaa tcctctcttc | 60 |
| cctggttggc actccgatcc cagctgtgcc tacgtagcgg agcaagacac ctttttctgc | 120 |
| gtgacgtcca ctttcattgc cttccccggt cttcctcttt atgcaagccg agatctgcag | 180 |
| aactggaaac tggcaagcaa tattttcaat cggcccagcc agatccctga tcttcgcgtc | 240 |
| acggatggac agcagtcggg tatctatgcg cccactctgc gctatcatga gggccagttc | 300 |
| tacttgatcg tttcgtacct gggcccgcag actaagggct tgctgttcac ctcgtctgat | 360 |
| ccgtacgacg atgccgcgtg gagcgatccg ctcgaattcg cggtacatgg catcgacccg | 420 |
| gatatcttct gggatcacga cgggacggtc tatgtcacgt ccgccgagga ccagatgatt | 480 |
| aagcagtaca cactcgatct gaagacgggg gcgattggcc cggttgacta cctctggaac | 540 |
| ggcaccggag gagtctggcc cgagggcccg cacatttaca agagagacgg atactactac | 600 |
| ctcatgatcg cagagggagg taccgagctc ggccactcgg agaccatggc gcgatctaga | 660 |
| acccggacag gtccctggga gccatacccg cacaatccgc tcttgtcgaa caagggcacc | 720 |
| tcggagtact ccagactgt gggccatgcg acttgttcc aggatgggaa cggcaactgg | 780 |
| tgggccgtgg cgttgagcac ccgatcaggg cctgcatgga gaactatcc catgggtcgg | 840 |
| gagacggtgc tcgccccgc cgcttgggag aagggtgagt ggcctgtcat tcagcctgtg | 900 |
| agaggccaaa tgcaggggcc gtttccacca ccaaataagc gagttcctcg cggcgagggc | 960 |
| ggatggatca agcaacccga caaagtggat ttcaggcccg gatcgaagat accggcgcac | 1020 |
| ttccagtact ggcgatatcc caagacagag gattttaccg tctcccctcg gggccacccg | 1080 |
| aatactcttc ggctcacacc ctcctttac aacctcaccg gaactgcgga cttcaagccg | 1140 |
| gatgatggcc tgtcgcttgt tatgcgcaaa cagaccgaca ccttgttcac gtacactgtg | 1200 |
| gacgtgtctt tgaccccaa ggttgccgat gaagaggcgg tgtgactgt tttccttacc | 1260 |
| cagcagcagc acatcgatct tggtattgtc cttctccaga caaccgaggg gctgtcgttg | 1320 |
| tccttccggt tccgcgtgga aggccgcggt aactacgaag tcctcttcc agaagccacc | 1380 |
| gtgcctgttc caaggaatg gtgtggacag accatccggc ttgagattca ggccgtgagt | 1440 |
| gacaccgagt atgtctttgc ggctgccccg gctcggcacc ctgcacagag gcaaatcatc | 1500 |
| agccgcgcca actcgttgat tgtcagtggt gatacgggac ggtttactgg ctcgcttgtt | 1560 |
| ggcgtgtatg ccacgtcgaa cgggggtgcc ggatccacgc ccgcatatat cagcagatgg | 1620 |
| agatacgaag gacggggcca gatgattgat tttggtcgag tggtcccgag ctactga | 1677 |

<210> SEQ ID NO 20
<211> LENGTH: 558
<212> TYPE: PRT
<213> ORGANISM: Aspergillus fumigatus

<400> SEQUENCE: 20

Met Ala Ala Pro Ser Leu Ser Tyr Pro Thr Gly Ile Gln Ser Tyr Thr
1               5                   10                  15

Asn Pro Leu Phe Pro Gly Trp His Ser Asp Pro Ser Cys Ala Tyr Val
            20                  25                  30

Ala Glu Gln Asp Thr Phe Phe Cys Val Thr Ser Thr Phe Ile Ala Phe
        35                  40                  45

Pro Gly Leu Pro Leu Tyr Ala Ser Arg Asp Leu Gln Asn Trp Lys Leu
    50                  55                  60

Ala Ser Asn Ile Phe Asn Arg Pro Ser Gln Ile Pro Asp Leu Arg Val
65                  70                  75                  80

-continued

Thr Asp Gly Gln Gln Ser Gly Ile Tyr Ala Pro Thr Leu Arg Tyr His
                    85                  90                  95

Glu Gly Gln Phe Tyr Leu Ile Val Ser Tyr Leu Gly Pro Gln Thr Lys
                100                 105                 110

Gly Leu Leu Phe Thr Ser Ser Asp Pro Tyr Asp Ala Ala Trp Ser
            115                 120                 125

Asp Pro Leu Glu Phe Ala Val His Gly Ile Asp Pro Asp Ile Phe Trp
        130                 135                 140

Asp His Asp Gly Thr Val Tyr Val Thr Ser Glu Ala Asp Gln Met Ile
145                 150                 155                 160

Lys Gln Tyr Thr Leu Asp Leu Lys Thr Gly Ala Ile Gly Pro Val Asp
                165                 170                 175

Tyr Leu Trp Asn Gly Thr Gly Gly Val Trp Pro Glu Gly Pro His Ile
            180                 185                 190

Tyr Lys Arg Asp Gly Tyr Tyr Tyr Leu Met Ile Ala Glu Gly Gly Thr
        195                 200                 205

Glu Leu Gly His Ser Glu Thr Met Ala Arg Ser Arg Thr Arg Thr Gly
    210                 215                 220

Pro Trp Glu Pro Tyr Pro His Asn Pro Leu Leu Ser Asn Lys Gly Thr
225                 230                 235                 240

Ser Glu Tyr Phe Gln Thr Val Gly His Ala Asp Leu Phe Gln Asp Gly
                245                 250                 255

Asn Gly Asn Trp Trp Ala Val Ala Leu Ser Thr Arg Ser Gly Pro Ala
            260                 265                 270

Trp Lys Asn Tyr Pro Met Gly Arg Glu Thr Val Leu Ala Pro Ala Ala
        275                 280                 285

Trp Glu Lys Gly Glu Trp Pro Val Ile Gln Pro Val Arg Gly Gln Met
    290                 295                 300

Gln Gly Pro Phe Pro Pro Asn Lys Arg Val Pro Arg Gly Glu Gly
305                 310                 315                 320

Gly Trp Ile Lys Gln Pro Asp Lys Val Asp Phe Arg Pro Gly Ser Lys
                325                 330                 335

Ile Pro Ala His Phe Gln Tyr Trp Arg Tyr Pro Lys Thr Glu Asp Phe
            340                 345                 350

Thr Val Ser Pro Arg Gly His Pro Asn Thr Leu Arg Leu Thr Pro Ser
        355                 360                 365

Phe Tyr Asn Leu Thr Gly Thr Ala Asp Phe Lys Pro Asp Asp Gly Leu
    370                 375                 380

Ser Leu Val Met Arg Lys Gln Thr Asp Thr Leu Phe Thr Tyr Thr Val
385                 390                 395                 400

Asp Val Ser Phe Asp Pro Lys Val Ala Asp Glu Glu Ala Gly Val Thr
                405                 410                 415

Val Phe Leu Thr Gln Gln Gln His Ile Asp Leu Gly Ile Val Leu Leu
            420                 425                 430

Gln Thr Thr Glu Gly Leu Ser Leu Ser Phe Arg Phe Arg Val Glu Gly
        435                 440                 445

Arg Gly Asn Tyr Glu Gly Pro Leu Pro Glu Ala Thr Val Pro Val Pro
    450                 455                 460

Lys Glu Trp Cys Gly Gln Thr Ile Arg Leu Glu Ile Gln Ala Val Ser
465                 470                 475                 480

Asp Thr Glu Tyr Val Phe Ala Ala Ala Pro Ala Arg His Pro Ala Gln
                485                 490                 495

Arg Gln Ile Ile Ser Arg Ala Asn Ser Leu Ile Val Ser Gly Asp Thr

```
             500                 505                 510
Gly Arg Phe Thr Gly Ser Leu Val Gly Val Tyr Ala Thr Ser Asn Gly
            515                 520                 525

Gly Ala Gly Ser Thr Pro Ala Tyr Ile Ser Arg Trp Arg Tyr Glu Gly
            530                 535                 540

Arg Gly Gln Met Ile Asp Phe Gly Arg Val Val Pro Ser Tyr
545                 550                 555

<210> SEQ ID NO 21
<211> LENGTH: 2320
<212> TYPE: DNA
<213> ORGANISM: Penicillium funiculosum

<400> SEQUENCE: 21
```

| | | | | | |
|---|---|---|---|---|---|
| atgggaaaga | tgtggcattc | gatcttggtt | gtgttgggct | tattgtctgt | cgggcatgcc | 60 |
| atcactatca | acgtgtccca | agtggcggc | aataagacca | gtcctttgca | atatggtctg | 120 |
| atgttcgagg | taatccttct | cttataccac | atataaaagt | tgcgtcattt | ctaagacaag | 180 |
| tcaaggacat | aaatcacggc | ggtgatggcg | gtctgtatgc | agagcttgtt | cgaaaccgag | 240 |
| cattccaagg | tagcaccgtc | tatccagcaa | acctcgatgg | atacgactcg | gtcaatggag | 300 |
| caatcctagc | gcttcagaat | ttgacaaacc | ctctatcacc | ctccatgcct | agctctctca | 360 |
| acgtcgccaa | ggggtccaac | aatggaagca | tcggtttcgc | aaatgaaggc | tggtggggga | 420 |
| tagaagtcaa | gccgcaaaga | tacgcgggct | cattctacgt | ccaggggac | tatcaaggag | 480 |
| atttcgacat | ctctcttcag | tcgaaattga | cacaagaagt | cttcgcaacg | gcaaaagtca | 540 |
| ggtcctcggg | caaacacgag | gactgggttc | aatacaagta | cgagttggtg | cccaaaaagg | 600 |
| cagcatcaaa | caccaataac | actctgacca | ttacttttga | ctcaaaggta | tgttaaattt | 660 |
| tgggtttagt | tcgatgtctg | gcaattgtct | tacgagaaac | gtagggattg | aaagacggat | 720 |
| ccttgaactt | caacttgatc | agcctatttc | ccccaactta | caacaatcgg | cccaatggcc | 780 |
| taagaatcga | cctggttgaa | gctatggctg | aactagaggg | ggtaagctct | tacaaatcaa | 840 |
| ctttatcttt | acgaagacta | atgtgaaaac | ttagaaattt | ctgcggtttc | caggcggtag | 900 |
| cgatgtggaa | ggtgtacaag | ctccttactg | gtataagtga | aatgaaacgg | taggagatct | 960 |
| caaggaccgt | tatagtaggc | ccagtgcatg | gacgtacgaa | gaaagcaatg | gaattggctt | 1020 |
| gattgagtac | atgaattggt | gtgatgacat | ggggcttgag | ccgagtgagt | gtattccatt | 1080 |
| cagcgtcaaa | tccagtgttc | taatcataca | catcagttct | tgccgtatgg | gatggacatt | 1140 |
| acctttcgaa | cgaagtgata | tcggaaaacg | atttgcagcc | atatatcgac | gacaccctca | 1200 |
| accaactgga | attcctgatg | ggtgccccag | atacgccata | tggtagttgg | cgtgcgtctc | 1260 |
| tgggctatcc | gaagccgtgg | acgattaact | acgtcgagat | tggaaacgaa | gacaatctat | 1320 |
| acggggact | agaaacatac | atcgcctacc | ggtttcaggc | atattcgac | gctataacag | 1380 |
| ctaaatatcc | ccatatgacg | gtcatggaat | ctttgacgga | gatgcctggt | ccggcggccg | 1440 |
| ctgcaagcga | ttaccatcaa | tattctactc | ctgatgggtt | tgtttcccag | ttcaactact | 1500 |
| ttgatcagat | gccagtcact | aatagaacac | tgaacggtat | gaaaacccc | cctttttaa | 1560 |
| atatgctttt | aatggtatta | accatctttc | ataggagaga | ttgcaaccgt | ttatccaaat | 1620 |
| aatcctagta | attcggtggc | ctggggaagc | ccattcccct | tgtatccttg | gtggattggg | 1680 |
| tccgttgcag | aagctgtttt | cctaattggt | gaagagagga | attcgccaaa | gataatcggt | 1740 |
| gctagctacg | tacggaattc | tacttttcga | gattttaaca | ttggataaga | aggactaacc | 1800 |

-continued

```
tcaatacagg ctccaatgtt cagaaatatc aacaattggc agtggtctcc aacactcatc    1860
gcttttgacg ctgactcgtc gcgtacaagt cgttcaacaa gctggcatgt gatcaaggta    1920 tgctaattt  cctcctcatt caaacccgca gatgtgagct aactttccga agcttctctc    1980
gacaaacaaa atcacgcaaa atttacccac gacttggagt ggcggtgaca taggtccatt    2040
atactgggta gctggacgaa acgacaatac aggatcgaac atattcaagg ccgctgttta    2100
caacagcacc tcagacgtcc ctgtcaccgt tcaatttgca ggatgcaacg caaagagcgc    2160
aaatttgacc atcttgtcat ccgacgatcc gaacgcatcg aactaccctg ggggcccga    2220 agttgtgaag actgagatcc agtctgtcac tgcaaatgct catggagcat ttgagttcag    2280
tctcccgaac ctaagtgtgg ctgttctcaa aacggagtaa                         2320
```

<210> SEQ ID NO 22
<211> LENGTH: 642
<212> TYPE: PRT
<213> ORGANISM: Penicillium funiculosum

<400> SEQUENCE: 22

```
Met Gly Lys Met Trp His Ser Ile Leu Val Val Gly Leu Leu Ser
1               5                   10                  15

Val Gly His Ala Ile Thr Ile Asn Val Ser Gln Ser Gly Gly Asn Lys
            20                  25                  30

Thr Ser Pro Leu Gln Tyr Gly Leu Met Phe Glu Asp Ile Asn His Gly
        35                  40                  45

Gly Asp Gly Gly Leu Tyr Ala Glu Leu Val Arg Asn Arg Ala Phe Gln
    50                  55                  60

Gly Ser Thr Val Tyr Pro Ala Asn Leu Asp Gly Tyr Asp Ser Val Asn
65                  70                  75                  80

Gly Ala Ile Leu Ala Leu Gln Asn Leu Thr Asn Pro Leu Ser Pro Ser
                85                  90                  95

Met Pro Ser Ser Leu Asn Val Ala Lys Gly Ser Asn Asn Gly Ser Ile
            100                 105                 110

Gly Phe Ala Asn Glu Gly Trp Trp Gly Ile Glu Val Lys Pro Gln Arg
        115                 120                 125

Tyr Ala Gly Ser Phe Tyr Val Gln Gly Asp Tyr Gln Gly Asp Phe Asp
    130                 135                 140

Ile Ser Leu Gln Ser Lys Leu Thr Gln Glu Val Phe Ala Thr Ala Lys
145                 150                 155                 160

Val Arg Ser Ser Gly Lys His Glu Asp Trp Val Gln Tyr Lys Tyr Glu
                165                 170                 175

Leu Val Pro Lys Lys Ala Ala Ser Asn Thr Asn Asn Thr Leu Thr Ile
            180                 185                 190

Thr Phe Asp Ser Lys Gly Leu Lys Asp Gly Ser Leu Asn Phe Asn Leu
        195                 200                 205

Ile Ser Leu Phe Pro Pro Thr Tyr Asn Asn Arg Pro Asn Gly Leu Arg
    210                 215                 220

Ile Asp Leu Val Glu Ala Met Ala Glu Leu Glu Gly Lys Phe Leu Arg
225                 230                 235                 240

Phe Pro Gly Gly Ser Asp Val Glu Gly Val Gln Ala Pro Tyr Trp Tyr
                245                 250                 255

Lys Trp Asn Glu Thr Val Gly Asp Leu Lys Asp Arg Tyr Ser Arg Pro
            260                 265                 270

Ser Ala Trp Thr Tyr Glu Glu Ser Asn Gly Ile Gly Leu Ile Glu Tyr
        275                 280                 285
```

```
Met Asn Trp Cys Asp Asp Met Gly Leu Glu Pro Ile Leu Ala Val Trp
            290                 295                 300

Asp Gly His Tyr Leu Ser Asn Glu Val Ile Ser Glu Asn Asp Leu Gln
305                 310                 315                 320

Pro Tyr Ile Asp Asp Thr Leu Asn Gln Leu Glu Phe Leu Met Gly Ala
                325                 330                 335

Pro Asp Thr Pro Tyr Gly Ser Trp Arg Ala Ser Leu Gly Tyr Pro Lys
            340                 345                 350

Pro Trp Thr Ile Asn Tyr Val Glu Ile Gly Asn Glu Asp Asn Leu Tyr
        355                 360                 365

Gly Gly Leu Glu Thr Tyr Ile Ala Tyr Arg Phe Gln Ala Tyr Tyr Asp
370                 375                 380

Ala Ile Thr Ala Lys Tyr Pro His Met Thr Val Met Glu Ser Leu Thr
385                 390                 395                 400

Glu Met Pro Gly Pro Ala Ala Ala Ser Asp Tyr His Gln Tyr Ser
                405                 410                 415

Thr Pro Asp Gly Phe Val Ser Gln Phe Asn Tyr Phe Asp Gln Met Pro
            420                 425                 430

Val Thr Asn Arg Thr Leu Asn Gly Glu Ile Ala Thr Val Tyr Pro Asn
            435                 440                 445

Asn Pro Ser Asn Ser Val Ala Trp Gly Ser Pro Phe Pro Leu Tyr Pro
450                 455                 460

Trp Trp Ile Gly Ser Val Ala Glu Ala Val Phe Leu Ile Gly Glu Glu
465                 470                 475                 480

Arg Asn Ser Pro Lys Ile Ile Gly Ala Ser Tyr Ala Pro Met Phe Arg
                485                 490                 495

Asn Ile Asn Asn Trp Gln Trp Ser Pro Thr Leu Ile Ala Phe Asp Ala
            500                 505                 510

Asp Ser Ser Arg Thr Ser Arg Ser Thr Ser Trp His Val Ile Lys Leu
            515                 520                 525

Leu Ser Thr Asn Lys Ile Thr Gln Asn Leu Pro Thr Thr Trp Ser Gly
530                 535                 540

Gly Asp Ile Gly Pro Leu Tyr Trp Val Ala Gly Arg Asn Asp Asn Thr
545                 550                 555                 560

Gly Ser Asn Ile Phe Lys Ala Ala Val Tyr Asn Ser Thr Ser Asp Val
                565                 570                 575

Pro Val Thr Val Gln Phe Ala Gly Cys Asn Ala Lys Ser Ala Asn Leu
            580                 585                 590

Thr Ile Leu Ser Ser Asp Asp Pro Asn Ala Ser Asn Tyr Pro Gly Gly
                595                 600                 605

Pro Glu Val Val Lys Thr Glu Ile Gln Ser Val Thr Ala Asn Ala His
            610                 615                 620

Gly Ala Phe Glu Phe Ser Leu Pro Asn Leu Ser Val Ala Val Leu Lys
625                 630                 635                 640

Thr Glu
```

<210> SEQ ID NO 23
<211> LENGTH: 739
<212> TYPE: DNA
<213> ORGANISM: Aspergillus fumigatus

<400> SEQUENCE: 23

```
atggtttctt tctcctacct gctgctggcg tgctccgcca ttggagctct ggctgccccc    60
```

-continued

```
gtcgaacccg agaccacctc gttcaatgag actgctcttc atgagttcgc tgagcgcgcc    120
ggcaccccaa gctccaccgg ctggaacaac ggctactact actccttctg gactgatggc    180
ggcggcgacg tgacctacac caatggcgcc ggtggctcgt actccgtcaa ctggaggaac    240
gtgggcaact ttgtcggtgg aaagggctgg aaccctggaa gcgctaggta ccgagctttg    300
tcaacgtcgg atgtgcagac ctgtggctga cagaagtaga accatcaact acggaggcag    360
cttcaacccc agcggcaatg ctacctggc tgtctacggc tggaccacca acccttgat    420 tgagtactac gttgttgagt cgtatggtac atacaacccc ggcagcggcg gtaccttcag    480
gggcactgtc aacaccgacg gtggcactta caacatctac acggccgttc gctacaatgc    540
tccctccatc gaaggcacca agaccttcac ccagtactgg tctgtgcgca cctccaagcg    600
taccggcggc actgtcacca tggccaacca cttcaacgcc tggagcagac tgggcatgaa    660
cctgggaact cacaactacc agattgtcgc cactgagggt taccagagca gcggatctgc    720
ttccatcact gtctactag                                                  739
```

```
<210> SEQ ID NO 24
<211> LENGTH: 228
<212> TYPE: PRT
<213> ORGANISM: Aspergillus fumigatus

<400> SEQUENCE: 24
```

Met Val Ser Phe Ser Tyr Leu Leu Ala Cys Ser Ala Ile Gly Ala
1               5                   10                  15

Leu Ala Ala Pro Val Glu Pro Glu Thr Thr Ser Phe Asn Glu Thr Ala
            20                  25                  30

Leu His Glu Phe Ala Glu Arg Ala Gly Thr Pro Ser Ser Thr Gly Trp
        35                  40                  45

Asn Asn Gly Tyr Tyr Tyr Ser Phe Trp Thr Asp Gly Gly Gly Asp Val
    50                  55                  60

Thr Tyr Thr Asn Gly Ala Gly Gly Ser Tyr Ser Val Asn Trp Arg Asn
65                  70                  75                  80

Val Gly Asn Phe Val Gly Gly Lys Gly Trp Asn Pro Gly Ser Ala Arg
                85                  90                  95

Thr Ile Asn Tyr Gly Gly Ser Phe Asn Pro Ser Gly Asn Gly Tyr Leu
            100                 105                 110

Ala Val Tyr Gly Trp Thr Thr Asn Pro Leu Ile Glu Tyr Tyr Val Val
        115                 120                 125

Glu Ser Tyr Gly Thr Tyr Asn Pro Gly Ser Gly Gly Thr Phe Arg Gly
    130                 135                 140

Thr Val Asn Thr Asp Gly Gly Thr Tyr Asn Ile Tyr Thr Ala Val Arg
145                 150                 155                 160

Tyr Asn Ala Pro Ser Ile Glu Gly Thr Lys Thr Phe Thr Gln Tyr Trp
                165                 170                 175

Ser Val Arg Thr Ser Lys Arg Thr Gly Gly Thr Val Thr Met Ala Asn
            180                 185                 190

His Phe Asn Ala Trp Ser Arg Leu Gly Met Asn Leu Gly Thr His Asn
        195                 200                 205

Tyr Gln Ile Val Ala Thr Glu Gly Tyr Gln Ser Ser Gly Ser Ala Ser
    210                 215                 220

Ile Thr Val Tyr
225

```
<210> SEQ ID NO 25
```

<211> LENGTH: 1002
<212> TYPE: DNA
<213> ORGANISM: Aspergillus fumigatus

<400> SEQUENCE: 25

```
atgatctcca tttcctcgct cagctttgga ctcgccgcta tcgccggcgc atatgctctt      60
ccgagtgaca aatccgtcag cttagcggaa cgtcagacga tcacgaccag ccagacaggc     120
acaaacaatg gctactacta ttccttctgg accaacggtg ccggatcagt gcaatataca     180
aatggtgctg gtggcgaata tagtgtgacg tgggcgaacc agaacggtgg tgactttacc     240
tgtgggaagg gctggaatcc agggagtgac cagtaggcaa cgcccgagaa ctatagaaga     300
ggacgcaaag aaagcactaa actctctact agtgacatta ccttctctgg cagcttcaat     360
ccttccggaa atgcttacct gtccgtgtat ggatggacta ccaaccccct agtcgaatac     420
tacatcctcg agaactatgg cagttacaat cctggctcgg gcatgacgca aagggcacc      480
gtcaccagcg atggatccac ctacgacatc tatgagcacc aacaggtcaa ccagccttcg     540
atcgtcggca cggccacctt caaccaatac tggtccatcc gccaaaacaa gcgatccagc     600
ggcacagtca ccaccgcgaa tcacttcaag gcctgggcta gtctggggat gaacctgggt     660
acccataact atcagattgt ttccactgag ggatatgaga gcagcggtac ctcgaccatc     720
actgtctcgt ctggtggttc ttcttctggt ggaagtggtg gcagctcgtc tactacttcc     780
tcaggcagct cccctactgg tggctccggc agtgtaagtc ttcttccata tggttgtggc     840
tttatgtgta ttctgactgt gatagtgctc tgctttgtgg ggccagtgcg gtggaattgg     900
ctggtctggt cctacttgct gctcttcggg cacttgccag tttcgaact cgtactactc      960
ccagtgcttg tagtaccttc ttgcagggtt atatccaagt ga                       1002
```

<210> SEQ ID NO 26
<211> LENGTH: 286
<212> TYPE: PRT
<213> ORGANISM: Aspergillus fumigatus

<400> SEQUENCE: 26

```
Met Ile Ser Ile Ser Ser Leu Ser Phe Gly Leu Ala Ala Ile Ala Gly
 1               5                  10                  15

Ala Tyr Ala Leu Pro Ser Asp Lys Ser Val Ser Leu Ala Glu Arg Gln
             20                  25                  30

Thr Ile Thr Thr Ser Gln Thr Gly Thr Asn Asn Gly Tyr Tyr Tyr Ser
         35                  40                  45

Phe Trp Thr Asn Gly Ala Gly Ser Val Gln Tyr Thr Asn Gly Ala Gly
     50                  55                  60

Gly Glu Tyr Ser Val Thr Trp Ala Asn Gln Asn Gly Gly Asp Phe Thr
 65                  70                  75                  80

Cys Gly Lys Gly Trp Asn Pro Gly Ser Asp His Asp Ile Thr Phe Ser
                 85                  90                  95

Gly Ser Phe Asn Pro Ser Gly Asn Ala Tyr Leu Ser Val Tyr Gly Trp
            100                 105                 110

Thr Thr Asn Pro Leu Val Glu Tyr Tyr Ile Leu Glu Asn Tyr Gly Ser
        115                 120                 125

Tyr Asn Pro Gly Ser Gly Met Thr His Lys Gly Thr Val Thr Ser Asp
    130                 135                 140

Gly Ser Thr Tyr Asp Ile Tyr Glu His Gln Gln Val Asn Gln Pro Ser
145                 150                 155                 160

Ile Val Gly Thr Ala Thr Phe Asn Gln Tyr Trp Ser Ile Arg Gln Asn
```

```
                        165                 170                 175
Lys Arg Ser Ser Gly Thr Val Thr Thr Ala Asn His Phe Lys Ala Trp
                180                 185                 190

Ala Ser Leu Gly Met Asn Leu Gly Thr His Asn Tyr Gln Ile Val Ser
            195                 200                 205

Thr Glu Gly Tyr Glu Ser Ser Gly Thr Ser Thr Ile Thr Val Ser Ser
        210                 215                 220

Gly Gly Ser Ser Gly Gly Ser Gly Gly Ser Ser Thr Thr Ser
225                 230                 235                 240

Ser Gly Ser Ser Pro Thr Gly Gly Ser Gly Cys Ser Ala Leu Trp
                245                 250                 255

Gly Gln Cys Gly Gly Ile Gly Trp Ser Gly Pro Thr Cys Cys Ser Ser
            260                 265                 270

Gly Thr Cys Gln Val Ser Asn Ser Tyr Tyr Ser Gln Cys Leu
        275                 280                 285

<210> SEQ ID NO 27
<211> LENGTH: 1053
<212> TYPE: DNA
<213> ORGANISM: Fusarium verticillioides

<400> SEQUENCE: 27
atgcagctca agtttctgtc ttcagcattg ttgctgtctt tgaccggcaa ttgcgctgcg      60
caagacacta atgatatccc tcctctgatc accgacctct ggtctgcgga tccctcggct     120
catgttttcg agggcaaact ctgggtttac ccatctcacg acatcgaagc caatgtcgtc     180
aacggcaccg gaggcgctca gtacgccatg agagattatc acacctattc catgaagacc     240
atctatggaa aagatcccgt tatcgaccat ggcgtcgctc tgtcagtcga tgatgtccca     300
tgggccaagc agcaaatgtg gctcctgac gcagcttaca agaacggcaa atattatctc     360
tacttccccg ccaaggataa agatgagatc ttcagaattg agttgctgt ctccaacaag     420 cccagcggtc ctttcaaggc cgacaagagc tggatccccg gtacttacag tatcgatcct     480
gctagctatg tcgacactaa tggcgaggca tacctcatct ggggcggtat ctggggcggc     540
cagcttcagg cctggcagga tcacaagacc tttaatgagt cgtggctcgg cgacaaagct     600
gctcccaacg gcaccaacgc cctatctcct cagatcgcca agctaagcaa ggacatgcac     660
aagatcaccg agacaccccg cgatctcgtc atcctggccc ccgagacagg caagcccctt     720
caagcagagg acaataagcg acgattttc gaggggccct gggttcacaa gcgcggcaag     780
ctgtactacc tcatgtactc taccggcgac acgcacttcc tcgtctacgc gacttccaag     840
aacatctacg gtccttatac ctatcagggc aagattctcg accctgttga tgggtggact     900
acgcatggaa gtattgttga gtacaaggga cagtggtggt tgttctttgc ggatgcgcat     960
acttctggaa aggattatct gagacaggtt aaggcgagga gatctggta tgacaaggat    1020 ggcaagattt tgcttactcg tcctaagatt tag                                1053

<210> SEQ ID NO 28
<211> LENGTH: 350
<212> TYPE: PRT
<213> ORGANISM: Fusarium verticillioides

<400> SEQUENCE: 28

Met Gln Leu Lys Phe Leu Ser Ser Ala Leu Leu Ser Leu Thr Gly
1               5                   10                  15

Asn Cys Ala Ala Gln Asp Thr Asn Asp Ile Pro Pro Leu Ile Thr Asp
```

```
                        20                  25                  30
Leu Trp Ser Ala Asp Pro Ser Ala His Val Phe Glu Gly Lys Leu Trp
                35                  40                  45

Val Tyr Pro Ser His Asp Ile Glu Ala Asn Val Val Asn Gly Thr Gly
        50                  55                  60

Gly Ala Gln Tyr Ala Met Arg Asp Tyr His Thr Tyr Ser Met Lys Thr
65                  70                  75                  80

Ile Tyr Gly Lys Asp Pro Val Ile Asp His Gly Val Ala Leu Ser Val
                85                  90                  95

Asp Asp Val Pro Trp Ala Lys Gln Gln Met Trp Ala Pro Asp Ala Ala
            100                 105                 110

Tyr Lys Asn Gly Lys Tyr Tyr Leu Tyr Phe Pro Ala Lys Asp Lys Asp
        115                 120                 125

Glu Ile Phe Arg Ile Gly Val Ala Val Ser Asn Lys Pro Ser Gly Pro
    130                 135                 140

Phe Lys Ala Asp Lys Ser Trp Ile Pro Gly Thr Tyr Ser Ile Asp Pro
145                 150                 155                 160

Ala Ser Tyr Val Asp Thr Asn Gly Glu Ala Tyr Leu Ile Trp Gly Gly
                165                 170                 175

Ile Trp Gly Gly Gln Leu Gln Ala Trp Gln Asp His Lys Thr Phe Asn
            180                 185                 190

Glu Ser Trp Leu Gly Asp Lys Ala Ala Pro Asn Gly Thr Asn Ala Leu
        195                 200                 205

Ser Pro Gln Ile Ala Lys Leu Ser Lys Asp Met His Lys Ile Thr Glu
    210                 215                 220

Thr Pro Arg Asp Leu Val Ile Leu Ala Pro Glu Thr Gly Lys Pro Leu
225                 230                 235                 240

Gln Ala Glu Asp Asn Lys Arg Arg Phe Phe Glu Gly Pro Trp Val His
                245                 250                 255

Lys Arg Gly Lys Leu Tyr Tyr Leu Met Tyr Ser Thr Gly Asp Thr His
            260                 265                 270

Phe Leu Val Tyr Ala Thr Ser Lys Asn Ile Tyr Gly Pro Tyr Thr Tyr
        275                 280                 285

Gln Gly Lys Ile Leu Asp Pro Val Asp Gly Trp Thr Thr His Gly Ser
    290                 295                 300

Ile Val Glu Tyr Lys Gly Gln Trp Trp Leu Phe Phe Ala Asp Ala His
305                 310                 315                 320

Thr Ser Gly Lys Asp Tyr Leu Arg Gln Val Lys Ala Arg Lys Ile Trp
                325                 330                 335

Tyr Asp Lys Asp Gly Lys Ile Leu Leu Thr Arg Pro Lys Ile
            340                 345                 350

<210> SEQ ID NO 29
<211> LENGTH: 1031
<212> TYPE: DNA
<213> ORGANISM: Penicillium funiculosum

<400> SEQUENCE: 29
atgagtcgca gcatccttcc gtacgcctct gttttcgccc tcctgggcgg ggctatcgcc      60
gaaccgtttt tggttctcaa tagcgatttt cccgatccca gtctcataga gacatccagc     120
ggatactatg cattcggtac caccggaaac ggagtcaatg cgcaggttgc ttcttcacca     180
gactttaata cctggacttt gctttccggc acagatgccc tcccgggacc atttccgtca     240
tgggtagctt cgtctccaca aatctgggcg ccagatgttt tggttaaggt atgttcttat     300
```

```
ggaataacag ttttaggagt aggtcagcca ggatattgac aaaattataa taggccgatg    360
gtacctatgt catgtacttt tcggcatctg ctgcgagtga ctcgggcaaa cactgcgttg    420
gtgccgcaac tgcgacctca ccggaaggac cttacacccc ggtcgatagc gctgttgcct    480
gtccattaga ccagggagga gctattgatg ccaatggatt tattgacacc gacggcacta    540
tatacgttgt atacaaaatt gatggaaaca gtctagacgg tgatggaacc acacatccta    600
cccccatcat gcttcaacaa atggaggcag acggaacaac cccaaccggc agcccaatcc    660
aactcattga ccgatccgac ctcgacggac ctttgatcga ggctcctagt ttgctcctct    720
ccaatggaat ctactacctc agtttctctt ccaactacta caacactaat tactacgaca    780
cttcatacgc ctatgcctcg tcgattactg gtccttggac caaacaatct gcgccttatg    840
caccttgtt ggttactgga accgagacta gcaatgacgg cgcattgagc gcccctggtg    900
gtgccgattt ctccgtcgat ggcaccaaga tgttgttcca cgcaaacctc aatggacaag    960
atatctcggg cggacgcgcc ttatttgctg cgtcaattac tgaggccagc gatgtggtta    1020
cattgcagta g                                                         1031
```

<210> SEQ ID NO 30
<211> LENGTH: 321
<212> TYPE: PRT
<213> ORGANISM: Penicillium funiculosum

<400> SEQUENCE: 30

```
Met Ser Arg Ser Ile Leu Pro Tyr Ala Ser Val Phe Ala Leu Leu Gly
1               5                   10                  15

Gly Ala Ile Ala Glu Pro Phe Leu Val Leu Asn Ser Asp Phe Pro Asp
                20                  25                  30

Pro Ser Leu Ile Glu Thr Ser Ser Gly Tyr Tyr Ala Phe Gly Thr Thr
            35                  40                  45

Gly Asn Gly Val Asn Ala Gln Val Ala Ser Ser Pro Asp Phe Asn Thr
        50                  55                  60

Trp Thr Leu Leu Ser Gly Thr Asp Ala Leu Pro Gly Pro Phe Pro Ser
65                  70                  75                  80

Trp Val Ala Ser Ser Pro Gln Ile Trp Ala Pro Asp Val Leu Val Lys
                85                  90                  95

Ala Asp Gly Thr Tyr Val Met Tyr Phe Ser Ala Ser Ala Ala Ser Asp
                100                 105                 110

Ser Gly Lys His Cys Val Gly Ala Ala Thr Ala Thr Ser Pro Glu Gly
            115                 120                 125

Pro Tyr Thr Pro Val Asp Ser Ala Val Ala Cys Pro Leu Asp Gln Gly
        130                 135                 140

Gly Ala Ile Asp Ala Asn Gly Phe Ile Asp Thr Asp Gly Thr Ile Tyr
145                 150                 155                 160

Val Val Tyr Lys Ile Asp Gly Asn Ser Leu Asp Gly Asp Gly Thr Thr
                165                 170                 175

His Pro Thr Pro Ile Met Leu Gln Gln Met Glu Ala Asp Gly Thr Thr
                180                 185                 190

Pro Thr Gly Ser Pro Ile Gln Leu Ile Asp Arg Ser Asp Leu Asp Gly
            195                 200                 205

Pro Leu Ile Glu Ala Pro Ser Leu Leu Leu Ser Asn Gly Ile Tyr Tyr
        210                 215                 220

Leu Ser Phe Ser Ser Asn Tyr Tyr Asn Thr Asn Tyr Tyr Asp Thr Ser
225                 230                 235                 240
```

```
Tyr Ala Tyr Ala Ser Ser Ile Thr Gly Pro Trp Thr Lys Gln Ser Ala
                245                 250                 255

Pro Tyr Ala Pro Leu Leu Val Thr Gly Thr Glu Thr Ser Asn Asp Gly
            260                 265                 270

Ala Leu Ser Ala Pro Gly Gly Ala Asp Phe Ser Val Asp Gly Thr Lys
        275                 280                 285

Met Leu Phe His Ala Asn Leu Asn Gly Gln Asp Ile Ser Gly Gly Arg
    290                 295                 300

Ala Leu Phe Ala Ala Ser Ile Thr Glu Ala Ser Asp Val Val Thr Leu
305                 310                 315                 320

Gln

<210> SEQ ID NO 31
<211> LENGTH: 2186
<212> TYPE: DNA
<213> ORGANISM: Fusarium verticillioides

<400> SEQUENCE: 31
atggttcgct tcagttcaat cctagcggct gcggcttgct tcgtggctgt tgagtcagtc    60
aacatcaagg tcgacagcaa gggcggaaac gctactagcg gtcaccaata tggcttcctt   120
cacgaggttg gtattgacac accactggcg atgattggga tgctaacttg agctaggat   180 atcaacaatt ccggtgatgg tggcatctac gctgagctca tccgcaatcg tgctttccag   240
tacagcaaga aataccctgt ttctctatct ggctggagac ccatcaacga tgctaagctc   300
tccctcaacc gtctcgacac tcctctctcc gacgctctcc ccgtttccat gaacgtgaag   360
cctggaaagg gcaaggccaa ggagattggt ttcctcaacg agggttactg gggaatggat   420
gtcaagaagc aaaagtacac tggctctttc tgggttaagg gcgcttacaa gggccacttt   480
acagcttctt tgcgatctaa ccttaccgac gatgtctttg gcagcgtcaa ggtcaagtcc   540
aaggccaaca gaagcagtg ggttgagcat gagtttgtgc ttactcctaa caagaatgcc   600
cctaacagca acaacacttt tgctatcacc tacgatccca aggtgagtaa caatcaaaac   660
tgggacgtga tgtatactga caatttgtag ggcgctgatg gagctcttga cttcaacctc   720
attagcttgt tccctcccac ctacaagggc cgcaagaacg tcttcgagt tgatcttgcc   780 gaggctctcg aaggtctcca ccccgtaagg tttaccgtct cacgtgtatc gtgaacagtc   840
gctgacttgt agaaaagagc ctgctgcgct tccccggtgg taacatgctc gagggcaaca   900
ccaacaagac ctggtgggac tggaaggata ccctcggacc tctccgcaac cgtcctggtt   960
tcgagggtgt ctggaactac cagcagaccc atggtcttgg aatcttggag tacctccagt  1020
gggctgagga catgaacctt gaaatcagta ggttctataa aattcagtga cggttatgtg  1080
catgctaaca gatttcagtt gtcggtgtct acgctggcct ctccctcgac ggctccgtca  1140
cccccaagga ccaactccag cccctcatcg acgacgcgct cgacgagatc gaattcatcc  1200
gaggtcccgt cacttcaaag tggggaaaga agcgcgctga gctcggccac ccaagccttt  1260
tcagactctc ctacgttgaa gtcggaaacg aggactggct cgctggttat cccactggct  1320
ggaactctta caaggagtac cgcttcccca tgttcctcga ggctatcaag aaagctcacc  1380
ccgatctcac cgtcatctcc tctggtgctt ctattgaccc cgttggtaag aaggatgctg  1440
gtttcgatat tcctgctcct ggaatcggtg actaccaccc ttaccgcgag cctgatgttc  1500
ttgttgagga gttcaacctg tttgataaca ataagtatgg tcacatcatt ggtgaggttg  1560
cttctaccca ccccaacggt ggaactggct ggagtggtaa ccttatgcct taccctggt   1620
```

```
ggatctctgg tgttggcgag gccgtcgctc tctgcggtta tgagcgcaac gccgatcgta    1680
ttcccggaac attctacgct cctatcctca agaacgagaa ccgttggcag tgggctatca    1740
ccatgatcca attcgccgcc gactccgcca tgaccacccg ctccaccagc tggtatgtct    1800
ggtcactctt cgcaggccac cccatgaccc atactctccc caccaccgcc gacttcgacc    1860
ccctctacta cgtcgctggt aagaacgagg acaagggaac tcttatctgg aagggtgctg    1920
cgtataacac caccaagggt gctgacgttc ccgtgtctct gtccttcaag ggtgtcaagc    1980
ccggtgctca agctgagctt actcttctga ccaacaagga aaggatcct tttgcgttca    2040 atgatcctca aagggcaac aatgttgttg atactaagaa gactgttctc aaggccgatg    2100
gaaagggtgc tttcaacttc aagcttccta acctgagcgt cgctgttctt gagaccctca    2160
agaagggaaa gccttactct agctag                                        2186
```

<210> SEQ ID NO 32
<211> LENGTH: 660
<212> TYPE: PRT
<213> ORGANISM: Fusarium verticillioides

<400> SEQUENCE: 32

```
Met Val Arg Phe Ser Ser Ile Leu Ala Ala Ala Cys Phe Val Ala
1               5                   10                  15

Val Glu Ser Val Asn Ile Lys Val Asp Ser Lys Gly Gly Asn Ala Thr
            20                  25                  30

Ser Gly His Gln Tyr Gly Phe Leu His Glu Asp Ile Asn Asn Ser Gly
        35                  40                  45

Asp Gly Gly Ile Tyr Ala Glu Leu Ile Arg Asn Arg Ala Phe Gln Tyr
    50                  55                  60

Ser Lys Lys Tyr Pro Val Ser Leu Ser Gly Trp Arg Pro Ile Asn Asp
65                  70                  75                  80

Ala Lys Leu Ser Leu Asn Arg Leu Asp Thr Pro Leu Ser Asp Ala Leu
                85                  90                  95

Pro Val Ser Met Asn Val Lys Pro Gly Lys Gly Lys Ala Lys Glu Ile
            100                 105                 110

Gly Phe Leu Asn Glu Gly Tyr Trp Gly Met Asp Val Lys Lys Gln Lys
        115                 120                 125

Tyr Thr Gly Ser Phe Trp Val Lys Gly Ala Tyr Lys Gly His Phe Thr
    130                 135                 140

Ala Ser Leu Arg Ser Asn Leu Thr Asp Asp Val Phe Gly Ser Val Lys
145                 150                 155                 160

Val Lys Ser Lys Ala Asn Lys Lys Gln Trp Val Glu His Glu Phe Val
                165                 170                 175

Leu Thr Pro Asn Lys Asn Ala Pro Ser Asn Thr Phe Ala Ile
            180                 185                 190

Thr Tyr Asp Pro Lys Gly Ala Asp Gly Ala Leu Asp Phe Asn Leu Ile
    195                 200                 205

Ser Leu Phe Pro Pro Thr Tyr Lys Gly Arg Lys Asn Gly Leu Arg Val
    210                 215                 220

Asp Leu Ala Glu Ala Leu Glu Gly Leu His Pro Ser Leu Leu Arg Phe
225                 230                 235                 240

Pro Gly Gly Asn Met Leu Glu Gly Asn Thr Asn Lys Thr Trp Trp Asp
                245                 250                 255

Trp Lys Asp Thr Leu Gly Pro Leu Arg Asn Arg Pro Gly Phe Glu Gly
            260                 265                 270
```

```
Val Trp Asn Tyr Gln Gln Thr His Gly Leu Gly Ile Leu Glu Tyr Leu
        275                 280                 285

Gln Trp Ala Glu Asp Met Asn Leu Glu Ile Ile Val Gly Val Tyr Ala
290                 295                 300

Gly Leu Ser Leu Asp Gly Ser Val Thr Pro Lys Asp Gln Leu Gln Pro
305                 310                 315                 320

Leu Ile Asp Asp Ala Leu Asp Glu Ile Glu Phe Ile Arg Gly Pro Val
                325                 330                 335

Thr Ser Lys Trp Gly Lys Lys Arg Ala Glu Leu Gly His Pro Lys Pro
                340                 345                 350

Phe Arg Leu Ser Tyr Val Glu Val Gly Asn Glu Asp Trp Leu Ala Gly
        355                 360                 365

Tyr Pro Thr Gly Trp Asn Ser Tyr Lys Glu Tyr Arg Phe Pro Met Phe
        370                 375                 380

Leu Glu Ala Ile Lys Lys Ala His Pro Asp Leu Thr Val Ile Ser Ser
385                 390                 395                 400

Gly Ala Ser Ile Asp Pro Val Gly Lys Lys Asp Ala Gly Phe Asp Ile
                405                 410                 415

Pro Ala Pro Gly Ile Gly Asp Tyr His Pro Tyr Arg Glu Pro Asp Val
                420                 425                 430

Leu Val Glu Glu Phe Asn Leu Phe Asp Asn Asn Lys Tyr Gly His Ile
        435                 440                 445

Ile Gly Glu Val Ala Ser Thr His Pro Asn Gly Gly Thr Gly Trp Ser
        450                 455                 460

Gly Asn Leu Met Pro Tyr Pro Trp Trp Ile Ser Gly Val Gly Glu Ala
465                 470                 475                 480

Val Ala Leu Cys Gly Tyr Glu Arg Asn Ala Asp Arg Ile Pro Gly Thr
                485                 490                 495

Phe Tyr Ala Pro Ile Leu Lys Asn Glu Asn Arg Trp Gln Trp Ala Ile
                500                 505                 510

Thr Met Ile Gln Phe Ala Ala Asp Ser Ala Met Thr Thr Arg Ser Thr
        515                 520                 525

Ser Trp Tyr Val Trp Ser Leu Phe Ala Gly His Pro Met Thr His Thr
        530                 535                 540

Leu Pro Thr Thr Ala Asp Phe Asp Pro Leu Tyr Tyr Val Ala Gly Lys
545                 550                 555                 560

Asn Glu Asp Lys Gly Thr Leu Ile Trp Lys Gly Ala Ala Tyr Asn Thr
                565                 570                 575

Thr Lys Gly Ala Asp Val Pro Val Ser Leu Ser Phe Lys Gly Val Lys
                580                 585                 590

Pro Gly Ala Gln Ala Glu Leu Thr Leu Leu Thr Asn Lys Glu Lys Asp
        595                 600                 605

Pro Phe Ala Phe Asn Asp Pro His Lys Gly Asn Asn Val Val Asp Thr
        610                 615                 620

Lys Lys Thr Val Leu Lys Ala Asp Gly Lys Gly Ala Phe Asn Phe Lys
625                 630                 635                 640

Leu Pro Asn Leu Ser Val Ala Val Leu Glu Thr Leu Lys Lys Gly Lys
                645                 650                 655

Pro Tyr Ser Ser
            660

<210> SEQ ID NO 33
<211> LENGTH: 2312
```

<212> TYPE: DNA
<213> ORGANISM: Chaetomium globosum

<400> SEQUENCE: 33

```
atggcgcccc tttcgcttcg ggccctctcg ctgctcgcgc tcacaggagc cgcagccgcg    60
gtgaccctat cggtcgcgaa ctctggcggt aatgatacgt ctccgtacat gtatggcatc   120
atgttcgagg acatcaatca gagcggtgac ggcgggctgt aagttctgtc gcggcttccc   180
ctgacaagct tgcatgatgc ttaactaaag tccttaggta cgccgagctg attcgcaacc   240
gagccttcca taatagctcc ctccaggcct ggaccgccgt gggggacagc actctcgagg   300
tcgtaacctc tgcaccgtta tcggatgccc tgcctcgctc ggtcaaggtc acgagtggaa   360
agggcaaggc gggcttgaag aatgccggct actggggaat ggacgtccag aagaccgaca   420
agtatagcgg cagcttctac tcgtacgcg cctacgacgg aaagtttacc ctctctctgg    480
tgtcggacat cacaaatgag accctggcca ccaccaagat caagtccagg tcggtggagc   540
atgcctggac cgagcacaag ttcgagcttc tcccgaccaa gagcgcggcg aacagcaaca   600
acagcttcgt gctggagttc cgcccctgcc accagacgga gctccagttc aacctcatca   660
gcttgttccc gccgacgtat aagaacaggc caacggcat cgccgagag ctcatggaga     720
agctcgcaga cctcaagccc agtttccttc ggattccagg aggcaacaac ctgtaagtgc   780
ttccggcgaa actagcagta gttgcctgag agacactaat ctcagcgaac aacagcgagg   840
gcaactatgc tggcaactac tggaactggt caagcacact tggcccgctg accgaccggc   900
ccggtcgtga cggcgtgtgg acgtacgcca cacggacgg catcgggctg gtcgagtaca    960
tgcactgggc cgaggacctc gacgtggagg ttgtgctggc ggtcgccgca ggcctgtacc  1020
tgaacgcgca tgtggtcccg gaggaggagc tgcacgtctt cgtggaggat gcgctgaacg  1080
agctcgagtt cctcatgggc gacgtctcga cccttgggg cgcgcgccgc gctaagctcg   1140
gctaccccaa gccgtggaac atcaagttcg tcgaggtcgg caacgaggac aacctgtggg  1200
gcggcctcga ctcgtacaag agctaccggc tgaagacttt ctacgacgcc atcaaggcga  1260
agtaccccga catctccatc ttttcgtcga ccgacgagtt tgtgtacaag gagtcgggcc  1320
aggactacca caagtacacc cggccggact actccgtgtc ccagttcgac ctgtttgaca  1380
actgggccga cggccacccc atcatcatcg gagagtgagt gaacggcgac ccccacctcc  1440
ccctaacgcg ggatcgcgag ctgatagatc accccaggta tgcgaccatc cagaacaaca  1500
cgggcaagct cgaggacacg gactgggacg cgcccaagaa caagtggtcc aactggatcg  1560
gctccgtcgc cgaggccgtc ttcatcctcg gagccgagcg caacggcgac cgggtctggg  1620
gcaccacctt tgcgccgatc ctccagaacc tcaacagcta ccaatgggct gtaagtacat  1680
acatacatac cgcaccccca accccaaccc ccccaaagcg cacctccacc cacccaccca  1740
aacacaccac aactacctag ctaacccgcc acacaaacaa acagcccgac ctaatctcct  1800
tcaccgccaa cccggccgac accacgccca gcgtctcgta cccgatcatc cagctgctcg  1860
cctcgcaccg catcacgcac accctccccg tcagcagcgc cgacgccttc ggcccggcct  1920
actgggtggc cggtcgcggc gccgacgacg gctcgtacat cctcaaggcg gccgtgtaca  1980
acagcacggg gggtgcggat gtaccggtga gggtgcagtt tgaggcgggg ggtggtggtg  2040
gtggtggtgg tggtggtggt ggtggtggtg gtgatgggaa ggggaagggt aaagggaagg  2100
gaggggaggg tggtgagggt gtgaagaagg gtgaccgcgc gcagttgacc gtgttgacgg  2160
cgccggaggg gccctgggcg cataatacgc cggagaataa gggggcggtc aagacgacag  2220
```

```
tgacgacgtt gaaggccggg aggggtgggg tgtttgagtt tagtctgccg gatttgtcgg    2280
tggcggtgtt ggtggtggag ggggagaagt ga                                   2312
```

<210> SEQ ID NO 34
<211> LENGTH: 670
<212> TYPE: PRT
<213> ORGANISM: Chaetomium globosum

<400> SEQUENCE: 34

```
Met Ala Pro Leu Ser Leu Arg Ala Leu Ser Leu Leu Ala Leu Thr Gly
1               5                   10                  15

Ala Ala Ala Ala Val Thr Leu Ser Val Ala Asn Ser Gly Gly Asn Asp
                20                  25                  30

Thr Ser Pro Tyr Met Tyr Gly Ile Met Phe Glu Asp Ile Asn Gln Ser
            35                  40                  45

Gly Asp Gly Gly Leu Tyr Ala Glu Leu Ile Arg Asn Arg Ala Phe His
        50                  55                  60

Asn Ser Ser Leu Gln Ala Trp Thr Ala Val Gly Asp Ser Thr Leu Glu
65                  70                  75                  80

Val Val Thr Ser Ala Pro Leu Ser Asp Ala Leu Pro Arg Ser Val Lys
                85                  90                  95

Val Thr Ser Gly Lys Gly Lys Ala Gly Leu Lys Asn Ala Gly Tyr Trp
            100                 105                 110

Gly Met Asp Val Gln Lys Thr Asp Lys Tyr Ser Gly Ser Phe Tyr Ser
        115                 120                 125

Tyr Gly Ala Tyr Asp Gly Lys Phe Thr Leu Ser Leu Val Ser Asp Ile
    130                 135                 140

Thr Asn Glu Thr Leu Ala Thr Thr Lys Ile Lys Ser Arg Ser Val Glu
145                 150                 155                 160

His Ala Trp Thr Glu His Lys Phe Glu Leu Leu Pro Thr Lys Ser Ala
                165                 170                 175

Ala Asn Ser Asn Asn Ser Phe Val Leu Glu Phe Arg Pro Cys His Gln
            180                 185                 190

Thr Glu Leu Gln Phe Asn Leu Ile Ser Leu Phe Pro Pro Thr Tyr Lys
        195                 200                 205

Asn Arg Pro Asn Gly Met Arg Arg Glu Leu Met Glu Lys Leu Ala Asp
    210                 215                 220

Leu Lys Pro Ser Phe Leu Arg Ile Pro Gly Gly Asn Asn Leu Glu Gly
225                 230                 235                 240

Asn Tyr Ala Gly Asn Tyr Trp Asn Trp Ser Ser Thr Leu Gly Pro Leu
                245                 250                 255

Thr Asp Arg Pro Gly Arg Asp Gly Val Trp Thr Tyr Ala Asn Thr Asp
            260                 265                 270

Gly Ile Gly Leu Val Glu Tyr Met His Trp Ala Glu Asp Leu Asp Val
        275                 280                 285

Glu Val Val Leu Ala Val Ala Ala Gly Leu Tyr Leu Asn Gly Asp Val
    290                 295                 300

Val Pro Glu Glu Glu Leu His Val Phe Val Glu Asp Ala Leu Asn Glu
305                 310                 315                 320

Leu Glu Phe Leu Met Gly Asp Val Ser Thr Pro Trp Gly Ala Arg Arg
                325                 330                 335

Ala Lys Leu Gly Tyr Pro Lys Pro Trp Asn Ile Lys Phe Val Glu Val
            340                 345                 350

Gly Asn Glu Asp Asn Leu Trp Gly Gly Leu Asp Ser Tyr Lys Ser Tyr
```

```
          355              360              365
Arg Leu Lys Thr Phe Tyr Asp Ala Ile Lys Ala Lys Tyr Pro Asp Ile
    370              375              380

Ser Ile Phe Ser Ser Thr Asp Glu Phe Val Tyr Lys Glu Ser Gly Gln
385              390              395              400

Asp Tyr His Lys Tyr Thr Arg Pro Asp Tyr Ser Val Ser Gln Phe Asp
            405              410              415

Leu Phe Asp Asn Trp Ala Asp Gly His Pro Ile Ile Ile Gly Glu Tyr
        420              425              430

Ala Thr Ile Gln Asn Asn Thr Gly Lys Leu Glu Asp Thr Asp Trp Asp
    435              440              445

Ala Pro Lys Asn Lys Trp Ser Asn Trp Ile Gly Ser Val Ala Glu Ala
    450              455              460

Val Phe Ile Leu Gly Ala Glu Arg Asn Gly Asp Arg Val Trp Gly Thr
465              470              475              480

Thr Phe Ala Pro Ile Leu Gln Asn Leu Asn Ser Tyr Gln Trp Ala Pro
            485              490              495

Asp Leu Ile Ser Phe Thr Ala Asn Pro Ala Asp Thr Thr Pro Ser Val
        500              505              510

Ser Tyr Pro Ile Ile Gln Leu Leu Ala Ser His Arg Ile Thr His Thr
    515              520              525

Leu Pro Val Ser Ser Ala Asp Ala Phe Gly Pro Ala Tyr Trp Val Ala
    530              535              540

Gly Arg Gly Ala Asp Asp Gly Ser Tyr Ile Leu Lys Ala Ala Val Tyr
545              550              555              560

Asn Ser Thr Gly Gly Ala Asp Val Pro Val Arg Val Gln Phe Glu Ala
            565              570              575

Gly Gly Gly Gly Gly Gly Gly Gly Gly Gly Gly Gly Gly Gly Gly Asp
        580              585              590

Gly Lys Gly Lys Gly Lys Gly Lys Gly Gly Glu Gly Gly Glu Gly Val
    595              600              605

Lys Lys Gly Asp Arg Ala Gln Leu Thr Val Leu Thr Ala Pro Glu Gly
    610              615              620

Pro Trp Ala His Asn Thr Pro Glu Asn Lys Gly Ala Val Lys Thr Thr
625              630              635              640

Val Thr Thr Leu Lys Ala Gly Arg Gly Gly Val Phe Glu Phe Ser Leu
            645              650              655

Pro Asp Leu Ser Val Ala Val Leu Val Val Glu Gly Glu Lys
        660              665              670

<210> SEQ ID NO 35
<211> LENGTH: 1002
<212> TYPE: DNA
<213> ORGANISM: Fusarium verticillioides

<400> SEQUENCE: 35
atgcgtcttc tatcgtttcc cagccatctc ctcgtggcct tcctaaccct caaagaggct    60
tcatccctcg ccctcagcaa acgggatagc cctgtcctcc ccggcctctg ggcggacccc   120
aacatcgcca tcgtcgacaa acatactac atcttcccta ccaccgacgg tttcgaaggc    180
tggggcggca acgtcttcta ctggtggaaa tcaaagatc tcgtatcatg acaaagagc     240 gacaagccat tccttactct caatggtacg aatggcaacg ttccctgggc tacaggtaat    300
gcctgggctc ctgctttcgc tgctcgcgga ggcaagtatt acttctacca tagtgggaat    360
```

```
aatccctctg tgagtgatgg gcataagagt attggtgcgg cggtggctga tcatcctgag      420
gggccgtgga aggcacagga taagccgatg atcaagggaa cttctgatga ggagattgtc      480
agcaaccagg ctatcgatcc cgctgccttt gaagaccctg agactggaaa gtggtatatc      540
tactggggaa acggtgtccc cattgtcgca gagctcaacg acgacatggt ctctctcaaa      600
gcaggctggc acaaaatcac aggtcttcag aatttccgcg agggtctttt cgtcaactat      660
cgcgatggaa catatcatct gacatactct atcgacgata cgggctcaga gaactatcgc      720
gttgggtacg ctacggcgga taaccccatt ggaccttgga catatcgtgg tgttcttctg      780
gagaaggacg aatcgaaggg cattcttgct acgggacata actccatcat caacattcct      840
ggaacggatg agtggtatat cgcgtatcat cgcttccata ttcccgatgg aaatgggtat      900
aatagggaga ctacgattga tagggtaccc atcgacaagg atacgggttt gtttggaaag      960
gttacgccga ctttgcagag tgttgatcct aggcctttgt ag                       1002
```

<210> SEQ ID NO 36
<211> LENGTH: 333
<212> TYPE: PRT
<213> ORGANISM: Fusarium verticillioides

<400> SEQUENCE: 36

```
Met Arg Leu Leu Ser Phe Pro Ser His Leu Leu Val Ala Phe Leu Thr
1               5                   10                  15

Leu Lys Glu Ala Ser Ser Leu Ala Leu Ser Lys Arg Asp Ser Pro Val
                20                  25                  30

Leu Pro Gly Leu Trp Ala Asp Pro Asn Ile Ala Ile Val Asp Lys Thr
            35                  40                  45

Tyr Tyr Ile Phe Pro Thr Thr Asp Gly Phe Glu Gly Trp Gly Gly Asn
        50                  55                  60

Val Phe Tyr Trp Trp Lys Ser Lys Asp Leu Val Ser Trp Thr Lys Ser
65                  70                  75                  80

Asp Lys Pro Phe Leu Thr Leu Asn Gly Thr Asn Gly Asn Val Pro Trp
                85                  90                  95

Ala Thr Gly Asn Ala Trp Ala Pro Ala Phe Ala Ala Arg Gly Gly Lys
            100                 105                 110

Tyr Tyr Phe Tyr His Ser Gly Asn Asn Pro Ser Val Ser Asp Gly His
        115                 120                 125

Lys Ser Ile Gly Ala Ala Val Ala Asp His Pro Glu Gly Pro Trp Lys
    130                 135                 140

Ala Gln Asp Lys Pro Met Ile Lys Gly Thr Ser Asp Glu Glu Ile Val
145                 150                 155                 160

Ser Asn Gln Ala Ile Asp Pro Ala Ala Phe Glu Asp Pro Glu Thr Gly
                165                 170                 175

Lys Trp Tyr Ile Tyr Trp Gly Asn Gly Val Pro Ile Val Ala Glu Leu
            180                 185                 190

Asn Asp Asp Met Val Ser Leu Lys Ala Gly Trp His Lys Ile Thr Gly
        195                 200                 205

Leu Gln Asn Phe Arg Glu Gly Leu Phe Val Asn Tyr Arg Asp Gly Thr
    210                 215                 220

Tyr His Leu Thr Tyr Ser Ile Asp Asp Thr Gly Ser Glu Asn Tyr Arg
225                 230                 235                 240

Val Gly Tyr Ala Thr Ala Asp Asn Pro Ile Gly Pro Trp Thr Tyr Arg
                245                 250                 255

Gly Val Leu Leu Glu Lys Asp Glu Ser Lys Gly Ile Leu Ala Thr Gly
```

|   |   | 260 |   |   |   | 265 |   |   |   | 270 |   |
|---|---|---|---|---|---|---|---|---|---|---|---|
| His | Asn | Ser | Ile | Ile | Asn | Ile | Pro | Gly | Thr | Asp | Glu | Trp | Tyr | Ile | Ala |
|   |   | 275 |   |   |   | 280 |   |   |   | 285 |   |

Tyr His Arg Phe His Ile Pro Asp Gly Asn Gly Tyr Asn Arg Glu Thr
            290             295             300

Thr Ile Asp Arg Val Pro Ile Asp Lys Asp Thr Gly Leu Phe Gly Lys
305             310             315             320

Val Thr Pro Thr Leu Gln Ser Val Asp Pro Arg Pro Leu
                325             330

<210> SEQ ID NO 37
<211> LENGTH: 1695
<212> TYPE: DNA
<213> ORGANISM: Fusarium verticillioides

<400> SEQUENCE: 37

```
atgctcttct cgctcgttct tcctacccct gcctttcaag ccagcctggc gctcggcgat      60
acatccgtta ctgtcgacac cagccagaaa ctccaggtca tcgatggctt tggtgtctca     120
gaagcctacg ccacgccaa acaattccaa aacctcggtc ctggaccaca gaaagagggc     180
ctcgatcttc tcttcaacac tacaaccggc gcaggcttat ccatcatccg aaacaagatc     240
ggctgcgacg cctccaactc catcaccagc accaacaccg acaacccaga taagcaggct     300
gtttaccatt ttgacggcga tgatgatggt caggtatggt ttagcaaaca ggccatgagc     360
tatggtgtag atactatcta cgctaatgct tggtctgcgc ctgtatacat gaagtcagcc     420
cagagtatgg gccgtctctg cggtacacct ggtgtgtcgt gctcctctgg agattggaga     480
catcgttacg ttgagatgat agctgagtac ctctcctact acaagcaggc tggcatccca     540
gtgtcgcacg ttggattcct caatgagggt gacggctcgg actttatgct ctcaactgcc     600
gaacaggctg cagatgtcat tcctcttcta cacagcgctt tgcagtccaa gggccttggc     660
gatatcaaga tgacgtgctg tgataacatc ggttggaagt cacagatgga ctataccgcc     720
aagctggctg agcttgaggt ggagaagtat ctatctgtca tcacatccca cgagtactcc     780
agcagcccca accagcctat gaacactaca ttgccaacct ggatgtccga gggagctgcc     840
aatgaccagg catttgccac agcgtggtac gtcaacggcg ttccaacga aggtttcaca     900
tgggcagtca gatcgcaca aggcatcgtc aatgccgacc tctcagcgta tatctactgg     960
gagggcgttg agaccaacaa caaggggtct ctatctcacg tcatcgacac ggacggtacc    1020
aagtttacca tatcctcgat tctctgggcc attgctcact ggtcgcgcca tattcgccct    1080
ggtgcgcata gactttcgac ttcaggtgtt gtgcaagata cgattgttgg tgcgtttgag    1140
aacgttgatg gcagtgtcgt catggtgctc accaactctg gcactgctgc tcagactgtg    1200
gacctgggtg tttcgggaag tagcttctca acagctcagg ctttcacttc ggatgctgag    1260
gcgcagatgg tcgataccaa ggtgactctg tccgacggtc gtgtcaaggt tacggtcccg    1320
gtgcacggtg tcgtcactgt gaagctcaca acagcaaaaa gctccaaacc ggtctcaact    1380
gctgtttctg cgcaatctgc ccccactcca actagtgtta agcacacctt gactcaccag    1440
aagacttctt caacaacact ctcgaccgcc aaggcccaa cctccactca gactacctct    1500
gtagttgagt cagccaaggc ggtgaaatac cctgtccccc ctgtagcatc caagggatcc    1560
tcgaagagtg ctcccaagaa gggtaccaag aagaccacta cgaagaaggg ctcccaccaa    1620
tcgcacaagg cgcatagtgc tactcatcgt cgatgccgcc atggaagtta ccgtcgtggc    1680
cactgcacca actaa                                                    1695
```

-continued

<210> SEQ ID NO 38
<211> LENGTH: 537
<212> TYPE: PRT
<213> ORGANISM: Fusarium verticillioides

<400> SEQUENCE: 38

```
Met Leu Phe Ser Leu Val Leu Pro Thr Leu Ala Phe Gln Ala Ser Leu
1               5                   10                  15

Ala Leu Gly Asp Thr Ser Val Thr Val Asp Thr Ser Gln Lys Leu Gln
            20                  25                  30

Val Ile Asp Gly Phe Gly Val Ser Glu Ala Tyr Gly His Ala Lys Gln
        35                  40                  45

Phe Gln Asn Leu Gly Pro Gly Pro Gln Lys Glu Gly Leu Asp Leu Leu
    50                  55                  60

Phe Asn Thr Thr Thr Gly Ala Gly Leu Ser Ile Ile Arg Asn Lys Ile
65                  70                  75                  80

Gly Cys Asp Ala Ser Asn Ser Ile Thr Ser Thr Asn Thr Asp Asn Pro
                85                  90                  95

Asp Lys Gln Ala Val Tyr His Phe Asp Gly Asp Asp Gly Gln Ser
            100                 105                 110

Ala Gln Ser Met Gly Arg Leu Cys Gly Thr Pro Gly Val Ser Cys Ser
        115                 120                 125

Ser Gly Asp Trp Arg His Arg Tyr Val Glu Met Ile Ala Glu Tyr Leu
    130                 135                 140

Ser Tyr Tyr Lys Gln Ala Gly Ile Pro Val Ser His Val Gly Phe Leu
145                 150                 155                 160

Asn Glu Gly Asp Gly Ser Asp Phe Met Leu Ser Thr Ala Glu Gln Ala
                165                 170                 175

Ala Asp Val Ile Pro Leu Leu His Ser Ala Leu Gln Ser Lys Gly Leu
            180                 185                 190

Gly Asp Ile Lys Met Thr Cys Cys Asp Asn Ile Gly Trp Lys Ser Gln
        195                 200                 205

Met Asp Tyr Thr Ala Lys Leu Ala Glu Leu Glu Val Glu Lys Tyr Leu
    210                 215                 220

Ser Val Ile Thr Ser His Glu Tyr Ser Ser Pro Asn Gln Pro Met
225                 230                 235                 240

Asn Thr Thr Leu Pro Thr Trp Met Ser Glu Gly Ala Ala Asn Asp Gln
                245                 250                 255

Ala Phe Ala Thr Ala Trp Tyr Val Asn Gly Gly Ser Asn Glu Gly Phe
            260                 265                 270

Thr Trp Ala Val Lys Ile Ala Gln Gly Ile Val Asn Ala Asp Leu Ser
        275                 280                 285

Ala Tyr Ile Tyr Trp Glu Gly Val Glu Thr Asn Asn Lys Gly Ser Leu
    290                 295                 300

Ser His Val Ile Asp Thr Asp Gly Thr Lys Phe Thr Ile Ser Ser Ile
305                 310                 315                 320

Leu Trp Ala Ile Ala His Trp Ser Arg His Ile Arg Pro Gly Ala His
                325                 330                 335

Arg Leu Ser Thr Ser Gly Val Val Gln Asp Thr Ile Val Gly Ala Phe
            340                 345                 350

Glu Asn Val Asp Gly Ser Val Val Met Val Leu Thr Asn Ser Gly Thr
        355                 360                 365

Ala Ala Gln Thr Val Asp Leu Gly Val Ser Gly Ser Ser Phe Ser Thr
```

Ala Gln Ala Phe Thr Ser Asp Ala Glu Ala Gln Met Val Asp Thr Lys
385                 390                 395                 400

Val Thr Leu Ser Asp Gly Arg Val Lys Val Thr Val Pro Val His Gly
                405                 410                 415

Val Val Thr Val Lys Leu Thr Ala Lys Ser Ser Lys Pro Val Ser
            420                 425                 430

Thr Ala Val Ser Ala Gln Ser Ala Pro Thr Pro Thr Ser Val Lys His
            435                 440                 445

Thr Leu Thr His Gln Lys Thr Ser Ser Thr Thr Leu Ser Thr Ala Lys
        450                 455                 460

Ala Pro Thr Ser Thr Gln Thr Thr Ser Val Val Glu Ser Ala Lys Ala
465                 470                 475                 480

Val Lys Tyr Pro Val Pro Pro Val Ala Ser Lys Gly Ser Ser Lys Ser
                485                 490                 495

Ala Pro Lys Lys Gly Thr Lys Lys Thr Thr Thr Lys Lys Gly Ser His
            500                 505                 510

Gln Ser His Lys Ala His Ser Ala Thr His Arg Arg Cys Arg His Gly
        515                 520                 525

Ser Tyr Arg Arg Gly His Cys Thr Asn
        530                 535

<210> SEQ ID NO 39
<211> LENGTH: 948
<212> TYPE: DNA
<213> ORGANISM: Fusarium verticillioides

<400> SEQUENCE: 39
atgtggaaac tcctcgtcag cggtcttgtc gccgtcgcgt ccctcagcgg cgtgaacgct      60
gcttatccta accctggtcc cgtcaccggc gatactcgtg ttcacgaccc tacggttgtc     120
aagactccca gcgtggata cttgctggct catactggcg ataacgtttc gctcaagact     180
tcttctgatc gaactgcttg gaaggatgca ggtgctgttt ccccaacgg tgcgccttgg     240
actacgcagt acaccaaggg cgacaagaac ctctgggccc ctgatatctc ctaccacaac     300
ggccagtact atctgtacta ctccgcctct tccttcggtc agcgtacctc tgccattttt     360
ctcgctacca gcaagaccgg tgcatccggc tcgtggacca accaaggcgt cgtcgtcgag     420
tccaacaaca caacgacta caatgccatt gacggaaatc tctttgtcga ctctgatgga     480
aaatggtggc tctccttcgg ctctttctgg tccggcatca agctcatcca actcgacccc     540
aagaccggca gcgcaccgg ctcaagcatg tactccctcg ccaaacgcga cgcctccgtc     600
gaaggcgccg tcgaggctcc gttcatcacc aaacgcggaa gcacctacta cctctgggtg     660
tcgttcgaca gtgttgcca gggcgctgct agcacgtacc gtgtcatggt tggacggtcg     720
agcagcatta ctggtcctta tgttgacaag gctggtaagc agatgatgtc tggtggagga     780
acggagatta tggctagtca cggatctatt catggaccgg gacataatgc tgttttcact     840
gataacgatg cggacgttct tgtctatcat tactacgata acgctggcac agcgctgttg     900
ggcatcaact tgctcagata tgacaatggc tggcctgttg cttattag                 948

<210> SEQ ID NO 40
<211> LENGTH: 315
<212> TYPE: PRT
<213> ORGANISM: Fusarium verticillioides

<400> SEQUENCE: 40

```
Met Trp Lys Leu Leu Val Ser Gly Leu Val Ala Val Ala Ser Leu Ser
1               5                   10                  15

Gly Val Asn Ala Ala Tyr Pro Asn Pro Gly Pro Val Thr Gly Asp Thr
            20                  25                  30

Arg Val His Asp Pro Thr Val Val Lys Thr Pro Ser Gly Gly Tyr Leu
        35                  40                  45

Leu Ala His Thr Gly Asp Asn Val Ser Leu Lys Thr Ser Ser Asp Arg
    50                  55                  60

Thr Ala Trp Lys Asp Ala Gly Ala Val Phe Pro Asn Gly Ala Pro Trp
65                  70                  75                  80

Thr Thr Gln Tyr Thr Lys Gly Asp Lys Asn Leu Trp Ala Pro Asp Ile
                85                  90                  95

Ser Tyr His Asn Gly Gln Tyr Tyr Leu Tyr Tyr Ser Ala Ser Ser Phe
            100                 105                 110

Gly Gln Arg Thr Ser Ala Ile Phe Leu Ala Thr Ser Lys Thr Gly Ala
            115                 120                 125

Ser Gly Ser Trp Thr Asn Gln Gly Val Val Val Glu Ser Asn Asn Asn
130                 135                 140

Asn Asp Tyr Asn Ala Ile Asp Gly Asn Leu Phe Val Asp Ser Asp Gly
145                 150                 155                 160

Lys Trp Trp Leu Ser Phe Gly Ser Phe Trp Ser Gly Ile Lys Leu Ile
                165                 170                 175

Gln Leu Asp Pro Lys Thr Gly Lys Arg Thr Gly Ser Ser Met Tyr Ser
            180                 185                 190

Leu Ala Lys Arg Asp Ala Ser Val Glu Gly Ala Val Glu Ala Pro Phe
            195                 200                 205

Ile Thr Lys Arg Gly Ser Thr Tyr Tyr Leu Trp Val Ser Phe Asp Lys
210                 215                 220

Cys Cys Gln Gly Ala Ala Ser Thr Tyr Arg Val Met Val Gly Arg Ser
225                 230                 235                 240

Ser Ser Ile Thr Gly Pro Tyr Val Asp Lys Ala Gly Lys Gln Met Met
            245                 250                 255

Ser Gly Gly Gly Thr Glu Ile Met Ala Ser His Gly Ser Ile His Gly
            260                 265                 270

Pro Gly His Asn Ala Val Phe Thr Asp Asn Asp Ala Asp Val Leu Val
            275                 280                 285

Tyr His Tyr Tyr Asp Asn Ala Gly Thr Ala Leu Leu Gly Ile Asn Leu
            290                 295                 300

Leu Arg Tyr Asp Asn Gly Trp Pro Val Ala Tyr
305                 310                 315
```

<210> SEQ ID NO 41
<211> LENGTH: 1352
<212> TYPE: DNA
<213> ORGANISM: Trichoderma reesei

<400> SEQUENCE: 41

```
atgaaagcaa acgtcatctt gtgcctcctg gccccctgg tcgccgctct ccccaccgaa      60
accatccacc tcgaccccga gctcgccgct ctccgcgcca acctcaccga gcgaacagcc     120
gacctctggg accgccaagc tctctcaaag catcgaccagc tcatcaagag aaaaggcaag    180
ctctactttg gcaccgccac cgaccgcggc ctcctccaac gggaaaagaa cgcggccatc     240
atccaggcag acctcggcca ggtgacgccg gagaacagca tgaagtggca gtcgctcgag     300
```

```
aacaaccaag gccagctgaa ctggggagac gccgactatc tcgtcaactt tgcccagcaa    360
aacggcaagt cgatacgcgg ccacactctg atctggcact cgcagctgcc tgcgtgggtg    420
aacaatatca acaacgcgga tactctgcgg caagtcatcc gcacccatgt ctctactgtg    480
gttgggcggt acaagggcaa gattcgtgct tgggtgagtt ttgaacacca catgcccctt    540
ttcttagtcc gctcctcctc ctcttggaac ttctcacagt tatagccgta tacaacattc    600
gacaggaaat ttaggatgac aactactgac tgacttgtgt gtgtgatggc gataggacgt    660
ggtcaatgaa atcttcaacg aggatggaac gctgcgctct tcagtctttt ccaggctcct    720
cggcgaggag tttgtctcga ttgcctttcg tgctgctcga gatgctgacc cttctgcccg    780
tctttacatc aacgactaca atctcgaccg cgccaactat ggcaaggtca acgggttgaa    840
gacttacgtc tccaagtgga tctctcaagg agttcccatt gacggtattg gtgagccacg    900
accccctaaat gtcccccatt agagtctctt tctagagcca aggcttgaag ccattcaggg    960
actgacacga gagccttctc tacaggaagc cagtcccatc tcagcggcgg cggaggctct   1020
ggtacgctgg gtgcgctcca gcagctggca acggtacccg tcaccgagct ggccattacc   1080
gagctggaca ttcaggggc accgacgacg gattacaccc aagttgttca agcatgcctg   1140
agcgtctcca gtgcgtcgg catcaccgtg tggggcatca gtgacaaggt aagttgcttc   1200
ccctgtctgt gcttatcaac tgtaagcagc aacaactgat gctgtctgtc tttacctagg   1260
actcgtggcg tgccagcacc aaccctcttc tgtttgacgc aaacttcaac cccaagccgg   1320
catataacag cattgttggc atcttacaat ag                                  1352
```

<210> SEQ ID NO 42
<211> LENGTH: 347
<212> TYPE: PRT
<213> ORGANISM: Trichoderma reesei

<400> SEQUENCE: 42

Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His
        115                 120                 125

Thr Leu Ile Trp His Ser Gln Leu Pro Ala Trp Val Asn Asn Ile Asn
    130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

```
Leu Gly Glu Glu Phe Val Ser Ile Ala Phe Arg Ala Ala Arg Asp Ala
            195                 200                 205

Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
            275                 280                 285

Pro Thr Thr Asp Tyr Thr Gln Val Val Gln Ala Cys Leu Ser Val Ser
    290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345

<210> SEQ ID NO 43
<211> LENGTH: 222
<212> TYPE: PRT
<213> ORGANISM: Trichoderma reesei

<400> SEQUENCE: 43

Met Val Ser Phe Thr Ser Leu Leu Ala Ala Ser Pro Pro Ser Arg Ala
1               5                   10                  15

Ser Cys Arg Pro Ala Ala Glu Val Glu Ser Val Ala Val Glu Lys Arg
                20                  25                  30

Gln Thr Ile Gln Pro Gly Thr Gly Tyr Asn Asn Gly Tyr Phe Tyr Ser
            35                  40                  45

Tyr Trp Asn Asp Gly His Gly Gly Val Thr Tyr Thr Asn Gly Pro Gly
    50                  55                  60

Gly Gln Phe Ser Val Asn Trp Ser Asn Ser Gly Asn Phe Val Gly Gly
65                  70                  75                  80

Lys Gly Trp Gln Pro Gly Thr Lys Asn Lys Val Ile Asn Phe Ser Gly
                85                  90                  95

Ser Tyr Asn Pro Asn Gly Asn Ser Tyr Leu Ser Val Tyr Gly Trp Ser
                100                 105                 110

Arg Asn Pro Leu Ile Glu Tyr Tyr Ile Val Glu Asn Phe Gly Thr Tyr
            115                 120                 125

Asn Pro Ser Thr Gly Ala Thr Lys Leu Gly Glu Val Thr Ser Asp Gly
    130                 135                 140

Ser Val Tyr Asp Ile Tyr Arg Thr Gln Arg Val Asn Gln Pro Ser Ile
145                 150                 155                 160

Ile Gly Thr Ala Thr Phe Tyr Gln Tyr Trp Ser Val Arg Arg Asn His
                165                 170                 175

Arg Ser Ser Gly Ser Val Asn Thr Ala Asn His Phe Asn Ala Trp Ala
            180                 185                 190

Gln Gln Gly Leu Thr Leu Gly Thr Met Asp Tyr Gln Ile Val Ala Val
            195                 200                 205

Glu Gly Tyr Phe Ser Ser Gly Ser Ala Ser Ile Thr Val Ser
```

<210> SEQ ID NO 44
<211> LENGTH: 797
<212> TYPE: PRT
<213> ORGANISM: Trichoderma reesei

<400> SEQUENCE: 44

Met Val Asn Asn Ala Ala Leu Leu Ala Leu Ser Ala Leu Leu Pro
1               5                   10                  15

Thr Ala Leu Ala Gln Asn Asn Gln Thr Tyr Ala Asn Tyr Ser Ala Gln
                20                  25                  30

Gly Gln Pro Asp Leu Tyr Pro Glu Thr Leu Ala Thr Leu Thr Leu Ser
            35                  40                  45

Phe Pro Asp Cys Glu His Gly Pro Leu Lys Asn Asn Leu Val Cys Asp
        50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
130                 135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205

Gly Ile Gln Gly Gly Val Asp Pro Glu His Leu Lys Val Ala Ala Thr
210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Arg Tyr Ala Lys Ser Arg Ser
            260                 265                 270

Leu Met Cys Ala Tyr Asn Ser Val Asn Gly Val Pro Ser Cys Ala Asn
        275                 280                 285

Ser Phe Phe Leu Gln Thr Leu Leu Arg Glu Ser Trp Gly Phe Pro Glu
290                 295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ser Ser Leu
            325                 330                 335

Arg Ala Gly Thr Asp Ile Asp Cys Gly Gln Thr Tyr Pro Trp His Leu
        340                 345                 350

Asn Glu Ser Phe Val Ala Gly Glu Val Ser Arg Gly Glu Ile Glu Arg
            355                 360                 365

Ser Val Thr Arg Leu Tyr Ala Asn Leu Val Arg Leu Gly Tyr Phe Asp
370                 375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Val Glu Gly Ile Val Leu
            405                 410                 415

Leu Lys Asn Asp Gly Thr Leu Pro Leu Ser Lys Val Arg Ser Ile
            420                 425                 430

Ala Leu Ile Gly Pro Trp Ala Asn Ala Thr Thr Gln Met Gln Gly Asn
            435                 440                 445

Tyr Tyr Gly Pro Ala Pro Tyr Leu Ile Ser Pro Leu Glu Ala Ala Lys
450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Lys Lys Ser
            485                 490                 495

Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
            515                 520                 525

Ile Lys Gln Leu Ser Glu Val Gly Lys Pro Leu Val Val Leu Gln Met
            530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
            595                 600                 605

Met Asn Leu Arg Pro Asp Gly Lys Ser Asn Pro Gly Gln Thr Tyr Ile
610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
            645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
            675                 680                 685

Lys Thr Glu Ser Pro Tyr Thr Ala Met Leu Phe Val Arg Thr Ser Asn
690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
            725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
            755                 760                 765

Leu Glu Phe Glu Leu Val Gly Glu Val Thr Ile Glu Asn Trp Pro
770                 775                 780

Leu Glu Glu Gln Gln Ile Lys Asp Ala Thr Pro Asp Ala

-continued

| 785 | 790 | 795 |

<210> SEQ ID NO 45
<211> LENGTH: 744
<212> TYPE: PRT
<213> ORGANISM: Trichoderma reesei

<400> SEQUENCE: 45

```
Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
            20                  25                  30

Val Pro Pro Ala Gly Thr Pro Trp Gly Thr Ala Tyr Asp Lys Ala Lys
                35                  40                  45

Ala Ala Leu Ala Lys Leu Asn Leu Gln Asp Lys Val Gly Ile Val Ser
            50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
            115                 120                 125

Gly Glu Glu Val Lys Ala Ser Gly Ile His Val Ile Leu Gly Pro Val
130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
            195                 200                 205

Asp Arg Thr Leu His Glu Leu Tyr Thr Trp Pro Phe Ala Asp Ala Val
            210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
            275                 280                 285

Thr Asp Phe Asn Gly Asn Asn Arg Leu Trp Gly Pro Ala Leu Thr Asn
            290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
            355                 360                 365
```

Ala Asn Ile Leu Pro Leu Lys Lys Pro Ala Ser Ile Ala Val Val Gly
             370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
                420                 425                 430

Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
        450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His
            500                 505                 510

Ser Val Gly Ala Ile Ile Leu Glu Gln Ile Leu Ala Leu Pro Gln Val
        515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
        595                 600                 605

Ser Tyr Thr Lys Phe Asn Tyr Ser Arg Leu Ser Val Leu Ser Thr Ala
        610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
        675                 680                 685

Asn Leu Thr Pro Gly Gln Ser Gly Thr Ala Thr Phe Asn Ile Arg Arg
        690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740

<210> SEQ ID NO 46
<211> LENGTH: 2031
<212> TYPE: DNA
<213> ORGANISM: Podospora anserina

<400> SEQUENCE: 46

```
atgatccacc tcaagccagc cctcgcggcg ttgttggcgc tgtcgacgca atgtgtggct    60
attgatttgt ttgtcaagtc ttcgggggga ataagacga ctgatatcat gtatggtctt   120
atgcacgagg atatcaacaa ctccggcgac ggcggcatct acgccgagct aatctccaac   180
cgcgcgttcc aagggagtga aagttcccc tccaacctcg acaactggag ccccgtcggt   240
ggcgctaccc ttaccttca gaagcttgcc aagccccttt cctctgcgtt gccttactcc   300
gtcaatgttg ccaaccccaa ggagggcaag gcaagggca aggacaccaa ggggaagaag   360
gttggcttgg ccaatgctgg gttttgggt atggatgtca agaggcagaa gtacactggt   420
agcttccacg ttactggtga gtacaaggt gactttgagg ttagcttgcg cagcgcgatt   480
accggggaga cctttggcaa gaaggtggtg aagggtggga gtaagaaggg gaagtggacc   540
gagaaggagt ttgagttggt gcctttcaag gatgcgccca acagcaacaa cacctttgtt   600
gtgcagtggg atgccgaggg cgcaaaggac ggatctttgg atctcaactt gatcagcttg   660
ttccctccga cattcaaggg aaggaagaat gggctgagaa ttgatcttgc gcagacgatg   720
gttgagctca agccgacctt cttgcgcttc cccggtggca acatgctcga gggtaacacc   780
ttggacactt ggtggaagtg gtacgagacc attggccctc tgaaggatcg cccgggcatg   840
gctggtgtct gggagtacca gcaaaccctt ggcttgggtc tggtcgagta catggagtgg   900
gccgatgaca tgaacttgga gcccattgtc ggtgtcttcg ctggtcttgc cctcgatggc   960
tcgttcgttc ccgaatccga gatgggatgg gtcatccaac aggctctcga cgaaatcgag  1020
ttcctcactg gcgatgctaa gaccaccaaa tgggtgccg tccgcgcgaa gcttggtcac  1080
cccaagcctt ggaaggtcaa gtgggttgag atcggtaacg aggattggct tgccggacgc  1140
cctgctggct tcgagtcgta catcaactac cgcttcccca tgatgatgaa ggccttcaac  1200
gaaaagtacc ccgacatcaa gatcatcgcc tcgccctcca tcttcgacaa catgacaatc  1260
cccgcgggtg ctgccggtga tcaccacccg tacctgactc ccgatgagtt cgttgagcga  1320
ttcgccaagt tcgataactt gagcaaggat aacgtgacgc tcatcggcga ggctgcgtcg  1380
acgcatccta acggtggtat cgcttgggag ggagatctca tgcccttgcc ttggtgggc  1440
ggcagtgttg ctgaggctat cttcttgatc agcactgaga gaaacggtga caagatcatc  1500
ggtgctactt acgcgcctgg tcttcgcagc ttggaccgct ggcaatggag catgacctgg  1560
gtgcagcatg ccgccgaccc ggccctcacc actcgctcga ccagtggta tgtctggaga  1620
atcctcgccc accacatcat ccgtgagacg ctcccggtcg atgccccggc cggcaagccc  1680
aactttgacc ctctgttcta cgttgccga aagagcgaga gtggcaccgg tatcttcaag  1740
gctgccgtct acaactcgac tgaatcgatc ccggtgtcgt tgaagtttga tggtctcaac  1800
gagggagcgg ttgccaactt gacggtgctt actgggccgg aggatccgta tggatacaac  1860
gaccccttca ctggtatcaa tgttgtcaag gagaagacca ccttcatcaa ggccggaaag  1920
ggcggcaagt tcaccttcac cctgccgggc ttgagtgttg ctgtgttgga gacggccgac  1980
gcggtcaagg gtggcaaggg aaagggcaag ggcaaggaa agggtaactg a            2031
```

<210> SEQ ID NO 47
<211> LENGTH: 2031
<212> TYPE: DNA
<213> ORGANISM: Artificial Sequence
<220> FEATURE:
<223> OTHER INFORMATION: synthesized codon optimized cDNA for P

| | |
|---|---|
| atgatccacc tcaagcccgc cctcgccgcc ctcctcgccc tcagcaccca atgcgtcgcc | 60 |
| atcgacctct tcgtcaagag cagcggcggc aacaagacca ccgacatcat gtacggcctc | 120 |
| atgcacgagg acatcaacaa cagcggcgac ggcggcatct acgccgagct gatcagcaac | 180 |
| cgcgccttcc agggcagcga gaagttcccc agcaacctcg acaactggtc cccgtcggc | 240 |
| ggcgccaccc tcaccctcca gaagctcgcc aagcccctgt cctctgccct ccctactcc | 300 |
| gtcaacgtcg ccaaccccaa ggagggtaag ggtaagggca aggacaccaa gggcaagaag | 360 |
| gtcggcctcg ccaacgccgg cttttggggc atggacgtca agcgccagaa atacaccggc | 420 |
| agcttccacg tcaccggcga gtacaagggc gacttcgagg tcagcctccg cagcgccatt | 480 |
| accggcgaga ccttcggcaa gaaggtcgtc aaggcgggca gcaagaaggg caagtggacc | 540 |
| gagaaggagt tcgagctggt ccccttcaag gacgccccca cagcaacaa caccttcgtc | 600 |
| gtccagtggg acgccgaggg cgccaaggac ggcagcctcg acctcaacct catcagcctc | 660 |
| ttcccgccca ccttcaaggg ccgcaagaac ggcctccgca tcgacctcgc ccagaccatg | 720 |
| gtcgagctga agcccacctt cctccgcttt cccggcggca acatgctcga gggcaacacc | 780 |
| ctcgacacct ggtggaagtg gtacgagacc atcggccccc tgaaggaccg ccctggcatg | 840 |
| gccggcgtct gggagtacca gcagacgctg ggcctcggcc tggtcgagta catggagtgg | 900 |
| gccgacgaca tgaacctcga gcccatcgtc ggcgtctttg ctggcctggc cctggatggc | 960 |
| agctttgtcc ccgagagcga gatgggctgg gtcatccagc aggctctcga tgagatcgag | 1020 |
| ttcctcaccg gcgacgccaa gaccaccaag tggggcgccg tccgcgccaa gctcggccac | 1080 |
| cctaagccct ggaaggtcaa atgggtcgag atcggcaacg aggactggct cgccggccga | 1140 |
| cctgccggct tcgagagcta catcaactac cgcttcccca tgatgatgaa ggccttcaac | 1200 |
| gagaaatacc ccgacatcaa gatcattgcc agccctcca tcttcgacaa catgaccatt | 1260 |
| ccagccggtg ctgccggtga ccaccacccc tacctcaccc ccgacgaatt tgtcgagcgc | 1320 |
| ttcgccaagt tcgacaacct cagcaaggac aacgtcaccc tcattggcga ggccgccagc | 1380 |
| acccacccca acggcggcat tgcctgggag gcgacctca tgcccctgcc ctggtggggc | 1440 |
| ggcagcgtcg ccgaggccat cttcctcatc agcaccgagc gcaacggcga caagatcatc | 1500 |
| ggcgccacct acgcccctgg cctccgatct ctcgaccgct ggcagtggag catgacctgg | 1560 |
| gtccagcacg ccgccgaccc tgccctcacc cccgcagca ccagctggta cgtctggcgc | 1620 |
| atcctcgccc accacatcat tcgcgagacc ctccccgtcg acgccccgc cggcaagccc | 1680 |
| aacttcgacc ccctcttcta cgtcgctggc aagtcggaga gcggcaccgg catcttcaag | 1740 |
| gccgccgtct acaacagcac cgagagcatc cccgtcagcc tcaagttcga cggcctcaac | 1800 |
| gagggcgccg tcgccaacct caccgtcctc accggccccg aggacccta cggctacaac | 1860 |
| gaccccttca ccggcatcaa cgtcgtcaag gaaaagacca ccttcatcaa ggccggcaag | 1920 |
| ggcggcaagt tcacctttac cctccccggc ctctctgtcg ccgtcctcga ccgccgac | 1980 |
| gccgtgaagg gtggcaaggg aaagggaaag ggcaagggta agggtaacta a | 2031 |

<210> SEQ ID NO 48
<211> LENGTH: 1020
<212> TYPE: DNA
<213> ORGANISM: Artificial Sequence
<220> FEATURE:
<223> OTHER INFORMATION: constructed GZ43A sequence

<400> SEQUENCE: 48

| | |
|---|---|
| atgtatcgga agttggccgt catctcggcc ttcttggcca cagctcgtgc taccaacgac | 60 |

```
gactgtcctc tcatcactag tagatggact gcggatcctt cggctcatgt ctttaacgac      120
accttgtggc tctacccgtc tcatgacatc gatgctggat ttgagaatga tcctgatgga      180
ggccagtacg ccatgagaga ttaccatgtc tactctatcg acaagatcta cggttccctg      240
ccggtcgatc acggtacggc cctgtcagtg gaggatgtcc cctgggcctc tcgacagatg      300
tgggctcctg acgctgccca caagaacggc aaatactacc tatacttccc tgccaaagac      360
aaggatgata tcttcagaat cggcgttgct gtctcaccaa ccccggcgg accattcgtc       420 cccgacaaga gttggatccc tcacactttc agcatcgacc ccgccagttt cgtcgatgat      480
gatgacagag cctacttggc atggggtggt atcatgggtg ccagcttca acgatggcag       540 gataagaaca agtacaacga atctggcact gagccaggaa acggcaccgc tgccttgagc      600
cctcagattg ccaagctgag caaggacatg cacactctgg cagagaagcc tcgcgacatg      660
ctcattcttg accccaagac tggcaagccg ctcctttctg aggatgaaga ccgacgcttc      720
ttcgaaggac cctggattca caagcgcaac aagatttact acctcaccta ctctactggc      780
acaacccact atcttgtcta tgcgacttca agaccccct atggtcctta cacctaccag       840
ggcagaattc tggagccagt tgatggctgg actactcact ctagtatcgt caagtaccag      900
ggtcagtggt ggctatttta tcacgatgcc aagacatctg gcaaggacta tcttcgccag      960
gtaaaggcta agaagatttg gtacgatagc aaaggaaaga tcttgacaaa gaagccttga     1020
```

<210> SEQ ID NO 49
<211> LENGTH: 1038
<212> TYPE: DNA
<213> ORGANISM: Artificial Sequence
<220> FEATURE:
<223> OTHER INFORMATION: constructed Gz43A sequence

<400> SEQUENCE: 49

```
atgtatcgga agttggccgt catctcggcc ttcttggcca cagctcgtgc tcaagacact       60
aatgacattc ctcccctgat caccgacctc tggtccgcag atccctcggc tcatgttttc      120
gaaggcaagc tctgggttta cccatctcac gacatcgaag ccaatgttgt caacggcaca      180
ggaggcgctc aatacgccat gagggattac catacctact ccatgaagag catctatggt      240
aaagatcccg ttgtcgacca cggcgtcgct ctctcagtcg atgacgttcc ctgggcgaag      300
cagcaaatgt gggctcctga cgcagctcat aagaacggca aatattatct gtacttcccc      360
gccaaggaca aggatgagat cttcagaatt ggagttgctg tctccaacaa gcccagcggt      420
cctttcaagg ccgacaagag ctggatccct ggcacgtaca gtatcgatcc tgctagctac      480
gtcgacactg ataacgaggc ctacctcatc tggggcggta tctggggcgg ccagctccaa      540
gcctggcagg ataaaaagaa ctttaacgag tcgtggattg gagacaaggc tgctcctaac      600
ggcaccaatg ccctatctcc tcagatcgcc aagctaagca aggacatgca caagatcacc      660
gaaacacccc gcgatctcgt cattctcgcc ccgagacag gcaagcctct tcaggctgag       720
gacaacaagc gacgattctt cgagggccct tggatccaca agcgcggcaa gctttactac      780
ctcatgtact ccaccggtga tacccacttc cttgtctacg ctacttccaa gaacatctac      840
ggtccttata cctaccgggg caagattctt gatcctgttg atgggtggac tactcatgga      900
agtattgttg agtataaggg acagtggtgg ctttttcttg ctgatgcgca tacgtctggt      960
aaggattacc ttcgacaggt gaaggcgagg aagatctggt atgacaagaa cggcaagatc     1020
ttgcttcacc gtccttag                                                   1038
```

<210> SEQ ID NO 50
<211> LENGTH: 1920
<212> TYPE: DNA
<213> ORGANISM: Artificial Sequence
<220> FEATURE:
<223> OTHER INFORMATION: synthesized codon optimized Pf51A sequence

<400> SEQUENCE: 50

| | | | | | |
|---|---|---|---|---|---|
| atgtaccgga | agctcgccgt | gatcagcgcc | ttcctggcga | ctgctcgcgc | catcaccatc | 60 |
| aacgtcagcc | agagcggcgg | caacaagacc | agcccgctcc | agtacggcct | catgttcgag | 120 |
| gacatcaacc | acggcggcga | cggcggcctc | tacgccgagc | tggtccggaa | ccgggccttc | 180 |
| cagggcagca | ccgtctaccc | ggccaacctc | gacggctacg | actcggtgaa | cggcgcgatt | 240 |
| ctcgcgctcc | agaacctcac | caacccgctc | agcccgagca | tgccctcgtc | gctgaacgtc | 300 |
| gccaagggct | cgaacaacgg | cagcatcggc | ttcgccaacg | aggggtggtg | gggcatcgag | 360 |
| gtcaagccgc | agcggtacgc | cggcagcttc | tacgtccagg | gcgactacca | gggcgacttc | 420 |
| gacatcagcc | tccagagcaa | gctcacccag | gaggtcttcg | cgacggcgaa | ggtccggtcg | 480 |
| agcggcaagc | acgaggactg | ggtccagtac | aagtacgagc | tggtcccgaa | gaaggccgcc | 540 |
| agcaacacca | acaacaccct | caccatcacc | ttcgacagca | agggcctcaa | ggacggcagc | 600 |
| ctcaacttca | acctcatcag | cctcttcccg | ccgacctaca | caaccggcc | gaacggcctc | 660 |
| cggatcgacc | tcgtcgaggc | catggcgag | ctggagggca | agttcctccg | cttccccggc | 720 |
| ggctcggacg | tggagggcgt | ccaggccccg | tactggtaca | agtggaacga | ccgtcggc | 780 |
| gacctcaagg | accgctactc | gcgcccgagc | gcctggacct | acgaggagag | caacggcatc | 840 |
| ggcctcatcg | agtacatgaa | ctggtgcgac | gacatgggcc | tcgagccgat | cctcgccgtc | 900 |
| tgggacggcc | actacctcag | caacgaggtc | atcagcgaga | cgacctcca | gccgtacatc | 960 |
| gacgacaccc | tcaaccagct | cgagttcctc | atgggcgccc | cggacactcc | ctacgggtct | 1020 |
| tggagggcta | gcctcggcta | cccgaagccg | tggaccatca | actacgtcga | gatcggcaac | 1080 |
| gaggacaacc | tctacggcgg | cctcgagacc | tacatcgcct | accggttcca | ggcctactac | 1140 |
| gacgccatca | ccgccaagta | cccgcacatg | accgtcatgg | agagcctcac | cgagatgccc | 1200 |
| ggccccgctg | ccgcggcgtc | ggactaccac | cagtactcga | cgcccgacgg | cttcgtcagc | 1260 |
| cagttcaact | acttcgacca | gatgccggtc | accaaccgca | cgctgaacgg | cgagatcgcc | 1320 |
| accgtctacc | ccaacaaccc | gagcaactcg | gtggcgtggg | gcagcccgtt | cccgctctac | 1380 |
| ccgtggtgga | tcgggtccgt | ggctgaggcc | gtcttcctca | tcggcgagga | gcggaacagc | 1440 |
| ccgaagatca | tcggcgccag | ctacgccccc | atgttccgca | acattaacaa | ctggcagtgg | 1500 |
| agcccgaccc | tgatcgcctt | cgacgccgac | agcagccgga | cgtcgcgctc | tacttcctgg | 1560 |
| cacgtcatca | agctcctcag | caccaacaag | atcacccaga | acctgccac | gacgtggtct | 1620 |
| gggggggaca | tcggcccgct | ctactgggtc | gccggccgga | acgacaacac | cggcagcaac | 1680 |
| atcttcaagg | ccgccgtcta | caacagcacc | agcgacgtcc | cggtcaccgt | ccagttcgcc | 1740 |
| ggctgcaacg | ccaagagcgc | caacctcacc | atcctctcgt | cggacgaccc | caacgccagc | 1800 |
| aactacccgg | cgccccga | ggtcgtcaag | accgagatcc | agagcgtcac | cgccaacgcc | 1860 |
| cacggcgcct | tcgagttcag | cctcccgaac | ctgtcggtgg | ctgtgctgaa | gacggagtag | 1920 |

<210> SEQ ID NO 51
<211> LENGTH: 17
<212> TYPE: PRT
<213> ORGANISM: Trichomonas reesei -continued

<400> SEQUENCE: 51

Met Tyr Arg Lys Leu Ala Val Ile Ser Ala Phe Leu Ala Thr Ala Arg
1               5                   10                  15

Ala

<210> SEQ ID NO 52
<211> LENGTH: 23
<212> TYPE: DNA
<213> ORGANISM: Artificial Sequence
<220> FEATURE:
<223> OTHER INFORMATION: synthetic primer

<400> SEQUENCE: 52
cacccatgct gctcaatctt cag                                         23

<210> SEQ ID NO 53
<211> LENGTH: 23
<212> TYPE: DNA
<213> ORGANISM: Artificial Sequence
<220> FEATURE:
<223> OTHER INFORMATION: synthetic primer

<400> SEQUENCE: 53
ttacgcagac ttggggtctt gag                                         23

<210> SEQ ID NO 54
<211> LENGTH: 24
<212> TYPE: DNA
<213> ORGANISM: Artificial Sequence
<220> FEATURE:
<223> OTHER INFORMATION: synthetic primer

<400> SEQUENCE: 54
caccatgtgg ctgacctccc catt                                        24

<210> SEQ ID NO 55
<211> LENGTH: 28
<212> TYPE: DNA
<213> ORGANISM: Artificial Sequence
<220> FEATURE:
<223> OTHER INFORMATION: synthetic primer

<400> SEQUENCE: 55
ttagctaaac tgccaccagt tgaagttg                                    28

<210> SEQ ID NO 56
<211> LENGTH: 26
<212> TYPE: DNA
<213> ORGANISM: Artificial Sequence
<220> FEATURE:
<223> OTHER INFORMATION: synthetic primer

<400> SEQUENCE: 56
caccatgcgc ttctcttggc tattgt                                      26

<210> SEQ ID NO 57
<211> LENGTH: 27
<212> TYPE: DNA
<213> ORGANISM: Artificial Sequence
<220> FEATURE:
<223> OTHER INFORMATION: synthetic primer

<400> SEQUENCE: 57
ctacaattct gatttcacaa aaacacc                                     27

<210> SEQ ID NO 58
<211> LENGTH: 22
<212> TYPE: DNA
<213> ORGANISM: Artificial Sequence
<220> FEATURE:
<223> OTHER INFORMATION: synthetic primer

<400> SEQUENCE: 58
caccatgcag ctcaagtttc tg                                              22

<210> SEQ ID NO 59
<211> LENGTH: 22
<212> TYPE: DNA
<213> ORGANISM: Artificial Sequence
<220> FEATURE:
<223> OTHER INFORMATION: synthetic primer

<400> SEQUENCE: 59
ctaaatctta ggacgagtaa gc                                              22

<210> SEQ ID NO 60
<211> LENGTH: 29
<212> TYPE: DNA
<213> ORGANISM: Artificial Sequence
<220> FEATURE:
<223> OTHER INFORMATION: synthetic primer

<400> SEQUENCE: 60
caccatggtt cgcttcagtt caatcctag                                       29

<210> SEQ ID NO 61
<211> LENGTH: 21
<212> TYPE: DNA
<213> ORGANISM: Artificial Sequence
<220> FEATURE:
<223> OTHER INFORMATION: synthetic primer

<400> SEQUENCE: 61
ctagctagag taaggctttc c                                               21

<210> SEQ ID NO 62
<211> LENGTH: 27
<212> TYPE: DNA
<213> ORGANISM: Artificial Sequence
<220> FEATURE:
<223> OTHER INFORMATION: synthetic primer

<400> SEQUENCE: 62
caccatgcac tacgctaccc tcaccac                                         27

<210> SEQ ID NO 63
<211> LENGTH: 22
<212> TYPE: DNA
<213> ORGANISM: Artificial Sequence
<220> FEATURE:
<223> OTHER INFORMATION: synthetic primer

<400> SEQUENCE: 63
tcaagtagag gggctgctca cc                                              22

<210> SEQ ID NO 64
<211> LENGTH: 27
<212> TYPE: DNA
<213> ORGANISM: Artificial Sequence
<220> FEATURE:

<223> OTHER INFORMATION: synthetic primer

<400> SEQUENCE: 64
caccatgaaa ctctctagct acctctg                                27

<210> SEQ ID NO 65
<211> LENGTH: 25
<212> TYPE: DNA
<213> ORGANISM: Artificial Sequence
<220> FEATURE:
<223> OTHER INFORMATION: synthetic primer

<400> SEQUENCE: 65
ctacgaaact gtgacagtca cgttg                                  25

<210> SEQ ID NO 66
<211> LENGTH: 30
<212> TYPE: DNA
<213> ORGANISM: Artificial Sequence
<220> FEATURE:
<223> OTHER INFORMATION: synthetic primer

<400> SEQUENCE: 66
caccatgctc ttctcgctcg ttcttcctac                             30

<210> SEQ ID NO 67
<211> LENGTH: 21
<212> TYPE: DNA
<213> ORGANISM: Artificial Sequence
<220> FEATURE:
<223> OTHER INFORMATION: synthetic primer

<400> SEQUENCE: 67
ttagttggtg cagtggccac g                                      21

<210> SEQ ID NO 68
<211> LENGTH: 29
<212> TYPE: DNA
<213> ORGANISM: Artificial Sequence
<220> FEATURE:
<223> OTHER INFORMATION: synthetic primer

<400> SEQUENCE: 68
caccatgaat cctttatctc tcggccttg                              29

<210> SEQ ID NO 69
<211> LENGTH: 23
<212> TYPE: DNA
<213> ORGANISM: Artificial Sequence
<220> FEATURE:
<223> OTHER INFORMATION: synthetic primer

<400> SEQUENCE: 69
cagccctcat agtcgtcttc ttc                                    23

<210> SEQ ID NO 70
<211> LENGTH: 24
<212> TYPE: DNA
<213> ORGANISM: Artificial Sequence
<220> FEATURE:
<223> OTHER INFORMATION: synthetic primer

<400> SEQUENCE: 70
caccatgcgt cttctatcgt ttcc                                   24

```
<210> SEQ ID NO 71
<211> LENGTH: 20
<212> TYPE: DNA
<213> ORGANISM: Artificial Sequence
<220> FEATURE:
<223> OTHER INFORMATION: synthetic primer

<400> SEQUENCE: 71
ctacaaaggc ctaggatcaa                                              20

<210> SEQ ID NO 72
<211> LENGTH: 27
<212> TYPE: DNA
<213> ORGANISM: Artificial Sequence
<220> FEATURE:
<223> OTHER INFORMATION: synthetic primer

<400> SEQUENCE: 72
caccatgcac tacgctaccc tcaccac                                      27

<210> SEQ ID NO 73
<211> LENGTH: 22
<212> TYPE: DNA
<213> ORGANISM: Artificial Sequence
<220> FEATURE:
<223> OTHER INFORMATION: synthetic primer

<400> SEQUENCE: 73
tcaagtagag gggctgctca cc                                           22

<210> SEQ ID NO 74
<211> LENGTH: 26
<212> TYPE: DNA
<213> ORGANISM: Artificial Sequence
<220> FEATURE:
<223> OTHER INFORMATION: synthetic primer

<400> SEQUENCE: 74
caccatgaag gtatactggc tcgtgg                                       26

<210> SEQ ID NO 75
<211> LENGTH: 25
<212> TYPE: DNA
<213> ORGANISM: Artificial Sequence
<220> FEATURE:
<223> OTHER INFORMATION: synthetic primer

<400> SEQUENCE: 75
ctatgcagct gtgaaagact caacc                                        25

<210> SEQ ID NO 76
<211> LENGTH: 25
<212> TYPE: DNA
<213> ORGANISM: Artificial Sequence
<220> FEATURE:
<223> OTHER INFORMATION: synthetic primer

<400> SEQUENCE: 76
caccatgtgg aaactcctcg tcagc                                        25

<210> SEQ ID NO 77
<211> LENGTH: 25
<212> TYPE: DNA
<213> ORGANISM: Artificial Sequence
<220> FEATURE:
<223> OTHER INFORMATION: synthetic primer
```

<400> SEQUENCE: 77
ctaataagca acaggccagc cattg  25

<210> SEQ ID NO 78
<211> LENGTH: 33
<212> TYPE: DNA
<213> ORGANISM: Artificial Sequence
<220> FEATURE:
<223> OTHER INFORMATION: synthetic primer

<400> SEQUENCE: 78
caccatgctt cagcgatttg cttatatttt acc  33

<210> SEQ ID NO 79
<211> LENGTH: 28
<212> TYPE: DNA
<213> ORGANISM: Artificial Sequence
<220> FEATURE:
<223> OTHER INFORMATION: synthetic primer

<400> SEQUENCE: 79
ttatgcgaac tgccaataat caaagttg  28

<210> SEQ ID NO 80
<211> LENGTH: 25
<212> TYPE: DNA
<213> ORGANISM: Artificial Sequence
<220> FEATURE:
<223> OTHER INFORMATION: synthetic primer

<400> SEQUENCE: 80
caccatgtac cggaagctcg ccgtg  25

<210> SEQ ID NO 81
<211> LENGTH: 24
<212> TYPE: DNA
<213> ORGANISM: Artificial Sequence
<220> FEATURE:
<223> OTHER INFORMATION: synthetic primer

<400> SEQUENCE: 81
ctactccgtc ttcagcacag ccac  24

<210> SEQ ID NO 82
<211> LENGTH: 40
<212> TYPE: DNA
<213> ORGANISM: Artificial Sequence
<220> FEATURE:
<223> OTHER INFORMATION: synthetic primer

<400> SEQUENCE: 82
ccgcggccgc accatggttt ctttctccta cctgctgctg  40

<210> SEQ ID NO 83
<211> LENGTH: 42
<212> TYPE: DNA
<213> ORGANISM: Artificial Sequence
<220> FEATURE:
<223> OTHER INFORMATION: synthetic primer

<400> SEQUENCE: 83
ccggcgcgcc cttactagta gacagtgatg gaagcagatc cg  42

<210> SEQ ID NO 84
<211> LENGTH: 38

```
<212> TYPE: DNA
<213> ORGANISM: Artificial Sequence
<220> FEATURE:
<223> OTHER INFORMATION: synthetic primer

<400> SEQUENCE: 84
ccgcggccgc accatgatct ccatttcctc gctcagct                              38

<210> SEQ ID NO 85
<211> LENGTH: 43
<212> TYPE: DNA
<213> ORGANISM: Artificial Sequence
<220> FEATURE:
<223> OTHER INFORMATION: synthetic primer

<400> SEQUENCE: 85
ccggcgcgcc cttatcactt ggatataacc ctgcaagaag gta                        43

<210> SEQ ID NO 86
<211> LENGTH: 25
<212> TYPE: DNA
<213> ORGANISM: Artificial Sequence
<220> FEATURE:
<223> OTHER INFORMATION: synthetic primer

<400> SEQUENCE: 86
caccatggca gctccaagtt tatcc                                            25

<210> SEQ ID NO 87
<211> LENGTH: 20
<212> TYPE: DNA
<213> ORGANISM: Artificial Sequence
<220> FEATURE:
<223> OTHER INFORMATION: synthetic primer

<400> SEQUENCE: 87
tcagtagctc gggaccactc                                                  20

<210> SEQ ID NO 88
<211> LENGTH: 28
<212> TYPE: DNA
<213> ORGANISM: Artificial Sequence
<220> FEATURE:
<223> OTHER INFORMATION: synthetic primer

<400> SEQUENCE: 88
caccatgaga tatagaacag ctgccgct                                         28

<210> SEQ ID NO 89
<211> LENGTH: 40
<212> TYPE: DNA
<213> ORGANISM: Artificial Sequence
<220> FEATURE:
<223> OTHER INFORMATION: synthetic primer

<400> SEQUENCE: 89
cgaccgccct gcggagtctt gcccagtggt cccgcgacag                            40

<210> SEQ ID NO 90
<211> LENGTH: 40
<212> TYPE: DNA
<213> ORGANISM: Artificial Sequence
<220> FEATURE:
<223> OTHER INFORMATION: synthetic primer

<400> SEQUENCE: 90
```
ctgtcgcggg accactgggc aagactccgc agggcggtcg    40

<210> SEQ ID NO 91
<211> LENGTH: 20
<212> TYPE: DNA
<213> ORGANISM: Artificial Sequence
<220> FEATURE:
<223> OTHER INFORMATION: synthetic primer

<400> SEQUENCE: 91
cctacgctac cgacagagtg    20

<210> SEQ ID NO 92
<211> LENGTH: 20
<212> TYPE: DNA
<213> ORGANISM: Artificial Sequence
<220> FEATURE:
<223> OTHER INFORMATION: synthetic primer

<400> SEQUENCE: 92
gtctagactg gaaacgcaac    20

<210> SEQ ID NO 93
<211> LENGTH: 21
<212> TYPE: DNA
<213> ORGANISM: Artificial Sequence
<220> FEATURE:
<223> OTHER INFORMATION: synthetic primer

<400> SEQUENCE: 93
gagttgtgaa gtcggtaatc c    21

<210> SEQ ID NO 94
<211> LENGTH: 35
<212> TYPE: DNA
<213> ORGANISM: Artificial Sequence
<220> FEATURE:
<223> OTHER INFORMATION: synthetic primer

<400> SEQUENCE: 94
caccatgaaa gcaaacgtca tcttgtgcct cctgg    35

<210> SEQ ID NO 95
<211> LENGTH: 43
<212> TYPE: DNA
<213> ORGANISM: Artificial Sequence
<220> FEATURE:
<223> OTHER INFORMATION: synthetic primer

<400> SEQUENCE: 95
ctattgtaag atgccaacaa tgctgttata tgccggcttg ggg    43

<210> SEQ ID NO 96
<211> LENGTH: 21
<212> TYPE: DNA
<213> ORGANISM: Artificial Sequence
<220> FEATURE:
<223> OTHER INFORMATION: synthetic primer

<400> SEQUENCE: 96
gagttgtgaa gtcggtaatc c    21

<210> SEQ ID NO 97
<211> LENGTH: 18
<212> TYPE: DNA
<213> ORGANISM: Artificial Sequence

```
<220> FEATURE:
<223> OTHER INFORMATION: synthetic primer

<400> SEQUENCE: 97
cacgaagagc ggcgattc                                                    18

<210> SEQ ID NO 98
<211> LENGTH: 23
<212> TYPE: DNA
<213> ORGANISM: Artificial Sequence
<220> FEATURE:
<223> OTHER INFORMATION: synthetic primer

<400> SEQUENCE: 98
cacccatgct gctcaatctt cag                                              23

<210> SEQ ID NO 99
<211> LENGTH: 23
<212> TYPE: DNA
<213> ORGANISM: Artificial Sequence
<220> FEATURE:
<223> OTHER INFORMATION: synthetic primer

<400> SEQUENCE: 99
ttacgcagac ttggggtctt gag                                              23

<210> SEQ ID NO 100
<211> LENGTH: 20
<212> TYPE: DNA
<213> ORGANISM: Artificial Sequence
<220> FEATURE:
<223> OTHER INFORMATION: synthetic primer

<400> SEQUENCE: 100
gcttgagtgt atcgtgtaag                                                  20

<210> SEQ ID NO 101
<211> LENGTH: 21
<212> TYPE: DNA
<213> ORGANISM: Artificial Sequence
<220> FEATURE:
<223> OTHER INFORMATION: synthetic primer

<400> SEQUENCE: 101
gcaacggcaa agccccactt c                                                21

<210> SEQ ID NO 102
<211> LENGTH: 32
<212> TYPE: DNA
<213> ORGANISM: Artificial Sequence
<220> FEATURE:
<223> OTHER INFORMATION: synthetic primer

<400> SEQUENCE: 102
gtagcggccg cctcatctca tctcatccat cc                                    32

<210> SEQ ID NO 103
<211> LENGTH: 24
<212> TYPE: DNA
<213> ORGANISM: Artificial Sequence
<220> FEATURE:
<223> OTHER INFORMATION: synthetic primer

<400> SEQUENCE: 103
caccatgcag ctcaagtttc tgtc                                             24
```

```
<210> SEQ ID NO 104
<211> LENGTH: 32
<212> TYPE: DNA
<213> ORGANISM: Artificial Sequence
<220> FEATURE:
<223> OTHER INFORMATION: synthetic primer

<400> SEQUENCE: 104
ggttactagt caactgcccg ttctgtagcg ag                              32

<210> SEQ ID NO 105
<211> LENGTH: 29
<212> TYPE: DNA
<213> ORGANISM: Artificial Sequence
<220> FEATURE:
<223> OTHER INFORMATION: synthetic primer

<400> SEQUENCE: 105
catgcgatcg cgacgttttg gtcaggtcg                                  29

<210> SEQ ID NO 106
<211> LENGTH: 40
<212> TYPE: DNA
<213> ORGANISM: Artificial Sequence
<220> FEATURE:
<223> OTHER INFORMATION: synthetic primer

<400> SEQUENCE: 106
gacagaaact tgagctgcat ggtgtgggac aacaagaagg                      40

<210> SEQ ID NO 107
<211> LENGTH: 29
<212> TYPE: DNA
<213> ORGANISM: Artificial Sequence
<220> FEATURE:
<223> OTHER INFORMATION: synthetic primer

<400> SEQUENCE: 107
caccatggtt cgcttcagtt caatcctag                                  29

<210> SEQ ID NO 108
<211> LENGTH: 22
<212> TYPE: DNA
<213> ORGANISM: Artificial Sequence
<220> FEATURE:
<223> OTHER INFORMATION: synthetic primer

<400> SEQUENCE: 108
gtggctagaa gatatccaac ac                                         22

<210> SEQ ID NO 109
<211> LENGTH: 29
<212> TYPE: DNA
<213> ORGANISM: Artificial Sequence
<220> FEATURE:
<223> OTHER INFORMATION: synthetic primer

<400> SEQUENCE: 109
catgcgatcg cgacgttttg gtcaggtcg                                  29

<210> SEQ ID NO 110
<211> LENGTH: 39
<212> TYPE: DNA
<213> ORGANISM: Artificial Sequence
<220> FEATURE:
<223> OTHER INFORMATION: synthetic primer
```

<400> SEQUENCE: 110
gaactgaagc gaaccatggt gtgggacaac aagaaggac                              39

<210> SEQ ID NO 111
<211> LENGTH: 21
<212> TYPE: DNA
<213> ORGANISM: Artificial Sequence
<220> FEATURE:
<223> OTHER INFORMATION: synthetic primer

<400> SEQUENCE: 111
gtagttatgc gcatgctaga c                                                21

<210> SEQ ID NO 112
<211> LENGTH: 22
<212> TYPE: DNA
<213> ORGANISM: Artificial Sequence
<220> FEATURE:
<223> OTHER INFORMATION: synthetic primer

<400> SEQUENCE: 112
gtggctagaa gatatccaac ac                                               22

<210> SEQ ID NO 113
<211> LENGTH: 504
<212> TYPE: PRT
<213> ORGANISM: Geobacillus stearothermophilus

<400> SEQUENCE: 113

```
Met Lys Val Val Asn Val Pro Ser Asn Gly Arg Glu Lys Phe Lys Lys
1               5                   10                  15
Asn Trp Lys Phe Cys Val Gly Thr Gly Arg Leu Gly Leu Ala Leu Gln
            20                  25                  30
Lys Glu Tyr Leu Asp His Leu Lys Leu Val Gln Glu Lys Ile Gly Phe
        35                  40                  45
Arg Tyr Ile Arg Gly His Gly Leu Leu Ser Asp Asp Val Gly Ile Tyr
    50                  55                  60
Arg Glu Val Glu Ile Asp Gly Glu Met Lys Pro Phe Tyr Asn Phe Thr
65                  70                  75                  80
Tyr Ile Asp Arg Ile Val Asp Ser Tyr Leu Ala Leu Asn Ile Arg Pro
                85                  90                  95
Phe Ile Glu Phe Gly Phe Met Pro Lys Ala Leu Ala Ser Gly Asp Gln
            100                 105                 110
Thr Val Phe Tyr Trp Lys Gly Asn Val Thr Pro Pro Lys Asp Tyr Asn
        115                 120                 125
Lys Trp Arg Asp Leu Ile Val Ala Val Ser His Phe Ile Glu Arg
    130                 135                 140
Tyr Gly Ile Glu Glu Val Arg Thr Trp Leu Phe Glu Val Trp Asn Glu
145                 150                 155                 160
Pro Asn Leu Val Asn Phe Trp Lys Asp Ala Asn Lys Gln Glu Tyr Phe
                165                 170                 175
Lys Leu Tyr Glu Val Thr Ala Arg Ala Val Lys Ser Val Asp Pro His
            180                 185                 190
Leu Gln Val Gly Gly Pro Ala Ile Cys Gly Gly Ser Asp Glu Trp Ile
        195                 200                 205
Thr Asp Phe Leu His Phe Cys Ala Glu Arg Arg Val Pro Val Asp Phe
    210                 215                 220
```

```
Val Ser Arg His Ala Tyr Thr Ser Lys Ala Pro His Lys Lys Thr Phe
225                 230                 235                 240

Glu Tyr Tyr Tyr Gln Glu Leu Glu Leu Glu Pro Pro Glu Asp Met Leu
            245                 250                 255

Glu Gln Phe Lys Thr Val Arg Ala Leu Ile Arg Gln Ser Pro Phe Pro
            260                 265                 270

His Leu Pro Leu His Ile Thr Glu Tyr Asn Thr Ser Tyr Ser Pro Ile
            275                 280                 285

Asn Pro Val His Asp Thr Ala Leu Asn Ala Ala Tyr Ile Ala Arg Ile
            290                 295                 300

Leu Ser Glu Gly Gly Asp Tyr Val Asp Ser Phe Ser Tyr Trp Thr Phe
305                 310                 315                 320

Ser Asp Val Phe Glu Glu Met Asp Val Pro Lys Ala Leu Phe His Gly
            325                 330                 335

Gly Phe Gly Leu Val Ala Leu His Ser Ile Pro Lys Pro Thr Phe His
            340                 345                 350

Ala Phe Thr Phe Phe Asn Ala Leu Gly Asp Glu Leu Leu Tyr Arg Asp
            355                 360                 365

Gly Glu Met Ile Val Thr Arg Arg Lys Asp Gly Ser Ile Ala Ala Val
370                 375                 380

Leu Trp Asn Leu Val Met Glu Lys Gly Glu Gly Leu Thr Lys Glu Val
385                 390                 395                 400

Gln Leu Val Ile Pro Val Ser Phe Ser Ala Val Phe Ile Lys Arg Gln
            405                 410                 415

Ile Val Asn Glu Gln Tyr Gly Asn Ala Trp Arg Val Trp Lys Gln Met
            420                 425                 430

Gly Arg Pro Arg Phe Pro Ser Arg Gln Ala Val Glu Thr Leu Pro Ser
            435                 440                 445

Ala Gln Pro His Val Met Thr Glu Gln Arg Arg Ala Thr Asp Gly Val
            450                 455                 460

Ile His Leu Ser Ile Val Leu Ser Lys Asn Glu Val Thr Leu Ile Glu
465                 470                 475                 480

Ile Glu Gln Val Arg Asp Glu Thr Ser Thr Tyr Val Gly Leu Asp Asp
            485                 490                 495

Gly Glu Ile Thr Ser Tyr Ser Ser
            500

<210> SEQ ID NO 114
<211> LENGTH: 500
<212> TYPE: PRT
<213> ORGANISM: Thermoanaerobacterium saccharolyticum

<400> SEQUENCE: 114

Met Ile Lys Val Arg Val Pro Asp Phe Ser Asp Lys Lys Phe Ser Asp
1               5                   10                  15

Arg Trp Arg Tyr Cys Val Gly Thr Gly Arg Leu Gly Leu Ala Leu Gln
            20                  25                  30

Lys Glu Tyr Ile Glu Thr Leu Lys Tyr Val Lys Glu Asn Ile Asp Phe
            35                  40                  45

Lys Tyr Ile Arg Gly His Gly Leu Leu Cys Asp Asp Val Gly Ile Tyr
            50                  55                  60

Arg Glu Asp Val Val Gly Asp Glu Val Lys Pro Phe Tyr Asn Phe Thr
65                  70                  75                  80

Tyr Ile Asp Arg Ile Phe Asp Ser Phe Leu Glu Ile Gly Ile Arg Pro
            85                  90                  95
```

```
Phe Val Glu Ile Gly Phe Met Pro Lys Lys Leu Ala Ser Gly Thr Gln
                100                 105                 110

Thr Val Phe Tyr Trp Glu Gly Asn Val Thr Pro Pro Lys Asp Tyr Glu
                115                 120                 125

Lys Trp Ser Asp Leu Val Lys Ala Val Leu His His Phe Ile Ser Arg
        130                 135                 140

Tyr Gly Ile Glu Glu Val Leu Lys Trp Pro Phe Glu Ile Trp Asn Glu
145                 150                 155                 160

Pro Asn Leu Lys Glu Phe Trp Lys Asp Ala Asp Glu Lys Glu Tyr Phe
                165                 170                 175

Lys Leu Tyr Lys Val Thr Ala Lys Ala Ile Lys Glu Val Asn Glu Asn
                180                 185                 190

Leu Lys Val Gly Gly Pro Ala Ile Cys Gly Gly Ala Asp Tyr Trp Ile
            195                 200                 205

Glu Asp Phe Leu Asn Phe Cys Tyr Glu Glu Asn Val Pro Val Asp Phe
            210                 215                 220

Val Ser Arg His Ala Thr Thr Ser Lys Gln Gly Glu Tyr Thr Pro His
225                 230                 235                 240

Leu Ile Tyr Gln Glu Ile Met Pro Ser Glu Tyr Met Leu Asn Glu Phe
                245                 250                 255

Lys Thr Val Arg Glu Ile Ile Lys Asn Ser His Phe Pro Asn Leu Pro
                260                 265                 270

Phe His Ile Thr Glu Tyr Asn Thr Ser Tyr Ser Pro Gln Asn Pro Val
            275                 280                 285

His Asp Thr Pro Phe Asn Ala Ala Tyr Ile Ala Arg Ile Leu Ser Glu
            290                 295                 300

Gly Gly Asp Tyr Val Asp Ser Phe Ser Tyr Trp Thr Phe Ser Asp Val
305                 310                 315                 320

Phe Glu Glu Arg Asp Val Pro Arg Ser Gln Phe His Gly Gly Phe Gly
                325                 330                 335

Leu Val Ala Leu Asn Met Ile Pro Lys Pro Thr Phe Tyr Thr Phe Lys
            340                 345                 350

Phe Phe Asn Ala Met Gly Glu Glu Met Leu Tyr Arg Asp Glu His Met
            355                 360                 365

Leu Val Thr Arg Arg Asp Asp Gly Ser Val Ala Leu Ile Ala Trp Asn
        370                 375                 380

Glu Val Met Asp Lys Thr Glu Asn Pro Asp Glu Asp Tyr Glu Val Glu
385                 390                 395                 400

Ile Pro Val Arg Phe Arg Asp Val Phe Ile Lys Arg Gln Leu Ile Asp
                405                 410                 415

Glu Glu His Gly Asn Pro Trp Gly Thr Trp Ile His Met Gly Arg Pro
            420                 425                 430

Arg Tyr Pro Ser Lys Glu Gln Val Asn Thr Leu Arg Glu Val Ala Lys
        435                 440                 445

Pro Glu Ile Met Thr Ser Gln Pro Val Ala Asn Asp Gly Tyr Leu Asn
        450                 455                 460

Leu Lys Phe Lys Leu Gly Lys Asn Ala Val Val Leu Tyr Glu Leu Thr
465                 470                 475                 480

Glu Arg Ile Asp Glu Ser Ser Thr Tyr Ile Gly Leu Asp Asp Ser Lys
                485                 490                 495

Ile Asn Gly Tyr
            500
```

<210> SEQ ID NO 115
<211> LENGTH: 302
<212> TYPE: PRT
<213> ORGANISM: Penicillium simplicissimum

<400> SEQUENCE: 115

Gln Ala Ser Val Ser Ile Asp Ala Lys Phe Lys Ala His Gly Lys Lys
1               5                   10                  15

Tyr Leu Gly Thr Ile Gly Asp Gln Tyr Thr Leu Thr Lys Asn Thr Lys
                20                  25                  30

Asn Pro Ala Ile Ile Lys Ala Asp Phe Gly Gln Leu Thr Pro Glu Asn
            35                  40                  45

Ser Met Lys Trp Asp Ala Thr Glu Pro Asn Arg Gly Gln Phe Thr Phe
    50                  55                  60

Ser Gly Ser Asp Tyr Leu Val Asn Phe Ala Gln Ser Asn Gly Lys Leu
65                  70                  75                  80

Ile Arg Gly His Thr Leu Val Trp His Ser Gln Leu Pro Gly Trp Val
                85                  90                  95

Ser Ser Ile Thr Asp Lys Asn Thr Leu Ile Ser Val Leu Lys Asn His
            100                 105                 110

Ile Thr Thr Val Met Thr Arg Tyr Lys Gly Lys Ile Tyr Ala Trp Asp
    115                 120                 125

Val Leu Asn Glu Ile Phe Asn Glu Asp Gly Ser Leu Arg Asn Ser Val
130                 135                 140

Phe Tyr Asn Val Ile Gly Glu Asp Tyr Val Arg Ile Ala Phe Glu Thr
145                 150                 155                 160

Ala Arg Ser Val Asp Pro Asn Ala Lys Leu Tyr Ile Asn Asp Tyr Asn
                165                 170                 175

Leu Asp Ser Ala Gly Tyr Ser Lys Val Asn Gly Met Val Ser His Val
            180                 185                 190

Lys Lys Trp Leu Ala Ala Gly Ile Pro Ile Asp Gly Ile Gly Ser Gln
    195                 200                 205

Thr His Leu Gly Ala Gly Ala Gly Ser Ala Val Ala Gly Ala Leu Asn
    210                 215                 220

Ala Leu Ala Ser Ala Gly Thr Lys Glu Ile Ala Ile Thr Glu Leu Asp
225                 230                 235                 240

Ile Ala Gly Ala Ser Ser Thr Asp Tyr Val Asn Val Asn Ala Cys
                245                 250                 255

Leu Asn Gln Ala Lys Cys Val Gly Ile Thr Val Trp Gly Val Ala Asp
            260                 265                 270

Pro Asp Ser Trp Arg Ser Ser Ser Pro Leu Leu Phe Asp Gly Asn
    275                 280                 285

Tyr Asn Pro Lys Ala Ala Tyr Asn Ala Ile Ala Asn Ala Leu
    290                 295                 300

<210> SEQ ID NO 116
<211> LENGTH: 329
<212> TYPE: PRT
<213> ORGANISM: Thermoascus aurantiacus

<400> SEQUENCE: 116

Met Val Arg Pro Thr Ile Leu Leu Thr Ser Leu Leu Leu Ala Pro Phe
1               5                   10                  15

Ala Ala Ala Ser Pro Ile Leu Glu Glu Arg Gln Ala Ala Gln Ser Val
                20                  25                  30

```
Asp Gln Leu Ile Lys Ala Arg Gly Lys Val Tyr Phe Gly Val Ala Thr
             35                  40                  45

Asp Gln Asn Arg Leu Thr Thr Gly Lys Asn Ala Ala Ile Ile Gln Ala
 50                      55                  60

Asp Phe Gly Gln Val Thr Pro Glu Asn Ser Met Lys Trp Asp Ala Thr
 65                      70                  75                  80

Glu Pro Ser Gln Gly Asn Phe Asn Phe Ala Gly Ala Asp Tyr Leu Val
                     85                  90                  95

Asn Trp Ala Gln Gln Asn Gly Lys Leu Ile Arg Gly His Thr Leu Val
                 100                 105                 110

Trp His Ser Gln Leu Pro Ser Trp Val Ser Ser Ile Thr Asp Lys Asn
             115                 120                 125

Thr Leu Thr Asn Val Met Lys Asn His Ile Thr Thr Leu Met Thr Arg
130                 135                 140

Tyr Lys Gly Lys Ile Arg Ala Trp Asp Val Val Asn Glu Ala Phe Asn
145                 150                 155                 160

Glu Asp Gly Ser Leu Arg Gln Thr Val Phe Leu Asn Val Ile Gly Glu
                 165                 170                 175

Asp Tyr Ile Pro Ile Ala Phe Gln Thr Ala Arg Ala Ala Asp Pro Asn
             180                 185                 190

Ala Lys Leu Tyr Ile Asn Asp Tyr Asn Leu Asp Ser Ala Ser Tyr Pro
         195                 200                 205

Lys Thr Gln Ala Ile Val Asn Arg Val Lys Gln Trp Arg Ala Ala Gly
     210                 215                 220

Val Pro Ile Asp Gly Ile Gly Ser Gln Thr His Leu Ser Ala Gly Gln
225                 230                 235                 240

Gly Ala Gly Val Leu Gln Ala Leu Pro Leu Leu Ala Ser Ala Gly Thr
                 245                 250                 255

Pro Glu Val Ala Ile Thr Glu Leu Asp Val Ala Gly Ala Ser Pro Thr
             260                 265                 270

Asp Tyr Val Asn Val Val Asn Ala Cys Leu Asn Val Gln Ser Cys Val
         275                 280                 285

Gly Ile Thr Val Trp Gly Val Ala Asp Pro Asp Ser Trp Arg Ala Ser
     290                 295                 300

Thr Thr Pro Leu Leu Phe Asp Gly Asn Phe Asn Pro Lys Pro Ala Tyr
305                 310                 315                 320

Asn Ala Ile Val Gln Asp Leu Gln Gln
                 325

<210> SEQ ID NO 117
<211> LENGTH: 485
<212> TYPE: PRT
<213> ORGANISM: Fusarium verticillioides

<400> SEQUENCE: 117

Met Asn Pro Leu Ser Leu Gly Leu Ala Ala Leu Ser Leu Leu Gly Tyr
1                5                  10                  15

Val Gly Val Asn Phe Val Ala Ala Phe Pro Thr Asp Ser Asn Ser Gly
                 20                  25                  30

Ser Glu Val Leu Ile Ser Val Asn Gly His Val Lys His Gln Glu Leu
             35                  40                  45

Asp Gly Phe Gly Ala Ser Gln Ala Phe Gln Arg Ala Glu Asp Ile Leu
         50                  55                  60

Gly Lys Asp Gly Leu Ser Lys Glu Gly Thr Gln His Val Leu Asp Leu
 65                      70                  75                  80
```

```
Leu Phe Ser Lys Asp Ile Gly Ala Gly Phe Ser Ile Leu Arg Asn Gly
            85                  90                  95

Ile Gly Ser Ser Asn Ser Ser Asp Lys Asn Phe Met Asn Ser Ile Glu
            100                 105                 110

Pro Phe Ser Pro Gly Ser Pro Gly Ala Lys Pro His Tyr Val Trp Asp
            115                 120                 125

Gly Tyr Asp Ser Gly Gln Leu Thr Val Ala Gln Glu Ala Phe Lys Arg
            130                 135                 140

Gly Leu Lys Phe Leu Tyr Gly Asp Ala Trp Ser Ala Pro Gly Tyr Met
145                 150                 155                 160

Lys Thr Asn His Asp Glu Asn Asn Gly Gly Tyr Leu Cys Gly Val Thr
            165                 170                 175

Gly Ala Ala Cys Ala Ser Gly Asp Trp Lys Gln Ala Tyr Ala Asp Tyr
            180                 185                 190

Leu Leu Gln Trp Val Glu Phe Tyr Arg Lys Ser Gly Val Lys Val Thr
            195                 200                 205

Asn Leu Gly Phe Leu Asn Glu Pro Gln Phe Ala Ala Pro Tyr Ala Gly
            210                 215                 220

Met Leu Ser Asn Gly Thr Gln Ala Ala Asp Phe Ile Arg Val Leu Gly
225                 230                 235                 240

Lys Thr Ile Arg Lys Arg Gly Ile His Asp Leu Thr Ile Ala Cys Cys
            245                 250                 255

Asp Gly Glu Gly Trp Asp Leu Gln Glu Asp Met Met Ala Gly Leu Thr
            260                 265                 270

Ala Gly Pro Asp Pro Ala Ile Asn Tyr Leu Ser Val Val Thr Gly His
            275                 280                 285

Gly Tyr Val Ser Pro Pro Asn His Pro Leu Ser Thr Thr Lys Lys Thr
            290                 295                 300

Trp Leu Thr Glu Trp Ala Asp Leu Thr Gly Gln Phe Thr Pro Tyr Thr
305                 310                 315                 320

Phe Tyr Asn Asn Ser Gly Gln Gly Glu Gly Met Thr Trp Ala Gly Arg
            325                 330                 335

Ile Gln Thr Ala Leu Val Asp Ala Asn Val Ser Gly Phe Leu Tyr Trp
            340                 345                 350

Ile Gly Ala Glu Asn Ser Thr Thr Asn Ser Ala Leu Ile Asn Met Ile
            355                 360                 365

Gly Asp Lys Val Ile Pro Ser Lys Arg Phe Trp Ala Phe Ala Ser Phe
            370                 375                 380

Ser Arg Phe Ala Arg Pro Gly Ala Arg Arg Ile Glu Ala Thr Ser Ser
385                 390                 395                 400

Val Pro Leu Val Thr Val Ser Ser Phe Leu Asn Thr Asp Gly Thr Val
            405                 410                 415

Ala Thr Gln Val Leu Asn Asn Asp Thr Val Ala His Ser Val Gln Leu
            420                 425                 430

Val Val Ser Gly Thr Gly Arg Asn Pro His Ser Leu Lys Pro Phe Leu
            435                 440                 445

Thr Asp Asn Ser Asn Asp Leu Thr Ala Leu Lys His Leu Lys Ala Thr
            450                 455                 460

Gly Lys Gly Ser Phe Gln Thr Thr Ile Pro Pro Arg Ser Leu Val Ser
465                 470                 475                 480

Phe Val Thr Asp Phe
            485
```

GLYCOSYL HYDROLASE ENZYMES AND USES THEREOF

1. CROSS-REFERENCE TO RELATED APPLICATIONS

This application is a continuation of U.S. application Ser. No. 13/498,069, filed Apr. 1, 2013, which is a U.S. National Stage Application of International Appl. No. PCT/US10/49849, filed Sep. 22, 2010, which claims priority to U.S. Provisional Application Nos. 61/245,273, filed Sep. 23, 2009, and 61/289,886, filed Dec. 23, 2009. All these previous applications are incorporated herein by reference in their entirety.

SEQUENCE LISTING

The sequence listing submitted via EFS on Jul. 27, 2015, in compliance with 37 C.F.R. § 1.52(e), is incorporated herein by reference. The sequence listing text file contains the file "31376-US-CNT_Sequence-Listing.txt" created on Jul. 27, 2015, which is 176 KB (180,752 bytes).

2. TECHNICAL FIELD

The present disclosure generally pertains to glycosyl hydrolase enzymes, compositions comprising such enzymes, and methods of using the enzymes and compositions, for example for the saccharification or conversion of cellulosic and hemicellulosic materials into sugars.

3. BACKGROUND

Bioconversion of renewable lignocellulosic biomass to a fermentable sugar that is subsequently fermented to produce alcohol (e.g., ethanol) as an alternative to liquid fuels has attracted the intensive attention of researchers since the 1970s, when the oil crisis occurred because OPEC decreased the output of petroleum (Bungay, H. R., "Energy: the biomass options". NY: Wiley; 1981; Olsson L, Hahn-Hagerdal B. Enzyme Microb Technol 1996, 18:312-31; Zaldivar, J et al., Appl Microbiol Biotechnol 2001, 56: 17-34; Galbe, M et al., Appl Microbiol Biotechnol 2002, 59:618-28). Ethanol has been widely used as a 10% blend to gasoline in the USA or as a neat fuel for vehicles in Brazil in the last two decades. The importance of fuel bioethanol will increase in parallel with skyrocketing prices for oil and gradual depletion of its sources. Additionally, fermentable sugars are increasingly used to produce plastics, polymers and other biobased products, and this industry is expected to expand substantially in the coming years. Thus, the demand for abundant low cost fermentable sugars, which can be used as a feed stock in lieu of petroleum based feedstocks, continues to grow.

Chiefly among the useful renewable feedstocks are cellulose and hemicellulose (xylans), which can be converted into fermentable sugars. The enzymatic conversion of these polysaccharides to soluble sugars, for example glucose, xylose, arabinose, galactose, mannose, and/or other hexoses and pentoses, occurs due to combined actions of various enzymes. For example, endo-1,4-β-glucanases (EG) and exo-cellobiohydrolases (CBH) catalyze the hydrolysis of insoluble cellulose to cellooligosaccharides (e.g., with cellobiose being a main product), while β-glucosidases (BGL) catalyzes the conversion of the oligosaccharides to glucose. Xylanases together with other accessory proteins (non-limiting examples of which include L-α-arabinofuranosidases, feruloyl and acetylxylan esterases, glucuronidases, and β-xylosidases) catalyze the hydrolysis of hemicelluloses.

The cell walls of plants are composed of a heterogeneous mixture of complex polysaccharides that interact through covalent and noncovalent means. Complex polysaccharides of higher plant cell walls include, for example, cellulose (β-1,4 glucan), which generally constitutes 35-50% of carbon found in cell wall components. Cellulose polymers self associate through hydrogen bonding, van der Waals interactions and hydrophobic interactions to form semi-crystalline cellulose microfibrils. These microfibrils also include noncrystalline regions, generally known as amorphous cellulose. The cellulose microfibrils are embedded in a matrix formed of hemicelluloses (including, e.g., xylans, arabinans, and mannans), pectins (e.g., galacturonans and galactans), and various other β-1,3 and β-1,4 glucans. These matrix polymers are often substituted with, for example, arabinose, galactose and/or xylose residues to yield highly complex arabinoxylans, arabinogalactans, galactomannans, and xyloglucans. The hemicellulose matrix is, in turn, surrounded by polyphenolic lignin.

The complexity of the matrix makes it difficult to degrade by microorganisms as lignin and hemicellulose components must be broken down before enzymes can act on the core cellulose microfibrils. Ordinarily, a consortium of different enzymatic activities is required to break down cell wall polymers to release the constituent monosaccharides. For saccharification of plant cell walls, the lignin must be permeabilized and hemicellulose disrupted to allow cellulose-degrading enzymes to act on their substrate.

Regardless of the type of cellulosic feedstock, the cost and hydrolytic efficiency of enzymes are major factors that restrict the commercialization of biomass bioconversion processes. The production costs of microbially produced enzymes are tightly connected with the productivity of the enzyme-producing strain and the final activity yield in the fermentation broth. The hydrolytic efficiency of a multienzyme complex depends both on properties of individual enzymes, the synergies among them, and their ratio in the multienzyme blend.

There exists a need in the art to identify enzyme and/or enzymatic blends/compositions that are capable of converting plant and/or other cellulosic or hemicellulosic materials into fermentable sugars with improved efficacy and yield.

4. SUMMARY

The disclosure provides certain glycosyl hydrolase polypeptides having hemicellulolytic activity, including, e.g., xylanases (e.g., endoxylanases), xylosidases (e.g., β-xylosidases), arabinofuranosidases (e.g., L-α-arabinofuranosidases), nucleic acids encoding these polypeptides, and methods for making and using the polypeptides and/or nucleic acids. The disclosure is based, in part, on the discovery of novel enzymes and variants having xylanase, β-xylosidase, and/or L-α-arabinofuranosidase activities. The disclosure is also based on the identification of enzyme blends (or compositions) that efficiently catalyze the hydrolysis of cellulosic and hemicellulosic materials. For purpose of this disclosure, an enzyme can be defined either as a polypeptide having the particular enzymatic activity or as that enzyme. For example, a xylanase can be referred to as a polypeptide having xylanase activity or as a xylanase enzyme, and a β-xylosidase can be referred to as either a polypeptide having R-xylosidase activity or a β-xylosidase enzyme.

The enzymes and/or enzyme blends/compositions of the disclosure can be used to produce sugars from biomass. The sugars so produced can be used by microorganisms for ethanol production or can be used to produce other bioproducts in various industrial applications. Therefore, the disclosure also provides industrial applications (e.g., saccharification processes in ethanol production) using the enzymes and/or enzyme blends/compositions described herein. The enzymes and/or enzyme blends/compositions of the present disclosure can be used to decrease enzyme costs in biofuel production.

In one aspect, the invention of the disclosure pertains to enzymes (including variants thereof), or enzyme blends/compositions that are useful for hydrolyzing the major components of a lignocellulosic biomass (including, e.g., cellulose, hemicellulose, and lignin) or any material comprising cellulose and/or hemicellulose. Such lignocellulosic biomass and/or material comprising cellulose and/or hemicellulose include, e.g., seeds, grains, tubers, plant waste or byproducts of food processing or industrial processing (e.g., stalks), corn (including, e.g., cobs, stover, and the like), grasses (e.g., Indian grass, such as *Sorghastrum nutans*; or, switchgrass, e.g., *Panicum* species, such as *Panicum virgatum*), wood (including, e.g., wood chips, processing waste), paper, pulp, recycled paper (e.g., newspaper).

The enzyme blends/compositions of the invention can be used to hydrolyze cellulose comprising a linear chain of β-1,4-linked glucose moieties, or hemicellulose, of a complex structure that varies from plant to plant.

The enzyme blends/compositions of the invention can comprise a number of different enzymes, including, e.g., cellulases and/or hemicellulases. For example, the enzymes blends/compositions of the invention can be used to hydrolyze biomass or a suitable feedstock. The enzyme blends/compositions of the invention desirably comprise mixtures of enzymes, selected from, e.g., xylanases, xylosidases, cellobiohydrolases, arabinofuranosidases, and/or other enzymes that can digest hemicellulose to monomer sugars. An enzyme blend/composition of the invention can comprise a mixture of two or more, three or more, or four or more enzymes selected from one or more xylanases, one or more xylosidases, one or more cellobiohydrolases, one or more arabinofuranosidases, and one or more other enzymes that are capable of converting hemicelluose to monomer sugars. The other enzymes that can digest hemicellulose to monomer sugars include, without limitation, a cellulase, a hemicellulase, or a composition comprising a cellulase or a hemicellulase. An enzyme blend/composition of the invention can comprise a mixture of two or more, three or more, or four or more enzymes selected from a xylanase, a xylosidase, a cellobiohydrolase, an arabinofuranosidase, and at least one other enzyme capable of converting hemicellulose to monomer sugars. A non-limiting example of an enzyme blend/composition of the invention comprises a mixture of a xylanase, a xylosidase, a cellobiohydrolase, an arabinofuranosidase, and a β-glucosidase. The enzyme blend/composition of the invention is suitably one that is non-naturally occurring.

As used herein, the term "naturally occurring composition" refers to a composition produced by a naturally occurring source, which comprises one or more enzymatic components or activities, wherein each of these components or activities is found at the ratio and level produced by the naturally-occurring source as it is found in nature, untouched and unmodified by the human hand. Accordingly, a naturally occurring composition is, for example, one that is produced by an organism unmodified with respect to the cellulolytic or hemicelluloytic enzymes such that the ratio or levels of the component enzymes are unaltered from that produced by the native organism in its native environment. A "non-naturally occurring composition," on the other hand, refers to a composition produced by: (1) combining component cellulolytic or hemicelluloytic enzymes either in a naturally occurring ratio or a non-naturally occurring, i.e., altered, ratio; or (2) modifying an organism to express, overexpress or underexpress one or more endogeneous or exogenous enzymes; or (3) modifying an organism such that at least one endogenous enzyme is deleted. A "non-naturally occurring composition" can also refer to a composition produced by a naturally-occurring and unmodified organism, but cultured in a man-made medium or environment that is different from the organism's native environment, such that the amounts or weight ratios of particular enzymes in the composition differ from those existing in a composition made by a native organism grown in its native habitat.

The enzyme blend/composition of the invention described herein is, for example, a fermentation broth. The fermentation broth can be one of a filamentous fungus, including, e.g., a *Trichoderma, Humicola, Fusarium, Aspergillus, Neurospora, Penicillium, Cephalosporium, Achlya, Podospora, Endothia, Mucor, Cochliobolus, Pyricularia*, or *Chrysosporium*. An exemplary fungus of *Trichoderma* spp. is a *Trichoderma reesei*. An exemplary fungus of *Penicillium* spp. is a *Penicillium funiculosum*. The fermentation broth can be, for example, a cell-free fermentation broth or a whole cell broth.

The enzyme blend/composition of the invention described herein is, in another example, a cellulase composition. The cellulase composition is a filamentous fungal cellulase composition, including, for example, a *Trichoderma*, such as a *Trichoderma reesei*, cellulase composition. The cellulase composition can be produced by a filamentous fungus, for example, a *Trichoderma*, such as a *Trichoderma reesei*.

For example, an enzyme blend/composition of the invention can comprise (a) one or more xylanase enzyme(s), wherein at least one of said one or more xylanase enzyme(s) is a *Trichoderma reesei* Xyn2, a *Trichoderma reesei* Xyn3, an AfuXyn2, or an AfuXyn5; (b) one or more β-xylosidase enzyme(s), wherein at least one of said one or more β-xylosidase enzyme(s) is a Group 1 β-xylosidase or a Group 2 β-xylosidase, wherein the Group 1 β-xylosidase is an Fv3A or an Fv43A, and the Group 2 β-xylosidase is a Pf43A, an Fv43D, an Fv39A, an Fv43E, an Fo43A, an Fv43B, a Pa51A, a Gz43A, or a *Trichoderma reesei* Bxl1; (c) one or more L-α-arabinofuranosidase enzyme(s), wherein at least one of said one or more L-α-arabinofuranosidase is an Af43A, an Fv43B, a Pf51A, a Pa51A, or an Fv51A; (d) one or more cellulase enzymes; and optionally (e) one or more other components. The enzyme blend/composition is suitably one that is non-naturally occurring. The one or more cellulase enzyme(s) of (d) is desirably able to achieve at least 0.00005 fraction product per mg protein per gram of phosphoric acid swollen cellulose (PASC) as determined by a calcofluor assay. In a non-limiting example, the combined weight of xylanase enzyme(s) in the composition can represent or constitute 5 wt. % to 45 wt. % (e.g., 5 wt. % to 25 wt. %, 5 wt. % to 15 wt. %, 10 wt. % to 15 wt. %) of the combined or total protein weight in the composition, whereas the combined weight of β-xylosidase enzyme(s) can represent or constitute 2 wt. % to 50 wt. % (e.g., 2 wt. % to 30 wt. %, 5 wt. % to 25 wt. %, 5 wt. % to 10 wt. %) of the total proteins in the composition, whereas the combined weight of L-α-arabinofuranosidase enzyme(s) can represent or constitute 2 wt. % to 50 wt. % (e.g., 2 wt. % to 30 wt. %, 2 wt. % to 20 wt. %, 5 wt. % to 15 wt. %, 5 wt. % to 10 wt. %) of the combined or total protein weight in the composition, whereas the combined weight of cellulase enzyme(s) can represent or constitute 30 wt. % to 80 wt. % (e.g., 40 wt. % to 70 wt. %, 50 wt. % to 60 wt. %) of the combined or total protein weight in the composition. The enzyme blend/composition as described herein is, for example, a fermentation broth composition. The fermentation broth is, for example, one of a filamentous fungus, including, without limitation, a *Trichoderma, Humicola, Fusarium, Aspergillus, Neurospora, Penicillium, Cephalosporium, Achlya, Podospora, Endothia, Mucor, Cochliobolus, Pyricularia,* or *Chrysosporium.* An exemplary fungus of *Trichoderma* spp. is a *Trichoderma reesei.* An exemplary fungus of *Penicillium* spp. is a *Penicillium funiculosum.* The fermentation can be, for example, a cell-free fermentation broth or a whole cell broth. The enzyme blend/composition as described herein can also be a cellulase composition, for example, a filamentous fungal cellulase composition. The cellulase composition, for example, can be produced by a filamentous fungus, such as by a *Trichoderma.*

For example, an enzyme blend/composition of the invention can comprise (a) one or more xylanase enzyme(s) wherein at least one of said one or more xylanase enzyme(s) is a *Trichoderma reesei* Xyn2, a *Trichoderma reesei* Xyn3, an AfuXyn2, or an AfuXyn5; (b) one or both of Group 1 β-xylosidase enzymes: Fv3A and Fv43A; (c) one or more of Group 2 β-xylosidase enzyme(s) selected from Pf43A, an Fv43D, an Fv39A, an Fv43E, an Fo43A, an Fv43B, a Pa51A, a Gz43A, and/or a *Trichoderma reesei* Bxl1; (d) one or more cellulase enzyme(s); and optionally (e) one or more other components. The one or more cellulase enzyme(s) of (e) is desirably able to achieve at least 0.00005 fraction product per mg protein per gram of phosphoric acid swollen cellulose (PASC) as determined by a calcofluor assay. The enzyme blend/composition is suitably one that is non-naturally occurring. In a non-limiting example, the combined weight of xylanase enzyme(s) in the composition can represent or constitute 5 wt. % to 45 wt. % (e.g., 5 wt. % to 25 wt. %, 5 wt. % to 15 wt. %, 10 wt. % to 15 wt. %) of the combined or total protein weight in the composition, whereas the combined weight of the Group 1 β-xylosidase enzyme(s) can constitute 2 wt. % to 50 wt. % (e.g., 2 wt. % to 30 wt. %, 5 wt. % to 25 wt. %, 5 wt. % to 10 wt. %) of the total protein weight in the composition, whereas the combined weight of the Group 2 β-xylosidase enzyme(s) can constitute 2 wt. % to 50 wt. % (e.g., 2 wt. % to 30 wt. %, 5 wt. % to 25 wt. %, 5 wt. % to 10 wt. %) of the total protein weight in the composition, and wherein the combined weight of the cellulase enzyme(s) can represent or constitute 30 wt. % to 80 wt. % (e.g., 40 wt. % to 70 wt. %, 50 wt. % to 60 wt. %) of the combined or total protein weight in the composition. The ratio of the weight of Group 1 β-xylosidase enzymes to the weight of Group 2 β-xylosidase enzymes can be, for example, 1:10 to 10:1 (e.g., 1:8 to 8:1, 1:6 to 6:1, 1:4 to 4:1, 1:2 to 2:1, or 1:1). The enzyme blend/composition can further comprise additional components, which may be accessory proteins or other protein/non-protein components. The additional components can constitute, for example, 1 wt. % to 50 wt. %, 1 wt. % to 10 wt. %, 2 wt. % to 5 wt. %, 5 wt. % to 10 wt. %, or 5 wt. % to 20 wt. % of the total weight of proteins in the composition. The enzyme blend/composition as described herein is, for example, a fermentation broth composition. The fermentation broth is, for example, one of a filamentous fungus, including, without limitation, a *Trichoderma, Humicola, Fusarium, Aspergillus, Neurospora, Penicillium, Cephalosporium, Achlya, Podospora, Endothia, Mucor, Cochliobolus, Pyricularia,* or *Chrysosporium.* An exemplary fungus of *Trichoderma* spp. is a *Trichoderma reesei.* An exemplary fungus of *Penicillium* spp. is a *Penicillium funiculosum.* The fermentation can be, for example, a cell-free fermentation broth or a whole cell broth. The enzyme blend/composition as described herein can also be a cellulase composition, for example, a filamentous fungal cellulase composition. The cellulase composition, for example, can be produced by a filamentous fungus, such as by a *Trichoderma.*

In further examples, an enzyme blend/composition of the invention can comprise (a) one or more xylanase enzyme(s) wherein at least one of said one or more xylanase enzyme(s) is a *Trichoderma reesei* Xyn2, a *Trichoderma reesei* Xyn3, an AfuXyn2, or an AfuXyn5; (b) one or more β-xylosidase enzyme(s) wherein at least one of the one or more β-xylosidase enzyme(s) is a Group 1 β-xylosidase enzyme Fv3A or Fv43A or a Group 2 β-xylosidase enzyme Pf43A, an Fv43D, an Fv39A, an Fv43E, an Fo43A, an Fv43B, a Pa51A, a Gz43A, and/or a *Trichoderma reesei* Bxl1; (c) one or more L-α-arabinofuranosidase enzyme(s), wherein at least one of said one or more L-α-arabinofuranosidase enzyme(s) is an Af43A, an Fv43B, a Pf51A, or an Fv51A; (d) one or more β-glucosidase enzyme(s); and optionally (e) one or more other components. The enzyme blend/composition is suitably one that is non-naturally occurring. In a non-limiting example, the combined weight of xylanase enzyme(s) in the composition can represent or constitute 5 wt. % to 45 wt. % (e.g., 5 wt. % to 25 wt. %, 5 wt. % to 15 wt. %, 10 wt. % to 15 wt. %) of the combined or total protein weight in the composition, whereas the combined weight of the β-xylosidase enzyme(s) can constitute 2 wt. % to 50 wt. % (e.g., 2 wt. % to 30 wt. %, 5 wt. % to 25 wt. %, 5 wt. % to 10 wt. %) of the total protein weight in the composition, whereas the combined weight of the L-α-arabinofuranosidase enzyme(s) can constitute 2 wt. % to 50 wt. % (e.g., 2 wt. % to 30 wt. %, 5 wt. % to 25 wt. %, 5 wt. % to 10 wt. %) of the total protein weight in the composition, and wherein the combined weight of the β-glucosidase enzyme(s) can constitute 2 wt. % to 50 wt. % (e.g., up to 50 wt. %, 2 wt. % to 10 wt. %, or 3 wt. % to 8 wt. %) of the combined or total protein weight in the composition. The enzyme blend/composition can further comprise additional components, which may be accessory proteins or other protein/non-protein components. The additional components can constitute, for example, 1 wt. % to 50 wt. %, 1 wt. % to 10 wt. %, 2 wt. % to 5 wt. %, 5 wt. % to 10 wt. %, or 5 wt. % to 20 wt. % of the total weight of proteins in the composition. The enzyme blend/composition as described herein is, for example, a fermentation broth composition. The fermentation broth is, for example, one of a filamentous fungus, including, without limitation, a *Trichoderma, Humicola, Fusarium, Aspergillus, Neurospora, Penicillium, Cephalosporium, Achlya, Podospora, Endothia, Mucor, Cochliobolus, Pyricularia,* or *Chrysosporium.* An exemplary fungus of *Trichoderma* spp. is a *Trichoderma reesei.* An exemplary fungus of *Penicillium* spp. is a *Penicillium funiculosum.* The fermentation can be, for example, a cell-free fermentation broth or a whole cell broth. The enzyme blend/composition as described herein can also be a cellulase composition, for example, a filamentous fungal cellulase composition. The cellulase composition, for example, can be produced by a filamentous fungus, such as by a *Trichoderma.*

An enzyme blend/composition of the invention can also comprise, for example, (a) one or more xylanase enzyme(s) wherein at least one of said one or more xylanase enzyme(s) is a *Trichoderma reesei* Xyn2, a *Trichoderma reesei* Xyn3, an AfuXyn2, or an AfuXyn5; (b) one or both of Group 1 β-xylosidase enzymes: Fv3A and Fv43A; (c) one or more of Group 2 β-xylosidase enzyme(s) selected from Pf43A, an Fv43D, an Fv39A, an Fv43E, an Fo43A, an Fv43B, a Pa51A, a Gz43A, and/or a *Trichoderma reesei* Bxl1; and (d) one or more β-glucosidase enzyme(s); and optionally (e) one or more other components. The enzyme blend/composition is suitably one that is non-naturally occurring. In a non-limiting example, the combined weight of xylanase enzyme(s) constitutes 5 wt. % to 45 wt. % (e.g., 5 wt. % to 25 wt. %, 5 wt. % to 15 wt. %, 10 wt. % to 15 wt. %) of the total weight of proteins in the composition, whereas the combined weight of Group 1 β-xylosidase enzyme(s) constitutes 2 wt. % to 50 wt. % (e.g., 2 wt. % to 30 wt. %, 5 wt. % to 25 wt. %, 5 wt. % to 10 wt. %) of the total weight of proteins in the composition, whereas the combined weight of Group 2 β-xylosidase enzyme(s) constitutes 2 wt. % to 50 wt. % (e.g., 2 wt. % to 30 wt. %, 5 wt. % to 25 wt. %, 5 wt. % to 10 wt. %) of the total weight of proteins in the composition, whereas the combined weight of β-glucosidase enzyme(s) constitutes 2 wt. % to 50 wt. % (e.g., 2 wt. % to 30 wt. %, 5 wt. % to 25 wt. %, 5 wt. % to 10 wt. %) of the total weight of proteins in the composition. The ratio of the weight of Group 1 β-xylosidase enzymes to the weight of Group 2 β-xylosidase enzymes can be, for example, 1:10 to 10:1, for example, 1:8 to 8:1, 1:6 to 6:1, 1:4 to 4:1, 1:2 to 2:1, or 1:1. The enzyme blend/composition can further comprise additional components, which may be accessory proteins or other protein/non-protein components. The additional components can constitute, for example, 1 wt. % to 50 wt. %, 1 wt. % to 10 wt. %, 2 wt. % to 5 wt. %, 5 wt. % to 10 wt. %, or 5 wt. % to 20 wt. % of the total weight of proteins in the composition. The enzyme blend/composition as described herein is, for example, a fermentation broth composition. The fermentation broth is, for example, one of a filamentous fungus, including, without limitation, a *Trichoderma*, *Humicola*, *Fusarium*, *Aspergillus*, *Neurospora*, *Penicillium*, *Cephalosporium*, *Achlya*, *Podospora*, *Endothia*, *Mucor*, *Cochliobolus*, *Pyricularia*, or *Chrysosporium*. An exemplary fungus of *Trichoderma* spp. is a *Trichoderma reesei*. An exemplary fungus of *Penicillium* spp. is a *Penicillium funiculosum*. The fermentation can be, for example, a cell-free fermentation broth or a whole cell broth. The enzyme blend/composition as described herein can also be a cellulase composition, for example, a filamentous fungal cellulase composition. The cellulase composition, for example, can be produced by a filamentous fungus, such as by a *Trichoderma*.

Moreover, an enzyme blend/composition of the invention can comprise, for example, (a) one or more xylanase enzyme(s) wherein at least one of said one or more xylanase enzyme(s) is a *Trichoderma reesei* Xyn2, a *Trichoderma reesei* Xyn3, an AfuXyn2, or an AfuXyn5; (b) one or more β-xylosidase enzyme(s) wherein at least one of said one or more β-xylosidase enzyme(s) is a Group 1 β-xylosidase or a Group 2 β-xylosidase, wherein Group 1 β-xylosidase can be an Fv3A or an Fv43A, and a Group 2 β-xylosidase can be a Pf43A, an Fv43D, an Fv39A, an Fv43E, an Fo43A, an Fv43B, a Pa51A, a Gz43A, and/or a *Trichoderma reesei* Bxl1; and (c) one or more L-α-arabinofuranosidase enzyme(s), wherein at least one of said one or more L-α-arabinofuranosidase enzyme(s) is an Af43A, an Fv43B, a Pf51A, or an Fv51A; and optionally (d) one or more other components. The enzyme blend/composition is suitably one that is non-naturally occurring. In a non-limiting example, the combined weight of the xylanase enzyme(s) constitutes 5 wt. % to 45 wt. % (e.g., 5 wt. % to 25 wt. %, 5 wt. % to 15 wt. %, 10 wt. % to 15 wt. %) of the total protein weight in the composition, whereas the combined weight of the β-xylosidase enzyme(s) constitutes 2 wt. % to 50 wt. % (e.g., 2 wt. % to 30 wt. %, 5 wt. % to 25 wt. %, 5 wt. % to 10 wt. %) of the total protein weight of the composition, whereas the combined weight of L-α-arabinofuranosidase enzyme(s) constitutes 2 wt. % to 50 wt. % (e.g., 2 wt. % to 30 wt. %, 5 wt. % to 25 wt. %, 5 wt. % to 10 wt. %) of the total protein weight of the composition. The enzyme blend/composition can further comprise additional components, which may be accessory proteins or other protein/non-protein components. The additional components can constitute, for example, 1 wt. % to 50 wt. %, 1 wt. % to 10 wt. %, 2 wt. % to 5 wt. %, 5 wt. % to 10 wt. %, or 5 wt. % to 20 wt. % of the total weight of proteins in the composition. The enzyme blend/composition as described herein is, for example, a fermentation broth composition. The fermentation broth is, for example, one of a filamentous fungus, including, without limitation, a *Trichoderma*, *Humicola*, *Fusarium*, *Aspergillus*, *Neurospora*, *Penicillium*, *Cephalosporium*, *Achlya*, *Podospora*, *Endothia*, *Mucor*, *Cochliobolus*, *Pyricularia*, or *Chrysosporium*. An exemplary fungus of *Trichoderma* spp. is a *Trichoderma reesei*. An exemplary fungus of *Penicillium* spp. is a *Penicillium funiculosum*. The fermentation can be, for example, a cell-free fermentation broth or a whole cell broth. The enzyme blend/composition as described herein can also be a cellulase composition, for example, a filamentous fungal cellulase composition. The cellulase composition, for example, can be produced by a filamentous fungus, such as by a *Trichoderma*.

An enzyme blend/composition of the invention can also be one that comprises (a) one or more xylanase enzyme(s) wherein at least one of said one or more xylanase enzyme(s) is a *Trichoderma reesei* Xyn2, a *Trichoderma reesei* Xyn3, an AfuXyn2, or an AfuXyn5; (b) one or both of Group 1 β-xylosidase enzymes: Fv3A and Fv43A; (c) one or more of Group 2 β-xylosidase enzyme(s) selected from Pf43A, an Fv43D, an Fv39A, an Fv43E, an Fo43A, an Fv43B, a Pa51A, a Gz43A, and/or a *Trichoderma reesei* Bxl1; and optionally (d) one or more other components. The enzyme blend/composition is suitably one that is non-naturally occurring. In a non-limiting example, the combined weight of xylanase enzyme(s) can constitute 5 wt. % to 45 wt. % (e.g., 5 wt. % to 25 wt. %, 5 wt. % to 15 wt. %, 10 wt. % to 15 wt. %) of the total protein weight in the composition, whereas the combined weight of Group 1 β-xylosidase enzyme(s) can constitute 2 wt. % 20 to 50 wt. % (e.g., 2 wt. % to 30 wt. %, 5 wt. % to 25 wt. %, 5 wt. % to 10 wt. %) of the total protein weight in the composition, whereas the combined weight of Group 2 β-xylosidase enzyme(s) can constitute 2 wt. % to 50 wt. % (e.g., 2 wt. % to 30 wt. %, 5 wt. % to 25 wt. %, 5 wt. % to 10 wt. %) of the total protein weight in the composition. The ratio of the weight of Group 1 β-xylosidase enzymes to the weight of Group 2 β-xylosidase enzymes can be, for example, 1:10 to 10:1, for example, 1:8 to 8:1, 1:6 to 6:1, 1:4 to 4:1, 1:2 to 2:1, or 1:1. The enzyme blend/composition can further comprise additional components, which may be accessory proteins or other protein/non-protein components. The additional components can constitute, for example, 1 wt. % to 50 wt. %, 1 wt. % to 10 wt. %, 2 wt. % to 5 wt. %, 5 wt. % to 10 wt. %, or 5 wt. % to 20 wt. % of the total weight of proteins in the composition. The enzyme blend/composition as described herein is, for example, a fermentation broth composition. The fermentation broth is, for example, one of a filamentous fungus, including, without limitation, a *Trichoderma, Humicola, Fusarium, Aspergillus, Neurospora, Penicillium, Cephalosporium, Achlya, Podospora, Endothia, Mucor, Cochliobolus, Pyricularia*, or *Chrysosporium*. An exemplary fungus of *Trichoderma* spp. is a *Trichoderma reesei*. An exemplary fungus of *Penicillium* spp. is a *Penicillium funiculosum*. The fermentation can be, for example, a cell-free fermentation broth or a whole cell broth. The enzyme blend/composition as described herein can also be a cellulase composition, for example, a filamentous fungal cellulase composition. The cellulase composition, for example, can be produced by a filamentous fungus, such as by a *Trichoderma*.

The enzymes, enzyme blends/compositions of the disclosure can be used in the food industry, e.g., for baking, for fruit and vegetable processing, in breaking down of agricultural waste, in the manufacture of animal feed, in pulp and paper production, in textile manufacture, or in household and industrial cleaning agents. The enzymes, and the enzymes in the enzyme blends/compositions of the disclosure are, for example, each independently produced by a microorganism, e.g., by a fungi or a bacteria.

The enzymes, enzyme blends/compositions of the disclosure can also be used as commercial enzymes or compositions to digest lignocellulose from any suitable sources, including all biological sources, such as plant biomasses, e.g., corn, grains, grasses (e.g., Indian grass, such as *Sorghastrum nutans*; or, switchgrass, e.g., *Panicum* species, such as *Panicum virgatum*), or, woods or wood processing byproducts, e.g., in the wood processing, pulp and/or paper industry, in textile manufacture, in household and industrial cleaning agents, and/or in biomass waste processing.

In another aspect, the disclosure provides isolated, synthetic or recombinant nucleic acids having at least about 70%, for example, at least about 71%, 72%, 73%, 74%, 75%, 76%, 77%, 78%, 79%, 80%, 81%, 82%, 83%, 84%, 85%, 86%, 87%, 88%; 89%, 90%, 91%, 92%, 93%, 94%, 95%, 96%, 97%, 98%, 99%, or complete (100%) sequence identity to a nucleic acid sequence of SEQ ID NO:1, 3, 5, 7, 9, 11, 13, 15, 17, 19, 21, 23, 25, 27, 29, 31, 33, 35, 37, 39, 41, 46, 47, 48, 49, or 50, over a region of at least about 10, e.g., at least about 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000, residues. Relatedly, the disclosure provides isolated, synthetic, or recombinant nucleic acids that are capable of hybridizing, under high stringency conditions, to a complement of 97%, 98%, 99%, or complete (100%) sequence identity to a nucleic acid sequence of SEQ ID NO:1, 3, 5, 7, 9, 11, 13, 15, 17, 19, 21, 23, 25, 27, 29, 31, 33, 35, 37, 39, 41, 46, 47, 48, 49, or 50, or to a fragment thereof. The fragment, for example, can be at least 150 contiguous residues in length, for example, at least 200, 250, or 300 contiguous residues in length. The present disclosure provides nucleic acids encoding a polypeptide having hemicellulolytic activity. Exemplary hemicellulolytic activity includes, without limitation, xylanase, β-xylosidase, and/or L-α-arabinofuranosidase activity. Exemplary polypeptides having hemicellulolytic activity include, without limitation, a xylanase, a β-xylosidase, and/or an L-α-arabinofuranosidase.

The disclosure further provides isolated, synthetic, or recombinant nucleic acids encoding an enzyme of the disclosure, including a polypeptide comprising the amino acid sequence of SEQ ID NO:2, 4, 6, 8, 10, 12, 14, 16, 18, 20, 22, 24, 26, 28, 30, 32, 34, 36, 38, 40, 42, 43, or 44, or a subsequence thereof (e.g., a catalytic domain ("CD") or carbohydrate binding module ("CBM")), or a suitable variant thereof. In some embodiments, a nucleic acid of the disclosure encodes the mature portion of a protein of amino acid sequence SEQ ID NO:2, 4, 6, 8, 10, 12, 14, 16, 18, 20, 22, 24, 26, 28, 30, 32, 34, 36, 38, 40, 42, 43, or 44, which is optionally operably linked to a heterologous signal sequence, e.g., the *Trichoderma reesei* CBHI signal sequence. The nucleic acid desirably encodes a polypeptide having hemicellulolytic activity, e.g., xylanase, β-xylosidase, and/or L-α-arabinofuranosidase activity. The nucleic acid of the disclosure encodes a hemicellulase, for example, a xylanase, a β-xylosidase, and/or an L-α-arabinofuranosidase, or a suitable variant thereof. Further nucleic acids of the disclosure are described in Section 6.2 below.

The disclosure additionally provides expression cassettes comprising a nucleic acid of the disclosure or a subsequence thereof. For example, the nucleic acid comprises at least about 70%, e.g., at least about 75%, 80%, 85%, 90%, 91%, 92%, 93%, 94%, 95%, 96%, 97%, 98%, or 99% sequence identity to a nucleic acid sequence of SEQ ID NO:1, 3, 5, 7, 9, 11, 13, 15, 17, 19, 21, 23, 25, 27, 29, 31, 33, 35, 37, 39, 41, 46, 47, 48, 49, or 50, over a region of at least about 10 residues, e.g., at least about 10, 20, 30, 40, 50, 75, 90, 100, 150, 200, 250, 300, 350, 400, or 500 residues. In another example, the nucleic acid encodes a polypeptide of SEQ ID NO:2, 4, 6, 8, 10, 12, 14, 16, 18, 20, 22, 24, 26, 28, 30, 32, 34, 36, 38, 40, 42, 43, or 44, wherein the nucleic acid is optionally operably linked to a promoter. The promoter can be, e.g., a fungal, viral, bacterial, mammalian, or plant promoter. The promoter can be a constitutive promoter or an inducible promoter. An exemplary suitable promoter is expressable in filamentous fungi, e.g., *Trichoderma reesei*. A suitable promoter can be derived from a filamentous fungus, e.g., *Trichoderma reesei*, e.g., a cellobiohydrolase I ("cbh1") gene promoter from *Trichoderma reesei*.

The disclosure further provides a recombinant cell engineered to express a nucleic acid of the disclosure or an expression cassette of the disclosure. For example, the nucleic acid comprises at least about 70%, e.g., at least about 75%, 80%, 85%, 90%, 91%, 92%, 93%, 94%, 95%, 96%, 97%, 98%, or 99% sequence identity to a nucleic acid sequence of SEQ ID NO:1, 3, 5, 7, 9, 11, 13, 15, 17, 19, 21, 23, 25, 27, 29, 31, 33, 35, 37, 39, 41, 46, 47, 48, 49, or 50, over a region of at least about 10, e.g., at least about 15, 20, 25, 50, 75, 100, 150, 200, 250, 300, 400, or 500 nucleotide residues. The nucleic acid can encode a polypeptide of SEQ ID NO:2, 4, 6, 8, 10, 12, 14, 16, 18, 20, 22, 24, 26, 28, 30, 32, 34, 36, 38, 40, 42, 43, or 44, wherein the nucleic acid is optionally operably linked to a promoter. The expression cassette can comprise the nucleic acid having at least about 70% (e.g., at least about 75%, 80%, 85%, 90%, 91%, 92%, 93%, 94%, 95%, 96%, 97%, 98%, or 99%) sequence identity to SEQ ID NO:1, 3, 5, 7, 9, 11, 13, 15, 17, 19, 21, 23, 25, 27, 29, 31, 33, 35, 37, 39, 41, 46, 47, 48, 49, or 50, over a region of at least about 10 nucleotide residues. For example, the expression cassette can comprise the nucleic acid encoding a polypeptide of SEQ ID NO:2, 4, 6, 8, 10, 12, 14, 16, 18, 20, 22, 24, 26, 28, 30, 32, 34, 36, 38, 40, 42, 43, or 44, wherein the nucleic acid is optionally operably linked to a promoter. The recombinant cell is desirably a recombinant bacterial cell, a recombinant mammalian cell, a recombinant fungal cell, a recombinant yeast cell, a recombinant insect cell, a recombinant algal cell, or a recombinant plant cell. For example, the recombinant cell is a recombinant filamentous fungal cell, such as a *Trichoderma, Humicola, Fusarium, Aspergillus, Neurospora, Penicillium, Cephalosporium, Achlya, Podospora, Endothia, Mucor, Cochliobolus, Pyricularia,* or *Chrysosporium* cell.

The disclosure provides transgenic plants comprising a nucleic acid of the disclosure or an expression cassette of the disclosure.

The disclosure provides isolated, synthetic or recombinant polypeptides comprising an amino acid sequence having at least about 80%, e.g., at least about 81%, 82%, 83%, 84%, 85%, 86%, 87%, 88%, 89%, 90%, 91%, 92%, 93%, 94%, 95%, 96%, 97%, 98%, or 99%, or complete (100%) sequence identity to a polypeptide of SEQ ID NO:2, 4, 6, 8, 10, 12, 14, 16, 18, 20, 22, 24, 26, 28, 30, 32, 34, 36, 38, 40, 42, 43, or 44, over a region of at least about 10, e.g., at least about 15, 20, 25, 30, 35, 40, 45, 50, 55, 60, 65, 70, 75, 80, 85, 90, 95, 100, 125, 150, 175, 200, 225, 250, 275, 300, 325, or 350 residues, or over the full length immature polypeptide, the full length mature polypeptide, the full length CD, or the full length CBM. Exemplary polypeptides include fragments of at least about 10, for example, at least about 15, 20, 25, 30, 35, 40, 45, 50, 75, 80, 85, 90, 95, 100, 150, 200, 250, 300, 350, 400, 450, 500, 550, 600 residues in length. In specific embodiments, the fragments comprise a CD and/or a CBM. Where a fragment comprises both a CD and a CBM of an enzyme of the disclosure, the fragment optionally includes a linker separating the CD and the CBM. The linker can be a native linker or a heterologous linker. In certain embodiments, the polypeptides of the disclosure have one or more hemicellulase activities. Polypeptides or peptide sequences of the disclosure include sequences encoded by the nucleic acids of the disclosure. Exemplary polypeptides are described in Section 6.1.

The disclosure additionally provides a chimeric or fusion protein comprising at least one domain of a polypeptide of the disclosure (e.g., the CD, the CBM, or both). The at least one domain can be operably linked to a second amino acid sequence, e.g., a signal peptide sequence.

Conversely, the disclosure provides a chimeric or fusion protein comprising a signal sequence of a polypeptide of the disclosure operably linked to a second sequence, e.g., encoding the amino acid sequence of a heterologous polypeptide that is not naturally associated with the signal sequence. Accordingly, the disclosure provides a recombinant polypeptide comprising residues 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, or 1 to 40 of a polypeptide of, e.g., SEQ ID NO:2, 4, 6, 8, 10, 12, 14, 16, 18, 20, 22, 24, 26, 28, 30, 32, 34, 36, 38, 40, 42, 43, or 44. Further exemplary chimeric or fusion polypeptides are described in Section 6.1.1.

The disclosure also provides methods of producing a recombinant polypeptide comprising: (a) culturing a host cell engineered to express a polypeptide of the disclosure; and (b) recovering the polypeptide. The recovery of the polypeptide includes, e.g., recovery of the fermentation broth comprising the polypeptide. In certain embodiments, recovery of the polypeptide can include further purification step(s).

The disclosure provides methods for hydrolyzing, breaking up, or disrupting a cellooligosaccharide, an arabinoxylan oligomer, or a glucan- or cellulose-comprising composition comprising contacting the composition with an enzyme, enzyme blend/composition of the disclosure under suitable conditions, wherein the enzyme, or enzyme blend/composition hydrolyzes, breaks up, or disrupts the cellooligosaccharide, arabinoxylan oligomer, or glucan- or cellulose-comprising composition.

The disclosure provides enzyme "blends" or compositions (also termed "enzyme blend/composition" herein), comprising a polypeptide of the disclosure, or a polypeptide encoded by a nucleic acid of the disclosure. In some embodiments, the polypeptide of the disclosure has one or more activities selected from xylanase, β-xylosidase, and L-α-arabinofuranosidase activities. In certain embodiments, the enzyme blends/compositions are used or are useful for depolymerization of cellulosic and hemicellulosic polymers to metabolizable carbon moieties. The enzyme blends of the disclosure can be in the form of a composition e.g., as a product of manufacture. The composition can be, e.g., a formulation, and can take the physical form of, e.g., a liquid or a solid. In exemplary embodiments, an enzyme blend/composition of the disclosure includes a cellulase comprising at least three different enzyme types selected from (1) an endoglucanase, (2) a cellobiohydrolase, and (3) a β-glucosidase; or at least three different enzymatic activities selected from (1) an endoglucanase activity catalyzing the cleavage of internal β-1,4 linkages of cellulosic or hemicellulosic materials, resulting in shorter glucooligosaccharides, (2) a cellobiohydrolase activity catalyzing the cleavage and release, in an "exo" manner, of cellobiose units (e.g., β-1,4 glucose-glucose disaccharide), and (3) a β-glucosidase activity catalyzing the release of glucose monomers from short cellooligosaccharides (e.g., cellobiose). Exemplary enzyme blends/compositions of the disclosure are described in Section 6.3.4. below.

In another aspect, the disclosure provides methods for processing a biomass material comprising lignocellulose comprising contacting a composition comprising a cellulose and/or a fermentable sugar with a polypeptide of the disclosure, or a polypeptide encoded by a nucleic acid of the disclosure, or an enzyme blend/composition (e.g., a product of manufacture) of the disclosure. Suitable biomass material comprising lignocellulose can be derived from an agricultural crop, a byproduct of a food or feed production, a lignocellulosic waste product, a plant residue, or a waste paper or waste paper product. The polypeptides of the disclosure can have one or more enzymatic activities selected from cellulase, endoglucanase, cellobiohydrolase, β-glucosidase, xylanase, mannanase, β-xylosidase, arabinofuranosidase, and other hemicellulase activities. Suitable plant residue can comprise grain, seeds, stems, leaves, hulls, husks, corncobs, corn stover, straw, grasses, wood, wood chips, wood pulp and sawdust. The grasses can be, e.g., Indian grass, or switchgrass. The grasses can also be, for example, *Miscanthus*. The paper waste can be, e.g., discarded or used photocopy paper, computer printer paper, notebook paper, notepad paper, typewriter paper, newspapers, magazines, cardboard, and various paper-based packaging materials. The paper waste can also be, for example, pulp.

The disclosure provides compositions (including enzymes, enzyme blends/compositions, e.g., products of manufacture of the disclosure) comprising a mixture of hemicellulose- and cellulose-hydrolyzing enzymes, and at least one biomass material. Optionally the biomass material comprises a lignocellulosic material derived from an agricultural crop. Alternatively the biomass material is a byproduct of a food or feed production. Suitable biomass material can also be a lignocellulosic waste product, a plant residue, a waste paper or waste paper product, or comprises a plant residue. The plant residue can, e.g., be one comprising grains, seeds, stems, leaves, hulls, husks, corncobs, corn stover, grasses, straw, wood, wood chips, wood pulp, or sawdust. Exemplary grasses include, without limitation, Indian grass or switchgrass. Exemplary grasses can also include *Miscanthus*. Exemplary paper waste include, without limitation, discarded or used photocopy paper, computer printer paper, notebook paper, notepad paper, typewriter paper, newspapers, magazines, cardboard and paper-based packaging materials. Exemplary paper waste can also include, e.g., pulp.

All publically available information as of the filing date, including, e.g., publications, patents, patent applications, GenBank sequences, and ATCC deposits cited herein are hereby expressly incorporated by reference.

5. BRIEF DESCRIPTION OF THE FIGURES AND TABLES

FIGS. 1A-1B: FIG. 1A: Fv3A nucleotide sequence (SEQ ID NO:1). FIG. 1B: Fv3A amino acid sequence (SEQ ID NO:2). SEQ ID NO:2 is the sequence of the immature Fv3A. Fv3A has a predicted signal sequence corresponding to positions 1 to 23 of SEQ ID NO:2 (underlined); cleavage of the signal sequence is predicted to yield a mature protein having a sequence corresponding to positions 24 to 766 of SEQ ID NO:2. The predicted conserved domain is in boldface type.

FIGS. 2A-2B: FIG. 2A: Pf43A nucleotide sequence (SEQ ID NO:3). FIG. 2B: Pf43A amino acid sequence (SEQ ID NO:4). SEQ ID NO:4 is the sequence of the immature Pf43A. Pf43A has a predicted signal sequence corresponding to positions 1 to of SEQ ID NO:4 (underlined); cleavage of the signal sequence is predicted to yield a mature protein having a sequence corresponding to positions 21 to 445 of SEQ ID NO:4. The predicted conserved domain is in boldface type, the predicted carbohydrate binding module ("CBM") is in uppercase type, and the predicted linker separating the CD and CBM is in italics.

FIGS. 3A-3B: FIG. 3A: Fv43E nucleotide sequence (SEQ ID NO:5). FIG. 3B: Fv43E amino acid sequence (SEQ ID NO:6). SEQ ID NO:6 is the sequence of the immature Fv43E. Fv43E has a predicted signal sequence corresponding to positions 1 to 18 of SEQ ID NO:6 (underlined); cleavage of the signal sequence is predicted to yield a mature protein having a sequence corresponding to positions 19 to 530 of SEQ ID NO:6. The predicted conserved domain is in boldface type.

FIGS. 4A-4B: FIG. 4A: Fv39A nucleotide sequence (SEQ ID NO:7). FIG. 4B: Fv39A amino acid sequence (SEQ ID NO:8). SEQ ID NO:8 is the sequence of the immature Fv39A. Fv39A has a predicted signal sequence corresponding to positions 1 to 19 of SEQ ID NO:8 (underlined); cleavage of the signal sequence is predicted to yield a mature protein having a sequence corresponding to positions 20 to 439 of SEQ ID NO:8. The predicted conserved domain is in boldface type.

FIGS. 5A-5B: FIG. 5A: Fv43A nucleotide sequence (SEQ ID NO:9). FIG. 5B: Fv43A amino acid sequence (SEQ ID NO:10). SEQ ID NO:10 is the sequence of the immature Fv43A. Fv43A has a predicted signal sequence corresponding to positions 1 to 22 of SEQ ID NO:10 (underlined); cleavage of the signal sequence is predicted to yield a mature protein having a sequence corresponding to positions 23 to 449 of SEQ ID NO:10. The predicted conserved domain is in boldface type, the predicted CBM is in uppercase type, and the predicted linker separating the conserved domain and CBM is in italics.

FIGS. 6A-6B: FIG. 6A: Fv43B nucleotide sequence (SEQ ID NO:11). FIG. 6B: Fv43B amino acid sequence (SEQ ID NO:12). SEQ ID NO:12 is the sequence of the immature Fv43B. Fv43B has a predicted signal sequence corresponding to positions 1 to 16 of SEQ ID NO:12 (underlined); cleavage of the signal sequence is predicted to yield a mature protein having a sequence corresponding to positions 17 to 574 of SEQ ID NO:12. The predicted conserved domain is in boldface type.

FIGS. 7A-7B: FIG. 7A: Pa51A nucleotide sequence (SEQ ID NO:13). FIG. 7B: Pa51A amino acid sequence (SEQ ID NO:14). SEQ ID NO:14 is the sequence of the immature Pa51A. Pa51A has a predicted signal sequence corresponding to positions 1 to 20 of SEQ ID NO:14 (underlined); cleavage of the signal sequence is predicted to yield a mature protein having a sequence corresponding to positions 21 to 676 of SEQ ID NO:14. The predicted L-α-arabinofuranosidase conserved domain is in boldface type. For expression purposes, the genomic DNA was codon optimized for expression in *T. reesei* (see FIG. 60B).

FIGS. 8A-8B: FIG. 8A: Gz43A nucleotide sequence (SEQ ID NO:15). FIG. 8B: Gz43A amino acid sequence (SEQ ID NO:16). SEQ ID NO:16 is the sequence of the immature Gz43A. Gz43A has a predicted signal sequence corresponding to positions 1 to 18 of SEQ ID NO:16 (underlined); cleavage of the signal sequence is predicted to yield a mature protein having a sequence corresponding to positions 19 to 340 of SEQ ID NO:16. The predicted conserved domain is in boldface type. For expression purposes, the Gz43A predicted signal sequence was replaced by the *T. reesei* CBH1 signal sequence (myrklavisaflatara (SEQ ID NO: 51)) in *T. reesei* (see FIG. 61).

FIGS. 9A-9B: FIG. 9A: Fo43A nucleotide sequence (SEQ ID NO:17). FIG. 9B: Fo43A amino acid sequence (SEQ ID NO:18). SEQ ID NO:18 is the sequence of the immature Fo43A. Fo43A has a predicted signal sequence corresponding to positions 1 to 20 of SEQ ID NO:18 (underlined); cleavage of the signal sequence is predicted to yield a mature protein having a sequence corresponding to positions 21 to 348 of SEQ ID NO:18. The predicted conserved domain is in boldface type. For expression purposes, the Fo43A predicted signal sequence was replaced by the *T. reesei* CBH1 signal sequence (myrklavisaflatara (SEQ ID NO:51)) (see FIG. 62).

FIGS. 10A-10B: FIG. 10A: Af43A nucleotide sequence (SEQ ID NO:19). FIG. 10B: Af43A amino acid sequence (SEQ ID NO:20). SEQ ID NO:20 is the sequence of the immature Af43A. The predicted conserved domain is in boldface type.

FIGS. 11A-11B: FIG. 11A: Pf51A nucleotide sequence (SEQ ID NO:21). FIG. 11B: Pf51A amino acid sequence (SEQ ID NO:22). SEQ ID NO:22 is the sequence of the immature Pf51A. Pf51A has a predicted signal sequence corresponding to positions 1 to 20 of SEQ ID NO:22 (underlined); cleavage of the signal sequence is predicted to yield a mature protein having a sequence corresponding to positions 21 to 642 of SEQ ID NO:22. The predicted L-α-arabinofuranosidase conserved domain is in boldface type. For expression purposes, the predicted Pf51A signal sequence was replaced by a codon optimized the *T. reesei* CBH1 signal sequence (myrklavisaflatara (SEQ ID NO:51)) (underlined) and the Pf51A nucleotide sequence was codon optimized for expression in *T. reesei* (see FIG. 63).

FIGS. 12A-12B: FIG. 12A: AfuXyn2 nucleotide sequence (SEQ ID NO:23). FIG. 12B: AfuXyn2 amino acid sequence (SEQ ID NO:24). SEQ ID NO:24 is the sequence of the immature AfuXyn2. AfuXyn2 has a predicted signal sequence corresponding to positions 1 to 18 of SEQ ID NO:24 (underlined); cleavage of the signal sequence is predicted to yield a mature protein having a sequence corresponding to positions 19 to 228 of SEQ ID NO:24. The predicted GH11 conserved domain is in boldface type.

FIGS. 13A-13B: FIG. 13A: AfuXyn5 nucleotide sequence (SEQ ID NO:25). FIG. 13B: AfuXyn5 amino acid sequence (SEQ ID NO:26). SEQ ID NO:26 is the sequence of the immature AfuXyn5. AfuXyn5 has a predicted signal sequence corresponding to positions 1 to 19 of SEQ ID NO:26 (underlined); cleavage of the signal sequence is predicted to yield a mature protein having a sequence corresponding to positions 20 to 313 of SEQ ID NO:26. The predicted GH11 conserved domain is in boldface type.

FIGS. 14A-14B: FIG. 14A: Fv43D nucleotide sequence (SEQ ID NO:27). FIG. 14B: Fv43D amino acid sequence (SEQ ID NO:28). SEQ ID NO:28 is the sequence of the immature Fv43D. Fv43D has a predicted signal sequence corresponding to positions 1 to 20 of SEQ ID NO:28 (underlined); cleavage of the signal sequence is predicted to yield a mature protein having a sequence corresponding to positions 21 to 350 of SEQ ID NO:28. The predicted conserved domain is in boldface type.

FIGS. 15A-15B: FIG. 15A: Pf43B nucleotide sequence (SEQ ID NO:29). FIG. 15B: Pf43B amino acid sequence (SEQ ID NO:30). SEQ ID NO:30 is the sequence of the immature Pf43B. Pf43B has a predicted signal sequence corresponding to positions 1 to 20 of SEQ ID NO:30 (underlined); cleavage of the signal sequence is predicted to yield a mature protein having a sequence corresponding to positions 21 to 321 of SEQ ID NO:30. The predicted conserved domain is in boldface type.

FIGS. 16A-16B: FIG. 16A: Fv51A nucleotide sequence (SEQ ID NO:31). FIG. 16B: Fv51A amino acid sequence (SEQ ID NO:32). SEQ ID NO:32 is the sequence of the immature Fv51A. Fv51A has a predicted signal sequence corresponding to positions 1 to 19 of SEQ ID NO:32 (underlined); cleavage of the signal sequence is predicted to yield a mature protein having a sequence corresponding to positions 20 to 660 of SEQ ID NO:32. The predicted L-α-arabinofuranosidase conserved domain is in boldface type.

FIGS. 17A-17B: FIG. 17A: Cg51B nucleotide sequence (SEQ ID NO:33). FIG. 17B: Cg51B amino acid sequence (SEQ ID NO:34). SEQ ID NO:34 is the sequence of the immature Cg51B. Cg51B has a predicted signal sequence corresponding to positions 1 to 20 of SEQ ID NO:34 (underlined); cleavage of the signal sequence is predicted to yield a mature protein having a sequence corresponding to positions 21 to 670 of SEQ ID NO:34. The predicted conserved domain is in boldface type.

FIGS. 18A-18B: FIG. 18A: Fv43C nucleotide sequence (SEQ ID NO:35). FIG. 18B: Fv43C amino acid sequence (SEQ ID NO:36). SEQ ID NO:36 is the sequence of the immature Fv43C. Fv43C has a predicted signal sequence corresponding to positions 1 to 22 of SEQ ID NO:36 (underlined); cleavage of the signal sequence is predicted to yield a mature protein having a sequence corresponding to positions 23 to 333 of SEQ ID NO:36. The predicted conserved domain is in boldface type.

FIGS. 19A-19B: FIG. 19A: Fv30A nucleotide sequence (SEQ ID NO:37). FIG. 19B: Fv30A amino acid sequence (SEQ ID NO:38). SEQ ID NO:38 is the sequence of the immature Fv30A. Fv30A has a predicted signal sequence corresponding to positions 1 to 19 of SEQ ID NO:38 (underlined); cleavage of the signal sequence is predicted to yield a mature protein having a sequence corresponding to positions 20 to 537 of SEQ ID NO:38.

FIGS. 20A-20B: FIG. 20A: Fv43F nucleotide sequence (SEQ ID NO:39). FIG. 20B: Fv43F amino acid sequence (SEQ ID NO:40). SEQ ID NO:40 is the sequence of the immature Fv43F. Fv43F has a predicted signal sequence corresponding to positions 1 to 20 of SEQ ID NO:40 (underlined); cleavage of the signal sequence is predicted to yield a mature protein having a sequence corresponding to positions 21 to 315 of SEQ ID NO:40.

FIGS. 21A-21B: FIG. 21A: *Trichoderma reesei* Xyn3 nucleotide sequence (SEQ ID NO:41). FIG. 21B: *Trichoderma reesei* Xyn3 amino acid sequence (SEQ ID NO:42). SEQ ID NO:42 is the sequence of the immature *Trichoderma reesei* Xyn3. *Trichoderma reesei* Xyn3 has a predicted signal sequence corresponding to positions 1 to 16 of SEQ ID NO:42 (underlined); cleavage of the signal sequence is predicted to yield a mature protein having a sequence corresponding to positions 17 to 347 of SEQ ID NO:42. The predicted conserved domain is in bold face type.

FIG. 22: Amino acid sequence of *Trichoderma reesei* Xyn2 (SEQ ID NO:43). The signal sequence is underlined. The predicted conserved domain is in bold face type. The coding sequence can be found in Törrönen et al. Biotechnology, 1992, 10:1461-65.

FIG. 23: Amino acid sequence of *Trichoderma reesei* Bxl1 (SEQ ID NO:44). The signal sequence is underlined. The predicted conserved domain is in bold face type. The coding sequence can be found in Margolles-Clark et al. Appl. Environ. Microbiol. 1996, 62(10):3840-46.

FIG. 24: Amino acid sequence of *Trichoderma reesei* Bgl1 (SEQ ID NO:45). The signal sequence is underlined. The predicted conserved domain is in bold face type. The coding sequence can be found in Barnett et al. Bio-Technology, 1991, 9(6):562-567.

FIG. 25: Cellulase activity assay using PASC hydrolysis with calcofluor detection.

Figure 26:
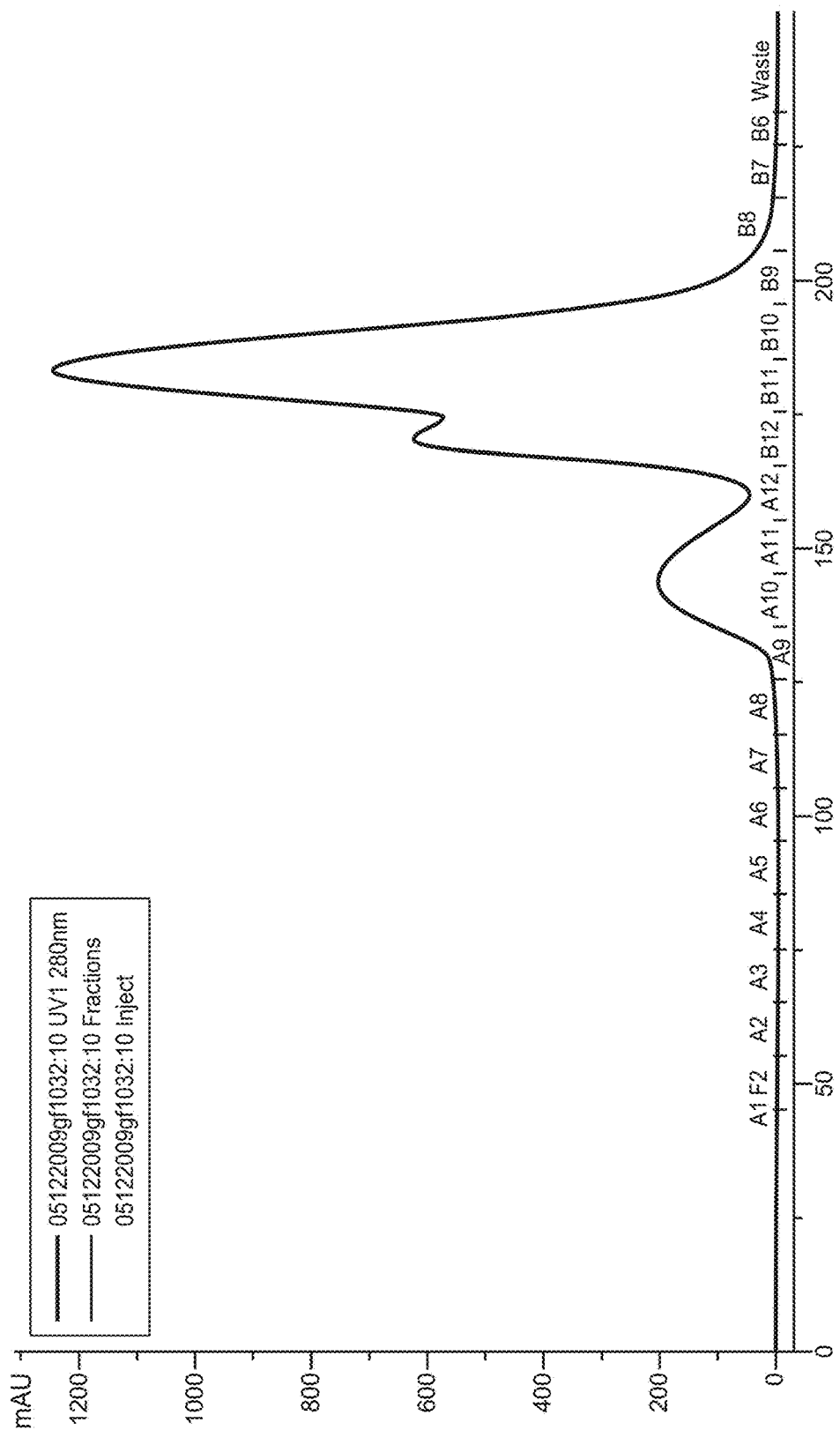

FIG. 26: Xylanase elution profile.

Figure 27:
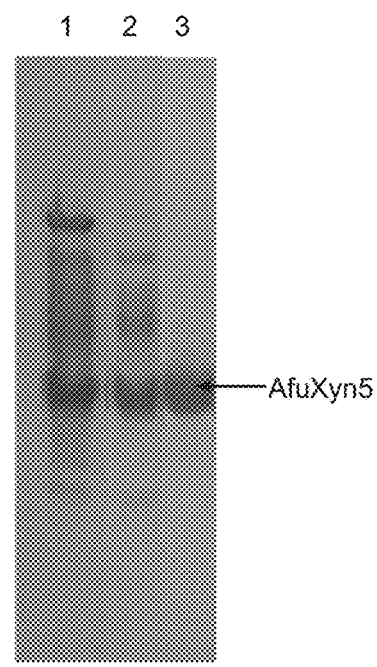

FIG. 27: SDS-PAGE detection of the two step separation of AfuXyn 5. Lane 1: Crude sample; Lane 2: Eluate from Phenyl column; Lane 3: Eluate from GF column.

Figure 28:
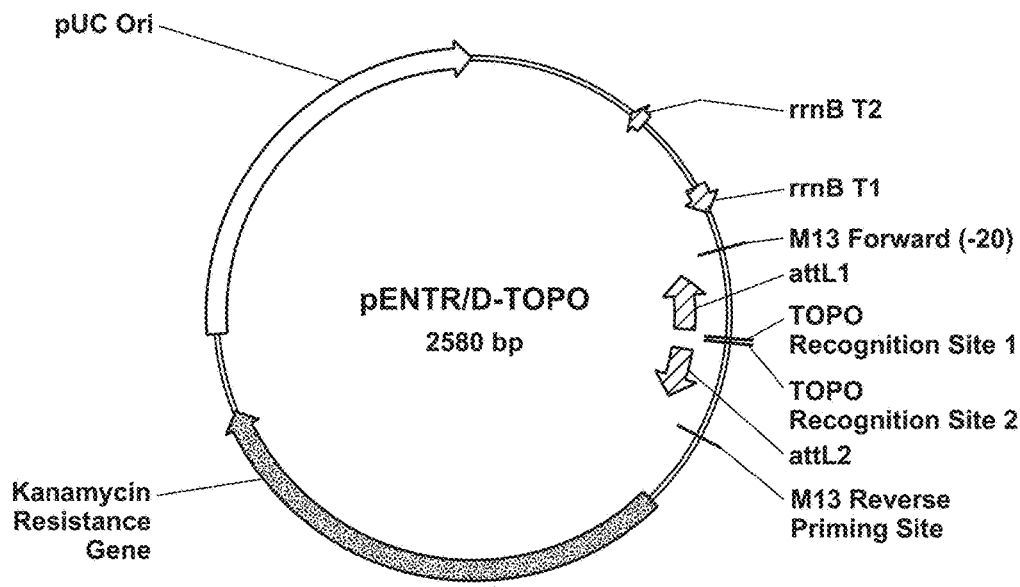

FIG. 28: pENTR/D-TOPO plasmid.

FIG. 29: pTrex3gM.

Figure 30A:
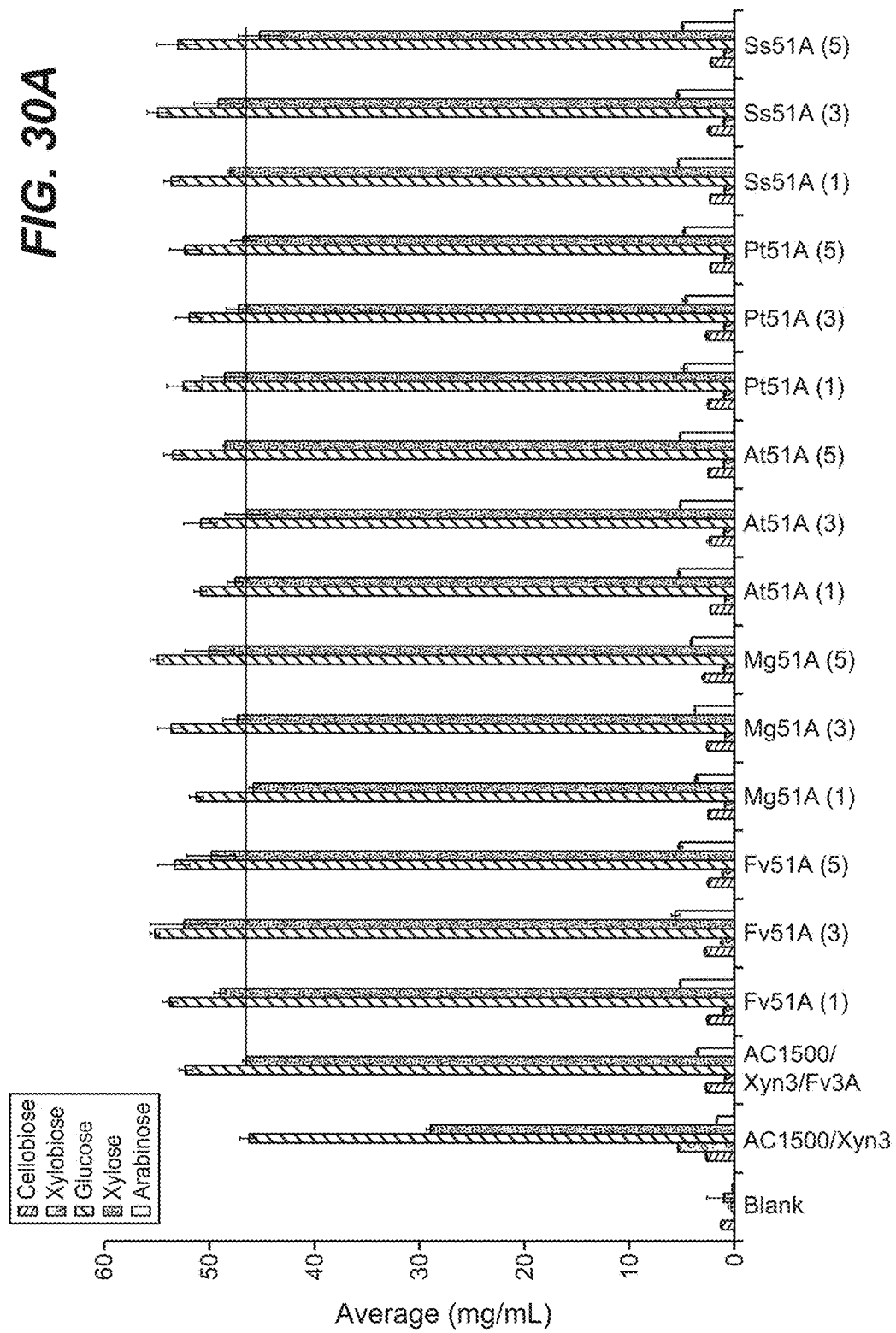

FIGS. 30A-30B: Performance of different enzymes on corncob substrate. Error bars represent the experimental errors associated with triplicate cob assays. The numbers in parenthesis along the x-axis represent the enzyme doses in mg of protein per g of cellulose.

Figure 31:
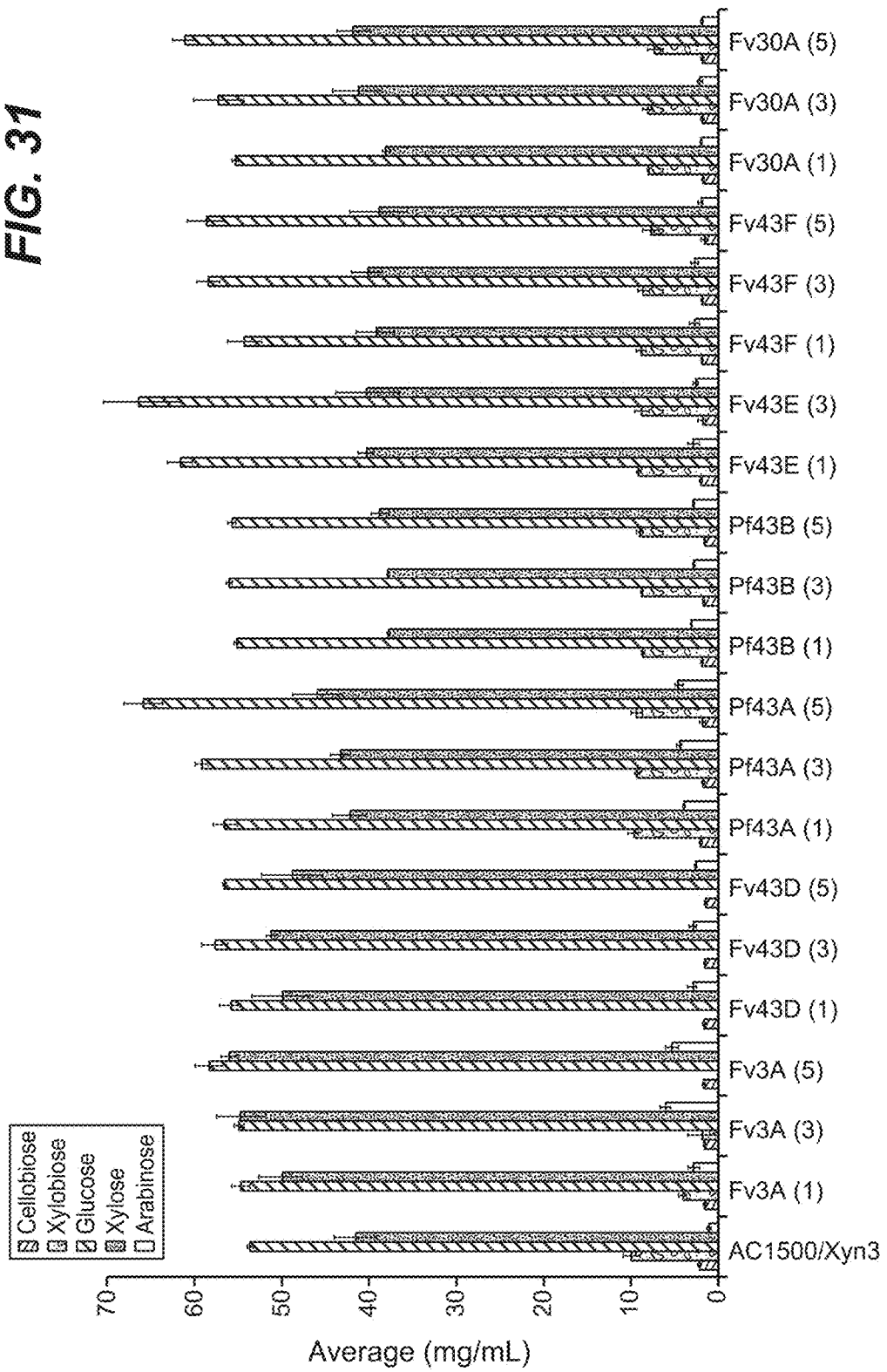

FIG. 31: Performance of different enzyme blends/compositions on corncob substrate. Error bars represent the experimental errors associated with triplicate cob assays. The numbers in parentheses along the x-axis represent the enzyme doses in mg of protein per g cellulose.

Figure 32:
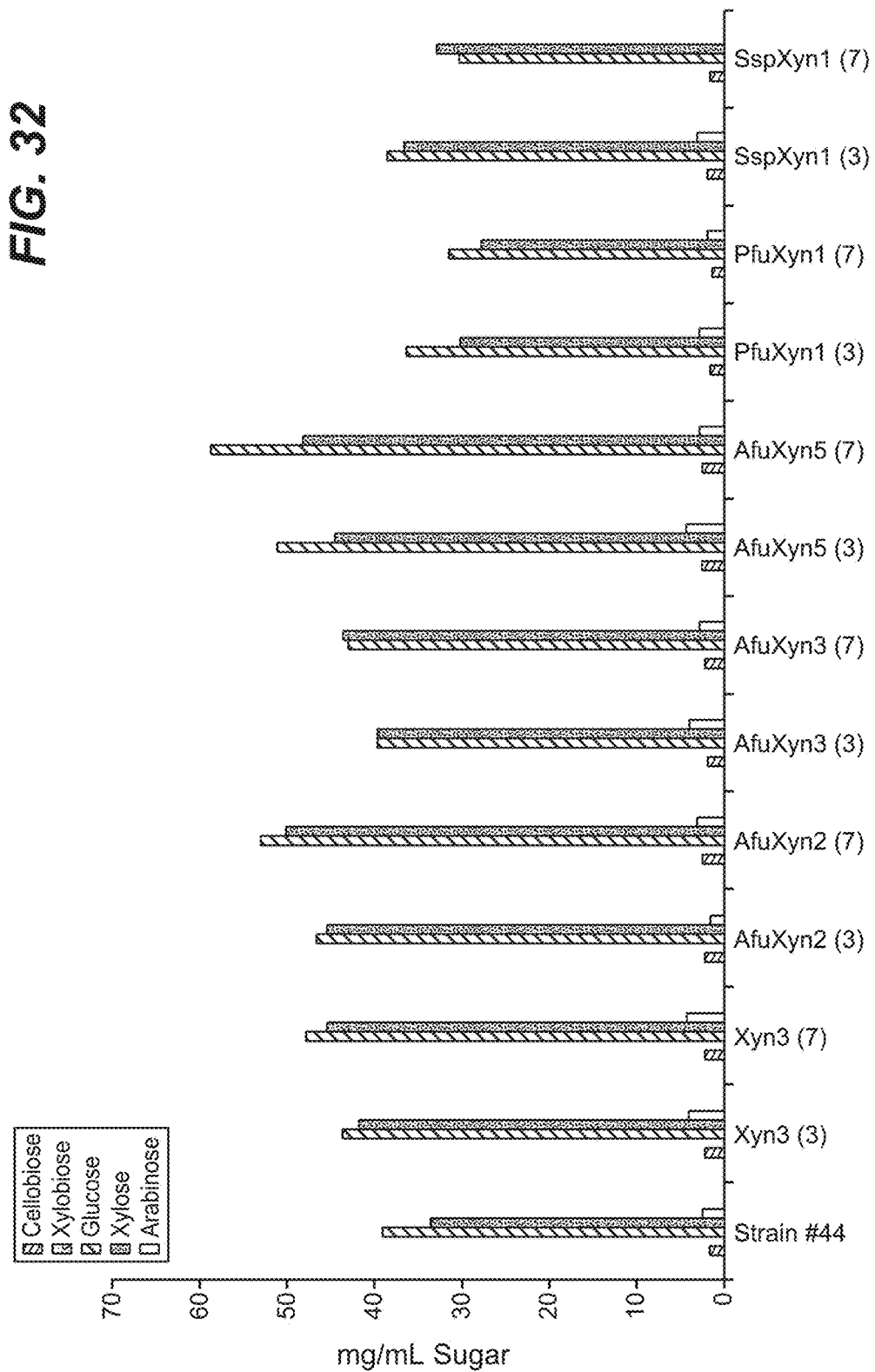

FIG. 32: Performance of different enzyme blends/compositions on corncob substrate. Error bars represent the experimental errors associated with triplicate cob assays. The numbers in parentheses along the x-axis represent the enzyme doses in mg of protein per g cellulose.

Figure 33:
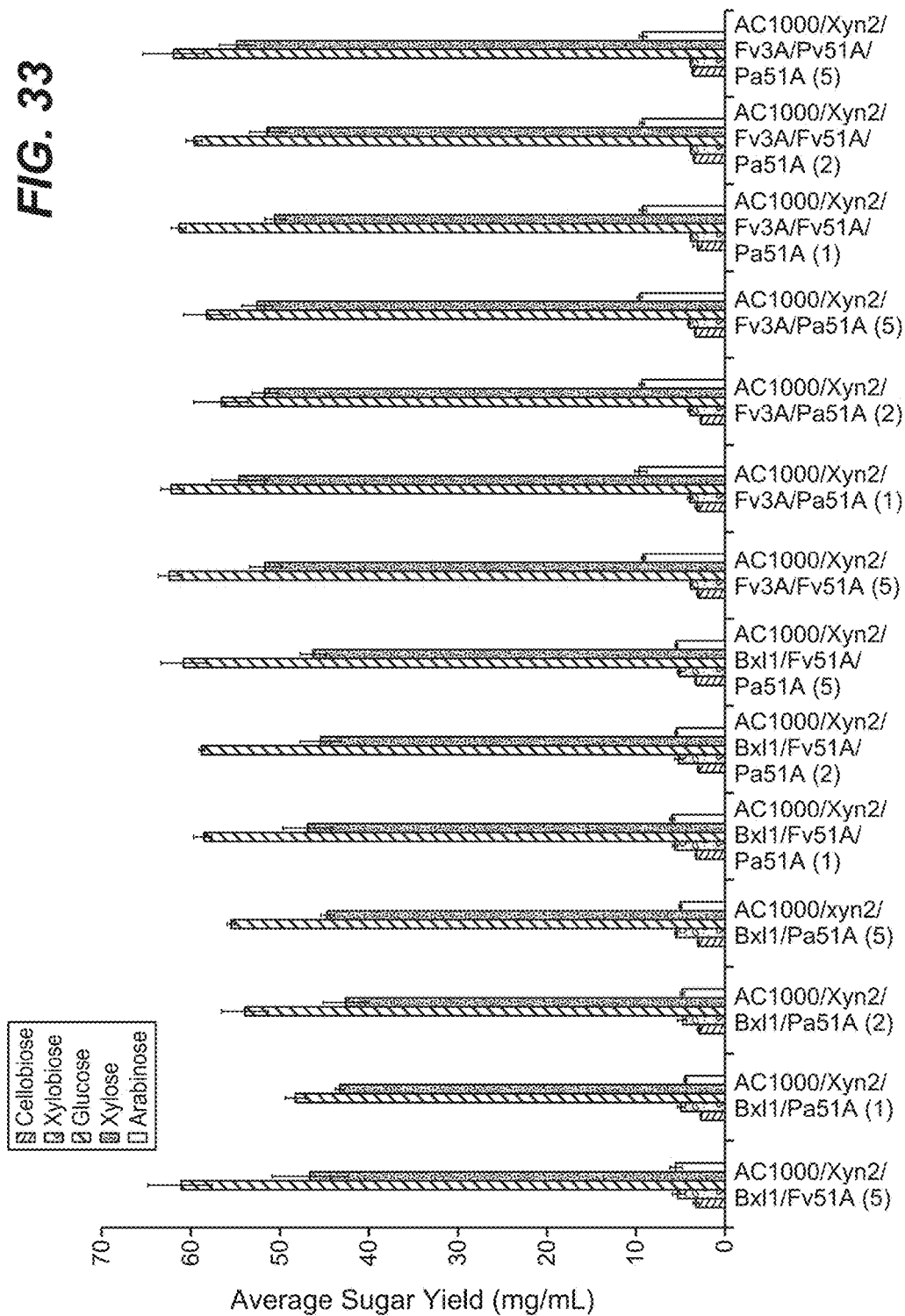

FIG. 33: Performance of different enzyme blends/compositions on corncob substrate. Error bars represent the experimental errors associated with triplicate cob assays. The numbers in parentheses along the x-axis represent the enzyme doses in mg of protein per g cellulose.

Figure 34:
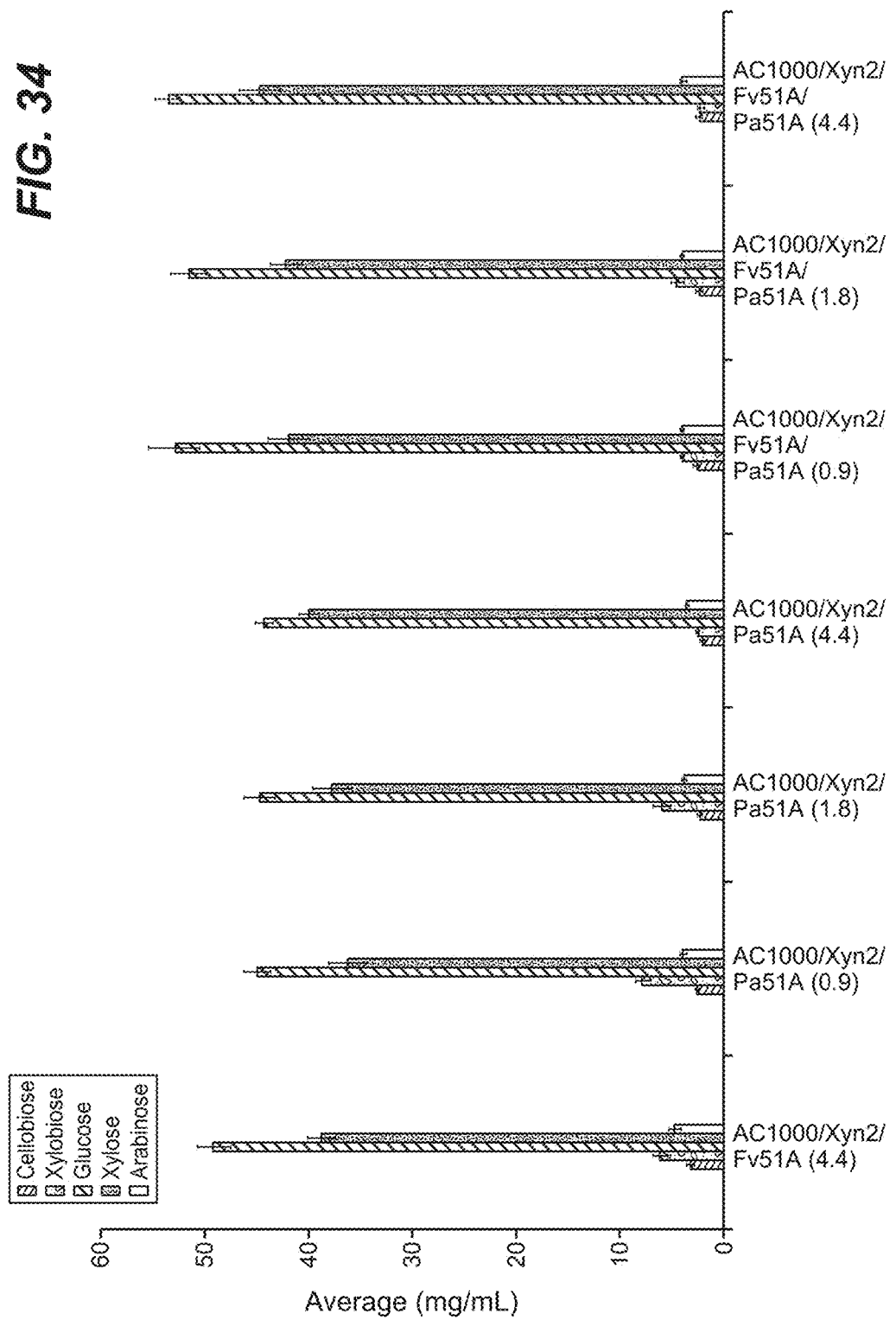

FIG. 34: Performance of different enzyme blends/compositions on corncob substrate. Error bars represent the experimental errors associated with triplicate cob assays.

The numbers in parentheses along the x-axis represent the enzyme doses in mg of protein per g cellulose.

Figure 35A:
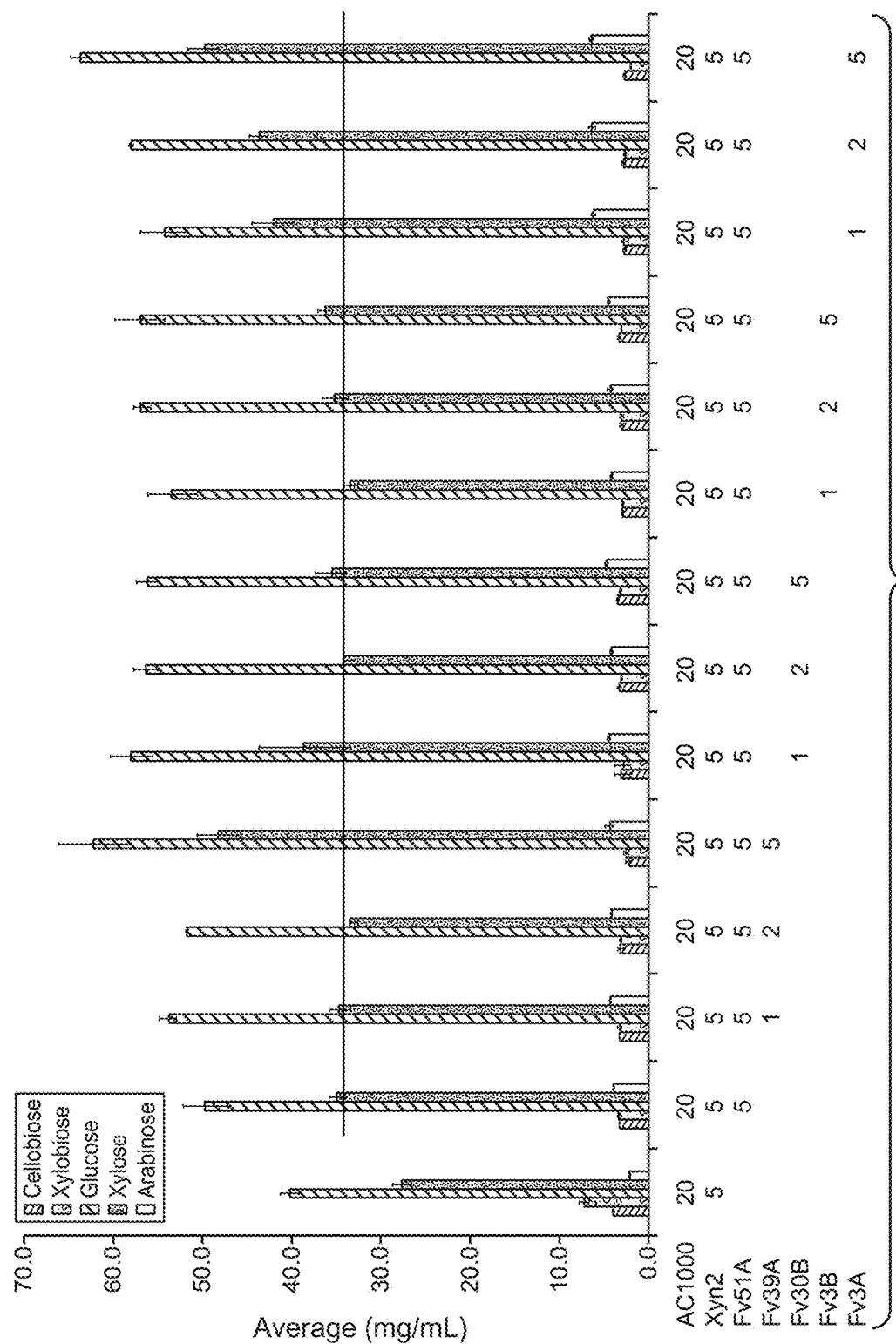
Figure 35B:
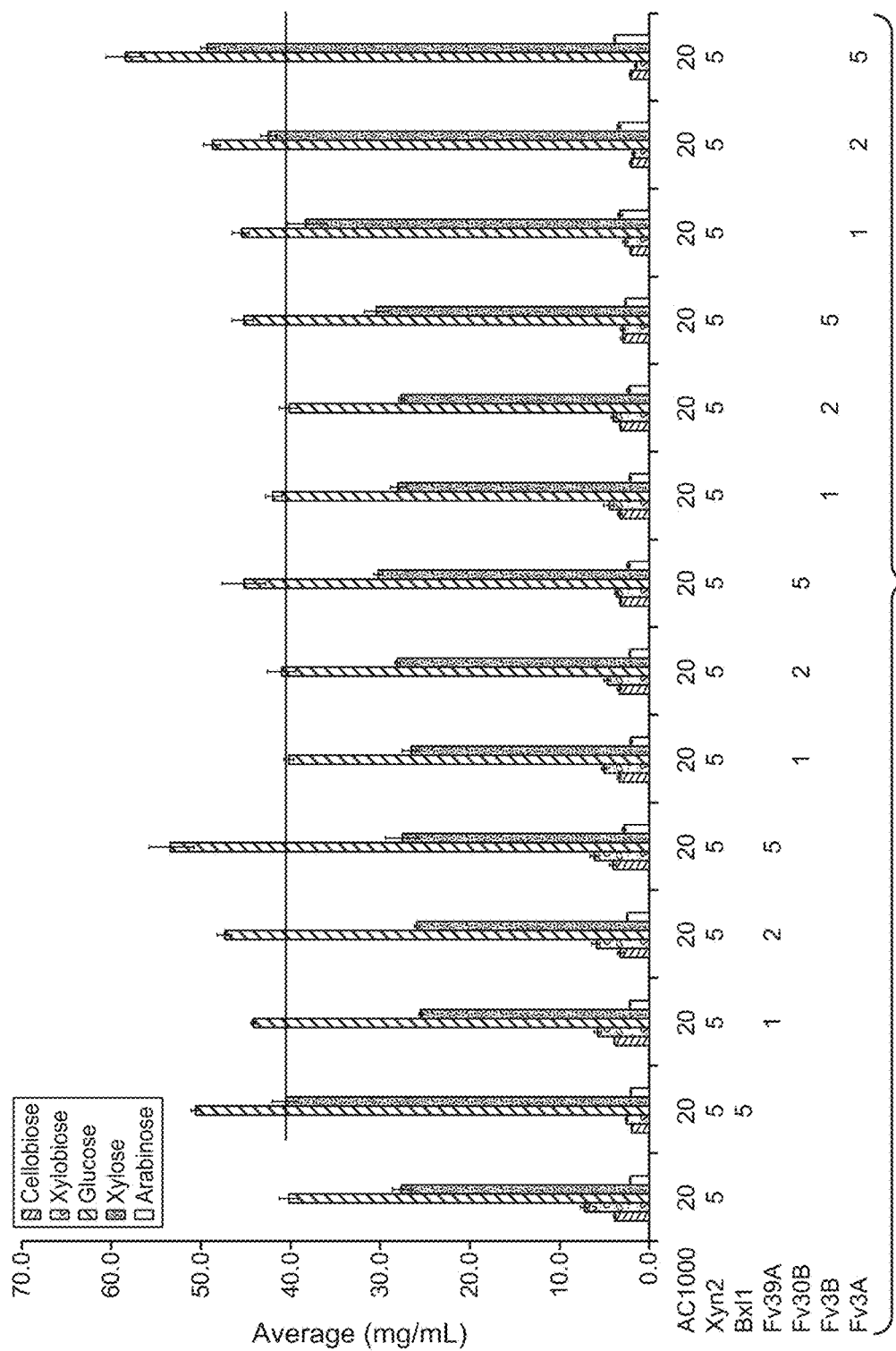

FIGS. 35A-35C: Performance of different enzyme blends/compositions on corncob substrate. Error bars represent the experimental errors associated with triplicate cob assays. The numbers along the x-axis represent the enzyme doses in mg of protein per g cellulose.

Figure 36:
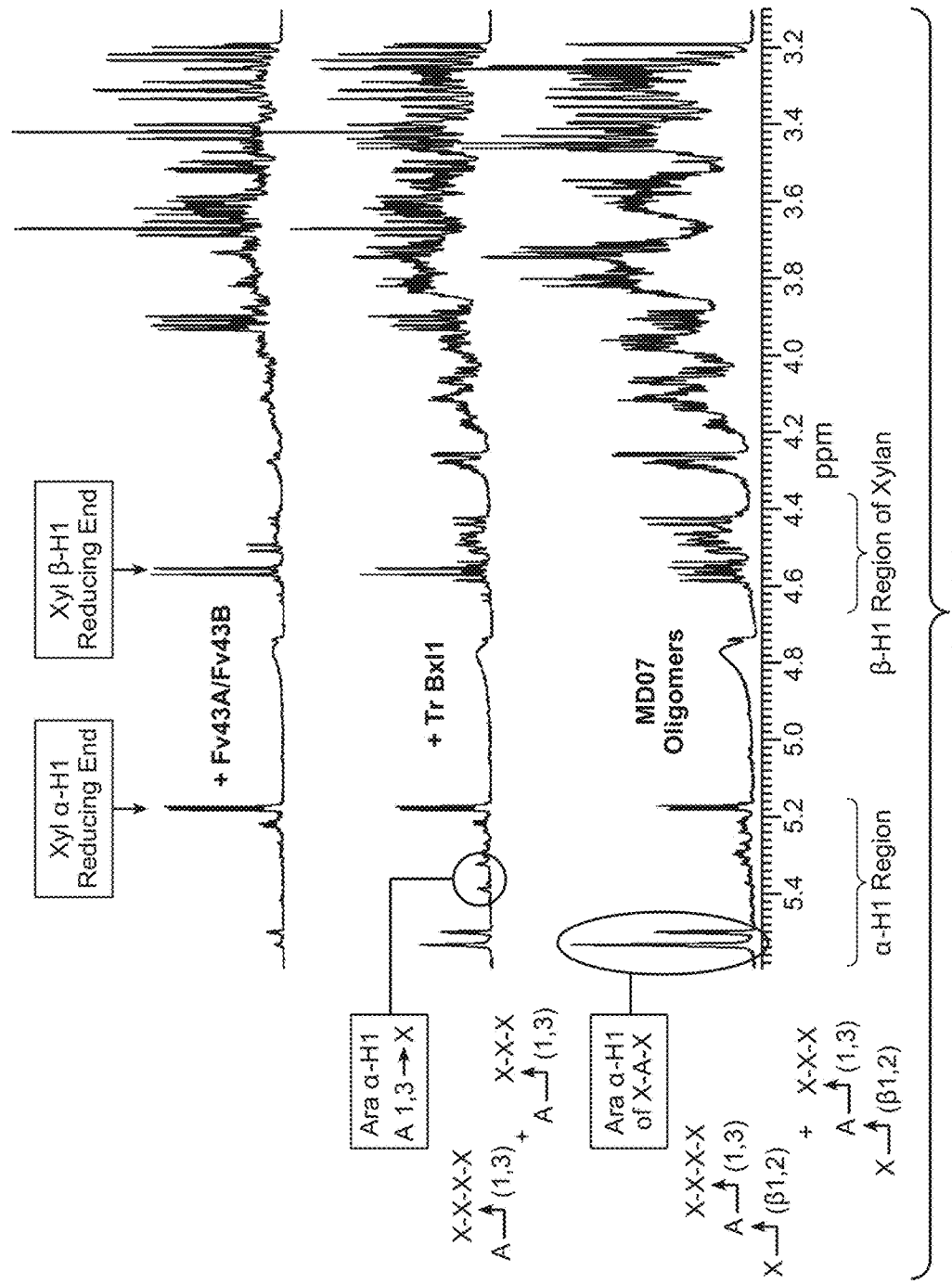

FIG. 36: Anomeric proton NMR region of short arabinoxylan oligomers shows cleavage by Fv43A plus Fv43B.

Figure 37:
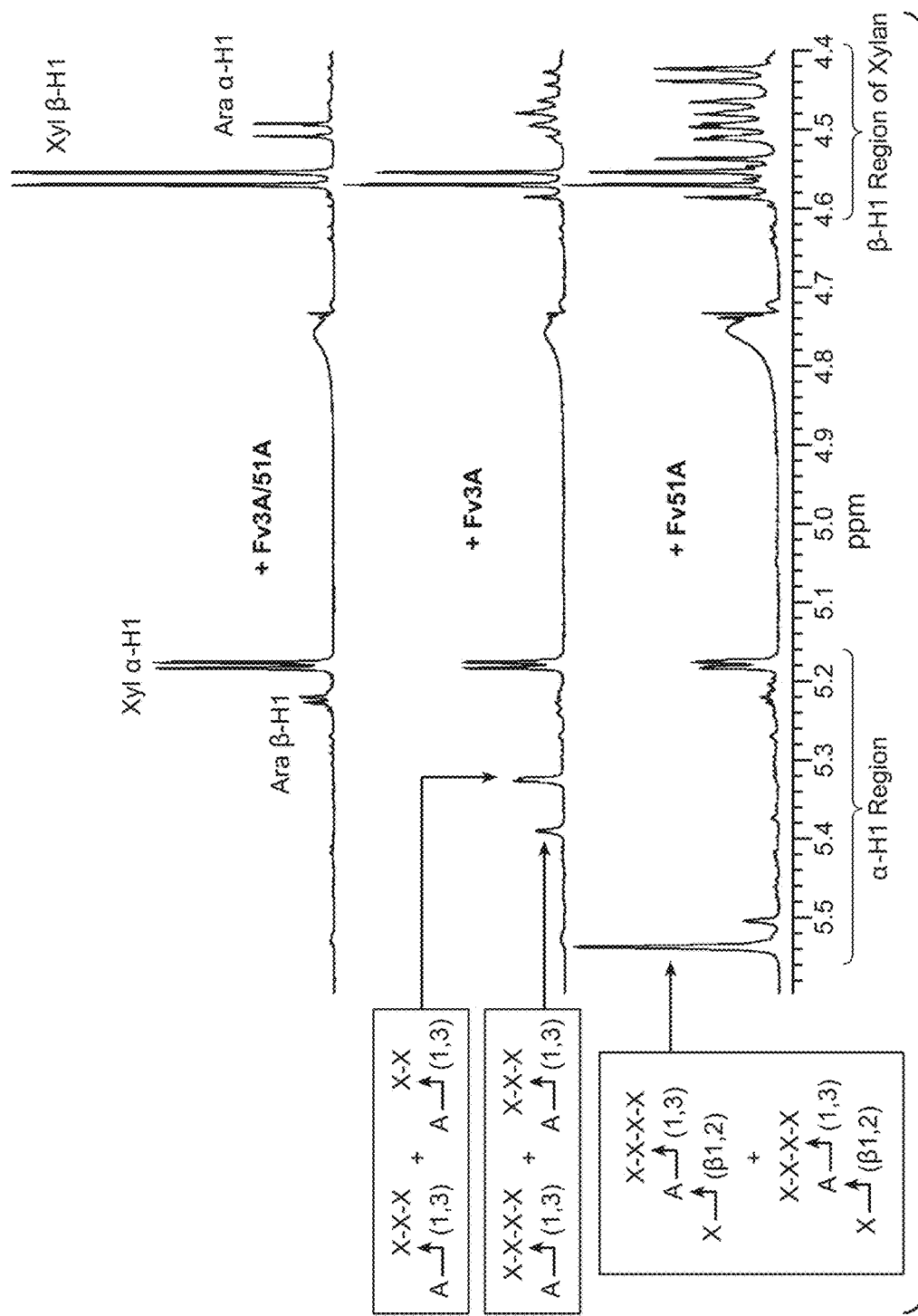

FIG. 37: Anomeric proton NMR region of short arabinoxylan oligomers shows cleavage of β-1,2-linked xylose from arabinose by Fv3A.

FIG. 38: Alignment between the amino acid sequences of *Trichoderma reesei* β-xylosidase and Fv3A.

Figure 39:
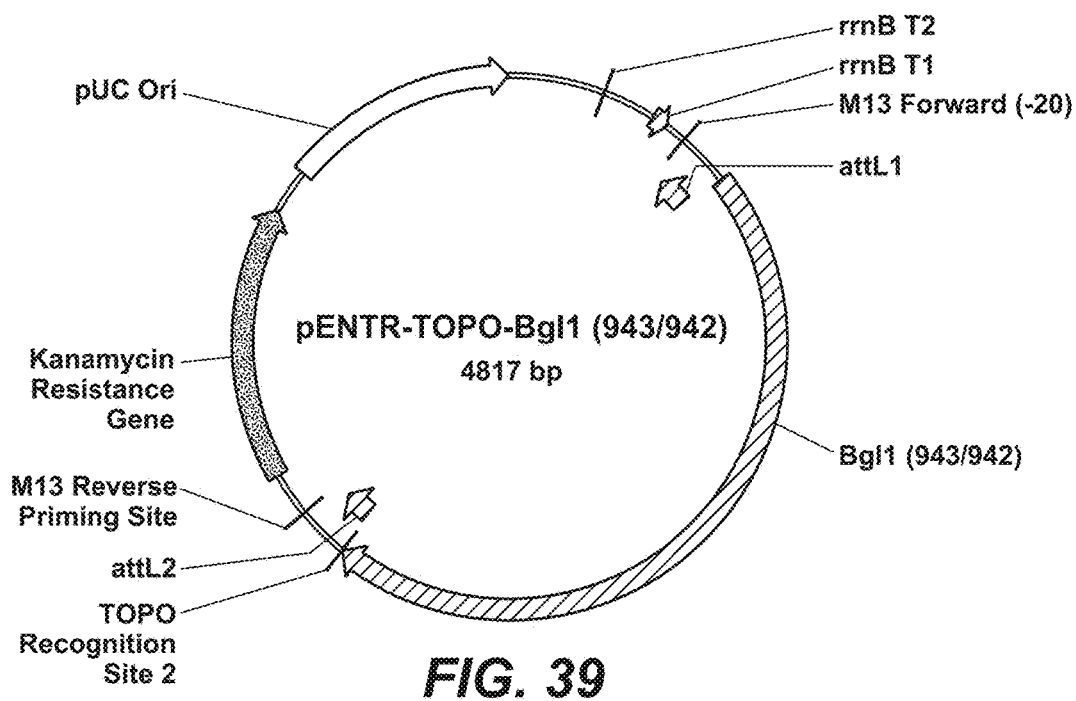

FIG. 39: pENTR-TOPO-Bgl1 (943/942) plasmid.

Figure 40:
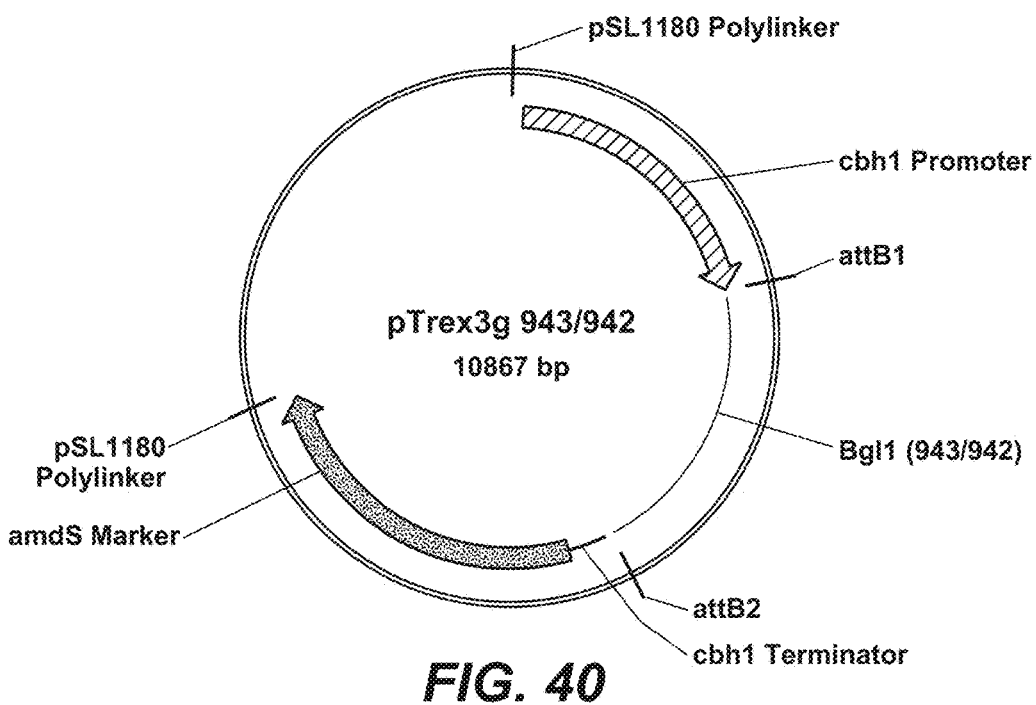

FIG. 40: pTrex3g 943/942 Bgl1 expression vector.

Figure 41:
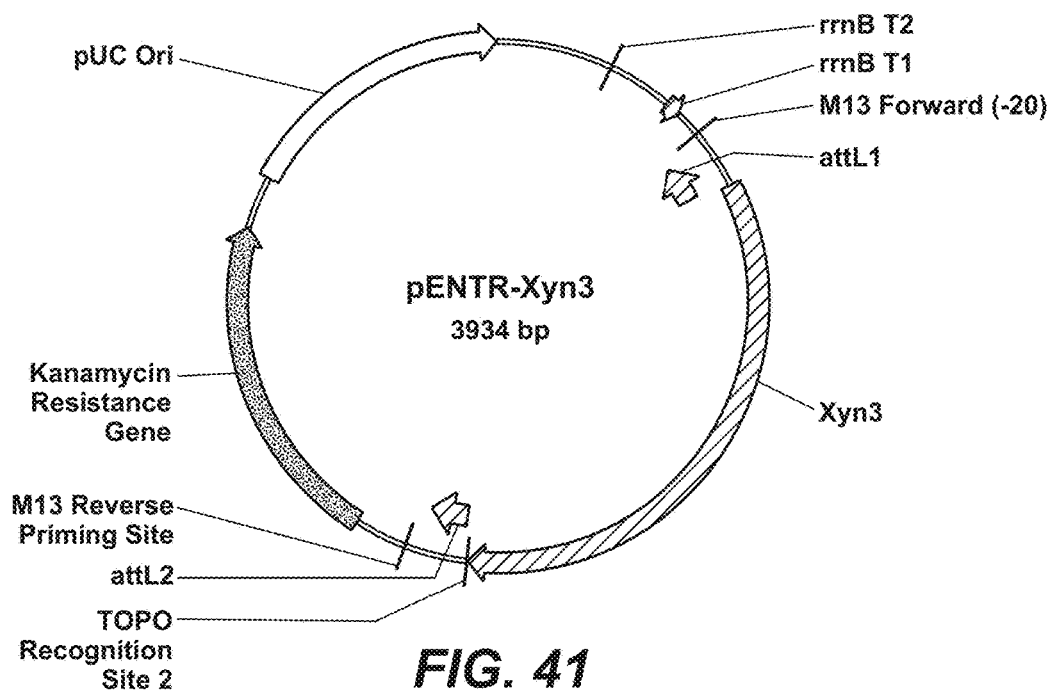

FIG. 41: pENTR-*Trichoderma reesei* Xyn3 plasmid.

Figure 42:
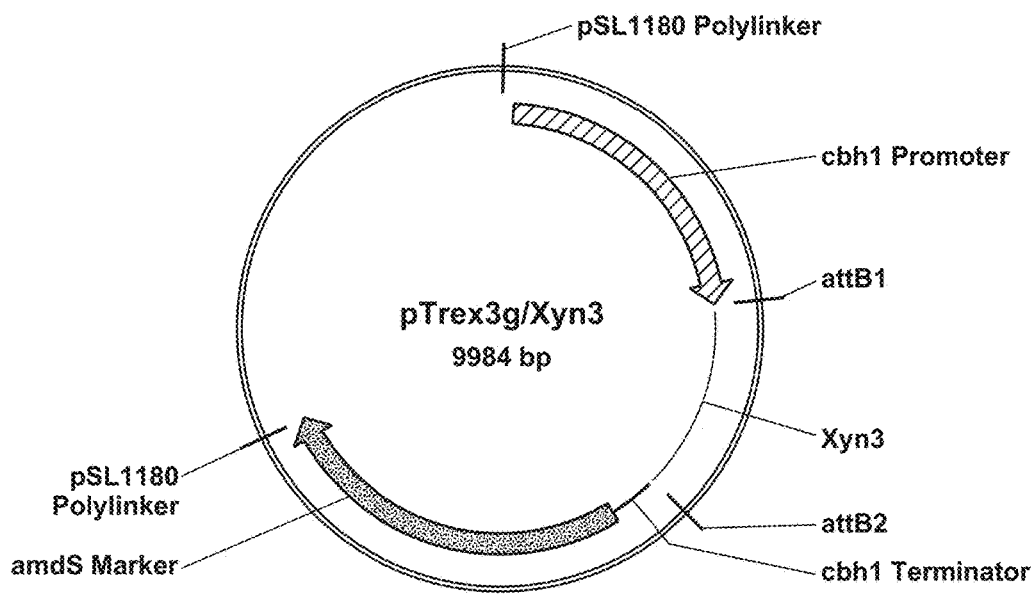

FIG. 42: pTrex3g/*Trichoderma reesei* Xyn3 expression vector.

Figure 43:
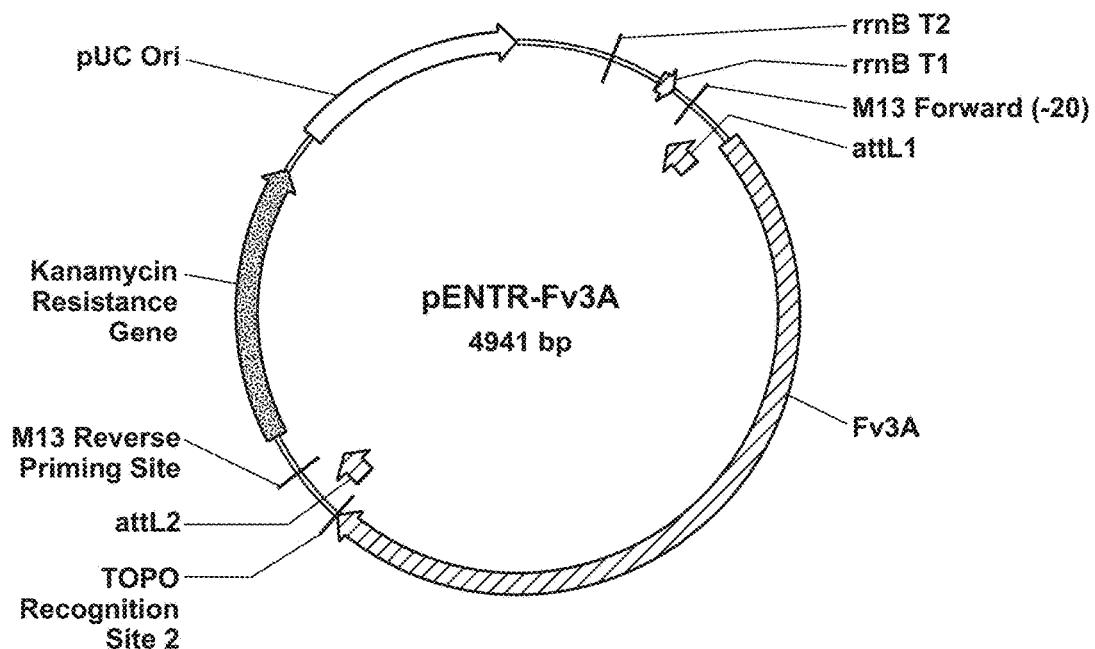

FIG. 43: pENTR-Fv3A plasmid.

Figure 44:
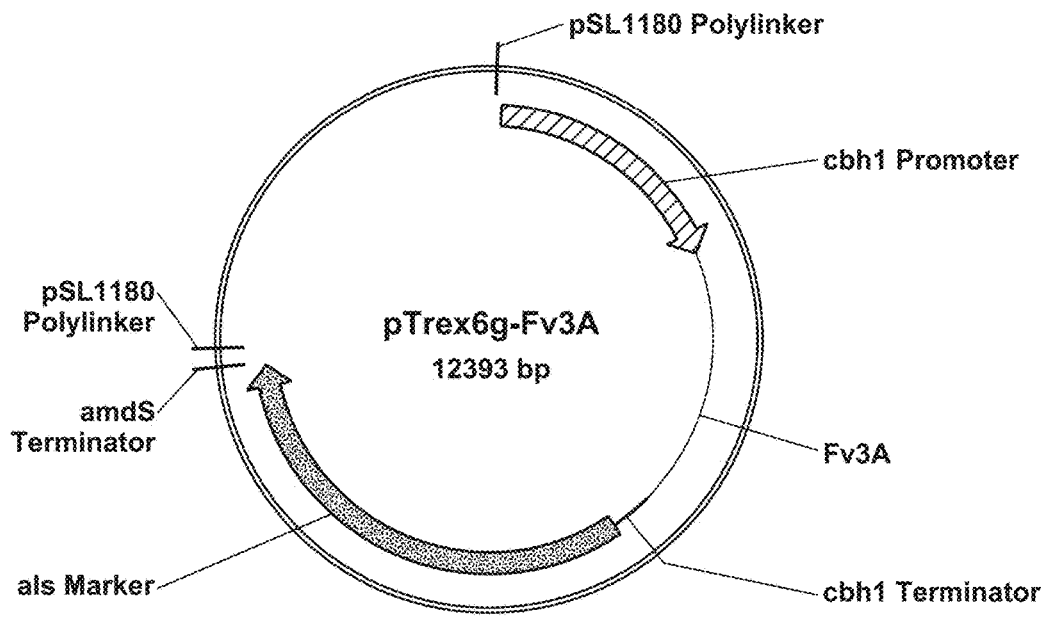

FIG. 44: pTrex6g/Fv3A expression vector.

Figure 45:
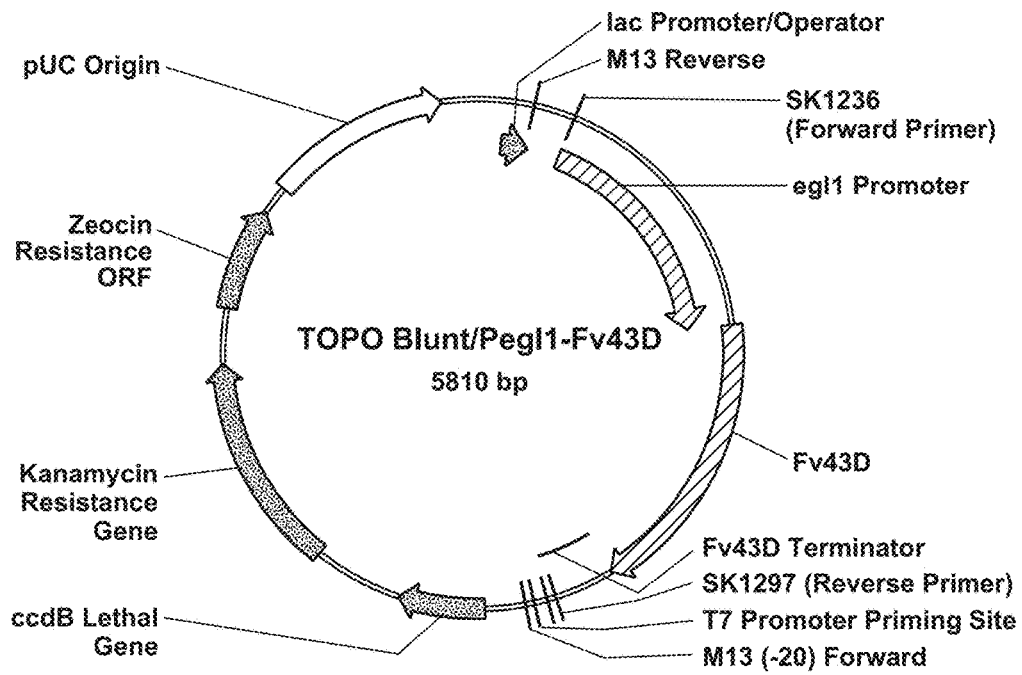

FIG. 45: TOPO Blunt/Pegl1-Fv43D plasmid.

Figure 46:
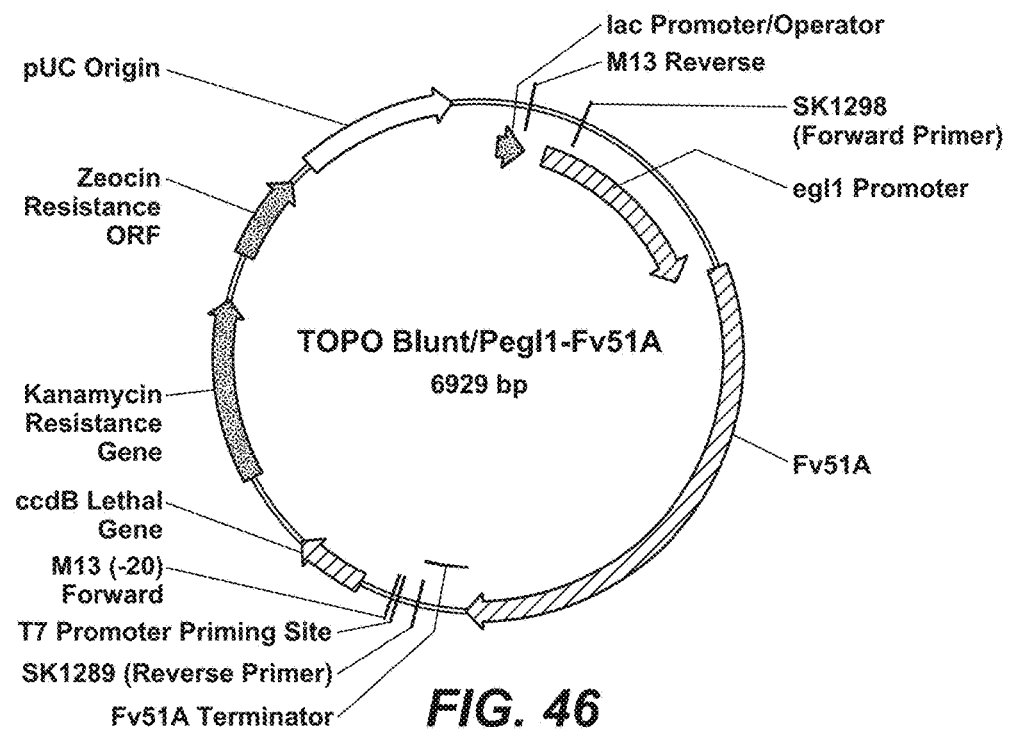

FIG. 46: TOPO Blunt/Pegl11-Fv51A plasmid.

Figure 47A:
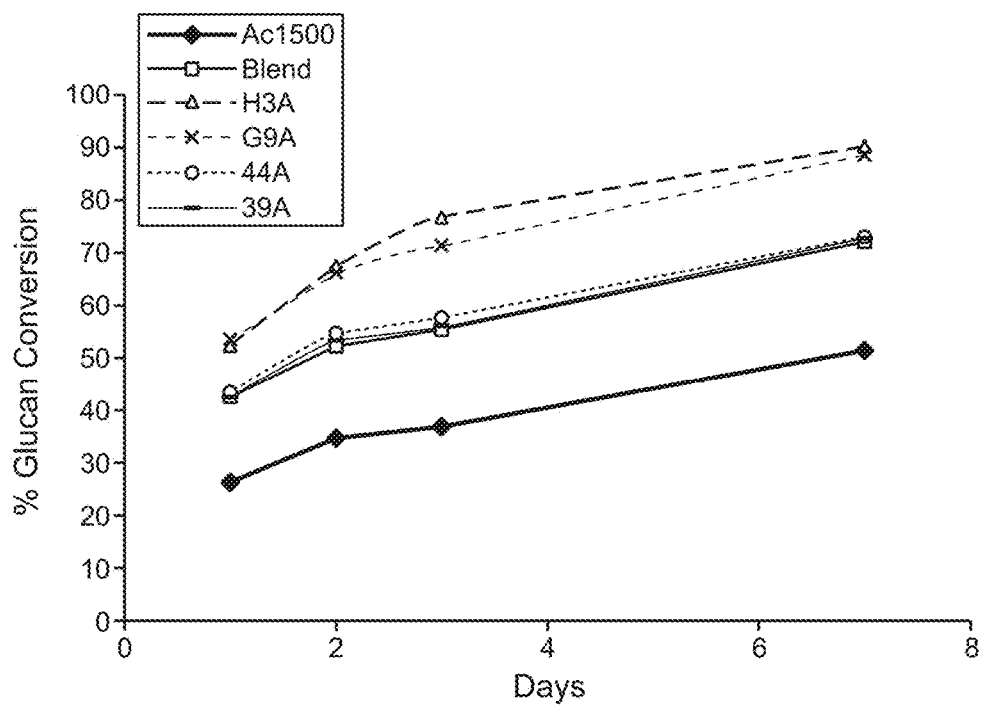
Figure 47B:
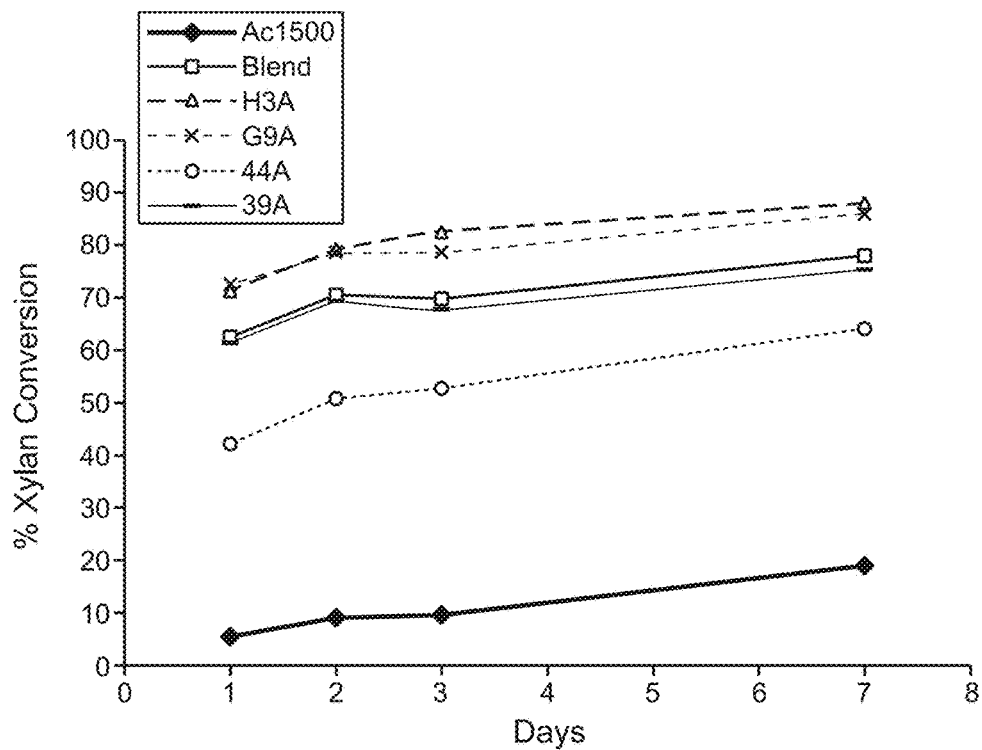
Figure 47C:
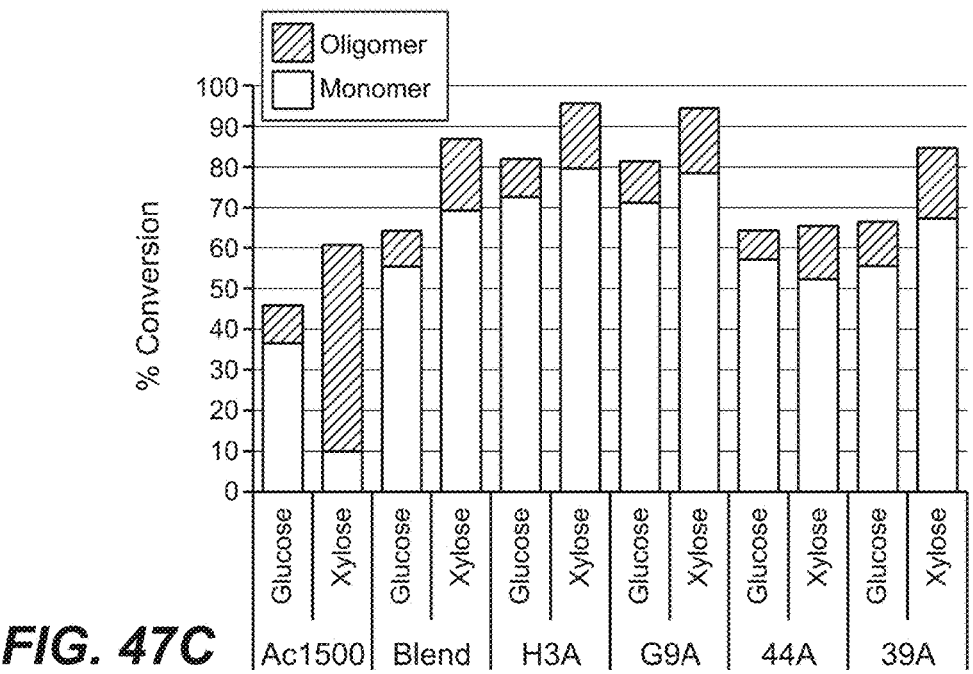
Figure 47D:
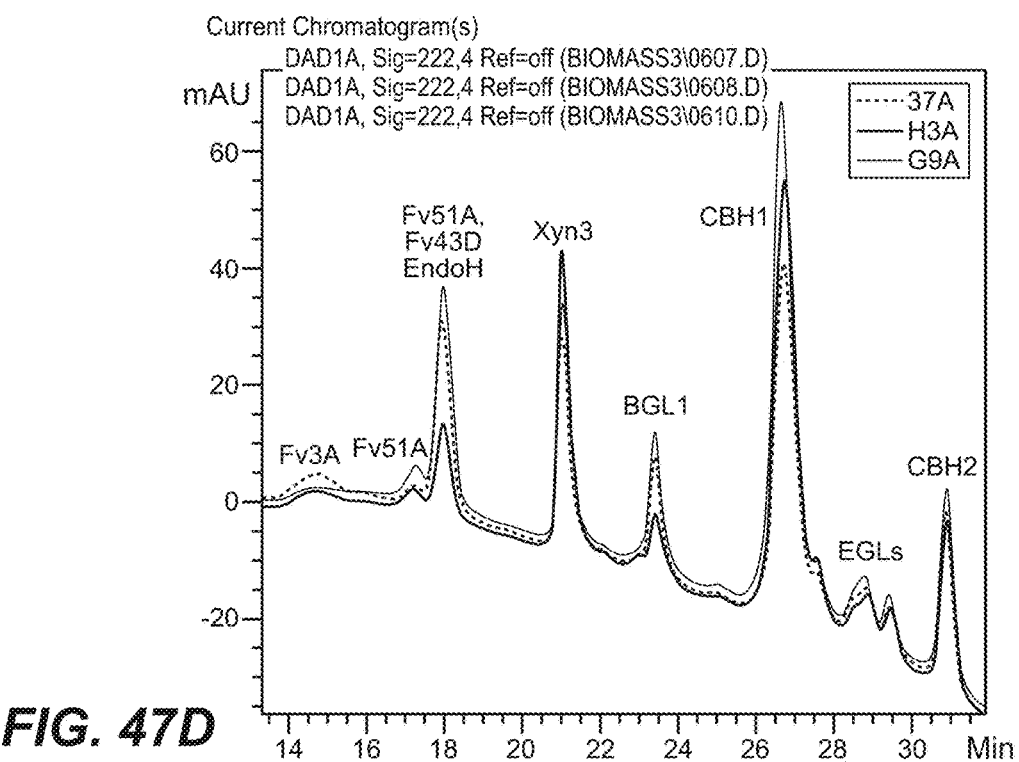

FIGS. 47A-47D: Glucan (FIG. 47A) and xylan (FIG. 47B) conversions to monomer sugars by secreted enzyme fermentation broths from *T. reesei* integrated expression strains. The 3-day sample was analyzed for the extent of conversion of glucan and xylan to both monomer and soluble oligomer products (FIG. 47C). FIG. 47D shows a chromatographic comparison of enzyme product from three *T. reesei* integrated expression strains. The experimental conditions are described in Example 1. Protein ratios differ across transformants and can be quantified as a percentage of the total integrated peak area. The "EGLs" marks the summed area of endoglucanase peaks. EndoH was added to the protein sample in small amounts as a reagent for HPLC analysis.

Figure 48A:
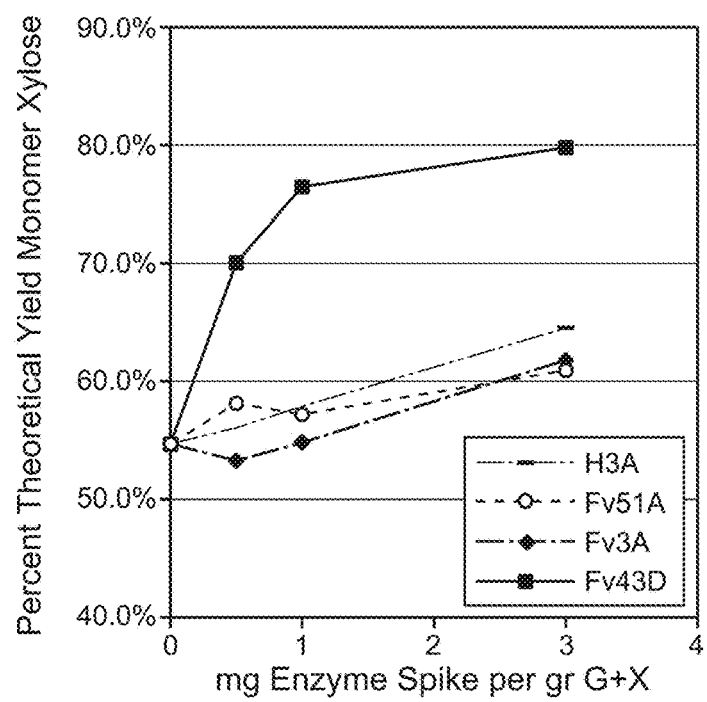
Figure 48B:
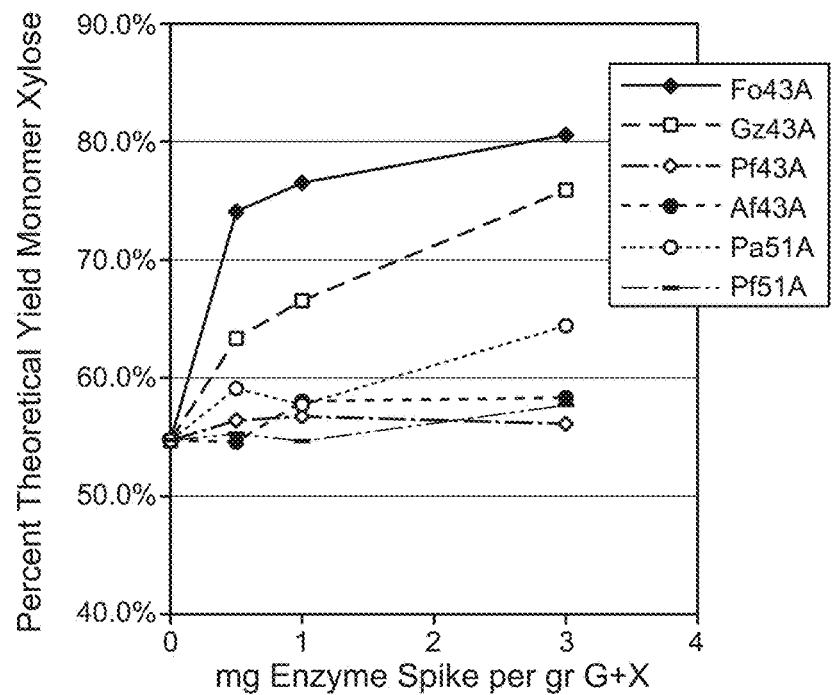

FIGS. 48A-48B: Saccharification increased in xylose monomer yield in response to hemicellulase addition to the enzyme composition produced by an integrated strain at 7 mg total protein per gram glucan+xylan in ammonia pretreated cob. FIG. 48A: Constituent *Fusarium verticillioides* hemicellulases in the enzyme composition produced by the integrated strain. FIG. 48B: Hemicellulases from other fungi.

Figure 49A:
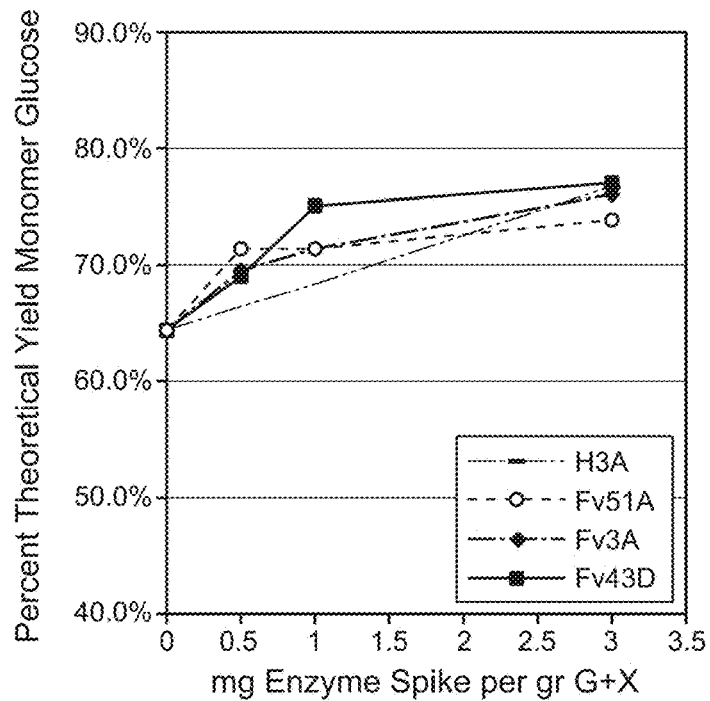
Figure 49B:
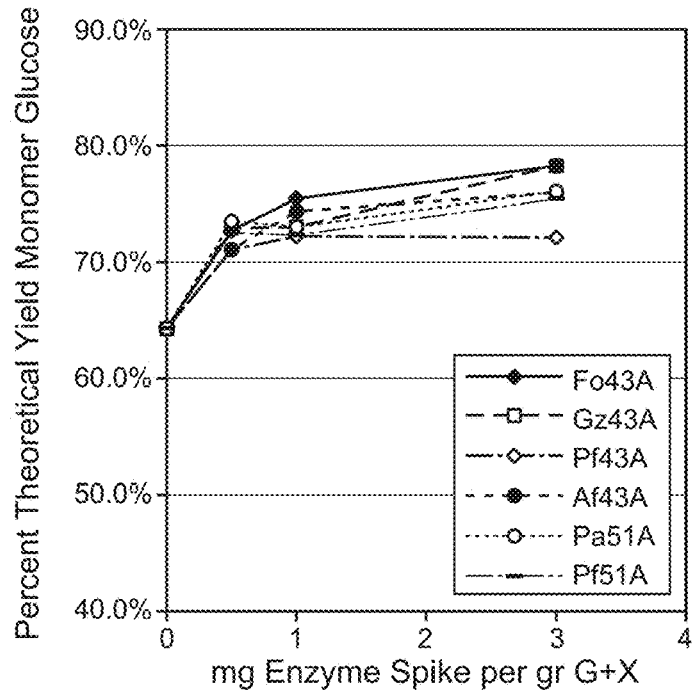

FIGS. 49A-49B: Saccharification increased in glucose monomer yield in response to hemicellulase addition to the enzyme composition produced by an integrated strain at 7 mg total protein per gram glucan+xylan in ammonia pretreated cob. FIG. 49A: Constituent *Fusarium verticillioides* hemicellulases in the enzyme composition produced by the integrated strain. FIG. 49B: Hemicellulases from other fungi.

Figure 50A:
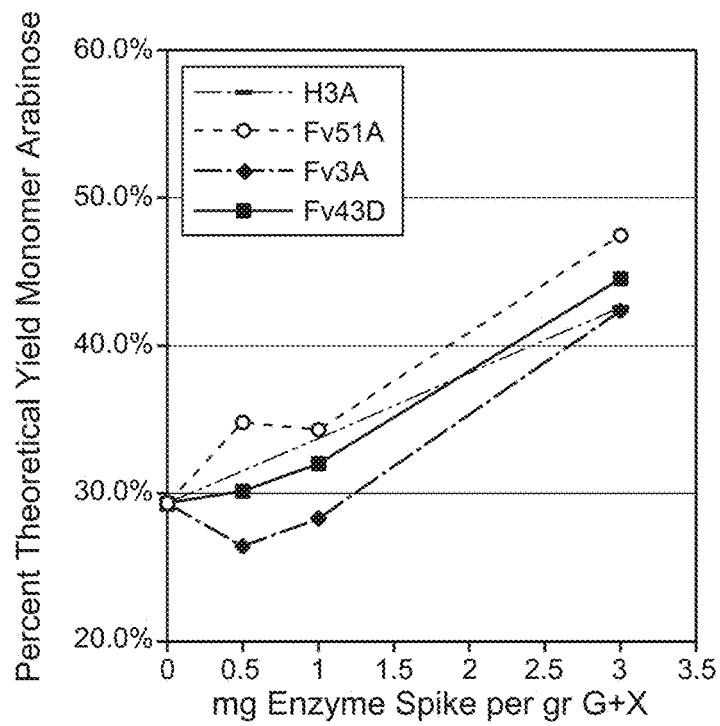
Figure 50B:
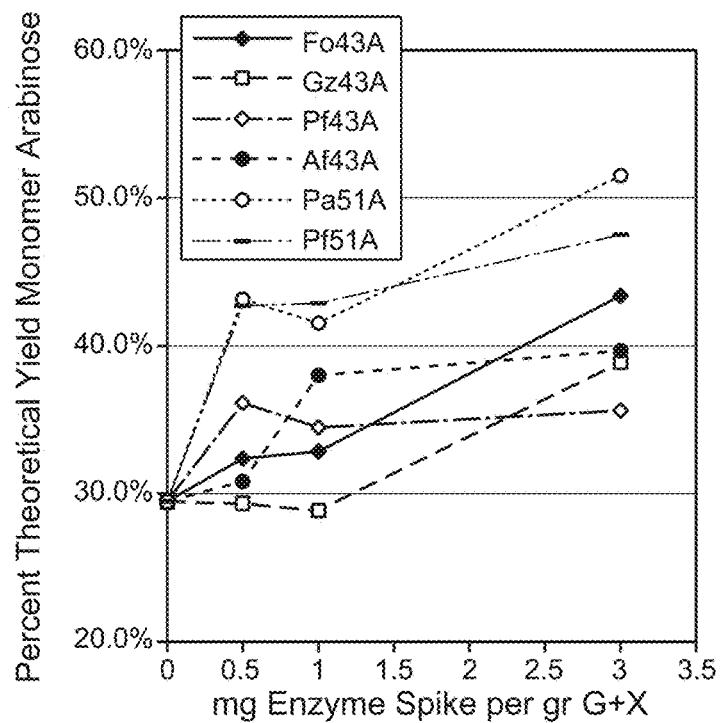

FIGS. 50A-50B: Saccharification increased in arabinose monomer yield in response to hemicellulase addition to the enzyme composition produced by an integrated strain at 7 mg total protein per gram glucan+xylan in ammonia pretreated cob. FIG. 50A: Constituent *Fusarium verticillioides* hemicellulases in the enzyme composition produced by an integrated strain. FIG. 50B: Hemicellulases from other fungi.

Figure 51:
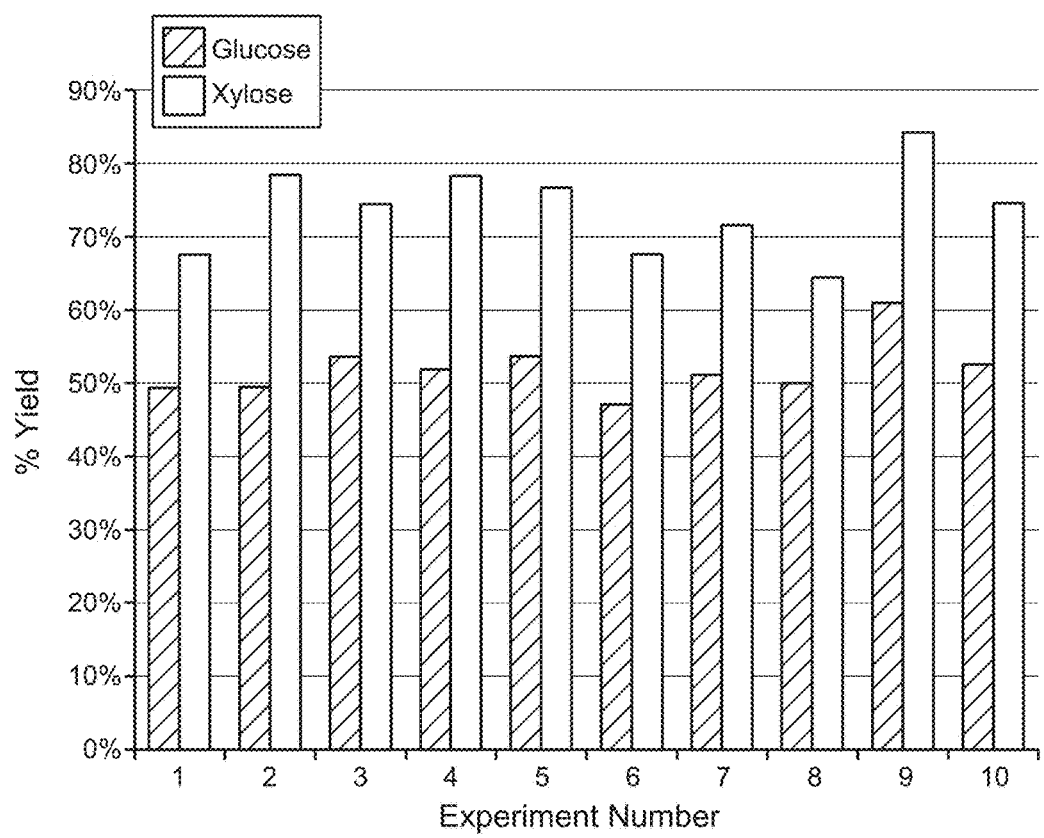

FIG. 51: A graphical presentation of the saccharification performance across pretreatment conditions. The X-axis corresponds to the experimental results listed in Table 12. Yields are calculated based on the theoretical amounts of glucan or xylan available in the raw switchgrass. All yields are based on monomeric sugars released after 3 days of saccharification with the enzyme cocktail.

Figure 52:
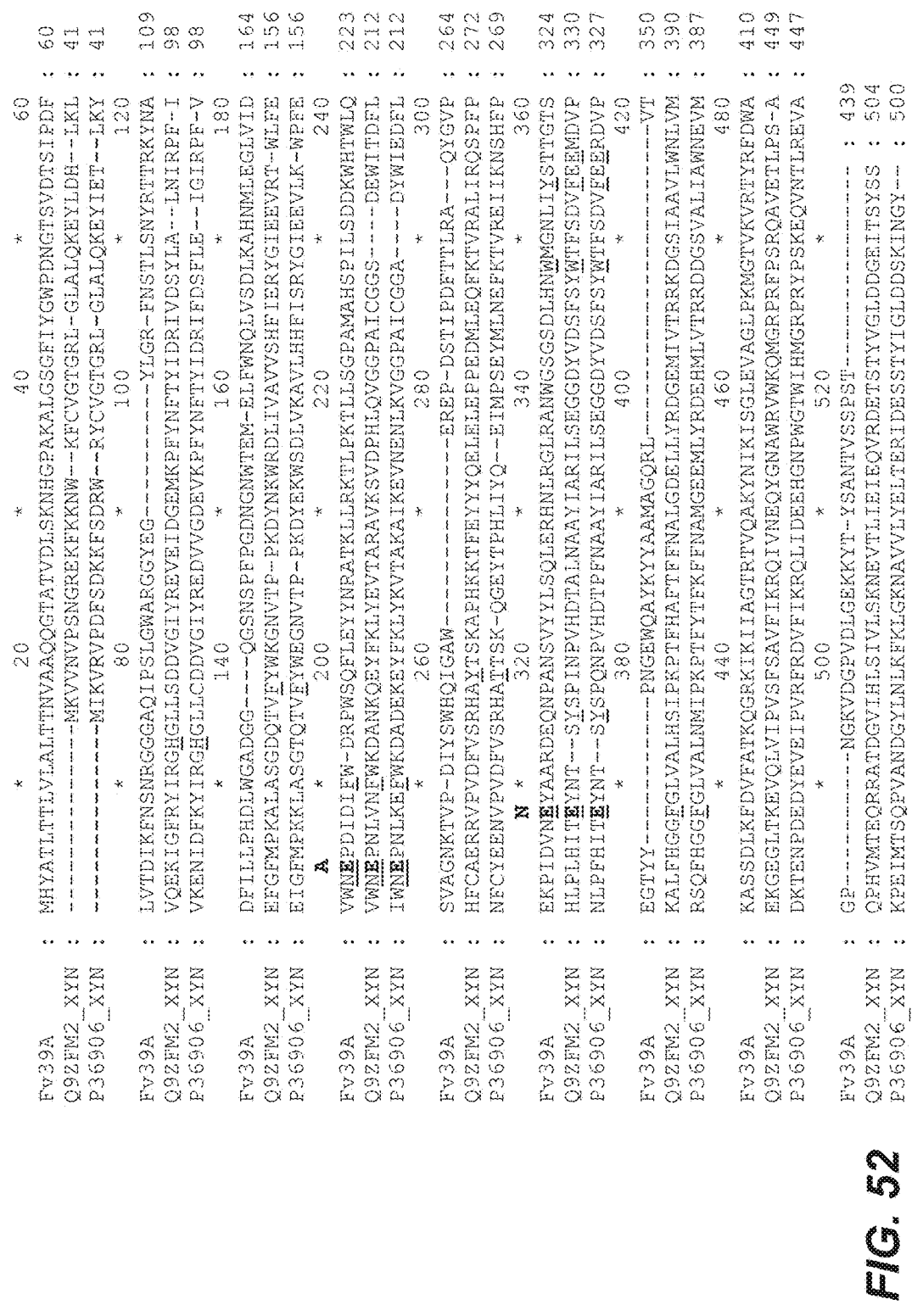

FIG. 52: Amino acid sequence alignment of a number of GH39 β-xylosidases. Underlined residues in bold face are the predicted catalytic general acid-base residue (marked with "A" above the alignment) and catalytic nucleophile residue (marked with "N" above the alignment). Underlined residues in normal face in the bottom two sequences are within 4 angstroms of the substrate in the active sites of the respective 3D structures (pdb: 1 uhv and 2bs9, respectively). Underlined residues in the Fv39A sequence are predicted to be within 4 angstroms of a bound substrate in the active site.

FIGS. 53A-53C: Amino acid sequence alignment of a number of GH43 family hydrolases. Amino acid residues highly conserved among members of the family are shown underlined and in bold face.

FIG. 54: Amino acid sequence alignment of a number of GH51 family enzymes. Amino acid residues highly conserved among members of the family are shown underlined and in bold type.

FIGS. 55A-55B: Amino acid sequence alignments of a number of GH10 and GH11 family endoxylanases. FIG. 55A; Alignment of GH10 family xylanases. Underlined residues in bold face are the catalytic nucleophile residues (marked with "N" above the alignment). FIG. 55B; Alignment of GH11 family xylanases. Underlined residues in bold face are the catalytic nucleophile residues and general acid base residues (marked with "N" and "A", respectively, above the alignment).

Figure 56A:
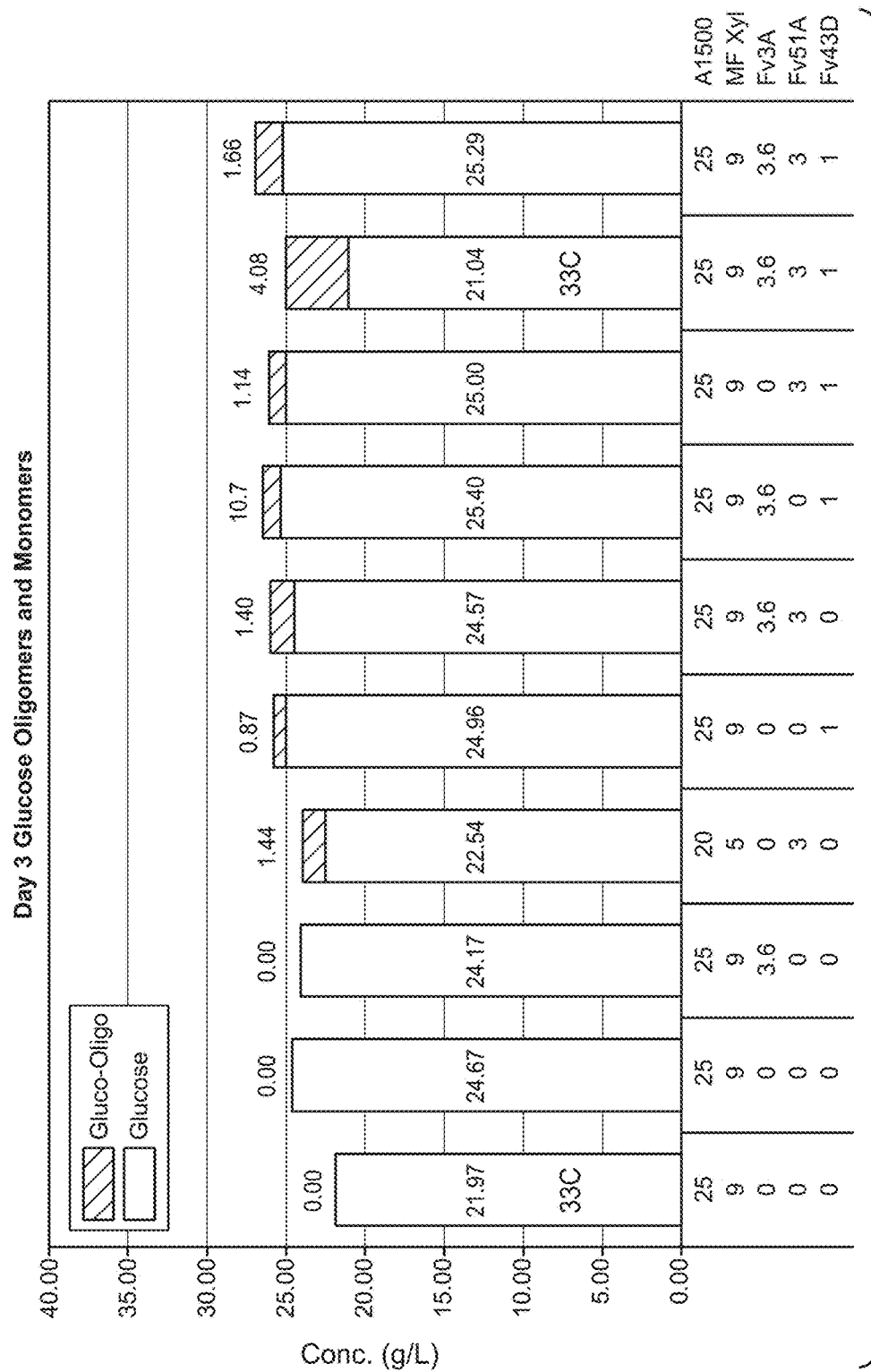
Figure 56B:
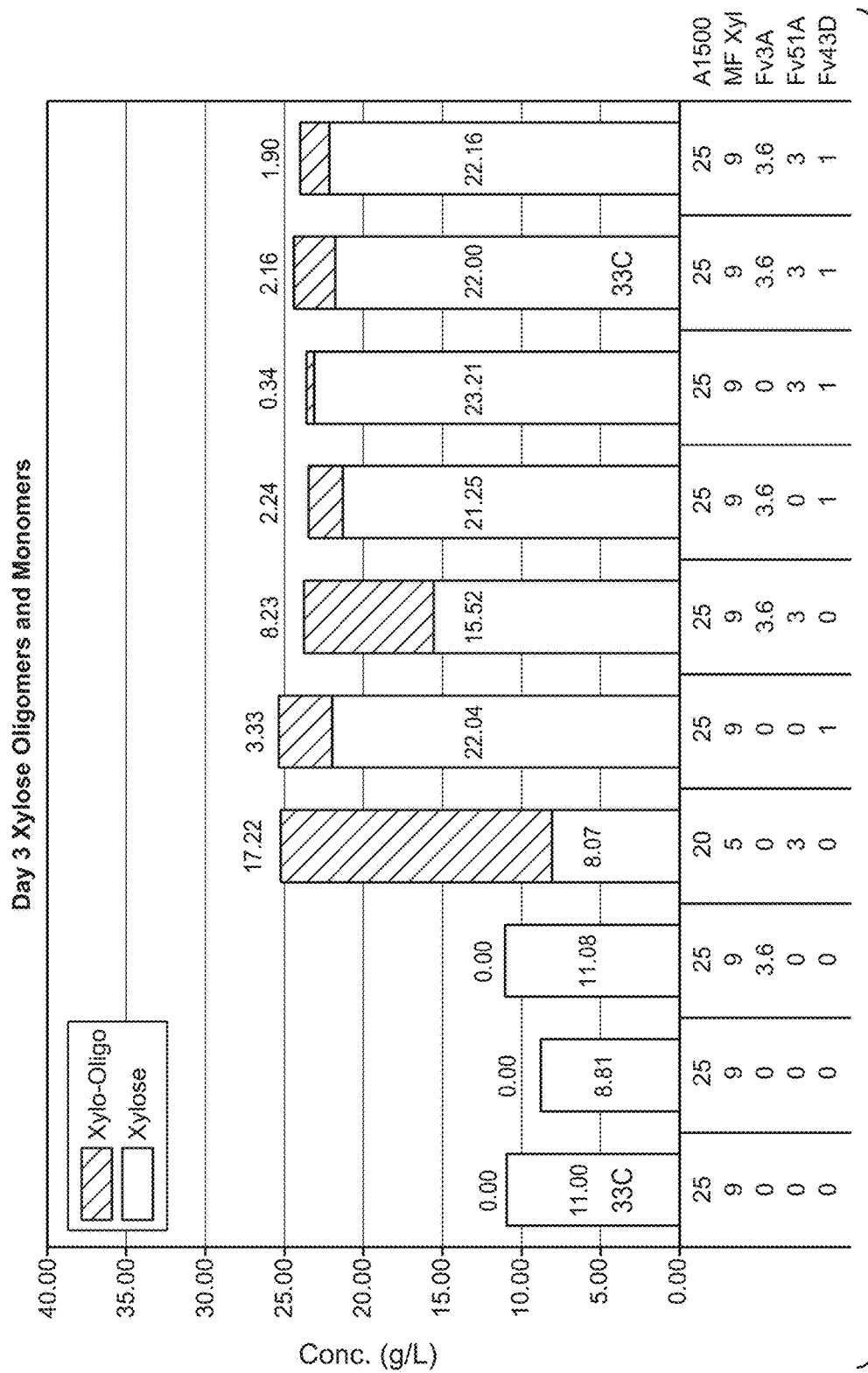

FIGS. 56A-56B: Saccharification of dilute ammonia pretreated switchgrass with various enzyme blends/compositions; FIG. 56A: glucan conversion; FIG. 56B: xylan conversion. The numbers below the figures on the x-axis refer to the amount of total mg of each protein in a given blend/composition per g of glucan or xylan, as described in Example 13.

Figure 57A:
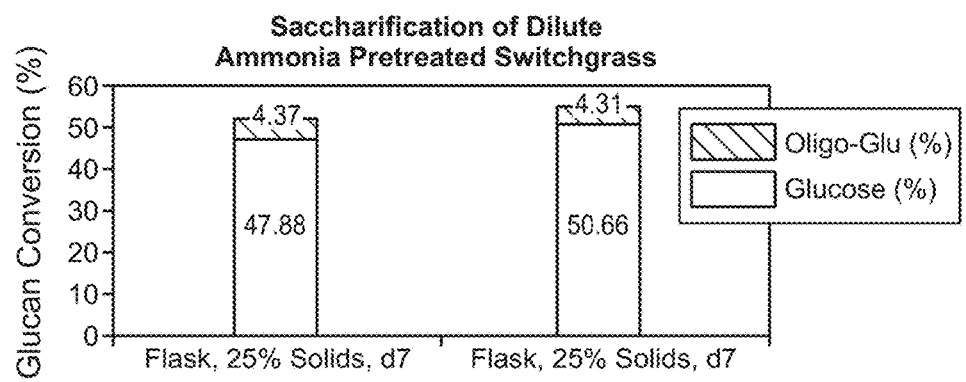
Figure 57B:
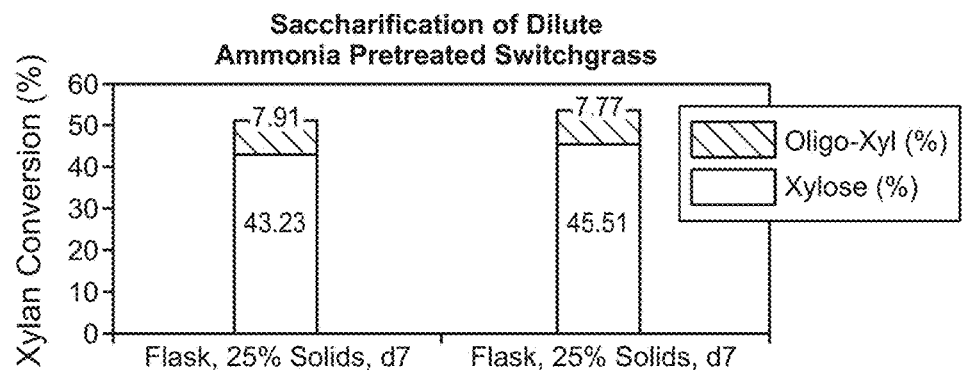

FIGS. 57A-57B: Saccharification of dilute ammonia pretreated switchgrass with an enzyme composition produced by integrated strain H3A; FIG. 57A: glucan conversion; FIG. 57B: xylan conversion. Experimental conditions are described in Example 14.

Figure 58A:
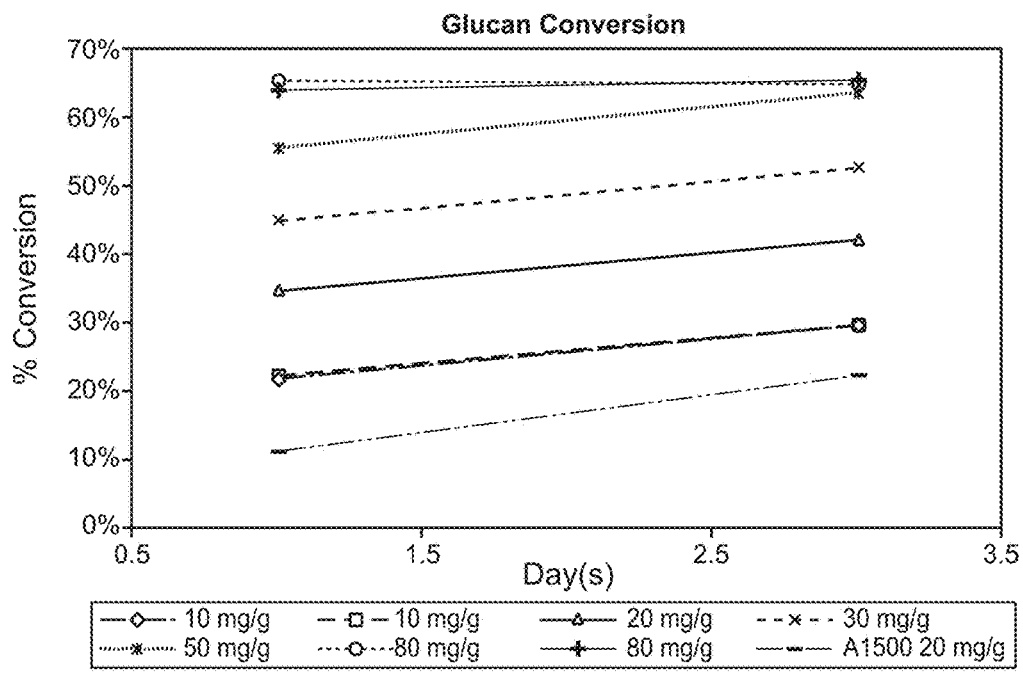
Figure 58B:
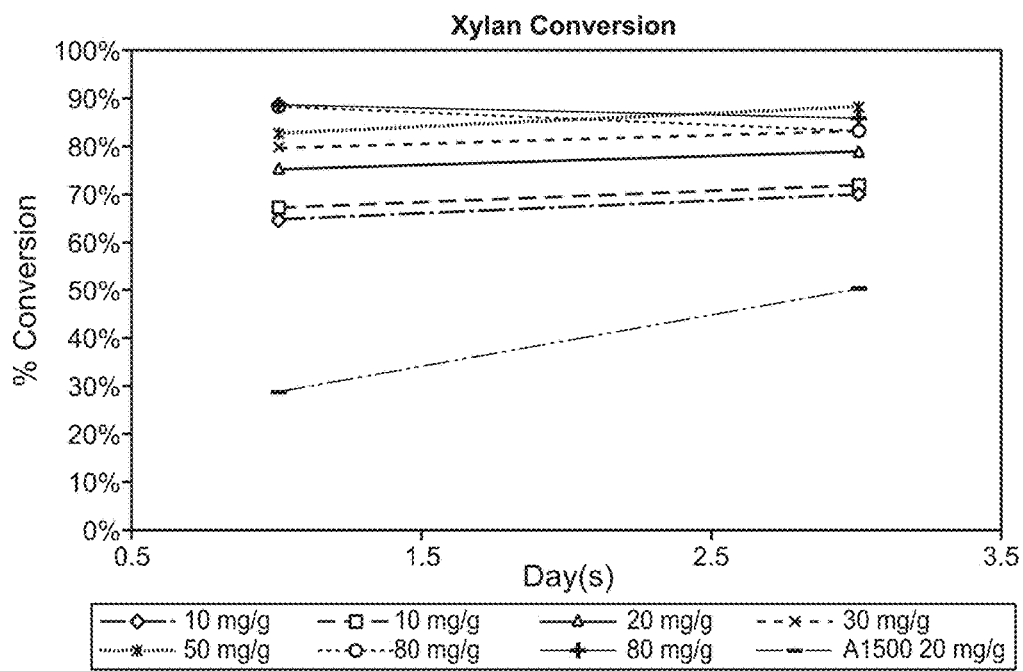
Figure 58C:
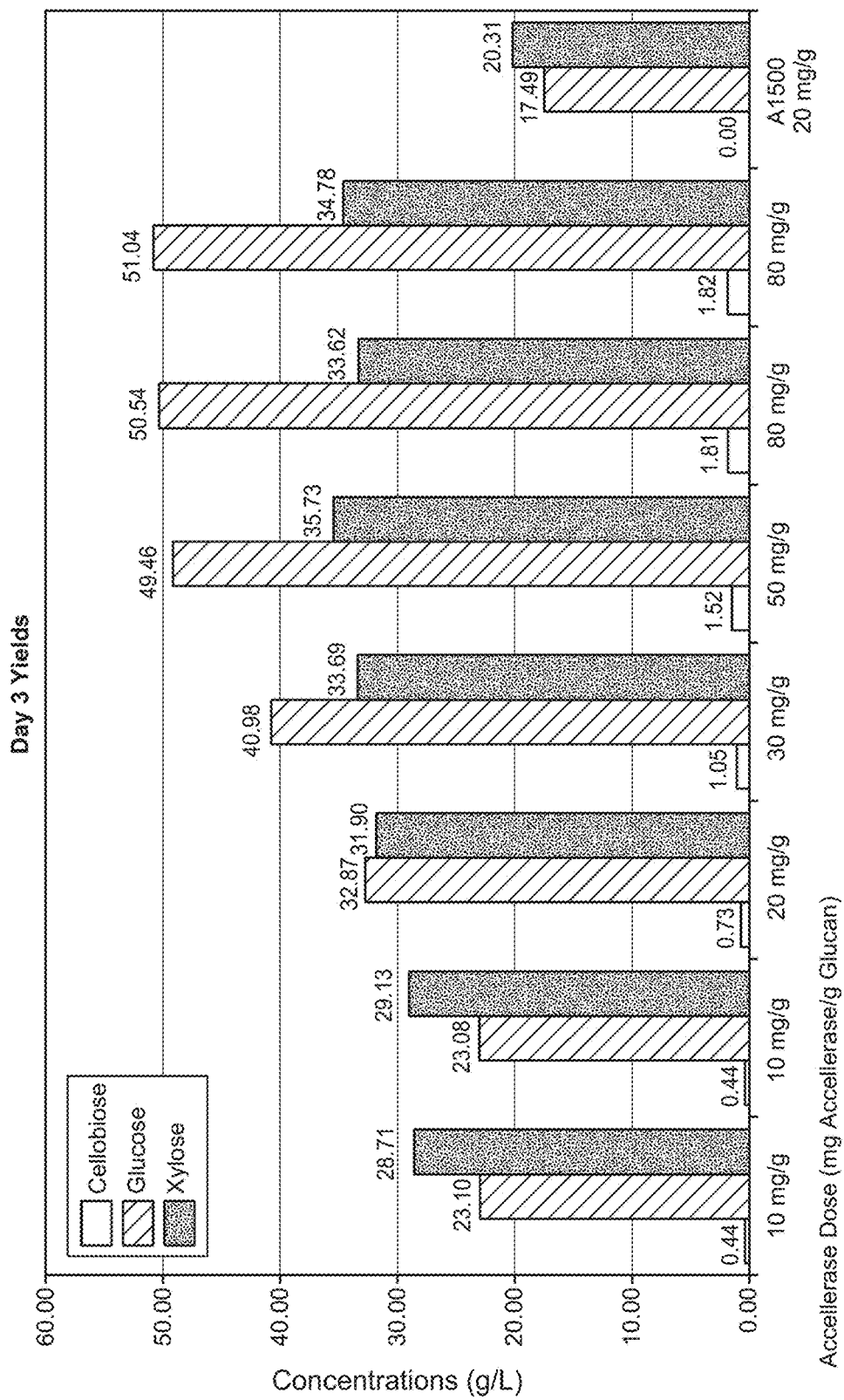

FIGS. 58A-58C: Saccharification of steam-expanded sugarcane bagasse with an enzyme composition produced by integrated strain H3A at different enzyme doses; FIG. 58A: glucan conversion; FIG. 58B: xylan conversion; FIG. 58C: 3-day glucan and xylan conversions. Experimental conditions are described in Example 17.

Figure 59A:
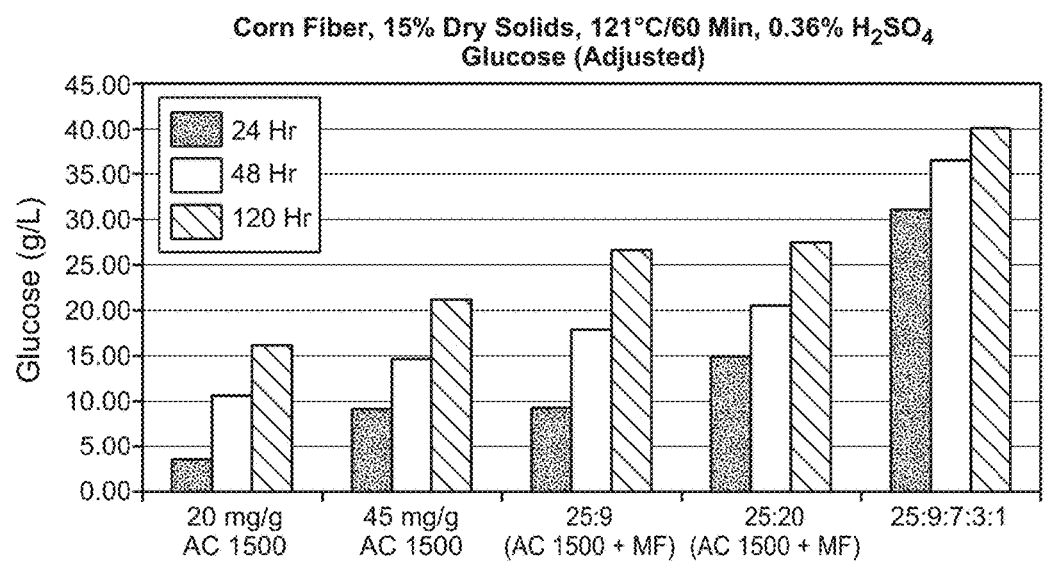
Figure 59B:
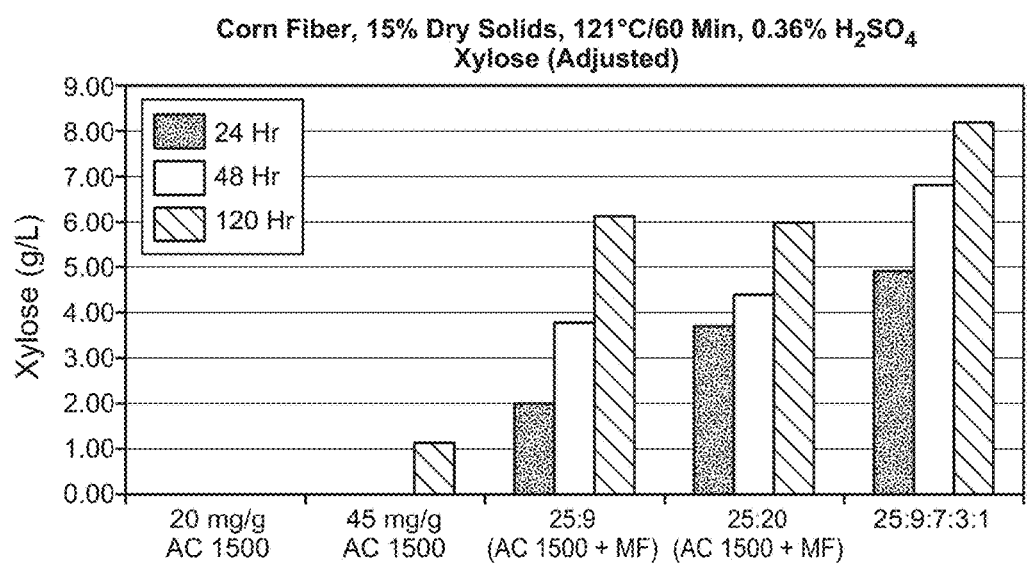
Figure 59C:
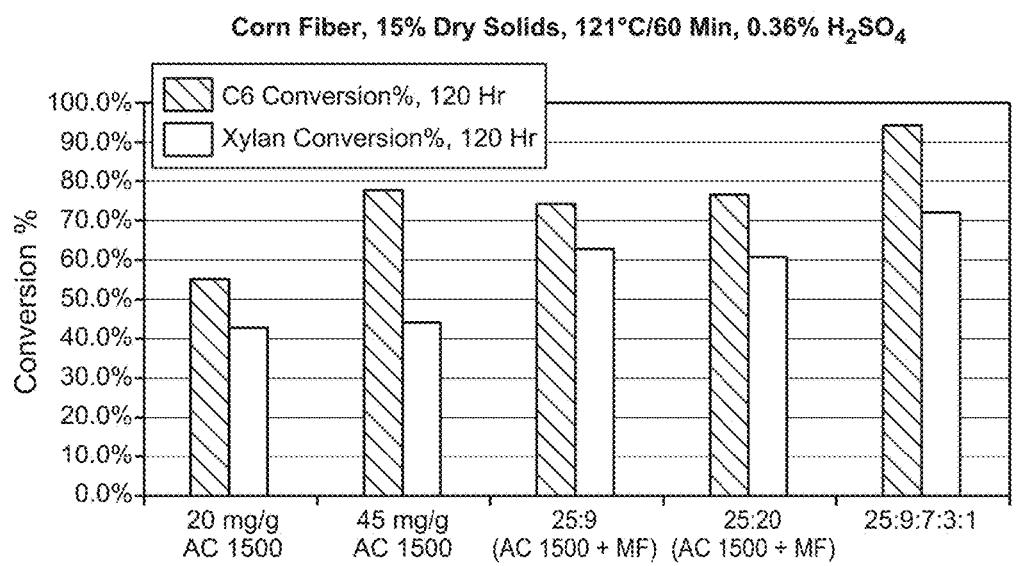

FIGS. 59A-59C: Saccharification of dilute-acid pretreated corn fiber with various enzymes or enzyme blends; FIG. 59A: glucan conversion; FIG. 59B: xylan conversion: FIG. 59C: 5-day glucan and xylan conversions. The adjusted sugar (glucose or xylose) reflected the sugar being produced from the enzymatic step minus the starting sugar levels. Ratios shown along the x-axis represent the enzyme dose in mg of total protein per gram of cellulose. Experimental conditions are described in Example 18.

FIGS. 60A-60B: FIG. 60A: Deduced cDNA for Pa51A (SEQ ID NO:46). FIG. 60B: Codon optimized cDNA for Pa51A (SEQ ID NO:47).

FIG. 61: Coding sequence for a construct comprising a CBH1 signal sequence (underlined) upstream of genomic DNA encoding mature Gz43A (SEQ ID NO:48).

FIG. 62: Coding sequence for a construct comprising a CBH1 signal sequence (underlined) upstream of genomic DNA encoding mature Fo43A (SEQ ID NO:49).

FIG. 63: Codon optimized coding sequence for a construct comprising a CBH1 signal sequence (underlined) upstream of codon optimized DNA encoding mature Pf51A (SEQ ID NO:50).

FIGS. 64A-64B: Amino acid sequence alignment of a number of GH3 family hydrolases. Amino acid residues highly conserved among members of the family are shown underlined and in bold face type. The box marks the predicted catalytic residue with flanking residues predicted to be involved in substrate binding.

FIG. 65: Amino acid sequence alignment of two representative Fusarium GH30 family hydrolases. Amino acid residues that are conserved among members of the family are shown underlined and in bold face type.

FIG. 66 and FIG. 67: Provide a summary of the sequence indentifiers used in the present disclosure for glycosyl hydrolase enzymes:

FIG. 68: Provides accession numbers for additional glycosyl hydrolase enzymes referred to in the Examples.

FIG. 69: Activity of expressed proteins on synthetic substrates pNPA and pNPX (as defined in Section 7.1.6 below) in terms relative to the Trichoderma reesei Quad delete host background activity. The Quad delete host background (or "XQuad") is defined as the activity of the expressed protein(s) in the Quad delete strain divided by the activity of the Quad delete background strain without the expressed protein(s). For example, a value of >1 indicates that the expressed protein have an activity greater than that of the background.

FIG. 70: Xylanase activity of purified candidate endo-xylanases with birchwood xylan, incubated at 50° C. pH 5.

FIG. 71: Percent conversion of cob arabinoxylan oligomers to monomer products based on total sugar available as determined by acid hydrolysis. See, Example 4.

FIG. 72A and FIG. 72B: Experiment results (as described in Example 7) defining the level of hemicellulase activity for hydrolyzing treated corncob to monomer sugars. The column entitled "run #" indicates the randomized experimental order. The column entitled "trial 190 " indicates the standard experimental design order. The column entitled "Quad" indicates fraction of the total protein that is from the culture supernatant for a growth of the Quad deleted T. reesei strain. The column entitled "Xyn3" indicates fraction of the total protein that is Trichoderma reesei Xyn3. The column entitled "Fv43D" indicates fraction of the total protein that is Fv43D. The column entitled "Fy51A" indicates fraction of the total protein that is Fv51A. The column entitled "Fv43A" indicates fraction of the total protein that is Fv43A. The column entitled "Fv43V" indicates fraction of the total protein that is Fv43B. The column entitled "loading (ug/mg carbo)" indicates the protein loaded into the saccharification reaction in units of micrograms of protein per milligram of carbohydrate. The column entitled "Xyl mg/mL, Glu mg/mL, Arab mg/mL and G+X+A mg/mL" indicate the concentration of xylose, glucose, arabinose, and the combination of those three sugar products that is detected at the end of the saccharification reaction. The columns entitled "Xyl %theor, Glu %theor, and Arab %theor" indicate the percent of theoretical yield of xylose, glucose, and arabinose reached at the end of the saccharification reaction.

FIG. 73: Calculated ratios of the seven enzymatic components for predicted maximal yield of glucose, xylose and arabinose from hydrolysis of corncob. The column "loading total mg/gr carb" indicates the total enzyme dose at wich the predictions are calculated. The rows entitled "Total mg/ml G+X+A, % Yield Glucose, % Yield Xylose, and % Yield Arabinose" indicate the response for which the optimum has been calculated. The column entitled "r2 data fit to model (includes both loadings)" indicates the r-squared statistical parameter for the model fit to data presented in Table 5. The columns entitled "fraction Accellerase, fraction Quad del sup, fraction purified Trichoderma reesei Xyn3, fraction purified Fv43D, fraction purified Fv51A, fraction purified Fv43A, and fraction purified Fv43B" indicate the fraction of that component that is calcuated to be optimal by the model fitted to the data in Table 5.

FIG. 74: Refinement of enzyme loadings for maximal hydrolytic conversion of corncob using blends including FV3A and Fv43D enzymes in 1.06 g. 14% dry solids pretreated cob reactions. The conditions for saccharification were as described in Example 7. Columns marked with enzyme names indicate the mg of each of the listed enzyme per gram of glucan or xylan used.

FIG. 75: Refinement of enzyme loadings for maximal conversion of corncob using blends containing Fv51A as the only L-α-arabinofuranosidase in 1.06 gr, 14% dry solids pretreated cob reactions. The conditions used for saccharification were as described in Example 7. Columns marked with enzyme names indicate the mg of each of the listed enzymes per gram of glucan or xylan used. Columns marked with carbohydrates indicate the mg per mL of each carbohydrate product producted based on measurements made with size exclusion chromatography. The >dp2 column includes all oligomers larger than a disaccharide.

FIG. 76: Sugar yields obtained from mixes A, B, C of purified hemicellulases tested in 1.06 g, 14% dry solids pretreated cob reactions. The conditions used for saccharification were as described in Example 7. Mix A: 6 mg Trichoderma reesei Xyn3, 4 mg Fv3A, 1 mg Fv51A per gram xylan. Mix B: 6 mg Trichoderma reesei Xyn3, 1 mg Fv43D, 3 mg Fv43A, 3 mg Fv43B per gram xylan, Mix C: 6 mg Trichoderma reesei Xyn3, 3 mg Fv3A, 1 mg Fv43D, 1 mg Fv51A per gram xylan. Columns marked with monomer sugars indicate the % yield of each of the listed monomer.

FIG. 77: Sugar yields from treatment of hemicellulose preparations made from corncob, sorghum, switchgrass and sugar cane bagasse by hemicellulase mixes A, B, C. The reations were run at 100-uL scale in 50 mM pH 5.0 Sodium Acetate buffer for 6 h at 48° C as described in Example 8. The % yield for each monomer sugar is shown.

FIG. 78: Concentration of the majority enzymes expressed by various T. reesei integrated expression strains (designated H3A, 39A, 69A, A10A, G6A, 102, 44A, 11A, G9A) as determined by percent of the integrated HPLC area.

FIG. 79: List of switchgrass pretreatment parameters and saccharification results from the various pretreatments.

FIG. 80: Saccharification results of a hardwood pulp with the enzyme composition produced by a T. reesei integrated strain, H3A, in reactions with different amounts of solids, enzymes, and incubation time.

FIG. 81: Saccharification of a hardwood pulp with the enzyme composition produced by an integrated strain H3A over a temperature range and a pH range.

Signal sequences listed below and in the figures were predicted. The predictions were made with the SignalP algorithm (available at www.cbs.dtu.dk). Domain predictions were made based on one or more of the Pfam, SMART, or NCBI databases.

6. DETAILED DESCRIPTION

Enzymes have traditionally been classified by substrate specificity and reaction products. In the pre-genomic era, function was regarded as the most amenable (andperhaps most useful) basis for comparing enzymes and assays for various enzymatic activities have been well-developed for many years, resulting in the familiar EC classification scheme. Cellulases and other glycosyl hydrolases, which act upon glycosidic bonds between two carbohydrate moieties (or a carbohydrate and non-carbohydrate moiety—as occurs in nitrophenol-glycoside derivatives) are, under this classification scheme, designated as EC 3.2.1.-, with the final number indicating the exact type of bond cleaved. For example, according to this scheme an endo-acting cellulase (1,4-β-endoglucanase) is designated EC 3.2.1.4.

With the advent of widespread genome sequencing projects, sequencing data have facilitated analyses and comparison of related genes and proteins. Additionally, a growing number of enzymes capable of acting on carbohydrate moieties (i.e., carbohydrases) have been crystallized and their 3-D structures solved. Such analyses have identified discreet families of enzymes with related sequence, which contain conserved three-dimensional folds that can be predicted based on their amino acid sequence. Further, it has been shown that enzymes with the same or similar three-dimensional folds exhibit the same or similar stereospecificity of hydrolysis, even when catalyzing different reactions (Henrissat et al., 1998, FEBS Lett 425(2): 352-4; Coutinho and Henrissat, 1999, in Genetics, biochemistry and ecology of cellulose degradation. T. Kimura. Tokyo, Uni Publishers Co: 15-23).

These findings form the basis of a sequence-based classification of carbohydrase modules, which is available in the form of an internet database, the Carbohydrate-Active enZYme server (CAZy), available at afmb.cnrs-mrs.fr/CAZY/index.html (Carbohydrate-active enzymes: an integrated database approach. See Cantarel et al., 2009, Nucleic Acids Res. 37 (Database issue):D233-38).

CAZy defines four major classes of carbohydrases distinguishable by the type of reaction catalyzed: Glycosyl Hydrolases (GH's), Glycosyltransferases (GT's), Polysaccharide Lyases (PL's), and Carbohydrate Esterases (CE's). The enzymes of the disclosure are glycosyl hydrolases. GH's are a group of enzymes that hydrolyze the glycosidic bond between two or more carbohydrates, or between a carbohydrate and a non-carbohydrate moiety. A classification system for glycosyl hydrolases, grouped by sequence similarity, has led to the definition of over 85 different families. This classification is available on the CAZy web site.

The enzymes of the disclosure belong, inter alia, to the glycosyl hydrolase families 3, 10, 11, 30, 39, 43, and/or 51.

Glycoside hydrolase family 3 ("GH3") enzymes include, e.g., β-glucosidase (EC:3.2.1.21); β-xylosidase (EC: 3.2.1.37); N-acetyl β-glucosaminidase (EC:3.2.1.52); glucan β-1,3-glucosidase (EC:3.2.1.58); cellodextrinase (EC: 3.2.1.74); exo-1,3-1,4-glucanase (EC:3.2.1); and β-galactosidase (EC 3.2.1.23). For example, GH3 enzymes can be those that have β-glucosidase, β-xylosidase, N-acetyl β-glucosaminidase, glucan β-1,3-glucosidase, cellodextrinase, exo-1,3-1,4-glucanase, and/or β-galactosidase activity. Generally, GH3 enzymes are globular proteins and can consist of two or more subdomains. A catalytic residue has been identified as an aspartate residue that, in β-glucosidases, located in the N-terminal third of the peptide and sits within the amino acid fragment SDW (Li et al. 2001, Biochem. J. 355:835-840). The corresponding sequence in Bgl1 from $T.$ reesei is T266D267W268 (counting from the methionine at the starting position), with the catalytic residue aspartate being the D267. The hydroxyl/aspartate sequence is also conserved in the GH3 β-xylosidases tested. For example, the corresponding sequence in $T.$ reesei Bxl1 is S310D311 and the corresponding sequence in Fv3A is S290D291.

Glycoside hydrolase family 39 ("GH39") enzymes have α-L-iduronidase (EC:3.2.1.76) or β-xylosidase (EC: 3.2.1.37) activity. The three-dimensional structure of two GH39 β-xylosidases, from *Thermoanaerobacterium saccharolyticum* (Uniprot Accession No. P36906) and *Geobacillus stearothermophilus* (Uniprot Accession No. Q9ZFM2), have been solved (see Yang et al. J. Mol. Biol. 2004, 335(1):155-65 and Czjzek et al., J. Mol. Biol. 2005, 353(4):838-46). The most highly conserved regions in these enzymes are located in their N-terminal sections, which have a classic (α/β)8 TIM barrel fold with the two key active site glutamic acids located at the C-terminal ends of β-strands 4 (acid/base) and 7 (nucleophile). Fv39A residues E168 and E272 are predicted to function as catalytic acid-base and nucleophile, respectively, based on a sequence alignment of the above-mentioned GH39 β-xylosidases from *Thermoanaerobacterium saccharolyticum* and *Geobacillus stearothermophilus* with Fv39A.

Glycoside hydrolase family 43 ("GH43") enzymes include, e.g., L-α-arabinofuranosidase (EC 3.2.1.55); β-xylosidase (EC 3.2.1.37); endo-arabinanase (EC 3.2.1.99); and/or galactan 1,3-β-galactosidase (EC 3.2.1.145). For example, GH43 enzymes can have L-α-arabinofuranosidase activity, β-xylosidase activity, endo-arabinanase activity, and/or galactan 1,3-β-galactosidase activity. GH43 family enzymes display a five-bladed-β-propeller-like structure. The propeller-like structure is based upon a five-fold repeat of blades composed of four-stranded β-sheets. The catalytic general base, an aspartate, the catalytic general acid, a glutamate, and an aspartate that modulates the pKa of the general base were identified through the crystal structure of *Cellvibrio japonicus* CjAbn43A, and confirmed by site-directed mutagenesis (see Nurizzo et al. Nat. Struct. Biol. 2002, 9(9) 665-8). The catalytic residues are arranged in three conserved blocks spread widely through the amino acid sequence (Pons et al. Proteins: Structure, Function and Bioinformatics, 2004, 54:424-432). Among the GH43 family enzymes tested for useful activities in biomass hydrolysis, the predicted catalytic residues are shown as the bold and underlined residues in the sequences of FIGS. 53A-53C. The crystal structure of the *Geobacillus stearothermophylus* xylosidase (Brux et al. J. Mol. Bio., 2006, 359:97-109) suggests several additional residues that may be important for substrate binding in this enzyme. Because the GH43 family enzymes tested for biomass hydrolysis had differing substrate preferences, these residues are not fully conserved in the sequences aligned in FIGS. 53A-53C. However among the xylosidases tested, several conserved residues that contribute to substrate binding, either through hydrophobic interaction or through hydrogen bonding, are conserved and are noted by single underlines in FIGS. 53A-53C.

Glycoside hydrolase family 51 ("GH51") enzymes have L-α-arabinofuranosidase (EC 3.2.1.55) and/or endoglucanase (EC 3.2.1.4) activity. High-resolution crystal structure of a GH51 L-α-arabinofuranosidase from *Geobacillus stearothermophilus* T-6 shows that the enzyme is a hexamer, with each monomer organized into two domains: an 8-barrel (β/α) and a 12-stranded β sandwich with jelly-roll topology (see Hovel et al. EMBO J. 2003, 22(19):4922-4932). It can be expected that the catalytic residues will be acidic and conserved across enzyme sequences in the family. When the amino acid sequences of Fv51A, Pf51A, and Pa51A are aligned with GH51 enzymes of more diverse sequence, 8 acidic residues remain conserved. Those are shown bold and underlined in FIG. 54.

Glycoside hydrolase family 10 ("GH10") enzymes also have an 8-barrel (β/α) structure. They hydrolyze in an endo fashion with a retaining mechanism that uses at least one acidic catalytic residue in a generally acid/base catalysis process (Pell et al., J. Biol. Chem., 2004, 279(10): 9597-9605). Crystal structures of the GH10 xylanases of *Penicillium simplicissimum* (Uniprot P56588) and *Thermoascus aurantiacus* (Uniprot P23360) complexed with substrates in the active sites have been solved (see Schmidt et al. Biochem., 1999, 38:2403-2412; and Lo Leggio et al. FEBS Lett. 2001, 509: 303-308). *Trichoderma reesei* Xyn3 residues that are important for substrate binding and catalysis can be derived from an alignment with the sequences of abovementioned GH10 xylanases from *Penicillium simplicissimum* and *Thermoascus aurantiacus* (FIG. 55A). *Trichoderma reesei* Xyn3 residue E282 is predicted to be the catalytic nucleophilic residue, whereas residues E91, N92, K95, Q97, S98, H128, W132, Q135, N175, E176, Y219, Q252, H254, W312, and/or W320 are predicted to be involved in substrate binding and/or catalysis.

Glycoside hydrolase family 11 ("GH11") enzymes have a β-jelly roll structure. They hydrolyze in an endo fashion with a retaining mechanism that uses at least one acidic catalytic residue in a generally acid/base catalysis process. Several other residues spread throughout their structure may contribute to stabilizing the xylose units in the substrate neighboring the pair of xylose monomers that are cleaved by hydrolysis. Three GH11 family endoxylanases were tested and their sequences are aligned in FIG. 55B. E118 (or E86 in mature *T. reesei* Xyn2) and E209 (or E177 in mature *T. reesei* Xyn2) have been identified as catalytic nucleophile and general/acid base residues in *Trichoderma reesei* Xyn2, respectively (see Havukainen et al. Biochem., 1996, 35:9617-24).

Glycoside hydrolase family 30 ("GH30") enzymes are retaining enzymes having glucosylceramidase (EC 3.2.1.45); β-1,6-glucanase (EC 3.2.1.75); β-xylosidase (EC 3.2.1.37); β-glucosidase (3.2.1.21) activity. The first GH30 crystal structure was the Gaucher disease-related human β-glucocerebrosidase solved by Grabowski, Gatt and Horowitz (Crit Rev Biochem Mol Biol 1990; 25(6) 385-414). GH30 have an (α/β)$_8$ TIM barrel fold with the two key active site glutamic acids located at the C-terminal ends of β-strands 4 (acid/base) and 7 (nucleophile) (Henrissat B, et al. Proc Natl Acad Sci USA, 92(15):7090-4, 1995; Jordan et al., Applied Microbiol Biotechnol, 86:1647, 2010). Glutamate 162 of Fv30A is conserved in 14 of 14 aligned GH30 proteins (13 bacterial proteins and one endo-b-xylanase from the fungi Biospora accession no. ADG62369) and glutamate 250 of Fv30A is conserved in 10 of the same 14, is an aspartate in another three and non-acidic in one. There are other moderately conserved acidic residues but no others are as widely conserved.

6.1 Polypeptides of the Disclosure

The disclosure provides isolated, synthetic or recombinant polypeptides comprising an amino acid sequence having at least about 80%, e.g., at least about 81%, 82%, 83%, 84%, 85%, 86%, 87%, 88%, 89%, 90%, 91%, 92%, 93%, 94%, 95%, 96%, 97%, 98%, 99%, or complete (100%) sequence identity to a polypeptide of SEQ ID NO:2, 4, 6, 8, 10, 12, 14, 16, 18, 20, 22, 24, 26, 28, 30, 32, 34, 36, 38, 40, 42, 43, 44, or 45, over a region of at least about 10, e.g., at least about 15, 20, 25, 30, 35, 40, 45, 50, 55, 60, 65, 70, 75, 80, 85, 90, 95, 100, 125, 150, 175, 200, 225, 250, 275, 300, 325, or 350 residues, or over the full length of the immature polypeptide, the full length mature polypeptide, the full length of the conserved domain, and/or the full length CBM. The conserved domain can be a predicted catalytic domain ("CD"). Exemplary polypeptides also include fragments of at least about 10, e.g., at least about 15, 20, 25, 30, 35, 40, 45, 50, 75, 80, 85, 90, 95, 100, 150, 200, 250, 300, 350, 400, 450, 500, 550, or 600 residues in length. The fragments can comprise a conserved domain and/or a CBM. Where a fragment comprises a conserved domain and a CBM of an enzyme, the fragment optionally includes a linker separating the two. The linker can be a native linker or a heterologous linker It is contemplated that the polypeptides of the disclosure can be encoded by a nucleic acid sequence having at least about 85%, about 86%, about 87%, about 88%, about 89%, or about 90% sequence identity to SEQ ID NO:1, 3, 5, 7, 9, 11, 13, 15, 17, 19, 21, 23, 25, 27, 29, 31, 33, 35, 37, 39, or 41, or by a nucleic acid sequence capable of hybridizing under high stringency conditions to a complement of SEQ ID NO:1, 3, 5, 7, 9, 11, 13, 15, 17, 19, 21, 23, 25, 27, 29, 31, 33, 35, 37, 39, or 41, or to a fragment thereof. Exemplary nucleic acids of the disclosure are described in Section 6.2 below.

The polypeptides of the disclosure include proteins having an amino acid sequence with at least 85%, e.g., at least 86%, 87%, 88%, 89%, 90%, 91%, 92%, 93%, 94%, 95%, 96%, 97%, 98%, or 99% sequence identity to at least 50 contiguous amino acid residues of the glycosyl hydrolase sequences of SEQ ID NO:2, 4, 6, 8, 10, 12, 14, 16, 18, 20, 22, 24, 26, 28, 30, 32, 34, 36, 38, 40, 42, 43, 44, or 45. For example, a polypeptide of the disclosure can include amino acid sequences having at least 85%, e.g., at least 86%, 87%, 88%, 89%, 90%, 91%, 92%, 93%, 94%, 95%, 96%, 97%, 98%, or 99% sequence identity to at least 10, e.g., at least 11, 12, 13, 14, 15, 20, 25, 30, 40, 50, 75, 100, 125, 150, 175, 200, 250, 300, or 350 contiguous amino acid residues of the glycosyl hydrolase sequences of SEQ ID NO:2, 4, 6, 8, 10, 12, 14, 16, 18, 20, 22, 24, 26, 28, 30, 32, 34, 36, 38, 40, 42, 43, 44, or 45. The contiguous amino acid sequence corresponds to the conserved domain and/or the CBM and/or the signal sequence.

Any of the amino acid sequences described herein can be produced together or in conjunction with at least 1, e.g., at least 2, 3, 5, 10, or 20 heterologous amino acids flanking each of the C- and/or N-terminal ends of the specified amino acid sequence, and or deletions of at least 1, e.g., at least 2, 3, 5, 10, or 20 amino acids from the C- and/or N-terminal ends of an enzyme of the disclosure.

Other variations also are within the scope of this disclosure. For example, one or more amino acid residues can be modified to increase or decrease the pI of an enzyme. The change of pI value can be achieved by removing a glutamate residue or substituting it with another amino acid residue.

The disclosure specifically provides an Fv3A, a Pf43A, an Fv43E, an Fv39A, an Fv43A, an Fv43B, a Pa51A, a Gz43A, an Fo43A, an Af43A, a Pf51A, an AfuXyn2, an AfuXyn5, a Fv43D, a Pf43B, Fv43B, a Fv51A, a *Trichoderma reesei* Xyn3, a *Trichoderma reesei* Xyn2, a *Trichoderma reesei* Bxl1, and/or a *Trichoderma reesei* Bgl1 polypeptide. A combination of one or more of these enzymes is suitably present in the enzyme blend/composition of the invention, for example, one that is non-naturally occurring.

Fv3A:

The amino acid sequence of Fv3A (SEQ ID NO:2) is shown in FIGS. 1B, 38, 64A and 64B. SEQ ID NO:2 is the sequence of the immature Fv3A. Fv3A has a predicted signal sequence corresponding to residues 1 to 23 of SEQ ID NO:2

(underlined); cleavage of the signal sequence is predicted to yield a mature protein having a sequence corresponding to residues 24 to 766 of SEQ ID NO:2. The predicted conserved domains are in boldface type in FIG. 1B. Fv3A was shown to have β-xylosidase activity, for example, in an enzymatic assay using p-nitrophenyl-β-xylopyranoside, xylobiose, mixed linear xylo-oligomers, branched arabinoxylan oligomers from hemicellulose, or dilute ammonia pretreated corncob as substrates. The predicted catalytic residue is D291, while the flanking residues, S290 and C292, are predicted to be involved in substrate binding (FIGS. 64A and 64B). E175 and E213 are conserved across other GH3 enzymes and are predicted to have catalytic functions. As used herein, "an Fv3A polypeptide" refers to a polypeptide and/or to a variant thereof comprising a sequence having at least 85%, e.g., at least 86%, 87%, 88%, 89%, 90%, 91%, 92%, 93%, 94%, 95%, 96%, 97%, 98%, 99%, or 100% sequence identity to at least 50, e.g., at least 75, 100, 125, 150, 175, 200, 250, 300, 350, 400, 450, 500, 550, 600, 650, or 700 contiguous amino acid residues among residues 24 to 766 of SEQ ID NO:2. An Fv3A polypeptide preferably is unaltered as compared to native Fv3A in residues D291, S290, C292, E175, and E213. An Fv3A polypeptide is preferably unaltered in at least 70%, 75%, 80%, 85%, 90%, 95%, 98%, or 99% of the amino acid residues that are conserved among Fv3A, *Trichoderma reesei* Bxl1 and/or *Trichoderma reesei* Bgl1, as shown in the alignment of FIGS. 64A and 64B. An Fv3A polypeptide suitably comprises the entire predicted conserved domain of native Fv3A as shown in FIG. 1B. An exemplary Fv3A polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Fv3A sequence as shown in FIG. 1B. The Fv3A polypeptide of the invention preferably has β-xylosidase activity.

Accordingly an Fv3A polypeptide of the invention suitably comprises an amino acid sequence with at least 90%, 91%, 92%, 93%, 94%, 95%, 96%, 97%, 98%, 99%, or 100% sequence identity to the amino acid sequence of SEQ ID NO:2, or to residues (i) 24-766, (ii) 73-321, (iii) 73-394, (iv) 395-622, (v) 24-622, or (vi) 73-622 of SEQ ID NO:2. The polypeptide suitably has β-xylosidase activity.

Pf43A:

The amino acid sequence of Pf43A (SEQ ID NO:4) is shown in FIGS. 2B and 53A-53C. SEQ ID NO:4 is the sequence of the immature Pf43A. Pf43A has a predicted signal sequence corresponding to residues 1 to 20 of SEQ ID NO:4 (underlined in FIG. 2B); cleavage of the signal sequence is predicted to yield a mature protein having a sequence corresponding to residues 21 to 445 of SEQ ID NO:4. The predicted conserved domain is in boldface type, the predicted CBM is in uppercase type, and the predicted linker separating the CD and CBM is in italics in FIG. 2B. Pf43A has been shown to have β-xylosidase activity, in, for example, an enzymatic assay using p-nitrophenyl-β-xylopyranoside, xylobiose, mixed linear xylo-oligomers, or ammonia pretreated corncob as substrates. The predicted catalytic residues include either D32 or D60, D145, and E206. The C-terminal region underlined in FIGS. 53A-53C is the predicted CBM. As used herein, "a Pf43A polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, 350, or 400 contiguous amino acid residues among residues 21 to 445 of SEQ ID NO:4. A Pf43A polypeptide preferably is unaltered as compared to the native Pf43A in residues D32 or D60, D145, and E206. A Pf43A is preferably unaltered in at least 70%, 80%, 90%, 95%, 98%, or 99% of the amino acid residues that are found conserved across a family of proteins including Pf43A and 1, 2, 3, 4, 5, 6, 7, or all 8 of other amino acid sequences in the alignment of FIGS. 53A-53C. A Pf43A polypeptide of the invention suitably comprises two or more or all of the following domains: (1) the predicted CBM, (2) the predicted conserved domain, and (3) the linker of Pf43A as shown in FIG. 2B. An exemplary Pf43A polypeptide of the invention comprises a sequence having at least 85%, 86%, 87%, 88%, 89%, 90%, 91%, 92%, 93%, 94%, 95%, 96%, 97%, 98%, 99%, or 100% identity to the mature Pf43A sequence as shown in FIG. 2B. The Pf43A polypeptide of the invention preferably has β-xylosidase activity.

Accordingly a Pf43A polypeptide of the invention suitably comprises an amino acid sequence with at least 90%, 91%, 92%, 93%, 94%, 95%, 96%, 97%, 98%, 99%, or 100% sequence identity to the amino acid sequence of SEQ ID NO:4, or to residues (i) 21-445, (ii) 21-301, (iii) 21-323, (iv) 21-444, (v) 302-444, (vi) 302-445, (vii) 324-444, or (viii) 324-445 of SEQ ID NO:4. The polypeptide suitably has β-xylosidase activity.

Fv43E:

The amino acid sequence of Fv43E (SEQ ID NO:6) is shown in FIGS. 3B and 53. SEQ ID NO:6 is the sequence of the immature Fv43E. Fv43E has a predicted signal sequence corresponding to residues 1 to 18 of SEQ ID NO:6 (underlined in FIG. 3B); cleavage of the signal sequence is predicted to yield a mature protein having a sequence corresponding to residues 19 to 530 of SEQ ID NO:6. The predicted conserved domain is marked in boldface type in FIG. 3B. Fv43E was shown to have β-xylosidase activity, in, for example, enzymatic assay using 4-nitophenyl-β-D-xylopyranoside, xylobiose, and mixed, linear xylo-oligomers, or ammonia pretreated corncob as substrates. The predicted catalytic residues include either D40 or D71, D155, and E241. As used herein, "an Fv43E polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, 350, 400, 450, or 500 contiguous amino acid residues among residues 19 to 530 of SEQ ID NO:6. An Fv43E polypeptide preferably is unaltered as compared to the native Fv43E in residues D40 or D71, D155, and E241. An Fv43E polypeptide is preferably unaltered in at least 70%, 80%, 90%, 95%, 98%, or 99% of the amino acid residues that are found to be conserved among a family of enzymes including Fv43E, and 1, 2, 3, 4, 5, 6, 7, or all other 8 amino acid sequences in the alignment of FIGS. 53A-53C. An Fv43E polypeptide suitably comprises the entire predicted conserved domain of native Fv43E as shown in FIG. 3B. An exemplary Fv43E polypeptide comprises a sequence having at least 85%, 86%, 87%, 88%, 89%, 90%, 91%, 92%, 93%, 94%, 95%, 96%, 97%, 98%, 99%, or 100% identity to mature Fv43E sequence as shown in FIG. 3B. The Fv43E polypeptide of the invention preferably has β-xylosidase activity.

Accordingly, an Fv43E polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:6, or to residues (i) 19-530, (ii) 29-530, (iii) 19-300, or (iv) 29-300 of SEQ ID NO:6. The polypeptide suitably has β-xylosidase activity.

Fv39A:

The amino acid sequence of Fv39A (SEQ ID NO:8) is shown in FIGS. 4B and 52. SEQ ID NO:8 is the sequence of the immature Fv39A. Fv39A has a predicted signal sequence corresponding to residues 1 to 19 of SEQ ID NO:8 (underlined in FIG. 4B); cleavage of the signal sequence is predicted to yield a mature protein having a sequence corresponding to residues 20 to 439 of SEQ ID NO:8. The predicted conserved domain is shown in boldface type in FIG. 4B. Fv39A was shown to have β-xylosidase activity in, for example, an enzymatic assay using p-nitophenyl-β-xylopyranoside, xylobiose or mixed, linear xylo-oligomers as substrates. Fv39A residues E168 and E272 are predicted to function as catalytic acid-base and nucleophile, respectively, based on a sequence alignment of the above-mentioned GH39 xylosidases from *Thermoanaerobacterium saccharolyticum* (Uniprot Accession No. P36906) and *Geobacillus stearothermophilus* (Uniprot Accession No. Q9ZFM2) with Fv39A. As used herein, "an Fv39A polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, 350, or 400 contiguous amino acid residues among residues 20 to 439 of SEQ ID NO:8. An Fv39A polypeptide preferably is unaltered as compared to native Fv39A in residues E168 and E272. An Fv39A polypeptide is preferably unaltered in at least 70%, 80%, 90%, 95%, 98%, or 99% of the amino acid residues that are conserved among a family or enzymes including Fv39A and xylosidases from *Thermoanaerobacterium saccharolyticum* and *Geobacillus stearothermophilus* (see above). An Fv39A polypeptide suitably comprises the entire predicted conserved domain of native Fv39A as shown in FIG. 4B. An exemplary Fv39A polypeptide comprises a sequence having at least 85%, 86%, 87%, 88%, 89%, 90%, 91%, 92%, 93%, 94%, 95%, 96%, 97%, 98%, 99%, or 100% identity to the mature Fv39A sequence as shown in FIG. 4B. The Fv39A polypeptide of the invention preferably has β-xylosidase activity.

Accordingly, an Fv39A polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:8, or to residues (i) 20-439, (ii) 20-291, (iii) 145-291, or (iv) 145-439 of SEQ ID NO:8. The polypeptide suitably has β-xylosidase activity.

Fv43A:

The amino acid sequence of Fv43A (SEQ ID NO:10) is provided in FIGS. 5B and 53A-53C. SEQ ID NO:10 is the sequence of the immature Fv43A. Fv43A has a predicted signal sequence corresponding to residues 1 to 22 of SEQ ID NO:10 (underlined in FIG. 5B); cleavage of the signal sequence is predicted to yield a mature protein having a sequence corresponding to residues 23 to 449 of SEQ ID NO:10. In FIG. 5B, the predicted conserved domain is in boldface type, the predicted CBM is in uppercase type, and the predicted linker separating the CD and CBM is in italics. Fv43A was shown to have β-xylosidase activity in, for example, an enzymatic assay using 4-nitrophenyl-β-D-xylopyranoside, xylobiose, mixed, linear xylo-oligomers, branched arabinoxylan oligomers from hemicellulose, and/ or linear xylo-oligomers as substrates. The predicted catalytic residues including either D34 or D62, D148, and E209. As used herein, "an Fv43A polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, 350, or 400 contiguous amino acid residues among residues 23 to 449 of SEQ ID NO:10. An Fv43A polypeptide preferably is unaltered, as compared to native Fv43A, at residues D34 or D62, D148, and E209, An Fv43A polypeptide is preferably unaltered in at least 70%, 80%, 90%, 95%, 98%, or 99% of the amino acid residues that are conserved among a family of enzymes including Fv43A and 1, 2, 3, 4, 5, 6, 7, 8, or all 9 other amino acid sequences in the alignment of FIGS. 5B and 53A-53C. An Fv43A polypeptide suitably comprises the entire predicted CBM of native Fv43A, and/or the entire predicted conserved domain of native Fv43A, and/or the linker of Fv43A as shown in FIG. 5B. An exemplary Fv43A polypeptide comprises a sequence having at least 85%, 86%, 87%, 88%, 89%, 90%, 91%, 92%, 93%, 94%, 95%, 96%, 97%, 98%, 99%, or 100% identity to the mature Fv43A sequence as shown in FIG. 5B. The Fv45A polypeptide of the invention preferably has β-xylosidase activity.

Accordingly an Fv43A polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:10, or to residues (i) 23-449, (ii) 23-302, (iii) 23-320, (iv) 23-448, (v) 303-448, (vi) 303-449, (vii) 321-448, or (viii) 321-449 of SEQ ID NO:10. The polypeptide suitably has β-xylosidase activity.

Fv43B:

The amino acid sequence of Fv43B (SEQ ID NO:12) is shown in FIGS. 6B and 53. SEQ ID NO:12 is the sequence of the immature Fv43B. Fv43B has a predicted signal sequence corresponding to residues 1 to 16 of SEQ ID NO:12 (underlined in FIG. 6B); cleavage of the signal sequence is predicted to yield a mature protein having a sequence corresponding to residues 17 to 574 of SEQ ID NO:12. The predicted conserved domain is in boldface type in FIG. 6B. Fv43B was shown to have both β-xylosidase and L-α-arabinofuranosidase activities, in, for example, a first enzymatic assay using 4-nitrophenyl-β-D-xylopyranoside and p-nitrophenyl-α-L-arabinofuranoside as substrates. It was shown, in a second enzymatic assay, to catalyze the release of arabinose from branched arabino-xylooligomers and to catalyze the increased xylose release from oligomer mixtures in the presence of other xylosidase enzymes. The predicted catalytic residues include either D38 or D68, D151, and E236. As used herein, "an Fv43B polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, 350, 400, 450, 500, or 550 contiguous amino acid residues among residues 17 to 574 of SEQ ID NO:12. An Fv43B polypeptide preferably is unaltered, as compared to native Fv43B, at residues D38 or D68, D151, and E236. An Fv43B polypeptide is preferably unaltered in at least 70%, 80%, 90%, 95%, 98%, or 99% of the amino acid residues that are conserved among a family of enzymes including Fv43B and 1, 2, 3, 4, 5, 6, 7, 8, or all 9 other amino acid sequences in the alignment of FIGS. 53A-53C. An Fv43B polypeptide suitably comprises the entire predicted conserved domain of native Fv43B as shown in FIGS. 6B and 53. An exemplary Fv43B polypeptide comprises a sequence having at least 85%, 86%, 87%, 88%, 89%, 90%, 91%, 92%, 93%, 94%, 95%, 96%, 97%, 98%, 99%, or 100% identity to the mature Fv43B sequence as shown in FIG. 6B. The Fv43B polypeptide of the present invention preferably has β-xylosidase activity, L-α-arabinofuranosidase activity, or both β-xylosidase and L-α-arabinofuranosidase activities.

Accordingly, an Fv43B polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:12, or to residues (i) 17-574, (ii) 27-574, (iii) 17-303, or (iv) 27-303 of SEQ ID NO:12. The polypeptide suitably has β-xylosidase activity, L-α-arabinofuranosidase activity, or both β-xylosidase and L-α-arabinofuranosidase activities.

Pa51A:

The amino acid sequence of Pa51A (SEQ ID NO:14) is shown in FIGS. 7B and 54. SEQ ID NO:14 is the sequence of the immature Pa51A. Pa51A has a predicted signal sequence corresponding to residues 1 to 20 of SEQ ID NO:14 (underlined in FIG. 7B); cleavage of the signal sequence is predicted to yield a mature protein having a sequence corresponding to residues 21 to 676 of SEQ ID NO:14. The predicted L-α-arabinofuranosidase conserved domain is in boldface type in FIG. 7B. Pa51A was shown to have both β-xylosidase activity and L-α-arabinofuranosidase activity in, for example, enzymatic assays using artificial substrates p-nitrophenyl-β-xylopyranoside and p-nitrophenyl-□α-L-arabinofuranoside. It was shown to catalyze the release of arabinose from branched arabino-xylo oligomers and to catalyze the increased xylose release from oligomer mixtures in the presence of other xylosidase enzymes. Conserved acidic residues include E43, D50, E257, E296, E340, E370, E485, and E493. As used herein, "a Pa51A polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, 350, 400, 450, 500, 550, 600, or 650 contiguous amino acid residues among residues 21 to 676 of SEQ ID NO:14. A Pa51A polypeptide preferably is unaltered, as compared to native Pa51A, at residues E43, D50, E257, E296, E340, E370, E485, and E493. A Pa51A polypeptide is preferably unaltered in at least 70%, 80%, 90%, 95%, 98%, or 99% of the amino acid residues that are conserved among a group of enzymes including Pa51A, Fv51A, and Pf51A, as shown in the alignment of FIG. 54. A Pa51A polypeptide suitably comprises the predicted conserved domain of native Pa51A as shown in FIG. 7B. An exemplary Pa51A polypeptide comprises a sequence having at least 85%, 86%, 87%, 88%, 89%, 90%, 91%, 92%, 93%, 94%, 95%, 96%, 97%, 98%, 99%, or 100% identity to the mature Pa51A sequence as shown in FIG. 7B. The Pa51A polypeptide of the invention preferably has β-xylosidase activity, L-α-arabinofuranosidase activity, or both β-xylosidase and L-α-arabinofuranosidase activities.

Accordingly, a Pa51A polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:14, or to residues (i) 21-676, (ii) 21-652, (iii) 469-652, or (iv) 469-676 of SEQ ID NO:14. The polypeptide suitably has β-xylosidase activity, L-α-arabinofuranosidase activity, or both β-xylosidase and L-α-arabinofuranosidase activities.

Gz43A:

The amino acid sequence of Gz43A (SEQ ID NO:16) is shown in FIGS. 8B and 53A-53C. SEQ ID NO:16 is the sequence of the immature Gz43A. Gz43A has a predicted signal sequence corresponding to residues 1 to 18 of SEQ ID NO:16 (underlined in FIG. 8B); cleavage of the signal sequence is predicted to yield a mature protein having a sequence corresponding to residues 19 to 340 of SEQ ID NO:16. The predicted conserved domain is in boldface type in FIG. 8B. Gz43A was shown to have β-xylosidase activity in, for example, an enzymatic assay using p-nitrophenyl-β-xylopyranoside, xylobiose or mixed, and/or linear xylo-oligomers as substrates. The predicted catalytic residues include either D33 or D68, D154, and E243. As used herein, "a Gz43A polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, or 300 contiguous amino acid residues among residues 19 to 340 of SEQ ID NO:16. A Gz43A polypeptide preferably is unaltered, as compared to native Gz43A, at residues D33 or D68, D154, and E243. A Gz43A polypeptide is preferably unaltered in at least 70%, 80%, 90%, 95%, 98%, or 99% of the amino acid residues that are conserved among a group of enzymes including Gz43A and 1, 2, 3, 4, 5, 6, 7, 8 or all 9 other amino acid sequences in the alignment of FIGS. 53A-53C. A Gz43A polypeptide suitably comprises the predicted conserved domain of native Gz43A as shown in FIG. 8B. An exemplary Gz43A polypeptide comprises a sequence having at least 85%, 86%, 87%, 88%, 89%, 90%, 91%, 92%, 93%, 94%, 95%, 96%, 97%, 98%, 99%, or 100% identity to the mature Gz43A sequence as shown in FIG. 8B. The Gz43A polypeptide of the invention preferably has β-xylosidase activity.

Accordingly a Gz43A polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:16, or to residues (i) 19-340, (ii) 53-340, (iii) 19-383, or (iv) 53-383 of SEQ ID NO:16. The polypeptide suitably has β-xylosidase activity.

Fo43A:

The amino acid sequence of Fo43A (SEQ ID NO:18) is shown in FIGS. 9B and 53A-53C. SEQ ID NO:18 is the sequence of the immature Fo43A. Fo43A has a predicted signal sequence corresponding to residues 1 to 20 of SEQ ID NO:18 (underlined in FIG. 9B); cleavage of the signal sequence is predicted to yield a mature protein having a sequence corresponding to residues 21 to 348 of SEQ ID NO:18. The predicted conserved domain is in boldface type in FIG. 9B. Fo43A was shown to have β-xylosidase activity in, for example, an enzymatic assay using p-nitrophenyl-β-xylopyranoside, xylobiose and/or mixed, linear xylo-oligomers as substrates. The predicted catalytic residues include either D37 or D72, D159, and E251. As used herein, "an Fo43A polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, or 300 contiguous amino acid residues among residues 18 to 344 of SEQ ID NO:18. An Fo43A polypeptide preferably is unaltered, as compared to native Fo43A, at residues D37 or D72, D159, and E251. An Fo43A polypeptide is preferably unaltered in at least 70%, 80%, 90%, 95%, 98%, or 99% of the amino acid residues that are conserved among a group of enzymes including Fo43A and 1, 2, 3, 4, 5, 6, 7, 8 or all 9 other amino acid sequences in the alignment of FIGS. 53A-53C. An Fo43A polypeptide suitably comprises the predicted conserved domain of native Fo43A as shown in FIG. 9B. An exemplary Fo43A polypeptide comprises a sequence having at least 85%, 86%, 87%, 88%, 89%, 90%, 91%, 92%, 93%, 94%, 95%, 96%, 97%, 98%, 99%, or 100% identity to the mature Fo43A sequence as shown in FIG. 9B. The Fo43A polypeptide of the invention preferably has β-xylosidase activity.

Accordingly an Fo43A polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:18, or to residues (i) 21-341, (ii) 107-341, (iii) 21-348, or (iv) 107-348 of SEQ ID NO:18. The polypeptide suitably has β-xylosidase activity.

Af43A:

The amino acid sequence of Af43A (SEQ ID NO:20) is shown in FIGS. 10B and 53A-53C. SEQ ID NO:20 is the sequence of the immature Af43A. The predicted conserved domain is in boldface type in FIG. 10B. Af43A was shown to have L-α-arabinofuranosidase activity in, for example, an enzymatic assay using p-nitrophenyl-□α-L-arabinofuranoside as a substrate. Af43A was shown to catalyze the release of arabinose from the set of oligomers released from hemicellulose via the action of endoxylanase. The predicted catalytic residues include either D26 or D58, D139, and E227. As used herein, "an Af43A polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, or 300 contiguous amino acid residues of SEQ ID NO:20. An Af43A polypeptide preferably is unaltered, as compared to native Af43A, at residues D26 or D58, D139, and E227. An Af43A polypeptide is preferably unaltered in at least 70%, 80%, 90%, 95%, 98%, or 99% of the amino acid residues that are conserved among a group of enzymes including Af43A and 1, 2, 3, 4, 5, 6, 7, 8, or all 9 other amino acid sequences in the alignment of FIGS. 53A-53C. An Af43A polypeptide suitably comprises the predicted conserved domain of native Af43A as shown in FIG. 10B. An exemplary Af43A polypeptide comprises a sequence having at least 85%, 86%, 87%, 88%, 89%, 90%, 91%, 92%, 93%, 94%, 95%, 96%, 97%, 98%, 99%, or 100% sequence identity to SEQ ID NO:20. The Af43A polypeptide of the invention preferably has L-α-arabinofuranosidase activity.

Accordingly an Af43A polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:20, or to residues (i) 15-558, or (ii) 15-295 of SEQ ID NO:20. The polypeptide suitably has L-α-arabinofuranosidase activity.

Pf51A:

The amino acid sequence of Pf51A (SEQ ID NO:22) is shown in FIGS. 11B and 54. SEQ ID NO:22 is the sequence of the immature Pf51A. Pf51A has a predicted signal sequence corresponding to residues 1 to 20 of SEQ ID NO:22 (underlined in FIG. 11B); cleavage of the signal sequence is predicted to yield a mature protein having a sequence corresponding to residues 21 to 642 of SEQ ID NO:22. The predicted L-α-arabinofuranosidase conserved domain is in boldface type in FIG. 11B. Pf51A was shown to have L-α-arabinofuranosidase activity in, for example, an enzymatic assay using 4-nitrophenyl-□α-L-arabinofuranoside as a substrate. Pf51A was shown to catalyze the release of arabinose from the set of oligomers released from hemicellulose via the action of endoxylanase. The predicted conserved acidic residues include E43, D50, E248, E287, E331, E360, E472, and E480. As used herein, "a Pf51A polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, 350, 400, 450, 500, 550, or 600 contiguous amino acid residues among residues 21 to 642 of SEQ ID NO:22. A Pf51A polypeptide preferably is unaltered, as compared to native Pf51A, at residues E43, D50, E248, E287, E331, E360, E472, and E480. A Pf51A polypeptide is preferably unaltered in at least 70%, 80%, 90%, 95%, 98%, or 99% of the amino acid residues that are conserved among Pf51A, Pa51A, and Fv51A, as shown in the alignment of FIG. 54. A Pf51A polypeptide suitably comprises the predicted conserved domain of native Pf51A shown in FIG. 11B. An exemplary Pf51A polypeptide comprises a sequence having at least 85%, 86%, 87%, 88%, 89%, 90%, 91%, 92%, 93%, 94%, 95%, 96%, 97%, 98%, 99%, or 100% identity to the mature Pf51A sequence shown in FIG. 11B. The Pf51A polypeptide of the invention preferably has L-α-arabinofuranosidase activity.

Accordingly a Pf51A polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:22, or to residues (i) 21-632, (ii) 461-632, (iii) 21-642, or (iv) 461-642 of SEQ ID NO:22. The polypeptide has L-α-arabinofuranosidase activity.

AfuXyn2:

The amino acid sequence of AfuXyn2 (SEQ ID NO:24) is shown in FIGS. 12B and 55B. SEQ ID NO:24 is the sequence of the immature AfuXyn2. AfuXyn2 has a predicted signal sequence corresponding to residues 1 to 18 of SEQ ID NO:24 (underlined in FIG. 12B); cleavage of the signal sequence is predicted to yield a mature protein having a sequence corresponding to residues 19 to 228 of SEQ ID NO:24. The predicted GH11 conserved domain is in boldface type in FIG. 12B. AfuXyn2 was shown to have endoxylanase activity indirectly by observing its ability to catalyze the increased xylose monomer production in the presence of xylobiosidase when the enzymes act on pretreated biomass or on isolated hemicellulose. The conserved catalytic residues include E124, E129, and E215. As used herein, "an AfuXyn2 polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, or 200 contiguous amino acid residues among residues 19 to 228 of SEQ ID NO:24. An AfuXyn2 polypeptide preferably is unaltered, as compared to native AfuXyn2, at residues E124, E129 and E215. An AfuXyn2 polypeptide is preferably unaltered in at least 70%, 80%, 90%, 95%, 98%, or 99% of the amino acid residues that are conserved among AfuXyn2, AfuXyn5, and *Trichoderma reesei* Xyn2, as shown in the alignment of FIG. 55B. An AfuXyn2 polypeptide suitably comprises the entire predicted conserved domain of native AfuXyn2 shown in FIG. 12B. An exemplary AfuXyn2 polypeptide comprises a sequence having at least 85%, 86%, 87%, 88%, 89%, 90%, 91%, 92%, 93%, 94%, 95%, 96%, 97%, 98%, 99%, or 100% identity to the mature AfuXyn2 sequence shown in FIG. 12B. The AfuXyn2 polypeptide of the invention preferably has xylanase activity.

AfuXyn5:

The amino acid sequence of AfuXyn5 (SEQ ID NO:26) is shown in FIGS. 13B and 55B. SEQ ID NO:26 is the sequence of the immature AfuXyn5. AfuXyn5 has a predicted signal sequence corresponding to residues 1 to 19 of SEQ ID NO:26 (underlined in FIG. 13B); cleavage of the signal sequence is predicted to yield a mature protein having a sequence corresponding to residues 20 to 313 of SEQ ID NO:26. The predicted GH11 conserved domains are in boldface type in FIG. 13B. AfuXyn5 was shown to have endoxylanase activity indirectly by observing its ability to catalyze increased xylose monomer production in the presence of xylobiosidase when the enzymes act on pretreated biomass or on isolated hemicellulose. The conserved catalytic residues include E119, E124, and E210. The predicted CBM is near the C-terminal end, characterized by numerous hydrophobic residues and follows the long serine-, threonine-rich series of amino acids. The region is shown underlined in FIG. 55B. As used herein, "an AfuXyn5 polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, or 275 contiguous amino acid residues among residues 20 to 313 of SEQ ID NO:26. An AfuXyn5 polypeptide preferably is unaltered, as compared to native AfuXyn5, at residues E119, E120, and E210. An AfuXyn5 polypeptide is preferably unaltered in at least 70%, 80%, 90%, 95%, 98%, or 99% of the amino acid residues that are conserved among AfuXyn5, AfuXyn2, and *Trichoderma reesei* Xyn2, as shown in the alignment of FIG. 55B. An AfuXyn5 polypeptide suitably comprises the entire predicted CBM of native AfuXyn5 and/or the entire predicted conserved domain of native AfuXyn5 (underlined) shown in FIG. 13B. An exemplary AfuXyn5 polypeptide comprises a sequence having at least 85%, 86%, 87%, 88%, 89%, 90%, 91%, 92%, 93%, 94%, 95%, 96%, 97%, 98%, 99%, or 100% identity to the mature AfuXyn5 sequence shown in FIG. 13B. The AfuXyn5 polypeptide of the invention preferably has xylanase activity.

Fv43D:

The amino acid sequence of Fv43D (SEQ ID NO:28) is shown in FIGS. 14B and 53A-53C. SEQ ID NO:28 is the sequence of the immature Fv43D. Fv43D has a predicted signal sequence corresponding to residues 1 to 20 of SEQ ID NO:28 (underlined in FIG. 14B); cleavage of the signal sequence is predicted to yield a mature protein having a sequence corresponding to residues 21 to 350 of SEQ ID NO:28. The predicted conserved domain is in boldface type in FIG. 14B. Fv43D was shown to have β-xylosidase activity in, for example, an enzymatic assay using p-nitophenyl-β-xylopyranoside, xylobiose, and/or mixed, linear xylo-oligomers as substrates. The predicted catalytic residues include either D37 or D72, D159, and E251. As used herein, "an Fv43D polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, or 320 contiguous amino acid residues among residues 21 to 350 of SEQ ID NO:28. An Fv43D polypeptide preferably is unaltered, as compared to native Fv43D, at residues D37 or D72, D159, and E251. An Fv43D polypeptide is preferably unaltered in at least 70%, 80%, 90%, 95%, 98%, or 99% of the amino acid residues that are conserved among a group of enzymes including Fv43D and 1, 2, 3, 4, 5, 6, 7, 8, or all 9 other amino acid sequences in the alignment of FIGS. 53A-53C. An Fv43D polypeptide suitably comprises the entire predicted CD of native Fv43D shown in FIG. 14B. An exemplary Fv43D polypeptide comprises a sequence having at least 85%, 86%, 87%, 88%, 89%, 90%, 91%, 92%, 93%, 94%, 95%, 96%, 97%, 98%, 99%, or 100% identity to the mature Fv43D sequence shown in FIG. 14B. The Fv43D polypeptide of the invention preferably has β-xylosidase activity.

Accordingly an Fv43D polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:28, or to residues (i) 20-341, (ii) 21-350, (iii) 107-341, or (iv) 107-350 of SEQ ID NO:28. The polypeptide suitably has β-xylosidase activity.

Pf43B:

The amino acid sequence of Pf43B (SEQ ID NO:30) is shown in FIGS. 15B and 53A-53C. SEQ ID NO:30 is the sequence of the immature Pf43B. Pf43B has a predicted signal sequence corresponding to residues 1 to 20 of SEQ ID NO:30 (underlined in FIG. 15B); cleavage of the signal sequence is predicted to yield a mature protein having a sequence corresponding to residues 21 to 321 of SEQ ID NO:30. The predicted conserved domain is in boldface type in FIG. 15B. Conserved acidic residues within the conserved domain include D32, D61, D148, and E212. Pf43B was shown to have β-xylosidase activity in, for example, an enzymatic assay using p-nitrophenyl-β-xylopyranoside, xylobiose, and/or mixed, linear xylo-oligomers as substrates. As used herein, "a Pf43B polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, or 280 contiguous amino acid residues among residues 21 to 321 of SEQ ID NO:30. A Pf43B polypeptide preferably is unaltered, as compared to native Pf43B, at residues D32, D61, D148, and E212. A Pf43B polypeptide is preferably unaltered in at least 70%, 80%, 90%, 95%, 98%, or 99% of the amino acid residues that are conserved among a group of enzymes including Pf43B and 1, 2, 3, 4, 5, 6, 7, 8, or all 9 other amino acid sequences in the alignment of FIGS. 53A-53C. A Pf43B polypeptide suitably comprises the predicted conserved domain of native Pf43B shown in FIG. 15B. An exemplary Pf43B polypeptide comprises a sequence having at least 85%, 86%, 87%, 88%, 89%, 90%, 91%, 92%, 93%, 94%, 95%, 96%, 97%, 98%, 99%, or 100% identity to the mature Pf43B sequence shown in FIG. 15B. The Pf43B polypeptide of the invention preferably has β-xylosidase activity.

Accordingly a Pf43B polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO:30. The polypeptide suitably has β-xylosidase activity.

Fv51A:

The amino acid sequence of Fv51A (SEQ ID NO:32) is shown in FIGS. 16B and 54. SEQ ID NO:32 is the sequence of the immature Fv51A. Fv51A has a predicted signal sequence corresponding to residues 1 to 19 of SEQ ID NO:32 (underlined in FIG. 16B); cleavage of the signal sequence is predicted to yield a mature protein having a sequence corresponding to residues 20 to 660 of SEQ ID NO:32. The predicted L-α-arabinofuranosidase conserved domain is in boldface type in FIG. 16B. Fv51A was shown to have L-α-arabinofuranosidase activity in, for example, an enzymatic assay using 4-nitrophenyl-□α-L-arabinofuranoside as a substrate. Fv51A was shown to catalyze the release of arabinose from the set of oligomers released from hemicellulose via the action of endoxylanase. Conserved residues include E42, D49, E247, E286, E330, E359, E479, and E487. As used herein, "an Fv51A polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, 350, 400, 450, 500, 550, 600, or 625 contiguous amino acid residues among residues 20 to 660 of SEQ ID NO:32. An Fv51A polypeptide preferably is unaltered, as compared to native Fv51A, at residues E42, D49, E247, E286, E330, E359, E479, and E487. An Fv51A polypeptide is preferably unaltered in at least 70%, 80%, 90%, 95%, 98%, or 99% of the amino acid residues that are conserved among Fv51A, Pa51A, and Pf51A, as shown in the alignment of FIG. 54. An Fv51A polypeptide suitably comprises the predicted conserved domain of native Fv51A shown in FIG. 16B. An exemplary Fv51A polypeptide comprises a sequence having at least 85%, 86%, 87%, 88%, 89%, 90%, 91%, 92%, 93%, 94%, 95%, 96%, 97%, 98%, 99%, or 100% identity to the mature Fv51A sequence shown in FIG. 16B. The Fv51A polypeptide of the invention preferably has L-α-arabinofuranosidase activity.

Accordingly an Fv51A polypeptide of the invention suitably comprise an amino acid sequence with at least 90%, 91%, 92%, 93%, 94%, 95%, 96%, 97%, 98%, 99% or 100% sequence identity to the amino acid sequence of SEQ ID NO:32, or to residues (i) 21-660, (ii) 21-645, (iii) 450-645, or (iv) 450-660 of SEQ ID NO:32. The polypeptide suitably has L-α-arabinofuranosidase activity.

Xyn3:

The amino acid sequence of *Trichoderma reesei* Xyn3 (SEQ ID NO:42) is shown in FIG. 21B. SEQ ID NO:42 is the sequence of the immature *Trichoderma reesei* Xyn3. *Trichoderma reesei* Xyn3 has a predicted signal sequence corresponding to residues 1 to 16 of SEQ ID NO:42 (underlined in FIG. 21B); cleavage of the signal sequence is predicted to yield a mature protein having a sequence corresponding to residues 17 to 347 of SEQ ID NO:42. The predicted conserved domain is in boldface type in FIG. 21B. *Trichoderma reesei* Xyn3 was shown to have endoxylanase activity indirectly by observation of its ability to catalyze increased xylose monomer production in the presence of xylobiosidase when the enzymes act on pretreated biomass or on isolated hemicellulose. The conserved catalytic residues include E91, E176, E180, E195, and E282, as determined by alignment with another GH10 family enzyme, the Xys1 delta from *Streptomyces halstedii* (Canals et al., 2003, Act Crystalogr. D Biol. 59:1447-53), which has 33% sequence identity to *Trichoderma reesei* Xyn3. As used herein, "a *Trichoderma reesei* Xyn3 polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, or 300 contiguous amino acid residues among residues 17 to 347 of SEQ ID NO:42. A *Trichoderma reesei* Xyn3 polypeptide preferably is unaltered, as compared to native *Trichoderma reesei* Xyn3, at residues E91, E176, E180, E195, and E282. A *Trichoderma reesei* Xyn3 polypeptide is preferably unaltered in at least 70%, 80%, 90%, 95%, 98%, or 99% of the amino acid residues that are conserved between *Trichoderma reesei* Xyn3 and Xys1 delta. A *Trichoderma reesei* Xyn3 polypeptide suitably comprises the entire predicted conserved domain of native *Trichoderma reesei* Xyn3 shown in FIG. 21B. An exemplary *Trichoderma reesei* Xyn3 polypeptide comprises a sequence having at least 85%, 86%, 87%, 88%, 89%, 90%, 91%, 92%, 93%, 94%, 95%, 96%, 97%, 98%, 99%, or 100% identity to the mature *Trichoderma reesei* Xyn3 sequence shown in FIG. 21B. The *Trichoderma reesei* Xyn3 polypeptide of the invention preferably has xylanase activity.

Xyn2:

The amino acid sequence of *Trichoderma reesei* Xyn2 (SEQ ID NO:43) is shown in FIGS. 22 and 55B. SEQ ID NO:43 is the sequence of the immature *Trichoderma reesei* Xyn2. *Trichoderma reesei* Xyn2 has a predicted prepropeptide sequence corresponding to residues 1 to 33 of SEQ ID NO:43 (underlined in FIG. 22); cleavage of the predicted signal sequence between positions 16 and 17 is predicted to yield a propeptide, which is processed by a kexin-like protease between positions 32 and 33, generating the mature protein having a sequence corresponding to residues 33 to 222 of SEQ ID NO:43. The predicted conserved domain is in boldface type in FIG. 22. *Trichoderma reesei* Xyn2 was shown to have endoxylanase activity indirectly by observation of its ability to catalyze an increased xylose monomer production in the presence of xylobiosidase when the enzymes act on pretreated biomass or on isolated hemicellulose. The conserved acidic residues include E118, E123, and E209. As used herein, "a *Trichoderma reesei* Xyn2 polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, or 175 contiguous amino acid residues among residues 33 to 222 of SEQ ID NO:43. A *Trichoderma reesei* Xyn2 polypeptide preferably is unaltered, as compared to a native *Trichoderma reesei* Xyn2, at residues E118, E123, and E209. A *Trichoderma reesei* Xyn2 polypeptide is preferably unaltered in at least 70%, 80%, 90%, 95%, 98%, or 99% of the amino acid residues that are conserved among *Trichoderma reesei* Xyn2, AfuXyn2, and AfuXyn5, as shown in the alignment of FIG. 55B. A *Trichoderma reesei* Xyn2 polypeptide suitably comprises the entire predicted conserved domain of native *Trichoderma reesei* Xyn2 shown in FIG. 22. An exemplary *Trichoderma reesei* Xyn2 polypeptide comprises a sequence having at least 85%, 86%, 87%, 88%, 89%, 90%, 91%, 92%, 93%, 94%, 95%, 96%, 97%, 98%, 99%, or 100% identity to the mature *Trichoderma reesei* Xyn2 sequence shown in FIG. 22. The *Trichoderma reesei* Xyn2 polypeptide of the invention preferably has xylanase activity.

Bxl1:

The amino acid sequence of *Trichoderma reesei* Bxl1 (SEQ ID NO:44) is shown in FIGS. 23 and 64. SEQ ID NO:44 is the sequence of the immature *Trichoderma reesei* Bxl1. *Trichoderma reesei* Bxl1 has a predicted signal sequence corresponding to residues 1 to 18 of SEQ ID NO:44 (underlined in FIG. 23); cleavage of the signal sequence is predicted to yield a mature protein having a sequence corresponding to residues 19 to 797 of SEQ ID NO:44. The predicted conserved domains are in boldface type in FIG. 23. *Trichoderma reesei* Bxl1 was shown to have β-xylosidase activity in, for example, an enzymatic assay using p-nitrophenyl-β-xylopyranoside, xylobiose and/or mixed, linear xylo-oligomers as substrates. The conserved acidic residues include E193, E234, and D310. As used herein, "a *Trichoderma reesei* Bxl1 polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, 350, 400, 450, 500, 550, 600, 650, 700, or 750 contiguous amino acid residues among residues 17 to 797 of SEQ ID NO:44. A *Trichoderma reesei* Bxl1 polypeptide preferably is unaltered, as compared to a native *Trichoderma reesei* Bxl1, at residues E193, E234, and D310. A *Trichoderma reesei* Bxl1 polypeptide is preferably unaltered in at least 70%, 80%, 90%, 95%, 98%, or 99% of the amino acid residues that are conserved among *Trichoderma reesei* Bxl1, Fv3A, and *Trichoderma reesei* Bgl1, as shown in the alignment of FIGS. 64A-64B. A *Trichoderma reesei* Bxl1 polypeptide suitably comprises the entire predicted conserved domains of native *Trichoderma reesei* Bxl1 shown in FIG. 23. An exemplary *Trichoderma reesei* Bxl1 polypeptide comprises a sequence having at least 85%, 86%, 87%, 88%, 89%, 90%, 91%, 92%, 93%, 94%, 95%, 96%, 97%, 98%, 99%, or 100% identity to the mature *Trichoderma reesei* Bxl1 sequence shown in FIG. 23. The *Trichoderma reesei* Bxl1 polypeptide of the invention preferably has β-xylosidase activity.

Accordingly a *Trichoderma reesei* Bxl1 polypeptide of the invention suitably comprises an amino acid sequence with at least 90%, 91%, 92%, 93%, 94%, 95%, 96%, 97%, 98%, 99% or 100% sequence identity to the amino acid sequence of SEQ ID NO: 44. The polypeptide suitably has β-xylosidase activity.

Bgl1:

The amino acid sequence of *Trichoderma reesei* Bgl1 (SEQ ID NO:45) is shown in FIGS. 24 and 64A-64B. *Trichoderma reesei* Bgl1 has a predicted signal sequence corresponding to residues 1 to 19 of SEQ ID NO:45 (underlined in FIG. 24); cleavage of the signal sequence is predicted to yield a mature protein having a sequence corresponding to residues 20 to 744 of SEQ ID NO:45. The predicted conserved domain is in boldface type in FIG. 24. *Trichoderma reesei* Bgl1 has been shown to have β-glucosidase activity by observation of a capacity to catalyze the hydrolysis of para-nitrophenyl-β-D-glucopyranoside to produce para-nitrophenol, and a capacity to catalyze the hydrolysis of cellobiose. The conserved acidic residues include D164, E197, and D267. As used herein, "a *Trichoderma reesei* Bgl1 polypeptide" refers to a polypeptide and/or a variant thereof comprising a sequence having at least 85%, 86%, 87%, 88%, 89%, 90%, 91%, 92%, 93%, 94%, 95%, 96%, 97%, 98%, 99%, or 100% sequence identity to at least 50, 75, 100, 125, 150, 175, 200, 250, 300, 350, 400, 450, 500, 550, 600, 650, 700, 750, or 780 contiguous amino acid residues among residues 20 to 744 of SEQ ID NO:45. A *Trichoderma reesei* Bgl1 polypeptide preferably is unaltered, as compared to a native Bgl1, at residues D164, E197, and D267. A *Trichoderma reesei* Bgl1 polypeptide is preferably unaltered in at least 70%, 80%, 90%, 95%, 98%, or 99% of the amino acid residues that are conserved among *Trichoderma reesei* Bgl1, Fv3A, and *Trichoderma reesei* Bxl1, as shown in the alignment of FIGS. 64A-64B. A *Trichoderma reesei* Bgl1 polypeptide suitably comprises the entire predicted conserved domain of native *Trichoderma reesei* Bgl1 shown in FIG. 24. An exemplary *Trichoderma reesei* Bgl1 polypeptide comprises a sequence having at least 85%, 86%, 87%, 88%, 89%, 90%, 91%, 92%, 93%, 94%, 95%, 96%, 97%, 98%, 99%, or 100% identity to the mature *Trichoderma reesei* Bgl1 sequence shown in FIG. 24. The *Trichoderma reesei* Bgl1 polypeptide of the invention preferably has β-glucosidase activity.

Accordingly, the present disclosure provides a number of isolated, synthetic, or recombinant hemicelluloytic polypeptides or variants as described below:

(1) a polypeptide comprising an amino acid sequence with at least 90%, at least 95%, at least 98%, at least 99%, or 100% sequence identity to the amino acid sequence corresponding to positions (i) 24 to 766 of SEQ ID NO:2; (ii) 73 to 321 of SEQ ID NO:2; (iii) 73 to 394 of SEQ ID NO:2; (iv) 395 to 622 of SEQ ID NO:2; (v) 24 to 622 of SEQ ID NO:2; or (iv) 73 to 622 of SEQ ID NO:2; the polypeptide preferably has β-xylosidase activity; or (2) a polypeptide comprising an amino acid sequence with at least 90%, at least 95%, at least 98%, at least 99%, or 100% sequence identity to the amino acid sequence corresponding to positions (i) 21 to 445 of SEQ ID NO:4; (ii) 21 to 301 of SEQ ID NO:4; (iii) 21 to 323 of SEQ ID NO:4; (iv) 21 to 444 of SEQ ID NO:4; (v) 302 to 444 of SEQ ID NO:4; (vi) 302 to 445 of SEQ ID NO:4; (vii) 324 to 444 of SEQ ID NO:4; or (viii) 324 to 445 of SEQ ID NO:4; the polypeptide preferably has β-xylosidase activity; or (3) a polypeptide comprising an amino acid sequence with at least 90%, at least 95%, at least 98%, at least 99%, or 100% sequence identity to the amino acid sequence corresponding to positions (i) 19 to 530 of SEQ ID NO:6; (ii) 29 to 530 of SEQ ID NO:6; (iii) 19 to 300 of SEQ ID NO:6; or (iv) 29 to 300 of SEQ ID NO:6; the polypeptide preferably has β-xylosidase activity; or (4) a polypeptide comprising an amino acid sequence with at least 90%, at least 95%, at least 98%, at least 99%, or 100% sequence identity to the amino acid sequence corresponding to positions (i) 20 to 439 of SEQ ID NO:8; (ii) 20 to 291 of SEQ ID NO:8; (iii) 145 to 291 of SEQ ID NO:8; or (iv) 145 to 439 of SEQ ID NO:8; the polypeptide preferably has β-xylosidase activity; or (5) a polypeptide comprising an amino acid sequence with at least 90%, at least 95%, at least 98%, at least 99%, or 100% sequence identity to the amino acid sequence corresponding to positions (i) 23 to 449 of SEQ ID NO:10; (ii) 23 to 302 of SEQ ID NO:10; (iii) 23 to 320 of SEQ ID NO:10; (iv) 23 to 448 of SEQ ID NO:10; (v) 303 to 448 of SEQ ID NO:10; (vi) 303 to 449 of SEQ ID NO:10; (vii) 321 to 448 of SEQ ID NO:10; or (viii) 321 to 449 of SEQ ID NO:10; the polypeptide preferably has β-xylosidase activity; or (6) a polypeptide comprising an amino acid sequence with at least 90%, at least 95%, at least 98%, at least 99%, or 100% sequence identity to the amino acid sequence corresponding to positions (i) 17 to 574 of SEQ ID NO:12; (ii) 27 to 574 of SEQ ID NO:12; (iii) 17 to 303 of SEQ ID NO:12; or (iv) 27 to 303 of SEQ ID NO:12; the polypeptide preferably has both β-xylosidase activity and L-α-arabinofuranosidase activity; or (7) a polypeptide comprising an amino acid sequence with at least 90%, at least 95%, at least 98%, at least 99%, or 100% sequence identity to the amino acid sequence corresponding to positions (i) 21 to 676 of SEQ ID NO:14; (ii) 21 to 652 of SEQ ID NO:14; (iii) 469 to 652 of SEQ ID NO:14; or (iv) 469 to 676 of SEQ ID NO:14; the polypeptide preferably has both β-xylosidase activity and L-α-arabinofuranosidase activity; or (8) a polypeptide comprising an amino acid sequence with at least 90%, at least 95%, at least 98%, at least 99%, or 100% sequence identity to the amino acid sequence corresponding to positions (i) 19 to 340 of SEQ ID NO:16; (ii) 53 to 340 of SEQ ID NO:16; (iii) 19 to 383 of SEQ ID NO:16; or (iv) 53 to 383 of SEQ ID NO:16; the polypeptide preferably has β-xylosidase activity; or (9) a polypeptide comprising an amino acid sequence with at least 90%, at least 95%, at least 98%, at least 99%, or 100% sequence identity to the amino acid sequence corresponding to positions (i) 21 to 341 of SEQ ID NO:18; (ii) 107 to 341 of SEQ ID NO:18; (iii) 21 to 348 of SEQ ID NO:18; or (iv) 107 to 348 of SEQ ID NO:18; the polypeptide preferably has β-xylosidase activity; or

(10) a polypeptide comprising an amino acid sequence with at least 90%, at least 95%, at least 98%, at least 99%, or 100% sequence identity to the amino acid sequence corresponding to positions (i) 15 to 558 of SEQ ID NO:20; or (ii) 15 to 295 of SEQ ID NO:20; the polypeptide preferably has L-α-arabinofuranosidase activity; or

(11) a polypeptide comprising an amino acid sequence with at least 90%, at least 95%, at least 98%, at least 99%, or 100% sequence identity to the amino acid sequence corresponding to positions (i) 21 to 632 of SEQ ID NO:22; (ii) 461 to 632 of SEQ ID NO:22; (iii) 21 to 642 of SEQ ID NO:22; or (iv) 461 to 642 of SEQ ID NO:22; the polypeptide preferably has L-α-arabinofuranosidase activity; or

(12) a polypeptide comprising an amino acid sequence with at least 90%, at least 95%, at least 98%, at least 99%, or 100% sequence identity to the amino acid sequence corresponding to positions (i) 20 to 341 of SEQ ID NO:28; (ii) 21 to 350 of SEQ ID NO:28; (iii) 107 to 341 of SEQ ID NO:28; or (iv) 107 to 350 of SEQ ID NO:28; the polypeptide has β-xylosidase activity; or

(13) a polypeptide comprising an amino acid sequence with at least 90%, at least 95%, at least 98%, at least 99%, or 100% sequence identity to the amino acid sequence corresponding to positions (i) 21 to 660 of SEQ ID NO:32; (ii) 21 to 645 of SEQ ID NO:32; (iii) 450 to 645 of SEQ ID NO:32; or (iv) 450 to 660 of SEQ ID NO:32; the polypeptide preferably has L-α-arabinofuranosidase activity.

The present disclosure provides also compositions (e.g., cellulase compositions, or enzyme blends/compositions) or fermentation broths enriched with one or more of the above-described polypeptides. The enzyme blend/composition is thus a non-naturally-occurring composition. The cellulase composition can be, for example, a filamentous fungal cellulase composition, such as a *Trichoderma* cellulase composition. The fermentation broth can be a fermentation broth of a filamentous fungus, for example, a *Trichoderma*, *Humicola*, *Fusarium*, *Aspergillus*, *Neurospora*, *Penicillium*, *Cephalosporium*, *Achlya*, *Podospora*, *Endothia*, *Mucor*, *Cochliobolus*, *Pyricularia*, or *Chrysosporium* fermentation broth. In particular, the fermentation broth can be, for example, one of *Trichoderma* spp. such as a *Trichoderma reesei*, or *Penicillium* spp., such as a *Penicillium funiculosum*. The fermentation broth can also suitably be a cell-free fermentation broth.

Additionally the instant disclosure provides host cells that are recombinantly engineered to express a polypeptide described above. The host cells can be, for example, filamentous fungal host cells, such as *Trichoderma*, *Humicola*, *Fusarium*, *Aspergillus*, *Neurospora*, *Penicillium*, *Cephalosporium*, *Achlya*, *Podospora*, *Endothia*, *Mucor*, *cochliobolus*, *Pyricularia*, or *Chrysosporium* cells. In particular, the host cells can be, for example, a *Trichoderma* spp. cell (such as a *Trichoderma reesei* cell), or a *Penicillium* cell (such as a *Penicillium funiculosum* cell), an *Aspergillus* cell (such as an *Aspergillus oryzae* or *Aspergillus nidulans* cell), or a *Fusarium* cell (such as a *Fusarium verticilloides* or *Fusarium oxysporum* cell).

6.1.1 Fusion Proteins

The present disclosure also provides a fusion protein that includes a domain of a protein of the present disclosure attached to one or more fusion segments, which are typically heterologous to the protein (i.e., derived from a different source than the protein of the disclosure). Suitable fusion segments include, without limitation, segments that can enhance a protein's stability, provide other desirable biological activity, and/or facilitate purification of the protein (e.g., by affinity chromatography). A suitable fusion segment can be a domain of any size that has the desired function (e.g., imparts increased stability, solubility, action or biological activity; and/or simplifies purification of a protein).

Fusion segments can be joined to amino and/or carboxyl termini of the domain(s) of a protein of the present disclosure. The fusion segments can be susceptible to cleavage. There may be some advantage in having this susceptibility, for example, it may enable straight-forward recovery of the protein of interest. Fusion proteins are preferably produced by culturing a recombinant cell transfected with a fusion nucleic acid that encodes a protein, which includes a fusion segment attached to either the carboxyl or amino terminal end, or fusion segments attached to both the carboxyl and amino terminal ends, of a protein, or a domain thereof.

Accordingly, proteins of the present disclosure also include expression products of gene fusions (e.g., an overexpressed, soluble, and active form of a recombinant protein), of mutagenized genes (e.g., genes having codon modifications to enhance gene transcription and translation), and of truncated genes (e.g., genes having signal sequences removed or substituted with a heterologous signal sequence).

Glycosyl hydrolases that utilize insoluble substrates are often modular enzymes. They usually comprise catalytic modules appended to one or more non-catalytic carbohydrate-binding domains (CBMs). In nature, CBMs are thought to promote the glycosyl hydrolase's interaction with its target substrate polysaccharide. Thus, the disclosure provides chimeric enzymes having altered substrate specificity; including, for example, chimeric enzymes having multiple substrates as a result of "spliced-in" heterologous CBMs. The heterologous CBMs of the chimeric enzymes of the disclosure can also be designed to be modular, such that they are appended to a catalytic module or catalytic domain (a "CD", e.g., at an active site), which can likewise be heterologous or homologous to the glycosyl hydrolase.

Thus, the disclosure provides peptides and polypeptides consisting of, or comprising, CBM/CD modules, which can be homologously paired or joined to form chimeric (heterologous) CBM/CD pairs. Thus, these chimeric polypeptides/peptides can be used to improve or alter the performance of an enzyme of interest. Accordingly, the disclosure provides chimeric enzymes comprising, e.g., at least one CBM of an enzyme of SEQ ID NO:2, 4, 6, 8, 10, 12, 14, 16, 18, 20, 22, 24, 26, 28, 30, 32, 34, 36, 38, 40, 42, 43, 44, or 45. A polypeptide of the disclosure, for example, includes an amino acid sequence comprising the CD and/or CBM of the glycosyl hydrolase sequence of SEQ ID NO:2, 4, 6, 8, 10, 12, 14, 16, 18, 20, 22, 24, 26, 28, 30, 32, 34, 36, 38, 40, 42, 43, 44, or 45. The polypeptide of the disclosure can thus suitably be a fusion protein comprising functional domains from two or more different proteins (e.g., a CBM from one protein linked to a CD from another protein).

The polypeptides of the disclosure can suitably be obtained and/or used in "substantially pure" form. For example, a polypeptide of the disclosure constitutes at least about 80 wt. % (e.g., at least about 85 wt. %, 90 wt. %, 91 wt. %, 92 wt. %, 93 wt. %, 94 wt. %, 95 wt. %, 96 wt. %, 97 wt. %, 98 wt. %, or 99 wt. %) of the total protein in a given composition, which also includes other ingredients such as a buffer or solution.

Also, the polypeptides of the disclosure can suitably be obtained and/or used in recombinant culture broths (e.g., a filamentous fungal culture broth). The recombinant culture broths can be non-naturally occurring; for example, the culture broth can be produced by a recombinant host cell that is engineered to express a heterologous polypeptide of the disclosure, or by a recombinant host cell that is engineered to express an endogenous polypeptide of the disclosure in greater or lesser amounts than the endogenous expression levels (e.g., in an amount that is 1-, 2-, 3-, 4-, 5-, or more-fold greater or less than the endogenous expression levels). Furthermore, the polypeptides of the disclosure can suitably be obtained and/or used as recombinant culture broths produced by "integrated" host cell strains that have been engineered to express a plurality of polypeptides of the disclosure in desired ratios. Exemplary desired ratios are described herein, for example, in Section 6.3.4 below.

6.2 Nucleic Acids and Host Cells

The present disclosure provides nucleic acids encoding a polypeptide of the disclosure, for example one described in Section 6.1 above.

The disclosure provides isolated, synthetic or recombinant nucleic acids comprising a nucleic acid sequence having at least about 70%, e.g., at least about 71%, 72%, 73%, 74%, 75%, 76%, 77%, 78%, 79%, 80%, 81%, 82%, 83%, 84%, 85%, 86%, 87%, 88%; 89%, 90%, 91%, 92%, 93%, 94%, 95%, 96%, 97%, 98%, or 99%, or complete (100%) sequence identity to a nucleic acid of SEQ ID NO:1, 3, 5, 7, 9, 11, 13, 15, 17, 19, 21, 23, 25, 27, 29, 31, 33, 35, 37, 39, 41, 46, 47, 48, 49, or 50, over a region of at least about 10, e.g., at least about 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 nucleotides. The present disclosure also provides nucleic acids encoding at least one polypeptide having a hemicellulolytic activity (e.g., a xylanase, β-xylosidase, and/or L-α-arabinofuranosidase activity).

Nucleic acids of the disclosure also include isolated, synthetic or recombinant nucleic acids encoding an enzyme having the sequence of SEQ ID NO:2, 4, 6, 8, 10, 12, 14, 16, 18, 20, 22, 24, 26, 28, 30, 32, 34, 36, 38, 40, 42, 43, 44, or 45, and subsequences thereof (e.g., a conserved domain or carbohydrate binding domain ("CBM"), and variants thereof. A nucleic acid of the disclosure can, for example, encode the mature portion of a protein of SEQ ID NO:2, 4, 6, 8, 10, 12, 14, 16, 18, 20, 22, 24, 26, 28, 30, 32, 34, 36, 38, 40, 42, 43, 44, or 45.

The disclosure specifically provides a nucleic acid encoding an Fv3A, a Pf43A, an Fv43E, an Fv39A, an Fv43B, a Pa51A, a Gz43A, an Fo43A, an Af43A, a Pf51A, an AfuXyn2, an AfuXyn5, a Fv43D, a Pf43B, an Fv43B, an Fv51A, a *Trichoderma reesei* Xyn3, a *Trichoderma reesei* Xyn2, a *Trichoderma reesei* Bxl1, or a *Trichoderma reesei* Bgl1 polypeptide.

For example, the disclosure provides an isolated nucleic acid molecule, wherein the nucleic acid molecule encodes:
(1) a polypeptide comprising an amino acid sequence with at least 90%, at least 95%, at least 98%, at least 99%, or 100% sequence identity to the amino acid sequence corresponding to positions (i) 24 to 766 of SEQ ID NO:2; (ii) 73 to 321 of SEQ ID NO:2; (iii) 73 to 394 of SEQ ID NO:2; (iv) 395 to 622 of SEQ ID NO:2; (v) 24 to 622 of SEQ ID NO:2; or (iv) 73 to 622 of SEQ ID NO:2; or
(2) a polypeptide comprising an amino acid sequence with at least 90%, at least 95%, at least 98%, at least 99%, or 100% sequence identity to the amino acid sequence corresponding to positions (i) 21 to 445 of SEQ ID NO:4; (ii) 21 to 301 of SEQ ID NO:4; (iii) 21 to 323 of SEQ ID NO:4; (iv) 21 to 444 of SEQ ID NO:4; (v) 302 to 444 of SEQ ID NO:4; (vi) 302 to 445 of SEQ ID NO:4; (vii) 324 to 444 of SEQ ID NO:4; or (viii) 324 to 445 of SEQ ID NO:4; or
(3) a polypeptide comprising an amino acid sequence with at least 90%, at least 95%, at least 98%, at least 99%, or 100% sequence identity to the amino acid sequence corresponding to positions (i) 19 to 530 of SEQ ID NO:6; (ii) 29 to 530 of SEQ ID NO:6; (iii) 19 to 300 of SEQ ID NO:6; or (iv) 29 to 300 of SEQ ID NO:6; or
(4) a polypeptide comprising an amino acid sequence with at least 90%, at least 95%, at least 98%, at least 99%, or 100% sequence identity to the amino acid sequence corresponding to positions (i) 20 to 439 of SEQ ID NO:8; (ii) 20 to 291 of SEQ ID NO:8; (iii) 145 to 291 of SEQ ID NO:8; or (iv) 145 to 439 of SEQ ID NO:8; or
(5) a polypeptide comprising an amino acid sequence with at least 90%, at least 95%, at least 98%, at least 99%, or 100% sequence identity to the amino acid sequence corresponding to positions (i) 23 to 449 of SEQ ID NO:10; (ii) 23 to 302 of SEQ ID NO:10; (iii) 23 to 320 of SEQ ID NO:10; (iv) 23 to 448 of SEQ ID NO:10; (v) 303 to 448 of SEQ ID NO:10; (vi) 303 to 449 of SEQ ID NO:10; (vii) 321 to 448 of SEQ ID NO:10; or (viii) 321 to 449 of SEQ ID NO:10; or
(6) a polypeptide comprising an amino acid sequence with at least 90%, at least 95%, at least 98%, at least 99%, or 100% sequence identity to the amino acid sequence corresponding to positions (i) 17 to 574 of SEQ ID NO:12; (ii) 27 to 574 of SEQ ID NO:12; (iii) 17 to 303 of SEQ ID NO:12; or (iv) 27 to 303 of SEQ ID NO:12; or
(7) a polypeptide comprising an amino acid sequence with at least 90%, at least 95%, at least 98%, at least 99%, or 100% sequence identity to the amino acid sequence corresponding to positions (i) 21 to 676 of SEQ ID NO:14; (ii) 21 to 652 of SEQ ID NO:14; (iii) 469 to 652 of SEQ ID NO:14; or (iv) 469 to 676 of SEQ ID NO:14; or
(8) a polypeptide comprising an amino acid sequence with at least 90%, at least 95%, at least 98%, at least 99%, or 100% sequence identity to the amino acid sequence corresponding to positions (i) 19 to 340 of SEQ ID NO:16; (ii) 53 to 340 of SEQ ID NO:16; (iii) 19 to 383 of SEQ ID NO:16; or (iv) 53 to 383 of SEQ ID NO:16; or
(9) a polypeptide comprising an amino acid sequence with at least 90%, at least 95%, at least 98%, at least 99%, or 100% sequence identity to the amino acid sequence corresponding to positions (i) 21 to 341 of SEQ ID NO:18; (ii) 107 to 341 of SEQ ID NO:18; (iii) 21 to 348 of SEQ ID NO:18; or (iv) 107 to 348 of SEQ ID NO:18; or
(10) a polypeptide comprising an amino acid sequence with at least 90%, at least 95%, at least 98%, at least 99%, or 100% sequence identity to the amino acid sequence corresponding to positions (i) 15 to 558 of SEQ ID NO:20; or (ii) 15 to 295 of SEQ ID NO:20; or
(11) a polypeptide comprising an amino acid sequence with at least 90%, at least 95%, at least 98%, at least 99%, or 100% sequence identity to the amino acid sequence corresponding to positions (i) 21 to 632 of SEQ ID NO:22; (ii) 461 to 632 of SEQ ID NO:22; (iii) 21 to 642 of SEQ ID NO:22; or (iv) 461 to 642 of SEQ ID NO:22; or
(12) a polypeptide comprising an amino acid sequence with at least 90%, at least 95%, at least 98%, at least 99%, or 100% sequence identity to the amino acid sequence corresponding to positions (i) 20 to 341 of SEQ ID NO:28; (ii) 21 to 350 of SEQ ID NO:28; (iii) 107 to 341 of SEQ ID NO:28; or (iv) 107 to 350 of SEQ ID NO:28; or
(13) a polypeptide comprising an amino acid sequence with at least 90%, at least 95%, at least 98%, at least 99%, or 100% sequence identity to the amino acid sequence corresponding to positions (i) 21 to 660 of SEQ ID NO:32; (ii) 21 to 645 of SEQ ID NO:32; (iii) 450 to 645 of SEQ ID NO:32; or (iv) 450 to 660 of SEQ ID NO:32.

The instant disclosure also provides:
(1) a nucleic acid having at least 90% (e.g., at least 90%, 91%, 92%, 93%, 94%, 95%, 96%, 97%, 98%, 99% or more) sequence identity to SEQ ID NO:1, or a nucleic acid that is capable of hybridizing under high stringency conditions to a complement of SEQ ID NO:1, or to a fragment thereof; or
(2) a nucleic acid having at least 90% (e.g., at least 90%, 91%, 92%, 93%, 94%, 95%, 96%, 97%, 98%, 99% or more) sequence identity to SEQ ID NO:3, or a nucleic acid that is capable of hybridizing under high stringency conditions to a complement of SEQ ID NO:3, or to a fragment thereof; or
(3) a nucleic acid having at least 90% (e.g., at least 90%, 91%, 92%, 93%, 94%, 95%, 96%, 97%, 98%, 99% or more) sequence identity to SEQ ID NO:5, or a nucleic acid that is capable of hybridizing under high stringency conditions to a complement of SEQ ID NO:5, or to a fragment thereof; or
(4) a nucleic acid having at least 90% (e.g., at least 90%, 91%, 92%, 93%, 94%, 95%, 96%, 97%, 98%, 99% or more) sequence identity to SEQ ID NO:7, or a nucleic acid that is capable of hybridizing under high stringency conditions to a complement of SEQ ID NO:7, or to a fragment thereof; or
(5) a nucleic acid having at least 90% (e.g., at least 90%, 91%, 92%, 93%, 94%, 95%, 96%, 97%, 98%, 99% or more) sequence identity to SEQ ID NO:9, or a nucleic acid that is capable of hybridizing under high stringency conditions to a complement of SEQ ID NO:9, or to a fragment thereof; or
(6) a nucleic acid having at least 90% (e.g., at least 90%, 91%, 92%, 93%, 94%, 95%, 96%, 97%, 98%, 99% or more) sequence identity to SEQ ID NO:11, or a nucleic acid that is capable of hybridizing under high stringency conditions to a complement of SEQ ID NO:11, or to a fragment thereof; or
(7) a nucleic acid having at least 90% (e.g., at least 90%, 91%, 92%, 93%, 94%, 95%, 96%, 97%, 98%, 99% or more) sequence identity to SEQ ID NO:13, or a nucleic acid that is capable of hybridizing under high stringency conditions to a complement of SEQ ID NO:13, or to a fragment thereof; or
(8) a nucleic acid having at least 90% (e.g., at least 90%, 91%, 92%, 93%, 94%, 95%, 96%, 97%, 98%, 99% or more) sequence identity to SEQ ID NO:15, or a nucleic acid that is capable of hybridizing under high stringency conditions to a complement of SEQ ID NO:15, or to a fragment thereof; or
(9) a nucleic acid having at least 90% (e.g., at least 90%, 91%, 92%, 93%, 94%, 95%, 96%, 97%, 98%, 99% or more) sequence identity to SEQ ID NO:17, or a nucleic acid that is capable of hybridizing under high stringency conditions to a complement of SEQ ID NO:17, or to a fragment thereof; or
(10) a nucleic acid having at least 90% (e.g., at least 90%, 91%, 92%, 93%, 94%, 95%, 96%, 97%, 98%, 99% or more) sequence identity to SEQ ID NO:19, or a nucleic acid that is capable of hybridizing under high stringency conditions to a complement of SEQ ID NO:19, or to a fragment thereof; or
(11) a nucleic acid having at least 90% (e.g., at least 90%, 91%, 92%, 93%, 94%, 95%, 96%, 97%, 98%, 99% or more) sequence identity to SEQ ID NO:21, or a nucleic acid that is capable of hybridizing under high stringency conditions to a complement of SEQ ID NO:21, or to a fragment thereof; or
(12) a nucleic acid having at least 90% (e.g., at least 90%, 91%, 92%, 93%, 94%, 95%, 96%, 97%, 98%, 99% or more) sequence identity to SEQ ID NO:27, or a nucleic acid that is capable of hybridizing under high stringency conditions to a complement of SEQ ID NO:27, or to a fragment thereof; or
(13) a nucleic acid having at least 90% (e.g., at least 90%, 91%, 92%, 93%, 94%, 95%, 96%, 97%, 98%, 99% or more) sequence identity to SEQ ID NO:31, or a nucleic acid that is capable of hybridizing under high stringency conditions to a complement of SEQ ID NO:31, or to a fragment thereof.

The disclosure also provides expression cassettes and/or vectors comprising the above-described nucleic acids.

Suitably, the nucleic acid encoding an enzyme of the disclosure is operably linked to a promoter. Specifically, where recombinant expression in a filamentous fungal host is desired, the promoter can be a filamentous fungal promoter. The nucleic acids can be, for example, under the control of heterologous promoters. The nucleic acids can also be expressed under the control of constitutive or inducible promoters. Examples of promoters that can be used include, but are not limited to, a cellulase promoter, a xylanase promoter, the 1818 promoter (previously identified as a highly expressed protein by EST mapping *Trichoderma*). For example, the promoter can suitably be a cellobiohydrolase, endoglucanase, or β-glucosidase promoter. A particularly suitable promoter can be, for example, a *T. reesei* cellobiohydrolase, endoglucanase, or β-glucosidase promoter. For example, the promoter is a cellobiohydrolase I (cbh1) promoter. Non-limiting examples of promoters include a cbh1, cbh2, egl1, egl2, egl3, egl4, egl5, pki1, gpd1, xyn1, or xyn2 promoter. Additional non-limiting examples of promoters include a *T. reesei* cbh1, cbh2, egl1, egl2, egl3, egl4, egl5, pki1, gpd1, xyn1, or xyn2 promoter.

The present disclosure provides host cells that are engineered to express one or more enzymes of the disclosure. Suitable host cells include cells of any microorganism (e.g., cells of a bacterium, a protist, an alga, a fungus (e.g., a yeast or filamentous fungus), or other microbe), and are preferably cells of a bacterium, a yeast, or a filamentous fungus.

Suitable host cells of the bacterial genera include, but are not limited to, cells of *Escherichia, Bacillus, Lactobacillus, Pseudomonas*, and *Streptomyces*. Suitable cells of bacterial species include, but are not limited to, cells of *Escherichia coli, Bacillus subtilis, Bacillus licheniformis, Lactobacillus brevis, Pseudomonas aeruginosa*, and *Streptomyces lividans*.

Suitable host cells of the genera of yeast include, but are not limited to, cells of *Saccharomyces, Schizosaccharomyces, Candida, Hansenula, Pichia, Kluyveromyces*, and *Phaffia*. Suitable cells of yeast species include, but are not limited to, cells of *Saccharomyces cerevisiae, Schizosaccharomyces pombe, Candida albicans, Hansenula polymorpha, Pichia pastoris, P. canadensis, Kluyveromyces marxianus*, and *Phaffia rhodozyma*.

Suitable host cells of filamentous fungi include all filamentous forms of the subdivision *Eumycotina*. Suitable cells of filamentous fungal genera include, but are not limited to, cells of *Acremonium, Aspergillus, Aureobasidium, Bjerkandera, Ceriporiopsis, Chrysoporium, Coprinus, Coriolus, Corynascus, Chaetomium, Cryptococcus, Filobasidium, Fusarium, Gibberella, Humicola, Hypocrea, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes*, and *Trichoderma*. Suitable cells can also include cells of various anamorph and teleomorph forms of these filamentous fungal genera.

Suitable cells of filamentous fungal species include, but are not limited to, cells of *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium lucknowense*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Coprinus cinereus*, *Coriolus hirsutus*, *Humicola insolens*, *Humicola lanuginosa*, *Mucor miehei*, *Myceliophthora thermophila*, *Neurospora crassa*, *Neurospora intermedia*, *Penicillium purpurogenum*, *Penicillium canescens*, *Penicillium solitum*, *Penicillium funiculosum*, *Phanerochaete chrysosporium*, *Phlebia radiate*, *Pleurotus eryngii*, *Talaromyces flavus*, *Thielavia terrestris*, *Trametes villosa*, *Trametes versicolor*, *Trichoderma harzianum*, *Trichoderma koningii*, *Trichoderma longibrachiatum*, *Trichoderma reesei*, and *Trichoderma viride*.

The disclosure further provides a recombinant host cell that is engineered to express one or more, two or more, three or more, four or more, or five or more of an Fv3A, a Pf43A, an Fv43E, an Fv39A, an Fv43A, an Fv43B, a Pa51A, a Gz43A, an Fo43A, an Af43A, a Pf51A, an AfuXyn2, an AfuXyn5 an Fv43D, a Pf43B, and an Fv51A polypeptide. The recombinant host cell is, for example, a recombinant *Trichoderma reesei* host cell. In a particular example, the disclosure provides a recombinant fungus, such as a recombinant *Trichoderma reesei*, that is engineered to express one or more, two or more, three or more, four or more, or five or more of an Fv3A, a Pf43A, an Fv43E, an Fv39A, an Fv43A, an Fv43B, a Pa51A, a Gz43A, an Fo43A, an Af43A, a Pf51A, an AfuXyn2, an AfuXyn5, an Fv43D, a Pf43B, and an Fv51A polypeptide. The disclosure provides a recombinant *Trichoderma reesei* host cell engineered to express 1, 2, 3, 4, 5, or more of an Fv3A, a Pf43A, an Fv43E, an Fv39A, an Fv43A, an Fv43B, a Pa51A, a Gz43A, an Fo43A, an Af43A, a Pf51A, an AfuXyn2, an AfuXyn5, an Fv43D, a Pf43B, and an Fv51A polypeptide.

The disclosure provides a host cell, for example, a recombinant fungal host cell or a recombinant filamentous fungus, engineered to recombinantly express at least one xylanase, at least one β-xylosidase, and one L-α-arabinofuranosidase. The disclosure also provides a recombinant host cell, e.g., a recombinant fungal host cell or a recombinant filamentous fungus such as a recombinant *Trichoderma reesei*, that is engineered to express 1, 2, 3, 4, 5, or more of an Fv3A, a Pf43A, an Fv43E, an Fv39A, an Fv43A, an Fv43B, a Pa51A, a Gz43A, an Fo43A, an Af43A, a Pf51A, an AfuXyn2, an AfuXyn5, an Fv43D, a Pf43B, and an Fv51A polypeptide, in addition to one or more of *Trichoderma reesei* Xyn2, *Trichoderma reesei* Xyn3, *Trichoderma reesei* Bxl1 and/or *Trichoderma reesei* Bgl1. The recombinant host cell is, for example, a *Trichoderma reesei* host cell. The recombinant fungus is, for example, a recombinant *Trichoderma reesei*. The disclosure provides a *Trichoderma reesei* host cell, or a recombinant *Trichoderma reesei* fungus, that is engineered to recombinantly express 1, 2, 3, 4, 5, or more of an Fv3A, a Pf43A, an Fv43E, an Fv39A, an Fv43A, an Fv43B, a Pa51A, a Gz43A, an Fo43A, an Af43A, a Pf51A, an AfuXyn2, an AfuXyn5, an Fv43D, a Pf43B, and an Fv51A polypeptide, in addition to recombinantly express one or more of *Trichoderma reesei* Xyn2, *Trichoderma reesei* Xyn3, *Trichoderma reesei* Bxl1 and/or *Trichoderma reesei* Bgl1.

The present disclosure also provides a recombinant host cell e.g., a recombinant fungal host cell or a recombinant organism, e.g., a filamentous fungus, such as a recombinant *Trichoderma reesei*, that is engineered to recombinantly express *Trichoderma reesei* Xyn3, *Trichoderma reesei* Bgl1, Fv3A, Fv43D, and Fv51A polypeptides. For example, the recombinant host cell is suitably a *Trichoderma reesei* host cell. The recombinant fungus is suitably a recombinant *Trichoderma reesei*. The disclosure provides, for example, a *Trichoderma reesei* host cell engineered to recombinantly express *Trichoderma reesei* Xyn3, *Trichoderma reesei* Bgl1, Fv3A, Fv43D, and Fv51A polypeptides.

Additionally the disclosure provides a recombinant host cell or recombinant fungus that is engineered to express an enzyme blend comprising suitable enzymes in ratios suitable for saccharification. The recombinant host cell is, for example, a fungal host cell. The recombinant fungus is, for example, a recombinant *Trichoderma reesei*. Exemplary enzyme ratios/amounts present in suitable enzyme blends are described in Section 6.3.4 below.

The disclosure further provides transgenic plants comprising a nucleic acid of the disclosure or an expression cassette of the disclosure. The transgenic plant can be, for example, a cereal plant, a corn plant, a potato plant, a tomato plant, a wheat plant, an oilseed plant, a rapeseed plant, a soybean plant, a rice plant, a barley plant, or a tobacco plant.

6.3 Enzyme Blends for Saccharification

The present disclosure provides a composition comprising an enzyme blend/composition that is capable of breaking down lignocellulose material. Such a multi-enzyme blend/composition comprises at least one polypeptide of the present disclosure, in combination with one or more additional polypeptides of the present disclosure, or one or more enzymes from other microorganisms, plants, or organisms. Synergistic enzyme combinations and related methods are contemplated. The disclosure includes methods for identifying the optimum ratios of the enzymes included in the blends/compositions for degrading a particular lignocellulosic material. These methods include, e.g., tests to identify the optimum enzyme blend/composition and ratios for efficient conversion of a given lignocellulosic substrate to its constituent sugars. The Examples below include assays that may be used to identify optimum ratios and blends/compositions of enzymes with which to degrade lignocellulosic materials.

6.3.1 Background

The cell walls of higher plants are comprised of a variety of carbohydrate polymer (CP) components. These CP interact through covalent and non-covalent means, providing the structural integrity required to form rigid cell walls and resist turgor pressure in plants. The major CP found in plants is cellulose, which forms the structural backbone of the cell wall. During cellulose biosynthesis, chains of poly-β-1,4-D-glucose self associate through hydrogen bonding and hydrophobic interactions to form cellulose microfibrils, which further self-associate to form larger fibrils. Cellulose microfibrils are often irregular structurally and contain regions of varying crystallinity. The degree of crystallinity of cellulose fibrils depends on how tightly ordered the hydrogen bonding is between and among its component cellulose chains. Areas with less-ordered bonding, and therefore more accessible glucose chains, are referred to as amorphous regions.

The general model for cellulose depolymerization to glucose involves a minimum of three distinct enzymatic activities. Endoglucanases cleave cellulose chains internally to shorter chains in a process that increases the number of accessible ends, which are more susceptible to exoglucanase activity than the intact cellulose chains. These exoglucanases (e.g., cellobiohydrolases) are specific for either reducing ends or non-reducing ends, liberating, in most cases, cellobiose, the dimer of glucose. The accumulating cellobiose is then subject to cleavage by cellobiases (e.g., β-1,4-glucosidases) to glucose.

Cellulose contains only anhydro-glucose. In contrast, hemicellulose contains a number of different sugar monomers. For instance, aside from glucose, sugar monomers in hemicellulose can also include xylose, mannose, galactose, rhamnose, and arabinose. Hemicelluloses mostly contain D-pentose sugars and occasionally small amounts of L-sugars. Xylose is typically present in the largest amount, but mannuronic acid and galacturonic acid also tend to be present. Hemicelluloses include xylan, glucuronoxylan, arabinoxylan, glucomannan, and xyloglucan.

The enzymes and multi-enzyme compositions of the disclosure are useful for saccharification of hemicellulose materials, including, e.g., xylan, arabinoxylan, and xylan- or arabinoxylan-containing substrates. Arabinoxylan is a polysaccharide composed of xylose and arabinose, wherein L-α-arabinofuranose residues are attached as branch-points to a β-(1,4)-linked xylose polymeric backbone.

Most biomass sources are rather complex, containing cellulose, hemicellulose, pectin, lignin, protein, and ash, among other components. Accordingly, in certain aspects, the present disclosure provides enzyme blends/compositions containing enzymes that impart a range or variety of substrate specificities when working together to degrade biomass into fermentable sugars in the most efficient manner. One example of a multi-enzyme blend/composition of the present invention is a mixture of cellobiohydrolase(s), xylanase(s), endoglucanase(s), β-glucosidase(s), β-xylosidase(s), and, optionally, accessory proteins. The enzyme blend/composition is suitably a non-naturally occurring composition.

Accordingly, the disclosure provides enzyme blends/compositions (including products of manufacture) comprising a mixture of xylan-hydrolyzing, hemicellulose- and/or cellulose-hydrolyzing enzymes, which include at least one, several, or all of a cellulase, including a glucanase; a cellobiohydrolase; an L-α-arabinofuranosidase; a xylanase; a β-glucosidase; and a β-xylosidase. Preferably each of the enzyme blends/compositions of the disclosure comprises at least one enzyme of the disclosure. The present disclosure also provides enzyme blends/compositions that are non-naturally occurring compositions. As used herein, the term "enzyme blends/compositions" refers to:

(1) a composition made by combining component enzymes, whether in the form of a fermentation broth or partially or completely isolated or purified;
(2) a composition produced by an organism modified to express one or more component enzymes; in certain embodiments, the organism used to express one or more component enzymes can be modified to delete one or more genes; in certain other embodiments, the organism used to express one or more component enzymes can further comprise proteins affecting xylan hydrolysis, hemicellulose hydrolysis, and/or cellulose hydrolysis;
(3) a composition made by combining component enzymes simultaneously, separately, or sequentially during a saccharification or fermentation reaction; and
(4) an enzyme mixture produced in situ, e.g., during a saccharification or fermentation reaction;
(5) a composition produced in accordance with any or all of the above (1)-(4).

The term "fermentation broth" as used herein refers to an enzyme preparation produced by fermentation that undergoes no or minimal recovery and/or purification subsequent to fermentation. For example, microbial cultures are grown to saturation, incubated under carbon-limiting conditions to allow protein synthesis (e.g., expression of enzymes). Then, once the enzyme(s) are secreted into the cell culture media, the fermentation broths can be used. The fermentation broths of the disclosure can contain unfractionated or fractionated contents of the fermentation materials derived at the end of the fermentation. For example, the fermentation broths of the invention are unfractionated and comprise the spent culture medium and cell debris present after the microbial cells (e.g., filamentous fungal cells) undergo a fermentation process. The fermentation broth can suitably contain the spent cell culture media, extracellular enzymes, and live or killed microbial cells. Alternatively, the fermentation broths can be fractionated to remove the microbial cells. In those cases, the fermentation broths can, for example, comprise the spent cell culture media and the extracellular enzymes.

Any of the enzymes described specifically herein can be combined with any one or more of the enzymes described herein or with any other available and suitable enzymes, to produce a suitable multi-enzyme blend/composition. The disclosure is not restricted or limited to the specific exemplary combinations listed below.

6.3.2 Biomass

The disclosure provides methods and processes for biomass saccharification, using enzymes, enzyme blends/compositions of the disclosure. The term "biomass," as used herein, refers to any composition comprising cellulose and/or hemicellulose (optionally also lignin in lignocellulosic biomass materials). As used herein, biomass includes, without limitation, seeds, grains, tubers, plant waste or byproducts of food processing or industrial processing (e.g., stalks), corn (including, e.g., cobs, stover, and the like), grasses (including, e.g., Indian grass, such as *Sorghastrum nutans*; or, switchgrass, e.g., *Panicum* species, such as *Panicum virgatum*), wood (including, e.g., wood chips, processing waste), paper, pulp, and recycled paper (including, e.g., newspaper, printer paper, and the like). Other biomass materials include, without limitation, potatoes, soybean (e.g., rapeseed), barley, rye, oats, wheat, beets, and sugar cane bagasse.

The disclosure provides methods of saccharification comprising contacting a composition comprising a biomass material, for example, a material comprising xylan, hemicellulose, cellulose, and/or a fermentable sugar, with a polypeptide of the disclosure, or a polypeptide encoded by a nucleic acid of the disclosure, or any one of the enzyme blends/compositions, or products of manufacture of the disclosure.

The saccharified biomass (e.g., lignocellulosic material processed by enzymes of the disclosure) can be made into a number of bio-based products, via processes such as, e.g., microbial fermentation and/or chemical synthesis. As used herein, "microbial fermentation" refers to a process of growing and harvesting fermenting microorganisms under suitable conditions. The fermenting microorganism can be any microorganism suitable for use in a desired fermentation process for the production of bio-based products. Suitable fermenting microorganisms include, without limitation, filamentous fungi, yeast, and bacteria. The saccharified biomass can, for example, be made it into a fuel (e.g., a biofuel such as a bioethanol, biobutanol, biomethanol, a biopropanol, a biodiesel, a jet fuel, or the like) via fermentation and/or chemical synthesis. The saccharified biomass can, for example, also be made into a commodity chemical (e.g., ascorbic acid, isoprene, 1,3-propanediol), lipids, amino acids, proteins, and enzymes, via fermentation and/or chemical synthesis.

6.3.3. Pretreatment

Prior to saccharification, biomass (e.g., lignocellulosic material) is preferably subject to one or more pretreatment step(s) in order to render xylan, hemicellulose, cellulose and/or lignin material more accessible or susceptable to enzymes and thus more amenable to hydrolysis by the enzyme(s) and/or enzyme blends/compositions of the disclosure.

In an exemplary embodiment, the pretreatment entails subjecting biomass material to a catalyst comprising a dilute solution of a strong acid and a metal salt in a reactor. The biomass material can, e.g., be a raw material or a dried material. This pretreatment can lower the activation energy, or the temperature, of cellulose hydrolysis, ultimately allowing higher yields of fermentable sugars. See, e.g., U.S. Pat. Nos. 6,660,506; 6,423,145.

Another exemplary pretreatment method entails hydrolyzing biomass by subjecting the biomass material to a first hydrolysis step in an aqueous medium at a temperature and a pressure chosen to effectuate primarily depolymerization of hemicellulose without achieving significant depolymerization of cellulose into glucose. This step yields a slurry in which the liquid aqueous phase contains dissolved monosaccharides resulting from depolymerization of hemicellulose, and a solid phase containing cellulose and lignin. The slurry is then subject to a second hydrolysis step under conditions that allow a major portion of the cellulose to be depolymerized, yielding a liquid aqueous phase containing dissolved/soluble depolymerization products of cellulose. See, e.g., U.S. Pat. No. 5,536,325.

A further exemplary method involves processing a biomass material by one or more stages of dilute acid hydrolysis using about 0.4% to about 2% of a strong acid; followed by treating the unreacted solid lignocellulosic component of the acid hydrolyzed material with alkaline delignification. See, e.g., U.S. Pat. No. 6,409,841.

Another exemplary pretreatment method comprises prehydrolyzing biomass (e.g., lignocellulosic materials) in a prehydrolysis reactor; adding an acidic liquid to the solid lignocellulosic material to make a mixture; heating the mixture to reaction temperature; maintaining reaction temperature for a period of time sufficient to fractionate the lignocellulosic material into a solubilized portion containing at least about 20% of the lignin from the lignocellulosic material, and a solid fraction containing cellulose; separating the solubilized portion from the solid fraction, and removing the solubilized portion while at or near reaction temperature; and recovering the solubilized portion. The cellulose in the solid fraction is rendered more amenable to enzymatic digestion. See, e.g., U.S. Pat. No. 5,705,369.

Further pretreatment methods can involve the use of hydrogen peroxide $H_2O_2$-See Gould, 1984, Biotech, and Bioengr. 26:46-52.

Pretreatment can also comprise contacting a biomass material with stoichiometric amounts of sodium hydroxide and ammonium hydroxide at a very low concentration. See Teixeira et al., 1999, Appl. Biochem. and Biotech. 77-79: 19-34.

Pretreatment can also comprise contacting a lignocellulose with a chemical (e.g., a base, such as sodium carbonate or potassium hydroxide) at a pH of about 9 to about 14 at moderate temperature, pressure, and pH. See PCT Publication WO2004/081185.

Ammonia is used, for example, in a preferred pretreatment method. Such a pretreatment method comprises subjecting a biomass material to low ammonia concentration under conditions of high solids. See, e.g., U.S. Patent Publication No. 20070031918 and PCT publication WO 06110901.

6.3.4 Exemplary Enzyme Blends

The present disclosure provides enzyme blends/compositions comprising one or more enzymes of the disclosure. One or more enzymes of the enzyme blends/compositions can be produced by a recombinant host cell or a recombinant organism. The enzyme blends/compositions are suitably non-naturally occurring compositions.

An enzyme blend/composition of the disclosure can suitably comprise a first polypeptide having β-xylosidase activity, and further comprises 1, 2, 3, or 4 of a second polypeptide having β-xylosidase activity, one or more polypeptides having L-α-arabinofuranosidase activity, one or more polypeptides having xylanase activity, and one or more polypeptides having cellulase activity. The first polypeptide having β-xylosidase activity is, for example, an Fv3A, a Pf43A, an Fv43E, an Fv43A, an Fv43B, a Pa51A, a Gz43A, an Fo43A, or an Fv39A polypeptide. The second polypeptide having 1-xylosidase activity, if present, is, for example, different from the first polypeptide having β-xylosidase activity, and is suitably an Fv3A, a Pf43A, an Fv43E, an Fv43A, an Fv43B, a Pa51A, a Gz43A, an Fv43D, an Fo43A, an Fv39A, or a Trichoderma reesei Bxl1 polypeptide. Each of the one or more polypeptides having L-α-arabinofuranosidase activity, if present, is, for example, an Af43A, a Pf51A, a Pa51A, an Fv43B, or an Fv51A polypeptide. Each of the one or more polypeptides having xylanase activity is, for example, a Trichoderma reesei Xyn, a Trichoderma reesei Xyn2, an AfuXyn2, or an AfuXyn5. Each of the one or more polypeptides having cellulase activity, if present, is, for example, an endoglucanase, for example, a Trichoderma reesei EG1 or EG2, a cellobiohydrolase, for example, a Trichoderma reesei CBH1 or CBH2, or a β-glucosidase, for example, a Trichoderma reesei Bgl1.

Another enzyme blend/composition of the disclosure can suitably comprise a first polypeptide having L-α-arabinofuranosidase activity, and further comprises 1, 2, 3, or 4 of a second polypeptide having L-α-arabinofuranosidase activity, one or more polypeptides having β-xylosidase activity, one or more polypeptides having xylanase activity, and/or one or more polypeptides having cellulase activity. The first L-α-arabinofuranosidase is an Af43A, a Pf51A, or an Fv51A polypeptide. The second L-α-arabinofuranosidase is different from the first L-α-arabinofuranosidase, and is, for example, an Af43A, a Pf51A, a Pa51A, an Fv43B, or an Fv51A polypeptide. Each of the one or more β-xylosidases is, for example, an Fv3A, a Pf43A, an Fv43E, an Fv43A, an Fv43B, a Pa51A, an Fv43D, a Gz43A, an Fo43A, an Fv39A, or a Trichoderma reesei Bxl1 polypeptide. In certain embodiments, each of the one or more xylanases is a Trichoderma reesei Xyn3, a Trichoderma reesei Xyn2, an AfuXyn2, or an AfuXyn5 polypeptide. In certain embodiments, each of the one or more cellulases is independently an endoglucanase, for example, a *Trichoderma reesei* EG1 or EG2 polypeptide, a cellobiohydrolase, for example, a *Trichoderma reesei* CBH1 or CBH2 polypeptide, or a β-glucosidase, for example, a *Trichoderma reesei* Bgl1 polypeptide.

Xylanases:

The xylanase(s) suitably constitutes about 0.05 wt. % to about 75 wt. % of the enzymes in an enzyme blend/composition of the disclosure (i.e., the percentage xylanase(s) is a weight percentage relative to the weight of all proteins in the composition) or a relative weight basis (i.e., wherein the percentage xylanase(s) is a weight percentage relative to the combined weight of xylanases, β-xylosidases, cellulases, L-α-arabinofuranosidases, and accessory proteins). The ratio of any pair of proteins relative to each other can be readily calculated in the enzyme blends/compositions of the disclosure. Blends/compositions comprising enzymes in any weight ratio derivable from the weight percentages disclosed herein are contemplated. The xylanase content can be in a range wherein the lower limit is 0.05 wt. %, 1 wt. %, 2 wt. %, 3 wt. %, 4 wt. %, 5 wt. %, 6 wt. %, 7 wt. %, 8 wt. %, 9 wt. %, 10 wt. %, 12 wt. %, 15 wt. %, 20 wt. %, 25 wt. %, 30 wt. %, 40 wt. %, 45 wt. %, or 50 wt. % of the total weight of enzymes in the enzyme blend/composition, and the upper limit is 10 wt. %, 15 wt. %, 20 wt. %, 25 wt. %, 30 wt. %, 35 wt. %, 40 wt. %, 50 wt. %, 55 wt. %, 60 wt. %, 65 wt. %, 70 wt. %, or 75 wt. % of the total weight of enzymes in the enzyme blend/composition. The one or more xylanases in an enzyme blend or composition can represent, for example, 5 wt. % to 20 wt. %, 10 wt. % to 15 wt. %, or 15 wt. % to 25 wt. % of the total enzymes in the enzyme blend/composition. Exemplary suitable xylanases for inclusion in the enzyme blends/compositions of the disclosure are described in Section 6.3.6 below.

L-α-arabinofuranosidases:

The L-α-arabinofuranosidase(s) suitably constitutes about 0.05 wt. % to about 75 wt. % of the total weight of all enzymes in a given enzyme blend/composition (i.e., wherein the percentage L-α-arabinofuranosidase(s) is a weight percentage relative to the weight of all proteins in the blend/composition) or a relative weight basis (i.e., wherein the percentage L-α-arabinofuranosidase(s) is a weight percentage relative to the combined weight of xylanases, β-xylosidases, cellulases, L-α-arabinofuranosidases, and accessory proteins). The ratio of any pair of proteins relative to each other can be readily calculated based on the disclosure. Blends/compositions comprising enzymes in any weight ratio derivable from the weight percentages disclosed herein are contemplated. The L-α-arabinofuranosidase content can be in a range wherein the lower limit is 0.05 wt. %, 1 wt. %, 2 wt. %, 3 wt. %, 4 wt. %, 5 wt. %, 6 wt. % 7 wt. %, 8 wt. %, 9 wt. %, 10 wt. %, 12 wt. %, 15 wt. %, 20 wt. %, 25 wt. %, 30 wt. %, 40 wt. %, 45 wt. %, or 50 wt. % of the total weight of enzymes in the blend/composition, and the upper limit is 10 wt. %, 15 wt. %, 20 wt. %, 25 wt. %, 30 wt. %, 35 wt. %, 40 wt. %, 50 wt. %, 55 wt. %, 60 wt. %, 65 wt. %, 70 wt. % or 75 wt. % of the total weight of enzymes in the blend/composition. For example, the one or more L-α-arabinofuranosidase(s) can suitably represent 2 wt. % to 25 wt. %; 5 wt. % to 20 wt. %; or 5 wt. % to 10 wt. % of the total weight of enzymes in the blend/composition. Exemplary suitable L-α-arabinofuranosidase(s) for inclusion in the enzyme blends/compositions of the disclosure are described in Section 6.3.8 below.

β-Xylosidases:

The β-xylosidase(s) suitably constitutes about 0.05 wt. % to about 75 wt. % of the total weight of enzymes in an enzyme blend/composition. The ratio of any pair of proteins relative to each other can be readily calculated based on the disclosure herein. Blends/compositions comprising enzymes in any weight ratio derivable from the weight percentages disclosed herein are contemplated. The β-xylosidase content can be in a range wherein the lower limit is about 0.05 wt. %, 1 wt. %, 2 wt. %, 3 wt. %, 4 wt. %, 5 wt. %, 6 wt. % 7 wt. %, 8 wt. %, 9 wt. %, 10 wt. %, 12 wt. %, 15 wt. %, 20 wt. %, 25 wt. %, 30 wt. %, 40 wt. %, 45 wt. %, or 50 wt. % of the total weight of enzymes in the blend/composition, and the upper limit is about 10 wt. %, 15 wt. %, 20 wt. %, 25 wt. %, 30 wt. %, 35 wt. %, 40 wt. %, 50 wt. %, 55 wt. %, 60 wt. %, 65 wt. %, 70 wt. %, or 75 wt. % of the total weight of enzymes in the blend/composition. For example, the β-xylosidase(s) can represent about 0.05 wt. % to about 75 wt. % of the total weight of enzymes in the blend/composition. Also, the β-xylosidase(s) can represent 0.05 wt. % to about 70 wt. %, about 1 wt. % to about 65 wt. %, about 1 wt. % to about 60 wt. %, about 2 wt. % to about 55 wt %, about 3 wt. % to about 50 wt. %, about 4 wt. % to about 45 wt. %, or about 5 wt. % to about 40 wt. % of the total weight of enzymes in the blend/composition. In yet a further example, the β-xylosidase(s) suitably represent 2 wt. % to 30 wt. %; 10 wt. % to 20 wt. %; or 5 wt. % to 10 wt. % of the total weight of enzymes in the blend/composition. Exemplary suitable β-xylosidase(s) are described in Section 6.3.7 below.

Cellulases:

The cellulase(s) suitably constitutes about 0.05 wt. % to about 90 wt. % of the total weight of enzymes in an enzyme blend/composition. Ratio of any pair of proteins relative to each other can be readily calculated based on the disclosure herein. Blends/compositions comprising enzymes in any weight ratio derivable from the weight percentages disclosed herein are contemplated. The cellulase content can be in a range wherein the lower limit is about 0.05 wt. %, 5 wt. %, 10 wt. %, 20 wt. %, 30 wt. %, 40 wt. %, 50 wt. %, 60 wt. %, 70 wt. % of the total weight of enzymes in the blend/composition, and the upper limit is about 20 wt. %, 30 wt. %, 40 wt. %, 50 wt. %, 60 wt. %, 70 wt. %, 80 wt. %, or 90 wt. % of the total weight of enzymes in the blend/composition. For example, the cellulase(s) suitably represents 30 wt. % to 80 wt. %, 50 wt. % to 70 wt. %, or 40 wt. % to 60 wt. % of the total weight of enzymes in the blend/composition. Exemplary suitable cellulases are described in Section 6.3.5 below. The cellulase components in an enzyme blend/composition of the disclosure are suitably capable of achieving at least about 0.005 fraction product per mg protein per gram of phosphoric acid swollen cellulose (PASC) as determined by a calcofluor assay. For example, the cellulase components in a blend/composition of the disclosure are capable of achieving a range of fraction product per mg protein per gram of PASC, wherein the lower limit of the range is about 0.005, 0.01, 0.015, 0.02, 0.03, 0.04, 0.05, 0.06, 0.075, or 0.1, and wherein the upper limit of the range is, 0.03, 0.04, 0.05, 0.06, 0.075, 0.1, 0.2, 0.3, 0.4, 0.5, 0.6, or 0.7. The cellulase components in a blend/composition of the disclosure can, for example, achieve 0.00005-0.0001, 0.0005-0.001, 0.001-0.005, 0.005-0.03, 0.01-0.06, 0.02-0.04, 0.01-0.03, 0.02-0.05, 0.02-0.04, 0.01-0.05, 0.015-0.035, or 0.015-0.075 product fraction product per mg protein per gram PASC as determined by a calcofluor assay. The cellulase can be, for example, a whole cellulase. The cellulase can also, for example, suitably be enriched with a 1-glucosidase.

Accessory Proteins:

The enzyme blend/composition may suitably further comprise one or more accessory proteins. The accessory protein content of an enzyme blend/composition can range from about 0 wt. % to about 60 wt. % of the total weight of proteins in an enzyme blend/composition. Ratio of any pair of proteins relative to each other can be readily determined based on the disclosure herein. Blends/compositions comprising enzymes in any weight ratio derivable from the weight percentages disclosed herein are contemplated. The accessory protein content can be in a range wherein the lower limit is 0 wt. %, 1 wt. %, 2 wt. %, 3 wt. %, 4 wt. %, 5 wt. %, 6 wt. %, 7 wt. %, 8 wt. %, 10 wt. %, 12 wt. %, 15 wt. %, 20 wt. %, 25 wt. %, or 35 wt. % of the total weight of proteins in the enzyme blend/composition, and the upper limit is 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. % 15 wt. %, 20 wt. %, 30 wt. %, 40 wt. %, 50 wt. %, or 60 wt. % of the total weight of proteins in the enzyme blend/composition. For example, the accessory protein(s) can suitably represent 0 wt. % to 2 wt. %, 5 wt. % to 10 wt. %, 20 wt. % to 50 wt. %, or 2 wt. % to 5 wt. % in the enzyme blend/composition. Exemplary suitable accessory proteins for inclusion in the enzyme blends/compositions of the disclosure are described in Section 6.3.9 below.

The present disclosure provides a first enzyme blend/composition for lignocellulose saccharification comprising:
(1) about 30 wt. % to about 80 wt. % (e.g., 30 wt. % to 80 wt. %, 35 wt. % to 75 wt. %, 40 wt. % to 70 wt. %, 40 wt. % to 60 wt. %, 50 wt. % to 70 wt. %, etc.) cellulase(s), e.g., whole cellulase or β-glucosidase enriched whole cellulase;
(2) about 3 wt. % to about 50 wt. % (e.g., 5 wt. % to 40 wt. %, 10 wt. % to 30 wt. %, 5 wt. % to 20 wt. %, 10 wt. % to 15 wt. %, 15 wt. % to 25 wt. %, etc.) xylanase(s), e.g., a Trichoderma reesei Xyn2, a Trichoderma reesei Xyn3, an AfuXyn2, an AfuXyn5, or a mixture of two or more of the foregoing enzymes;
(3) about 2 wt. % to about 40 wt. % (e.g., 2 wt. % to 35 wt. %, 5 wt. % to 30 wt. %, 10 wt. % to 25 wt. %, 2 wt. % to 30 wt. %, 10 wt. % to 20 wt. %, 5 wt. % to 10 wt. %, etc.) β-xylosidase(s), e.g., an Fv3A, a Pf43A, an Fv43D, an Fv39A, an Fv43E, an Fv43A, an Fv43B, a Pa51A, an Fo43A, a Gz43A, a Trichoderma reesei Bxl1, or a mixture of two or more of the foregoing enzymes;
(4) about 2 wt. % to about 40 wt. % (e.g., 2 wt. % to 35 wt. %, 5 wt. % to 30 wt. %, 10 wt. % to 25 wt. %, 2 wt. % to 25 wt. %, 5 wt. % to 20 wt. %, 5 wt. % to 10 wt. %, etc) L-α-arabinofuranosidase(s), e.g., an Af43A, an Fv43B, a Pa51A, a Pf51A, an Fv51A, or a mixture of two or more of the foregoing enzymes; and
(5) about 0 wt. % to about 50 wt. % (2 wt. % to 40 wt. %, 5 wt. % to 30 wt. %, 10 wt. % to 25 wt. %, 0 wt. % to 2 wt. %, 5 wt. % to 10 wt. %, 20 wt. % to 50 wt. %, 2 wt. % to 5 wt. %, etc) accessory protein(s).

The present disclosure provides a second enzyme blend/composition for lignocellulose saccharification comprising:
(1) about 30 wt. % to about 80 wt. % (e.g., 30 wt. % to 80 wt. %, 35 wt. % to 75 wt. %, 40 wt. % to 70 wt. %, 40 wt. % to 60 wt. %, 50 wt. % to 70 wt. %, etc.) cellulase(s), e.g., whole cellulase or β-glucosidase enriched whole cellulase, or about 2 wt. % to about 10 wt. % (e.g., 2 wt. % to 8 wt. %, 4 wt. % to 6 wt. %, 2 wt. % to 4 wt. %, 6 wt. % to 8 wt. %, 8 wt. % to 10 wt. %, 2 wt. % to 10 wt. %, etc) β-glucosidase(s), e.g., a Trichoderma reesei Bgl1;
(2) about 3 wt. % to about 50 wt. % (e.g., 5 wt. % to 40 wt. %, 10 wt. % to 30 wt. %, 5 wt. % to 20 wt. %, 10 wt. % to 15 wt. %, 15 wt. % to 25 wt. %, etc.) xylanase(s), e.g., a Trichoderma reesei Xyn2, a Trichoderma reesei Xyn3, an AfuXyn2, an AfuXyn5, or a mixture of two or more of the foregoing enzymes;
(3) about 2 wt. % to about 40 wt. % (e.g., 2 wt. % to 35 wt. %, 5 wt. % to 30 wt. %, 10 wt. % to 25 wt. %, 2 wt. % to 30 wt. %, 10 wt. % to 20 wt. %, 5 wt. % to 10 wt. %, etc.) of at least two β-xylosidase(s), wherein at least one β-xylosidase is selected from Group 1 and at least one β-xylosidase is selected from Group 2;
wherein:
Group 1: an Fv3A, an Fv43A, or a mixture thereof;
Group 2: an Fv43D, a Pa51A, a Gz43A, a Trichoderma reesei Bxl1, a Pf43A, an Fv43E, an Fv39A, an Fo43A, an Fv43B, or a mixture of two or more of the foregoing enzymes;
(4) about 2 wt. % to about 25 wt. % (e.g., 2 wt. % to 25 wt. %, 5 wt. % to 20 wt. %, 5 wt. % to 10 wt. %, etc) L-α-arabinofuranosidase(s), e.g., an Af43A, an Fv43B, a Pa51A, a Pf51A, Fv51A, or a mixture of two or more of the foregoing enzymes; and
(5) about 0 wt. % to about 50 wt. % (2 wt. % to 40 wt. %, 5 wt. % to 30 wt. %, 10 wt. % to 25 wt. %, 0 wt. % to 2 wt. %, 5 wt. % to 10 wt. %, 20 wt. % to 50 wt. %, 2 wt. % to 5 wt. %, etc) accessory protein(s).

The present disclosure provides a third enzyme blend/composition for lignocellulose saccharification comprising:
(1) about 3 wt. % to about 50 wt. % (e.g., 5 wt. % to 40 wt. %, 10 wt. % to 30 wt. %, 5 wt. % to 20 wt. %, 10 wt. % to 15 wt. %, 15 wt. % to 25 wt. %, etc.) xylanase(s), e.g., a Trichoderma reesei Xyn2, a Trichoderma reesei Xyn3, an AfuXyn2, an AfuXyn5, or a mixture of two or more of the foregoing enzymes; and
(2) about 2 wt. % to 40 wt. % (e.g., 2 wt. % to 35 wt. %, 5 wt. % to 30 wt. %, 10 wt. % to 25 wt. %, 2 wt. % to 30 wt. %, 10 wt. % to 20 wt. %, 5 wt. % to 10 wt. %, etc.) of at least two β-xylosidase(s), wherein at least one β-xylosidase is selected from Group 1 and at least one β-xylosidase is selected from Group 2;
wherein:
Group 1: an Fv3A, an Fv43A, or a mixture thereof;
Group 2: an Fv43D, a Pa51A, a Gz43A, a Trichoderma reesei Bxl1, a Pf43A, an Fv43E, an Fv39A, an Fo43A, an Fv43B, or a mixture of two or more of the foregoing enzymes.

The present disclosure provides a fourth enzyme blend/composition for lignocellulose saccharification comprising:
(1) about 5 wt. % to about 25 wt. % (e.g., 2 wt. % to 25 wt. %, 5 wt. % to 20 wt. %, 5 wt. % to 10 wt. %, etc) xylanase(s), e.g., a Trichoderma reesei Xyn2, a Trichoderma reesei Xyn3, an AfuXyn2, an AfuXyn5, or a mixture of two or more of the foregoing enzymes;
(2) about 2 wt. % to about 30 wt. % (e.g., 2 wt. % to 30 wt. %, 10 wt. % to 20 wt. %, 5 wt. % to 10 wt. %, etc.) β-xylosidase(s), e.g., an Fv3A, a Pf43A, an Fv43D, an Fv39A, an Fv43E, an Fv43A, an Fv43B, a Pa51A, a Gz43A, an Fo43A, a Trichoderma reesei Bxl1, or a mixture of two or more of the foregoing enzymes; and
(3) about 2 wt. % to about 50 wt. % (e.g., 2 wt. % to 5 wt. %, 5 wt. % to 45 wt. %, 10 wt. % to 40 wt. %, 15 wt. % to 30 wt. %, 10 wt. % to 25 wt. %, 5 wt. % to 20 wt. %, 15 wt. % to 40 wt. %, etc) β-glucosidase(s), e.g., a Trichoderma reesei Bgl1.

The present disclosure provides a fifth enzyme blend/composition for lignocellulose saccharification comprising:

(1) about 5 wt. % to about 25 wt. % (e.g., 2 wt. % to 25 wt. %, 5 wt. % to 20 wt. %, 5 wt. % to 10 wt. %, etc) xylanase(s), e.g., a *Trichoderma reesei* Xyn2, a *Trichoderma reesei* Xyn3, an AfuXyn2, an AfuXyn5, or a mixture of two or more of the foregoing enzymes; and (2) about 2 wt. % to about 30 wt. % (e.g., 2 wt. % to 30 wt. %, 10 wt. % to 20 wt. %, 5 wt. % to 10 wt. %, etc.) β-xylosidase(s), e.g., an Fv3A, a Pf43A, an Fv43D, an Fv39A, an Fv43E, an Fv43A, an Fv43B, a Pa51A, a Gz43A, an Fo43A, a *Trichoderma reesei* Bxl1, or a mixture of two or more of the foregoing enzymes.

The present disclosure provides a sixth enzyme blend/composition for lignocellulose saccharification comprising:

(1) about 2 wt. % to about 50 wt. % (e.g., 2 wt. % to 5 wt. %, 5 wt. % to 45 wt. %, 10 wt. % to 40 wt. %, 15 wt. % to 30 wt. %, 10 wt. % to 25 wt. %, 5 wt. % to 20 wt. %, 15 wt. % to 40 wt. %, etc) β-glucosidase(s), e.g., a Bgl1;

(2) about 3 wt. % to about 50 wt. % (e.g., 5 wt. % to 40 wt. %, 10 wt. % to 30 wt. %, 5 wt. % to 20 wt. %, 10 wt. % to 15 wt. %, 15 wt. % to 25 wt. %, etc.) xylanase(s), e.g., a *Trichoderma reesei* Xyn2, a *Trichoderma reesei* Xyn3, an AfuXyn2, an AfuXyn5, or a mixture of two or more of the foregoing enzymes;

(3) about 2 wt. % to 40 wt. % (e.g., 2 wt. % to 35 wt. %, 5 wt. % to 30 wt. %, 10 wt. % to 25 wt. %, 2 wt. % to 30 wt. %, 10 wt. % to 20 wt. %, 5 wt. % to 10 wt. %, etc.) β-xylosidase(s), e.g., an Fv3A, a Pf43A, an Fv43D, an Fv39A, an Fv43E, an Fv43A, an Fv43B, a Pa51A, a Gz43A, an Fo43A, a *Trichoderma reesei* Bxl1, or a mixture of two or more of the foregoing enzymes; and (4) about 2 wt. % to about 25 wt. % (e.g., 2 wt. % to 25 wt. %, 5 wt. % to 20 wt. %, 5 wt. % to 10 wt. %, etc) L-α-arabinofuranosidase(s), e.g., an Af43A, an Fv43B, a Pa51A, a Pf51A, Fv51A, or a mixture of two or more of the foregoing enzymes.

The sixth enzyme blend/composition for lignocellulose saccharification above can, for example, comprise about 2 wt. % to about 40 wt. % of at least two β-xylosidase, wherein at least one β-xylosidase is selected from Group 1 and at least one β-xylosidase is selected from Group 2; wherein:

Group 1: an Fv3A, an Fv43A, or a mixture thereof;
Group 2: an Fv43D, a Pa51A, a Gz43A, a *Trichoderma reesei* Bxl1, a Pf43A, an Fv43E, an Fv39A, an Fo43A, an Fv43B, or a mixture of two or more of the foregoing enzymes.

Where an enzyme blend/composition of the disclosure contains both Group 1 and a Group 2 β-xylosidases, the ratio of Group 1 to Group 2 β-xylosidases is preferably 1:10 to 10:1. For example, the ratio is suitably 1:2 to 2:1, 2:5 to 5:2, 3:8 to 8:3, 1:4 to 4:1, 1:5 to 5:1, 1:7 to 7:1, or any range between any pair the foregoing endpoints (e.g., 1:10 to 2:1, 4:1 to 2:5, 3:8 to 5:1, etc.). A particular example of a suitable ratio is approximately 1:1.

Where an enzyme blend/composition of the disclosure contains an Fv43A as a β-xylosidase, the blend/composition can further contain Fv43B as an L-α-arabinofuranosidase.

An enzyme blend/composition of the disclosure is, for example, suitably part of a saccharification reaction mixture containing biomass in addition to the components of the enzyme blend/composition. For example, the saccharification reaction mixture can be characterized by 1, 2, 3 or all 4 of the following features:

(1) the total weight of xylanase(s) per kg of hemicellulase in said saccharification reaction mixture is in a range in which the lower limit is about 0.5 g, 1 g, 2 g, 3 g, 4 g, 5 g, 7 g, or 10 g, and the upper limit is independently about 5 g, 7 g, 10 g, 15 g, 20 g, 30 g, or 40 g; for example, the total weight of xylanase(s) per kg of hemicellulase in the reaction mixture can be 0.5 g to 40 g, 0.5g to 30 g, 0.5 g to 20 g, 0.5 to 10 g, 0.5 to 5 g, 1 g to 40 g, 2 g to 40 g, 3 g to 40 g, 5 g to 40 g, 7 g to 30 g, 10g to 30 g, 5 g to 20 g, or 5 g to 30 g.

(ii) the total weight of β-xylosidase(s) per kg of hemicellulase in said saccharification reaction mixture is in a range in which the lower limit is about 0.5 g, 1 g, 2 g, 3 g, 4 g, 5 g, 7 g, or 10 g and the upper limit is independently about 5 g, 7 g, 10 g, 15 g, 20 g, 30 g, 40 g, or 50 g; for example, the total weight of β-xylosidase(s) per kg of hemicellulase in the reaction mixture can be 0.5 g to 40 g, 0.5 to 50 g, 0.5 g to 30 g, 0.5 g to 20 g, 0.5 g to 10 g, 0.5 g to 5g, 1 g to 40 g, 2 g to 40 g, 3 g to 40 g, 5 g to 40 g, 7 g to 30 g, 10g, to 30 g, 5 g to 30 g, 5 g to 20g.

(iii) the total weight of L-α-arabinofuranosidase(s) per kg of hemicellulase in said saccharification reaction mixture is in a range in which the lower limit is about 0.2 g, 0.5 g, 1 g, 1.5 g, 2 g, 2.5 g, 3 g, 4 g, or 5 g and the upper limit is independently about 2 g, 3 g, 4 g, 5 g, 7 g, 10 g, 15 g, or 20 g; for example, the total weight of L-α-arabinofuranosidase(s) per kg of hemicellulase in the reaction mixture can be 0.2 g to 20 g, 0.5 g to 20 g, 1 g to 20 g, 2 g to 20 g, 2.5 g to 20 g, 3 g to 15 g, 4 g to 20 g, 5 g to 15 g, 5 g to 10g, 5 g to 20 g, or 2.5 g to 15g.

(iv) the total weight of cellulase(s) per kg of cellulase in said saccharification reaction mixture is in a range in which the lower limit is about 1 g, 3 g, 5 g, 7 g, 10 g, 12 g, 15 g, 18 g, or 20g, and the upper limit is independently about 10 g, 15 g, 18 g, 20 g, 25 g, 30g, 50 g, 75 g, or 100g; for example, the total weight of cellulase(s) per kg of cellulase in said reaction mixture can be 1 g to 100 g, 3 g to 100 g, 5 g to 100 g, 7 g to 100 g, 12 g to 100 g, 15g to 100 g, 18 g to 100 g, 3 g to 75 g, 5 g to 50 g, 7 g to 75 g, 10 g to 75 g, 10 g to 50 g, 12 g to 75 g, 12 g to 50 g, 15 g to 75 g, 15 g to 50 g, 18 g to 30 g, 18 g to 75 g.

6.3.5. Cellulases

The enzyme blends/compositions of the disclosure can comprise one or more cellulases. Cellulases are enzymes that hydrolyze cellulose (β-1,4-glucan or β D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and β-glucosidases (β-D-glucoside glucohydrolase; EC 3.2.1.21) ("BG") (Knowles et al., 1987, Trends in Biotechnology 5(9):255-261; Shulein, 1988, Methods in Enzymology, 160:234-242). Endoglucanases act mainly on the amorphous parts of the cellulose fiber, whereas cellobiohydrolases are also able to degrade crystalline cellulose.

Cellulases for use in accordance with the methods and compositions of the disclosure can be obtained from, or produced recombinantly from, inter alia, one or more of the following organisms: *Crinipellis scapella, Macrophomina phaseolina, Myceliophthora thermophila, Sordaria fimicola,*

*Volutella colletotrichoides, Thielavia terrestris, Acremonium* sp., *Exidia glandulosa, Fomes fomentarius, Spongipellis* sp., *Rhizophlyctis rosea, Rhizomucor pusillus, Phycomyces niteus, Chaetostylum fresenii, Diplodia gossypina, Ulospora bilgramii, Saccobolus dilutellus, Penicillium verruculosum, Penicillium chrysogenum, Thermomyces verrucosus, Diaporthe syngenesia, Colletotrichum lagenarium, Nigrospora* sp., *Xylaria hypoxylon, Nectria pinea, Sordaria macrospora, Thielavia thermophila, Chaetomium mororum, Chaetomium virscens, Chaetomium brasiliensis, Chaetomium cunicolorum, Syspastospora boninensis, Cladorrhinum foecundissimum, Scytalidium thermophila, Gliocladium catenulatum, Fusarium oxysporum* ssp. *lycopersici, Fusarium oxysporum* ssp. *passiflora, Fusarium solani, Fusarium anguioides, Fusarium poae, Humicola nigrescens, Humicola grisea, Panaeolus retirugis, Trametes sanguinea, Schizophyllum commune, Trichothecium roseum, Microsphaeropsis* sp., *Acsobolus stictoideus* spej., *Poronia punctata, Nodulisporum* sp., *Trichoderma* sp. (e.g., *Trichoderma reesei*) and *Cylindrocarpon* sp.

For example, a cellulase for use in the method and/or composition of the disclosure is a whole cellulase and/or is capable of achieving at least 0.1 (e.g. 0.1 to 0.4) fraction product as determined by the calcofluor assay described in Section 7.1.10 below.

6.3.5.1 β-Glucosidase

The enzyme blends/compositions of the disclosure can optionally comprise one or more β-glucosidases. The term "β-glucosidase" as used herein refers to a β-D-glucoside glucohydrolase classified as EC 3.2.1.21, and/or members of certain GH families, including, without limitation, members of GH families 1, 3, 9 or 48, which catalyze the hydrolysis of cellobiose to release β-D-glucose.

Suitable β-glucosidase can be obtained from a number of microorganisms, by recombinant means, or be purchased from commercial sources. Examples of β-glucosidases from microorganisms include, without limitation, ones from bacteria and fungi. For example, a β-glucosidase of the present disclosure is suitably obtained from a filamentous fungus.

The β-glucosidases can be obtained, or produced recombinantly, from, inter alia, *Aspergillus aculeatus* (Kawaguchi et al. Gene 1996, 173: 287-288), *Aspergillus kawachi* (Iwashita et al. Appl. Environ. Microbiol. 1999, 65: 5546-5553), *Aspergillus oryzae* (WO 2002/095014), *Cellulomonas biazotea* (Wong et al. Gene, 1998, 207:79-86), *Penicillium funiculosum* (WO 2004/078919), *Saccharomycopsis fibuligera* (Machida et al. Appl. Environ. Microbiol. 1988, 54: 3147-3155), *Schizosaccharomyces pombe* (Wood et al. Nature 2002, 415: 871-880), or *Trichoderma reesei* (e.g., β-glucosidase 1 (U.S. Pat. No. 6,022,725), β-glucosidase 3 (U.S. Pat. No. 6,982,159), β-glucosidase 4 (U.S. Pat. No. 7,045,332), β-glucosidase 5 (U.S. Pat. No. 7,005,289), β-glucosidase 6 (U.S. Publication No. 20060258554), β-glucosidase 7 (U.S. Publication No. 20060258554)).

The β-glucosidase can be produced by expressing an endogenous or exogenous gene encoding a β-glucosidase. For example, β-glucosidase can be secreted into the extracellular space e.g., by Gram-positive organisms (e.g., *Bacillus* or *Actinomycetes*), or eukaryotic hosts (e.g., *Trichoderma, Aspergillus, Saccharomyces*, or *Pichia*). The β-glucosidase can be, in some circumstances, overexpressed or underexpressed.

The β-glucosidase can also be obtained from commercial sources. Examples of commercial β-glucosidase preparation suitable for use in the present disclosure include, for example, *Trichoderma reesei* β-glucosidase in Accellerase® BG (Danisco US Inc., Genencor); NOVOZYM™ 188 (a β-glucosidase from *Aspergillus niger*); *Agrobacterium* sp. β-glucosidase, and *Thermatoga maritima* β-glucosidase from Megazyme (Megazyme International Ireland Ltd., Ireland).

Moreover, the β-glucosidase can be a component of a whole cellulase, as described in Section 6.3.5.4 below.

β-glucosidase activity can be determined by a number of suitable means known in the art, such as the assay described by Chen et al., in Biochimica et Biophysica Acta 1992, 121:54-60, wherein 1 pNPG denotes 1 μmoL of Nitrophenol liberated from 4-nitrophenyl-β-D-glucopyranoside in 10 min at 50° C. (122° F.) and pH 4.8.

6.3.5.2 Endoglucanases

The enzyme blends/compositions of the disclosure optionally comprise one or more endoglucanase. Any endoglucanase (EC 3.2.1.4) can be used in the methods and compositions of the present disclosure. An endoglucanse can be produced by expressing an endogenous or exogenous endoglucanase gene. The endoglucanase can be, in some circumstances, overexpressed or underexpressed.

For example, *Trichoderma reesei* EG1 (Penttila et al., Gene 1986, 63:103-112) and/or EG2 (Saloheimo et al., Gene 1988, 63:11-21) are suitably used in the methods and compositions of the present disclosure.

A thermostable *Thielavia terrestris* endoglucanase (Kvesitadaze et al., Applied Biochem. Biotech. 1995, 50:137-143) is, in another example, used in the methods and compositions of the present disclosure. Moreover, a *Trichoderma reesei* EG3 (Okada et al. Appl. Environ. Microbiol. 1988, 64:555-563), EG4 (Saloheimo et al. Eur. J. Biochem. 1997, 249:584-591), EG5 (Saloheimo et al. Molecular Microbiology 1994, 13:219-228), EG6 (U.S. Patent Publication No. 20070213249), or EG7 (U.S. Patent Publication No. 20090170181), an *Acidothermus cellulolyticus* EI endoglucanase (U.S. Pat. No. 5,536,655), a *Humicola insolens* endoglucanase V (EGV) (Protein Data Bank entry 4ENG), a *Staphylotrichum coccosporum* endoglucanase (U.S. Patent Publication No. 20070111278), an *Aspergillus aculeatus* endoglucanase F1-CMC (Ooi et al. Nucleic Acid Res. 1990, 18:5884), an *Aspergillus kawachii* IFO 4308 endoglucanase CMCase-1 (Sakamoto et al. Curr. Genet. 1995, 27:435-439), an *Erwinia carotovara* (Saarilahti et al. Gene 1990, 90:9-14); or an *Acremonium thermophilum* ALKO4245 endoglucanase (U.S. Patent Publication No. 20070148732) can also be used. Additional suitable endoglucanases are described in, e.g., WO 91/17243, WO 91/17244, WO 91/10732, U.S. Pat. No. 6,001,639.

6.3.5.3 Cellobiohydrolases

Any cellobiohydrolase (EC 3.2.1.91) ("CBH") can be optionally used in the methods and blends/compositions of the present disclosure. The cellobiohydrolase can be produced by expressing an endogeneous or exogenous cellobiohydrolase gene.

The cellobiohydrolase can be, in some circumstances, overexpressed or under expressed.

For example, *Trichoderma reesei* CBHI (Shoemaker et al. Bio/Technology 1983, 1:691-696) and/or CBHII (Teeri et al. Bio/Technology 1983, 1:696-699) can be suitably used in the methods and blends/compositions of the present disclosure.

Suitable CBHs can be selected from an *Agaricus bisporus* CBH1 (Swiss Prot Accession No. Q92400), an *Aspergillus aculeatus* CBH1 (Swiss Prot Accession No. 059843), an *Aspergillus nidulans* CBHA (GenBank Accession No. AF420019) or CBHB (GenBank Accession No. AF420020), an *Aspergillus niger* CBHA (GenBank Accession No. AF156268) or CBHB (GenBank Accession No. AF156269), a *Claviceps purpurea* CBH1 (Swiss Prot Accession No. 000082), a *Cochliobolus carbonarum* CBH1 (Swiss Prot Accession No. Q00328), a *Cryphonectria parasitica* CBH1 (Swiss Prot Accession No. Q00548), a *Fusarium oxysporum* CBH1 (Cel7A) (Swiss Prot Accession No. P46238), a *Humicola grisea* CBH1.2 (GenBank Accession No. U50594), a *Humicola grisea* var. thermoidea CBH1 (GenBank Accession No. D63515) a CBHI.2 (GenBank Accession No. AF123441), or an exo1 (GenBank Accession No. AB003105), a *Melanocarpus albomyces* Cel7B (GenBank Accession No. AJ515705), a *Neurospora crassa* CBHI (GenBank Accession No. X77778), a *Penicillium funiculosum* CBHI (Cel7A) (U.S. Patent Publication No. 20070148730), a *Penicillium janthinellum* CBHI (GenBank Accession No. S56178), a *Phanerochaete chrysosporium* CBH (GenBank Accession No. M22220), or a CBHI-2 (Cel7D) (GenBank Accession No. L22656), a *Talaromyces emersonii* CBH1A (GenBank Accession No. AF439935), a *Trichoderma viride* CBH1 (GenBank Accession No. X53931), or a *Volvariella volvacea* V14 CBH1 (GenBank Accession No. AF156693).

6.3.5.4 Whole Cellulases

An enzyme blend/composition of the disclosure can further comprise a whole cellulase. As used herein, a "whole cellulase" refers to either a naturally occurring or a non-naturally occurring cellulase-containing composition comprising at least 3 different enzyme types: (1) an endoglucanase, (2) a cellobiohydrolase, and (3) a β-glucosidase, or comprising at least 3 different enzymatic activities: (1) an endoglucanase activity, which catalyzes the cleavage of internal β-1,4 linkages, resulting in shorter glucooligosaccharides, (2) a cellobiohydrolase activity, which catalyzes an "exo"-type release of cellobiose units (β-1,4 glucose-glucose disaccharide), and (3) a β-glucosidase activity, which catalyzes the release of glucose monomer from short cellooligosaccharides (e.g., cellobiose).

A "naturally occurring cellulase-containing" composition is one produced by a naturally occurring source, which comprises one or more cellobiohydrolase-type, one or more endoglucanase-type, and one or more β-glucosidase-type components or activities, wherein each of these components or activities is found at the ratio and level produced in nature, untouched by the human hand. Accordingly, a naturally occurring cellulase-containing composition is, for example, one that is produced by an organism unmodified with respect to the cellulolytic enzymes such that the ratio or levels of the component enzymes are unaltered from that produced by the native organism in nature. A "non-naturally occurring cellulase-containing composition" refers to a composition produced by: (1) combining component cellulolytic enzymes either in a naturally occurring ratio or a non-naturally occurring, i.e., altered, ratio; or (2) modifying an organism to overexpress or underexpress one or more cellulolytic enzymes; or (3) modifying an organism such that at least one cellulolytic enzyme is deleted. A "non-naturally occurring cellulase containing" composition can also refer to a composition resulting from adjusting the culture conditions for a naturally-occurring organism, such that the naturally-occurring organism grows under a non-native condition, and produces an altered level or ratio of enzymes. Accordingly, in some embodiments, the whole cellulase preparation of the present disclosure can have one or more EGs and/or CBHs and/or β-glucosidases deleted and/or overexpressed.

In the present disclosure, a whole cellulase preparation can be from any microorganism that is capable of hydrolyzing a cellulosic material. In some embodiments, the whole cellulase preparation is a filamentous fungal whole cellulase. For example, the whole cellulase preparation can be from an *Acremonium*, *Aspergillus*, *Emericella*, *Fusarium*, *Humicola*, *Mucor*, *Myceliophthora*, *Neurospora*, *Penicillium*, *Scytalidium*, *Thielavia*, *Tolypocladium*, or *Trichoderma* species. The whole cellulase preparation is, for example, an *Aspergillus aculeatus*, *Aspergillus awamori*, *Aspergillus foetidus*, *Aspergillus japonicus*, *Aspergillus nidulans*, *Aspergillus niger*, or *Aspergillus oryzae* whole cellulase. Moreover, the whole cellulase preparation can be a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* whole cellulase preparation. The whole cellulase preparation can also be a *Humicola insolens*, *Humicola lanuginosa*, *Mucor miehei*, *Myceliophthora thermophila*, *Neurospora crassa*, *Penicillium purpurogenum*, *Penicillium funiculosum*, *Scytalidium thermophilum*, or *Thielavia terrestris* whole cellulase preparation. Moreover, the whole cellulase preparation can be a *Trichoderma harzianum*, *Trichoderma koningii*, *Trichoderma longibrachiatum*, *Trichoderma reesei* (e.g., RL-P37 (Sheir-Neiss G et al. Appl. Microbiol. Biotechnology, 1984, 20, pp. 46-53), QM9414 (ATCC No. 26921), NRRL 15709, ATCC 13631, 56764, 56466, 56767), or a *Trichoderma viride* (e.g., ATCC 32098 and 32086) whole cellulase preparation.

The whole cellulase preparation can, in particular, suitably be a *Trichoderma reesei* RutC30 whole cellulase preparation, which is available from the American Type Culture Collection as *Trichoderma reesei* ATCC 56765. For example, the whole cellulase preparation can also suitably be a whole cellulase of *Penicillium funiculosum*, which is available from the American Type Culture Collection as *Penicillium funiculosum* ATCC Number: 10446.

The whole cellulase preparation can also be obtained from commercial sources. Examples of commercial cellulase preparations suitable for use in the methods and compositions of the present disclosure include, for example, CELLUCLAST™ and Cellic™ (Novozymes A/S) and LAMINEX™ BG, IndiAge™ 44L, Primafast™ 100, Primafast™ 200, Spezyme™ CP, Accellerase® 1000 and Accellerase® 1500 (Danisco US. Inc., Genencor).

Suitable whole cellulase preparations can be made using any microorganism cultivation methods known in the art, especially fermentation, resulting in the expression of enzymes capable of hydrolyzing a cellulosic material. As used herein, "fermentation" refers to shake flask cultivation, small- or large-scale fermentation, such as continuous, batch, fed-batch, or solid state fermentations in laboratory or industrial fermenters performed in a suitable medium and under conditions that allow the cellulase and/or enzymes of interest to be expressed and/or isolated.

Generally, the microorganism is cultivated in a cell culture medium suitable for production of enzymes capable of hydrolyzing a cellulosic material. The cultivation takes place in a suitable nutrient medium comprising carbon and nitrogen sources and inorganic salts, using procedures and variations known in the art. Suitable culture media, temperature ranges and other conditions for growth and cellulase production are known in the art. As a non-limiting example, a typical temperature range for the production of cellulases by *Trichoderma reesei* is 24° C. to 28° C.

The whole cellulase preparation can be used as it is produced by fermentation with no or minimal recovery and/or purification. For example, once cellulases are secreted into the cell culture medium, the cell culture medium containing the cellulases can be used directly. The whole cellulase preparation can comprise the unfractionated contents of fermentation material, including the spent cell culture medium, extracellular enzymes and cells. On the other hand, the whole cellulase preparation can also be subject to further processing in a number of routine steps, e.g., precipitation, centrifugation, affinity chromatography, filtration, or the like. For example, the whole cellulase preparation can be concentrated, and then used without further purification. The whole cellulase preparation can, for example, be formulated to comprise certain chemical agents that decrease cell viability or kills the cells after fermentation. The cells can, for example, be lysed or permeabilized using methods known in the art.

The endoglucanase activity of the whole cellulase preparation can be determined using carboxymethyl cellulose (CMC) as a substrate. A suitable assay measures the production of reducing ends created by the enzyme mixture acting on CMC wherein 1 unit is the amount of enzyme that liberates 1 μmoL of product/min (Ghose, T. K., Pure & Appl. Chem. 1987, 59, pp. 257-268).

The whole cellulase can be a β-glucosidase-enriched cellulase. The β-glucosidase-enriched whole cellulase generally comprises a β-glucosidase and a whole cellulase preparation. The β-glucosidase-enriched whole cellulase compositions can be produced by recombinant means. For example, such a whole cellulase preparation can be achieved by expressing a β-glucosidase in a microorganism capable of producing a whole cellulase. The β-glucosidase-enriched whole cellulase composition can also, for example, comprise a whole cellulase preparation and a β-glucosidase. For instance, the β-glucosidase-enriched whole cellulase composition can suitably comprise at least 5 wt. %, 7 wt. %, 10 wt. %, 15 wt. % or 20 wt. %, and up to 25 wt. %, 30 wt. %, 35 wt. %, 40 wt. %, or 50 wt. % β-glucosidase based on the total weight of proteins in that blend/composition.

6.3.6 Xylanases

The enzyme blends/compositions of the disclosure, for example, can, comprise one or more Group A xylanases, which may be a *Trichoderma reesei* Xyn2, a *Trichoderma reesei* Xyn3, an AfuXyn2, or an AfuXyn5. Suitable *Trichoderma reesei* Xyn2, *Trichoderma reesei* Xyn3, AfuXyn2, or AfuXyn5 polypeptides are described in Section 6.1 above.

The enzyme blends/compositions of the disclosure optionally comprise one or more xylanases in addition to or in place of the one or more Group A xylanases. Any xylanase (EC 3.2.1.8) can be used as the additional one or more xylanases. Suitable xylanases include, e.g., a *Caldocellum saccharolyticum* xylanase (Luthi et al. 1990, Appl. Environ. Microbiol. 56(9):2677-2683), a *Thermatoga maritima* xylanase (Winterhalter & Liebel, 1995, Appl. Environ. Microbiol. 61(5):1810-1815), a *Thermatoga* Sp. Strain FJSS-B.1 xylanase (Simpson et al. 1991, Biochem. J. 277, 413-417), a *Bacillus circulans* xylanase (BcX) (U.S. Pat. No. 5,405,769), an *Aspergillus niger* xylanase (Kinoshita et al. 1995, Journal of Fermentation and Bioengineering 79(5): 422-428), a *Streptomyces lividans* xylanase (Shareck et al. 1991, Gene 107:75-82; Morosoli et al. 1986 Biochem. J. 239:587-592; Kluepfel et al. 1990, Biochem. J. 287:45-50), a *Bacillus subtilis* xylanase (Bernier et al. 1983, Gene 26(1):59-65), a *Cellulomonas fimi* xylanase (Clarke et al., 1996, FEMS Microbiology Letters 139:27-35), a *Pseudomonas fluorescens* xylanase (Gilbert et al. 1988, Journal of General Microbiology 134:3239-3247), a *Clostridium thermocellum* xylanase (Dominguez et al., 1995, Nature Structural Biology 2:569-576), a *Bacillus pumilus* xylanase (Nuyens et al. Applied Microbiology and Biotechnology 2001, 56:431-434; Yang et al. 1998, Nucleic Acids Res. 16(14B): 7187), a *Clostridium acetobutylicum* P262 xylanase (Zappe et al. 1990, Nucleic Acids Res. 18(8):2179), or a *Trichoderma harzianum* xylanase (Rose et al. 1987, J. Mol. Biol. 194(4):755-756).

The xylanase can be produced by expressing an endogenous or exogenous gene encoding a xylanase. The xylanase can be, in some circumstances, overexpressed or underexpressed.

6.3.7 β-Xylosidases

The enzyme blends/compositions of the disclosure, for example, can suitably comprise one or more β-xylosidases. For example, the β-xylosidase is a Group 1 β-xylosidase enzyme (e.g., an Fv3A or an Fv43A) or a Group 2 β-xylosidase enzyme (e.g., a Pf43A, an Fv43D, an Fv39A, an Fv43E, an Fo43A, an Fv43B, a Pa51A, a Gz43A, or a *Trichoderma reesei* Bxl1). These polypeptides are described in Section 0 above. For example, an enzyme blend/composition of the disclosure can suitably comprise one or more Group 1 β-xylosidases and one or more Group 2 β-xylosidases.

The enzyme blends/compositions of the disclosure can optionally comprise one or more β-xylosidases, in addition to or in place of the Group 1 and/or Group 2 β-xylosidases above. Any β-xylosidase (EC 3.2.1.37) can be used as the additional β-xylosidases. Suitable β-xylosidases include, for example, a *Talaromyces emersonii* Bxl1 (Reen et al. 2003, Biochem Biophys Res Commun. 305(3):579-85), a *Geobacillus stearothermophilus* β-xylosidases (Shallom et al. 2005, Biochemistry 44:387-397), a *Scytalidium thermophilum* β-xylosidases (Zanoelo et al. 2004, J. Ind. Microbiol. Biotechnol. 31:170-176), a *Trichoderma lignorum* β-xylosidases (Schmidt, 1998, Methods Enzymol. 160:662-671), an *Aspergillus awamori* β-xylosidases (Kurakake et al. 2005, Biochim. Biophys. Acta 1726:272-279), an *Aspergillus versicolor* β-xylosidases (Andrade et al. 2004, Process Biochem. 39:1931-1938), a *Streptomyces* sp. β-xylosidases (Pinphanichakarn et al. 2004, World J. Microbiol. Biotechnol. 20:727-733), a *Thermotoga maritima* β-xylosidases (Xue and Shao, 2004, Biotechnol. Lett. 26:1511-1515), a *Trichoderma* sp. SY β-xylosidases (Kim et al. 2004, J. Microbiol. Biotechnol. 14:643-645), an *Aspergillus niger* β-xylosidases (Oguntimein and Reilly, 1980, Biotechnol. Bioeng. 22:1143-1154), or a *Penicillium wortmanni* β-xylosidases (Matsuo et al. 1987, Agric. Biol. Chem. 51:2367-2379).

The β-xylosidase can be produced by expressing an endogenous or exogenous gene encoding a β-xylosidase. The β-xylosidase can be, in some circumstances, overexpressed or underexpressed.

6.3.8 L-α-Arabinofuranosidases

The enzyme blends/compositions of the disclosure can, for example, suitably comprise one or more L-α-arabinofuranosidases. The L-α-arabinofuranosidase is, for example, an Af43A, an Fv43B, a Pf51A, a Pa51A, or an Fv51A. Af43A, Fv43B, Pf51A, Pa51A, and Fv51A polypeptides are described in Section 6.1 above.

The enzyme blends/compositions of the disclosure optionally comprise one or more L-α-arabinofuranosidases in addition to or in place of the foregoing L-α-arabinofuranosidases. L-α-arabinofuranosidases (EC 3.2.1.55) from any suitable organism can be used as the additional L-α- arabinofuranosidases. Suitable L-α-arabinofuranosidases include, e.g., an L-α-arabinofuranosidases of *Aspergillus oryzae* (Numan & Bhosle, J. Ind. Microbiol. Biotechnol. 2006, 33:247-260), *Aspergillus sojae* (Oshima et al. J. Appl. Glycosci. 2005, 52:261-265), *Bacillus brevis* (Numan & Bhosle, J. Ind. Microbiol. Biotechnol. 2006, 33:247-260), *Bacillus stearothermophilus* (Kim et al., J. Microbiol. Biotechnol. 2004, 14:474-482), *Bifidobacterium breve* (Shin et al., Appl. Environ. Microbiol. 2003, 69:7116-7123), *Bifidobacterium longum* (Margolles et al., Appl. Environ. Microbiol. 2003, 69:5096-5103), *Clostridium thermocellum* (Taylor et al., Biochem. J. 2006, 395:31-37), *Fusarium oxysporum* (Panagiotou et al., Can. J. Microbiol. 2003, 49:639-644), *Fusarium oxysporum* f. sp. *dianthi* (Numan & Bhosle, J. Ind. Microbiol. Biotechnol. 2006, 33:247-260), *Geobacillus stearothermophilus* T-6 (Shallom et al., J. Biol. Chem. 2002, 277:43667-43673), *Hordeum vulgare* (Lee et al., J. Biol. Chem. 2003, 278:5377-5387), *Penicillium chrysogenum* (Sakamoto et al., Biophys. Acta 2003, 1621:204-210), *Penicillium* sp. (Rahman et al., Can. J. Microbiol. 2003, 49:58-64), *Pseudomonas cellulosa* (Numan & Bhosle, J. Ind. Microbiol. Biotechnol. 2006, 33:247-260), *Rhizomucor pusillus* (Rahman et al., Carbohydr. Res. 2003, 338:1469-1476), *Streptomyces chartreusis, Streptomyces thermoviolacus, Thermoanaerobacter ethanolicus, Thermobacillus xylanilyticus* (Numan & Bhosle, J. Ind. Microbiol. Biotechnol. 2006, 33:247-260), *Thermomonospora fusca* (Tuncer and Ball, Folia Microbiol. 2003, (Praha) 48:168-172), *Thermotoga maritima* (Miyazaki, Extremophiles 2005, 9:399-406), *Trichoderma* sp. SY (Jung et al. Agric. Chem. Biotechnol. 2005, 48:7-10), *Aspergillus kawachii* (Koseki et al., Biochim. Biophys. Acta 2006, 1760:1458-1464), *Fusarium oxysporum* f. sp. *dianthi* (Chacon-Martinez et al., Physiol. Mol. Plant Pathol. 2004, 64:201-208), *Thermobacillus xylanilyticus* (Debeche et al., Protein Eng. 2002, 15:21-28), *Humicola insolens, Meripilus giganteus* (Sorensen et al., Biotechnol. Prog. 2007, 23:100-107), or *Raphanus sativus* (Kotake et al. J. Exp. Bot. 2006, 57:2353-2362).

The L-α-arabinofuranosidase can be produced by expressing an endogenous or exogenous gene encoding an L-α-arabinofuranosidase. The L-α-arabinofuranosidase can be, in some circumstances, overexpressed or underexpressed.

6.3.9 Accessory Proteins

The enzyme blends/compositions of the disclosure can, for example, suitably further comprise one or more accessory proteins. Examples of accessory proteins include, without limitation, mannanases (e.g., endomannanases, exomannanases, and β-mannosidases), galactanases (e.g., endo- and exo-galactanases), arabinases (e.g., endo-arabinases and exo-arabinases), ligninases, amylases, glucuronidases, proteases, esterases (e.g., ferulic acid esterases, acetyl xylan esterases, coumaric acid esterases or pectin methyl esterases), lipases, glycoside hydrolase Family 61 polypeptides, xyloglucanases, CIP1, CIP2, swollenin, expansins, and cellulose disrupting proteins. Examples of accessory proteins can also include CIP1-like proteins, CIP2-like proteins, cellobiose dehydrogenases and manganese peroxidases. In particular embodiments, the cellulose disrupting proteins are cellulose binding modules.

6.4 Further Applications

In addition to saccharification of biomass, the enzymes and/or enzyme blends/compositions of the disclosure can be used in industrial, agricultural, food and feed, as well as food and feed supplement processing processes. Exemplary applications are described below.

6.4.1 Wood, Paper and Pulp Treatments

The enzymes, enzyme blends/compositions, and methods of the disclosure can be used in wood, wood product, wood waste or by-product, paper, paper product, paper or wood pulp, Kraft pulp, or wood or paper recycling treatment or industrial process. These processes include, e.g., treatments of wood, wood pulp, paper waste, paper, or pulp, or deinking of wood or paper. The enzymes, enzyme blends/compositions of the disclosure can be, for example, used to treat/pretreat paper pulp, or recycled paper or paper pulp, and the like. The enzymes, enzyme blends/compositions of the disclosure can be used to increase the "brightness" of the paper when they are included in the paper, pulp, recycled paper or paper pulp treatment/pretreatment. It can be appreciated that the higher the grade of paper, the greater the brightness; the brightness can impact the scan capability of optical scanning equipment. As such, the enzymes, enzyme blends/compositions, and methods/processes can be used to make high grade, "bright" papers, including inkjet, laser and photo printing quality paper.

The enzymes, enzyme blends/compositions of the disclosure can be used to process or treat a number of other cellulosic material, including, e.g., fibers from wood, cotton, hemp, flax or linen.

Accordingly, the disclosure provides wood, wood pulp, paper, paper pulp, paper waste or wood or paper recycling treatment processes using an enzyme, enzyme blend/composition of the disclosure.

The enzymes, enzyme blends/compositions of the disclosure can be used for deinking printed wastepaper, such as newspaper, or for deinking noncontact-printed wastepaper, e.g., xerographic and laser-printed paper, and mixtures of contact and noncontact-printed wastepaper, as described in U.S. Pat. No. 6,767,728 or 6,426,200; Neo, J. Wood Chem. Tech. 1986, 6(2):147. They can also be used to produce xylose from a paper-grade hardwood pulp in a process involving extracting xylan contained in pulp into a liquid phase, subjecting the xylan contained in the obtained liquid phase to conditions sufficient to hydrolyze xylan to xylose, and recovering the xylose. The extracting step, for example, can include at least one treatment of an aqueous suspension of pulp or an alkali-soluble material by an enzyme or an enzyme blend/composition (see, U.S. Pat. No. 6,512,110). The enzymes, enzyme blends/compositions of the disclosure can be used to dissolve pulp from cellulosic fibers such as recycled paper products made from hardwood fiber, a mixture of hardwood fiber and softwood fiber, waste paper, e.g., from unprinted envelopes, de-inked envelopes, unprinted ledger paper, de-inked ledger paper, and the like, as described in, e.g., U.S. Pat. No. 6,254,722.

6.4.2 Treating Fibers and Textiles

The disclosure provides methods of treating fibers and fabrics using one or more enzymes, enzyme blends/compositions of the disclosure. The enzymes, enzyme blends/compositions can be used in any fiber- or fabric-treating method, which are known in the art. See, e.g., U.S. Pat. Nos. 6,261,828; 6,077,316; 6,024,766; 6,021,536; 6,017,751; 5,980,581; U.S. Patent Publication No. 20020142438 A1. For example, enzymes, enzyme blends/compositions of the disclosure can be used in fiber and/or fabric desizing. The feel and appearance of a fabric can be, for example, improved by a method comprising contacting the fabric with an enzyme or enzyme blend/composition of the disclosure in a solution. Optionally, the fabric is treated with the solution under pressure. The enzymes, enzyme blends/composition of the disclosure can also be used to remove stains.

The enzymes, enzyme blends/compositions of the disclosure can be used to treat a number of other cellulosic material, including fibers (e.g., fibers from cotton, hemp, flax or linen), sewn and unsewn fabrics, e.g., knits, wovens, denims, yarns, and toweling, made from cotton, cotton blends or natural or manmade cellulosics or blends thereof. The textile treating processes can be used in conjunction with other textile treatments, e.g., scouring and/or bleaching. Scouring, for example, is the removal of non-cellulosic material from the cotton fiber, e.g., the cuticle (mainly consisting of waxes) and primary cell wall (mainly consisting of pectin, protein and xyloglucan).

6.4.3 Treating Foods and Food Processing

The enzymes, enzyme blends/compositions of the disclosure have numerous applications in food processing industry. They can, for example, be used to improve extraction of oil from oil-rich plant material, e.g., oil-rich seeds. The enzymes, enzyme blends/compositions of the disclosure can be used to extract soybean oil from soybeans, olive oil from olives, rapeseed oil from rapeseed, or sunflower oil from sunflower seeds.

The enzymes, enzyme blends/compositions of the disclosure can also be used to separate components of plant cell materials. For example, they can be used to separate plant cells into components. The enzymes, enzyme blends/compositions of the disclosure can also be used to separate crops into protein, oil, and hull fractions. The separation process can be performed using known methods.

The enzymes, enzyme blends/compositions of the disclosure can, in addition to the uses above, be used to increase yield in the preparation of fruit or vegetable juices, syrups, extracts and the like. They can also be used in the enzymatic treatment of various plant cell wall-derived materials or waste materials from, e.g., cereals, grains, wine or juice production, or agricultural residues such as, e.g., vegetable hulls, bean hulls, sugar beet pulp, olive pulp, potato pulp, and the like. Further, they can be used to modify the consistency and/or appearance of processed fruits or vegetables. Additionally, they can be used to treat plant material so as to facilitate processing of the plant material (including foods), purification or extraction of plant components. The enzymes, enzyme blends/compositions of the disclosure can be used to improve feed value, decrease the water binding capacity, improve the degradability in waste water plants and/or improve the conversion of plant material to ensilage, and the like.

The enzymes, enzyme blends/compositions of the disclosure can also be used in baking applications. In some embodiments, they are used to create non-sticky doughs that are not difficult to machines and to reduce biscuit sizes. They can also be used to hydrolyze arabinoxylans to prevent rapid rehydration of the baked product that can lead to loss of crispiness and reduced shelf-life. For example, they are used as additives in dough processing.

6.4.4 Animal Feeds and Food or Feed or Food Additives

The disclosure provides methods for treating animal feeds and foods and food or feed additives (supplements) using enzymes, enzyme blends/compositions of the disclosure. Animals including mammals (e.g., humans), birds, fish, and the like. The disclosure provides animal feeds, foods, and additives (supplements) comprising enzymes, enzyme blends/compositions of the disclosure. Treating animal feeds, foods and additives using enzymes of the disclosure can help in the availability of nutrients, e.g., starch, protein, and the like, in the animal feed or additive (supplements). By breaking down difficult to digest proteins or indirectly or directly unmasking starch (or other nutrients), the enzymes, enzyme blends/compositions can make nutrients more accessible to other endogenous or exogenous enzymes. They can also simply cause the release of readily digestible and easily absorbed nutrients and sugars.

When added to animal feed, enzymes, enzyme blends/compositions of the disclosure improve the in vivo breakdown of plant cell wall material partly by reducing the intestinal viscosity (see, e.g., Bedford et al., Proceedings of the 1st Symposium on Enzymes in Animal Nutrition, 1993, pp. 73-77), whereby a better utilization of the plant nutrients by the animal is achieved. Thus, by using enzymes, enzyme blends/compositions of the disclosure in feeds, the growth rate and/or feed conversion ratio (i.e., the weight of ingested feed relative to weight gain) of the animal can be improved.

The animal feed additive of the disclosure may be a granulated enzyme product which can be readily mixed with feed components. Alternatively, feed additives of the disclosure can form a component of a pre-mix. The granulated enzyme product of the disclosure may be coated or uncoated. The particle size of the enzyme granulates can be compatible with that of the feed and/or the pre-mix components. This provides a safe and convenient mean of incorporating enzymes into feeds. Alternatively, the animal feed additive of the disclosure can be a stabilized liquid composition. This may be an aqueous- or oil-based slurry. See, e.g., U.S. Pat. No. 6,245,546.

An enzyme, enzyme blend/composition of the disclosure can be supplied by expressing the enzymes directly in transgenic feed crops (e.g., as transgenic plants, seeds and the like), such as grains, cereals, corn, soy bean, rape seed, lupin and the like. As discussed above, the disclosure provides transgenic plants, plant parts and plant cells comprising a nucleic acid sequence encoding a polypeptide of the disclosure. The nucleic acid is expressed such that the enzyme of the disclosure is produced in recoverable quantities. The xylanase can be recovered from any plant or plant part. Alternatively, the plant or plant part containing the recombinant polypeptide can be used as such for improving the quality of a food or feed, e.g., improving nutritional value, palatability, and rheological properties, or to destroy an antinutritive factor.

The disclosure provides methods for removing oligosaccharides from feed prior to consumption by an animal subject using an enzyme, enzyme blend/composition of the disclosure. In this process a feed is formed to have an increased metabolizable energy value. In addition to enzymes, enzyme blends/compositions of the disclosure, galactosidases, cellulases, and combinations thereof can be used.

The disclosure provides methods for utilizing an enzyme, an enzyme blend/composition of the disclosure as a nutritional supplement in the diets of animals by preparing a nutritional supplement containing a recombinant enzyme of the disclosure, and administering the nutritional supplement to an animal to increase the utilization of hemicellulase contained in food ingested by the animal.

6.4.5 Waste Treatment

The enzymes, enzyme blends/compositions of the disclosure can be used in a variety of other industrial applications, e.g., in waste treatment. For example, in one aspect, the disclosure provides a solid waste digestion process using the enzymes, enzyme blends/compositions of the disclosure. The methods can comprise reducing the mass and volume of substantially untreated solid waste. Solid waste can be treated with an enzymatic digestive process in the presence of an enzymatic solution (including the enzymes, enzyme blends/compositions of the disclosure) at a controlled temperature. This results in a reaction without appreciable bacterial fermentation from added microorganisms. The solid waste is converted into a liquefied waste and any residual solid waste. The resulting liquefied waste can be separated from said any residual solidified waste. See, e.g., U.S. Pat. No. 5,709,796.

6.4.6 Detergent, Disinfectant and Cleaning Compositions

The disclosure provides detergent, disinfectant or cleanser (cleaning or cleansing) compositions comprising one or more enzymes, enzyme blends/compositions of the disclosure, and methods of making and using these compositions. The disclosure incorporates all known methods of making and using detergent, disinfectant or cleanser compositions. See, e.g., U.S. Pat. Nos. 6,413,928; 6,399,561; 6,365,561; 6,380,147.

In specific embodiments, the detergent, disinfectant or cleanser compositions can be a one- and two-part aqueous composition, a non-aqueous liquid composition, a cast solid, a granular form, a particulate form, a compressed tablet, a gel and/or a paste and a slurry form. The enzymes, enzyme blends/compositions of the disclosure can also be used as a detergent, disinfectant, or cleanser additive product in a solid or a liquid form. Such additive products are intended to supplement or boost the performance of conventional detergent compositions, and can be added at any stage of the cleaning process.

The present disclosure provides cleaning compositions including detergent compositions for cleaning hard surfaces, detergent compositions for cleaning fabrics, dishwashing compositions, oral cleaning compositions, denture cleaning compositions, and contact lens cleaning solutions.

When the enzymes of the disclosure are components of compositions suitable for use in a laundry machine washing method, the compositions can comprise, in addition to an enzyme, enzyme blend/composition of the disclosure, both a surfactant and a builder compound. They can additionally comprise one or more detergent components, e.g., organic polymeric compounds, bleaching agents, additional enzymes, suds suppressors, dispersants, lime-soap dispersants, soil suspension and anti-redeposition agents, and corrosion inhibitors.

Laundry compositions of the disclosure can also contain softening agents, as additional detergent components. Such compositions containing carbohydrase can provide fabric cleaning, stain removal, whiteness maintenance, softening, color appearance, dye transfer inhibition and sanitization when formulated as laundry detergent compositions.

The disclosure thus further provides a process of saccharification a biomass material comprising hemicellulose. Such a biomass material can optionally comprise cellulose. Exemplary biomass materials include, without limitation, corcob, switchgrass, sorghum, and/or bagasse. Accordingly the disclosure provides a process of saccharification, comprising treating a biomass material herein comprising hemicelluose and optionally cellose with an enzyme blend/composition as described herein. The enzyme blend/composition used in such a process of the invention include 0.5 g to 40 g (e.g., 0.5 g to 20 g, 0.5 g to 30 g, 0.5 g to 40 g, 0.5 g to 15 g, 0.5 g to 10 g, 0.5 g to 5 g, 0.5 g to 7 g, etc) of polypeptides having xylanase activity per kg of hemicellulose in the biomass material. The enzyme blend/composition used in such a process of the invention can also include 1 g to 40 g (e.g., 2 g to 20 g, 3 g to 7 g, 1 g to 5 g, or 2 g to 5 g, etc.) of polypeptides having xylanase activity per kg of hemicellulose in the biomass material. The enzyme blend/composition used in such a process can include 0.5 g to 50 g (e.g., 0.5 g to 50 g, 0.5 g to 45 g, 0.5 g to 40 g, 0.5 g to 30 g, 0.5 g to 25 g, 0.5 g to 20 g, 0.5 g to 15 g, 0.5 g to 10 g, etc) of polypeptides having β-xylosidase activity per kg of hemicellulose in the biomass material. The enzyme blend/composition used in such a process can also include 1 g to 50 g (e.g., 2 g to 40 g, 4 g to 20 g, 4 g to 10 g, 2 g to 10 g, 3 g to 7 g, etc.) of polypeptide having β-xylosidase activity per kg of hemicellulose in the biomass material. The enzyme blend/composition used in such a process of the invention can include 0.2 g to 20 g (e.g., 0.2 g to 18 g, 0.2 g to 15 g, 0.3 g to 10 g, 0.2 g to 8 g, 0.2 g to 5 g, etc) of polypeptides having L-α-arabinofuranosidase activity per kg of hemicellulose in the biomass material. The enzyme blend/composition used in such a process of the invention can include 0.5 g to 20 g (e.g., 1 g to 10 g, 1 g to 5 g, 2 g to 6 g, 0.5 g to 4 g, or 1 g to 3 g, etc) of polypeptides having L-α-arabinofuranosidase activity per kg of hemicellulose in the biomass material. The enzyme blend/composition can also include 1 g to 100 g (e.g., 1 g to 100 g, 2 g to 80 g, 3 g to 50 g, 5 g to 40 g, 2 g to 20 g, 10 g to 30 g, or 12 g to 18 g, etc) of polypeptides having cellulase activity per kg of cellulose in the biomass material. Optionally, the amount of polypeptides having 3-glucosidase activity can constitute up to 50% of the total weight of polypeptides having cellulase activity.

A suitable process of the invention preferably yields 60% to 90% xylose from the hemicellulose xylan of the biomass material treated. Suitable biomass materials include one or more of, for example, corncob, switchgrass, sorghum, and/or bagasse. As such, a process of the invention preferably yields at least 70% (e.g. at least 75%, at least 80%) xylose from hemicellulose xylan from one or more of these biomass materials. For example, the process yields 60% to 90% of xylose from hemicellulose xylan of a biomass material comprising hemicellulose, including, without limitation, corncob, switchgrass, sorghum, and/or bagasse.

The process of the invention optionally further comprises recovering monosaccharides.

The invention is further illustrated by the following examples. The examples are provided for illustrative purposes only. They are not to be construed as limiting the scope or content of the invention in any way.

7. EXAMPLE 1: REPRESENTATIVE EXPERIMENTAL METHODS

7.1 Materials and Methods

The following assays/methods were used in Example 1 and subsequent examples. Any deviations from the protocols provided below are indicated.

7.1.1 Preparation of Hemicellulose from Plant Tissues

Hemicellulose preparations were prepared using a modification of the NaOH/sonication procedure described by Erbringerova et al. (Carbohydrate Polymers 1998, 37:231). Dry plant material was ground to pass a 1 mm screen and 10 g of this material was suspended in 250 mL of 5% (wt/v) NaOH. The suspension was heated to 80° C. without stirring for 30 min then sonicated for 15 min at ambient temperature using a probe sonicator at high setting. The suspension was returned to 80° C. for an additional 30 min then allowed to cool to room temperature. Solids were removed from the suspension by centrifugation at 3000×g for 15 min and the resulting supernatant was decanted into 1 L of ethanol which was cooled on ice. After 30 min the resulting precipitate was recovered by first decanting the clear liquid above the precipitate then filtration without allowing the precipitate to fully air dry. The filter cake was first washed with 200 mL of cold, 80% ethanol then removed from the filter without allowing it to air dry. The filter cake was re-dissolved in 200 mL of water and the pH of the solution was adjusted to 5.5 with acetic acid. The extracted carbohydrate was re-precipitated by addition to 1 L of ethanol on ice and the resulting precipitate was again recovered by filtration as above. The filter cake was frozen and remaining solvent and water was removed by lyophylization. Yield of recovered carbohydrate ranged from 6 to 23% of the starting plant material depending on the tissue and the preparation.

7.1.2 Dilute Ammonia Pretreatment of Biomass Substrates

Corncob and switchgrass were pretreated prior to enzymatic hydrolysis according to the methods and processing ranges described in WO06110901A (unless otherwise noted).

7.1.3 Compositional Analysis of Biomass

The 2-step acid hydrolysis methods described in "Determination of structural carbohydrates and lignin in the biomass" (National Renewable Energy Laboratory, Golden, Colo. 2008, available at www.nrel.gov/biomass/pdfs/42618.pdf) were used to measure the composition of biomass substrates. Enzymatic hydrolysis results are reported in terms of percent conversion with respect to the theoretical yield from the starting glucan and xylan content of the substrate.

7.1.4 Preparation of Crude Oligomers from Ammonia Pretreated Corncob

Crude oligomers for screening hemicellulases were prepared from corncob by the following procedure. Hammer-milled corncob (~¼ in mean diameter) plus 6% ammonia (w/w) was heated to 145° C. with direct injection of steam into a stirred pressure reactor. After 20 min excess ammonia was flashed out of the reactor at a final vacuum of ~0.1 bar. The ammonia pretreated cob was then placed in a sterile stirred reactor for enzyme saccharification. Enough water was added to obtain a final total solids loading of 25% (w/w) after all additions are made. The pH of the reactor was maintained at pH 5.3 with 4 N sulfuric acid and the temperature controlled at 47° C. Spezyme® CP, Multifect® Xylanase (Danisco US Inc., Genencor), and Novo 188 (Novozymes, Denmark) were added at loadings of 20, 10 and 5 mg/g of cellulose, respectively, and allowed to saccharify the pretreated cob to sugars and oligomers for 116 h. The material was then cooled to 33° C. and the pH adjusted to 5.8 with 4 N NaOH. The glucose and xylose were then fermented to ethanol by adding a seed culture of a recombinant $Zymomonas$ $mobilis$ strain (10% total volume, ATCC accession no. PTA-1798) as described in U.S. Pat. No. 7,354,755. The fermentation progress was followed until all of the glucose and ~95% of the xylose was consumed. A 0.5 L aliquot of the fermentation broth was clarified by centrifugation (21,000×g) for 20 min followed by filtration of the supernatant through a 0.2 micron filtering unit (Nalgene). The ethanol was removed from the filtered fermentation broth on a rotovap maintained at 35° C. under house vacuum. The total volume of the final liquor was reduced by ~4× by the latter procedure.

7.1.5 Total Protein Assays

Different total protein determination methods were employed depending on the nature of the protein sample (i.e., purified, fermentation broth, commercial product, etc.). The BCA protein assay is an example of a colorimetric assay that measures protein concentration with a spectrophotometer.

Reagents:

BCA Protein Assay Kit (Pierce Chemical, Product #23227), 50 mM Sodium Acetate buffer pH 5.0, 15% trichloroacetic acid (TCA), 0.1 N NaOH, BSA stock solution, Reagent A, Reagent B (from protein assay kit)

Procedure:

Enzyme dilutions were prepared in test tubes using 50 mM Sodium Acetate buffer. Diluted enzyme solution (0.1 mL) was added to 2 mL Eppendorf centrifuge tubes containing 1 mL 15% TCA. The tubes were vortexed and placed in an ice bath for 10 min. The samples were then centrifuged at 14,000 rpm for 6 min. The supernatant was poured out, the pellet resuspended in 1 mL 0.1 N NaOH, and the tubes vortexed until the pellet dissolved. BSA standard solutions were prepared from a stock solution of 2 mg/mL. BCA working solution was prepared by mixing 0.5 mL Reagent B with 25 mL Reagent A. The resuspended protein (0.1 mL each) was added to 3 Eppendorf centrifuge tubes. Two mL Pierce BCA working solution was added to each of the sample and serially diluted BSA standard Eppendorf tubes. All tubes were incubated in a 37° C. water bath for 30 min. The samples were then cooled to room temperature (15 min) and the absorbance measured at 562 nm in a spectrophotometer.

Calculations:

Average values for each BSA protein standard absorbance were calculated and plotted, absorbance on x-axis and concentration (mg/mL) on the y-axis. A linear curve fit was applied and the equation for the line calculated using the formula:

$$y=mx+b$$

The raw concentration of the enzyme samples was calculated by substituting the absorbance for the x-value. The total protein concentration was calculated by multiplying with the dilution factor.

The total protein of purified samples was determined by A280 (see, e.g., Pace et al., Protein Science, 1995, 4:2411).

Some protein samples were measured using the Biuret method as modified by Weichselbaum and Gornall using Bovine Serum Albumin as a calibrator (modified Biuret) (Weichselbaum, Amer. J. Clin. Path. 1960, 16:40; Gornall et al., J. Biol. Chem. 1949, 177:752).

Total protein content of fermentation products was also sometimes measured as total nitrogen by combustion, capture and measurement of released nitrogen, either by Kjeldahl (rtech laboratories, www.rtechlabs.com) or in-house by the DUMAS method (TruSpec CN, www.leco.com) (SADER, et al. Archives of Veterinary Science, 9(2):73-79, 2004). For complex protein-containing samples, e.g. fermentation broths, an average 16% N content, and the conversion factor of 6.25 for nitrogen to protein was used. In some cases, total precipitable protein was measured to remove interfering non-protein nitrogen. A 12.5% final TCA concentration was used and the protein-containing TCA pellet was resuspended in 0.1 M NaOH.

In other cases, Coomassie Plus—the Better Bradford Assay (Thermo Scientific, Rockford, Ill. product #23238) was used according to manufacturer recommendation.

7.1.6 Synthetic Substrate (Para-Nitrophenyl Substrate) Activity Assays

Active protein from $T.$ $reesei$ expression of cloned genes was confirmed with model substrate assays. Cellulase and hemicellulase activities on the synthetic substrates, such as 4-nitrophenyl α-L-arabinofuranoside (pNPA, Sigma N3641) and 4-nitrophenyl β-D-glucopyranoside (pNPG, Sigma N7006), and 4-nitrophenyl β-D-xylopyranoside (pNPX, Sigma N2132) were measured as follows: Substrate solution was prepared by dissolving 30 mg of synthetic substrate in 100 mL 50 mM Sodium Acetate buffer, pH 4.8. Sodium carbonate (1 M) was prepared for reaction quenching. Substrate solution (100 μL) was dispensed into Costar 96 well plates (Cat no. 9017). 20 μL of enzyme sample was dispensed into a microtiter plate well. The microtiter plate was incubated at 50° C. for 10 min using a Thermomixer R heating and cooling shaker (Eppendorf). 50 μL of 1 M sodium carbonate was added to each well to quench the reaction. Absorbance at 400 nm wavelength was read with SpectraMax 340C384 Microplate Spectrophotometer (Molecular Devices). Units per mL were determined by using a p-nitrophenol standard curve. A Quad-delete *Trichoderma* host, from which the cbh1, cbh2, egl1 and egl2 genes were deleted (see WO 05/001036), was analyzed with the enzyme samples as a control for the activity of enzymes expressed in this background.

7.1.7 Cob Saccharification Assay

Typically, Corncob saccharification in a microtiter plate format was performed in accordance with the following procedures. The biomass substrate, dilute ammonia pretreated corncob, was diluted in water and pH-adjusted with sulfuric acid to create a pH 5, 7% cellulose slurry that was used directly in the assay. The enzymes tested included: commercial cellulase products, e.g. Accellerase® 1000, Accellerase® 1500 (Danisco US Inc., Genencor), *T. reesei* fermentation broths, and purified enzymes. The enzymes were loaded based on mg total protein per gram of cellulose (as determined by compositional analysis) in the corncob substrate. The enzymes were diluted in 50 mM Sodium Acetate pH 5.0 to obtain the desired loading concentration at the required volume. Forty microliters of enzyme solution was added to 70 mg of dilute-ammonia pretreated corncob at 7% cellulose per well (equivalent to 4.5% cellulose final). The assay plate was incubated at room temperature for 10 min. The assay plates were covered with aluminum plate sealers and the plates incubated at 50° C., 200 rpm, for three days. At the end of the incubation period, the saccharification reaction was quenched by adding 100 μL of 100 mM glycine buffer, pH 10.0 per well and the plate was centrifuged for 5 min at 3,000 rpm. Ten microliters of the supernatant were added to 200 μL of MilliQ water in a 96-well HPLC plate and the soluble sugars were measured by HPLC.

This describes a typical method that was used in multiple Examples herein. In certain Examples, corncob saccharification was measured using a modified protocol. The modifications are described with the individual examples.

7.1.8 Sugar Analysis by HPLC

Typically, samples from cob saccharification hydrolysis were prepared by centrifugation to clear insoluble material, filtration through a 0.22 μm nylon filter (Spin-X centrifuge tube filter, Corning Incorporated, Corning, N.Y.) and dilution to an appropriate concentration of soluble sugars with distilled water. Monomer sugars were determined on a Shodex Sugar SH-G SH1011, 8×300 mm with a 6×50 mm SH-1011P guard column (www.shodex.net). Solvent was 0.01 N $H_2SO_4$ run at 0.6 mL/min. Column temperature was 50° C. and detection was made using a refractive index detector. External standards of glucose, xylose and arabinose were run with each sample set. Certain examples herein use a protocol to achieve the same end with a somewhat modified set of protocols. The specific modifications to the protocols are described with individual examples.

Oligomeric sugars were separated by size exclusion chromatography using a Tosoh Biosep G2000PW column 7.5 mm×60 cm (www.tosohbioscience.de). The solvent was distilled water at 0.6 mL/min and the column was run at room temperature. Six carbon sugar standards used for size calibration were: stachyose, raffinose, cellobiose and glucose; and 5 carbon sugars were: xylohexose, xylopentose, xylotetrose, xylotriose, xylobiose and xylose. Xylo-oligomers were obtained from Megazyme (www.megazyme.com). Detection was by refractive index and when reported quantitatively results are either as peak area units or relative peak areas by percent.

Total soluble sugars were determined by acid hydrolysis of the centrifuged and filter clarified samples described above. The clarified sample was diluted 1:1 with 0.8 N $H_2SO_4$ and the resulting solution was autoclaved in a capped vial for a total cycle time of 1 h at 121° C. Results are reported without correction for loss of monomer sugar during the hydrolysis.

7.1.9 Protein Analysis by HPLC

To separate and quantify the enzymes contained in broth from 14L fermentations of the integrated expression strains, liquid chromatography (LC) and mass spectroscopy (MS) were performed. Enzyme samples were first treated with a recombinantly expressed endoH glycosidase from *S. plicatus* (e.g., NEB P0702L). EndoH was used at a ratio of 0.01-0.03 μg endoH protein per μg sample total protein and incubated for 3 h at 37° C., pH 4.5-6.0 to enzymatically remove N-linked gycosylation prior to HPLC analysis. Approximately 50 μg of protein was then injected for hydrophobic interaction chromatography using an Agilent 1100 HPLC system with an HIC-phenyl column and a high-to-low salt gradient over 35 min was performed on samples of concentrated fermentation broth. The gradient was achieved using high salt buffer A: 4 M ammonium sulphate containing 20 mM potassium phosphate pH 6.75 and low salt buffer B: 20 mM potassium phosphate pH 6.75. Peaks were detected with UV light at 222 nm and fractions were collected and identified by mass spectroscopy.

7.1.10 Cellulase Activity Assay Using Calcofluor White

Cellulase activity was measured on PASC using a calcofluor white detection method (Appl. Biochem. Biotechnol. 161:313-317). All chemicals used were of analytical grade. Avicel PH-101 was purchased from FMC BioPolymer (Philadelphia, Pa.). Calcofluor white was purchased from Sigma (St. Louis, Mo.). Phosphoric acid swollen cellulose (PASC) was prepared from Avicel PH-101 using an adapted protocol of Walseth, TAPPI 1971, 35:228 and Wood, Biochem. J. 1971, 121:353-362. In short, Avicel was solubilized in concentrated phosphoric acid then precipitated using cold deionized water. After the cellulose was collected and washed with more water to neutralize the pH, it was diluted to 1% solids in 50 mM Sodium Acetate buffer, pH 5.0.

All enzyme dilutions were made into 50 mM Sodium Acetate buffer, pH 5.0. GC220 Cellulase (Danisco US Inc., Genencor) was diluted to 2.5, 5, 10, and 15 mg protein/g PASC, to produce a linear calibration curve. Samples to be tested were diluted to fall within the range of the calibration curve, i.e. to obtain a response of 0.1 to 0.4 fraction product. 150 μL of cold 1% PASC was added to 20 μL of enzyme solution in 96-well microtiter plates. The plate was covered and incubated for 2 h at 50° C., 200 rpm in an Innova incubator/shaker. The reaction was quenched with 100 μL of 50 μg/mL Calcofluor in 100 mM Glycine, pH 10. Fluorescence was read on a fluorescence microplate reader (SpectraMax M5 by Molecular Devices) at excitation wavelength Ex=365 nm and emission wavelength Em=435 nm. The result (shown in FIG. 25) is expressed as the fraction product according to the equation:

$$FP=1-(FI\ sample-FI\ buffer)/(FI\ zero\ enzyme-FI\ buffer),$$

wherein FP is fraction product, and FI=fluorescence units.

7.1.11 Cultivation of *Fusarium verticillioides* and Purification of Major Hemicellulase Activities Detected in the Extracellular Protein Wild type *Fusarium verticillioides* source was as described in Table 1 of Fuchs et al., Fungal Genetics and Biology 2004, 41:852-863. The fungus was grown using destarched corn grain fiber using a modification of the method described in Li et al., Applied Biochemistry and Biotechnology 2005, (121-124):321-334.

Starch was removed from the dried corn pericarp fraction from a corn dry mill fractionation by slurrying 200 g of corn pericarp in 3 L of tap water and heating to 80° C. with 5 mL (500 mg) of high temperature amylase Liquozyme SC DS (Novozymes, Denmark). The mixture was stirred occasionally with a spatula and held at 80° C. for 30 min then allowed to cool to room temperature for about 2 h. The resulting slurry was decanted onto a 20 mesh screen to partially de-water. The solids on the screen were further washed with 4 L of tap water then air dried overnight before a final drying in an oven at 60° C. The dried material was ground to pass a 1 mm screen in a knife mill before use.

The *F. verticillioides* culture was maintained on potato dextrose agar (Sigma P6685) and a rich growth media of 24 g/L potato dextrose was inoculated with mycelia from the plate. The growth culture was incubated for 3 days at 30° C. with agitation at 130 rpm. After 3 days growth the 150 mL of the resulting cell mass and spent media were used to inoculate a corn pericarp induction media. The induction media was 80 g destarched corn pericarp in 1 L base media (15 g $KH_2PO_4$, 5 g ammonium sulfate, 20 g yeast extract, 0.5 g magnesium sulfate and 1 g Tween 80 at pH 4.8). The culture was maintained at 30° C. with agitation at 130 rpm for 7 days.

Extracellular protein was separated from the spent grain and fungal cell mass by centrifugation at 2,000×G for 20 min. The partially clarified supernatant was passed first through a 0.45 μm filter and then through a 0.22 μm filter. The clarified filtrate was stored at 4° C. until used. The filtrate was concentrated approximately 14-fold with Amicon ultra-4 centrifugal filters with a 30 kD cutoff (Millipore).

L-α-arabinofuranosidase (LARF) and β-xylosidase (BXL) activities were purified from the fungal supernatant by first exchanging the proteins into 50 mM pH 6.3 (N-Morpholino) ethanesulphonic acid-NaOH (MES) buffer, then applying protein onto a GE Health Sciences Q-Sepharose Fast Flow quaternary amine anion exchange column (20 mL bed volume equilibrated with MES buffer). The protein purification system used was a GH Health Sciences Akta system using Unicorn software. Proteins were eluted with a 0-0.5 M NaCl gradient in MES buffer.

Activity in column fractions was monitored using either 4-nitrophenyl β-D-xylopyranoside (for BXL activity) or 4-nitrophenyl α-L-arabinofuranoside (for LARF activity). In both cases, 2 μL of the column fraction was added to 95 μL of 50 mM pH 5.0 Sodium Acetate buffer and 5 μL of the p-nitrophenyl substrate, mixed and incubated 2 min at 23° C. 100 μL of 1 N sodium carbonate stop solution was added and absorbance at 405 nm was read.

Active enzyme fractions from the anion exchange system were collected, concentrated on Amicon Centriprep filtration, and applied to a GE Health Sciences SP-Sepharose Fast Flow sulfopropyl cation exchange column (20 mL bed equilibrated with Sodium Acetate buffer) using the same protein purification system described above. Proteins were eluted with a 0-1 M NaCl gradient in Sodium Acetate buffer, and activity in the fractions was monitored as described above. Active fractions were then collected, pooled and concentrated if necessary. Proteins in active fractions were identified by MS-MS.

7.1.12 Protein Identification by MS-MS

The identification of a representative set of *Fusarium verticillioides* family GH54 L-α-arabinofuranosidase (LARF), family GH51 LARF, two family GH3 β-xylosidases and a family GH30 β-xylosidase (BXL) is described below.

For the identification of GH54 LARF, 200 μL of 1 N HCl (EM Industries, Hawthorne, N.Y.) was added to 250 μL of "Fraction B3" (0.35 mg protein) from the purification procedure described above and the sample iced for 10 min. Next, 200 μL of 50% TCA (Sigma-Aldrich, St. Louis, Mo.) was added and samples were iced for another 10 min to precipitate protein. Samples were centrifuged for 2 min at 16,000 rcf and the supernatants were discarded. The pelleted protein was washed with 90% cold acetone (J.T. Baker, Phillipsburg, N.J.), then centrifuged for 1 min at 16,000 rcf. The supernatant was discarded and the pellet was left to air dry. First, 30 μL of 8 M urea (MP Biomedicals, Solon, Ohio) was added to the pellet, then 4 μL of 0.2 M DTT (Sigma-Aldrich, St. Louis, Mo.). Sample was incubated at 52° C. for 30 min and then 4 μL of 0.44 M iodoacetamide (Sigma-Aldrich, St. Louis, Mo.) was added and the solution incubated at room temperature in the dark for 30 min. Next, 120 μL of 0.1% n-octyl B-D-glucopyranoside water (Sigma-Aldrich, St. Louis, Mo.) was added slowly, and then sample was divided into two equal parts. To half the sample, 7.5 μg Trypsin (Promega Corp., Madison, Wis.) was added, and to the other half, 4 μg of AspN (Roche Applied Science, Indianapolis, Ind.) was added. Both samples were incubated at 37° C. for 1 h. Samples were quenched with 10% Trifluoroacetic Acid (Thermoscientific, Waltham, Mass.) for a final volume of 0.1% TFA. Both samples were run on a Thermofinnigan (San Jose, Calif.) LCQ-Deca electrospray ionization (ESI) ion-trap mass spectrometer. A Vydac C18 column (5 u, 300 A, 0.2×150 mm, Michrom Bioresources, Auburn, Calif.) was run at a flow rate of 200 μL/min. The injection volumes were 50 μL, and were filtered through an on-line trapping cartridge (Peptide CapTrap, Michrom Bioresources, Auburn, Calif.) before loading onto the column. Separation of the digests was performed with a gradient as follows (Solvent A: 0.1% trifluoroacetic acid in $H_2O$ (J.T. Baker, Phillipsburg, N.J.), Solvent B: 0.08% trifluoroacetic acid in acetonitrile (J.T. Baker, Phillipsburg, N.J.)). For the identification of GH51 LARF, the two GH3 β-xylosidases, and GH30 β-xylosidase, the method described above was used, except samples were digested with Chymotrypsin (7.5 μg, Sigma-Aldrich, St. Louis, Mo.) in addition to Trypsin and AspN. The TurboSequest search engine within Bioworks 3.31 (Thermo, San Jose) was used to identify proteins from the *Fusarium verticillioides* protein database. The protein database was downloaded from the BROAD Institute at www.broadinstitute.org/annotation/genome/fusarium_verticillioides/MultiDownloads.html.

7.1.13 Induction of *Fusarium verticillioides* Enzymes by Dilute Aqueous Ammonia Pretreated Switchqrass For induction of *Fusarium verticillioides* enzymes in response to dilute aqueous ammonia pretreated switchgrass, switchgrass was ground to <1 mm diameter, then pretreated with 6% ammonia based on dry weight at 50% initial dry matter at 160° *C. maximum* temperature for 90 min. The resulting material was 43.3% solids and contained 0.336% residual ammonia.

Wild type *F. verticillioides* culture was maintained on potato dextrose agar (Sigma P6685) and a rich growth media of 24 g/L potato dextrose was inoculated with mycelia from the plate. The growth culture was incubated for 3 days at 24° C. with agitation at 140 rpm, during which time it became turbid with *Fusarium* cells. After 3 days growth, 4 flasks each containing 100 mL of base Christakapoulos media (0.1% $KH_2PO_4$, 0.03% $CaCl_2$, 0.03% $MgSO_4 \times 7\ H_2O$, 2.61% $Na_2HPO_4 \times 7\ H_2O$, 0.134% $NaH_2PO_4 \times 1\ H_2O$, 1.0% anhydrous ammonium phosphate) were inoculated with 4 mL of the resulting cell suspension. To the suspension, two grams dry matter of dilute aqueous ammonia-pretreated switchgrass was added as the sole carbon source.

After addition of the pretreated switchgrass, the pH was adjusted to 6.5 and the flask was swirled at 180 rpm at 23° C. for 168 h. Prior to size exclusion chromatography, samples were analyzed at different time points by Bradford assay for protein, p-nitrophenyl arabinofuranosidase, p-nitrophenyl xylosidase and p-nitrophenyl glucosidase activities, and by SDS-PAGE gels for induction of enzymes. Intact non-pretreated switchgrass, 2% glucose and no carbon source were included as parallel controls and were found to lead to much lower levels of enzyme induction than was the case for dilute aqueous ammonia-pretreated switchgrass carbon source.

7.1.14 Size Exclusion Chromatography Fractionation of the *Fusarium verticillioides* Culture Broth The *Fusarium verticillioides* culture media containing the expressed enzymes from the 168-h induction described above was centrifuged at 3,500×g to remove debris and cells. The supernatant was filtered through a 0.4 m filter yielding a clear deep yellow liquid. The liquid was concentrated (~4×) two times in a large Amicon ultra 10K MW cutoff concentrator (UFC901024). A 1.7 mL concentrated sample was set aside for size exclusion chromatography (SEC) and assayed for protein content by BCA assay as described earlier. The concentrated protein sample was loaded onto a Superdex 16/60 SEC column equilibrated with 50 mM Sodium Acetate buffer pH 5.0. The column was eluted at 1 mL/min at 4° C. Absorbance of the sample at 214 nm and 280 nm were monitored. After elution of the void volume, 1 mL fractions were collected in a deep well polypropylene microtiter plate. The protein-containing fractions were aggregated into a separate deep well plate and all fractions were measured for total protein concentration by BCA assay, and p-nitrophenyl arabinosidase, p-nitrophenyl xylosidase, and p-nitrophenyl glucosidase activities as described in Example 1 (Synthetic substrate activity assays).

7.1.15 Purification of a NUMBER OF GH43, GH51 and GH3 HOMOLOGS (SECTION 8.1 BELOW) from *T. reesei* Fermentation by Cation Exchange Chromatography Shake flask-scale enzyme production from wild type *Trichoderma reesei* cultures was performed as described in WO 2005/001036. The extracellular enzyme preparations were concentrated by Amicon Centriprep filtration if necessary, and applied to a GE Health Sciences SP-Sepharose Fast Flow sulfopropyl cation exchange column (20 mL bed equilibrated with Sodium Acetate buffer) using a GE Health Sciences Akta system protein purification system using Unicorn software. Proteins were eluted with a 0-1 M NaCl gradient in Sodium Acetate buffer and activity in the fractions were monitored as described above. Active fractions were then collected, pooled and concentrated if necessary. Activity in column fractions was monitored using either 4-nitrophenyl β-D-xylopyranoside (for BXL activity) or 4-nitrophenyl α-L-arabinofuranoside (for LARF activity). In both cases, 2 μL of the column fraction was added to 95 μL of 50 mM pH 5.0 Sodium Acetate buffer and 5 μL of the p-nitrophenyl substrate, mixed and incubated 2 min at 23° C. One hundred microliters of 1 N sodium carbonate stop solution was added and the absorbance was measured at 405 nm. In some cases an anion exchange protein purification step was useful before the cation exchange. In this case, the enzyme fractions were exchanged into 50 mM pH 6.3 (N-Morpholino) ethanesulphonic acid-NaOH (MES) buffer, and then the protein sample was applied onto a GE Health Sciences Q-Sepharose Fast Flow quaternary amine anion exchange column (20 mL bed volume equilibrated with MES buffer). The Akta protein purification system as described for the cation exchange step was used. Proteins were eluted with a 0-0.5 M NaCl gradient in MES buffer. The active enzymes were then exchanged into 50 mM, pH 5.0 Sodium Acetate buffer before cation exchange chromatography.

7.1.16 Purification of Xylanases

Xylanase purification was conducted in two stages:

Stage 1: Hydrophobic interaction chromatography (HIC). $(NH_4)_2SO_4$ was added to fermentation supernatant to achieve a final concentration of 1 M. The separation column used was a Hiprep Phenyl (highsub), 16/10, 20 mL. Buffer A: 20 mM sodium phosphate, pH 6.0. Buffer B: Buffer A+1 M $(NH4)_2SO_4$. Stepwise Elution: 45% B; 0% B; water+10% glycerol.

Stage 2: Gel filtration (GF). Eluate of 0% B from the HIC column was collected and loaded on a HiLoad 26/60 Superdex 75 prep grade (320 mL, GE Healthcare) column. The mobile phase was 20 mM sodium phosphate, pH 6.8, containing 0.15 M NaCl. The elution profile is shown in FIG. 26. FIG. 27 shows the SDS-PAGE detection of the two step separation of AfuXyn 5.

The Applied Biosystems BIOCAD® Vision and Amersham Pharmacia Biotech AKTA Explorer were used for protein purification of *T. reesei* XYN3. Approximately 150 mL of Xylanase 3, from an ultrafiltration concentrate, was loaded onto a Sephadex G-25M desalting column (total volume ~525 mL) equilibrated in 10 mM TES buffer, pH 6.8. 300-400 mL of this desalted sample was then loaded onto an anion-exchange column (high density quaternary amine resin; Applied Biosystems Inc.). The bound protein was then eluted using a salt gradient between 0-1 M sodium chloride using 8-column volumes of 25 mM TES buffer. Elution of the protein occurred between 0-250 mM sodium chloride, and was detected using 10% Bis-Tris NUPAGE® SDS-PAGE (Novex).

The eluted Xylanase 3-containing samples were concentrated to 10 mL with Vivaspin 5,000 MWCO (molecular weight cut-off) membrane concentrators (Vivascience; GE Healthcare). The concentrate was then loaded onto a High Load 26/60 Superdex 200 (ID no 17-1071-01; GE Healthcare). The column was equilibrated with 25 mM TES buffer, pH 6.8, containing 100 mM sodium chloride, and the bound protein was eluted over 8-column volumes of the TES buffer with sodium chloride.

The purity of the eluted protein was assessed using 10% Bis-Tris NUPAGE® SDS-PAGE (Novex), and determined to be greater than 95% pure.

7.1.17 Purification of Fv43D

The ultrafiltration concentrate (UFC) of *Fusarium verticillioides* 43D was buffer exchanged and dialyzed against 50 mM Sodium Acetate buffer, pH 4.0, overnight. The dialyzed material was passed through a HiTrap 1 mL column prepacked with sulfopropyl sepharose fast flow resin (GE Healthcare) designed for use with a syringe. The purified Fv43D was eluted with 50 mM Sodium Acetate buffer, pH 4.0, with 250 mM sodium chloride. The UFC and Sodium Acetate buffer were pushed through the column using a 5 mL syringe fitted with a GE Healthcare connector. The purified Fv43D was dialyzed overnight against 50 mM Sodium Acetate buffer, pH 4.0. The purified protein was assayed by SDS-PAGE, HPLC, and mass spectroscopy to demonstrate homogeneity.

7.1.18 Purification of Fv51A

The ultrafiltration concentrate (UFC) of *Fusarium verticillioides* 51A was buffer exchanged and dialyzed against 50 mM Sodium Acetate buffer, pH 5.0, overnight. The dialyzed material was passed through a RESOURCE 15 6 mL column prepacked with methyl sulfonate media (GE Healthcare). The UFC was loaded at 1 mL/min against 50 mM Sodium Acetate buffer, pH 5.0, and eluted at 5 mL/min against 50 mM Sodium Acetate buffer, pH 5.0, using a 0 to 250 mM sodium chloride gradient. The eluted fractions were collected and assayed by SDS-PAGE. Fractions with purified Fv51A were concentrated using a 10,000 MWCO Vivaspin concentrator from Sartorius Stemdim Biotech. The purified Fv51A was dialyzed against 50 mM Sodium Acetate buffer, pH 5.0, overnight. The purified protein was assayed by SDS-PAGE, HPLC, and mass spectroscopy to demonstrate homogeneity. The AKTA Explorer 100 system from GE Healthcare was used for the purification of Fv51A.

8. EXAMPLE 2: EXPRESSION OF INDIVIDUAL HEMICELLULASE GENES FROM VARIOUS SPECIES IN *TRICHODERMA REESEI*

8.1 *Fusarium verticillioides* Genes

The sequence for Fv51A was obtained by searching the *Fusarium verticillioides* genome in the Broad Institute database (www.broadinstitute.org/) for GH51 arabinofuranosidase homologs.

The following genes from *Fusarium verticillioides* were expressed in *Trichoderma reesei*: Fv3A, Fv43A, Fv43B, Fv43D, Fv51A, Fv3B, Fv43C, Fv39A, Fv43E, Fv30A, Fv30B, and Fv43F. Fv3A sequence was obtained by searching for GH3 β-xylosidase homologs in *Fusarium verticillioides* genome. The annotated sequence lacked a signal sequence and the gene prediction program Augustus (augustus.gobics.de/) was used to identify upstream sequence which contained a signal sequence. Sequences for Fv39A, Fv43A, Fv43B, Fv43D, Fv43E, and Fv30A were obtained by searching the *Fusarium verticillioides* genome for GH39, GH30, and GH43 β-xylosidase homologs.

Open reading frames of the hemicellulase genes of interest were amplified by PCR using purified/extracted genomic DNA from *Fusarium verticillioides* as the template. The PCR thermocycler used was DNA Engine Tetrad 2 Peltier Thermal Cycler (BioRad Laboratories). The DNA polymerase used was PfuUltra II Fusion HS DNA Polymerase (Stratagene). The primers used to amplify the open reading frames were as follows:

Fv3A:
Forward primer MH124
(SEQ ID NO: 52)
(5'-CACCCATGCTGCTCAATCTTCAG-3')

Reverse primer MH125
(SEQ ID NO: 53)
(5'-TTACGCAGACTTGGGGTCTTGAG-3')

Fv43A:
Forward primer MH075
(SEQ ID NO: 54)
(5'-CACCATGTGGCTGACCTCCCCATT-3')

Reverse primer MH076
(SEQ ID NO: 55)
(5'-TTAGCTAAACTGCCACCAGTTGAAGTTG-3')

Fv43B:
Forward primer MH077
(SEQ ID NO: 56)
(5'-CACCATGCGCTTCTCTTGGCTATTGT-3')

Reverse primer MH078
(SEQ ID NO: 57)
(5'-CTACAATTCTGATTTCACAAAAACACC-3')

Fv43D:
Forward primer MH081
(SEQ ID NO: 58)
(5'-CACCATGCAGCTCAAGTTTCTG-3')

Reverse primer MH082
(SEQ ID NO: 59)
(5'-CTAAATCTTAGGACGAGTAAGC-3')

Fv51A:
Forward primer SK1159
(SEQ ID NO: 60)
(5'-CACCATGGTTCGCTTCAGTTCAATCCTAG-3')

Reverse primer SK1160
(SEQ ID NO: 61)
(5'-CTAGCTAGAGTAAGGCTTTCC-3')

Fv39A:
Forward: MH116
(SEQ ID NO: 62)
(5'-CACCATGCACTACGCTACCCTCACCAC-3')

Reverse: MH117
(SEQ ID NO: 63)
(5'-TCAAGTAGAGGGGCTGCTCACC-3')

Fv3B:
Forward primer MH126
(SEQ ID NO: 64)
(5'-CAC CAT GAA ACT CTC TAG CTA CCT CTG-3')

Reverse primer MH127
(SEQ ID NO: 65)
(5'-CTA CGA AAC TGT GAC AGT CAC GTT G-3')

Fv30A:
Forward primer MH112
(SEQ ID NO: 66)
(5'-CAC CAT GCT CTT CTC GCT CGT TCT TCC TAC-3')

Reverse primer MH113
(SEQ ID NO: 67)
(5'-TTA GTT GGT GCA GTG GCC ACG-3')

Fv30B:
Forward primer MH114
(SEQ ID NO: 68)
(5'-CAC CAT GAA TCC TTT ATC TCT CGG CCT TG-3')

Reverse primer MH115
(SEQ ID NO: 69)
(5'-CAG CCC TCA TAG TCG TCT TCT TC-3')

Fv43C:
Forward primer MH079
(SEQ ID NO: 70)
(5'-CAC CAT GCG TCT TCT ATC GTT TCC-3')

Reverse primer MH080
(SEQ ID NO: 71)
(5'-CTA CAA AGG CCT AGG ATC AA-3')

Fv39A:
Forward primer MH116
(SEQ ID NO: 72)
(5'-CAC CAT GCA CTA CGC TAC CCT CAC CAC-3')

-continued

```
Reverse primer MH117
                                              (SEQ ID NO: 73)
(5'-TCA AGT AGA GGG GCT GCT CAC C-3')

Fv43E:
Forward primer MH147
                                              (SEQ ID NO: 74)
(5'-CAC CAT GAA GGT ATA CTG GCT CGT GG-3')

Reverse primer MH148
                                              (SEQ ID NO: 75)
(5'-CTA TGC AGC TGT GAA AGA CTC AAC C-3')

Fv43F:
Forward primer MH149
                                              (SEQ ID NO: 76)
(5'-CACCATGTGGAAACTCCTCGTCAGC-3')

Reverse primer MH150
                                              (SEQ ID NO: 77)
(5'-CTA ATA AGC AAC AGG CCA GCC ATT G-3')
```

The forward primers included four additional nucleotides (sequences—CACC) at the 5'-end to facilitate directional cloning into pENTR/D-TOPO (Invitrogen, Carlsbad, Calif.) (FIG. 28). The PCR conditions for amplifying the open reading frames were as follows (except for Fv51A): Step 1: 94° C. for 2 min. Step 2: 94° C. for 30 sec. Step 3: 57° C. for 30 sec. Step 4: 72° C. for 30-45 sec. Steps 2, 3 and 4 were repeated for an additional 29 cycles. Step 5: 72° C. for 2 min. For Fv51A, the following conditions were used: Step 1: 94° C. for 2 min. Step 2: 94° C. for 30 sec. Step 3: 56° C. for 30 sec. Step 4: 72° C. for 45 sec. Steps 2, 3, 4 were repeated for an additional 25 cycles. Step 5: 4° C. hold.

Figure 29:
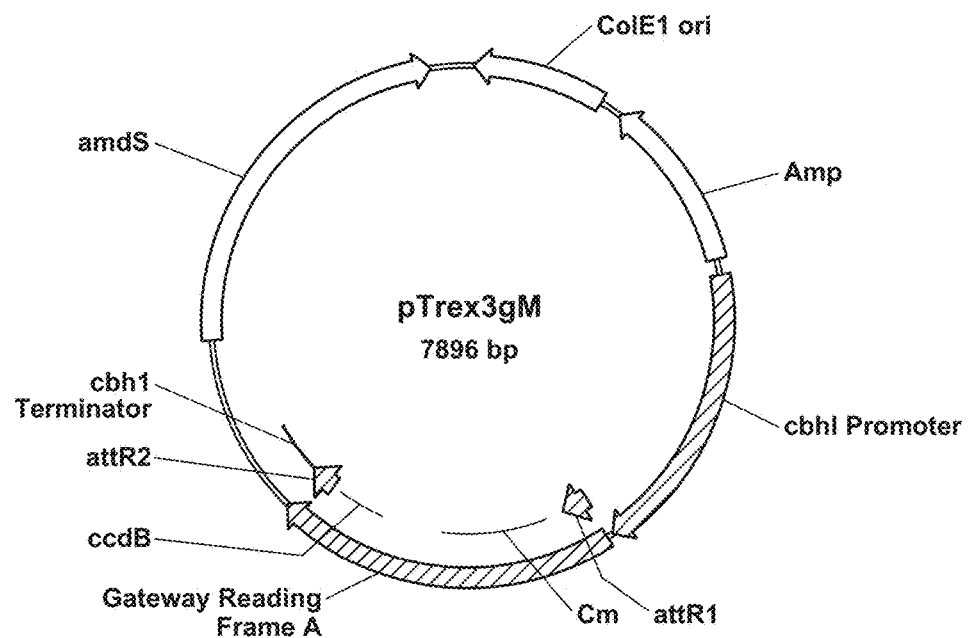

The PCR products of the corresponding hemicellulase open reading frames were purified using a Qiaquick PCR Purification Kit (Qiagen, Valencia, Calif.). The purified PCR products were cloned into the pENTR/D-TOPO vector, transformed into TOP10 chemically competent E. coli cells (Invitrogen, Carlsbad, Calif.) and plated on LA plates with 50 ppm kanamycin. Plasmid DNA was obtained from the E. coli transformants using a QIAspin plasmid preparation kit (Qiagen). Sequence data for the DNA inserted in the pENTR/D-TOPO vector was obtained using M13 forward and reverse primers (Sequetech, Mountain View, Calif.). A pENTR/D-TOPO vector with the correct DNA sequence of the corresponding hemicellulase open reading frame was recombined with the pTrex3gM destination vector (WO 05/001036, FIG. 29) using LR clonase reaction mixture (Invitrogen, Carlsbad, Calif.) according to the manufacturer's instructions. The product of the LR clonase reaction was subsequently transformed into TOP10 chemically competent E. coli cells which were then plated on LA containing 50 ppm carbenicillin. The resulting expression vectors were pTrex3gM plasmids containing the corresponding hemicellulase open reading frames that resulted from the recombination event between the attR1 and attR2 sites of pTrex3gM and the attL1 and attL2 sites of pENTR/D-TOPO; and the Aspergillus nidulans acetamidase selection marker (amdS). DNA of the expression vectors containing the corresponding hemicellulase open reading frames were isolated using a Qiagen miniprep kit and used for biolistic transformation of Trichoderma reesei spores.

Biolistic transformation of Trichoderma reesei with the pTrex3gM expression vector containing the corresponding hemicellulase open reading frame was performed using the following protocol. Transformation of the Trichoderma reesei cellulase quad delete (Δcbh1, Δcbh2, Δeg1, Δeg2) strain by helium-bombardment was accomplished using a Biolistic® PDS-1000/He Particle Delivery System from Bio-Rad (Hercules, Calif.) following the manufacturer's instructions (see patent publications WO 05/001036 and US 2006/0003408). Transformants were transferred to fresh acetamide selection plates (see patent publication WO 2009114380). Stable transformants were inoculated into filter microtiter plates (Corning), containing 200 µL/well of Glycine Minimal media (6.0 g/L glycine; 4.7 g/L $(NH_4)_2SO_4$; 5.0 g/L $KH_2PO_4$; 1.0 g/L $MgSO_4.7H_2O$; 33.0 g/L PIPPS; pH 5.5) with post sterile addition of ~2% glucose/sophorose mixture (U.S. Pat. No. 7,713,725) as the carbon source, 10 mL/L of 100 g/L of $CaCl_2$, 2.5 mL/L of T. reesei trace elements (400×): 175 g/L Citric acid anhydrous; 200 g/L $FeSO_4.7H_2O$; 16 g/L $ZnSO_4.7H_2O$; 3.2 g/L $CuSO_4.5H_2O$; 1.4 g/L $MnSO_4.H_2O$; 0.8 g/L $H_3Bo_3$). Transformants were grown in liquid culture for 5 days in an $O_2$-rich chamber housed in a 28° C. incubator. The supernatant samples from the filter microtiter plate were collected on a vacuum manifold. Supernatant samples were run on 4-12% NuPAGE gels (Invitrogen, Carlsbad, Calif.) according to the manufacturer's instructions to check for expression. The gel was stained with Simply Blue stain (Invitrogen, Carlsbad, Calif.). Purification of GH43, GH51 and GH3 enzymes from T. reesei fermentations was performed by cation exchange chromatography as described in Example 1.

8.2 Genes from Other Species

Pf43A and Pf51A sequences were obtained by sequencing of the Penicillium funiculosum genome. The queries used for the searches of the P. funiculosum genome were other fungal GH43 and GH51 homologs available in the public genomes. A gene prediction program named Augustus (augustus.gobics.de/) was used to verify the intron sequences, along with the start codon. Fv43D sequence was used to query the Gibberella zeae (Fusarium graminearum) and Fusarium oxysporum genomes available in the Broad Institute database and retrieve sequences for Gz43A and Fo43A respectively. The genes for Gz43A and Fo43A were synthesized by GeneArt (Geneart GmbH, Regensburg, Germany) with the CBH1 signal sequence in place of the native signal sequence. Neither gene contained introns. The Pf51A gene was codon-optimized and synthesized by GeneArt with the CBH1 signal sequence in place of the native signal sequence.

Pf43A and Pf51A were cloned and expressed in Trichoderma reesei using the following primers:

```
Pf43A: MH151
                                              (SEQ ID NO: 78)
(5'-CACCATGCTTCAGCGATTTGCTTATATTTTACC-3')

Pf43A: MH152
                                              (SEQ ID NO: 79)
(5'-TTATGCGAACTGCCAATAATCAAAGTTG-3')

Pf51A: SK1168
                                              (SEQ ID NO: 80)
(5'-CACCATGTACCGGAAGCTCGCCGTG-3')

Pf51A: SK1169:
                                              (SEQ ID NO: 81)
(5'-CTACTCCGTCTTCAGCACAGCCAC-3')
```

Three genes were cloned from Aspergillus fumigatus for expression in Trichoderma reesei: GH11 xylanase 2 (AfuXyn2), GH11 xylanase 5 (AfuXyn5), and GH43 Af43A. The primers for AfuXyn2, AfuXyn5, and Af43A cloning primers are shown below:

AfuXyn2:
A.fumi-Q4WG11-F:
(SEQ ID NO: 82)
(5'-CCGCGGCCGCACCATGGTTTCTTTCTCCTACCTGCTGCTG-3')

A.fumi-Q4WG11-R:
(SEQ ID NO: 83)
(5'-CCGGCGCGCCCTTACTAGTAGACAGTGATGGAAGCAGATCCG-3')

AfuXyn5:
A.fumi-Q4WFZ8-F:
(SEQ ID NO: 84)
(5'-CCGCGGCCGCACCATGATCTCCATTTCCTCGCTCAGCT-3')

A.fumi-Q4WFZ8-R:
(SEQ ID NO: 85)
(5'-CCGGCGCGCCCTTATCACTTGGATATAACCCTGCAAGAAGGTA-3')

Af43A:
SK1203:
(SEQ ID NO: 86)
(5'-CACCATGGCAGCTCCAAGTTTATCC-3')

SK1204-
(SEQ ID NO: 87)
(5' TCAGTAGCTCGGGACCACTC-3')

The methods used for cloning and expression of all these genes were similar to the procedure described for cloning of the *Fusarium* genes. Additional genes including those listed in FIG. 68, were cloned in a similar manner.

9. EXAMPLE 3: TESTING FOR ACTIVITY OF NOVEL HEMICELLULASES ON SYNTHETIC SUBSTRATES

The activities of Fv3A, Fv43A, Fv43B, Fv43D and a number of other proteins in, for example, FIG. 69, were tested on synthetic substrates pNPX and pNPA as described in Synthetic substrate activity assay in Example 1. *T. reesei* Bxl1 was used in at 0.7 g/L. The other enzyme samples, and the Quad-delete host control, were added by volume from growth cultures (microtiter plate or shake flask scale). Therefore, the absolute activity cannot be compared across samples but is an indication of an active expressed protein with the relative pNPX and pNPA activity shown in FIG. 69. Activity on para-nitrophenyl substrates is not used as a predictor of performance in biomass saccharification.

10. EXAMPLE 4: HYDROLYSIS OF PRETREATED CORNCOB BY CELLULASE AND HEMICELLULASE PREPARATIONS 10.1 Saccharification Performance of Expressed Proteins The saccharification performance of expressed proteins as additions to an enzyme mixture with an L-α-arabinofuranosidase deficiency was evaluated. L-α-arabinofuranosidase candidates were evaluated in a 4-day cob saccharification assay by addition to an enzyme mixture of Accellerase® 1500/*T. reesei* Xyn3/Fv3A. The screen was conducted as described in the corncob Saccharification Assay (Example 1) with the following enzymes and amounts/concentrations:

Accellerase® 1500, TP (Total Nitrogen) 54.2 mg/mL
*Trichoderma reesei* Xyn3, 2.9 mg/mL TP (purified)
Fv3A, 3.2 mg/mL TP (purified)
Fv51A, 7.8 mg/mL TP (purified)
Mg51A, 6.8 mg/mL TP (TCA/BCA)
At51A, 6.7 mg/mL TP (TCA/BCA)
Pt51A, 3.3 mg/mL TP (TCA/BCA)
Ss51A, 3.0 mg/mL TP (TCA/BCA)
Vd51A, 6.8 mg/mL TP (TCA/BCA)
Cg51B, 3.6 mg/mL TP (TCA/BCA)
Af43A, 2.6 mg/mL TP (TCA/BCA)
Pf43A, 2 mg/mL TP (TCA/BCA)
Fv43E, 1.37 mg/mL TP (TCA/BCA)

The total protein (TP) of purified samples was determined by A280 unless otherwise noted. The total protein of unpurified samples was determined by BCA according to manufacturer instructions, unless otherwise noted. Accellerase® 1500 was added at 20 mg protein/g cellulose; *Trichoderma reesei* Xyn3 was added at 5 mg protein/g cellulose; Fv3A was added at 5 mg protein/g cellulose. Fv51A, Mg51A, At51A, Pt51A, Ss51A, Vd51A, Cg51B, Af43A, Pf43A, or Fv43E were added at 1, 3, and 5 mg protein/g cellulose. Following 4 days incubation, 50° C., 200 rpm, the assay plate was quenched and analyzed by HPLC for soluble sugars.

Enzymes were found that enhanced glucose or xylose or arabinose yield, or reduced cellobiose or xylobiose concentration in this enzyme mixture. Results are shown in FIGS. 30A and 30B.

The saccharification performance of expressed proteins was also evaluated as additions to the enzyme mixture with an L-α-arabinofuranosidase and β-xylosidase deficiency. β-xylosidase candidates were evaluated in a 3 day cob saccharification assay by addition to an enzyme mixture of Accellerase® 1500/*T. reesei* Xyn3. The screen was conducted as described in the corncoob saccharification assay (Example 1) with the following enzymes and amounts/concentrations:

Accellerase® 1500, TP (total nitrogen) 54.2 mg/mL
*Trichoderma reesei* Xyn3, 2.9 mg/mL (purified)
Fv3A, 3.2 mg/mL (purified)
Fv43D, 6.8 mg/mL (purified)
Pf43A, 2 mg/mL TP (BCA)
Pf43B, 2.7 mg/mL TP (BCA)
Fv43E, 1.37 mg/mL TP (BCA)
Fv43F, 2.8 mg/mL TP (BCA)
Fv30A, 2.7 mg/mL TP (BCA)

Accellerase® 1500 was added at 17.9 mg protein/g cellulose; *T. reesei* Xyn3 was added at 5 mg protein/g cellulose. Fv3A, Fv43D, Pf43A, Pf43B, Fv43E, Fv43F, or Fv30A were added at 1, 3, and 5 mg protein/g cellulose (Fv43E was only added at 1 and 3 mg/g). Following 3 days incubation, 50° C., 200 rpm, the assay plate was quenched and analyzed by HPLC for soluble sugars. Results are shown in FIG. 31. Enzymes were found that enhanced glucose, or xylose or arabinose yield, or reduced cellobiose or xylobiose concentration in this enzyme mixture.

The saccharification performance of expressed proteins was also evaluated as additions to the enzyme mix with a xylanase deficiency. During the construction of the *Trichoderma reesei* integrated expression strains (described in Example 9 below), one *T. reesei* strain (strain #44) was isolated that over-expressed Bgl1, Fv3A, Fv51A, Fv43D proteins but did not over-express endo-xylanase. This strain was used as the background to which candidate xylanases were added for performance screening. Endo-xylanase candidates were evaluated in a 3 day cob saccharification assay by addition to the enzyme products from strain #44. The screen was conducted as described in the corncob saccharification assay (Example 1) with the following enzymes and amounts/concentrations:

Strain #44 enzyme product 78.6 mg/mL TP (modified Biuret)
*Trichoderma reesei* Xyn3 2.9 mg/mL TP (purified)
AfuXyn2 3.3 mg/mL TP (purified)
AfuXyn3 5.8 mg/mL TP (purified)

AfuXyn5 14.8 mg/mL TP (purified)
PfuXyn1 1.9 mg/mL TP (purified)
SspXyn1 1.2 mg/mL TP (purified)

The enzyme composition produced by Strain #44 was added at 20 mg protein/g cellulose; candidate xylanase enzymes were added at 3 and 7 mg protein/g cellulose. Following 3 days incubation, at 50° C., 200 rpm, the assay plate was quenched and analyzed by HPLC for soluble sugars. Enzymes were found that enhanced xylose, or glucose, or arabinose yield, or reduced cellobiose or xylobiose concentration in this enzyme mixture. Results are shown in FIG. 32.

The saccharification performance of expressed Fv51A and Pa51A proteins in enzyme mixtures with L-α-arabinofuranosidase deficiency was evaluated and compared. Fv51A and Pa51A were evaluated in a 3 day cob saccharification assay by addition to an enzyme mixture of Accellerase® 1000/T. reesei Xyn2/Bxl1 or Fv3A. The screen was conducted as described in the corncob saccharification assay (Example 1) with the following enzymes and amounts/concentrations:

Accellerase® 1000, 60.6 mg/mL TP (total nitrogen)
Trichoderma reesei Xyn2 4.1 mg/mL TP (purified)
Trichoderma reesei Bxl1 69 mg/mL TP (TCA/total nitrogen)
Fv3A 65 mg/mL TP (TCA/total nitrogen)
Fv51A 43 mg/mL TP (TCA/BCA)
Pa51A 85.4 mg/mL TP (TCA/total nitrogen)

Accellerase® 1000 was added at 20 mg protein/g cellulose; Trichoderma reesei Xyn2 was added at 5 mg protein/g cellulose; Trichoderma reesei Bxl1 or Fv3A was added at 5 mg protein/g cellulose. Fv51A was added at 5 mg protein/g cellulose. Pa51A was added at 1, 2, or 5 mg protein/g cellulose. Following 3 days incubation, at 50° C., 200 rpm, the assay plate was quenched and analyzed by HPLC for soluble sugars. Enzyme combinations were found that enhanced xylose, or glucose, or arabinose yield, or reduced cellobiose or xylobiose concentration in this enzyme mixture. Results are shown in FIG. 33.

Fv51A and Pa51A also were evaluated in a 3 day cob saccharification assay by addition to an enzyme mixture of Accellerase® 1000/Trichoderma reesei Xyn2. Purified Fv51A (29 mg/mL TP) and Pa51A (29 mg/mL) were used in this part of the study. Accellerase® 1000 was added at 17.5 mg protein/g cellulose; Trichoderma reesei Xyn2 was added at 4.4 mg protein/g cellulose. Fv51A was added at 4.4 mg protein/g cellulose. Pa51A was added at 0.9, 1.8, and 4.4 mg protein/g cellulose. Following 3 days incubation, at 50° C., 200 rpm, the assay plate was quenched and analyzed by HPLC for soluble sugars. Enzyme combinations were found that enhanced xylose, or glucose, or arabinose yield in this enzyme mixture. Results are shown in FIG. 34.

The saccharification performance of expressed proteins was also evaluated as additions to the enzyme mix with β-xylosidase deficiency. β-xylosidase candidates were evaluated in a 3 day cob saccharification assay by addition to an enzyme mixture of Accellerase® 1000/Trichoderma reesei Xyn2/Fv51A. The screen was conducted as described in the corncob saccharification assay (Example 1) with the following enzymes and amounts/concentrations:

Accellerase® 1000, TP (TCA/Total nitrogen) 60.6 mg/mL
Trichoderma reesei Xyn2, 4.1 mg/mL TP (purified)
Fv3A, 65 mg/mL TP (TCA/Total nitrogen)
Fv3B, 62.9 mg/mLTP (TCA/Total nitrogen)
Fv39A, 47.5 mg/mL TP (TCA/Total nitrogen)
Fv30B, 62.9 mg/mL TP (TCA/Total nitrogen)
Fv51A, 43 mg/mL TP (TCA/BCA)

Accellerase® 1000 was added at 20 mg protein/g cellulose; Trichoderma reesei Xyn2 was added at 5 mg protein/g cellulose; Fv51A was added at 5 mg protein/g cellulose. Fv39A, Fv30B, Fv3A, or Fv3B were added at 1, 2, or 5 mg protein/g cellulose. Following 3 days incubation, at 50° C., 200 rpm, the assay plate was quenched and analyzed by HPLC for soluble sugars. Enzymes and combinations were found that enhanced glucose or xylose or arabinose yield, or reduced cellobiose or xylobiose concentration in this enzyme mixture, with or without another β-xylosidase (T. reesei Bxl1). Results are shown in FIGS. 35A-35C.

10.2 Activity of Candidate Endo-Xylanases with Birchwood Xylan

The activity of candidate endo-xylanases was evaluated using birchwood xylan as a substrate using the following assay. Ninety microliters of a 1% (wt/vol) birchwood xylan (Sigma X0502) stock solution was added to wells in a 96-well microtiter plate and pre-incubated at 50° C. for 10 min. Enzyme dilutions and xylose standards were added (10 µL) to the microtiter plate and the plates incubated at 50° C. for 10 min. Meanwhile, 100 µL of DNS solution was added to PCR tubes. Following the 10-min incubation, 60 µL of the enzyme reaction was transferred to the PCR tubes containing the DNS solution. The tubes were incubated in a thermocycler at 95° C. for 5 min, and then cooled to 4° C. One hundred microliters of the reaction mixture was transferred to a 96-well plate, and absorbance at 540 nm was measured. A xylose standard curve was generated and used to calculate the activity. One xylanase unit is defined as the amount of enzyme required to generate 1 µmole of xylose reducing sugar equivalents per minute under the conditions of the assay. Results are shown in FIG. 70.

10.3 Enzyme Hydrolysis of Arabinoxylan Oligomers from Saccharified Corncob

In this study, enzyme hydrolysis of the arabinoxylan oligomers remaining after digestion of dilute ammonia pretreated corncob with cellulase and hemicellulase preparations was monitored. Preparation of crude oligomers is described in Example 1. Total oligomer sugars were determined by HPLC (see Example 1) after acid hydrolysis of the crude oligomers with 2% (v/v) sulfuric acid in a sealed vial at 121° C. for 30 min. The sugar concentrations were corrected for a small amount of sugar degradation as determined by control samples of known sugar mixtures treated by the same procedure. The concentration of total sugars in the crude oligomer preparation determined by this method was 45 g/L glucose, 168 g/L xylose, and 46 g/L arabinose. When accounting for monomer sugar present in crude oligomers before acid hydrolysis, 86% of the glucose, 90% of the xylose, and 43% of the arabinose was present in oligomeric form. Various β-xylosidases, arabinofuranosidases, and mixtures thereof were tested for increased conversion of arabinose monomer from the crude oligomers preparation. The crude oligomer preparation was diluted 20-fold to 12 g/L oligomers in 50 mM Sodium Acetate buffer, pH 5.0, and maintained at 50° C. in a heating block in capped 1.5 mL Eppendorf tubes. Enzymes were added at final concentrations of 0.06-0.09 g/L and incubated for 24 h to reach completion. Samples were then removed for HPLC analysis of momomer sugars as described in Example 1. The results are listed in FIG. 71 as % conversion to monomer sugar based on total sugar as determined by acid hydrolysis.

To obtain the highest yields (44-71%) of arabinose from the remaining arabinoxylan oligomers in the crude oligomer mix, the data in FIG. 71 show that binary combinations of Fv3A+Fv51A, Fv3A+Fv43B, and Fv43A+Fv43B provide the best results. From the sequence families and activity on artificial substrates, it is deduced that Fv3A is a β-xylosidase and Fv51A is an L-α-arabinofuranosidase.

It is known that arabinose sugars in arabinoxylan from corncob are frequently linked to xylose at both the 2 and 3 carbon positions of the arabinose sugar. Thus the activity of Fv3A is likely to hydrolyze the xyl(1-2)ara linkage which then makes available the ara(1-3) xyl linkage to hydrolysis by the L-α-arabinofuranosidase. Of the β-xylosidases tested only Fv3A and Fv43A appeared to have this activity. Also in this screening only Fv43B appeared to have L-α-arabinofuranosidase activity among the Family 43 members from *Fusarium verticillioides*. Results are shown in FIG. 71.

11. EXAMPLE 5: SUBSTRATE RANGE OF B-XYLOSIDASES FOR EFFECTIVE CORNCOB HYDROLYSIS

In this example, the substrate range of 3 β-xylosidases and their relation to effective conversion of corncob xylooligomers to monomer sugars were determined. Preparation of corncob hydrolysate containing oligomeric sugars and assay of monomer sugars was performed as described in Example 1. The proton NMR spectra of oligomeric sugars with degree of polymerization (DP) greater than 2 as separated by size exclusion chromatography on Bio-Gel P2 were determined (FIG. 36 and FIG. 37). The spectra of oligomers before enzyme treatment is labeled "MD07 oligomers" in the bottom panel of FIG. 36 and spectra of the same oligo containing fractions after enzyme treatments are in the remaining panels of FIG. 36 and FIG. 37 labeled with the treatment enzyme.

The Bio-gel P2 fractions containing oligomers of greater than DP2 (5-10 mg) were lyophilized then dissolved in 0.7 mL of a $D_2O$ solution containing 0.5 mM 2,2-dimethyl-2-silapentane-5-sulfonate (DSS) as internal standard. Aliquots of 0.55 mL were used for the NMR samples in order to optimize suppression of the residual water peak. Standard versions of the Varian 2D correlation pulse sequences were used, with optimization of the $^{13}C$ spectral width for the heteronuclear experiments. Spectra were acquired on a Varian Unity Inova using a high sensitivity cryoprobe operating at 500 MHz. Structure elucidation was done by identifying the correlations that characterize the spin-system for the individual sugar residues and then identifying the inter-glycosidic correlations.

The arabinose containing oligomers as determined by NMR, are dominated by one or more branched structures in which arabinose is linked β-1→3 to a xylose residue in a polymer fragment. The arabinose residue in the resulting branch is further substituted by a xylose residue linked β-1→2 to the arabinose. Little arabinose without this second substitution is present in the remaining xylo-oligomers. *T. reesei* Bxl1 is not very effective at cleaving the furthest out xylose 1→2 to arabinose bond as evidenced by the remaining signals at 5.5 to 5.55 ppm in the spectra. The combination of the Fv43A that is effective on longer chain xylose oligomers and the Fv43B L-α-arabinofuranosidase removes most but not all of the branched species with signals in the 5.5 ppm range and unlike treatment with the *T. reesei* Bxl1, leaves none of the signal at 5.35 that is attributable to remaining arabinose branched to xylose oligomer.

The anomeric proton region of the spectra of the remaining xylo-oligomers after treatment with the Fv51A alone or in combination with the Fv3A show different results. The L-α-arabinofuranosidase alone is not effective at reducing the complexity of signals in the region. The Fv3A β-xylosidase removes essentially all of the xylose subtending the arabinose branch leaving mostly simply linked arabinose 1→3 xylose oligomer structures. Addition of the L-α-arabinofuranosidase to the β-xylosidase results in a fairly complete conversion to monomer sugars as evidenced by the increase in signal coming from the α and β anomeric protons of reducing sugars.

It can thus be concluded that the increased effectiveness of one β-xylosidase over another is likely to be due to the substrate range in terms of the structural complexity of the aglycon allowable as substrate.

12. EXAMPLE 6: SEQUENCE COMPARISON AND CRITICAL RESIDUES IN DETERMINING SUBSTRATE RANGE IN GH3 B-XYLOSIDASES

The *T. reesei* β-xylosidase (Bxl1) is 61% similar to the *F. verticillioides* ortholog (Fv3A) and shares 42% sequence identity as shown in the alignment of FIG. 38. Fv3A has much broader substrate range than Bxl1, which is likely to be attributable to the non-conserved amino acids among the two proteins.

13. EXAMPLE 7: DETERMINATION OF DEFINED HEMICELLULASE ACTIVITY FOR CORNCOB HYDROLYSIS TO MONOMER SUGARS

Pretreated corncob as described in Example 1 was used as water slurry adjusted to about pH 5 with $H_2SO_4$ in water at 18.6 g dry corncob solids/100 g of total slurry. 0.78 g of the slurry was added to 4 mL glass vials and sufficient pH 5.0, 50 mM Sodium Acetate buffer was added to give a total reaction weight of 1.06 g after the desired enzyme additions. The hemicellulases were added as the purified preparations described in Example 1. Supernatant from the quad deleted *T. reesei* strain (Quad in FIG. 72A, FIG. 72B and FIG. 73) is the concentrate of background proteins expressed by the *T. reesei* strain deleted in 4 major cellulase activities (described in WO 05/001036). Accellerase® 1000 is a whole cellulase mixture with high β-glucosidase activity. The vials were incubated at 230 rpm in an orbital shaker at 48° C. for 72 h then 2 mL of water was added. A sub-sample was taken and further diluted, centrifuged and filtered for HPLC analysis for monomer sugars as described in Example 1. Experimental results defining useful amounts of defined hemicellulase activity for hydrolyzing pretreated corncob to monomer sugars is shown in FIG. 72A and FIG. 72B.

The results from the design-of-experiments (DoE) were fit to a surface model and used to determine best ratios of the 7 enzyme components for best yield of glucose, xylose and arabinose at the two total protein concentrations tested. Results of the ratios for the seven enzyme components are shown in FIG. 73.

Another exploration of the ratios (FIG. 74) was conducted including Fv3A, and again including Fv43D and holding that activity constant at a low level. The reaction set up and reaction conditions were identical to those described for the full DoE experiment.

Reactions (run numbers) 20, 21, and 22 contain only the whole cellulase enzyme mix and at the 21 mg/g of glucan loading monomerized about 48% of the glucose present in the cob and 24% of the xylose. Addition of the endoxy-lanase, *Trichoderma reesei* Xyn3 allowed decrease of the whole cellulase protein load while retaining about the same glucose monomer yield and increased the xylose monomer yield to about 40% (run#1). All the combinations that gave arabinose yields of above 40% required the combination of Fv43D, Fv43A and Fv43B or Fv51A or of Fv3A and Fv51A or Fv43B. Those combinations also tended to have highest release of xylose to monomer sugar.

Another set of reactions aimed at refining the required mix of hemicellulases was run holding both the loading of whole cellulase constant and the loading of the endoxylanase constant. Accellerase® 1000 whole cellulase preparation was held constant at 12 mg/g glucan and purified *T. reesei* Xyn3 endoxylanase was held at 6 mg/g xylan. Fv51A was the only L-α-arabinofuranosidase in the mixture, at different doses. Other reaction conditions remained the same but the hydrolysate was analyzed by size exclusion chromatography as described in Example 1. The quantitation of individual sugars was performed by peak area only and the results are shown in FIG. 75.

All combinations released similar amounts of glucose and about the same amount of total soluble xylose. The degree of reduction to monomer xylose varied by treatment. Without added activity to convert oligomer to monomer about 50% of the solubilized xylose remained oligomeric unless at least a β-xylosidase was added. Fv3A at 2 mg Fv3A protein/g xylan reduced >DP2 oligomers to 3.6 mg/mL. Addition of 2 mg Fv51A protein/g xylan to the 2 mg Fv3A protein/g xylan further decreased the >DP2 oligomers to 1.5 mg/mL. About 2 mg of Fv51A/g xylan appeared to be sufficient to reduce the >DP2 oligomers to a minimum when the required 2 mg/g Fv3A was present (FIG. 75).

A mix of 6 mg/g xylan *T. reesei* Xyn3, 2 mg/g Fv3A and either 1 or 2 mg/g Fv51A is a suitable loading to reduce total cob arabinoxylan to monomer sugars. The addition of Fv43D to the mix aids in taking the xylobiose or other DP2 oligomers to monomer. Arabinose hydrolysis to monomer was not measured in this experiment.

14. EXAMPLE 8: EFFECTIVENESS OF HEMICELLULASES AT PRODUCING MONOMER SUGARS FROM CORNCOB

In this example, the effectiveness of a set of purified hemicellulase activities at producing monomer xylose and arabinose sugars when acting alone on diluted ammonia pretreated corncob is demonstrated. Three mixtures (Mixes A, B, & C) of purified hemicellulases were prepared and used to hydrolyze hemicellulose in pretreated cob in 1 g total, 14% solids reactions prepared as in Example 1 and run under the conditions described in Example 1. Monomer sugars were analyzed by HPLC as described in Example 1 after 72 h of reaction and the amounts obtained are shown in FIG. 76.

Mix A: 6 mg *Trichoderma reesei* Xyn3; 4 mg Fv3A; 1 mg Fv51A/g xylan

Mix B: 6 mg *Trichoderma reesei* Xyn3; 1 mg Fv43D; 3 mg Fv43A; 3 mg Fv43B/g xylan Mix C: 6 mg *Trichoderma reesei* Xyn3; 3 mg Fv3A; 1 mg Fv43D; 1 mg Fv51A/g xylan In this experiment the defined hemicellulase sets yielded slightly less monomer sugar than seen in earlier experiments which included activities to solubilize cellulose. The yields were still greater than those seen with endoxylanase-only addition to whole cellulase preparations. The hemicellulase activities are effective in taking xylan to monomer.

The same set of mixtures was used on hemicellulose preparations made from corncob, total stover from grain sorghum, switchgrass and sugar cane bagasse using the procedures in the general methods in accordance with Example 1. Stock suspensions of each hemicellulose preparation at 100 mg/mL in 50 mM pH 5.0 Sodium Acetate buffer were made and the pH was checked. Each of them was diluted to 10 mg preparation per mL with more 50 mM acetate buffer. Aliquots of each enzyme mixture were added to 100 μL of the 10 mg/mL suspension and the reactions were run in duplicate, incubated at 48° C. for 6 h with agitation. Reactions were diluted with 100 μL of water, centrifuged and filtered before HPLC analysis for monomer sugars as described in Example 1. 200 μL of each hemicellulose suspension was diluted with 200 μL of 0.8 N H$_2$SO$_4$, autoclaved at 121° C. for 30 min on liquid cycle then filtered and sugars analyzed by HPLC as described in Example 1. Results shown in FIG. 77 are reported as the average monomer sugar released by the enzyme mixture as a percentage of the acid hydrolysable sugar present in the reaction.

Mixes A and C performed well on hemicellulose from cob and as seen in other experiments on whole pretreated cob. Mixtures containing Fv3A increase conversion of arabinose to monomer and give a slight advantage in conversion of xylose to monomer. All 3 mixtures work well on hemicellulose purified from other monocots. The mixing of one endoxylanase, either one or two β-xylosidases, one of which has substrate specificity beyond two or three xylose units linked β 1→4 and an L α-arabinofuranosidase results in an effective hemicellulase blend against monocot hemicellulose.

15. EXAMPLE 9: CONSTRUCTION OF THE INTEGRATED EXPRESSION STRAIN OF *TRICHODERMA REESEI*

An integrated expression strain of *Trichoderma reesei* was constructed that co-expressed five genes: *T. reesei* β-glucosidase gene bgl1, *T. reesei* endoxylanase gene xyn3, *F. verticillioides* β-xylosidase gene fv3A, *F. verticillioides* β-xylosidase gene fv43D, and *F. verticillioides* α-arabinofuranosidase gene fv51A.

The construction of the expression cassettes for these different genes and the transformation of *T. reesei* strain are described below.

15.1 Construction of the β-Glucosidase Expression Cassette

The N-terminal portion of the native *T. reesei* f-glucosidase gene bgl1 was codon optimized by DNA 2.0 (Menlo Park, USA). This synthesized portion comprised of the first 447 bases of the coding region. This fragment was PCR amplified using primers SK943 and SK941. The remaining region of the native bgl1 gene was PCR amplified from a genomic DNA sample extracted from *T. reesei* strain RL-P37, using primer SK940 and SK942. These two PCR fragments of the bgl1 gene were fused together in a fusion PCR reaction, using primers SK943 and SK942:

```
Forward Primer SK943:
                                     (SEQ ID NO: 88)
(5'-CACCATGAGATATAGAACAGCTGCCGCT-3')

Reverse Primer SK941:
                                    (SEQ ID NO: 89))
(5'-CGACCGCCCTGCGGAGTCTTGCCCAGTGGTCCCGCGACAG-3')

Forward Primer SK940:
                                     (SEQ ID NO: 90)
(5'-CTGTCGCGGGACCACTGGGCAAGACTCCGCAGGGCGGTCG-3')

Reverse Primer SK942:
                                     (SEQ ID NO: 91)
(5'-CCTACGCTACCGACAGAGTG-3')
```

The resulting fusion PCR fragments were cloned into the Gateway® Entry vector pENTR™/D-TOPO®, and transformed into *E. coli* One Shot® TOP10 Chemically Competent cells (Invitrogen) resulting in the intermediate vector, pENTRY-943/942 (FIG. 39). The nucleotide sequence of the inserted DNA was determined. The pENTRY-943/942 vector with the correct bgl1 sequence was recombined with pTrex3g using a LR Clonase® reaction protocol outlined by Invitrogen. The LR clonase reaction mixture was transformed into *E. coli* One Shot® TOP10 Chemically Competent cells (Invitrogen), resulting in the final expression vector, pTrex3g 943/942 (FIG. 40). The vector also contains the *Aspergillus nidulans* amdS gene encoding acetamidase as a selectable marker for transformation of *T. reesei*. The expression cassette was PCR amplified with primers SK745 and SK771 to generate product for transformation of the strain, using the electroporation method described in WO 08153712.

```
Forward Primer SK771:
                                        (SEQ ID NO: 94)
(5'-GTCTAGACTGGAAACGCAAC-3')

Reverse Primer SK745:
                                        (SEQ ID NO: 95)
(5'-GAGTTGTGAAGTCGGTAATCC-3')
```

15.2 Construction of the Endoxylanase Expression Cassette

The native *T. reesei* endoxylanase gene xyn3 was PCR amplified from a genomic DNA sample extracted from *T. reesei*, using primers xyn3F-2 and xyn3R-2.

```
Forward Primer xyn3F-2:
                                        (SEQ ID NO: 94)
(5'-CACCATGAAAGCAAACGTCATCTTGTGCCTCCTGG-3')

Reverse Primer (xyn3R-2):
                                        (SEQ ID NO: 95)
(5'-CTATTGTAAGATGCCAACAATGCTGTTATATGCCGGCTTGGGG-3')
```

The resulting PCR fragments were cloned into the Gateway® Entry vector pENTR™/D-TOPO®, and transformed into *E. coli* One Shot® TOP10 Chemically Competent cells (Invitrogen) resulting in the intermediate vector, pENTR/Xyn3 (FIG. 41). The nucleotide sequence of the inserted DNA was determined. The pENTR/Xyn3 vector with the correct xyn3 sequence was recombined with pTrex3g using a LR Clonase® reaction protocol outlined by Invitrogen. The LR clonase reaction mixture was transformed into *E. coli* One Shot® TOP10 Chemically Competent cells (Invitrogen), resulting in the final expression vector, pTrex3g/Xyn3 (FIG. 42). The vector also contains the *Aspergillus nidulans* amdS gene encoding acetamidase as a selectable marker for transformation of *T. reesei*. The expression cassette was PCR amplified with primers SK745 and SK822 to generate product for transformation of the strain, using the electroporation method.

```
Forward Primer SK745:
                                        (SEQ ID NO: 96)
(5'-GAGTTGTGAAGTCGGTAATCC-3')

Reverse Primer SK822:
                                        (SEQ ID NO: 97)
(5'-CACGAAGAGCGGCGATTC-3')
```

15.3 Construction of the β-Xylosidase Fv3A Expression Cassette

The *F. verticilloides* β-xylosidase fv3A gene was amplified from a *F. verticilloides* genomic DNA sample using the primers MH124 and MH125.

```
Forward Primer MH124:
                                        (SEQ ID NO: 98)
(5'-CAC CCA TGC TGC TCA ATC TTC AG-3')

Reverse Primer MH125:
                                        (SEQ ID NO: 99)
(5'-TTA CGC AGA CTT GGG GTC TTG AG-3')
```

The PCR fragments were cloned into the Gateway® Entry vector pENTR™/D-TOPO®, and transformed into *E. coli* One Shot® TOP10 Chemically Competent cells (Invitrogen) resulting in the intermediate vector, pENTR-Fv3A (FIG. 43). The nucleotide sequence of the inserted DNA was determined. The pENTRY-Fv3A vector with the correct fv3A sequence was recombined with pTrex6g using a LR Clonase® reaction protocol outlined by Invitrogen. The LR clonase reaction mixture was transformed into *E. coli* One Shot® TOP10 Chemically Competent cells (Invitrogen), resulting in the final expression vector, pTrex6g/Fv3A (FIG. 44). The vector also contains a chlorimuron ethyl resistant mutant of the native *T. reesei* acetolactate synthase (als) gene, designated alsR, which is used together with its native promoter and terminator as a selectable marker for transformation of *T. reesei* (WO2008/039370 A1). The expression cassette was PCR amplified with primers SK1334, SK1335 and SK1299 to generate product for transformation of *T. reesei*, using the electroporation method (see, e.g., WO2008153712 A2).

```
Forward Primer SK1334:
                                        (SEQ ID NO: 100)
(5'-GCTTGAGTGTATCGTGTAAG-3')

Forward Primer SK1335:
                                        (SEQ ID NO: 101)
(5'-GCAACGGCAAAGCCCCACTTC-3')

Reverse Primer SK1299:
                                        (SEQ ID NO: 102)
(5'-GTAGCGGCCGCCTCATCTCATCTCATCCATCC-3')
```

15.4 Construction of the β-Xylosidase Fv43D Expression Cassette

For the construction of the *F. verticilloides* β-xylosidase Fv43D expression cassette, the fv43D gene product was amplified from *F. verticilloides* genomic DNA using the primers SK1322 and SK1297. A region of the promoter of the endoglucanase gene egl1 was PCR amplified from *T. reesei* genomic DNA extracted from strain RL-P37, using the primers SK1236 and SK1321. These two PCR amplified DNA fragments were subsequently fused together in a fusion PCR reaction using the primers SK1236 and SK1297. The resulting fusion PCR fragment was cloned into pCR-Blunt II-TOPO vector (Invitrogen) to give the plasmid TOPO Blunt/Pegl1-Fv43D (FIG. 45) and *E. coli* One Shot® TOP10 Chemically Competent cells (Invitrogen) were transformed using this plasmid. Plasmid DNA was extracted from several *E. coli* clones and confirmed by restriction digest.

```
Forward Primer SK1322:
                                        (SEQ ID NO: 103)
(5'-CACCATGCAGCTCAAGTTTCTGTC-3')
```

```
-continued
Reverse Primer SK1297:
                                        (SEQ ID NO: 104)
(5'-GGTTACTAGTCAACTGCCCGTTCTGTAGCGAG-3')

Forward Primer SK1236:
                                        (SEQ ID NO: 105)
(5'-CATGCGATCGCGACGTTTTGGTCAGGTCG-3')

Reverse Primer SK1321:
                                        (SEQ ID NO: 106)
(5'-GACAGAAACTTGAGCTGCATGGTGTGGGACAACAAGAAGG-3')
```

The expression cassette was PCR amplified from TOPO Blunt/Pegl1-Fv43D with primers SK1236 and SK1297 to generate product for transformation of *T. reesei*, using the electroporation method as described in WO2008153712A2.

15.5 Construction of the α-Arabinofuranosidase Expression Cassette

For the construction of the *F. verticilloides* α-arabinofuranosidase gene fv51A expression cassette, the fv51A gene product was amplified from *F. verticilloides* genomic DNA using the primers SK1159 and SK1289. A region of the promoter of the endoglucanase gene egl1 was PCR amplified from *T. reesei* genomic DNA sample extracted from strain RL-P37, using the primers SK1236 and SK1262. These two PCR amplified DNA fragments were subsequently fused together in a fusion PCR reaction using the primers SK1236 and SK1289. The resulting fusion PCR fragment was cloned into pCR-Blunt II-TOPO vector (Invitrogen) to give the plasmid TOPO Blunt/Pegl11-Fv51A (FIG. 46) and *E. coli* One Shot® TOP10 Chemically Competent cells (Invitrogen) were transformed using this plasmid.

```
Forward Primer SK1159:
                                        (SEQ ID NO: 107)
(5'-CACCATGGTTCGCTTCAGTTCAATCCTAG-3')

Reverse Primer SK1289:
                                        (SEQ ID NO: 108)
(5'-GTGGCTAGAAGATATCCAACAC-3')

Forward Primer SK1236:
                                        (SEQ ID NO: 109)
(5'-CATGCGATCGCGACGTTTTGGTCAGGTCG-3')

Reverse Primer SK1262:
                                        (SEQ ID NO: 110)
(5'-GAACTGAAGCGAACCATGGTGTGGGACAACAAGAAGGAC-3')
```

The expression cassette was PCR amplified with primers SK1298 and SK1289 to generate product for transformation of *T. reesei* using the electroporation method.

```
Forward Primer SK1298:
                                        (SEQ ID NO: 111)
(5'-GTAGTTATGCGCATGCTAGAC-3')

Reverse Primer SK1289:
                                        (SEQ ID NO: 112)
(5'-GTGGCTAGAAGATATCCAACAC-3')
```

15.6 Co-Transformation of *T. reesei* with the β-Glucosidase and Endoxylanase Expression Cassettes A *Trichoderma reesei* mutant strain, derived from RL-P37 (Sheir-Neiss, G et al. Appl. Microbiol. Biotechnol. 1984, 20:46-53) and selected for high cellulase production was co-transformed with the β-glucosidase expression cassette (cbh1 promoter, *T. reesei* β-glucosidase1 gene, cbh1 terminator, and amdS marker), and the endoxylanase expression cassette (cbh1 promoter, *T. reesei* xyn3, and cbh1 terminator) using PEG-mediated transformation (Penttila, M et al. Gene 1987, 61(2):155-64). Numerous transformants were isolated and examined for β-glucosidase and endoxylanase production. One transformant called *T. reesei* strain #229 was used for transformation with the other expression cassettes.

15.7 Co-Transformation of *T. reesei* Strain #229 with Two β-Xylosidase and α-Arabinofuranosidase Expression Cassettes

*T. reesei* strain #229 was co-transformed with the β-xylosidase fv3A expression cassette (cbh1 promoter, fv3A gene, cbh1 terminator, and alsR marker), the β-xylosidase fv43D expression cassette (egl1 promoter, fv43D gene, native fv43D terminator), and the fv51A α-arabinofuranosidase expression cassette (egl1 promoter, fv51A gene, fv51A native terminator) using electroporation. Transformants were selected on Vogels agar plates containing chlorimuron ethyl (80 ppm). Vogels agar was prepared as follows, per liter.

| | |
|---|---|
| 50 × Vogels Stock Solution (below) | 20 mL |
| BBL Agar | 20 g |
| With deionized H$_2$O bring to | 980 mL |
| post-sterile addition: | |
| 50% Glucose | 20 mL |

50×Vogels Stock Solution (WO 2005/001036), per liter: In 750 mL deionized H2O dissolve successively:

| | |
|---|---|
| Na$_3$Citrate*2H$_2$O | 125.00 g |
| KH$_2$PO$_4$ (Anhydrous) | 250.00 g |
| NH$_4$NO$_3$ (Anhydrous) | 100 g |
| MgSO4*7H$_2$O | 10.00 g |
| CaCl$_2$*2H$_2$O | 5.00 g |
| Vogels Trace Element Solution | 5.0 mL |
| Vogels Biotin Solution | 2.5 mL |
| With deionized H$_2$O, | bring to 1 L |

Numerous transformants were isolated and examined for β-xylosidase and L-α-arabinofuranosidase production. Transformants were also screened for biomass conversion performance according to the cob saccharification assay described in Example 1. Examples of *T. reesei* integrated expression strains described herein are H3A, 39A, A10A, 11A, and G9A, which express all of the genes for *T. reesei* beta-glucosidase 1, *T. reesei* Xyn3, Fv3A, Fv51A, and Fv43D, at different ratios (FIG. 78). Examples of *T. reesei* integrated expression strains described herein also include 44A, 69A, G6A and 102, and each includes most of the genes for *T. reesei* beta-glucosidase 1, *T. reesei* XYN3, Fv3A, Fv51A, and Fv43D, expressed at different ratios. Strain 44A lacked overexpressed *T. reesei* XYN3; strain 69A lacked Fv51A (confirmed by Western Blot, not shown); strains G6A and 102 lacked Fv3A (FIG. 78), as determined by HPLC protein analysis (Example 1).

16. EXAMPLE 10: SACCHARIFICATION PERFORMANCE OF *T. REESEI* INTEGRATED EXPRESSION STRAINS ON AMMONIA PRETREATED CORNCOB

The saccharification performance of enzyme compositions produced by *T. reesei* integrated expression strains on dilute ammonia pretreated corncob was evaluated. *T. reesei* enzyme samples were generated as either ultrafiltration concentrates (UFC) or centrate. For the generation of UFC, *T. reesei* fermentation broths (14L-scale) were obtained after cell separation by centrifugation, concentrated using membrane-ultrafiltration through a Millipore 10 kD molecular weight cut off membrane. Then pH was adjusted to 4.8. The cell-separated broth was then polished by filtration, using FW6 Buchner filtration. Each enzyme sample was assayed for total protein concentration using the modified Biuret method.

The saccharification performance was evaluated in vials or in shake flasks. Each enzyme preparation was assayed for saccharification performance on 20% dry solids (DS) loading of dilute ammonia pretreated corncob (see, WO2006/110901). All saccharification reactions were then titrated with sulfuric acid to pH 5.0 and sodium azide was added to a final concentration of 0.01% (w/v), for microbial contamination control. Each saccharification reaction was then dosed with 20 mg of total protein (TP) enzyme preparation per g of substrate glucan or xylan, as appropriate. Accellerase® 1500 (Ac1500) and the integrated strain UFC's were dosed at 20 mg total protein/g glucan. An enzyme blend was prepared in a ratio of 25:9:4:3:1 Accellerase® 1500:Xyn3: Fv3A:Fv51A: FV43D. In the blend, Accellerase® 1500 was dosed at 20 mg total protein/g glucan and the hemicellulases were dosed per g xylan (4.3 mg Xyn3/g of xylan, 1.7 mg Fv3A/g of xylan, 1.4 mg Fv51A/g of xylan, 0.5 mg Fv43D/g of xylan). Each saccharification reaction was incubated at 50° C. in a rotary shaker set to 200 rpm, then sampled and diluted 10× (v/v) before monomeric sugar concentration was determined using HPLC analysis (detailed in Section 16.1 below under the "monomeric HPLC analysis" section) after 1, 2, 3 and 7 days of saccharification (FIGS. 47A, 47B). On day 3 of saccharification, each reaction was also sampled by weight (w/w) for oligomeric sugar concentration by HPLC analysis (Section 16.1, FIG. 47C). These results show that the enzyme compositions produced by integrated strains H3A and G9A provide better glucose and xylose yields than Accellerase®1500 or enzyme blends created from individually expressed enzymes.

A chromatographic comparison of the enzyme composition produced by three different integrated strains is shown in FIG. 47D.

16.1 HPLC Analysis

Monomeric Sugar HPLC Analysis:

Each sample was analyzed by HPLC using a BioRad Aminex HPX-87H ion exclusion column (300 mm×7.8 mm). All day 1, 2, 3, and 7 samples were diluted 10× volumetrically with 5 mM sulfuric acid, filtered through a 0.2 µm filter before injection into the HPLC and run under manufacture specifications.

Oligomeric Sugar HPLC Analysis (Acid Hydrolysis):

Day 3 saccharification samples were diluted 10× by weight with Milli-Q water, then sulfuric acid was added to the final concentration of 4% (w/w). A xylose and glucose standard (sugar recovery standard—"SRS") of known concentration was also prepared and measured for monomeric sugar HPLC analysis as stated above, and oligomer sugar HPLC analysis. Oligomer HPLC samples and were then autoclaved at 121° C. for 15 min, and filtered through a 0.2 µm filter before injection into the HPLC BioRad Aminex HPX-87H ion exclusion column (300 mm×7.8 mm), and run under manufacturer specifications. Oligomer sugar concentration was determined by multiplying the percent retained xylose and glucose concentration of the sugar recovery standard (SRS) after acid hydrolysis, by the post acid hydrolysis HPLC sugar concentrations of each sample, then subtracting the monomeric sugar concentration determined in the "monomeric sugar HPLC Analysis" section above.

17. EXAMPLE 11: IDENTIFICATION OF PHYLOGENETICALLY BROAD ENZYME CLASSES WHICH CAN IMPROVE THE SACCHARIFICATION PERFORMANCE OF *T. REESEI* INTEGRATED EXPRESSION STRAIN

In this example, enzyme activities which limit the efficacy of enzyme compositions produced by a *T. reesei* integrated expression strain were identified and enzymes from different species which can compensate for those limiting activities or which could substitute for integrated strain components are exemplified.

0.95g of pretreated corncob as described in Example 1 was added to 20 mL glass vials. Sufficient pH 5.0, 50 mM Sodium Acetate buffer and 1 N $H_2SO_4$ were added to give a total reaction weight of 3.00 g at 22 g dry corncob solids/100g of total slurry, pH 5.0 post enzyme additions. The *T. reesei* enzyme composition produced by integrated strain H3A (FIGS. 48A, 49A, and 50A) was added as an ultrafiltered (i.e., cell-free) concentrate to 7 mg total protein per g of glucan and xylan combined in the feedstock to all vials. In addition, candidate hemicellulases were added as the ultrafiltered preparations from 14 L fermentation cultures expressed by *T. reesei* Quad delete strain (described in WO 05/001036). The candidate hemicellulases were added at 0, 0.5, 1.0 or 3.0 mg enzyme protein per g of glucan and xylan combined. The hemicellulases included constituents of the enzyme composition produced by the integrated strain itself including:

*Fusarium verticillioides* Fv3A
*Fusarium verticillioides* Fv51A
*Fusarium verticillioides* Fv43D As well as enzymes from different fungi

*Fusarium oxysporum* Fo43A
*Gibberella zeae* Gz43A
*Penicillium funiculosum* Pf43A
*Aspergillus fumigatus* Af43A
*Podospora anserina* Pa51A
*Penicillium funiculosum* Pf51A The vials were incubated at 180 rpm in an orbital shaker at 48° C. for 72 h. Then 12 mL of water was added. A sub-sample was taken and further diluted, centrifuged and filtered for HPLC analysis for monomer sugars as described in Example 1.

The results shown in FIG. 48A and FIG. 48B demonstrate that addition of β-xylosidase activities such as *Fusarium verticillioides* Fv43D and *Fusarium oxysporum* Fo43A markedly improved monomer xylose release relative to 7 mg *T. reesei* integrated strain total protein per g of Glucan and Xylan combined. Significant improvements were even observed at the low additions of 0.5 and 1.0 mg/g.

The results shown in FIG. 49A and FIG. 49B demonstrate that addition of all of the hemicellulases lead to a significant increase in monomer glucose, even >10% at hemicellulase loadings of 1-3 mg per g of Glucan and Xylan combined.

The results shown in FIG. 50A and FIG. 50B demonstrate that addition of GH51 enzymes such as *Fusarium verticillioides* Fv51A, and especially *Podospora anserine* Pa51A and *Penicillium funiculosum* Pfu51A, led to an increase in monomer arabinose level.

18. EXAMPLE 12: SACCHARIFICATION OF VARIOUSLY PRETREATED SWITCHGRASS BY CELLULASE AND HEMICELLULASE PREPARATIONS

The saccharification performance of expressed cellulases and hemicellulases on pretreated raw switchgrass was evaluated. A range of conditions for dilute ammonia pretreatment of switchgrass were evaluated for saccharification performance with an enzyme cocktail composed of enzymes described herein. Pretreatment conditions vary and pretreatment efficacy affects enzymatic hydrolysis performance.

Pretreatment of raw switchgrass was performed in sealed, 6"×½", stainless steel tubes that were immersed in a heated sand bath. A slurry of raw switchgrass, water, and ammonium hydroxide (~28% solution) was mixed to the desired percent solids and percent ammonia and then loaded into a pretreatment tube. Tubes were then held at the desired temperature (+/−2° C.) for the desired time and then quenched in ice water for approximately 1 min before being brought to room temperature. The pretreated slurry was removed from the tubes and allowed to dry overnight in the hood (>90% solids attainable).

Dried pretreated solids were then saccharified at 10% solids, pH 5, 50° C., 200 rpm using Accellerase® 1500, Xyn 3, Fv3A, Fv51A, and Fv43D (25, 9, 7, 3, 1 mg total protein/g glucan or xylan respectively). A 5 mL total hydrolysate volume in 20 mL scintillation vials was used.

Glucan and xylan yields were based on monomeric glucose and xylose released compared to the glucan or xylan available from the raw biomass. Monomeric sugar concentrations were measured by HPLC (BioRad Aminex HPX 87-H column).

Pretreatment time, temperature, percent solids, and percent $NH_3$, were varied over a wide range in order to optimize saccharification results. Each pretreatment condition that had both glucan and xylan yields better than ~50% is considered a strong performer. The pretreatment parameters that performed strongly are listed in FIG. 79 along with their respective glucan, xylan, and total percent yields. Glucan and Xylan conversions are based on monomeric sugars released during saccharification as compared to glucan or xylan theoretically available in the raw switchgrass. Total conversion is glucose and xylose only (FIG. 51).

19. EXAMPLE 13: SACCHARIFICATION OF PRETREATED SWITCHGRASS BY CELLULASE AND HEMICELLULASE PREPARATIONS

In addition to the above Examples, the saccharification performance of enzyme mixes and enzyme compositions produced by an integrated strain was tested on several substrates, pretreatments and conditions. These experiments show the range of performance using the enzyme mix or an integrated strain product. They demonstrate good performance across a range of substrates and pretreatments, pH, and temperatures.

Dilute ammonia pretreated switchgrass was prepared according to the methods and process ranges in WO06110901A: Switchgrass (38.7% glucan, 22.2% xylan, 2.5% arabinan, 23.2% lignin) was hammer-milled to pass through a 1 mm screen, then pretreated at 160° C. for 90 min with 6% $NH_3$ (weight/weight DM, added as $NH_4OH$). This pretreated substrate was treated with enzyme mixes containing Accellerase® 1500, Multifect® Xylanase (both commercial products of Danisco A/S, Genencor Division, Palo Alto, Calif.), Fv3A, Fv51A, and Fv43D in a total reaction mass of 50g at 15% solids. The total protein (TP) of the commercial products was determined by Biuret assay. The other enzymes were ultra-filtration concentrates (UFCs) following expression in cellulase quad-deleted strains of *T. reesei*, with TP determined by Total Nitrogen analysis of TCA-precipitable protein. All reactions were dosed with Accellerase® 1500 at 25 mg TP/g Glucan and Multifect® Xylanase (MF Xyl) at 9 mg TP/g Xylan, and Fv3A, Fv51A, and Fv43D were added as indicated in FIGS. 56A-56B at 3.6 mg TP/g Xylan, 3.0 mg TP/g Xylan and 1.0 mg TP/g Xylan, respectively. All enzymes were dosed relative to the starting carbohydrate contents of the switchgrass before pretreatment. The saccharification reactions were carried out at 47° C. and 33° C. at pH 5.3 for three days.

The results at 33° C. showed that addition of Fv3A, Fv51A, and Fv43D increased glucan conversion (FIG. 56A) and more than doubled the xylan conversion (FIG. 56B). The results at 47° C. showed that addition of Fv3A, Fv51A, and Fv43D gave some increased glucan conversion (FIG. 56A) and more than doubled the xylan conversion (F FIG. igure 56B). Additions of Fv51A or Fv43D, alone, gave large increases in xylan conversion, especially to xylo-oligomers or xylose monomers, respectively. Addition of Fv3A alone increased xylose yields, but in combination with Fv51A gave a large increase in xylan conversion to monomer.

20. EXAMPLE 14: SACCHARIFICATION OF PRETREATED SWITCHGRASS BY AN INTEGRATED *T. REESEI* STRAIN

The saccharification performance of an enzyme composition produced by an integrated *T. reesei* strain (H3A) was evaluated on dilute ammonia pretreated switchgrass prepared according to the methods and process ranges in WO006110901A: Switchgrass (37% glucan, 21% xylan, 5% arabinan, 18% lignin) was hammer-milled to pass through a 1 mm screen, then pretreated at 160° C. for 90 min with 10.0% $NH_3$ (weight/weight DM, added as $NH_4OH$). In duplicate 500 mL glass Erlenmeyer flasks, 50 g of pretreated slurry at 25% solids was saccharified at 48° C., pH 5.3 for 7 days, with supernatant from the integrated strain was dosed at 14 mg TP/g of carbohydrate (glucan plus xylan). TP of H3A was determined by Total Nitrogen analysis of TCA-precipitable protein. Enzymes were dosed relative to the starting carbohydrate contents of the switchgrass before pretreatment.

At the end of 7 days, high levels of glucan conversion (52-55%, FIG. 57A) and xylan conversion (51%-53%, (FIG. 57B) were measured by HPLC. These results show that the enzyme composition produced by the integrated strain can saccharify dilute ammonia pretreated switchgrass at high solids (25% dry matter).

21. EXAMPLE 15: SACCHARIFICATION OF HARDWOOD PULP BY AN INTEGRATED *T. REESEI* STRAIN

The saccharification performance of an enzyme composition produced by integrated *T reesei* strain H3A was evaluated on industrial hardwood unbleached pulp (derived from Kraft process and oxygen delignification, Smurfit Kappa Cellulose Du Pin, Biganos, France) with the following composition: Glucan 75.1%, Xylan 19.1%, Acid soluble lignin 2.2%. The enzymatic saccharification studies were carried out using NREL standard assay method LAP-009 "Enzymatic Saccharification of Lignocellulosic Biomass"

(www.nrel.gov/biomass/pdfs/42629.pdf), except that the cellulose loading was different (varying from 9.3-20%) and a total mass of 100 g was used. The experimental condition was 200 rpm and pH 5.0, 50° C. Enzyme was dosed at 20 mg TP/g glucan (based on final dry matter) at the start of the experiment. Samples were taken at timed intervals if they were liquefied, and then analyzed by HPLC for sugar concentration. Glucose, xylose, and cellobiose concentration were determined using a Waters HPLC system (Alliance system, Waters Corp., Milford, Mass.). The HPLC column used for sugar analysis was from BioRad (Aminex HPX-87H ion exclusion column (300 mm×7.8 mm), BioRad Inc., Hercules, Calif.). All samples were diluted 10× with 5 mM sulfuric acid, filtered through a 0.2 μm filter before injection into the HPLC. As indicated (FIG. 80) two experiments were carried out in "fed-batch" mode: Pretreated hardwood pulp to an initial dry matter content of 7.0% at Time 0 and the rest of the substrate was added at discrete times in four equal portions during the first 24 h to bring the final dry solids loading to 20%.

Results showed high levels of glucan and xylan conversion to monomers (up to 89% and 90%, respectively) with the enzyme composition produced by integrated strain H3A. Conversions increased with higher enzyme loadings and longer saccharification times. Conversion was lower when the solids were at 20% than at 15%, but this lower conversion at 20% could be partially mitigated by using a fed-batch process.

22. EXAMPLE 16: SACCHARIFICATION OF HARDWOOD PULP BY AN INTEGRATED *T. REESEI* STRAIN OVER A RANGE OF TEMPERATURE AND PH

The saccharification performance of an enzyme composition produced by an integrated *T. reesei* strain (H3A) on industrial hardwood unbleached pulp (as used in the preceding example) at 7% cellulose loading and 20 mg TP/g glucan of integrated strain supernatant (based on final dry matter and composition of the pretreated substrate) was tested at temperatures from 45° C.-60° C. and pH's from 4.65-5.4 (buffered in 0.1 M sodium citrate). Results after 2 days saccharification are shown in FIG. 81 and show good glucan and xylan conversions over the whole range of conditions tested. These results suggested optimum conditions for saccharification of this substrate as pH 4.9 and 50° C. but good conversions are seen even at pH 5.0, 60° C. In a follow-up experiment at 50° C., including lower pH's (and otherwise unchanged experimental conditions) good saccharifications were seen at pH 3.8, pH 4.0 and pH 4.25, with glucose & xylose titers of 45.1 & 9.7 g/L; 50.0 & 11.4 g/L; and 57.2 & 13.2 g/L, respectively.

23. EXAMPLE 17: SACCHARIFICATION OF STEAM-EXPANDED SUGARCANE BAGASSE WITH AN ENZYME COMPOSITION PRODUCED BY AN INTEGRATED STRAIN AT DIFFERENT ENZYME DOSES

The saccharification performance of an enzyme composition produced by an integrated *T reesei* strain (H3A) on steam-expanded sugarcane bagasse was evaluated at 7% cellulose loading. The bagasse was pretreated by steam injection in a StakeTech reactor at 210 psig, 200° C. with a 4 min residence time. The pretreated material had the following composition: Glucan 40.9%, Xylan 20.8%, Lignin 27%. The integrated strain supernatant was dosed at 10, 20, 30, 50 or 80 mg TP/g glucan (based on final dry matter and composition of the pretreated substrate). Saccharification was carried out in a 5 mL reaction volume at 50° C., pH 5 for 3 days. The results (FIGS. 58A-C) showed that the integrated strain product out-performed Accellerase®1500 (20 mg protein/g glucan) in glucan conversion to glucose (FIG. 58A and FIG. 58C) and, especially, xylan conversion to xylose (FIG. 58B and FIG. 58C) even at half the Accellerase® 1500 dose. Glucan conversion, especially at Day 1, increased significantly as the dose of H3A total protein increased (FIG. 58A and FIG. 58C), whereas xylan conversion was more rapid, with little increase from Day 1 to Day 3, and very high, even at the lowest dose of H3A total protein (FIG. 58B and FIG. 58C).

24. EXAMPLE 18: SACCHARIFICATION OF DILUTE-ACID PRETREATED CORN FIBER WITH VARIOUS ENZYMES

The saccharification performance of enzyme mixtures on dilute sulfuric acid pretreated corn fiber was evaluated in a 250 mL shake flask. In a typical experiment, corn fiber (initial composition 38% C6 sugars and 27% C5 sugars) was adjusted to 15% DS (dry solids) and 0.36% (w/w %) sulfuric acid was added. Corn fiber slurry was then autoclaved at 121° C. for 60 min. The slurry was then adjusted to pH 5.0 using 6 N NaOH. The sugar content of the pretreated sample was 21 g/L glucose and 12 g/L xylose. Enzymes were added to the pretreated substrate as follows (as indicated in FIGS. 59A, 59B, 59C); Accellerase® 1500 (AC 1500): 20 mg TP/g glucan and 45 mg TP/g glucan; Accellerase® 1500+Multifect® Xylanase (MF): (25 mg/g glucan+9 mg TP/g xylan) and (25 mg TP/g glucan+20 mg TP/g xylan); Accellerase® 1500+Xyn 3+Fv3A+Fv51A+Fv43D: (25 mg TP/g glucan+9 mg TP/g xylan+7 mg TP/g xylan+3 mg TP/g xylan+1 mg TP/g xylan) (the full enzyme "blend"). The total protein (TP) of the commercial products (Accellerase® 1500 and Multifect® Xylanase: Danisco US Inc., Genencor) were determined by Biuret assay. The other enzymes were ultra-filtration concentrates (UFCs) following expression in cellulase quad-deleted strains of *T. reesei* (as described earlier)—their TP were determined by Total Nitrogen analysis of TCA-precipitable protein. All enzymes were dosed relative to the starting carbohydrate contents of the corn fiber before pretreatment. Enzymatic saccharification was carried out at 200 rpm and 50° C. for 24 h, 48 h and 120 h. Samples were withdrawn at different time intervals and analyzed for the formation of glucose and xylose sugars by HPLC. The adjusted sugar (glucose or xylose) reflected the sugar being produced from the enzymatic step, with the starting sugars subtracted.

The results show that the full enzyme blend out-performed the (Accellerase® 1500+Multifect® Xylanase) ("AC 1500+MF") in glucan conversion and in xylan conversion, even when both were dosed at the same total protein. The full enzyme blend gave almost complete glucan conversion of this substrate after 5 days saccharification.

25. SPECIFIC EMBODIMENTS AND INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the disclosure(s).

What is claimed is:

1. A non-naturally occurring composition comprising:
   (a) a first polypeptide having β-xylosidase activity, wherein the first polypeptide has at least 90% sequence identity to the amino acid sequence of SEQ ID NO:28 or the amino acid sequence corresponding to residues (i) 20-341, (ii) 21-350, (iii) 107-341, or (iv) 107-350 of SEQ ID NO:28; and
   (b) a second polypeptide having xylanase activity;
   wherein the non-naturally occurring composition comprises one or more polypeptides produced from a host cell, wherein the host cell is engineered to express the first polypeptide having β-xylosidase activity and wherein the first polypeptide is heterologous to the host cell.

2. The composition of claim 1, wherein the second polypeptide is a *Trichoderma* xylanase or an *Aspergillus* xylanase.

3. The composition of claim 2, wherein the *Trichoderma* xylanase is a *Trichoderma reesei* Xyn3 polypeptide or a *Trichoderma reesei* Xyn2 polypeptide, or the *Aspergillus* xylanase is an *Aspergillus fumigatus* AfuXyn2 polypeptide or an *Aspergillus fumigatus* AfuXyn5 polypeptide, wherein:
   said *Trichoderma reesei* Xyn3 polypeptide has at least 90% sequence identity to SEQ ID NO:42, or to residues 17-347 of SEQ ID NO:42, or is encoded by a nucleic acid having at least 90% sequence identity to SEQ ID NO:41;
   said *Trichoderma reesei* Xyn2 polypeptide has at least 90% sequence identity to SEQ ID NO:43, or to residues 33-222 of SEQ ID NO:43;
   said *Aspergillus fumigatus* AfuXyn2 polypeptide has at least 90% sequence identity to SEQ ID NO:24, or to residues 19-228 of SEQ ID NO:24, or is encoded by a nucleic acid having at least 90% sequence identity to SEQ ID NO:23;
   said *Aspergillus fumigatus* AfuXyn5 polypeptide has at least 90% sequence identity to SEQ ID NO:26, or to residues 20-313 of SEQ ID NO:26, or is encoded by a nucleic acid having at least 90% sequence identity to SEQ ID NO:25.

4. The composition of claim 1, further comprising one or more accessory proteins selected from the group consisting of mannanases, galactanases, arabinases, ligninases, amylases, glucuronidases, proteases, esterases, lipases, xyloglucanases, glycoside hydrolase Family 61 polypeptides, CIP1, CIP2, swollenin, expansins, CIP1-like proteins, CIP2-like proteins, cellobiose dehydrogenases, and manganese peroxidases.

5. The composition of claim 1, further comprising a biomass.

6. The composition of claim 5, wherein the biomass is pretreated biomass, optionally wherein the biomass is ammonia-pretreated.

7. The composition of claim 6, wherein the combined weight of polypeptides having xylanase activity is 0.5 g to 40 g per 1 kg of hemicellulose in the biomass, or the combined weight of polypeptides having β-xylosidase activity is 0.5 g to 50 g per 1 kg of hemicellulose in the biomass.

8. The composition of claim 7, wherein the biomass comprises one or more of corncob, corn stover, corn fiber, switchgrass, sorghum, paper, pulp, sugarcane bagasse, or *Miscanthus*.

9. A fermentation broth comprising the composition of claim 1.

10. The fermentation broth of claim 9, which is the fermentation broth of a filamentous fungus, wherein the filamentous fungus is a *Trichoderma, Humicola, Fusarium, Aspergillus, Myceliophthora, Neurospora, Penicillium, Cephalosporium, Achlya, Podospora, Endothia, Mucor, Cochliobolus, Pyricularia, Phanerochaete,* or *Chrysosporium*.

11. A saccharification process comprising treating a material comprising hemicellulose with the composition of claim 1.

12. The process of claim 11, wherein the material comprising hemicellulose is one or more of corncob, corn stover, corn fiber, switchgrass, sorghum, paper, pulp, sugarcane bagasse, or *Miscanthus*;
   optionally wherein the process yields at least 60% xylose from hemicellulose xylan of the material comprising hemicellulose.

* * * * *